United States Patent
Narain et al.

(10) Patent No.: US 9,797,905 B2
(45) Date of Patent: Oct. 24, 2017

(54) USE OF MARKERS IN THE DIAGNOSIS AND TREATMENT OF PROSTATE CANCER

(71) Applicant: Berg LLC, Nashville, TN (US)

(72) Inventors: Niven Rajin Narain, Cambridge, MA (US); Rangaprasad Sarangarajan, Boylston, MA (US); Vivek K. Vishnudas, Bedford, MA (US)

(73) Assignee: Berg LLC, Nashville, TN (US)

( * ) Notice: Subject to any disclaimer, the term of this patent is extended or adjusted under 35 U.S.C. 154(b) by 0 days.

(21) Appl. No.: 15/059,238

(22) Filed: Mar. 2, 2016

(65) Prior Publication Data

US 2016/0178632 A1  Jun. 23, 2016

Related U.S. Application Data

(62) Division of application No. 13/929,723, filed on Jun. 27, 2013, now abandoned.

(60) Provisional application No. 61/665,201, filed on Jun. 27, 2012, provisional application No. 61/718,081, filed on Oct. 24, 2012, provisional application No. 61/718,064, filed on Oct. 24, 2012, provisional application No. 61/672,090, filed on Jul. 16, 2012, provisional application No. 61/673,094, filed on Jul. 18, 2012, provisional application No. 61/702,523, filed on Sep. 18, 2012, provisional application No. 61/718,080, filed on Oct. 24, 2012.

(51) Int. Cl.
*G01N 33/53*  (2006.01)
*G01N 33/574*  (2006.01)
*G01N 33/68*  (2006.01)
*C12Q 1/68*  (2006.01)

(52) U.S. Cl.
CPC ..... *G01N 33/57434* (2013.01); *C12Q 1/6886* (2013.01); *G01N 33/6893* (2013.01); *C12Q 2600/106* (2013.01); *C12Q 2600/118* (2013.01); *C12Q 2600/158* (2013.01); *G01N 2333/47* (2013.01); *G01N 2333/4742* (2013.01); *G01N 2800/50* (2013.01); *G01N 2800/56* (2013.01)

(58) Field of Classification Search
None
See application file for complete search history.

(56) References Cited

U.S. PATENT DOCUMENTS

| | | |
|---|---|---|
| 5,288,614 A | 2/1994 | Bodenmueller et al. |
| 5,399,482 A | 3/1995 | Bodenmueller et al. |
| 6,207,380 B1 | 3/2001 | Billing-Medel et al. |
| 6,329,179 B1 | 12/2001 | Kopreski |
| 7,901,902 B2 | 3/2011 | Bae et al. |
| 8,008,032 B2 | 8/2011 | Forsyth et al. |
| 8,030,031 B2 | 10/2011 | Kopreski |
| 8,076,080 B2 | 12/2011 | Tada et al. |
| 8,293,485 B2 | 10/2012 | Krizman et al. |
| 8,383,357 B2 | 2/2013 | Haley et al. |
| 8,492,328 B2 | 7/2013 | Huang et al. |
| 8,524,493 B2 | 9/2013 | Panabieres et al. |
| 8,557,777 B2 | 10/2013 | Perambakam et al. |
| 8,609,345 B2 | 12/2013 | Krisman et al. |
| 8,642,349 B1 | 2/2014 | Yeatman |
| 8,669,058 B2 | 3/2014 | Liew |
| 8,741,587 B2 | 6/2014 | Roessler et al. |
| 8,748,108 B2 | 6/2014 | McKeegan et al. |
| 8,889,361 B2 | 11/2014 | Chen |
| 8,980,573 B2 | 3/2015 | Rollinger et al. |
| 2002/0012931 A1 | 1/2002 | Waldman et al. |
| 2002/0137086 A1 | 9/2002 | Olek et al. |
| 2003/0073144 A1 | 4/2003 | Benson et al. |
| 2003/0225528 A1 | 12/2003 | Baker et al. |
| 2004/0029151 A1 | 2/2004 | Mahadevappa et al. |
| 2004/0109863 A1 | 6/2004 | Emtage |
| 2005/0064455 A1 | 3/2005 | Baker et al. |
| 2005/0259483 A1 | 11/2005 | Nakamura et al. |
| 2006/0019256 A1 | 1/2006 | Clarke et al. |
| 2006/0057127 A1 | 3/2006 | Liu et al. |
| 2006/0134663 A1 | 6/2006 | Harkin et al. |
| 2006/0172303 A1 | 8/2006 | Lehnert |
| 2007/0042945 A1 | 2/2007 | Bodary et al. |
| 2007/0048297 A1 | 3/2007 | Rosen et al. |
| 2007/0048738 A1 | 3/2007 | Donkena et al. |
| 2007/0054271 A1 | 3/2007 | Polyak et al. |
| 2007/0099209 A1 | 5/2007 | Clarke et al. |
| 2007/0099251 A1 | 5/2007 | Zhang et al. |
| 2007/0105114 A1 | 5/2007 | Li et al. |
| 2007/0122856 A1 | 5/2007 | Georges et al. |
| 2007/0141587 A1 | 6/2007 | Baker et al. |
| 2007/0207508 A1 | 9/2007 | Yao et al. |

(Continued)

FOREIGN PATENT DOCUMENTS

| | | |
|---|---|---|
| EP | 1124572 A2 | 8/2001 |
| EP | 1678503 A2 | 7/2006 |

(Continued)

OTHER PUBLICATIONS

Tockman et al (Cancer Res., 1992, 52:2711s-2718s).*
Ernst et al. "Decrease and Gain of Gene Expression Are Equally Discriminatory Markers for Prostate Carcinoma" Am. J. Pathol. Jun. 2002; 160(6) p. 2169-2180.
Glen et al. "Eight-Plex iTRAQ Analysis of Variant Metastatic Human Prostate Cancer Cells Identifies Candidate Biomarkers of Progression: An Exploratory Study" The Prostate (2010) 70 p. 1313-1332.

(Continued)

*Primary Examiner* — Sean Aeder
(74) *Attorney, Agent, or Firm* — McCarter & English, LLP; Elizabeth A. Hanley, Esq.; Jill Mello

(57) ABSTRACT

The invention provides method for diagnosis, monitoring, and prognosis of prostate cancer using one or more of keratin 4, keratin 7, keratin 8, keratin 15, keratin 18, keratin 19, tubulin-beta 3, filamin B, and LY9, and PSA. The invention provides kits for practicing the methods of the invention.

33 Claims, 14 Drawing Sheets

(56) References Cited

U.S. PATENT DOCUMENTS

| | | |
|---|---|---|
| 2007/0218496 A1 | 9/2007 | Kitagawa et al. |
| 2007/0220621 A1 | 9/2007 | Clarke et al. |
| 2007/0231822 A1 | 10/2007 | Mitas |
| 2008/0003624 A1 | 1/2008 | Takata et al. |
| 2008/0305558 A1 | 12/2008 | Loveday et al. |
| 2009/0081659 A1 | 3/2009 | Hornbeck et al. |
| 2009/0098533 A1 | 4/2009 | Munnes et al. |
| 2009/0176235 A1 | 7/2009 | Cargill et al. |
| 2009/0186024 A1 | 7/2009 | Nevins et al. |
| 2009/0186815 A1 | 7/2009 | Boutros et al. |
| 2009/0215636 A1 | 8/2009 | Krizman et al. |
| 2009/0221004 A1 | 9/2009 | Hong |
| 2009/0232773 A1 | 9/2009 | Kato et al. |
| 2010/0093556 A1* | 4/2010 | Clarke .................. C12N 5/0693 506/9 |
| 2010/0184125 A1 | 7/2010 | Huang et al. |
| 2010/0216660 A1 | 8/2010 | Nikolsky et al. |
| 2010/0279957 A1 | 11/2010 | Potti et al. |
| 2010/0330593 A1 | 12/2010 | Alper |
| 2011/0171124 A1 | 7/2011 | Bugaj et al. |
| 2011/0177525 A1 | 7/2011 | Shuber et al. |
| 2011/0177967 A1 | 7/2011 | Carstens et al. |
| 2011/0212464 A1 | 9/2011 | Hagmann et al. |
| 2011/0212465 A1 | 9/2011 | Roessler et al. |
| 2011/0236903 A1 | 9/2011 | McClelland et al. |
| 2011/0265197 A1 | 10/2011 | Depinho et al. |
| 2011/0271359 A1 | 11/2011 | Langham |
| 2011/0311443 A1 | 12/2011 | Schubert |
| 2012/0021929 A1 | 1/2012 | Swiatek-de Lange et al. |
| 2012/0071335 A1 | 3/2012 | Manaresi et al. |
| 2012/0087862 A1 | 4/2012 | Hood et al. |
| 2012/0101084 A1 | 4/2012 | Haley et al. |
| 2012/0183552 A1 | 7/2012 | Joseloff et al. |
| 2012/0244531 A1 | 9/2012 | Lee et al. |
| 2013/0022974 A1 | 1/2013 | Chinnaiyan et al. |
| 2013/0029868 A1 | 1/2013 | Orfao De Matos Correia E Vale |
| 2013/0095503 A1 | 4/2013 | Lu |
| 2013/0131194 A1 | 5/2013 | Skog et al. |
| 2013/0203164 A1 | 8/2013 | Rosen et al. |
| 2013/0244256 A1 | 9/2013 | Clarke et al. |
| 2013/0260388 A1 | 10/2013 | Shen et al. |
| 2013/0288233 A1 | 10/2013 | Murray |
| 2013/0316361 A1 | 11/2013 | Bastia et al. |
| 2013/0317083 A1 | 11/2013 | Rigoutsos |
| 2014/0011861 A1 | 1/2014 | McClelland et al. |
| 2014/0045915 A1 | 2/2014 | Skog et al. |
| 2014/0065612 A1 | 3/2014 | Tsai et al. |
| 2014/0066319 A1 | 3/2014 | Gertler et al. |
| 2014/0106981 A1 | 4/2014 | Hood et al. |
| 2014/0162888 A1 | 6/2014 | Kuslich et al. |
| 2014/0235479 A1 | 8/2014 | Depinho et al. |
| 2014/0242069 A1 | 8/2014 | Sin et al. |
| 2014/0271672 A1 | 9/2014 | Iakoubova et al. |
| 2014/0286961 A1 | 9/2014 | Bergstein |
| 2014/0343451 A1 | 11/2014 | Pannell et al. |
| 2014/0364326 A1 | 12/2014 | Guergova-Kuras et al. |
| 2015/0051104 A1 | 2/2015 | Schubert |
| 2015/0056614 A1 | 2/2015 | Mikolajczyk |
| 2015/0079590 A1 | 3/2015 | Pandolfi et al. |
| 2015/0086570 A1 | 3/2015 | Violette et al. |
| 2015/0125456 A1 | 5/2015 | Kim et al. |
| 2015/0152474 A1 | 6/2015 | Pawlowski et al. |
| 2015/0153363 A1 | 6/2015 | Jarvi et al. |

FOREIGN PATENT DOCUMENTS

| | | |
|---|---|---|
| EP | 1845167 B1 | 10/2007 |
| EP | 1364069 B1 | 4/2009 |
| EP | 2057465 A2 | 5/2009 |
| EP | 2177615 A1 | 4/2010 |
| EP | 1861715 B1 | 8/2010 |
| EP | 2270226 A2 | 1/2011 |
| EP | 2403877 A1 | 1/2012 |
| EP | 2520935 A2 | 11/2012 |
| WO | 0023100 A2 | 4/2000 |
| WO | 02/14500 A2 | 2/2002 |
| WO | 2004/076614 A3 | 10/2004 |
| WO | 2005/043165 A2 | 5/2005 |
| WO | 2006/048291 A2 | 5/2006 |
| WO | WO-2007071947 A1 | 6/2007 |
| WO | 2008/079269 A2 | 7/2008 |
| WO | 2008/121307 A2 | 10/2008 |
| WO | 2010/100899 A1 | 9/2010 |
| WO | WO-2011040532 A1 | 4/2011 |
| WO | 2011/053837 A1 | 7/2011 |
| WO | 2011/073131 A1 | 10/2011 |
| WO | 2011/149402 A2 | 12/2011 |
| WO | 2012/006634 A2 | 1/2012 |
| WO | 2012/021969 A1 | 2/2012 |
| WO | 2012/024543 A1 | 2/2012 |
| WO | 2012/031008 A2 | 3/2012 |
| WO | 2012/077139 A1 | 6/2012 |
| WO | 2012/083338 A1 | 6/2012 |
| WO | 2012/101283 A1 | 8/2012 |
| WO | 2012/116248 A1 | 8/2012 |
| WO | 2012135397 A2 | 10/2012 |
| WO | 2013/022995 A2 | 2/2013 |
| WO | 2014/041185 A2 | 3/2014 |
| WO | 2014/160499 A2 | 10/2014 |
| WO | 2014/163557 A1 | 10/2014 |
| WO | 2015/042465 A1 | 3/2015 |

OTHER PUBLICATIONS

Alaiya, A. et al., Proteomics-Based Signature for Human Benign Prostate Hyperplasia and Prostate Adenocarinoma, International Journal of Oncology, Feb. 8, 2011, vol. 38, No. 4, pp. 1047-1057.

Hudson, DL et al., "Epithelial Cell Differentiation Pathways in the Human Prostate: Identification of Intermediate Phenotypes by Keratin Expression," Journal of Histochemistry & Cytochemistry, Feb. 1, 2001, vol. 29, No. 22, pp. 271-278.

Ploussard G., et al., "Class III Beta-Tubulin Expression Predicts Prostate Tumor Aggressiveness and Patient Response to Docetaxel-Based Chemotherapy," Nov. 2, 2010, vol. 70, No. 22, pp. 9253-9264.

Sakamoto, K., et al., "Down-Regulation of Keratin 4 and Keratin 13 Expression in Oral Squamous Cell Carcinoma and Epithelial Dysplasia: A Clue for Histopathogenesis", Histopathology, Mar. 3, 2011, vol. 58, No. 4, pp. 531-542.

Tobias-Machado, M. et al., "Cytokeratin 19 Exp[ression by Reverse Transcriptase—Polymer Chain Reaction in the Peripheral Blood and Prostate Cancer Patients", Tumori May 2005, vol. 91, No. 3, pp. 248-252.

Van Den Eertwegh, AJM et al., "Combined Immunotherapy With Granulocyte-Macrophage Colony-Stimulating Factor-Transduced Allogenic Prostate Cancer Cells and Ipilimumab in Patients with Metastatic Castration-Resistant Prostate Cancer: A Phase 1 Dose-Escalation Trial", Lancet Oncology, Feb. 10, 2012, vol. 13, No. 5, p. 509-517.

Narain et al., "Abstract 538: Identification and validation of novel prostate cancer biomarkers using the Berg Interrogative Biology (TM) platform" www.cancerres.aacrjournals.org, Aug. 1, 2015 p. 1-2.

Higano et al., "Phase 1/2 Dose-Escalation Study of a GM-CSF-Secreting, Allogeneic, Cellular Immunotherapy for Metastatic Hormone-Refractory Prostate Cancer" Wiley InterScience, Jul. 21, 2008, p. 975-984.

Panteleakou Z. et al. Detection of Circulating Tumor Cells in Prostate Cancer Patients: Methodological Pitfalls and Clinical Relevance. Molecular Medicine. 2009;15(3-4):101-114.

Baldassarre M. et al. Filamins Regulate Cell Spreading and Initiation of Cell Migration. 2009, PLoS ONE 4 (11): e7830.

Bedolla RG et al. Nuclear vs. Cytoplasmic Localization of Filamin A in Prostate Cancer: Immunohistochemical Correlation with Metastases. 2009, Clin Cancer Res. 15 (3): 788-796.

Loy CJ et al. Filamin-A Fragment Localizes to the Nucleus to Regulate Androgen Receptor and Coactivator Functions. 2003, International Journal of Oncology 44 (2): 467-472.

(56) References Cited

OTHER PUBLICATIONS

Filella X et al. Measurement of Complexed PSA in the Differential Diagnosis Between Prostate Cancer and Benign Prostate Hyperplasia. 2000, The Prostate 42 (3): 181-185.

* cited by examiner

Mean FLNB Levels in Human Serum n=2

PSA Levels in Human Serum

| Marker | AUC |
|---|---|
| PSA | 0.87 |
| FLNB | 0.78 |
| PSA + FLNB | 0.975 |

Linear scoring function

ROC curves for PSA, FLNB, LY9 and combinations

Non-Linear scoring function

ROC curves for PSA, FLNB, LY9 and combinations:
Non-linear model:

USE OF MARKERS IN THE DIAGNOSIS AND TREATMENT OF PROSTATE CANCER

CROSS REFERENCE TO RELATED APPLICATIONS

This application is a divisional application of U.S. Ser. No. 13/929,723, filed on Jun. 27, 2013, which claims priority to U.S. Provisional Application Ser. No. 61/665,201, filed Jun. 27, 2012; U.S. Provisional Application Ser. No. 61/672,090, filed Jul. 16, 2012; U.S. Provisional Application Ser. No. 61/673,094, filed Jul. 18, 2012; U.S. Provisional Application Ser. No. 61/702,523, filed Sep. 18, 2012, and U.S. Provisional Application Ser. Nos. 61/718,064, 61/718,080, and 61/718,081 all filed on Oct. 24, 2012. Each of these applications are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Mar. 2, 2016, is named 119992-06605.txt and is 461,575 bytes in size.

FIELD OF THE INVENTION

The invention relates to treatment, prevention, reduction, diagnosis, monitoring, and prognosis of abnormal prostate states, including benign prostate hyperplasia and oncological disorders, especially prostate cancer, in humans using filamin B, lymphocyte antigen 9 (LY9), keratins and tubulin, specifically using keratins 4, 7, 8, 15, 18, and 19, and tubulin-beta 3, particularly keratins 7, 15, or 19. The filamin B, lymphocyte antigen 9 (LY9), keratins and tubulin can further be used in conjunction with prostate specific antigen (PSA) for the treatment, prevention, reduction, diagnosis, monitoring, and prognosis of abnormal prostate states, including benign prostate hyperplasia and oncological disorders, especially prostate cancer. The invention also relates to panels and kits for use in practicing the methods of the invention.

BACKGROUND OF THE INVENTION

Oncological disorders, such as cancer, are presently one of the leading causes of death in developed nations and is a serious threat to modern society. Cancer can develop in any tissue of any organ at any age. Worldwide, more than 10 million people are diagnosed with cancer every year and it is estimated that this number will grow to 15 million new cases every year by 2020. It is believed that cancer causes six million deaths every year or 12% of the deaths worldwide.

Prostate cancer is a form of cancer that develops in the prostate, a gland in the male reproductive system. Most prostate cancers are slow growing. However, there are cases of aggressive prostate cancers. The cancer cells may metastasize from the prostate to other parts of the body, particularly to the bones and lymph nodes. Prostate cancer may cause pain, difficulty in urinating, problems during sexual intercourse, or erectile dysfunction. Other symptoms can potentially develop during later stages of the disease.

Rates of detection of prostate cancers vary widely across the world, with detection rates in south and east Asia being lower than those in Europe, and especially in the United States. Prostate cancer tends to develop in men over the age of fifty and, although it is one of the most prevalent types of cancer in men, many never have symptoms or undergo therapy for prostate cancer, and eventually die of other causes. Further, treatment of prostate cancer may do more harm to the subject than the prostate cancer itself. Prostate specific antigen (PSA) screening has lead to a significant rise in the number of men diagnosed with prostate cancer with an associated increase in potentially unnecessary biopsies preformed. Despite its limitations, including a positive predictive value of only 25-40%, PSA remains the only generally accepted biomarker for prostate cancer.

Prostate cancer is, in most cases, slow-growing and symptom-free. Moreover, since men with the condition are typically older, they often die of causes unrelated to the prostate cancer, such as heart/circulatory disease, pneumonia, other unrelated cancers, or old age. On the other hand, the more aggressive prostate cancers account for more cancer-related deaths among men in the United States than any other cancer except lung cancer.

About two-thirds of prostate cancer cases are slow growing, whereas the other third are more aggressive and fast developing. It is important to be able to distinguish between aggressive and non-aggressive forms of the disease, and further, to distinguish prostate cancer from benign prostate hyperplasia (BPH). Commonly used screening tests, e.g., for prostate specific antigen (PSA) cannot distinguish between prostate cancer and BPH.

SUMMARY OF THE INVENTION

The present invention is based, at least in part, on Applicants' discovery that keratins 4, 7, 8, 15, 18, and 19, tubulin-beta 3, filamin B (FLNB), and lymphocyte antigen 9 (LY9) are differentially regulated in prostate cancer cells.

Accordingly, the invention provides methods for diagnosing, monitoring (e.g., of disease progression or treatment), prognosing, treating, alleviating symptoms of, inhibiting progression of, or preventing, an oncological disease state, e.g., prostate cancer, in a mammal. The invention further provides panels and kits for practicing the methods of the invention.

In one aspect, the invention provides methods for diagnosing an abnormal prostate state in a subject comprising:

(1) determining a level of one or more prostate cancer related markers selected from the group consisting of filamin B, LY9, keratin 4, keratin 7, keratin 8, keratin 15, keratin 18, keratin 19, and tubulin-beta 3 in a biological sample from the subject; and (2) comparing the level of the one or more prostate cancer related markers in the biological sample with the level of the one or more prostate cancer related markers in a normal control sample, wherein an altered level of the one or more prostate cancer related markers in the biological sample relative to the normal control sample is indicative of an abnormal prostate state in the subject.

In certain embodiments, the one or more prostate cancer related markers is selected from the group consisting of filamin B, LY9, and keratin 19. In certain embodiments, an increased level of one or more prostate cancer related markers selected from the group consisting of filamin B, LY9, and keratin 19 in the biological sample relative to a normal control sample is indicative of an abnormal prostate state in the subject.

In certain embodiments, no increase in the detected level of expression of each of the one or more prostate-cancer related markers selected from the group consisting of filamin B, LY9, and keratin 19 in the biological sample relative to a normal control sample is indicative of a normal prostate state in the subject. In such embodiments, levels of one, two, or all three of filamin B, LY9, and keratin 19 can be detected. For the marker levels detected, none of the markers have increased levels.

In certain embodiments, the method further comprises detecting the level of prostate specific antigen (PSA) in the biological sample and preferably further comprising comparing the level of PSA in the biological sample to the level of PSA in a normal control sample. In certain embodiments, an increase in the level of one or more prostate cancer related markers selected from the group consisting of filamin B, LY9, and keratin 19 in the biological sample relative to the normal control sample, in combination with an increase in the level of PSA in the biological sample as compared to the level of PSA in the normal control sample has greater predictive value of the subject having an abnormal prostate state than the predictive value of a single marker alone. In certain embodiments, no increase in the detected level of expression of each of the one or more prostate-cancer related markers selected from the group consisting of filamin B, LY9, and keratin 19 in the biological sample relative to the normal control sample, in combination with a decreased or normal level of PSA in the biological sample as compared to the level of PSA in the normal control sample has a greater predictive value of the subject having a normal prostate state than any single marker alone.

Throughout the methods, kits, and panels of the invention, one or more of filamin B, LY9 and keratin 19 is understood as any of filamin B; LY9; keratin 19; filamin B and LY9; filamin B and keratin 19; LY9 and keratin 19; or filamin B, LY9, and keratin 19.

In certain embodiments of the invention, the abnormal prostate state is prostate cancer.

In certain embodiments of the invention, the prostate cancer is androgen-dependent prostate cancer. In certain embodiments of the invention, the prostate cancer is androgen-independent prostate cancer. In certain embodiments of the invention, the prostate cancer is aggressive prostate cancer. In certain embodiments of the invention, the prostate cancer is non-aggressive prostate cancer.

In certain embodiments of the invention, the abnormal prostate state is benign prostate hyperplasia.

In another aspect, the invention provides a method for identifying a subject as being at increased risk for developing prostate cancer, the method comprising:

(1) determining a level of one or more prostate cancer related markers selected from the group consisting of filamin B, LY9, keratin 4, keratin 7, keratin 8, keratin 15, keratin 18, keratin 19, and tubulin-beta 3 in a biological sample from the subject; and (2) comparing the level of the one or more prostate cancer related markers in the biological sample with the level of the one or more prostate cancer related markers in a normal control sample, wherein an altered level of the one or more prostate cancer related markers in the biological sample relative to the control sample is indicative of an increased risk for developing prostate cancer in the subject.

In certain embodiments, the one or more prostate cancer related markers is selected from the group consisting of filamin B, LY9, and keratin 19. In certain embodiments, an increased level of one or more prostate cancer related markers selected from the group consisting of filamin B, LY9, and keratin 19 in the biological sample relative to the normal control sample is indicative of an increased risk for developing prostate cancer in the subject. In certain embodiments, no increase in the detected level of expression of each of the one or more prostate-cancer related markers selected from the group consisting of filamin B, LY9, and keratin 19 in the biological sample relative to the normal control sample is indicative of no increased risk for developing prostate cancer in the subject.

In certain embodiments, the method further comprises detecting the level of prostate specific antigen (PSA) in the biological sample and preferably further comprises comparing the level of PSA in the biological sample to the level of PSA in a normal control sample. In certain embodiments, an increase in the level of one or more prostate cancer related markers selected from the group consisting of filamin B, LY9, and keratin 19 in the biological sample relative to the normal control sample, in combination with an increase in the level of PSA in the biological sample as compared to the level of PSA in the normal control sample has greater predictive value of an increased risk for developing prostate cancer in the subject than an increase in any of the individual markers alone. In certain embodiments, no increase in the detected level of expression of each of the one or more prostate-cancer related markers selected from the group consisting of filamin B, LY9, and keratin 19 in the biological sample relative to the normal control sample, in combination with a decreased or normal level of PSA in the biological sample as compared to the level of PSA in the normal control sample, has greater predictive value of no increased risk for developing prostate cancer in the subject than any single marker alone.

In the embodiments of the invention, one or more prostate cancer markers selected from the group consisting of filamin B, LY9 and keratin 19 is: filamin B; LY9; keratin 19; filamin B and LY9; filamin B and keratin 19; LY9 and keratin 19; or filamin B, LY9, and keratin 19.

In certain embodiments of the diagnostic or prognostic methods of the invention, one or more prostate cancer related markers is selected from the group consisting of keratin 4, keratin 7, keratin 8, keratin 15, keratin 18, and tubulin beta-3. In certain embodiments, one or more prostate cancer related markers is selected from the group consisting of keratin 7, keratin 8, and keratin 15. In certain embodiments, one or more prostate cancer related markers is selected from the group consisting of keratin 7 and keratin 15. In certain embodiments, one or more prostate cancer markers is selected from the group consisting of keratin 7, 15, and 19. In certain embodiments, the diagnostic and prognostic methods of the invention further comprise detecting the level of prostate specific antigen (PSA) in the biological sample, and preferably further comprise comparing the level of PSA in the biological sample to a level of PSA in a control sample.

In certain embodiments, the control sample for PSA is the same control sample as for the other prostate cancer related markers of the invention. In certain embodiments, the control sample for PSA is different from the control sample for the other prostate cancer related markers of the invention In certain embodiments of the diagnostic methods of the invention, wherein one or more prostate cancer related markers is selected from the group consisting of keratin 4, keratin 7, keratin 8, keratin 15, keratin 18, and tubulin beta-3, an increased level of one or more of the prostate cancer related markers in the biological sample relative to a normal control sample is indicative of an abnormal prostate state in the subject. In certain embodiments of the diagnostic methods of the invention, wherein one or more prostate cancer related markers is selected from the group consisting of keratin 4, keratin 7, keratin 8, keratin 15, keratin 18, and tubulin beta-3, a decreased or normal level of one or more of the prostate cancer related markers in the biological sample relative to a normal control sample is indicative of an abnormal prostate state in the subject. In certain embodiments of the diagnostic methods of the invention, wherein one or more prostate cancer related markers is selected from the group consisting of keratin 4, keratin 7, keratin 8, keratin 15, keratin 18, and tubulin beta-3, an increased level of one or more of the prostate cancer related markers in the biological sample relative to a normal control sample is indicative of a normal prostate state in the subject. In certain embodiments of the diagnostic methods of the invention, wherein one or more prostate cancer related markers is selected from the group consisting of keratin 4, keratin 7, keratin 8, keratin 15, keratin 18, and tubulin beta-3, a decreased or normal level of one or more of the prostate cancer related markers in the biological sample relative to a normal control sample is indicative of a normal prostate state in the subject.

In certain embodiments of the prognostic methods of the invention, wherein one or more prostate cancer related markers is selected from the group consisting of keratin 4, keratin 7, keratin 8, keratin 15, keratin 18, and tubulin beta-3, an increased level of one or more of the prostate cancer related markers in the biological sample relative to a normal control sample is indicative of an increased risk of developing prostate cancer in the subject. In certain embodiments of the prognostic methods of the invention, wherein one or more prostate cancer related markers is selected from the group consisting of keratin 4, keratin 7, keratin 8, keratin 15, keratin 18, and tubulin beta-3, a decreased or normal level of one or more of the prostate cancer related markers in the biological sample relative to a normal control sample is indicative of an increased risk of developing prostate cancer in the subject. In certain embodiments of the prognostic methods of the invention, wherein one or more prostate cancer related markers is selected from the group consisting of keratin 4, keratin 7, keratin 8, keratin 15, keratin 18, and tubulin beta-3, an increased level of one or more of the prostate cancer related markers in the biological sample relative to a normal control sample is indicative of no increased risk of developing prostate cancer in the subject. In certain embodiments of the prognostic methods of the invention, wherein one or more prostate cancer related markers is selected from the group consisting of keratin 4, keratin 7, keratin 8, keratin 15, keratin 18, and tubulin beta-3, a decreased or normal level of one or more of the prostate cancer related markers in the biological sample relative to a normal control sample is indicative of no increased risk of developing prostate cancer in the subject.

In certain embodiments of the diagnostic methods of the invention, wherein one or more prostate cancer related markers is selected from the group consisting of keratin 4, keratin 7, keratin 8, keratin 15, keratin 18, and tubulin beta-3, the method further comprises detecting the level of prostate specific antigen (PSA) in the biological sample, and preferably further comprises comparing the level of PSA in the biological sample to the level of PSA in a normal control sample. In certain embodiments of the diagnostic methods of the invention, wherein one or more prostate cancer related markers is selected from the group consisting of keratin 4, keratin 7, keratin 8, keratin 15, keratin 18, and tubulin beta-3, an increase in the level of one or more of the prostate cancer related markers in the biological sample relative to the normal control sample, in combination with an increase in the level of PSA in the biological sample as compared to the level of PSA in the normal control sample is indicative of an abnormal prostate state in the subject wherein the method has greater diagnostic or predictive value than the value of any of the individual markers alone. In certain embodiments of the diagnostic methods of the invention, wherein one or more prostate cancer related markers is selected from the group consisting of keratin 4, keratin 7, keratin 8, keratin 15, keratin 18, and tubulin beta-3, an decrease in the level of one or more of the prostate cancer related markers in the biological sample relative to the normal control sample, in combination with an increase in the level of PSA in the biological sample as compared to the level of PSA in the normal control sample is indicative of an abnormal prostate state in the subject wherein the method has greater diagnostic or predictive value than the value of any of the individual markers alone. In certain embodiments of the diagnostic methods of the invention, wherein one or more prostate cancer related markers is selected from the group consisting of keratin 4, keratin 7, keratin 8, keratin 15, keratin 18, and tubulin beta-3, a decreased or normal level of one or more of the prostate cancer related markers in the biological sample relative to the normal control sample, in combination with a decreased or normal level of PSA in the biological sample as compared to the level of PSA in the normal control sample, is indicative of a normal prostate state in the subject. In certain embodiments of the diagnostic methods of the invention, wherein one or more prostate cancer related markers is selected from the group consisting of keratin 4, keratin 7, keratin 8, keratin 15, keratin 18, and tubulin beta-3, an increased or normal level of one or more of the prostate cancer related markers in the biological sample relative to the normal control sample, in combination with a decreased or normal level of PSA in the biological sample as compared to the level of PSA in the normal control sample, is indicative of a normal prostate state in the subject.

In certain embodiments of the prognostic methods of the invention, wherein one or more prostate cancer related markers is selected from the group consisting of keratin 4, keratin 7, keratin 8, keratin 15, keratin 18, and tubulin beta-3, the method further comprises detecting the level of prostate specific antigen (PSA) in the biological sample, and preferably further comprises comparing the level of PSA in the biological sample to the level of PSA in a normal control sample. In certain embodiments of the prognostic methods of the invention, wherein one or more prostate cancer related markers is selected from the group consisting of keratin 4, keratin 7, keratin 8, keratin 15, keratin 18, and tubulin beta-3, an increase in the level of one or more of the prostate cancer related markers in the biological sample relative to the normal control sample, in combination with an increase in the level of PSA in the biological sample as compared to the level of PSA in the normal control sample is indicative of an increased risk for the subject of developing prostate cancer wherein the method has greater diagnostic or predictive value than the value of any of the individual markers alone. In certain embodiments of the prognostic methods of the invention, wherein one or more prostate cancer related markers is selected from the group consisting of keratin 4, keratin 7, keratin 8, keratin 15, keratin 18, and tubulin beta-3, an decrease in the level of one or more of the prostate cancer related markers in the biological sample relative to the normal control sample, in combination with an increase in the level of PSA in the biological sample as compared to the level of PSA in the normal control sample is indicative of an increased risk for the subject of developing prostate cancer wherein the method has greater diagnostic or predictive value than the value of any of the individual markers alone. In certain embodiments of the prognostic methods of the invention, wherein one or more prostate cancer related markers is selected from the group consisting of keratin 4, keratin 7, keratin 8, keratin 15, keratin 18, and tubulin beta-3, a decreased or normal level of one or more of the prostate cancer related markers in the biological sample relative to the normal control sample, in combination with a decreased or normal level of PSA in the biological sample as compared to the level of PSA in the normal control sample, is indicative of an decreased risk or normal risk of developing prostate cancer in the subject wherein the method has greater diagnostic or predictive value than the value of any of the individual markers alone. In certain embodiments of the prognostic methods of the invention, wherein one or more prostate cancer related markers is selected from the group consisting of keratin 4, keratin 7, keratin 8, keratin 15, keratin 18, and tubulin beta-3, an increased or normal level of one or more of the prostate cancer related markers in the biological sample relative to the normal control sample, in combination with a decreased or normal level of PSA in the biological sample as compared to the level of PSA in the normal control sample, is indicative of a decreased risk or normal risk of developing prostate cancer in the subject wherein the method has greater diagnostic or predictive value than the value of any of the individual markers alone.

In various embodiments of any of the diagnostic or prognostic methods of the invention, the method may further comprise comparing the level of the one or more prostate cancer related markers in the biological sample with the level of the one or more prostate cancer related markers in a control sample selected from the group consisting of: a sample obtained from the same subject at an earlier time point than the biological sample, a sample from a subject with benign prostatic hyperplasia (BPH), a sample from a subject with non-metastatic prostate cancer, a sample from a subject with metastatic prostate cancer, a sample from a subject with androgen sensitive prostate cancer, a sample from a subject with androgen insensitive prostate cancer, a sample from a subject with aggressive prostate cancer, and a sample from a subject with non-aggressive prostate cancer. In such embodiments, comparison with one or more additional control sample can facilitate differentiating between two prostate cancer states selected from the group consisting of: normal prostate and prostate cancer, benign prostate hyperplasia and prostate cancer, benign prostate hyperplasia and normal prostate, androgen dependent and androgen independent prostate cancer, aggressive prostate cancer and non-aggressive prostate cancer, and metastatic prostate cancer and non-metastatic prostate cancer; or differentiating between any two or more of normal prostate, prostate cancer, benign prostate hyperplasia, androgen dependent prostate cancer, androgen independent prostate cancer, aggressive prostate cancer, non-aggressive prostate cancer, metastatic prostate cancer, and non-metastatic prostate cancer.

In certain embodiments of the invention, when a tumor is present, the method further comprises detecting the size of the prostate tumor in the subject.

In certain embodiments of the diagnostic and prognostic methods the invention, the method further comprises obtaining a sample from a subject.

In certain embodiments of the diagnostic and prognostic methods the invention, the method further comprises selecting a subject who has or is suspected of having prostate cancer.

In certain embodiments of the invention, the method further comprises selecting a treatment regimen for the subject based on the level of the one or more prostate cancer markers. In certain embodiments of the invention, the method further comprises treating the subject with a treatment regimen based on the level of the one or more prostate cancer markers. In certain embodiments, a treatment regimen comprises one or more treatments selected from the group consisting of surgery, radiation, hormone therapy, antibody therapy, growth factor therapy, cytokine therapy, and chemotherapy.

In yet another aspect, the invention provides methods for monitoring prostate cancer in a subject, the method comprising (1) determining a level of one or more prostate cancer related markers selected from the group consisting of filamin B, LY9, keratin 4, keratin 7, keratin 8, keratin 15, keratin 18, keratin 19, and tubulin-beta 3 in a first biological sample obtained at a first time from a subject having prostate cancer;

(2) determining a level of expression of the one or more prostate cancer related markers in a second biological sample obtained from the subject at a second time, wherein the second time is after or later than, the first time; and (3) comparing the level of the one or more prostate cancer related markers in the second sample with the level of the one or more prostate cancer related markers in the first sample, wherein a change in the level of the one or more prostate cancer related markers in the second sample as compared to the first sample is indicative of a change in prostate cancer status in the subject.

In certain embodiments, the subject is actively treated for prostate cancer prior to obtaining the second sample. That is, the subject is undergoing active treatment for prostate cancer.

In certain embodiments, the subject is not actively treated for prostate cancer prior to obtaining the second sample. That is, the subject is being monitored using watchful waiting.

In certain embodiments, one or more prostate cancer related markers is selected from the group consisting of filamin B, LY9, and keratin 19. In certain embodiments, an increased level of one or more prostate cancer related markers selected from the group consisting of filamin B, LY9, and keratin 19 in the second biological sample as compared to the first biological sample is indicative of progression of the prostate cancer in the subject. In certain embodiments, no increase in the detected level of expression of each of the one or more prostate-cancer related markers selected from the group consisting of filamin B, LY9, and keratin 19 in the second biological sample as compared to the first biological sample is indicative of non-progression of the prostate cancer in the subject.

In certain embodiments, the methods further comprise determining the level of prostate specific antigen (PSA) in the first biological sample and the second biological sample and preferably, further comprising comparing the level of PSA in the second biological sample to the level of PSA in the first biological sample. In certain embodiments, an increased level of the one or more prostate cancer related markers selected from the group consisting of filamin B, LY9, and keratin 19 in the second biological sample relative to the level of the one or more prostate cancer related markers in the first biological sample, in combination with an increase in the level of PSA in the second biological sample relative to the level of PSA in the first biological sample has greater predictive value of progression of the prostate cancer in the subject than any single marker alone. In certain embodiments, no increase in the detected level of expression of each of the one or more prostate-cancer related markers selected from the group consisting of filamin B, LY9, and keratin 19 in the second biological sample relative to the level of the one or more prostate cancer related markers in the first biological sample, in combination with a decreased or same level of PSA in the second biological sample relative to the level of PSA in the first biological sample has greater predictive value of non-progression of the prostate cancer in the subject than any single marker alone.

In embodiments of the invention, the one or more prostate cancer related markers selected from the group consisting of filamin B, LY9, and keratin 19 is: filamin B; LY9; keratin 19; filamin B and LY9; filamin B and keratin 19; LY9 and keratin 19; or filamin B, LY9, and keratin 19.

In certain embodiments of the monitoring methods of the invention, the one or more prostate cancer markers is selected from the group consisting of keratin 4, keratin 7, keratin 8, keratin 15, keratin 18, and tubulin beta-3. In certain embodiments of the monitoring methods of the invention, the one or more prostate cancer related markers is selected from the group consisting of keratin 7, keratin 8, and keratin 15. In certain embodiments of the monitoring methods of the invention, the one or more prostate cancer related markers is selected from the group consisting of keratin 7, keratin 15, and keratin 19. In certain embodiments of the monitoring methods of the invention, the one or more prostate cancer related markers is selected from the group consisting of keratin 7 and keratin 15.

In certain embodiments of the monitoring methods of the invention, wherein the one or more prostate cancer markers is selected from the group consisting of keratin 4, keratin 7, keratin 8, keratin 15, keratin 18, and tubulin beta-3, the methods further comprise determining the level of prostate specific antigen (PSA) in the first biological sample and the second biological sample, and preferably further comprise comparing the level of PSA in the second biological sample to the level of PSA in the first biological sample.

In certain embodiments of the monitoring methods of the invention, wherein one or more prostate cancer related markers is selected from the group consisting of keratin 4, keratin 7, keratin 8, keratin 15, keratin 18, and tubulin beta-3, an increased level of one or more of the prostate cancer related markers in the second sample relative to a first sample is indicative of prostate tumor progression in the subject. In certain embodiments of the monitoring methods of the invention, wherein one or more prostate cancer related markers is selected from the group consisting of keratin 4, keratin 7, keratin 8, keratin 15, keratin 18, and tubulin beta-3, a decreased or normal level of one or more of the prostate cancer related markers in the second sample relative to a first sample is indicative of prostate tumor progression in the subject. In certain embodiments of the monitoring methods of the invention, wherein one or more prostate cancer related markers is selected from the group consisting of keratin 4, keratin 7, keratin 8, keratin 15, keratin 18, and tubulin beta-3, an increased level of one or more of the prostate cancer related markers in the second sample relative to a first sample is indicative of no prostate tumor progression in the subject. In certain embodiments of the monitoring methods of the invention, wherein one or more prostate cancer related markers is selected from the group consisting of keratin 4, keratin 7, keratin 8, keratin 15, keratin 18, and tubulin beta-3, a decreased or normal level of one or more of the prostate cancer related markers in the second sample relative to a first sample is indicative of no prostate tumor progression in the subject.

In certain embodiments of the monitoring methods of the invention, wherein one or more prostate cancer related markers is selected from the group consisting of keratin 4, keratin 7, keratin 8, keratin 15, keratin 18, and tubulin beta-3, the method further comprises detecting the level of prostate specific antigen (PSA) in the second sample, and preferably further comprises comparing the level of PSA in the second sample to the level of PSA in a first sample. In certain embodiments of the monitoring methods of the invention, wherein one or more prostate cancer related markers is selected from the group consisting of keratin 4, keratin 7, keratin 8, keratin 15, keratin 18, and tubulin beta-3, an increase in the level of one or more of the prostate cancer related markers in the second sample relative to the first sample, in combination with an increase in the level of PSA in the second sample as compared to the level of PSA in the first sample is indicative of prostate tumor progression in the subject wherein the method has greater diagnostic or predictive value than the value of any of the individual markers alone. In certain embodiments of the monitoring methods of the invention, wherein one or more prostate cancer related markers is selected from the group consisting of keratin 4, keratin 7, keratin 8, keratin 15, keratin 18, and tubulin beta-3, an decrease in the level of one or more of the prostate cancer related markers in the second sample relative to the first sample, in combination with an increase in the level of PSA in the second sample as compared to the level of PSA in the first sample is indicative of prostate tumor progression in the subject wherein the method has greater diagnostic or predictive value than the value of any of the individual markers alone wherein the method has greater diagnostic or predictive value than the value of any of the individual markers alone. In certain embodiments of the monitoring methods of the invention, wherein one or more prostate cancer related markers is selected from the group consisting of keratin 4, keratin 7, keratin 8, keratin 15, keratin 18, and tubulin beta-3, a decreased or normal level of one or more of the prostate cancer related markers in the second sample relative to the first sample, in combination with a decreased or normal level of PSA in the second sample as compared to the level of PSA in the first sample, is indicative of no prostate tumor progression in the subject. In certain embodiments of the monitoring methods of the invention, wherein one or more prostate cancer related markers is selected from the group consisting of keratin 4, keratin 7, keratin 8, keratin 15, keratin 18, and tubulin beta-3, an increased or normal level of one or more of the prostate cancer related markers in the second sample relative to the first sample, in combination with a decreased or normal level of PSA in the second sample as compared to the level of PSA in the first sample, is indicative of no prostate tumor progression in the subject wherein the method has greater diagnostic or predictive value than the value of any of the individual markers alone.

In certain embodiments of the monitoring methods of the invention, the methods further comprise comparing the level of the one or more prostate cancer related markers in the first biological sample or the second biological sample with the level of the one or more prostate cancer related markers in a control sample selected from the group consisting of: a normal control sample, a sample from a subject with benign prostatic hyperplasia (BPH), a sample from a subject with non-metastatic prostate cancer, a sample from a subject with metastatic prostate cancer, a sample from a subject with androgen sensitive prostate cancer, a sample from a subject with androgen insensitive prostate cancer, a sample from a subject with aggressive prostate cancer, and a sample from a subject with non-aggressive prostate cancer.

In certain embodiments of the monitoring methods of the invention, the methods further comprise detecting the size of the prostate tumor in the subject.

In certain embodiments of the monitoring methods of the invention, the methods further comprise obtaining a first sample and a second sample from the subject.

In certain embodiments of the monitoring methods of the invention, the methods further comprise selecting and/or administering a different treatment regimen for the subject based on progression of the prostate cancer in the subject.

In certain embodiments of the monitoring methods of the invention, the methods further comprise comprises maintaining a treatment regimen for the subject based on non-progression of the prostate cancer in the subject.

In certain embodiments, the treatment regimens comprise one or more treatments selected from the group consisting of: surgery, radiation, hormone therapy, antibody therapy, growth factor therapy, cytokine therapy, and chemotherapy.

In certain embodiments of the monitoring methods of the invention, the methods further comprise withholding an active treatment of the prostate cancer in the subject based on non-progression of the prostate cancer in the subject. In certain embodiments, the active treatment is one or more treatments selected from the group consisting of: surgery, radiation, hormone therapy, antibody therapy, growth factor therapy, cytokine therapy, and chemotherapy.

In still another aspect, the invention provides methods for detecting a set of prostate cancer related markers, the method comprising:

(1) analyzing a biological sample from a subject for a level of two or more prostate cancer related markers of a set of prostate cancer related markers, wherein the set of prostate cancer related markers comprises filamin B, LY9, keratin 4, keratin 7, keratin 8, keratin 15, keratin 18, keratin 19, and tubulin-beta 3;

(2) detecting each of the two or more prostate specific makers in the biological sample, thereby detecting the set of prostate cancer related biomarkers.

In certain embodiments, the set of prostate cancer related markers comprises filamin B, LY9, and keratin 19. In certain embodiments, the two or more prostate cancer related markers are: filamin B and LY9; filamin B and keratin 19; LY9 and keratin 19; or filamin B, LY9, and keratin 19. In certain embodiments, the set of prostate cancer related markers comprises keratin 4, keratin 7, keratin 8, keratin 15, keratin 18, and tubulin beta-3. In certain embodiments, the set of prostate cancer related markers comprises keratin 7, keratin 8, and keratin 15. In certain embodiments, the set of prostate cancer related markers comprises keratin 7, keratin 15, and keratin 19. In certain embodiments, the set of prostate cancer related markers comprises keratin 7 and keratin 15.

In various embodiments of any of the methods of the invention, the step of detecting or determining a level of one or more prostate cancer related markers in a biological sample comprises isolating a component of the biological sample.

In various embodiments of any of the methods of the invention, the step of detecting or determining a level of one or more prostate cancer related markers in a biological sample comprises labeling a component of the biological sample.

In various embodiments of any of the methods of the invention, the step of detecting or determining a level of one or more prostate cancer related markers in a biological sample comprises processing the biological sample.

In various embodiments of any of the methods of the invention, the step of detecting or determining a level of one or more prostate cancer related markers in a biological sample comprises contacting a prostate cancer related marker to be detected with a prostate cancer related marker binding agent.

In various embodiments of any of the methods of the invention, the step of detecting or determining a level of one or more prostate cancer related markers in a biological sample comprises forming a complex between a prostate cancer related marker to be detected and a prostate cancer related marker binding agent.

In various embodiments of any of the methods of the invention, the step of detecting or determining a level of one or more prostate cancer related markers in a biological sample comprises contacting each of the one or more prostate cancer related markers with a prostate cancer related marker binding agent.

In various embodiments of any of the methods of the invention, the step of detecting or determining a level of one or more prostate cancer related markers in a biological sample comprises forming a complex between each of the one or more prostate cancer related markers and a prostate cancer related marker binding agent.

In various embodiments of any of the methods of the invention, the step of detecting or determining a level of one or more prostate cancer related markers in a biological sample comprises attaching a prostate cancer related marker to be detected to a solid surface.

In yet another aspect, the invention provides a panel of reagents for use in a detection method, the panel comprising at least two detection reagents, wherein each detection reagent is specific for the detection of at least one prostate cancer related marker of a set of prostate cancer related markers, wherein the set of prostate cancer specific markers comprises two or more prostate cancer related markers selected from the group consisting of filamin B, LY9, keratin 4, keratin 7, keratin 8, keratin 15, keratin 18, keratin 19, tubulin-beta 3 and PSA.

In certain embodiments, the set of prostate cancer specific markers comprises two or more prostate cancer related markers selected from the group consisting of filamin B, LY9, and keratin 19. In certain embodiments, the two or more prostate cancer related markers is: filamin B and LY9; filamin B and keratin 19; LY9 and keratin 19; or filamin B, LY9, and keratin 19.

In certain embodiments, the set of prostate cancer specific markers comprises two or more prostate cancer related markers selected from the group consisting of keratin 4, keratin 7, keratin 8, keratin 15, keratin 18, and tubulin beta-3. In certain embodiments, the set of prostate cancer specific markers comprises two or more prostate cancer related markers selected from the group consisting of keratin 7, keratin 8, and keratin 15. In certain embodiments, the set of prostate cancer specific markers comprises keratin 7 and keratin 15.

In certain embodiments, the set of prostate cancer specific markers further comprises PSA. In certain embodiments, the panel of reagents comprises a detection reagent specific for the detection of PSA.

In yet another aspect, the invention provides for the use of any of the foregoing panels of the invention in any of the methods provided by the invention.

In still another aspect, the invention provides a kit for the diagnosis, monitoring, or characterization of an abnormal prostate state, comprising: at least one reagent specific for the detection of a level of at least one prostate cancer related marker selected from the group consisting of keratin 4, keratin 7, keratin 8, keratin 15, keratin 18, keratin 19, and tubulin-beta 3, filamin B, and LY9.

In certain embodiments, the kit further comprises instructions for the diagnosis, monitoring, or characterization of an abnormal prostate state based on the level of the at least one prostate cancer related marker selected from the group consisting of keratin 4, keratin 7, keratin 8, keratin 15, keratin 18, keratin 19, and tubulin-beta 3, filamin B, and LY9 detected.

In certain embodiments, the kit further comprises instructions to detect the level of PSA in a sample in which the at least one prostate cancer related marker selected from the group consisting of keratin 4, keratin 7, keratin 8, keratin 15, keratin 18, keratin 19, and tubulin-beta 3, filamin B, and LY9 is detected.

In certain embodiments, the kit further comprises at least one reagent specific for the detection of a level of PSA.

In one embodiment, the invention provides a kit comprising at least one reagent specific for the detection of a level of at least one prostate cancer related marker selected from the group consisting of keratin 4, keratin 7, keratin 8, keratin 15, keratin 18, keratin 19, tubulin-beta 3, filamin B, and LY9 and at least one reagent specific for the detection of a level of PSA.

Further, the invention provides methods for diagnosing prostate cancer comprising determining a level of expression of one or more (e.g., 1, 2, 3, 4, 5, 6, 7, 8, or 9) markers selected from the group consisting of keratin 4, keratin 7, keratin 8, keratin 15, keratin 18, keratin 19, tubulin-beta 3, filamin B (FLNB), and lymphocyte antigen 9 (LY9) in a biological sample obtained from a subject; and comparing the level of expression of the one or more markers in the biological sample obtained from the subject with the level of expression of the corresponding one or more markers in a control sample, wherein a modulation in the level of expression of the one or more markers in the biological sample is an indication that the subject is afflicted with prostate cancer. In certain embodiments, an increase in the level of expression of filamin B (FLNB), lymphocyte antigen 9 (LY9), or keratin 19 in the biological sample as compared to a normal control sample is an indication that the subject is afflicted with prostate cancer.

The invention further provides methods prognosing whether a subject is predisposed to developing prostate cancer, the method comprising determining the level of expression of one or more (e.g., 1, 2, 3, 4, 5, 6, 7, 8, or 9) markers selected from the group consisting of keratin 4, keratin 7, keratin 8, keratin 15, keratin 18, keratin 19, tubulin-beta 3, filamin B (FLNB), and lymphocyte antigen 9 (LY9) present in a biological sample obtained from the subject; and comparing the level of expression of the one or more markers present in the biological sample obtained from the subject with the level of expression of the corresponding markers in a control sample, wherein a modulation in the level of expression of the one or more markers in the biological sample obtained from the subject with the level of expression of the corresponding marker in a control sample is an indication that the subject is predisposed to developing prostate cancer. In certain embodiments, an increase in the level of expression of filamin B (FLNB), lymphocyte antigen 9 (LY9), or keratin 19 in the biological sample as compared to a normal control sample is an indication that the subject is predisposed to prostate cancer.

The invention further provides methods for monitoring the treatment of prostate cancer in a subject, the methods comprising determining a level of expression of one or more (e.g., 1, 2, 3, 4, 5, 6, 7, 8, or 9) markers selected from the group consisting of keratin 4, keratin 7, keratin 8, keratin 15, keratin 18, keratin 19, tubulin-beta 3, filamin B (FLNB), and lymphocyte antigen 9 (LY9) present in a first sample obtained from the subject prior to administering at least a portion of a treatment regimen to the subject; determining a level of expression of a corresponding one or more markers in a second sample obtained from the subject following administration of at least a portion of the treatment regimen to the subject; and comparing the level of expression of the one or more markers in the first sample with the expression level of the corresponding one or more markers in the second sample, wherein a modulation in the level of expression of the one or more in the second sample as compared to the one or more markers in the first sample is an indication of a modulation in prostate cancer status in the subject. In certain embodiments, an decrease in the level of expression of filamin B (FLNB), lymphocyte antigen 9 (LY9), or keratin 19 in the biological sample as compared to the control sample is an indication that the subject is responding to treatment for prostate cancer.

In certain embodiments, methods of diagnosing, prognosing, and monitoring the treatment of prostate cancer by detecting the level of one or more (e.g., 1, 2, 3, 4, 5, 6, 7, 8, or 9) markers selected from the group consisting of keratin 4, keratin 7, keratin 8, keratin 15, keratin 18, keratin 19, tubulin-beta 3, filamin B (FLNB), and lymphocyte antigen 9 (LY9) further include detection of prostate specific antigen (PSA) for the diagnosing, prognosing, and monitoring the treatment of prostate cancer.

The invention also provides methods for diagnosing prostate cancer comprising determining a level of expression of keratin 7 or keratin 15 in a biological sample obtained from a subject; and comparing the level of expression of keratin 7 or keratin 15 in the biological sample obtained from the subject with the level of expression of keratin 7 or keratin 15 in a control sample, wherein an modulation in the level of expression of keratin 7 or keratin 15 in the biological sample as compared to the control sample is an indication that the subject is afflicted with prostate cancer.

The invention provides methods of prognosing whether a subject is predisposed to developing prostate cancer, the method comprising determining the level of expression of keratin 7 or keratin 15 present in a biological sample obtained from the subject; and comparing the level of expression of keratin 7 or keratin 15 present in the biological sample obtained from the subject with the level of expression of keratin 7 or keratin 15 in a control sample, wherein a modulation in the level of expression of keratin 7 or keratin 15 in the biological sample obtained from the subject with the level of expression of keratin 7 or keratin 15 in a control sample is an indication that the subject is predisposed to developing prostate cancer.

The invention provides methods for monitoring the treatment of prostate cancer in a subject, the methods comprising determining a level of expression of keratin 7 or keratin 15 present in a first sample obtained from the subject prior to administering at least a portion of a treatment regimen to the subject; determining a level of expression of keratin 7 or keratin 15 in a second sample obtained from the subject following administration of at least a portion of the treatment regimen to the subject; and comparing the level of expression of keratin 7 or keratin 15 in the first sample with the expression level of keratin 7 or keratin 15 in the second sample, wherein a modulation in the level of expression of keratin 7 or keratin 15 in the second sample as compared to keratin 7 or keratin 15 in the first sample is an indication that the therapy is modulating prostate cancer in the subject.

The invention also provides methods for diagnosing prostate cancer comprising determining a level of expression of keratin 19 in a biological sample obtained from a subject; and comparing the level of expression of keratin 19 in the biological sample obtained from the subject with the level of expression of keratin 19 in a control sample, wherein an increase in the level of expression of keratin 19 in the biological sample as compared to a normal control sample is an indication that the subject is afflicted with prostate cancer.

The invention provides methods prognosing whether a subject is predisposed to developing prostate cancer, the method comprising determining the level of expression of keratin 19 present in a biological sample obtained from the subject; and comparing the level of expression of keratin 19 present in the biological sample obtained from the subject with the level of expression of keratin 19 in a control sample, wherein a modulation in the level of expression of keratin 19 in the biological sample obtained from the subject with the level of expression of keratin 19 in a normal control sample is an indication that the subject is predisposed to developing prostate cancer.

The invention provides methods for monitoring the treatment of prostate cancer in a subject, the methods comprising determining a level of expression of keratin 19 present in a first sample obtained from the subject prior to administering at least a portion of a treatment regimen to the subject; determining a level of expression of keratin 19 in a second sample obtained from the subject following administration of at least a portion of the treatment regimen to the subject; and comparing the level of expression of keratin 19 in the first sample with the expression level of keratin 19 in the second sample, wherein a decrease in the level of expression of keratin 19 in the second sample as compared to keratin 19 in the first sample is an indication that the subject is responding to treatment for prostate cancer.

In certain embodiments, methods of diagnosing, prognosing, and monitoring the treatment of prostate cancer by detecting the level of keratin 7, 15, or 19 further include detection of filamin B for the diagnosing, prognosing, and monitoring the treatment of prostate cancer. In certain embodiments, methods of diagnosing, prognosing, and monitoring the treatment of prostate cancer by detecting the level of keratin 7, 15, or 19 further include detection of LY9 for the diagnosing, prognosing, and monitoring the treatment of prostate cancer. In certain embodiments, methods of diagnosing, prognosing, and monitoring the treatment of prostate cancer by detecting the level of keratin 7, 15, or 19 further include detection of PSA for the diagnosing, prognosing, and monitoring the treatment of prostate cancer. In certain embodiments, methods of diagnosing, prognosing, and monitoring the treatment of prostate cancer by detecting the level of keratin 7, 15, or 19 further include detection of filamin B for the diagnosing, prognosing, and monitoring the treatment of prostate cancer. In certain embodiments, methods of diagnosing, prognosing, and monitoring the treatment of prostate cancer by detecting the level of keratin 7, 15, or 19 further include detection of keratin 4 for the diagnosing, prognosing, and monitoring the treatment of prostate cancer. In certain embodiments, methods of diagnosing, prognosing, and monitoring the treatment of prostate cancer by detecting the level of keratin 7, 15, or 19 further include detection of keratin 8 for the diagnosing, prognosing, and monitoring the treatment of prostate cancer. In certain embodiments, methods of diagnosing, prognosing, and monitoring the treatment of prostate cancer by detecting the level of keratin 7, 15, or 19 further include detection of keratin 18 for the diagnosing, prognosing, and monitoring the treatment of prostate cancer. In certain embodiments, methods of diagnosing, prognosing, and monitoring the treatment of prostate cancer by detecting the level of keratin 7, 15, or 19 further include detection of tubulin-beta 3 for the diagnosing, prognosing, and monitoring the treatment of prostate cancer.

In certain embodiments, keratin 7, 15, or 19 is keratin 7. In certain embodiments, keratin 7, 15, or 19 is keratin 15. In certain embodiments, keratin 7, 15, or 19 is keratin 19. In certain embodiments, keratin 7, 15, or 19 is keratin 7 and 15. In certain embodiments, keratin 7, 15, or 19 is keratin 7 and 19. In certain embodiments, keratin 7, 15, or 19 is keratin 15 and 19. In certain embodiments, keratin 7, 15, or 19 is keratin 7, 15, and 19.

In certain embodiments, filamin B, LY9, or keratin 19 is filamin B. In certain embodiments, filamin B, LY9, or keratin 19 is LY9. In certain embodiments, filamin B, LY9, or keratin 19 is keratin 19. In certain embodiments, filamin B, LY9, or keratin 19 is filamin B and LY9. In certain embodiments, filamin B, LY9, or keratin 19 is filamin B and keratin 19. In certain embodiments, filamin B, LY9, or keratin 19 is LY9, and keratin 19. In certain embodiments, filamin B, LY9, or keratin 19 is filamin B, LY9, and keratin 19.

In certain embodiments, the control sample is a sample from a normal subject or normal tissue. In certain embodiments, the control sample is a sample from the same subject from an earlier time point than the biological sample. In certain embodiments, the control sample is a sample from a subject with benign prostatic hyperplasia (BPH).

In certain embodiments, diagnosing includes differentiating between normal prostate and prostate cancer. In certain embodiments, diagnosing includes differentiating between benign prostate hyperplasia and prostate cancer.

The invention provides methods of characterizing prostate cancer status in a subject, the method comprising determining the level of expression of one or more (e.g., 1, 2, 3, 4, 5, 6, 7, 8, or 9) markers selected from the group consisting of keratin 4, keratin 7, keratin 8, keratin 15, keratin 18, keratin 19, tubulin-beta 3, filamin B (FLNB), and lymphocyte antigen 9 (LY9) present in a biological sample obtained from the subject; and comparing the level of expression of the one or more markers present in the biological sample obtained from the subject with the level of expression of the one or more markers in a control sample, wherein the level of expression of the one or more markers in the biological sample obtained from the subject compared to the level of expression of the corresponding marker in a control sample is an indication of the prostate cancer status in the subject.

The invention provides methods of characterizing prostate cancer status in a subject, the method comprising determining the level of expression of keratin 7, 15, or 19 present in a biological sample obtained from the subject; and comparing the level of expression of keratin 7, 15, or 19 present in the biological sample obtained from the subject with the level of expression of keratin 7, 15, or 19 in a control sample, wherein the level of expression of keratin 7, 15, or 19 in the biological sample obtained from the subject compared to the level of expression of keratin 7, 15, or 19 in a control sample is an indication of the prostate cancer status in the subject.

In certain embodiments, the methods further comprises detection of the level of expression of prostate specific antigen (PSA) in the biological sample in which the expression level of filamin B or LY9 is detected in the methods of characterization of prostate cancer. In certain embodiments, the method further includes comparing the level of expression of PSA in the biological sample with the level of PSA in a control sample. In certain embodiments, the results from the detection of the expression level of PSA is used in conjunction with the results from detection of the level of one or more (e.g., 1, 2, 3, 4, 5, 6, or 7) markers selected from the group consisting of keratin 4, keratin 7, keratin 8, keratin 15, keratin 18, keratin 19, and tubulin-beta 3 in the methods of characterization of prostate cancer.

In certain embodiments, the control sample is a sample from a normal subject or normal tissue. In certain embodiments, the control sample is a sample from the same subject from an earlier time point than the biological sample. In certain embodiments, the control sample is a sample from a subject with benign prostatic hyperplasia (BPH). In certain embodiments, the control sample is a sample from a subject with androgen dependent prostate cancer. In certain embodiments, the control sample is a sample from a subject with androgen independent prostate cancer. In certain embodiments, the control sample is a sample from a subject with an aggressive prostate cancer. In certain embodiments, the control sample is a sample from a subject with a non-aggressive prostate cancer.

In certain embodiments of the invention, characterizing includes differentiating between normal prostate and prostate cancer. In certain embodiments, characterizing includes differentiating between benign prostate hyperplasia and prostate cancer. In certain embodiments, characterizing includes differentiating between androgen sensitive and androgen insensitive prostate cancer. In certain embodiments, characterizing includes differentiating between aggressive prostate cancer and non-aggressive prostate cancer. In certain embodiments, characterizing includes differentiating between any two or more of normal prostate, prostate cancer, benign prostate hyperplasia, androgen sensitive prostate cancer, androgen insensitive prostate cancer, aggressive prostate cancer, non-aggressive prostate cancer, metastatic prostate cancer and non-metastatic prostate cancer. In certain embodiments, characterizing includes detecting a change in status from androgen independent prostate cancer to androgen dependent prostate cancer. In certain embodiments, characterizing includes detecting a change in status from androgen independent prostate cancer to androgen dependent prostate cancer in response prior to a change in response to treatment. In certain embodiments, characterizing includes detecting a change in the size or relative aggressiveness of the prostate cancer. In certain embodiments, characterizing includes detecting a change from non-metastatic to metastatic prostate cancer.

In certain embodiments of the invention, an increase in the expression level of keratin 19 is an indication of increased pathology of prostate cancer or increased likelihood of developing prostate cancer. In certain embodiments of the invention, a decrease in the expression level of keratin 19 is an indication of decreased pathology of prostate cancer or decreased likelihood of developing prostate cancer. In certain embodiments of the invention, no significant change in the expression level of keratin 19 is an indication of no significant change in prostate cancer status.

In certain embodiments of the invention, an increase in the expression level of filamin B or LY9 is an indication of increased pathology of prostate cancer or increased likelihood of developing prostate cancer. In certain embodiments of the invention, a decrease in the expression level of filamin B or LY9 is an indication of decreased pathology of prostate cancer or decreased likelihood of developing prostate cancer. In certain embodiments of the invention, no significant change in the expression level of filamin B or LY9 is an indication of no significant change in prostate cancer status.

In certain embodiments, methods of the invention further comprise obtaining a biological sample from a subject.

In certain embodiments, methods of the invention further comprise selecting a subject for having or being suspected of having prostate cancer.

In certain embodiments, methods of the invention further comprise selection of a regimen for treatment of the subject including one or more treatments selected from the group consisting of surgery, radiation, hormone therapy, antibody therapy, therapy with growth factors, cytokines, and chemotherapy.

In certain embodiments, the method further comprises selection of the one ore more specific treatment regimens for the subject based on the results of the methods.

In certain embodiments, the method further comprises changing the treatment regimen of the subject based on the results of the methods.

In certain embodiments, the method further comprises a change in hormone based therapy based on monitoring of the subject based on the results of the methods.

In certain embodiments, the method further comprises not treating the subject with one or more treatments selected from the group consisting of surgery, radiation, hormone therapy, antibody therapy, therapy with growth factors, cytokines, or chemotherapy for an interval prior to performing a subsequent diagnostic, prognostic, or monitoring method provided herein.

The invention provides methods of treating a subject with prostate cancer by determining a level of expression of one or more (e.g., 1, 2, 3, 4, 5, 6, 7, 8, or 9) markers selected from the group consisting of keratin 4, keratin 7, keratin 8, keratin 15, keratin 18, keratin 19, tubulin-beta 3, filamin B (FLNB), and lymphocyte antigen 9 (LY9), present in a first sample obtained from the subject having prostate cancer; determining a level of expression of the one or more markers in a second sample obtained from the subject after administration of at least a portion of a treatment for prostate cancer; comparing the level of expression of the one or more markers in the first sample with the expression level of the one or more markers in the second sample, wherein a modulated level of expression of the one or more markers in the second sample as compared to the one or more markers in the first sample is an indication that the subject is an indication of modulation of prostate cancer in the subject; and selecting a treatment for the subject based on the expression level of the one or more (e.g., 1, 2, 3, 4, 5, 6, 7, 8, or 9) markers selected from the group consisting of keratin 4, keratin 7, keratin 8, keratin 15, keratin 18, keratin 19, tubulin-beta 3, filamin B (FLNB), and lymphocyte antigen 9 (LY9). For example, a decrease in the level of filamin B, LY9, or keratin 19 is an indication that the subject is responding to treatment. An increase in the level of filamin B, LY9, or keratin 19 is an indication that the subject is not responding to treatment.

As used herein, modulation is understood as a change in an expression level of a marker, particularly a statistically significant change in an expression level of a marker as compared to an appropriate control. The meaning of an increase or a decrease in an expression level of the marker as compared to a control depends, at least, on the specific identity of the marker and the control used. Such considerations are well understood by those of skill in the art. The meaning of the modulation in the expression level(s) of markers can be determined based on the teachings provided herein.

In certain embodiments, the treatment method further comprises determining a level of expression of PSA in the first sample and determining a level of expression of PSA in the second sample. In certain embodiments, the treatment of the subject is maintained upon detection of a decrease in the expression level of at least one of filamin B, LY9, keratin 19, or PSA in the second sample, indicating that the subject was responsive to the treatment. In certain embodiments, the treatment of the subject is discontinued upon detection of a decrease in the expression level of at least one of filamin B, LY9, keratin 19, or PSA in the second sample, indicating that disease is no longer present or minimized such that treatment is no longer required. In certain embodiments, a new treatment of the subject is initiated upon detection of a decrease in the expression level of at least one of filamin B, LY9, keratin 19, or PSA in the second sample, e.g., resection after shrinkage of the tumor. In certain embodiments, the treatment of the subject is discontinued upon detection of an increase in the expression level of at least one of filamin B, LY9, keratin 19, or PSA in the second sample, indication of a lack of response or discontinuation of response to the treatment. In certain embodiments, a new treatment of the subject is initiated upon detection of an increase in the expression level of at least one of filamin B, LY9, keratin 19, or PSA in the second sample, e.g., due to lack of response or discontinuation of response to treatment. One of skill in the art can select appropriate methods of treatment of a subject based, at least in part, on his response, or non-response, to treatments being used as determined by the expression level of the markers.

The invention provides method of selecting a subject with prostate cancer for administration of active treatment, rather than watchful waiting, by determining a level of expression of filamin B, LY9, or keratin 19, present in a first sample obtained from the subject having prostate cancer wherein the subject has not been actively treated for prostate cancer; determining a level of expression of filamin B, LY9, or keratin 19 in a second sample obtained from the subject; comparing the level of expression of filamin B, LY9, or keratin 19 in the first sample obtained at an earlier time point with the expression level of filamin B, LY9, or keratin 19 in the second sample; wherein a decreased level of expression of filamin B, LY9, or keratin 19 in the second sample as compared to filamin B, LY9, or keratin 19 in the first sample is an indication that the subject should not be administered active treatment for prostate cancer; and selecting against active treatment of a subject for prostate cancer.

The invention also provides methods of selecting a subject with prostate cancer for administration of active treatment by determining a level of expression of one or more (e.g., 1, 2, 3, 4, 5, 6, 7, 8, or 9) markers selected from the group consisting of keratin 4, keratin 7, keratin 8, keratin 15, keratin 18, keratin 19, tubulin-beta 3, filamin B (FLNB), and lymphocyte antigen 9 (LY9), present in a first sample obtained from the subject having prostate cancer wherein the subject has not been actively treated for prostate cancer; determining a level of expression of the corresponding one or more markers in a second sample obtained from the subject; comparing the level of expression of the one or more markers in the first sample obtained at an earlier time point with the expression level of the one or more markers in the second sample; wherein an modulated level of expression of the one or more markers in the second sample as compared to the one or more markers in the first sample is considered in determining if a subject should be actively treated for prostate cancer.

In certain embodiments, actively treating the subject for prostate cancer comprises treating the subject with one or more therapies such as hormone therapy, chemotherapy, radiation therapy, and surgery.

In certain embodiments, methods of subject selection further comprise determining a level of expression of PSA in the first sample and determining a level of expression of PSA in the second sample. In certain embodiments, a decreased level of expression of PSA in the second sample as compared to the level of expression of PSA in the first sample is an indication that the subject should not be administered active treatment for prostate cancer. In certain embodiments, an increased level of expression of PSA in the second sample as compared to the level of expression of PSA in the first sample is an indication that the subject should be administered active treatment for prostate cancer.

In certain embodiments of any of the methods provided herein, filamin B or LY9 is understood as filamin B and LY9. In certain embodiments of any of the methods provided herein, filamin B or LY9 is understood as filamin B. In certain embodiments of any of the methods provided herein, filamin B or LY9 is understood as LY9.

In certain embodiments of any of the methods provided herein, keratin 7, 15, or 19 is understood as keratin 7. In certain embodiments of any of the methods provided herein, keratin 7, 15, or 19 is understood as keratin 15. In certain embodiments of any of the methods provided herein, keratin 7, 15, or 19 is understood as keratin 19. In certain embodiments of any of the methods provided herein, keratin 7, 15, or 19 is understood as keratin 7 and 15. In certain embodiments of any of the methods provided herein, keratin 7, 15, or 19 is understood as keratin 15 and 19. In certain embodiments of any of the methods provided herein, keratin 7, 15, or 19 is understood as keratin 7 and 19. In certain embodiments of any of the methods provided herein, keratin 7, 15, or 19 is understood as keratin 7, 15, and 19.

In certain embodiments, one or more markers selected from any group provided herein does not include keratin 4. In certain embodiments, one or more markers selected from any group provided herein does not include keratin 7. In certain embodiments, one or more markers selected from any group provided herein does not include keratin 8. In certain embodiments, one or more markers selected from any group provided herein does not include keratin 15. In certain embodiments, one or more markers selected from any group provided herein does not include keratin 18. In certain embodiments, one or more markers selected from any group provided herein does not include keratin 19. In certain embodiments, one or more markers selected from any group provided herein does not include tubulin-beta 3. In certain embodiments, one or more markers selected from any group provided herein does not include filamin B. In certain embodiments, one or more markers selected from any group provided herein does not include LY9. In certain embodiments, one or more markers selected from any group provided herein does not include PSA.

In certain embodiments of any of the methods provided herein, the methods further comprising obtaining a biological sample from the subject.

The invention provides methods of identifying a compound for treating prostate cancer comprising obtaining a test cell; contacting the test cell with a test compound; determining the level of expression of one or more (e.g., 1, 2, 3, 4, 5, 6, 7, 8, or 9) markers selected from the group consisting of keratin 4, keratin 7, keratin 8, keratin 15, keratin 18, keratin 19, tubulin-beta 3, filamin B (FLNB), and lymphocyte antigen 9 (LY9) in the test cell; comparing the level of expression of the one or more markers in the test cell with a control cell not contacted by the test compound; and selecting a test compound that modulates the level of expression of the one or more markers in the test cell, thereby identifying a compound for treating a disorder in a subject. In certain embodiments, the methods further include identifying a compound that modulates the level of expression of PSA.

The invention provides methods of identifying a compound for treating prostate cancer comprising obtaining a test cell; contacting the test cell with a test compound; determining the level of expression of keratin 7, 15, or 19 in the test cell; comparing the level of expression of keratin 7, 15, or 19 in the test cell with a control cell not contacted by the test compound; and selecting a test compound that modulates the level of expression of keratin 7, 15, or 19 in the test cell, thereby identifying a compound for treating a disorder in a subject.

The invention provides methods of identifying a compound for treating prostate cancer comprising obtaining a test cell; contacting the test cell with a test compound; determining the level of expression of filamin B or LY9 in the test cell; comparing the level of expression of filamin B or LY9 in the test cell with a control cell not contacted by the test compound; and selecting a test compound that modulates the level of expression of filamin B or LY9 in the test cell, thereby identifying a compound for treating a disorder in a subject.

In certain embodiments, the methods of identifying a compound for treating prostate cancer further include identifying a compound that modulates the level of expression of PSA.

In certain embodiments, the test cell is contacted with the agent in vitro.

In certain embodiments, the test cell is contacted with the agent in vivo. In certain embodiments, the test cell is present in a xenogenic model of cancer. In certain embodiments, the test cell is present in an animal model of prostate cancer. In certain embodiments, the level of expression of one or more (e.g., 1, 2, 3, 4, 5, 6, 7, 8, or 9) markers selected from the group consisting of keratin 4, keratin 7, keratin 8, keratin 15, keratin 18, keratin 19, tubulin-beta 3, filamin B (FLNB), and lymphocyte antigen 9 (LY9) is detected in the test cell by detection of the expression level of one or more (e.g., 1, 2, 3, 4, 5, 6, 7, 8, or 9) markers selected from the group consisting of keratin 4, keratin 7, keratin 8, keratin 15, keratin 18, keratin 19, tubulin-beta 3, filamin B (FLNB), and lymphocyte antigen 9 (LY9) in a biological sample in the organism containing the test cell.

The invention provides kits for the diagnosis, monitoring, or characterization of prostate cancer comprising at least one reagent specific for the detection of the level of expression of one or more (e.g., 1, 2, 3, 4, 5, 6, 7, 8, or 9) markers selected from the group consisting of keratin 4, keratin 7, keratin 8, keratin 15, keratin 18, keratin 19, tubulin-beta 3, filamin B (FLNB), and lymphocyte antigen 9 (LY9) in a sample.

In certain embodiments, the kit further comprises instructions for the diagnosis, monitoring, or characterization of prostate cancer based on the level of expression of one or more (e.g., 1, 2, 3, 4, 5, 6, 7, 8, or 9) markers selected from the group consisting of keratin 4, keratin 7, keratin 8, keratin 15, keratin 18, keratin 19, tubulin-beta 3, filamin B (FLNB), and lymphocyte antigen 9 (LY9). In certain embodiments, the kit includes instructions to detect the level of expression of PSA in the same sample in which the level of expression of one or more (e.g., 1, 2, 3, 4, 5, 6, 7, 8, or 9) markers selected from the group consisting of keratin 4, keratin 7, keratin 8, keratin 15, keratin 18, keratin 19, tubulin-beta 3, filamin B (FLNB), and lymphocyte antigen 9 (LY9) is detected. In certain embodiments, the kit includes at least one reagent specific for the detection of the level of expression of PSA. In certain embodiments, the kits include at least one antibody or nucleic acid for binding to f one or more (e.g., 1, 2, 3, 4, 5, 6, 7, 8, or 9) markers selected from the group consisting of keratin 4, keratin 7, keratin 8, keratin 15, keratin 18, keratin 19, tubulin-beta 3, filamin B (FLNB), and lymphocyte antigen 9 (LY9) for use in the methods provided herein. In certain embodiments, the kit includes at least one antibody or nucleic acid for binding to keratin 7 and one antibody or nucleic acid for binding to keratin 15. In certain embodiments, the kits further include at least one antibody or nucleic acid for binding to PSA for use in the methods provided herein. The kits may further provide instructions for practicing the methods provided herein.

Where applicable or not specifically disclaimed, any one of the embodiments described herein are contemplated to be able to combine with any other one or more embodiments, even though the embodiments are described under different aspects of the invention.

calculated (B) based on the analysis. The combination of PSA and FLNB was more sensitive than either marker alone.

Figure 10A:
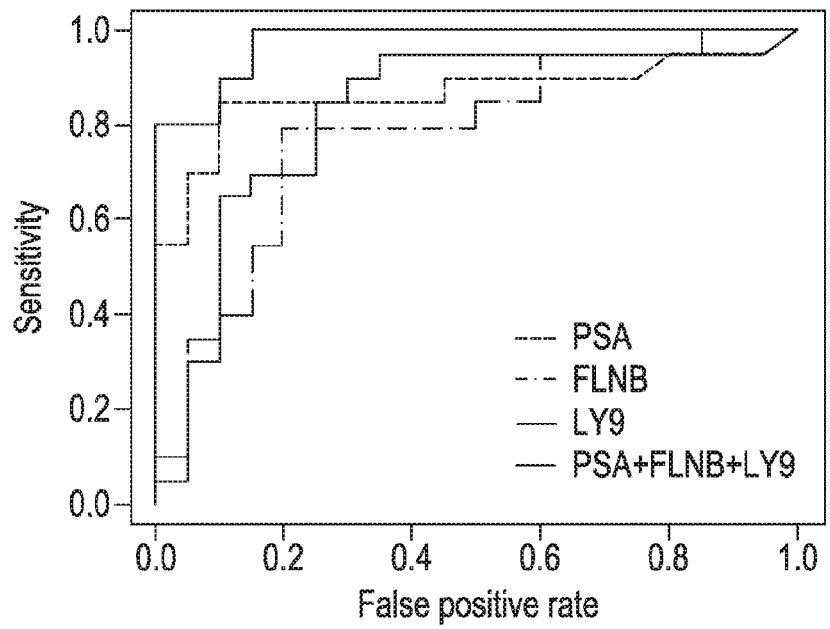
Figure 10B:
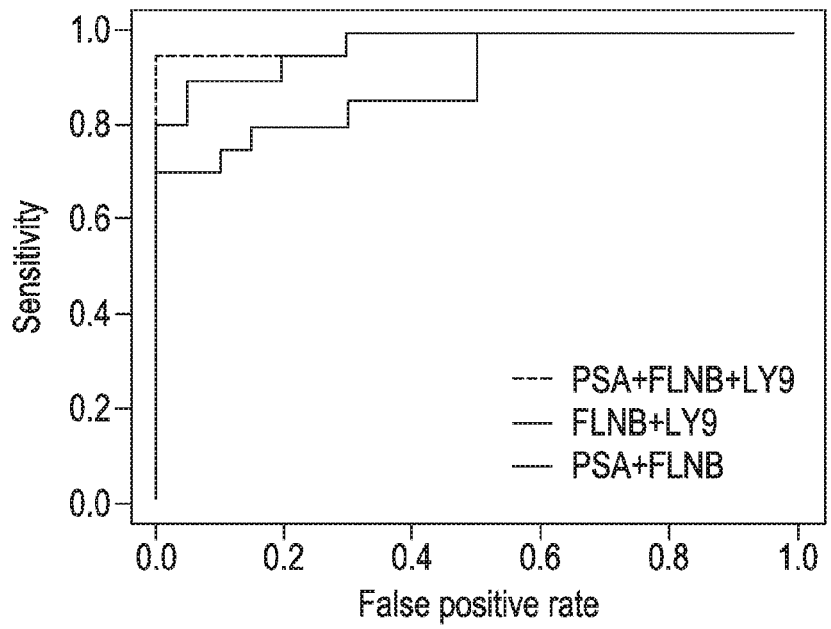

FIGS. 10A-B: ROC curve analysis of PSA, FLNB, LY9 and combinations of PSA, FLNB, and LY9 using linear (A) and non-linear (B) scoring functions. The combination of PSA, LY9, and FLNB was more sensitive than any marker alone.

DETAILED DESCRIPTION OF THE INVENTION

Definitions

As used herein, each of the following terms has the meaning associated with it in this section.

A "patient" or "subject" to be treated by the method of the invention can mean either a human or non-human animal, preferably a mammal. By "subject" is meant any animal, including horses, dogs, cats, pigs, goats, rabbits, hamsters, monkeys, guinea pigs, rats, mice, lizards, snakes, sheep, cattle, fish, and birds. A human subject may be referred to as a patient. It should be noted that clinical observations described herein were made with human subjects and, in at least some embodiments, the subjects are human.

"Therapeutically effective amount" means the amount of a compound that, when administered to a patient for treating a disease, is sufficient to effect such treatment for the disease, e.g., the amount of such a substance that produces some desired local or systemic effect at a reasonable benefit/risk ratio applicable to any treatment, e.g., is sufficient to ameliorate at least one sign or symptom of the disease, e.g., to prevent progression of the disease or condition, e.g., prevent tumor growth, decrease tumor size, induce tumor cell apoptosis, reduce tumor angiogenesis, prevent metastasis. When administered for preventing a disease, the amount is sufficient to avoid or delay onset of the disease. The "therapeutically effective amount" will vary depending on the compound, its therapeutic index, solubility, the disease and its severity and the age, weight, etc., of the patient to be treated, and the like. For example, certain compounds discovered by the methods of the present invention may be administered in a sufficient amount to produce a reasonable benefit/risk ratio applicable to such treatment. Administration of a therapeutically effective amount of a compound may require the administration of more than one dose of the compound.

"Preventing" or "prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease). Prevention does not require that the disease or condition never occurs in the subject. Prevention includes delaying the onset or severity of the disease or condition.

The term "prophylactic" or "therapeutic" treatment refers to administration to the subject of one or more agents or interventions to provide the desired clinical effect. If it is administered prior to clinical manifestation of the unwanted condition (e.g., disease or other unwanted state of the host animal) then the treatment is prophylactic, i.e., it protects the host against developing at least one sign or symptom of the unwanted condition, whereas if administered after manifestation of the unwanted condition, the treatment is therapeutic (i.e., it is intended to diminish, ameliorate, or maintain at least one sign or symptom of the existing unwanted condition or side effects therefrom).

As used herein, "treatment", particularly "active treatment" refers to performing an intervention to treat prostate cancer in a subject, e.g., reduce at least one of the growth rate, reduction of tumor burden, reduce or maintain the tumor size, or the malignancy (e.g., likelihood of metastasis) of the tumor; or to increase apoptosis in the tumor by one or more of administration of a therapeutic agent, e.g., chemotherapy or hormone therapy; administration of radiation therapy (e.g., pellet implantation, brachytherapy), or surgical resection of the tumor, or any combination thereof appropriate for treatment of the subject based on grade and stage of the tumor and other routine considerations. Active treatment is distinguished from "watchful waiting" (i.e., not active treatment) in which the subject and tumor are monitored, but no interventions are performed to affect the tumor. Watchful waiting can include administration of agents that alter effects caused by the tumor (e.g., incontinence, erectile dysfunction) that are not administered to alter the growth or pathology of the tumor itself.

The term "therapeutic effect" refers to a local or systemic effect in animals, particularly mammals, and more particularly humans caused by a pharmacologically active substance. The term thus means any substance intended for use in the diagnosis, cure, mitigation, treatment, or prevention of disease, or in the enhancement of desirable physical or mental development and conditions in an animal or human. A therapeutic effect can be understood as a decrease in tumor growth, decrease in tumor growth rate, stabilization or decrease in tumor burden, stabilization or reduction in tumor size, stabilization or decrease in tumor malignancy, increase in tumor apoptosis, and/or a decrease in tumor angiogenesis.

The terms "disorders", "diseases", and "abnormal state" are used inclusively and refer to any deviation from the normal structure or function of any part, organ, or system of the body (or any combination thereof). A specific disease is manifested by characteristic symptoms and signs, including biological, chemical, and physical changes, and is often associated with a variety of other factors including, but not limited to, demographic, environmental, employment, genetic, and medically historical factors. Certain characteristic signs, symptoms, and related factors can be quantitated through a variety of methods to yield important diagnostic information. As used herein the disorder, disease, or abnormal state is an abnormal prostate state, including benign prostate hyperplasia and cancer, particularly prostate cancer. The abnormal prostate state of prostate cancer can be further subdivided into stages and grades of prostate cancer as provided, for example in Prostate. In: Edge S B, Byrd D R, Compton C C, et al., eds.: AJCC Cancer Staging Manual. 7th ed. New York, N.Y.: Springer, 2010, pp 457-68 (incorporated herein by reference). Further, abnormal prostate states can be classified as one or more of benign prostate hyperplasia (BPH), androgen sensitive prostate cancer, androgen insensitive or resistant prostate cancer, aggressive prostate cancer, non-aggressive prostate cancer, metastatic prostate cancer, and non-metastatic prostate cancer.

A subject at "increased risk for developing prostate cancer" may or may not develop prostate cancer. Identification of a subject at increased risk for developing prostate cancer should be monitored for additional signs or symptoms of prostate cancer. The methods provided herein for identifying a subject with increased risk for developing prostate cancer can be used in combination with assessment of other known risk factors or signs of prostate cancer including, but not limited to decreased urinary stream, urgency, hesitancy, nocturia, incomplete bladder emptying, and age.

The term "expression" is used herein to mean the process by which a polypeptide is produced from DNA. The process involves the transcription of the gene into mRNA and the translation of this mRNA into a polypeptide. Depending on the context in which used, "expression" may refer to the production of RNA, or protein, or both.

The terms "level of expression of a gene", "gene expression level", "level of a marker", and the like refer to the level of mRNA, as well as pre-mRNA nascent transcript(s), transcript processing intermediates, mature mRNA(s) and degradation products, or the level of protein, encoded by the gene in the cell.

The term "specific identification" is understood as detection of a marker of interest with sufficiently low background of the assay and cross-reactivity of the reagents used such that the detection method is diagnostically useful. In certain embodiments, reagents for specific identification of a marker bind to only one isoform of the marker. In certain embodiments, reagents for specific identification of a marker bind to more than one isoform of the marker. In certain embodiments, reagents for specific identification of a marker bind to all known isoforms of the marker.

The term "modulation" refers to upregulation (i.e., activation or stimulation), down-regulation (i.e., inhibition or suppression) of a response, or the two in combination or apart. A "modulator" is a compound or molecule that modulates, and may be, e.g., an agonist, antagonist, activator, stimulator, suppressor, or inhibitor.

The term "control sample," as used herein, refers to any clinically relevant comparative sample, including, for example, a sample from a healthy subject not afflicted with an oncological disorder, e.g., prostate cancer, or a sample from a subject from an earlier time point, e.g., prior to treatment, an earlier tumor assessment time point, at an earlier stage of treatment. A control sample can be a purified sample, protein, and/or nucleic acid provided with a kit. Such control samples can be diluted, for example, in a dilution series to allow for quantitative measurement of levels of analytes, e.g., markers, in test samples. A control sample may include a sample derived from one or more subjects. A control sample may also be a sample made at an earlier time point from the subject to be assessed. For example, the control sample could be a sample taken from the subject to be assessed before the onset of an oncological disorder, e.g., prostate cancer, at an earlier stage of disease, or before the administration of treatment or of a portion of treatment. The control sample may also be a sample from an animal model, or from a tissue or cell lines derived from the animal model of oncological disorder, e.g., prostate cancer. The level of activity or expression of one or more (e.g., 1, 2, 3, 4, 5, 6, 7, 8, or 9) markers selected from the group consisting of keratin 4, keratin 7, keratin 8, keratin 15, keratin 18, keratin 19, tubulin-beta 3, filamin B (FLNB), lymphocyte antigen 9 (LY9), and PSA in a control sample consists of a group of measurements may be determined, e.g., based on any appropriate statistical measure, such as, for example, measures of central tendency including average, median, or modal values. Different from a control is preferably statistically significantly different from a control.

The term "control level" refers to an accepted or predetermined level of a marker in a subject sample. A control level can be a range of values. Marker levels can be compared to a single control value, to a range of control values, to the upper level of normal, or to the lower level of normal as appropriate for the assay.

In one embodiment, the control is a standardized control, such as, for example, a control which is predetermined using an average of the levels of expression of one or more markers from a population of subjects having no cancer, especially subjects having no prostate cancer. In still other embodiments of the invention, a control level of a marker in a non-cancerous sample(s) derived from the subject having cancer. For example, when a biopsy or other medical procedure reveals the presence of cancer in one portion of the tissue, the control level of a marker may be determined using the non-affected portion of the tissue, and this control level may be compared with the level of the marker in an affected portion of the tissue.

In certain embodiments, the control can be from a subject, or a population of subject, having an abnormal prostate state. For example, the control can be from a subject suffering from benign prostate hyperplasia (BPH), androgen sensitive prostate cancer, androgen insensitive or resistant prostate cancer, aggressive prostate cancer, non-aggressive prostate cancer, metastatic prostate cancer, or non-metastatic prostate cancer. It is understood that not all markers will have different levels for each of the abnormal prostate states listed. It is understood that a combination of maker levels may be most useful to distinguish between abnormal prostate states, possibly in combination with other diagnostic methods. Further, marker levels in biological samples can be compared to more than one control sample (e.g., normal, abnormal, from the same subject, from a population control). Marker levels can be used in combination with other signs or symptoms of an abnormal prostate state to provide a diagnosis for the subject.

A control can also be a sample from a subject at an earlier time point, e.g., a baseline level prior to suspected presence of disease, before the diagnosis of a disease, at an earlier assessment time point during watchful waiting, before the treatment with a specific agent (e.g., chemotherapy, hormone therapy) or intervention (e.g., radiation, surgery). In certain embodiments, a change in the level of the marker in a subject can be more significant than the absolute level of a marker, e.g., as compared to control.

As used herein, a sample obtained at an "earlier time point" is a sample that was obtained at a sufficient time in the past such that clinically relevant information could be obtained in the sample from the earlier time point as compared to the later time point. In certain embodiments, an earlier time point is at least four weeks earlier. In certain embodiments, an earlier time point is at least six weeks earlier. In certain embodiments, an earlier time point is at least two months earlier. In certain embodiments, an earlier time point is at least three months earlier. In certain embodiments, an earlier time point is at least six months earlier. In certain embodiments, an earlier time point is at least nine months earlier. In certain embodiments, an earlier time point is at least one year earlier. Multiple subject samples (e.g., 3, 4, 5, 6, 7, or more) can be obtained at regular or irregular intervals over time and analyzed for trends in changes in marker levels. Appropriate intervals for testing for a particular subject can be determined by one of skill in the art based on ordinary considerations.

As used herein, "changed as compared to a control" sample or subject is understood as having a level of the analyte or diagnostic or therapeutic indicator (e.g., marker) to be detected at a level that is statistically different than a sample from a normal, untreated, or abnormal state control sample. Changed as compared to control can also include a difference in the rate of change of the level of one or more markers obtained in a series of at least two subject samples obtained over time. Determination of statistical significance is within the ability of those skilled in the art, e.g., the number of standard deviations from the mean that constitute a positive or negative result.

As used herein, the term "obtaining" is understood herein as manufacturing, purchasing, or otherwise coming into possession of.

As used herein, "detecting", "detection", "determining", and the like are understood that an assay performed for identification of a specific marker in a sample, e.g., one or more (e.g., 1, 2, 3, 4, 5, 6, 7, 8, or 9) markers selected from the group consisting of keratin 4, keratin 7, keratin 8, keratin 15, keratin 18, keratin 19, tubulin-beta 3, filamin B (FLNB), lymphocyte antigen 9 (LY9), and PSA. The amount of marker expression or activity detected in the sample can be none or below the level of detection of the assay or method.

As used herein, "greater predictive value" is understood as an assay that has significantly greater sensitivity and/or specificity, preferably greater sensitivity and specificity, than the test to which it is compared. The predictive value of a test can be determined using an ROC analysis. In an ROC analysis a test that provides perfect discrimination or accuracy between normal and disease states would have an area under the curve (AUC)=1, whereas a very poor test that provides no better discrimination than random chance would have AUC=0.5. As used herein, a test with a greater predictive value will have a statistically improved AUC as compared to another assay. The assays are preformed in an appropriate subject population.

The articles "a" and "an" are used herein to refer to one or to more than one (i.e. to at least one) of the grammatical object of the article. By way of example, "an element" means one element or more than one element.

The term "including" is used herein to mean, and is used interchangeably with, the phrase "including but not limited to."

The term "or" is used inclusively herein to mean, and is used interchangeably with, the term "and/or," unless context clearly indicates otherwise. For example, as used herein, filamin B or LY9 is understood to include filamin B alone, LY9 alone, and the combination of filamin B and LY9.

The term "such as" is used herein to mean, and is used interchangeably, with the phrase "such as but not limited to."

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term about.

The recitation of a listing of chemical group(s) in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, "one or more" is understood as each value 1, 2, 3, 4, 5, 6, 7, 8, 9, 10, and any value greater than 10.

Reference will now be made in detail to exemplary embodiments of the invention. While the invention will be described in conjunction with the exemplary embodiments, it will be understood that it is not intended to limit the invention to those embodiments. To the contrary, it is intended to cover alternatives, modifications, and equivalents as may be included within the spirit and scope of the invention as defined by the appended claims.

Keratins

Keratin 4

Keratin 4, also known as K4; CK4; CK-4; CYK4, is a member of the keratin gene family. The type II cytokeratins consist of basic or neutral proteins which are arranged in pairs of heterotypic keratin chains coexpressed during differentiation of simple and stratified epithelial tissues. This type II cytokeratin is specifically expressed in differentiated layers of the mucosal and esophageal epithelia with family member KRT13. Mutations in these genes have been associated with White Sponge Nevus, characterized by oral, esophageal, and anal leukoplakia. The type II cytokeratins are clustered in a region of chromosome 12q12-q13.

As used herein, keratin 4 refers to both the gene and the protein unless clearly indicated otherwise by context. The NCBI Gene ID for human keratin 4 is 3851 and detailed information can be found at www.ncbi.nlm.nih.gov/gene/3851 (incorporated herein by reference in the version available on the filing date of the application to which this application claims priority). Homo sapiens keratin 4, GenBank Accession No. NM_002272 amino acid and nucleotide sequences, respectively, are provided in SEQ ID NOs: 1 and 2. (The GenBank number is incorporated herein by reference in the version available on the filing date of the application to which this application claims priority.)

It is understood that the invention includes the use of any fragments of keratin 4 sequences as long as the fragment can allow for the specific identification of keratin 4. Moreover, it is understood that there are naturally occurring variants of keratin 4 which may or may not be associated with a specific disease state, the use of which are also included in this application.

Keratin 7

Keratin 7, also known as CK7, K2C7, K7, SCL, CK-7; cytokeratin 7; cytokeratin-7; keratin, 55K type II cytoskeletal; keratin, simple epithelial type I, K7; keratin, type II cytoskeletal 7; keratin-7; sarcolectin; type II mesothelial keratin K7; and type-II keratin Kb7, is a member of the keratin gene family. The type II cytokeratins consist of basic or neutral proteins which are arranged in pairs of heterotypic keratin chains coexpressed during differentiation of simple and stratified epithelial tissues. This type II cytokeratin is specifically expressed in the simple epithelia lining the cavities of the internal organs and in the gland ducts and blood vessels. The genes encoding the type II cytokeratins are clustered in a region of chromosome 12q12-q13. Alternative splicing may result in several transcript variants; however, not all variants have been fully described.

As used herein, keratin 7 refers to both the gene and the protein unless clearly indicated otherwise by context. The NCBI Gene ID for human keratin 7 is 3855 and detailed information can be found at www.ncbi.nlm.nih.gov/gene/3855 (incorporated herein by reference in the version available on the filing date of the application to which this application claims priority). Homo sapiens keratin 7, GenBank Accession No. NM_005556 amino acid and nucleotide sequences, respectively, are provided in SEQ ID NOs: 3 and 4. (The GenBank number is incorporated herein by reference in the version available on the filing date of the application to which this application claims priority.)

It is understood that the invention includes the use of any fragments of keratin 7 sequences as long as the fragment can allow for the specific identification of keratin 7. Moreover, it is understood that there are naturally occurring variants of keratin 7 which may or may not be associated with a specific disease state, the use of which are also included in this application.

Keratin 8

Keratin 8, also known as K8; KO; CK8; CK-8; CYK8; K2C8; CARD2 is a member of the type II keratin family clustered on the long arm of chromosome 12. Type I and type II keratins heteropolymerize to form intermediate-sized filaments in the cytoplasm of epithelial cells. The product of this gene typically dimerizes with keratin 18 to form an intermediate filament in simple single-layered epithelial cells. This protein plays a role in maintaining cellular structural integrity and also functions in signal transduction and cellular differentiation. Mutations in this gene cause cryptogenic cirrhosis. Alternatively spliced transcript variants have been found for this gene.

As used herein, keratin 8 refers to both the gene and the protein unless clearly indicated otherwise by context. The NCBI Gene ID for human keratin 8 is 3856 and detailed information can be found at www.ncbi.nlm.nih.gov/gene/3856 (incorporated herein by reference in the version available on the filing date of the application to which this application claims priority). Homo sapiens keratin 8, variant 1, GenBank Accession No. NM_001256282 amino acid and nucleotide sequences, respectively, are provided in SEQ ID NOs: 5 and 6; and homo sapiens keratin 8, variant 3, GenBank Accession No. NM_001256293 amino acid and nucleotide sequences, respectively, are provided in SEQ ID NOs: 7 and 8. (The GenBank numbers are incorporated herein by reference in the version available on the filing date of the application to which this application claims priority.)

It is understood that the invention includes the use of either on of or both of the variants of keratin 8 provided in the sequence listing and any fragments of keratin 8 sequences as long as the fragment can allow for the specific identification of keratin 8. Moreover, it is understood that there are naturally occurring variants of keratin 8 which may or may not be associated with a specific disease state, the use of which are also included in this application.

Keratin 15

Keratin 15, also known as K15; CK15; K1CO, is a member of the keratin gene family. The keratins are intermediate filament proteins responsible for the structural integrity of epithelial cells and are subdivided into cytokeratins and hair keratins. Most of the type I cytokeratins consist of acidic proteins which are arranged in pairs of heterotypic keratin chains and are clustered in a region on chromosome 17q21.2.

As used herein, keratin 15 refers to both the gene and the protein unless clearly indicated otherwise by context. The NCBI Gene ID for human keratin 15 is 3866 and detailed information can be found at www.ncbi.nlm.nih.gov/gene/3866 (incorporated herein by reference in the version available on the filing date of the application to which this application claims priority). Homo sapiens keratin 15, GenBank Accession No. NM_002275 amino acid and nucleotide sequences, respectively, are provided in SEQ ID NOs: 9 and 10. (The GenBank number is incorporated herein by reference in the version available on the filing date of the application to which this application claims priority.)

It is understood that the invention includes the use of any fragments of keratin 15 sequences as long as the fragment can allow for the specific identification of keratin 15. Moreover, it is understood that there are naturally occurring variants of keratin 15 which may or may not be associated with a specific disease state, the use of which are also included in this application.

Keratin 18

Keratin 18, also known as K18; CYK18, encodes the type I intermediate filament chain keratin 18. Keratin 18, together with its filament partner keratin 8, are perhaps the most commonly found members of the intermediate filament gene family. They are expressed in single layer epithelial tissues of the body. Mutations in this gene have been linked to cryptogenic cirrhosis. Two transcript variants encoding the same protein have been found for this gene.

As used herein, keratin 15 refers to both the gene and the protein unless clearly indicated otherwise by context. The NCBI Gene ID for human keratin 18 is 3875 and detailed information can be found at www.ncbi.nlm.nih.gov/gene/3875 (incorporated herein by reference in the version available on the filing date of the application to which this application claims priority). Homo sapiens keratin 18, variant 1, GenBank Accession No. NM_000224 amino acid and nucleotide sequences, respectively, are provided in SEQ ID NOs: 11 and 12, and homo sapiens keratin 18, variant 2, GenBank Accession No. 199187 amino acid and nucleotide sequences, respectively, are provided in SEQ ID NOs: 13 and 14. (The GenBank numbers are incorporated herein by reference in the version available on the filing date of the application to which this application claims priority.)

It is understood that the invention includes the use of either on of or both of the variants of keratin 18 provided in the sequence listing and any fragments of keratin 18 sequences as long as the fragment can allow for the specific identification of keratin 18. Moreover, it is understood that there are naturally occurring variants of keratin 18 which may or may not be associated with a specific disease state, the use of which are also included in this application.

Keratin 19

Keratin 19, also known as K19; CK19; K1CS, is a member of the keratin gene family. The keratins are intermediate filament proteins responsible for the structural integrity of epithelial cells and are subdivided into cytokeratins and hair keratins. The type I cytokeratins consist of acidic proteins which are arranged in pairs of heterotypic keratin chains. Unlike its related family members, this smallest known acidic cytokeratin is not paired with a basic cytokeratin in epithelial cells. It is specifically expressed in the periderm, the transiently superficial layer that envelopes the developing epidermis. The type I cytokeratins are clustered in a region of chromosome 17q12-q21.

As used herein, keratin 19 refers to both the gene and the protein unless clearly indicated otherwise by context. The NCBI Gene ID for human keratin 19 is 3880 and detailed information can be found at www.ncbi.nlm.nih.gov/gene/3880 (incorporated herein by reference in the version available on the filing date of the application to which this application claims priority). Homo sapiens keratin 19, GenBank Accession No. NM_002276 amino acid and nucleotide sequences, respectively, are provided in SEQ ID NOs: 15 and 16. (The GenBank number is incorporated herein by reference in the version available on the filing date of the application to which this application claims priority.)

It is understood that the invention includes the use of any fragments of keratin 19 sequences as long as the fragment can allow for the specific identification of keratin 19. Moreover, it is understood that there are naturally occurring variants of keratin 19 which may or may not be associated with a specific disease state, the use of which are also included in this application.

Tubulin-Beta 3

Tubulin-beta 3, also known as CDCBM; TUBB4; beta-4; CFEOM3A, is a class III member of the beta tubulin protein family. Beta tubulins are one of two core protein families (alpha and beta tubulins) that heterodimerize and assemble to form microtubules. This protein is primarily expressed in neurons and may be involved in neurogenesis and axon guidance and maintenance. Mutations in this gene are the cause of congenital fibrosis of the extraocular muscles type 3. Alternate splicing results in multiple transcript variants. A pseudogene of this gene is found on chromosome 6.

As used herein, Tubulin-beta 3 refers to both the gene and the protein unless clearly indicated otherwise by context. The NCBI Gene ID for human Tubulin-beta 3 is 10381 and detailed information can be found at www.ncbi.nlm.nih.gov/gene/10381 (incorporated herein by reference in the version available on the filing date of the application to which this application claims priority). Homo sapiens Tubulin-beta 3, variant 2, GenBank Accession No. NM_001197181 amino acid and nucleotide sequences, respectively, are provided in SEQ ID NOs: 17 and 18. Homo sapiens Tubulin-beta 3, variant 1, GenBank Accession No. NM_006086 amino acid and nucleotide sequences, respectively, are provided in SEQ ID NOs: 19 and 20. (The GenBank numbers are incorporated herein by reference in the versions available on the filing date of the application to which this application claims priority.)

It is understood that the invention includes the use of any fragments of Tubulin-beta 3 sequences as long as the fragment can allow for the specific identification of Tubulin-beta 3. Moreover, it is understood that there are naturally occurring variants of Tubulin-beta 3 which may or may not be associated with a specific disease state, the use of which are also included in this application.

Filamin B

Filamin B is also known as filamin-3, beta-filamin, ABP-280 homolog, filamin homolog 1, thyroid autoantigen, actin binding protein 278, actin-binding-like protein, Larsen syndrome 1 (autosomal dominant), AOI; FH1; SCT; TAP; LRS1; TABP; FLN-B; FLN1L; ABP-278; and ABP-280. The gene encodes a member of the filamin family. The encoded protein interacts with glycoprotein Ib alpha as part of the process to repair vascular injuries. The platelet glycoprotein Ib complex includes glycoprotein Ib alpha, and it binds the actin cytoskeleton. Mutations in this gene have been found in several conditions: atelosteogenesis type 1 and type 3; boomerang dysplasia; autosomal dominant Larsen syndrome; and spondylocarpotarsal synostosis syndrome. Multiple alternatively spliced transcript variants that encode different protein isoforms have been described for this gene.

As used herein, filamin B refers to both the gene and the protein unless clearly indicated otherwise by context. The NCBI gene ID for filamin B is 2317 and detailed information can be found at www.ncbi.nlm.nih.gov/gene/2317 (incorporated herein by reference in the version available on the filing date of the application to which this application claims priority). Homo sapiens filamin B, beta (FLNB), RefSeqGene on chromosome 3, locus NG_012801 is shown in SEQ ID NO: 21. Homo sapiens filamin B, beta (FLNB), transcript variant 1, GenBank Accession No. NM_001164317.1 amino acid and nucleotide sequences, respectively, are provided in SEQ ID NOs: 22 and 23. Homo sapiens filamin B, beta (FLNB), transcript variant 3, GenBank Accession No. NM_001164318.1 amino acid and nucleotide sequences, respectively, are provided in SEQ ID NOs: 24 and 25. Homo sapiens filamin B, beta (FLNB), transcript variant 4, GenBank Accession No. NM_001164319.1 amino acid and nucleotide sequences, respectively, are provided in SEQ ID NOs: 26 and 27. Homo sapiens filamin B, beta (FLNB), transcript variant 2, GenBank Accession No. NM_001457.3 amino acid and nucleotide sequences, respectively, are provided in SEQ ID NOs: 28 and 29. (Each GenBank number is incorporated herein by reference in the version available on the filing date of the application to which this application claims priority.)

It is understood that the invention includes the use of any combination of one or more of the filamin B sequences provided in the sequence listing or any fragments thereof as long as the fragment can allow for the specific identification of filamin B. Methods of the invention and reagents can be used to detect single isoforms of filamin B, combinations of filamin B isoforms, or all of the filamin B isoforms simultaneously. Unless specified, filamin B can be considered to refer to one or more isoforms of filamin B, including total filamin B. Moreover, it is understood that there are naturally occurring variants of filamin B, which may or may not be associated with a specific disease state, the use of which are also included in the instant application.

Lymphocyte Antigen 9

Lymphocyte antigen 9 (LY9) is also known as RP11-312J18.1, CD229, SLAMF3, hly9, mLY9, T-lymphocyte surface antigen Ly-9; and cell surface molecule Ly-9. LY9 belongs to the SLAM family of immunomodulatory receptors (see SLAMF1; MIM 603492) and interacts with the adaptor molecule SAP (SH2D1A; MIM 300490) (Graham et al., 2006).

As used herein, LY9 refers to both the gene and the protein unless clearly indicated otherwise by context. The NCBI gene ID for LY9 is 4063 and detailed information can be found at www.ncbi.nlm.nih.gov/gene/4063 (incorporated herein by reference in the version available on the filing date of the application to which this application claims priority).

Homo sapiens lymphocyte antigen 9 (LY9), transcript variant 2, GenBank Accession No. NM_001033667 amino acid and nucleotide sequences, respectively, are provided in SEQ ID NOs: 30 and 31. Homo sapiens lymphocyte antigen 9 (LY9), transcript variant 3, GenBank Accession No. NM_001261456 amino acid and nucleotide sequences, respectively, are provided in SEQ ID NOs: 32 and 33. Homo sapiens lymphocyte antigen 9 (LY9), transcript variant 4, GenBank Accession No. NM_001261457 amino acid and nucleotide sequences, respectively, are provided in SEQ ID NOs: 34 and 35. Homo sapiens lymphocyte antigen 9 (LY9), transcript variant 1, GenBank Accession No. NM_002348 is shown amino acid and nucleotide sequences, respectively, are provided in SEQ ID NOs: 36 and 37. (Each GenBank number is incorporated herein by reference in the version available on the filing date of the application to which this application claims priority.)

It is understood that the invention includes the use of any combination of one or more of the LY9 sequences provided in the sequence listing or any fragments thereof as long as the fragment can allow for the specific identification of LY9. Methods of the invention and reagents can be used to detect single isoforms of LY9, combinations of LY9 isoforms, or all of the LY9 isoforms simultaneously. Unless specified, LY9 can be considered to refer to one or more isoforms of LY9, including total LY9. Moreover, it is understood that there are naturally occurring variants of LY9, which may or may not be associated with a specific disease state, the use of which are also included in the instant application.

Prostate Specific Antigen

Prostate-specific antigen (PSA) is also known as kallikrein-3, seminin, P-30 antigen, semenogelase, gamma-seminoprotein, APS, hK3, and KLK2A1. Kallikreins are a subgroup of serine proteases having diverse physiological functions. Growing evidence suggests that many kallikreins are implicated in carcinogenesis and some have potential as novel cancer and other disease biomarkers. This gene is one of the fifteen kallikrein subfamily members located in a cluster on chromosome 19. Its protein product is a protease present in seminal plasma. It is thought to function normally in the liquefaction of seminal coagulum, presumably by hydrolysis of the high molecular mass seminal vesicle protein. Serum level of this protein, called PSA in the clinical setting, is useful in the diagnosis and monitoring of prostatic carcinoma. Alternate splicing of this gene generates several transcript variants encoding different isoforms.

As used herein, PSA refers to both the gene and the protein, in both processed and unprocessed forms, unless clearly indicated otherwise by context. The NCBI gene ID for PSA is 354 and detailed information can be found at www.ncbi.nlm.nih.gov/gene/354 (incorporated herein by reference in the version available on the filing date of the application to which this application claims priority).

Homo sapiens PSA is located on chromosome 19 at 19q13.41Sequence: NC_000019.9 (51358171 . . . 51364020). Four splice variants of human PSA are known: Prostate-specific antigen isoform 3 preproprotein, NM_001030047.1; Prostate-specific antigen isoform 4 preproprotein, NM_001030048.1; Prostate-specific antigen isoform 6 preproprotein, NM_001030050.1; and Prostate-specific antigen isoform 1 preproprotein, NM_001648.2. (Each GenBank number is incorporated herein by reference in the version available on the filing date of the application to which this application claims priority).

It is understood that the invention includes the use of any combination of one or more of the PSA sequences provided in the sequence listing or any fragments thereof as long as the fragment can allow for the specific identification of PSA. Methods of the invention and reagents can be used to detect single isoforms of PSA, combinations of PSA isoforms, or all of the PSA isoforms simultaneously. Unless specified, PSA can be considered to refer to one or more isoforms of PSA, including total PSA. Moreover, it is understood that there are naturally occurring variants of PSA, which may or may not be associated with a specific disease state, the use of which are also included in the instant application.

Treatment of Disease States

The present invention provides methods for use of one or more (e.g., 1, 2, 3, 4, 5, 6, 7, 8, or 9) markers selected from the group consisting of keratin 4, keratin 7, keratin 8, keratin 15, keratin 18, keratin 19, tubulin-beta 3, filamin B (FLNB), and lymphocyte antigen 9 (LY9) to treat disease states in a subject, e.g., a mammal, e.g., a human.

The present invention also provides methods for treatment of a subject with prostate cancer with a therapeutic, e.g., a nucleic acid based therapeutic, that modulates the expression or activity of one or more (e.g., 1, 2, 3, 4, 5, 6, 7, 8, or 9) markers selected from the group consisting of keratin 4, keratin 7, keratin 8, keratin 15, keratin 18, keratin 19, tubulin-beta 3, filamin B (FLNB), and lymphocyte antigen 9 (LY9).

The invention also provides methods for selection and/or administration of known treatment agents, especially hormone based therapies vs. non-hormone based therapies, and aggressive or active treatment vs. "watchful waiting", depending on the detection of a change in the level of one or more (e.g., 1, 2, 3, 4, 5, 6, 7, 8, or 9) markers selected from the group consisting of keratin 4, keratin 7, keratin 8, keratin 15, keratin 18, keratin 19, tubulin-beta 3, filamin B (FLNB), and lymphocyte antigen 9 (LY9), as compared to a control. The selection of treatment regimens can further include the detection of PSA to assist in selection of the therapeutic methods. Selection of treatment methods can also include other diagnostic considerations and patient characteristics including results from imaging studies, tumor size or growth rates, risk of poor outcomes, disruption of daily activities, and age.

As used herein, the term "aggressive oncological disorder", such as aggressive prostate cancer, refers to an oncological disorder involving a fast-growing tumor. An aggressive oncological disorder typically does not respond, responds poorly, or loses response to therapeutic treatment. For example, an prostate cancer may be considered to become an aggressive prostate cancer upon loss of response to hormone therapy, necessitating treatment with chemotherapy, surgery, and/or radiation. As used herein, an aggressive prostate cancer, for example, is one that will likely or has metastasized. As used herein, an aggressive prostate cancer is one that will result in significant changes in quality of life as the tumor grows. Active treatment is therapeutically indicated for an aggressive oncological disorder, e.g., aggressive prostate cancer.

As used herein, the term "non-aggressive oncological disorder" such as a non-aggressive prostate cancer, refers to an oncological disorder involving a slow-growing tumor. A non-aggressive oncological disorder typically responds favorably or moderately to therapeutic treatment or grows so slowly that immediate treatment is not warranted. A non-aggressive prostate tumor is one that a person skilled in the art, e.g., an oncologist, may decide to not actively treat with routine interventions for the treatment of cancer, e.g., chemotherapy, radiation, surgery, as the active treatment may do more harm than the disease, particularly in an older subject. A non-aggressive prostate tumor is one that a person skilled in the art may decide to monitor with "watchful waiting" rather than subjecting the person to any active therapeutic interventions to alter the presence or growth of the tumor (e.g., radiation, surgery, chemotherapy, hormone therapy).

Diagnostic/Prognostic Uses of the Invention

The invention provides methods for diagnosing an abnormal prostate state, e.g., BPH or an oncological disease state, e.g., prostate cancer, in a subject. The invention further provides methods for prognosing or monitoring progression or monitoring response of an abnormal prostate state, e.g., BPH or prostate cancer, to a therapeutic treatment during active treatment or watchful waiting.

The invention provides, in one embodiment, methods for diagnosing an oncological disorder, e.g., prostate cancer. The methods of the present invention can be practiced in conjunction with any other method used by the skilled practitioner to prognose the occurrence or recurrence of an oncologic disorder and/or the survival of a subject being treated for an oncologic disorder. The diagnostic and prognostic methods provided herein can be used to determine if additional and/or more invasive tests or monitoring should be performed on a subject. It is understood that a disease as complex as an oncological disorder is rarely diagnosed using a single test. Therefore, it is understood that the diagnostic, prognostic, and monitoring methods provided herein are typically used in conjunction with other methods known in the art. For example, the methods of the invention may be performed in conjunction with a morphological or cytological analysis of the sample obtained from the subject, imaging analysis, and/or physical exam. Cytological methods would include immunohistochemical or immunofluorescence detection (and quantitation if appropriate) of any other molecular marker either by itself, in conjunction with other markers. Other methods would include detection of other markers by in situ PCR, or by extracting tissue and quantitating other markers by real time PCR. PCR is defined as polymerase chain reaction.

Methods for assessing tumor progression during watchful waiting or the efficacy of a treatment regimen, e.g., chemotherapy, radiation therapy, surgery, hormone therapy, or any other therapeutic approach useful for treating an oncologic disorder in a subject are also provided. In these methods the amount of marker in a pair of samples (a first sample obtained from the subject at an earlier time point or prior to the treatment regimen and a second sample obtained from the subject at a later time point, e.g., at a later time point when the subject has undergone at least a portion of the treatment regimen) is assessed. It is understood that the methods of the invention include obtaining and analyzing more than two samples (e.g., 3, 4, 5, 6, 7, 8, 9, or more samples) at regular or irregular intervals for assessment of marker levels. Pairwise comparisons can be made between consecutive or non-consecutive subject samples. Trends of marker levels and rates of change of marker levels can be analyzed for any two or more consecutive or non-consecutive subject samples.

The invention also provides a method for determining whether an oncologic disorder, e.g., prostate cancer, is aggressive. The method comprises determining the amount of a marker present in a sample and comparing the amount to a control amount of the marker present in one or more control samples, as defined in Definitions, thereby determining whether an oncologic disorder is aggressive. Marker levels can be compared to marker levels in samples obtained at different times from the same subject or marker levels from normal or abnormal prostate state subjects. A rapid increase in the level of marker may be indicative of a more aggressive cancer than a slow increase or no increase or change in the marker level.

The methods of the invention may also be used to select a compound that is capable of modulating, i.e., decreasing, the aggressiveness of an oncologic disorder, e.g., prostate cancer. In this method, a cancer cell is contacted with a test compound, and the ability of the test compound to modulate the expression and/or activity of a marker in the invention in the cancer cell is determined, thereby selecting a compound that is capable of modulating aggressiveness of an oncologic disorder.

Using the methods described herein, a variety of molecules, may be screened in order to identify molecules which modulate, e.g., increase or decrease the expression and/or activity of a marker of the invention, i.e., keratin 4, keratin 7, keratin 8, keratin 15, keratin 18, keratin 19, tubulin-beta 3, filamin B (FLNB), and lymphocyte antigen 9 (LY9), optionally in combination with PSA. Compounds so identified can be provided to a subject in order to inhibit the aggressiveness of an oncological disorder in the subject, to prevent the recurrence of an oncological disorder in the subject, or to treat an oncological disorder in the subject.

Markers of the Invention

The invention relates to markers (hereinafter "biomarkers", "markers" or "markers of the invention"). The preferred markers of the invention are one or more (e.g., 1, 2, 3, 4, 5, 6, 7, 8, or 9) markers selected from the group consisting of keratin 4, keratin 7, keratin 8, keratin 15, keratin 18, keratin 19, tubulin-beta 3, filamin B (FLNB), and lymphocyte antigen 9 (LY9). Methods of the invention also include use of the marker PSA in conjunction with one or more (e.g., 1, 2, 3, 4, 5, 6, 7, 8, or 9) markers selected from the group consisting of keratin 4, keratin 7, keratin 8, keratin 15, keratin 18, keratin 19, tubulin-beta 3, filamin B (FLNB), and lymphocyte antigen 9 (LY9).

The invention provides nucleic acids and proteins (e.g., isolated nucleic acids and isolated proteins or fragments thereof) that are encoded by, or correspond to, the markers (hereinafter "marker nucleic acids" and "marker proteins," respectively). These markers are particularly useful in screening for the presence of an altered prostate state, e.g., BPH or prostate cancer, in assessing aggressiveness and metastatic potential of an oncologic disorder, assessing the androgen dependent status of an oncological disorder, assessing whether a subject is afflicted with an oncological disorder, identifying a composition for treating an oncological disorder, assessing the efficacy of a compound for treating an oncological disorder, monitoring the progression of an oncological disorder, prognosing the aggressiveness of an oncological disorder, prognosing the survival of a subject with an oncological disorder, prognosing the recurrence of an oncological disorder, and prognosing whether a subject is predisposed to developing an oncological disorder.

In some embodiments of the present invention, other biomarkers can be used in connection with the methods of the present invention. As used herein, the term "one or more biomarkers" is intended to mean that one or more (e.g., 1, 2, 3, 4, 5, 6, 7, 8, or 9) markers selected from the group consisting of keratin 4, keratin 7, keratin 8, keratin 15, keratin 18, keratin 19, tubulin-beta 3, filamin B (FLNB), and lymphocyte antigen 9 (LY9), are assayed, optionally in combination with PSA, and, in various embodiments, more than one other biomarker may be assayed, such as two, three, four, five, six, seven, eight, nine, or more biomarkers in the list may be assayed. One or more of keratin 4, keratin 7, keratin 8, keratin 15, keratin 18, and keratin 19 can be assayed in combination with one or more of filamin B, LY9, and PSA. Filamin B can be used in conjunction with one or more other biomarkers, e.g., LY9 or PSA, known to be associated with prostate cancer. LY9 can be used in conjunction with one or more other biomarkers, e.g., filamin B or PSA, known to be associated with prostate cancer. That is, any combination of the filamin B and LY9 biomarkers, optionally with PSA can be used, e.g., filamin B; LY9; filamin B and PSA; filamin B and LY9; LY9 and PSA; filamin B, LY9, and PSA; all of which can optionally be combined with other markers, e.g., one or more of keratins 4, 7, 8, 15, 18, 19, or tubulin-beta 3.

Methods, kits, and panels provided herein include any combination of 1, 2, 3,4, 5, 6, 7, 8, or 9 markers of the set filamin B, LY9, keratin 4, keratin 7, keratin 8, keratin 15, keratin 18, keratin 19, and tubulin-beta 3. Such combinations include any of the following marker sets:

Marker sets with one member: filamin B; LY9; keratin 4; keratin 7; keratin 8; keratin 15; keratin 18; keratin 19; and tubulin-beta 3. Any single marker can be used in combination with PSA.

Marker sets with two members: filamin B, LY9; filamin B, keratin 4; filamin B, keratin 7; filamin B, keratin 8; filamin B, keratin 15; filamin B, keratin 18; filamin B, keratin 19; filamin B, tubulin-beta 3; LY9, keratin 4; LY9, keratin 7; LY9, keratin 8; LY9, keratin 15; LY9, keratin 18; LY9, keratin 19; LY9, tubulin-beta 3; keratin 4, keratin 7; keratin 4, keratin 8; keratin 4, keratin 15; keratin 4, keratin 18; keratin 4, keratin 19; keratin 4, tubulin-beta 3; keratin 7, keratin 8; keratin 7, keratin 15; keratin 7, keratin 18; keratin 7, keratin 19; keratin 7, tubulin-beta 3; keratin 8, keratin 15; keratin 8, keratin 18; keratin 8, keratin 19; keratin 8, tubulin-beta 3; keratin 15, keratin 18; keratin 15, keratin 19; keratin 15, tubulin-beta 3; keratin 18, tubulin-beta 3; keratin 18, keratin 19; and keratin 19, tubulin-beta 3. Any marker set can be used in combination with PSA.

Marker sets with three members: filamin B, LY9, keratin 4; filamin B, LY9, keratin 7; filamin B, LY9, keratin 8; filamin B, LY9, keratin 15; filamin B, LY9, keratin 18; filamin B, LY9, keratin 19; filamin B, LY9, tubulin-beta 3; filamin B, keratin 4, keratin 7; filamin B, keratin 4, keratin 8; filamin B, keratin 4, keratin 15; filamin B, keratin 4, keratin 18; filamin B, keratin 4, keratin 19; filamin B, keratin 4, tubulin-beta 3; filamin B, keratin 7, keratin 8; filamin B, keratin 7, keratin 15; filamin B, keratin 7, keratin 18; filamin B, keratin 7, keratin 19; filamin B, keratin 7, tubulin-beta 3; filamin B, keratin 8, keratin 15; filamin B, keratin 8, keratin 18; filamin B, keratin 8, keratin 19; filamin B, keratin 8, tubulin-beta 3; filamin B, keratin 15, keratin 18; filamin B, keratin 15, keratin 19; filamin B, keratin 15, tubulin-beta 3; filamin B, keratin 18, keratin 19; filamin B, keratin 18, tubulin-beta 3; filamin B, keratin 19, tubulin-beta 3; LY9, keratin 4, keratin 7; LY9, keratin 4, keratin 8; LY9, keratin 4, keratin 15; LY9, keratin 4, keratin 18; LY9, keratin 4, keratin 19; LY9, keratin 4, tubulin-beta 3; LY9, keratin 7, keratin 8; LY9, keratin 7, keratin 15; LY9, keratin 7, keratin 18; LY9, keratin 7, keratin 19; LY9, keratin 7, tubulin-beta 3; LY9, keratin 8, keratin 15; LY9, keratin 8, keratin 18; LY9, keratin 8, keratin 19; LY9, keratin 8, tubulin-beta 3; LY9, keratin 15, keratin 18; LY9, keratin 15, keratin 19; LY9, keratin 15, tubulin-beta 3; LY9, keratin 18, keratin 19; LY9, keratin 18, tubulin-beta 3; LY9, keratin 19, tubulin-beta 3; keratin 4, keratin 7, keratin 8; keratin 4, keratin 7, keratin 15; keratin 4, keratin 7, keratin 18; keratin 4, keratin 7, keratin 19; keratin 4, keratin 7, tubulin-beta 3; keratin 4, keratin 8, keratin 15; keratin 4, keratin 8, keratin 18; keratin 4, keratin 8, keratin 19; keratin 4, keratin 8, tubulin-beta 3; keratin 4, keratin 15, keratin 18; keratin 4, keratin 15, keratin 19; keratin 4, keratin 15, tubulin-beta 3; keratin 4, keratin 18, keratin 19; keratin 4, keratin 19, tubulin-beta 3; keratin 7, keratin 8, keratin 15; keratin 7, keratin 8, keratin 18; keratin 7, keratin 8, keratin 19; keratin 7, keratin 8, tubulin-beta 3; keratin 7, keratin 8, tubulin-beta 3; keratin 7, keratin 15, keratin 18; keratin 7, keratin 15, keratin 19; keratin 7, keratin 15, tubulin-beta 3; keratin 7, keratin 18, keratin 19; keratin 7, keratin 18, tubulin-beta 3; keratin 15, keratin 18, keratin 19; keratin 15, keratin 18, tubulin-beta 3; and keratin 18, keratin 19, tubulin-beta 3. Any marker set can be used in combination with PSA.

Marker sets with four members: filamin B, LY9, keratin 4, keratin 7; filamin B, LY9, keratin 4, keratin 8; filamin B, LY9, keratin 4, keratin 15; filamin B, LY9, keratin 4, keratin 18; filamin B, LY9, keratin 4, keratin 19; filamin B, LY9, keratin 4, tubulin-beta 3; filamin B, keratin 4, keratin 7, keratin 8; filamin B, keratin 4, keratin 7, keratin 15; filamin B, keratin 4, keratin 7, keratin 18; filamin B, keratin 4, keratin 7, tubulin-beta 3; filamin B, keratin 4, keratin 7, tubulin-beta 3; filamin B, keratin 7, keratin 8, keratin 15; filamin B, keratin 7, keratin 8, keratin 18; filamin B, keratin 7, keratin 8, keratin 19; filamin B, keratin 7, keratin 8, tubulin-beta 3; filamin B, keratin 8, keratin 15, keratin 18; filamin B, keratin 8, keratin 15, keratin 19; filamin B, keratin 8, keratin 15, tubulin-beta 3; filamin B, keratin 15, keratin 18, keratin 19; filamin B, keratin 15, keratin 18, tubulin-beta 3; filamin B, keratin 18, keratin 19, and tubulin-beta 3; LY9, keratin 4, keratin 7, keratin 8; LY9, keratin 4, keratin 7, keratin 15; LY9, keratin 4, keratin 7, keratin 18; LY9, keratin 4, keratin 7, keratin 19; LY9, keratin 4, keratin 7, tubulin-beta 3; LY9, keratin 7, keratin 8, keratin 15; LY9, keratin 7, keratin 8, keratin 18; LY9, keratin 7, keratin 8, keratin 19; LY9, keratin 7, keratin 8, tubulin-beta 3; LY9, keratin 8, keratin 15, keratin 18; LY9, keratin 8, keratin 15, keratin 19; LY9, keratin 8, keratin 15, tubulin-beta 3; LY9, keratin 15, keratin 18, keratin 19; LY9, keratin 15, keratin 18, tubulin-beta 3; LY9, keratin 18, keratin 19, and tubulin-beta 3; keratin 4, keratin 7, keratin 8, keratin 15; keratin 4, keratin 7, keratin 8, keratin 18; keratin 4, keratin 7, keratin 8, keratin 19; keratin 4, keratin 7, keratin 8, tubulin-beta 3; keratin 4, keratin 8, keratin 15, keratin 18; keratin 4, keratin 8, keratin 15, keratin 19; keratin 4, keratin 8, keratin 15, tubulin-beta 3; keratin 4, keratin 15, keratin 18, keratin 19; keratin 4, keratin 15, keratin 18, tubulin-beta 3; keratin 4, keratin 18, keratin 19, tubulin-beta 3; keratin 8, keratin 15, keratin 18, keratin 19; keratin 8, keratin 15, keratin 18, tubulin-beta 3; and keratin 15, keratin 18, keratin 19, tubulin-beta 3. Any marker set can be used in combination with PSA.

Marker sets with five members: keratin 8, keratin 15, keratin 18, keratin 19 tubulin-beta 3; keratin 7, keratin 15, keratin 18, keratin 19 tubulin-beta 3; keratin 7, keratin 8, keratin 18, keratin 19 tubulin-beta 3; keratin 7, keratin 8, keratin 15, keratin 19 tubulin-beta 3; keratin 7, keratin 8, keratin 15, keratin 18 tubulin-beta 3; keratin 7, keratin 8, keratin 15, keratin 18, keratin 19; keratin 4, keratin 15, keratin 18, keratin 19 tubulin-beta 3; keratin 4, keratin 8, keratin 18, keratin 19 tubulin-beta 3; keratin 4, keratin 8, keratin 15, keratin 19 tubulin-beta 3; keratin 4, keratin 8, keratin 15, keratin 18 tubulin-beta 3; keratin 4, keratin 8, keratin 15, keratin 18, keratin 19; LY9, keratin 15, keratin 18, keratin 19, tubulin-beta 3; LY9, keratin 8, keratin 18, keratin 19 tubulin-beta 3; LY9, keratin 8, keratin 15, keratin 19 tubulin-beta 3; LY9, keratin 8, keratin 15, keratin 18, and tubulin-beta 3; LY9, keratin 8, keratin 15, keratin 18, keratin 19; filamin B, keratin 15, keratin 18, keratin 19 tubulin-beta 3; filamin B, keratin 8, keratin 18, keratin 19 tubulin-beta 3; filamin B, keratin 8, keratin 15, keratin 19 tubulin-beta 3; filamin B, keratin 8, keratin 15, keratin 18, and tubulin-beta 3; filamin B, keratin 8, keratin 15, keratin 18, keratin 19; filamen B, LY9, keratin 18, keratin 19 tubulin-beta 3; filamen B, LY9, keratin 15, keratin 19 tubulin-beta 3; filamen B, LY9, keratin 15, keratin 18, tubulin-beta 3; filamen B, LY9, keratin 15, keratin 18, keratin 19; filamen B, keratin 4, keratin 18, keratin 19 tubulin-beta 3; filamen B, keratin 4, keratin 15, keratin 19 tubulin-beta 3; filamen B, keratin 4, keratin 15, keratin 18, tubulin-beta 3; filamen B, keratin 4, keratin 15, keratin 18, keratin 19; filamen B keratin 7, keratin 18, keratin 19 tubulin-beta 3; filamen B keratin 7, keratin 15, keratin 19, tubulin-beta 3; filamen B keratin 7, keratin 15, keratin 18, tubulin-beta 3; filamen B keratin 7, keratin 15, keratin 18, keratin 19; filamen B, keratin 8, keratin 18, keratin 19 tubulin-beta 3; filamen B, keratin 8, keratin 15, keratin 19 tubulin-beta 3; filamen B, keratin 8, keratin 15, keratin 18 tubulin-beta 3; filamen B, keratin 8, keratin 15, keratin 18, keratin 19; LY9, keratin 4, keratin 18, keratin 19 and tubulin-beta 3; LY9, keratin 4, keratin 15, keratin 19 tubulin-beta 3; LY9, keratin 4, keratin 15, keratin 18, tubulin-beta 3; LY9, keratin 4, keratin 15, keratin 18, keratin 19; LY9, keratin 7, keratin 18, keratin 19 tubulin-beta 3; LY9, keratin 7, keratin 15, keratin 19 tubulin-beta 3; LY9, keratin 7, keratin 15, keratin 18, and tubulin-beta 3; LY9, keratin 7, keratin 15, keratin 18, keratin 19; LY9, keratin 8, keratin 18, keratin 19 tubulin-beta 3; LY9, keratin 8, keratin 15, keratin 19 tubulin-beta 3; LY9, keratin 8, keratin 15, keratin 18, and tubulin-beta 3; LY9, keratin 8, keratin 15, keratin 18, keratin 19; keratin 4, keratin 7, keratin 18, keratin 19 tubulin-beta 3; keratin 4, keratin 7, keratin 15, keratin 19 tubulin-beta 3; keratin 4, keratin 7, keratin 15, keratin 18, and tubulin-beta 3; keratin 4, keratin 7, keratin 15, keratin 18, keratin 19; keratin 4, keratin 8, keratin 18, keratin 19 tubulin-beta 3; keratin 4, keratin 8, keratin 15, keratin 19 tubulin-beta 3; keratin 4, keratin 8, keratin 15, keratin 18, and tubulin-beta 3; keratin 4, keratin 8, keratin 15, keratin 18, keratin 19; keratin 7, keratin 8, keratin 18, keratin 19 tubulin-beta 3; keratin 7, keratin 8, keratin 15, keratin 19 tubulin-beta 3; keratin 7, keratin 8, keratin 15, keratin 18, and tubulin-beta 3; keratin 7, keratin 8, keratin 15, keratin 18, keratin 19; filamen B, LY9, keratin 4, keratin 19, tubulin-beta 3; filamen B, LY9, keratin 4, keratin 18, tubulin-beta 3; filamen B, LY9, keratin 4, keratin 18, keratin 19; filamen B, LY9, keratin 7, keratin 19, tubulin-beta 3; filamen B, LY9, keratin 7, keratin 18, tubulin-beta 3; filamen B, LY9, keratin 7, keratin 18, keratin 19; filamen B, LY9, keratin 8, keratin 19, tubulin-beta 3; filamen B, LY9, keratin 8, keratin 18, tubulin-beta 3; filamen B, LY9, keratin 8, keratin 18, keratin 19; filamen B, LY9, keratin 15, keratin 19, tubulin-beta 3; filamen B, LY9, keratin 15, keratin 18, tubulin-beta 3; filamen B, LY9, keratin 15, keratin 18, keratin 19; filamen B, keratin 4, keratin 7, keratin 19, tubulin-beta 3; filamen B, keratin 4, keratin 7, keratin 18, tubulin-beta 3; filamen B, keratin 4, keratin 7, keratin 18, keratin 19; filamen B, keratin 4, keratin 8, keratin 19, tubulin-beta 3; filamen B, keratin 4, keratin 8, keratin 18, tubulin-beta 3; filamen B, keratin 4, keratin 8, keratin 18, keratin 19; filamen B, keratin 4, keratin 15, keratin 19, tubulin-beta 3; filamen B, keratin 4, keratin 15, keratin 18, tubulin-beta 3; filamen B, keratin 4, keratin 15, keratin 18, keratin 19; filamen B, keratin 7, keratin 8, keratin 19, tubulin-beta 3; filamen B, keratin 7, keratin 8, keratin 18, tubulin-beta 3; filamen B, keratin 7, keratin 8, keratin 18, keratin 19; filamen B, keratin 8, keratin 15, keratin 19, tubulin-beta 3; filamen B, keratin 8, keratin 15, keratin 18, tubulin-beta 3; filamen B, keratin 8, keratin 15, keratin 18, keratin 19; LY9, keratin 4, keratin 7, keratin 19, tubulin-beta 3; LY9, keratin 4, keratin 7, keratin 18, tubulin-beta 3; LY9, keratin 4, keratin 7, keratin 18, keratin 19; LY9, keratin 4, keratin 8, keratin 19, tubulin-beta 3; LY9, keratin 4, keratin 8, keratin 18, tubulin-beta 3; LY9, keratin 4, keratin 8, keratin 18, keratin 19; LY9, keratin 4, keratin 15, keratin 19, tubulin-beta 3; LY9, keratin 4, keratin 15, keratin 18, tubulin-beta 3; LY9, keratin 4, keratin 15, keratin 18, keratin 19; LY9, keratin 7, keratin 8, keratin 19, tubulin-beta 3; LY9, keratin 7, keratin 8, keratin 18, tubulin-beta 3; LY9, keratin 7, keratin 8, keratin 18, keratin 19; LY9, keratin 7, keratin 15, keratin 19, tubulin-beta 3; LY9, keratin 7, keratin 15, keratin 18, tubulin-beta 3; LY9, keratin 7, keratin 15, keratin 18, keratin 19; LY9, keratin 8, keratin 15, keratin 19, tubulin-beta 3; LY9, keratin 8, keratin 15, keratin 18, tubulin-beta 3; LY9, keratin 8, keratin 15, keratin 18, keratin 19; keratin 4, keratin 7, keratin 8, keratin 19, tubulin-beta 3; keratin 4, keratin 7, keratin 8, keratin 18, tubulin-beta 3; keratin 4, keratin 7, keratin 8, keratin 18, keratin 19; keratin 4, keratin 7, keratin 15, keratin 19, tubulin-beta 3; keratin 4, keratin 7, keratin 15, keratin 18, tubulin-beta 3; keratin 4, keratin 7, keratin 15, keratin 18, keratin 19; keratin 4, keratin 8, keratin 15, keratin 19, tubulin-beta 3; keratin 4, keratin 8, keratin 15, keratin 18, tubulin-beta 3; keratin 4, keratin 8, keratin 15, keratin 18, keratin 19; keratin 7, keratin 8, keratin 15, keratin 19, tubulin-beta 3; keratin 7, keratin 8, keratin 15, keratin 18, tubulin-beta 3; and keratin 7, keratin 8, keratin 15, keratin 18, keratin 19. Any marker set can be used in combination with PSA.

Marker sets with six members: keratin 7, keratin 8, keratin 15, keratin 18, keratin 19, and tubulin-beta 3; keratin 4, keratin 8, keratin 15, keratin 18, keratin 19, and tubulin-beta 3; keratin 4, keratin 7, keratin 15, keratin 18, keratin 19, tubulin-beta 3; keratin 4, keratin 7, keratin 8, keratin 18, keratin 19, tubulin-beta 3; keratin 4, keratin 7, keratin 8, keratin 15, keratin 19, tubulin-beta 3; keratin 4, keratin 7, keratin 8, keratin 15, keratin 18, tubulin-beta 3; keratin 4, keratin 7, keratin 8, keratin 15, keratin 18, keratin 19; LY9, keratin 8, keratin 15, keratin 18, keratin 19, tubulin-beta 3; LY9, keratin 7, keratin 15, keratin 18, keratin 19, tubulin-beta 3; LY9, keratin 7, keratin 8, keratin 18, keratin 19, tubulin-beta 3; LY9, keratin 7, keratin 8, keratin 15, keratin 19, tubulin-beta 3; LY9, keratin 7, keratin 8, keratin 15, keratin 18, tubulin-beta 3; LY9, keratin 7, keratin 8, keratin 15, keratin 18, keratin 19; LY9, keratin 4, keratin 15, keratin 18, keratin 19, tubulin-beta 3; LY9, keratin 4, keratin 8, keratin 18, keratin 19, tubulin-beta 3; LY9, keratin 4, keratin 8, keratin 15, keratin 19, tubulin-beta 3; LY9, keratin 4, keratin 8, keratin 15, keratin 18, tubulin-beta 3; LY9, keratin 4, keratin 8, keratin 15, keratin 18, keratin 19; LY9, keratin 4, keratin 7, keratin 18, keratin 19, and tubulin-beta 3; LY9, keratin 4, keratin 7, keratin 15, keratin 19, and tubulin-beta 3; LY9, keratin 4, keratin 7, keratin 15, keratin 18, tubulin-beta 3; LY9, keratin 4, keratin 7, keratin 15, keratin 18, keratin 19; LY9, keratin 4, keratin 7, keratin 8, keratin 19, tubulin-beta 3; LY9, keratin 4, keratin 7, keratin 8, keratin 18, tubulin-beta 3; LY9, keratin 4, keratin 7, keratin 8, keratin 18, keratin 19; LY9, keratin 4, keratin 7, keratin 8, keratin 15, tubulin-beta 3; LY9, keratin 4, keratin 7, keratin 8, keratin 15, keratin 19; and LY9, keratin 4, keratin 7, keratin 8, keratin 15, keratin 18. Any marker set can be used in combination with PSA.

Marker sets with seven members: keratin 4, keratin 7, keratin 8, keratin 15, keratin 18, keratin 19, tubulin-beta 3; LY9, keratin 7, keratin 8, keratin 15, keratin 18, keratin 19, tubulin-beta 3; LY9, keratin 4, keratin 8, keratin 15, keratin 18, keratin 19, tubulin-beta 3; LY9, keratin 4, keratin 7, keratin 15, keratin 18, keratin 19, tubulin-beta 3; LY9, keratin 4, keratin 7, keratin 8, keratin 18, keratin 19, tubulin-beta 3; LY9, keratin 4, keratin 7, keratin 8, keratin 15, keratin 19, tubulin-beta 3; LY9, keratin 4, keratin 7, keratin 8, keratin 15, keratin 18, tubulin-beta 3; LY9, keratin 4, keratin 7, keratin 8, keratin 15, keratin 18, keratin 19; filamin B, keratin 7, keratin 8, keratin 15, keratin 18, keratin 19, tubulin-beta 3; filamin B, keratin 4, keratin 8, keratin 15, keratin 18, keratin 19, tubulin-beta 3; filamin B, keratin 4, keratin 7, keratin 15, keratin 18, keratin 19, tubulin-beta 3; filamin B, keratin 4, keratin 7, keratin 8, keratin 18, keratin 19, tubulin-beta 3; filamin B, keratin 4, keratin 7, keratin 8, keratin 15, keratin 19, tubulin-beta 3; filamin B, keratin 4, keratin 7, keratin 8, keratin 15, keratin 18, tubulin-beta 3; filamin B, keratin 4, keratin 7, keratin 8, keratin 15, keratin 18, keratin 19; filamin B, LY9, keratin 8, keratin 15, keratin 18, keratin 19, tubulin-beta 3; filamin B, LY9, keratin 7, keratin 15, keratin 18, keratin 19, tubulin-beta 3; filamin B, LY9, keratin 7, keratin 8, keratin 18, keratin 19, tubulin-beta 3; filamin B, LY9, keratin 7, keratin 8, keratin 15, keratin 19, tubulin-beta 3; filamin B, LY9, keratin 7, keratin 8, keratin 15, keratin 18, tubulin-beta 3; filamin B, LY9, keratin 7, keratin 8, keratin 15, keratin 18, keratin 19; filamin B, LY9, keratin 4, keratin 15, keratin 18, keratin 19, tubulin-beta 3; filamin B, LY9, keratin 4, keratin 8, keratin 18, keratin 19, tubulin-beta 3; filamin B, LY9, keratin 4, keratin 8, keratin 15, keratin 19, tubulin-beta 3; filamin B, LY9, keratin 4, keratin 8, keratin 15, keratin 18, tubulin-beta 3; filamin B, LY9, keratin 4, keratin 8, keratin 15, keratin 18, keratin 19; filamin B, LY9, keratin 4, keratin 7, keratin 18, keratin 19, and tubulin-beta 3; filamin B, LY9, keratin 4, keratin 7, keratin 15, keratin 19, and tubulin-beta 3; filamin B, LY9, keratin 4, keratin 7, keratin 15, keratin 18, tubulin-beta 3; filamin B, LY9, keratin 4, keratin 7, keratin 15, keratin 18, keratin 19; filamin B, LY9, keratin 4, keratin 7, keratin 8, keratin 19, tubulin-beta 3; filamin B, LY9, keratin 4, keratin 7, keratin 8, keratin 18, tubulin-beta 3; filamin B, LY9, keratin 4, keratin 7, keratin 8, keratin 18, keratin 19; filamin B, LY9, keratin 4, keratin 7, keratin 8, keratin 15, tubulin-beta 3; filamin B, LY9, keratin 4, keratin 7, keratin 8, keratin 15, keratin 19; and filamin B, LY9, keratin 4, keratin 7, keratin 8, keratin 15, keratin 18. Any marker set can be used in combination with PSA.

Marker sets with eight members:LY9, keratin 4, keratin 7, keratin 8, keratin 15, keratin 18, keratin 19, tubulin-beta 3; filamin B, keratin 4, keratin 7, keratin 8, keratin 15, keratin 18, keratin 19, tubulin-beta 3; filamin B, LY9,keratin 7, keratin 8, keratin 15, keratin 18, keratin 19, tubulin-beta 3; filamin B, LY9, keratin 4, keratin 8, keratin 15, keratin 18, keratin 19, tubulin-beta 3; filamin B, LY9, keratin 4, keratin 7, keratin 15, keratin 18, keratin 19, tubulin-beta 3; filamin B, LY9, keratin 4, keratin 7, keratin 8, keratin 18, keratin 19, tubulin-beta 3; filamin B, LY9, keratin 4, keratin 7, keratin 8, keratin 15, keratin 19, tubulin-beta 3; filamin B, LY9, keratin 4, keratin 7, keratin 8, keratin 15, keratin 18, tubulin-beta 3; and filamin B, LY9, keratin 4, keratin 7, keratin 8, keratin 15, keratin 18, keratin 19. Any marker set can be used in combination with PSA.

Marker sets with nine members: filamin B, LY9, keratin 4, keratin 7, keratin 8, keratin 15, keratin 18, keratin 19, and tubulin-beta 3.

Any marker set can be used in combination with PSA.

The invention provides for the use of various combinations and sub-combinations of markers. It is understood that any single marker or combination of the markers provided herein can be used in the invention unless clearly indicated otherwise. Further, any single marker or combination of the markers of the invention can be used in conjunction with PSA.

Throughout the application, one or more of filamin B, LY9 and keratin 19 is understood as any of: filamin B; LY9; keratin 19; filamin B and LY9; filamin B and keratin 19; LY9 and keratin 19; or filamin B, LY9, and keratin 19. Further, any single marker or combination of the markers of the invention can be used in conjunction with PSA.

Throughout the application, combination of the filamin B and LY9 with PSA is understood as any of filamin B; LY9; filamin B and PSA; filamin B and LY9; LY9 and PSA; filamin B, LY9, and PSA.

Throughout the application, one or more prostate cancer markers selected from the group consisting of keratin 4, keratin 7, keratin 8, keratin 15, keratin 18, and tubulin beta-3 is understood as any of keratin 4; keratin 7; keratin 8; keratin 15; keratin 18; tubulin beta-3; keratin 4 and keratin 7; keratin 4 and keratin 8; keratin 4 and keratin 15; keratin 4 and keratin 18; keratin 4 and tubulin beta-3; keratin 7 and keratin 8; keratin 7 and keratin 15; keratin 7 and keratin 18; keratin 7 and tubulin beta-3; keratin 8 and keratin 15; keratin 8 and keratin 18; keratin 8 and tubulin beta-3; keratin 15 and keratin 18; keratin 15 and tubulin beta-3; keratin 18 and tubulin beta-3; keratin 4, keratin 7 and keratin 8; keratin 4, keratin 7 and keratin 15; keratin 4, keratin 7 and keratin 18; keratin 4, keratin 7 and tubulin beta-3; keratin 4, keratin 8 and keratin 15; keratin 4, keratin 8 and keratin 18; keratin 4, keratin 8 and tubulin beta-e; keratin 4, keratin 15 and keratin 18; keratin 4, keratin 15 and tubulin beta-e; keratin 4, keratin 18 and tubulin beta-3; keratin 4, keratin 7, keratin 8 and keratin 15; keratin 4, keratin 7, keratin 8 and keratin 18; keratin 4, keratin 7, keratin 8 and tubulin beta-3; keratin 4, keratin 8, keratin 15 and keratin 18; keratin 4, keratin 8, keratin 15 and tubulin beta-3; keratin 4, keratin 15, keratin 18 and tubulin beta-3; keratin 4, keratin 7, keratin 8, keratin 15 and keratin 18; keratin 4, keratin 7, keratin 8, keratin 15, and tubulin beta-3; keratin 4, keratin 7, keratin 8, keratin 18, and tubulin beta-3; keratin 4, keratin 7, keratin 15, keratin 18, and tubulin beta-3; keratin 4, keratin 8, keratin 15, keratin 18, and tubulin beta-3; or keratin 7, keratin 8, keratin 15, keratin 18, and tubulin beta-3. Further, any single marker or combination of the markers of the invention can be used in conjunction with PSA.

Throughout the application, one or more prostate cancer markers selected from the group consisting of keratin 7, 15, and 19 is understood as any of keratin 7; keratin 15; keratin 19; keratin 7 and 15; keratin 7 and 19; keratin 15 and 19; and keratin 7, 15, and 19. Further, any single marker or combination of the markers of the invention can be used in conjunction with PSA.

Throughout the application, one or more prostate cancer markers selected from the group consisting of keratin 7, 8, and 15 is understood as any of keratin 7; keratin 8; keratin 15; keratin 7 and 8; keratin 7 and 15; keratin 8 and 15; and keratin 7, 8, and 15. Further, any single marker or combination of the markers of the invention can be used in conjunction with PSA.

Throughout the application, one or more prostate cancer markers selected from the group consisting of keratin 7 and 15 is understood as any of keratin 7; keratin 15; or keratin 7 and 15. Further, any single marker or combination of the markers of the invention can be used in conjunction with PSA.

Throughout the application, one or more prostate cancer markers selected from the group consisting filamin B, LY9, or keratin 19 is understood as any of filamin B; LY9; keratin 19; filamin B and LY9; filamin B and keratin 19; LY9, and keratin 19; and filamin B, LY9, and keratin 19. Further, any single marker or combination of the markers of the invention can be used in conjunction with PSA.

In certain embodiments, methods of diagnosing, prognosing, and monitoring the treatment of prostate cancer by detecting the level sets of markers including of keratin 7, 15, or 19 and filamin B; keratin 7, 15, 19 or LY9; keratin 7, 15, 19, or PSA; keratin 4, 7, 15, or 19; keratin 7, 8, 15, or 19; keratin 7, 15, 18, or 19; and keratin 7, 15, 19, or tubulin-beta 3.

A "marker" is a gene whose altered level of expression in a tissue or cell from its expression level in normal or healthy tissue or cell is associated with a disease state, such as an abnormal prostate state. In a preferred embodiment, the marker is detected in a blood sample, e.g., serum or plasma. In one embodiment, the marker is detected in serum. In one embodiment, the marker is detected in plasma. In certain embodiments, the serum or plasma can be further processed to remove abundant blood proteins (e.g., albumin) or proteins that are not marker proteins prior to analysis. A "marker nucleic acid" is a nucleic acid (e.g., mRNA, cDNA) encoded by or corresponding to a marker of the invention. Such marker nucleic acids include DNA (e.g., cDNA) comprising the entire or a partial sequence of any of the nucleic acid sequences provided herein or the complement of such a sequence. The marker nucleic acids also include RNA comprising the entire or a partial sequence of any of the nucleic acid sequences provided herein or the complement of such a sequence, wherein all thymidine residues are replaced with uridine residues. A "marker protein" is a protein encoded by or corresponding to a marker of the invention. A marker protein comprises the entire or a partial sequence of any of the amino acid sequences provided herein. The terms "protein" and "polypeptide" are used interchangeably.

A "biological sample" or a "subject sample" is a body fluid or tissue in which a prostate cancer related marker may be present. In certain embodiments the sample is blood or a blood product (e.g., serum or plasma). In certain embodiments, the sample is a tissue sample, e.g., a tissue sample from at or near the site of the prostate hyperplasia or tumor, or the suspected prostate hyperplasia or tumor. A tissue sample can be obtained, for example, during biopsy or surgical resection of the prostate. A tissue sample can include one or more of normal tissue, hyperplasia, and cancerous tissue. Methods of distinguishing between such tissue types are known, e.g., histological analysis, immunohistochemical analysis. In certain embodiments, the control sample can be a normal portion of sample tissue removed from a subject.

An "oncological disorder-associated" body fluid is a fluid which, when in the body of a subject, contacts, or passes through oncological cells or into which cells or proteins shed from oncological cells are capable of passing. Exemplary oncological disorder-associated body fluids include blood fluids (e.g. whole blood, blood serum, blood having platelets removed therefrom), and are described in more detail below. Many oncological disorder-associated body fluids can have oncological cells therein, particularly when the cells are metastasizing. Cell-containing fluids which can contain oncological cells include, but are not limited to, whole blood, blood having platelets removed therefrom, lymph, prostatic fluid, urine, and semen.

The "normal" level of expression of a marker is the level of expression of the marker in cells of a human subject or patient or a population of subjects not afflicted with an oncological disorder or an abnormal prostate state, e.g., BPH or prostate cancer.

An "over-expression", "higher level of expression", "higher level", and the like of a marker refers to an expression level in a test sample that is greater than the standard error of the assay employed to assess expression, and is preferably at least 25% more, at least 50% more, at least 75% more, at least two, at least three, at least four, at least five, at least six, at least seven, at least eight, at least nine, or at least ten times the expression level of the marker in a control sample (e.g., sample from a healthy subject not having the marker associated disease, i.e., an abnormal prostate state) and preferably, the average expression level of the marker or markers in several control samples.

A "lower level of expression" or "lower level" of a marker refers to an expression level in a test sample that is less than 90%, 85%, 80%, 75%, 70%, 65%, 60%, 55%, 50%, 45%, 40%, 35%, 30%, 25%, 20%, 15%, or 10% of the expression level of the marker in a control sample (e.g., sample from a healthy subjects not having the marker associated disease, i.e., an abnormal prostate state) and preferably, the average expression level of the marker in several control samples.

A "transcribed polynucleotide" or "nucleotide transcript" is a polynucleotide (e.g. an mRNA, hnRNA, a cDNA, or an analog of such RNA or cDNA) which is complementary to or having a high percentage of identity (e.g., at least 80% identity) with all or a portion of a mature mRNA made by transcription of a marker of the invention and normal post-transcriptional processing (e.g. splicing), if any, of the RNA transcript, and reverse transcription of the RNA transcript.

"Complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

"Identical" or "identity" as used herein, refers to nucleotide sequence similarity between two regions of the same nucleic acid strand or between regions of two different nucleic acid strands. When a nucleotide residue position in both regions is occupied by the same nucleotide residue, then the regions are identical at that position. A first region is identical to a second region if at least one nucleotide residue position of each region is occupied by the same residue. Identity between two regions is expressed in terms of the proportion of nucleotide residue positions of the two regions that are occupied by the same nucleotide residue. By way of example, a region having the nucleotide sequence 5'-ATTGCC-3' and a region having the nucleotide sequence 5'-TATGGC-3' share 50% identity. Preferably, the first region comprises a first portion and the second region comprises a second portion, whereby, at least about 50%, and preferably at least about 75%, at least about 90%, or at least about 95% of the nucleotide residue positions of each of the portions are occupied by the same nucleotide residue. More preferably, all nucleotide residue positions of each of the portions are occupied by the same nucleotide residue.

"Proteins of the invention" encompass marker proteins and their fragments; variant marker proteins and their fragments; peptides and polypeptides comprising an at least a 15 amino acid segment of a marker or variant marker protein; and fusion proteins comprising a marker or variant marker protein, or an at least a 15 amino acid segment of a marker or variant marker protein. In certain embodiments, a protein of the invention is a peptide sequence or epitope large enough to permit the specific binding of an antibody to the marker.

The invention further provides antibodies, antibody derivatives and antibody fragments which specifically bind with the marker proteins and fragments of the marker proteins of the present invention. Unless otherwise specified herewithin, the terms "antibody" and "antibodies" broadly encompass naturally-occurring forms of antibodies (e.g., IgG, IgA, IgM, IgE) and recombinant antibodies such as single-chain antibodies, chimeric and humanized antibodies and multi-specific antibodies, as well as fragments and derivatives of all of the foregoing, which fragments and derivatives have at least an antigenic binding site. Antibody derivatives may comprise a protein or chemical moiety conjugated to an antibody.

In certain embodiments, the positive or negative fold change refers to that of any gene described herein.

As used herein, "positive fold change" refers to "up-regulation" or "increase (of expression)" of a gene that is listed herein.

As used herein, "negative fold change" refers to "down-regulation" or "decrease (of expression)" of a gene that is listed herein.

Various aspects of the invention are described in further detail in the following subsections.

Isolated Nucleic Acid Molecules

One aspect of the invention pertains to isolated nucleic acid molecules, including nucleic acids which encode a marker protein or a portion thereof. Isolated nucleic acids of the invention also include nucleic acid molecules sufficient for use as hybridization probes to identify marker nucleic acid molecules, and fragments of marker nucleic acid molecules, e.g., those suitable for use as PCR primers for the amplification of a specific product or mutation of marker nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid molecule. In one embodiment, an "isolated" nucleic acid molecule (preferably a protein-encoding sequences) is free of sequences which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. In another embodiment, an "isolated" nucleic acid molecule, such as a cDNA molecule, can be substantially free of other cellular material, or culture medium when produced by recombinant techniques, or substantially free of chemical precursors or other chemicals when chemically synthesized. A nucleic acid molecule that is substantially free of cellular material includes preparations having less than about 30%, 20%, 10%, or 5% of heterologous nucleic acid (also referred to herein as a "contaminating nucleic acid").

A nucleic acid molecule of the present invention can be isolated using standard molecular biology techniques and the sequence information in the database records described herein. Using all or a portion of such nucleic acid sequences, nucleic acid molecules of the invention can be isolated using standard hybridization and cloning techniques (e.g., as described in Sambrook et al., ed., *Molecular Cloning: A Laboratory Manual*, 2nd ed., Cold Spring Harbor Laboratory Press, Cold Spring Harbor, N.Y., 1989).

A nucleic acid molecule of the invention can be amplified using cDNA, mRNA, or genomic DNA as a template and appropriate oligonucleotide primers according to standard PCR amplification techniques. The nucleic acid so amplified can be cloned into an appropriate vector and characterized by DNA sequence analysis. Furthermore, nucleotides corresponding to all or a portion of a nucleic acid molecule of the invention can be prepared by standard synthetic techniques, e.g., using an automated DNA synthesizer.

In another preferred embodiment, an isolated nucleic acid molecule of the invention comprises a nucleic acid molecule which has a nucleotide sequence complementary to the nucleotide sequence of a marker nucleic acid or to the nucleotide sequence of a nucleic acid encoding a marker protein. A nucleic acid molecule which is complementary to a given nucleotide sequence is one which is sufficiently complementary to the given nucleotide sequence that it can hybridize to the given nucleotide sequence thereby forming a stable duplex.

Moreover, a nucleic acid molecule of the invention can comprise only a portion of a nucleic acid sequence, wherein the full length nucleic acid sequence comprises a marker nucleic acid or which encodes a marker protein. Such nucleic acids can be used, for example, as a probe or primer. The probe/primer typically is used as one or more substantially purified oligonucleotides. The oligonucleotide typically comprises a region of nucleotide sequence that hybridizes under stringent conditions to at least about 15, more preferably at least about 25, 50, 75, 100, 125, 150, 175, 200, 250, 300, 350, or 400 or more consecutive nucleotides of a nucleic acid of the invention.

Probes based on the sequence of a nucleic acid molecule of the invention can be used to detect transcripts or genomic sequences corresponding to one or more markers of the invention. In certain embodiments, the probes hybridize to nucleic acid sequences that traverse splice junctions. The probe comprises a label group attached thereto, e.g., a radioisotope, a fluorescent compound, an enzyme, or an enzyme co-factor. Such probes can be used as part of a diagnostic test kit or panel for identifying cells or tissues which express or mis-express the protein, such as by measuring levels of a nucleic acid molecule encoding the protein in a sample of cells from a subject, e.g., detecting mRNA levels or determining whether a gene encoding the protein or its translational control sequences have been mutated or deleted.

The invention further encompasses nucleic acid molecules that differ, due to degeneracy of the genetic code, from the nucleotide sequence of nucleic acids encoding a marker protein (e.g., protein having the sequence provided in the sequence listing), and thus encode the same protein.

It will be appreciated by those skilled in the art that DNA sequence polymorphisms that lead to changes in the amino acid sequence can exist within a population (e.g., the human population). Such genetic polymorphisms can exist among individuals within a population due to natural allelic variation and changes known to occur in cancer. An allele is one of a group of genes which occur alternatively at a given genetic locus. In addition, it will be appreciated that DNA polymorphisms that affect RNA expression levels can also exist that may affect the overall expression level of that gene (e.g., by affecting regulation or degradation).

As used herein, the phrase "allelic variant" refers to a nucleotide sequence which occurs at a given locus or to a polypeptide encoded by the nucleotide sequence.

As used herein, the terms "gene" and "recombinant gene" refer to nucleic acid molecules comprising an open reading frame encoding a polypeptide corresponding to a marker of the invention. Such natural allelic variations can typically result in 1-5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the invention.

In another embodiment, an isolated nucleic acid molecule of the invention is at least 15, 20, 25, 30, 40, 60, 80, 100, 150, 200, 250, 300, 350, 400, 450, 550, 650, 700, 800, 900, 1000, 1200, 1400, 1600, 1800, 2000, 2200, 2400, 2600, 2800, 3000, 3500, 4000, 4500, or more nucleotides in length and hybridizes under stringent conditions to a marker nucleic acid or to a nucleic acid encoding a marker protein. As used herein, the term "hybridizes under stringent conditions" is intended to describe conditions for hybridization and washing under which nucleotide sequences at least 60% (65%, 70%, preferably 75%) identical to each other typically remain hybridized to each other. Such stringent conditions are known to those skilled in the art and can be found in sections 6.3.1-6.3.6 of *Current Protocols in Molecular Biology*, John Wiley & Sons, N.Y. (1989). A preferred, non-limiting example of stringent hybridization conditions are hybridization in 6× sodium chloride/sodium citrate (SSC) at about 45° C., followed by one or more washes in 0.2×SSC, 0.1% SDS at 50-65° C.

Nucleic Acid Therapeutics

Nucleic acid therapeutics are well known in the art. Nucleic acid therapeutics include both single stranded and double stranded (i.e., nucleic acid therapeutics having a complementary region of at least 15 nucleotides in length that may be one or two nucleic acid strands) nucleic acids that are complementary to a target sequence in a cell. Nucleic acid therapeutics can be delivered to a cell in culture, e.g., by adding the nucleic acid to culture media either alone or with an agent to promote uptake of the nucleic acid into the cell. Nucleic acid therapeutics can be delivered to a cell in a subject, i.e., in vivo, by any route of administration. The specific formulation will depend on the route of administration.

As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Such conditions can, for example, be stringent conditions, where stringent conditions may include: 400 mM NaCl, 40 mM PIPES pH 6.4, 1 mM EDTA, 50° C. or 70° C. for 12-16 hours followed by washing. Other conditions, such as physiologically relevant conditions as may be encountered inside an organism, can apply. The skilled person will be able to determine the set of conditions most appropriate for a test of complementarity of two sequences in accordance with the ultimate application of the hybridized nucleotides.

Sequences can be "fully complementary" with respect to each when there is base-pairing of the nucleotides of the first nucleotide sequence with the nucleotides of the second nucleotide sequence over the entire length of the first and second nucleotide sequences. However, where a first sequence is referred to as "substantially complementary" with respect to a second sequence herein, the two sequences can be fully complementary, or they may form one or more, but generally not more than 4, 3 or 2 mismatched base pairs upon hybridization, while retaining the ability to hybridize under the conditions most relevant to their ultimate application. However, where two oligonucleotides are designed to form, upon hybridization, one or more single stranded overhangs as is common in double stranded nucleic acid therapeutics, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, may yet be referred to as "fully complementary" for the purposes described herein.

"Complementary" sequences, as used herein, may also include, or be formed entirely from, non-Watson-Crick base pairs and/or base pairs formed from non-natural and modified nucleotides, in as far as the above requirements with respect to their ability to hybridize are fulfilled. Such non-Watson-Crick base pairs includes, but not limited to, G:U Wobble or Hoogstein base pairing.

The terms "complementary," "fully complementary", and "substantially complementary" herein may be used with respect to the base matching between the sense strand and the antisense strand of a dsRNA, or between an antisense nucleic acid or the antisense strand of dsRNA and a target sequence, as will be understood from the context of their use.

As used herein, a polynucleotide that is "substantially complementary to at least part of" a messenger RNA (mRNA) refers to a polynucleotide that is substantially complementary to a contiguous portion of the mRNA of interest (e.g., an mRNA encoding filamin B, LY9, a keratin, tubulin-beta 3, or PSA) including a 5' UTR, an open reading frame (ORF), or a 3' UTR. For example, a polynucleotide is complementary to at least a part of filamin B, LY9, a keratin, tubulin-beta 3, or PSA mRNA if the sequence is substantially complementary to a non-interrupted portion of an mRNA encoding filamin B, LY9, a keratin, tubulin-beta 3, or PSA.

Nucleic acid therapeutics typically include chemical modifications to improve their stability and to modulate their pharmacokinetic and pharmacodynamic properties. For example, the modifications on the nucleotides can include, but are not limited to, LNA, HNA, CeNA, 2'-methoxyethyl, 2'-O-alkyl, 2'-O-allyl, 2'-C-allyl, 2'-fluoro, 2'-deoxy, 2'-hydroxyl, and combinations thereof.

Nucleic acid therapeutics may further comprise at least one phosphorothioate or methylphosphonate internucleotide linkage. The phosphorothioate or methylphosphonate internucleotide linkage modification may occur on any nucleotide of the sense strand or antisense strand or both (in nucleic acid therapeutics including a sense strand) in any position of the strand. For instance, the internucleotide linkage modification may occur on every nucleotide on the sense strand or antisense strand; each internucleotide linkage modification may occur in an alternating pattern on the sense strand or antisense strand; or the sense strand or antisense strand may contain both internucleotide linkage modifications in an alternating pattern. The alternating pattern of the internucleotide linkage modification on the sense strand may be the same or different from the antisense strand, and the alternating pattern of the internucleotide linkage modification on the sense strand may have a shift relative to the alternating pattern of the internucleotide linkage modification on the antisense strand.

Single Stranded Nucleic Acid Therapeutics

Antisense nucleic acid therapeutic agent single stranded nucleic acid therapeutics, typically about 16 to 30 nucleotides in length and are complementary to a target nucleic acid sequence in the target cell, either in culture or in an organism.

Patents directed to antisense nucleic acids, chemical modifications, and therapeutic uses are provided, for example, in U.S. Pat. No. 5,898,031 related to chemically modified RNA-containing therapeutic compounds, and U.S. Pat. No. 6,107,094 related methods of using these compounds as therapeutic agent. U.S. Pat. No. 7,432,250 related to methods of treating patients by administering single-stranded chemically modified RNA-like compounds; and U.S. Pat. No. 7,432,249 related to pharmaceutical compositions containing single-stranded chemically modified RNA-like compounds. U.S. Pat. No. 7,629,321 is related to methods of cleaving target mRNA using a single-stranded oligonucleotide having a plurality RNA nucleosides and at least one chemical modification. Each of the patents listed in the paragraph are incorporated herein by reference.

Double Stranded Nucleic Acid Therapeutics

In many embodiments, the duplex region is 15-30 nucleotide pairs in length. In some embodiments, the duplex region is 17-23 nucleotide pairs in length, 17-25 nucleotide pairs in length, 23-27 nucleotide pairs in length, 19-21 nucleotide pairs in length, or 21-23 nucleotide pairs in length.

In certain embodiments, each strand has 15-30 nucleotides.

The RNAi agents that are used in the methods of the invention include agents with chemical modifications as disclosed, for example, in Publications WO 2009/073809 and WO/2012/037254, the entire contents of each of which are incorporated herein by reference.

An "RNAi agent," "double stranded RNAi agent," double-stranded RNA (dsRNA) molecule, also referred to as "dsRNA agent," "dsRNA", "siRNA", "iRNA agent," as used interchangeably herein, refers to a complex of ribonucleic acid molecules, having a duplex structure comprising two anti-parallel and substantially complementary, as defined below, nucleic acid strands. As used herein, an RNAi agent can also include dsiRNA (see, e.g., US Patent publication 20070104688, incorporated herein by reference). In general, the majority of nucleotides of each strand are ribonucleotides, but as described herein, each or both strands can also include one or more non-ribonucleotides, e.g., a deoxyribonucleotide and/or a modified nucleotide. In addition, as used in this specification, an "RNAi agent" may include ribonucleotides with chemical modifications; an RNAi agent may include substantial modifications at multiple nucleotides. Such modifications may include all types of modifications disclosed herein or known in the art. Any such modifications, as used in a siRNA type molecule, are encompassed by "RNAi agent" for the purposes of this specification and claims.

The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5'-end of the respective other strand forming the duplex structure, the connecting RNA chain is referred to as a "hairpin loop." Where the two strands are connected covalently by means other than an uninterrupted chain of nucleotides between the 3'-end of one strand and the 5'-end of the respective other strand forming the duplex structure, the connecting structure is referred to as a "linker." The RNA strands may have the same or a different number of nucleotides. The maximum number of base pairs is the number of nucleotides in the shortest strand of the dsRNA minus any overhangs that are present in the duplex. In addition to the duplex structure, an RNAi agent may comprise one or more nucleotide overhangs. The term "siRNA" is also used herein to refer to an RNAi agent as described above.

In another aspect, the agent is a single-stranded antisense RNA molecule. An antisense RNA molecule is complementary to a sequence within the target mRNA. Antisense RNA can inhibit translation in a stoichiometric manner by base pairing to the mRNA and physically obstructing the translation machinery, see Dias, N. et al., (2002) Mol Cancer Ther 1:347-355. The antisense RNA molecule may have about 15-30 nucleotides that are complementary to the target mRNA. For example, the antisense RNA molecule may have a sequence of at least 15, 16, 17, 18, 19, 20 or more contiguous nucleotides complementary to the filamin B or LY9 sequences provided herein.

The term "antisense strand" refers to the strand of a double stranded RNAi agent which includes a region that is substantially complementary to a target sequence (e.g., a human TTR mRNA). As used herein, the term "region complementary to part of an mRNA encoding transthyretin" refers to a region on the antisense strand that is substantially complementary to part of a TTR mRNA sequence. Where the region of complementarity is not fully complementary to the target sequence, the mismatches are most tolerated in the terminal regions and, if present, are generally in a terminal region or regions, e.g., within 6, 5, 4, 3, or 2 nucleotides of the 5' and/or 3' terminus.

The term "sense strand," as used herein, refers to the strand of a dsRNA that includes a region that is substantially complementary to a region of the antisense strand.

The invention also includes molecular beacon nucleic acids having at least one region which is complementary to a nucleic acid of the invention, such that the molecular beacon is useful for quantitating the presence of the nucleic acid of the invention in a sample. A "molecular beacon" nucleic acid is a nucleic acid comprising a pair of complementary regions and having a fluorophore and a fluorescent quencher associated therewith. The fluorophore and quencher are associated with different portions of the nucleic acid in such an orientation that when the complementary regions are annealed with one another, fluorescence of the fluorophore is quenched by the quencher. When the complementary regions of the nucleic acid are not annealed with one another, fluorescence of the fluorophore is quenched to a lesser degree. Molecular beacon nucleic acids are described, for example, in U.S. Pat. No. 5,876,930.

Isolated Proteins and Antibodies

One aspect of the invention pertains to isolated marker proteins and biologically active portions thereof, as well as polypeptide fragments suitable for use as immunogens to raise antibodies directed against a marker protein or a fragment thereof. In one embodiment, the native marker protein can be isolated from cells or tissue sources by an appropriate purification scheme using standard protein purification techniques. In another embodiment, a protein or peptide comprising the whole or a segment of the marker protein is produced by recombinant DNA techniques. Alternative to recombinant expression, such protein or peptide can be synthesized chemically using standard peptide synthesis techniques.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the polypeptide of interest.

Biologically active portions of a marker protein include polypeptides comprising amino acid sequences sufficiently identical to or derived from the amino acid sequence of the marker protein, which include fewer amino acids than the full length protein, and exhibit at least one activity of the corresponding full-length protein. Typically, biologically active portions comprise a domain or motif with at least one activity of the corresponding full-length protein. A biologically active portion of a marker protein of the invention can be a polypeptide which is, for example, 10, 25, 50, 100 or more amino acids in length. Moreover, other biologically active portions, in which other regions of the marker protein are deleted, can be prepared by recombinant techniques and evaluated for one or more of the functional activities of the native form of the marker protein.

Preferred marker proteins are encoded by nucleotide sequences provided in the sequence listing. Other useful proteins are substantially identical (e.g., at least about 40%, preferably 50%, 60%, 70%, 80%, 90%, 91%, 92%, 93%, 94%, 95%, 96%, 97%, 98% or 99%) to one of these sequences and retain the functional activity of the corresponding naturally-occurring marker protein yet differ in amino acid sequence due to natural allelic variation or mutagenesis.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. Preferably, the percent identity between the two sequences is calculated using a global alignment. Alternatively, the percent identity between the two sequences is calculated using a local alignment. The percent identity between the two sequences is a function of the number of identical positions shared by the sequences (i.e., % identity=# of identical positions/total # of positions (e.g., overlapping positions)×100). In one embodiment the two sequences are the same length. In another embodiment, the two sequences are not the same length.

The determination of percent identity between two sequences can be accomplished using a mathematical algorithm. A preferred, non-limiting example of a mathematical algorithm utilized for the comparison of two sequences is the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the BLASTN and BLASTX programs of Altschul, et al. (1990) *J. Mol. Biol.* 215:403-410. BLAST nucleotide searches can be performed with the BLASTN program, score=100, wordlength=12 to obtain nucleotide sequences homologous to a nucleic acid molecules of the invention. BLAST protein searches can be performed with the BLASTP program, score=50, wordlength=3 to obtain amino acid sequences homologous to a protein molecules of the invention. To obtain gapped alignments for comparison purposes, a newer version of the BLAST algorithm called Gapped BLAST can be utilized as described in Altschul et al. (1997) *Nucleic Acids Res.* 25:3389-3402, which is able to perform gapped local alignments for the programs BLASTN, BLASTP and BLASTX. Alternatively, PSI-Blast can be used to perform an iterated search which detects distant relationships between molecules. When utilizing BLAST, Gapped BLAST, and PSI-Blast programs, the default parameters of the respective programs (e.g., BLASTX and BLASTN) can be used. See http://www.ncbi.nlm.nih.gov. Another preferred, non-limiting example of a mathematical algorithm utilized for the comparison of sequences is the algorithm of Myers and Miller, (1988) *CABIOS* 4:11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson and Lipman (1988) *Proc. Natl. Acad. Sci. USA* 85:2444-2448. When using the FASTA algorithm for comparing nucleotide or amino acid sequences, a PAM120 weight residue table can, for example, be used with a k-tuple value of 2.

The percent identity between two sequences can be determined using techniques similar to those described above, with or without allowing gaps. In calculating percent identity, only exact matches are counted.

Another aspect of the invention pertains to antibodies directed against a protein of the invention. In preferred embodiments, the antibodies specifically bind a marker protein or a fragment thereof. The terms "antibody" and "antibodies" as used interchangeably herein refer to immunoglobulin molecules as well as fragments and derivatives thereof that comprise an immunologically active portion of an immunoglobulin molecule, (i.e., such a portion contains an antigen binding site which specifically binds an antigen, such as a marker protein, e.g., an epitope of a marker protein). An antibody which specifically binds to a protein of the invention is an antibody which binds the protein, but does not substantially bind other molecules in a sample, e.g., a biological sample, which naturally contains the protein. Examples of an immunologically active portion of an immunoglobulin molecule include, but are not limited to, single-chain antibodies (scAb), F(ab) and F(ab')$_2$ fragments.

An isolated protein of the invention or a fragment thereof can be used as an immunogen to generate antibodies. The full-length protein can be used or, alternatively, the invention provides antigenic peptide fragments for use as immunogens. The antigenic peptide of a protein of the invention comprises at least 8 (preferably 10, 15, 20, or 30 or more) amino acid residues of the amino acid sequence of one of the proteins of the invention, and encompasses at least one epitope of the protein such that an antibody raised against the peptide forms a specific immune complex with the protein. Preferred epitopes encompassed by the antigenic peptide are regions that are located on the surface of the protein, e.g., hydrophilic regions. Hydrophobicity sequence analysis, hydrophilicity sequence analysis, or similar analyses can be used to identify hydrophilic regions. In preferred embodiments, an isolated marker protein or fragment thereof is used as an immunogen.

The invention provides polyclonal and monoclonal antibodies. The term "monoclonal antibody" or "monoclonal antibody composition", as used herein, refers to a population of antibody molecules that contain only one species of an antigen binding site capable of immunoreacting with a particular epitope. Preferred polyclonal and monoclonal antibody compositions are ones that have been selected for antibodies directed against a protein of the invention. Particularly preferred polyclonal and monoclonal antibody preparations are ones that contain only antibodies directed against a marker protein or fragment thereof. Methods of making polyclonal, monoclonal, and recombinant antibody and antibody fragments are well known in the art.

Predictive Medicine

The present invention pertains to the field of predictive medicine in which diagnostic assays, prognostic assays, pharmacogenomics, and monitoring clinical trials are used for prognostic (predictive) purposes to thereby treat an individual prophylactically. Accordingly, one aspect of the present invention relates to diagnostic assays for determining the level of expression of one or more marker proteins or nucleic acids, in order to determine whether an individual is at risk of developing a disease or disorder, such as, without limitation, an oncological disorder, e.g., prostate cancer. Such assays can be used for prognostic or predictive purposes to thereby prophylactically treat an individual prior to the onset of the disorder.

Yet another aspect of the invention pertains to monitoring the influence of agents (e.g., drugs or other compounds administered either to inhibit an oncological disorder, e.g., prostate cancer, or to treat or prevent any other disorder (i.e. in order to understand any carcinogenic effects that such treatment may have)) on the expression or activity of a marker of the invention in clinical trials. These and other agents are described in further detail in the following sections.

A. Diagnostic Assays

An exemplary method for detecting the presence or absence or change of expression level of a marker protein or nucleic acid in a biological sample involves obtaining a biological sample (e.g. an oncological disorder-associated body fluid) from a test subject and contacting the biological sample with a compound or an agent capable of detecting the polypeptide or nucleic acid (e.g., mRNA, genomic DNA, or cDNA). The detection methods of the invention can thus be used to detect mRNA, protein, cDNA, or genomic DNA, for example, in a biological sample in vitro as well as in vivo.

Methods provided herein for detecting the presence, absence, change of expression level of a marker protein or nucleic acid in a biological sample include obtaining a biological sample from a subject that may or may not contain the marker protein or nucleic acid to be detected, contacting the sample with a marker-specific binding agent (i.e., one or more marker-specific binding agents) that is capable of forming a complex with the marker protein or nucleic acid to be detected, and contacting the sample with a detection reagent for detection of the marker—marker-specific binding agent complex, if formed. It is understood that the methods provided herein for detecting an expression level of a marker in a biological sample includes the steps to perform the assay. In certain embodiments of the detection methods, the level of the marker protein or nucleic acid in the sample is none or below the threshold for detection.

The methods include formation of either a transient or stable complex between the marker and the marker-specific binding agent. The methods require that the complex, if formed, be formed for sufficient time to allow a detection reagent to bind the complex and produce a detectable signal (e.g., fluorescent signal, a signal from a product of an enzymatic reaction, e.g., a peroxidase reaction, a phosphatase reaction, a beta-galactosidase reaction, or a polymerase reaction).

In certain embodiments, all markers are detected using the same method. In certain embodiments, all markers are detected using the same biological sample (e.g., same body fluid or tissue). In certain embodiments, different markers are detected using various methods. In certain embodiments, markers are detected in different biological samples.

1. Protein Detection

In certain embodiments of the invention, the marker to be detected is a protein. Proteins are detected using a number of assays in which a complex between the marker protein to be detected and the marker specific binding agent would not occur naturally, for example, because one of the components is not a naturally occurring compound or the marker for detection and the marker specific binding agent are not from the same organism (e.g., human marker proteins detected using marker-specific binding antibodies from mouse, rat, or goat). In a preferred embodiment of the invention, the marker protein for detection is a human marker protein. In certain detection assays, the human markers for detection are bound by marker-specific, non-human antibodies, thus, the complex would not be formed in nature. The complex of the marker protein can be detected directly, e.g., by use of a labeled marker-specific antibody that binds directly to the marker, or by binding a further component to the marker—marker-specific antibody complex. In certain embodiments, the further component is a second marker-specific antibody capable of binding the marker at the same time as the first marker-specific antibody. In certain embodiments, the further component is a secondary antibody that binds to a marker-specific antibody, wherein the secondary antibody preferably linked to a detectable label (e.g., fluorescent label, enzymatic label, biotin). When the secondary antibody is linked to an enzymatic detectable label (e.g., a peroxidase, a phosphatase, a beta-galactosidase), the secondary antibody is detected by contacting the enzymatic detectable label with an appropriate substrate to produce a colorimetric, fluorescent, or other detectable, preferably quantitatively detectable, product. Antibodies for use in the methods of the invention can be polyclonal, however, in a preferred embodiment monoclonal antibodies are used. An intact antibody, or a fragment or derivative thereof (e.g., Fab or F(ab')$_2$) can be used in the methods of the invention. Such strategies of marker protein detection are used, for example, in ELISA, RIA, western blot, and immunofluorescence assay methods.

In certain detection assays, the marker present in the biological sample for detection is an enzyme and the detection reagent is an enzyme substrate. For example, the enzyme can be a protease and the substrate can be any protein that includes an appropriate protease cleavage site. Alternatively, the enzyme can be a kinase and the substrate can be any substrate for the kinase. In preferred embodiments, the substrate which forms a complex with the marker enzyme to be detected is not the substrate for the enzyme in a human subject.

In certain embodiments, the marker—marker-specific binding agent complex is attached to a solid support for detection of the marker. The complex can be formed on the substrate or formed prior to capture on the substrate. For example, in an ELISA, RIA, immunoprecipitation assay, western blot, immunofluorescence assay, in gel enzymatic assay the marker for detection is attached to a solid support, either directly or indirectly. In an ELISA, RIA, or immunofluorescence assay, the marker is typically attached indirectly to a solid support through an antibody or binding protein. In a western blot or immunofluorescence assay, the marker is typically attached directly to the solid support. For in-gel enzyme assays, the marker is resolved in a gel, typically an acrylamide gel, in which a substrate for the enzyme is integrated.

2. Nucleic Acid Detection

In certain embodiments of the invention, the marker is a nucleic acid. Nucleic acids are detected using a number of assays in which a complex between the marker nucleic acid to be detected and a marker-specific probe would not occur naturally, for example, because one of the components is not a naturally occurring compound. In certain embodiments, the analyte comprises a nucleic acid and the probe comprises one or more synthetic single stranded nucleic acid molecules, e.g., a DNA molecule, a DNA-RNA hybrid, a PNA, or a modified nucleic acid molecule containing one or more artificial bases, sugars, or backbone moieties. In certain embodiments, the synthetic nucleic acid is a single stranded is a DNA molecule that includes a fluorescent label. In certain embodiments, the synthetic nucleic acid is a single stranded oligonucleotide molecule of about 12 to about 50 nucleotides in length. In certain embodiments, the nucleic acid to be detected is an mRNA and the complex formed is an mRNA hybridized to a single stranded DNA molecule that is complementary to the mRNA. In certain embodiments, an RNA is detected by generation of a DNA molecule (i.e., a cDNA molecule) first from the RNA template using the single stranded DNA that hybridizes to the RNA as a primer, e.g., a general poly-T primer to transcribe poly-A RNA. The cDNA can then be used as a template for an amplification reaction, e.g., PCR, primer extension assay, using a marker-specific probe. In certain embodiments, a labeled single stranded DNA can be hybridized to the RNA present in the sample for detection of the RNA by fluorescence in situ hybridization (FISH) or for detection of the RNA by northern blot.

For example, in vitro techniques for detection of mRNA include northern hybridizations, in situ hybridizations, and rtPCR. In vitro techniques for detection of genomic DNA include Southern hybridizations. Techniques for detection of mRNA include PCR, northern hybridizations and in situ hybridizations. Methods include both qualitative and quantitative methods.

A general principle of such diagnostic, prognostic, and monitoring assays involves preparing a sample or reaction mixture that may contain a marker, and a probe, under appropriate conditions and for a time sufficient to allow the marker and probe to interact and bind, thus forming a complex that can be removed and/or detected in the reaction mixture. These assays can be conducted in a variety of ways known in the art, e.g., ELISA assay, PCR, FISH.

3. Detection of Expression Levels

Marker levels can be detected based on the absolute expression level or a normalized or relative expression level. Detection of absolute marker levels may be preferable when monitoring the treatment of a subject or in determining if there is a change in the prostate cancer status of a subject. For example, the expression level of one or more markers can be monitored in a subject undergoing treatment for prostate cancer, e.g., at regular intervals, such a monthly intervals. A modulation in the level of one or more markers can be monitored over time to observe trends in changes in marker levels. Expression levels of one or more of filamin B, LY9, or keratin 19 in the subject may be higher than the expression level of those markers in a normal sample, but may be lower than the prior expression level, thus indicating a benefit of the treatment regimen for the subject. Similarly, rates of change of marker levels can be important in a subject who is not subject to active treatment for prostate cancer (e.g., watchful waiting). Changes, or not, in marker levels may be more relevant to treatment decisions for the subject than marker levels present in the population. Rapid changes in marker levels in a subject who otherwise appears to have a normal prostate may be indicative of an abnormal prostate state, even if the markers are within normal ranges for the population.

As an alternative to making determinations based on the absolute expression level of the marker, determinations may be based on the normalized expression level of the marker. Expression levels are normalized by correcting the absolute expression level of a marker by comparing its expression to the expression of a gene that is not a marker, e.g., a housekeeping gene that is constitutively expressed. Suitable genes for normalization include housekeeping genes such as the actin gene, or epithelial cell-specific genes. This normalization allows the comparison of the expression level in one sample, e.g., a patient sample, to another sample, e.g., a non-cancer sample, or between samples from different sources.

Alternatively, the expression level can be provided as a relative expression level as compared to an appropriate control, e.g., population control, adjacent normal tissue control, earlier time point control, etc. Preferably, the samples used in the baseline determination will be from non-cancer cells. The choice of the cell source is dependent on the use of the relative expression level. Using expression found in normal tissues as a mean expression score aids in validating whether the marker assayed is cancer specific (versus normal cells). In addition, as more data is accumulated, the mean expression value can be revised, providing improved relative expression values based on accumulated data. Expression data from cancer cells provides a means for grading the severity of the cancer state.

Diagnostic, Prognostic, and Treatment Methods

The invention provides methods for detecting an abnormal prostate state in a subject by (1) contacting a biological sample from a subject with a panel of one or more detection reagents wherein each detection reagent is specific for one prostate-cancer related protein; wherein the prostate-cancer related proteins are selected from the prostate-cancer related protein set as follows: filamin B, LY9, keratin 4, keratin 7, keratin 8, keratin 15, keratin 18, keratin 19, and tubulin-beta 3;

(2) measuring the amount of each prostate-cancer related marker detected in the biological sample by each detection reagent; and (3) comparing the level of expression of the one or more prostate-cancer related protein in the biological sample obtained from the subject with a level of expression of the one or more prostate-cancer related protein in a normal control sample, thereby detecting an abnormal prostate state.

In certain embodiments, detecting an abnormal prostate state comprises diagnosing prostate cancer status in a subject. In certain embodiments, an abnormal prostate state comprises identifying a predisposed to developing prostate cancer.

The invention provides methods for monitoring the treatment of prostate cancer in a subject by (1) contacting a first biological sample obtained from the subject prior to administering at least a portion of a treatment regimen to the subject with a panel of one or more detection reagents wherein each detection reagent is specific for one prostate-cancer related protein; wherein the prostate-cancer related proteins are selected from the prostate protein set as follows: filamin B, LY9, keratin 4, keratin 7, keratin 8, keratin 15, keratin 18, keratin 19, and tubulin-beta 3;

(2) contacting a second biological sample obtained from the subject after administering at least a portion of a treatment regimen to the subject with a panel of one or more detection reagents wherein each detection reagent is specific for one prostate-cancer related protein; wherein the prostate-cancer related proteins are selected from the prostate protein set as follows: filamin B, LY9, keratin 4, keratin 7, keratin 8, keratin 15, keratin 18, keratin 19, and tubulin-beta 3;

(3) measuring the amount of prostate-cancer related marker detected in each the first biological sample and the second biological sample by each detection reagent; and (4) comparing the level of expression of the one or more prostate-cancer related markers in the first sample with the expression level of the one or more prostate-cancer related markers in the second sample, thereby monitoring the treatment of prostate cancer in the subject.

The invention provides method of selecting for administration of active treatment or against administration of active treatment of prostate cancer in a subject by (1) contacting a first biological sample obtained from the subject prior to administering a treatment regimen to the subject with a panel of one or more detection reagents wherein each detection reagent is specific for one prostate-cancer related protein; wherein the prostate-cancer related proteins are selected from the prostate protein set as follows: filamin B, LY9, keratin 4, keratin 7, keratin 8, keratin 15, keratin 18, keratin 19, and tubulin-beta 3;

(2) contacting a second biological sample obtained from the subject prior to administering a treatment regimen to the subject with a panel of one or more detection reagents wherein each detection reagent is specific for one prostate-cancer related protein; wherein the prostate-cancer related proteins are selected from the prostate protein set as follows: filamin B, LY9, keratin 4, keratin 7, keratin 8, keratin 15, keratin 18, keratin 19, and tubulin-beta 3;

(3) measuring the amount of prostate-cancer related marker detected in each the first biological sample and the second biological sample by each detection reagent; and (4) comparing the level of expression of the one or more prostate-cancer related markers in the first sample with the expression level of the one or more prostate-cancer related markers in the second sample, wherein selecting for administration of active treatment or against administration of active treatment of prostate cancer is based on the presence or absence of changes in the level of expression of one or more markers between the first sample and the second sample.

In certain embodiments of the diagnostic and monitoring methods provided herein, one or more prostate-cancer related markers is two or more markers. In certain embodiments of the diagnostic and monitoring methods provided herein, one or more prostate-cancer related markers is three or more markers. In certain embodiments of the diagnostic and monitoring methods provided herein, one or more prostate-cancer related markers is four or more markers. In certain embodiments of the diagnostic and monitoring methods provided herein, one or more prostate-cancer related markers is five or more markers. In certain embodiments of the diagnostic and monitoring methods provided herein, one or more prostate-cancer related markers is six or more markers. In certain embodiments of the diagnostic and monitoring methods provided herein, one or more prostate-cancer related markers is seven or more markers. In certain embodiments of the diagnostic and monitoring methods provided herein, one or more prostate-cancer related markers is eight or more markers. In certain embodiments of the diagnostic and monitoring methods provided herein, one or more prostate-cancer related markers is nine or more markers.

In certain embodiments of the diagnostic methods provided herein, an increase in the level of expression of one or more prostate-cancer related markers selected from the group consisting of filamin B, LY9, and keratin 19 in the biological sample as compared to the level of expression of the one or more prostate-cancer related markers in a normal control sample is an indication that the subject is afflicted with prostate cancer. In certain embodiments of the diagnostic methods provided herein, no increase in the detected expression level of one or more of filamin B, LY9, and keratin 19 in the biological sample as compared to the expression level in a normal control sample is an indication that the subject is not afflicted with prostate cancer or not predisposed to developing prostate cancer.

In certain embodiments of the diagnostic methods provided herein, an increase in the level of expression of one or more prostate-cancer related markers selected from the group consisting of filamin B, LY9, and keratin 19 in the biological sample as compared to the level of expression of the one or more prostate-cancer related markers in a normal control sample is an indication that the subject is predisposed to developing prostate cancer.

In certain embodiments of the monitoring methods provided herein, no increase in the detected level of expression of any of the one or more prostate-cancer related markers selected from the group consisting of filamin B, LY9, and keratin 19 in the second sample as compared to the level of expression of the one or more prostate-cancer related markers in the first sample is an indication that the therapy is efficacious for treating prostate cancer in the subject. In certain embodiments the monitoring methods provided herein, further comprise comparing the level of expression of one or more prostate-cancer related markers selected from the group consisting of filamin B, LY9, and keratin 19 in the first sample or the level of expression of one or more prostate-cancer related markers selected from the group consisting of filamin B, LY9, and keratin 19 in the second sample with the expression of the one or more prostate-cancer related markers in a control sample.

In certain embodiments of the monitoring methods provided herein, an increase in the level of expression of the one or more prostate-cancer related markers selected from the group consisting of filamin B, LY9, and keratin 19 in the second sample as compared to the level of expression of the one or more prostate-cancer related markers in the first sample is an indication for selection of active treatment of prostate cancer in the subject. In certain embodiments of the monitoring methods provided herein, no increase in the detected level of expression of any of the one or more prostate-cancer related markers selected from the group consisting of filamin B, LY9, and keratin 19 in the second sample as compared to the level of expression of the one or more prostate-cancer related markers in the first sample is an indication against selection of active treatment of prostate cancer in the subject. In certain embodiments of the monitoring methods provided herein, wherein an increased expression level of one or more of filamin B, LY9, and keratin 19 in the second sample as compared to the expression level in the first sample is an indication that the therapy is not efficacious in the treatment of prostate cancer.

In certain embodiments of the diagnostic and monitoring methods provided herein, the one or more prostate-cancer related markers is selected from the group of keratin 4, keratin 7, keratin 8, keratin 15, keratin 18, and tubulin beta-3. In certain embodiments of the diagnostic and monitoring methods provided herein, the one or more prostate-cancer related markers is selected from the group of keratin 7, keratin 8, and keratin 15. In certain embodiments of the diagnostic and monitoring methods provided herein, the one or more prostate-cancer related markers is selected from the group of keratin 7, keratin 15, and keratin 19. In certain embodiments of the diagnostic and monitoring methods provided herein, the one or more prostate-cancer related markers is keratin 7 or keratin 15. In certain embodiments of the diagnostic and monitoring methods provided herein, the one or more prostate-cancer related markers selected from the group consisting of keratin 4, keratin 7, keratin 8, keratin 15, keratin 18, and tubulin beta-3 in the biological sample is compared to the level of the one or more prostate-cancer related markers in a normal control sample is indicative of a modulation in prostate cancer status.

In certain embodiments of the monitoring methods provided herein, modulation of the level of expression of the one or more prostate-cancer related markers selected from the group consisting of keratin 4, keratin 7, keratin 8, keratin 15, keratin 18, and tubulin beta-3 in the second sample as compared to the level of expression of the one or more prostate-cancer related markers selected from the group consisting of keratin 4, keratin 7, keratin 8, keratin 15, keratin 18, and tubulin beta-3 in the first sample is indicative of a change in prostate cancer status in response to treatment of the prostate cancer in the subject. In certain embodiments of the monitoring methods provided herein, the methods further comprise comparing the level of expression of one or more prostate-cancer related markers selected from the group consisting of keratin 4, keratin 7, keratin 8, keratin 15, keratin 18, and tubulin beta-3 in the first sample; or the level of expression of one or more prostate-cancer related markers selected from the group consisting of keratin 4, keratin 7, keratin 8, keratin 15, keratin 18, and tubulin beta-3 in the second sample to the level of expression of one or more prostate-cancer related markers in a normal control sample.

In certain embodiments the diagnostic methods provided herein further comprise detecting the level of expression of prostate specific antigen (PSA) in the biological sample and preferably further comprise comparing the level of expression of PSA in the biological sample to a PSA expression level in a normal control sample. In certain embodiments, the combination of PSA level with one or more of the prostate-cancer maker levels increases the predictive value of the method.

In certain embodiments the monitoring methods provided herein further comprise detecting the level of expression of prostate specific antigen (PSA) in the first sample and the second sample, and preferably further comprising comparing the level of expression of PSA in the first sample with the level of expression of PSA in the second sample. In certain monitoring methods, the change in PSA level in combination with the change in prostate-cancer maker level increases the predictive value of the method.

In certain embodiments the diagnostic and monitoring methods provided herein further comprise comparing the detected level of the one or more prostate markers in the biological samples with one or more control samples wherein the control sample is one or more of a sample from the same subject at an earlier time point than the biological sample, a sample from a subject with benign prostatic hyperplasia (BPH), a sample from a subject with non-metastatic prostate cancer, a sample from a subject with metastatic prostate cancer, a sample from a subject with androgen sensitive prostate cancer, a sample from a subject with androgen insensitive prostate cancer, a sample from a subject with aggressive prostate cancer, and sample obtained from a subject with non-aggressive prostate cancer. Comparison of the marker levels in the biological samples with control samples from subjects with various normal and abnormal prostate states facilitates the differentiation between various prostate states including normal prostate and prostate cancer, benign prostate hyperplasia and prostate cancer,benign prostate hyperplasia and normal prostate, androgen dependent and androgen independent prostate cancer, aggressive prostate cancer and non-aggressive prostate cancer,aggressive prostate cancer and non-aggressive prostate cancer, or between any two or more prostate states including normal prostate, prostate cancer, benign prostate hyperplasia, androgen dependent prostate cancer, androgen independent prostate cancer, aggressive prostate cancer, non-aggressive prostate cancer, metastatic prostate cancer, and non-metastatic prostate cancer.

In certain embodiments the diagnostic and monitoring methods provided herein further comprising detecting the size of the prostate tumor in the subject. In certain embodiments the monitoring methods provided herein further comprise detecting a change in the size or relative aggressiveness of the tumor. In certain embodiments, the size of the prostate tumor in the subject is detected prior to administering the at least a portion of a treatment regimen to the subject. In certain embodiments, the size of the prostate tumor in the subject is detected after administering the at least a portion of a treatment regimen to the subject. Certain monitoring methods, further comprise comparing the size of the prostate tumor in the subject prior to administering the at least a portion of a treatment regimen to the subject to the size of the prostate tumor in the subject after administering the at least a portion of a treatment regimen to the subject.

In certain embodiments the diagnostic and monitoring methods provided herein further comprising obtaining a subject sample.

In certain embodiments the diagnostic and monitoring methods provided herein further comprising selecting a treatment regimen for the subject based on the level expression of one or more of the prostate-cancer related markers provided in claims 1.

In certain embodiments the diagnostic and monitoring methods provided herein further comprising selecting a subject for having or being suspected of having prostate cancer.

In certain embodiments the diagnostic and monitoring methods provided herein further comprising treating the subject with a regimen including one or more treatments selected from the group consisting of surgery, radiation, hormone therapy, antibody therapy, therapy with growth factors, cytokines, and chemotherapy.

In certain embodiments the diagnostic and monitoring methods provided herein further comprising selecting the one or more specific treatment regimens for the subject based on the results of the diagnostic and monitoring methods provided herein. In certain embodiments, the treatment method is maintained based on the results from the diagnostic or prognostic methods. n certain embodiments, the treatment method is changed based on the results from the diagnostic or prognostic methods.

In certain embodiments, a change the treatment regimen comprises changing a hormone based therapy treatment. In certain embodiments, treatments for prostate cancer include one or more of surgery, radiation, hormone therapy, antibody therapy, therapy with growth factors, cytokines, or chemotherapy based on the results of a method of any one of claims 1-64 for an interval prior to performing a subsequent diagnostic, prognostic, or monitoring method provided herein.

In certain embodiments of the diagnostic and monitoring methods provided herein, the method of detecting a level comprises isolating a component of the biological sample.

In certain embodiments of the diagnostic and monitoring methods provided herein, the method of detecting a level comprises labeling a component of the biological sample.

In certain embodiments of the diagnostic and monitoring methods provided herein, the method of detecting a level comprises amplifying a component of a biological sample.

In certain embodiments of the diagnostic and monitoring methods provided herein, the method of detecting a level comprises forming a complex with a probe and a component of a biological sample. In certain embodiments, forming a complex with a probe comprises forming a complex with at least one non-naturally occurring reagent. In certain embodiments of the diagnostic and monitoring methods provided herein, the method of detecting a level comprises processing the biological sample. In certain embodiments of the diagnostic and monitoring methods provided herein, the method of detecting a level of at least two markers comprises a panel of markers. In certain embodiments of the diagnostic and monitoring methods provided herein, the method of detecting a level comprises attaching the marker to be detected to a solid surface.

The invention provides methods of selecting for administration of active treatment or against administration of active treatment of prostate cancer in a subject comprising:

(1) detecting a level of one or more markers selected from the group consisting of filamin B, LY9, keratin 4, keratin 7, keratin 8, keratin 15, keratin 18, keratin 19, and tubulin-beta in a first sample obtained from the subject having prostate cancer wherein the subject has not been actively treated for prostate cancer;

(2) detecting a level of one or more markers selected from the group consisting of filamin B, LY9, keratin 4, keratin 7, keratin 8, keratin 15, keratin 18, keratin 19, and tubulin-beta 3 in a second sample from the subject;

(3) comparing the level of one or more markers selected from the group consisting of filamin B, LY9, keratin 4, keratin 7, keratin 8, keratin 15, keratin 18, keratin 19, and tubulin-beta 3 in the first sample with the level of one or more markers selected from the group consisting of filamin B, LY9, keratin 4, keratin 7, keratin 8, keratin 15, keratin 18, keratin 19, and tubulin-beta 3 in the second sample;

wherein selecting for administration of active treatment or against administration of active treatment of prostate cancer is based on the presence or absence of changes in the level of expression of one or more markers between the first sample and the second sample.

In certain embodiments, the method further comprising obtaining a third sample obtained from the subject, detecting a level of one or more markers selected from the group consisting of filamin B, LY9, keratin 4, keratin 7, keratin 8, keratin 15, keratin 18, keratin 19, and tubulin-beta 3 in the third sample, and comparing the level of one or more markers selected from the group consisting of filamin B, LY9, keratin 4, keratin 7, keratin 8, keratin 15, keratin 18, keratin 19, and tubulin-beta 3 in the third sample with the level of the one or more markers in the first sample or the one or more markers in the second sample.

In certain embodiments, an increased level of one or more of filamin B, LY9, and keratin 19 in the second sample as compared to the level of one or more of filamin B, LY9, and keratin 19 in the first sample is an indication that the therapy is not efficacious in the treatment of prostate cancer.

In certain embodiments, an increased of one or more of filamin B, LY9, and keratin 19 in the second sample as compared to the level of one or more of filamin B, LY9, and keratin 19 in the first sample is an indication for selecting active treatment for prostate cancer.

In certain embodiments, the method further comprises comparing the level of one or more markers selected from the group consisting of filamin B, LY9, and keratin 19 in the first sample or the level of one or more markers selected from the group consisting of filamin B, LY9, and keratin 19 in the second sample with the level of one or more of filamin B, LY9, and keratin 19 in a control sample. In certain embodiments, the method comprises detecting the level of one or more of keratin 4, keratin 7, keratin 8, keratin 15, keratin 18, and tubulin beta-3 in the first sample; detecting the level of one or more of keratin 4, keratin 7, keratin 8, keratin 15, keratin 18, and tubulin beta-3 in the second sample; and comparing the level of the one or more of one or more of keratin 4, keratin 7, keratin 8, keratin 15, keratin 18, and tubulin beta-3 in the second sample with the one or more of the level of keratin 4, keratin 7, keratin 8, keratin 15, keratin 18, and tubulin beta-3 in the first sample. In certain embodiments, the method comprises detection of a subset of keratins such as keratin 7, keratin 8, and keratin 15; keratin 7, 15, and 19; and keratin 7 or keratin 15. In certain embodiments, the method further comprises comparing the level of one or more of keratin 4, keratin 7, keratin 8, keratin 15, keratin 18, and tubulin beta-3 in the first sample; or the level of expression of one or more of keratin 4, keratin 7, keratin 8, keratin 15, keratin 18, and tubulin beta-3 in the second sample to the level of one or more of keratin 4, keratin 7, keratin 8, keratin 15, keratin 18, and tubulin beta-3 in a control sample.

In certain embodiments, no change in the level of expression of one or more markers selected from the group consisting of filamin B, LY9, keratin 4, keratin 7, keratin 8, keratin 15, keratin 18, keratin 19, and tubulin-beta 3 between the first sample and the second sample is an indication for selecting against active treatment for prostate cancer.

In certain embodiments, the methods further comprise detecting the level of prostate specific antigen (PSA) in the first sample and the second sample, and then preferably further comprising comparing the level of PSA in the first sample with the level of PSA in the second sample.

In certain embodiments, a decrease in the level of one or more of filamin B, LY9, and keratin 19 in the second sample as compared to the level of one or more of filamin B, LY9, and keratin 19 in the first sample in combination with a decrease in the level of PSA in the second sample as compared to the level of PSA in the first sample has greater predictive value that the therapy is efficacious in treating prostate cancer in the subject than analysis of a single marker alone.

In certain embodiments, a decrease in the level of one or more of filamin B, LY9, and keratin 19 in the second sample as compared to the level of one or more of filamin B, LY9, and keratin 19 in the first sample in combination with a decrease in the level of expression of PSA in the second sample as compared to the level of PSA in the first sample has greater predictive value that for selecting against active treatment for prostate cancer than analysis of a single marker alone.

Monitoring Clinical Trials

Monitoring the influence of agents (e.g., drug compounds) on the level of expression of a marker of the invention can be applied not only in basic drug screening or monitoring the treatment of a single subject, but also in clinical trials. For example, the effectiveness of an agent to affect marker expression can be monitored in clinical trials of subjects receiving treatment for an oncological disorder. In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate) comprising the steps of (i) obtaining a pre-administration sample from a subject prior to administration of the agent; (ii) detecting the level of expression of one or more selected markers of the invention (e.g., filamin B, LY9, keratin 4, keratin 7, keratin 8, keratin 15, keratin 18, keratin 19, tubulin-beta 3, optionally in combination with PSA) in the pre-administration sample; (iii) obtaining one or more post-administration samples from the subject; (iv) detecting the level of expression of the marker(s) in the post-administration samples; (v) comparing the level of expression of the marker(s) in the pre-administration sample with the level of expression of the marker(s) in the post-administration sample or samples; and (vi) altering the administration of the agent to the subject accordingly. For example, increased expression of the marker gene(s) during the course of treatment may indicate ineffective dosage and the desirability of increasing the dosage. Conversely, decreased expression of the marker gene(s) may indicate efficacious treatment and no need to change dosage.

Kits

The invention also provides compositions and kits for diagnosing, prognosing, or monitoring a disease or disorder, recurrence of a disorder, or survival of a subject being treated for a disorder (e.g., an abnormal prostate state, BPH, an oncologic disorder, e.g., prostate cancer). These kits include one or more of the following: a detectable antibody that specifically binds to a marker of the invention, a detectable antibody that specifically binds to a marker of the invention, reagents for obtaining and/or preparing subject tissue samples for staining, and instructions for use.

The invention also encompasses kits for detecting the presence of a marker protein or nucleic acid in a biological sample. Such kits can be used to determine if a subject is suffering from or is at increased risk of developing an abnormal prostate state. For example, the kit can comprise a labeled compound or agent capable of detecting a marker protein or nucleic acid in a biological sample and means for determining the amount of the protein or mRNA in the sample (e.g., an antibody which binds the protein or a fragment thereof, or an oligonucleotide probe which binds to DNA or mRNA encoding the protein). Kits can also include instructions for use of the kit for practicing any of the methods provided herein or interpreting the results obtained using the kit based on the teachings provided herein. The kits can also include reagents for detection of a control protein in the sample not related to the abnormal prostate state, e.g., actin for tissue samples, albumin in blood or blood derived samples for normalization of the amount of the marker present in the sample. The kit can also include the purified marker for detection for use as a control or for quantitation of the assay performed with the kit.

Kits include panel of reagents for use in a method to diagnose prostate cancer in a subject (or to identify a subject predisposed to developing prostate cancer, etc.), the panel comprising at least two detection reagents, wherein each detection reagent is specific for one prostate cancer-specific protein, wherein said prostate cancer-specific proteins are selected from the prostate cancer-specific protein sets provided herein.

For antibody-based kits, the kit can comprise, for example: (1) a first antibody (e.g., attached to a solid support) which binds to a first marker protein; and, optionally, (2) a second, different antibody which binds to either the first marker protein or the first antibody and is conjugated to a detectable label. In certain embodiments, the kit includes (1) a second antibody (e.g., attached to a solid support) which binds to a second marker protein; and, optionally, (2) a second, different antibody which binds to either the second marker protein or the second antibody and is conjugated to a detectable label. The first and second marker proteins are different. In an embodiment, the first and second markers are markers of the invention, e.g., keratin 4, keratin 7, keratin 8, keratin 15, keratin 18, keratin 19, tubulin-beta 3, filamin B, LY9, and PSA. In certain embodiments, neither the first marker nor the second marker is PSA. In certain embodiments, the kit comprises a third antibody which binds to a third marker protein which is different from the first and second marker proteins, and a second different antibody that binds to either the third marker protein or the antibody that binds the third marker protein wherein the third marker protein is different from the first and second marker proteins.

For oligonucleotide-based kits, the kit can comprise, for example: (1) an oligonucleotide, e.g., a detectably labeled oligonucleotide, which hybridizes to a nucleic acid sequence encoding a marker protein or (2) a pair of primers useful for amplifying a marker nucleic acid molecule. In certain embodiments, the kit can further include, for example: (1) an oligonucleotide, e.g., a second detectably labeled oligonucleotide, which hybridizes to a nucleic acid sequence encoding a second marker protein or (2) a pair of primers useful for amplifying the second marker nucleic acid molecule. The first and second markers are different. In an embodiment, the first and second markers are markers of the invention, e.g., keratin 4, keratin 7, keratin 8, keratin 15, keratin 18, keratin 19, tubulin-beta 3, filamin B, LY9, and PSA. In certain embodiments, neither the first marker nor the second marker is PSA. In certain embodiments, the kit can further include, for example: (1) an oligonucleotide, e.g., a third detectably labeled oligonucleotide, which hybridizes to a nucleic acid sequence encoding a third marker protein or (2) a pair of primers useful for amplifying the third marker nucleic acid molecule wherein the third marker is different from the first and second markers. In certain embodiments, the kit includes a third primer specific for each nucleic acid marker to allow for detection using quantitative PCR methods.

For chromatography methods, the kit can include markers, including labeled markers, to permit detection and identification of one or more markers of the invention, e.g., keratin 4, keratin 7, keratin 8, keratin 15, keratin 18, keratin 19, tubulin-beta 3, filamin B, LY9, and optionally PSA, by chromatography. In certain embodiments, kits for chromatography methods include compounds for derivatization of one or more markers of the invention. In certain embodiments, kits for chromatography methods include columns for resolving the markers of the method.

Reagents specific for detection of a marker of the invention, e.g., keratin 4, keratin 7, keratin 8, keratin 15, keratin 18, keratin 19, tubulin-beta 3, filamin B, LY9, and PSA, allow for detection and quantitation of the marker in a complex mixture, e.g., serum, tissue sample. In certain embodiments, the reagents are species specific. In certain embodiments, the reagents are not species specific. In certain embodiments, the reagents are isoform specific. In certain embodiments, the reagents are not isoform specific. In certain embodiments, the reagents detect total keratin 8, keratin 18, filamin B, PSA, or LY9.

In certain embodiments, the kits for the diagnosis, monitoring, or characterization of prostate cancer comprise at least one reagent specific for the detection of the level of expression of at least one marker selected from the group consisting of keratin 4, keratin 7, keratin 8, keratin 15, keratin 18, keratin 19, and tubulin-beta 3, filamin B, and LY9. In certain embodiments, the kits further comprise instructions for the diagnosis, monitoring, or characterization of prostate cancer based on the level of expression of the at least one marker selected from the group consisting of keratin 4, keratin 7, keratin 8, keratin 15, keratin 18, keratin 19, and tubulin-beta 3, filamin B, and LY9. In certain embodiments, the kits further comprise instructions to detect the level of PSA in a sample in which the at least one marker selected from the group consisting of keratin 4, keratin 7, keratin 8, keratin 15, keratin 18, keratin 19, and tubulin-beta 3, filamin B, and LY9 is detected. In certain embodiments, the kits further comprise at least one reagent for the specific detection of PSA.

The invention provides kits comprising at least one reagent specific for the detection of a level of expression of at least one marker selected from the group consisting of keratin 4, keratin 7, keratin 8, keratin 15, keratin 18, keratin 19, and tubulin-beta 3, filamin B, and LY9 and at least one reagent specific for the detection of a level of expression of PSA.

In certain embodiments, the kits can also comprise, e.g., a buffering agents, a preservative, a protein stabilizing agent, reaction buffers. The kit can further comprise components necessary for detecting the detectable label (e.g., an enzyme or a substrate). The kit can also contain a control sample or a series of control samples which can be assayed and compared to the test sample. The controls can be control serum samples or control samples of purified proteins or nucleic acids, as appropriate, with known levels of target markers. Each component of the kit can be enclosed within an individual container and all of the various containers can be within a single package, along with instructions for interpreting the results of the assays performed using the kit.

The kits of the invention may optionally comprise additional components useful for performing the methods of the invention.

Panels

The invention provides panels of reagents for detection of one or more prostate-related marker in a subject sample and at least one control reagent. In certain embodiments, the control reagent is to detect the marker for detection in the biological sample wherein the panel is provided with a control sample containing the marker for use as a positive control and optionally to quantitate the amount of marker present in the biological sample. In certain embodiments, the panel includes a detection reagent for a maker not related to an abnormal prostate state that is known to be present or absent in the biological sample to provide a positive or negative control, respectively. The panel can be provided with reagents for detection of a control protein in the sample not related to the abnormal prostate state, e.g., actin for tissue samples, albumin in blood or blood derived samples for normalization of the amount of the marker present in the sample. The panel can be provided with a purified marker for detection for use as a control or for quantitation of the assay performed with the panel.

In a preferred embodiment, the panel includes reagents for detection of two or more markers of the invention (e.g., 2, 3, 4, 5, 6, 7, 8, 9), preferably in conjunction with a control reagent. In the panel, each marker is detected by a reagent specific for that marker. In certain embodiments, the panel further includes a reagent for the detection of PSA. In certain embodiments, the panel includes replicate wells, spots, or portions to allow for analysis of various dilutions (e.g., serial dilutions) of biological samples and control samples. In a preferred embodiment, the panel allows for quantitative detection of one or more markers of the invention.

In certain embodiments, the panel is a protein chip for detection of one or more markers. In certain embodiments, the panel is an ELISA plate for detection of one or more markers. In certain embodiments, the panel is a plate for quantitative PCR for detection of one or more markers.

In certain embodiments, the panel of detection reagents is provided on a single device including a detection reagent for one or more markers of the invention and at least one control sample. In certain embodiments, the panel of detection reagents is provided on a single device including a detection reagent for two or more markers of the invention and at least one control sample. In certain embodiments, multiple panels for the detection of different markers of the invention are provided with at least one uniform control sample to facilitate comparison of results between panels.

Screening Assays

The invention also provides methods (also referred to herein as "screening assays") for identifying modulators, i.e., candidate or test compounds or agents (e.g., proteins, peptides, peptidomimetics, peptoids, small molecules or other drugs), which modulate the state of the diseased cell by modulating the expression and/or activity of a marker of the invention, i.e., keratin 4, keratin 7, keratin 8, keratin 15, keratin 18, keratin 19, tubulin-beta 3, filamin B, or LY9; optionally in combination with PSA. Such assays typically comprise a reaction between a marker of the invention and one or more assay components. The other components may be either the test compound itself, or a combination of test compounds and a natural binding partner of a marker of the invention. Compounds identified via assays such as those described herein may be useful, for example, for modulating, e.g., inhibiting, ameliorating, treating, or preventing the disease. Compounds identified for modulating the expression level of one or more of keratin 4, keratin 7, keratin 8, keratin 15, keratin 18, keratin 19, tubulin-beta 3, filamin B, or LY9; optionally in combination with PSA, are preferably further tested for activity useful in the treatment of cancer, preferably prostate cancer, e.g., inhibiting tumor cell growth, inhibiting tumor angiogenesis, inducing tumor cell apoptosis, etc.

The test compounds used in the screening assays of the present invention may be obtained from any available source, including systematic libraries of natural and/or synthetic compounds. Test compounds may also be obtained by any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann et al., 1994, *J. Med. Chem.* 37:2678-85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, 1997, *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten, 1992, *Biotechniques* 13:412-421), or on beads (Lam, 1991, *Nature* 354:82-84), chips (Fodor, 1993, *Nature* 364:555-556), bacteria and/or spores, (Ladner, U.S. Pat. No. 5,223,409), plasmids (Cull et al, 1992, *Proc Natl Acad Sci USA* 89:1865-1869) or on phage (Scott and Smith, 1990, *Science* 249:386-390; Devlin, 1990, *Science* 249:404-406; Cwirla et al, 1990, *Proc. Natl. Acad. Sci.* 87:6378-6382; Felici, 1991, *J. Mol. Biol.* 222:301-310; Ladner, supra.).

The screening methods of the invention comprise contacting a cell, e.g., a diseased cell, especially a prostate cancer cell, with a test compound and determining the ability of the test compound to modulate the expression and/or activity of filamin B, LY9, or keratin 19, optionally in combination with PSA, in the cell. The expression and/or activity of filamin B, LY9, or keratin 19; optionally in combination with PSA, can be determined using any methods known in the art, such as those described herein.

In another embodiment, the invention provides assays for screening candidate or test compounds which are substrates of a marker of the invention or biologically active portions thereof. In yet another embodiment, the invention provides assays for screening candidate or test compounds which bind to a marker of the invention or biologically active portions thereof. Determining the ability of the test compound to directly bind to a marker can be accomplished, for example, by any method known in the art.

This invention further pertains to novel agents identified by the above-described screening assays. Accordingly, it is within the scope of this invention to further use an agent identified as described herein in an appropriate animal model. For example, an agent capable of modulating the expression and/or activity of a marker of the invention identified as described herein can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatment as described above.

This invention is further illustrated by the following examples which should not be construed as limiting. The contents of all references and published patents and patent applications cited throughout the application are hereby incorporated by reference.

Exemplification of the Invention:

This invention is further illustrated by the following examples which should not be construed as limiting. The contents of all references, GenBank Accession and Gene numbers, and published patents and patent applications cited throughout the application are hereby incorporated by reference.

EXAMPLE 1

Identification of Keratins and Tubulin as Prostate Cancer Markers

Figure 1:
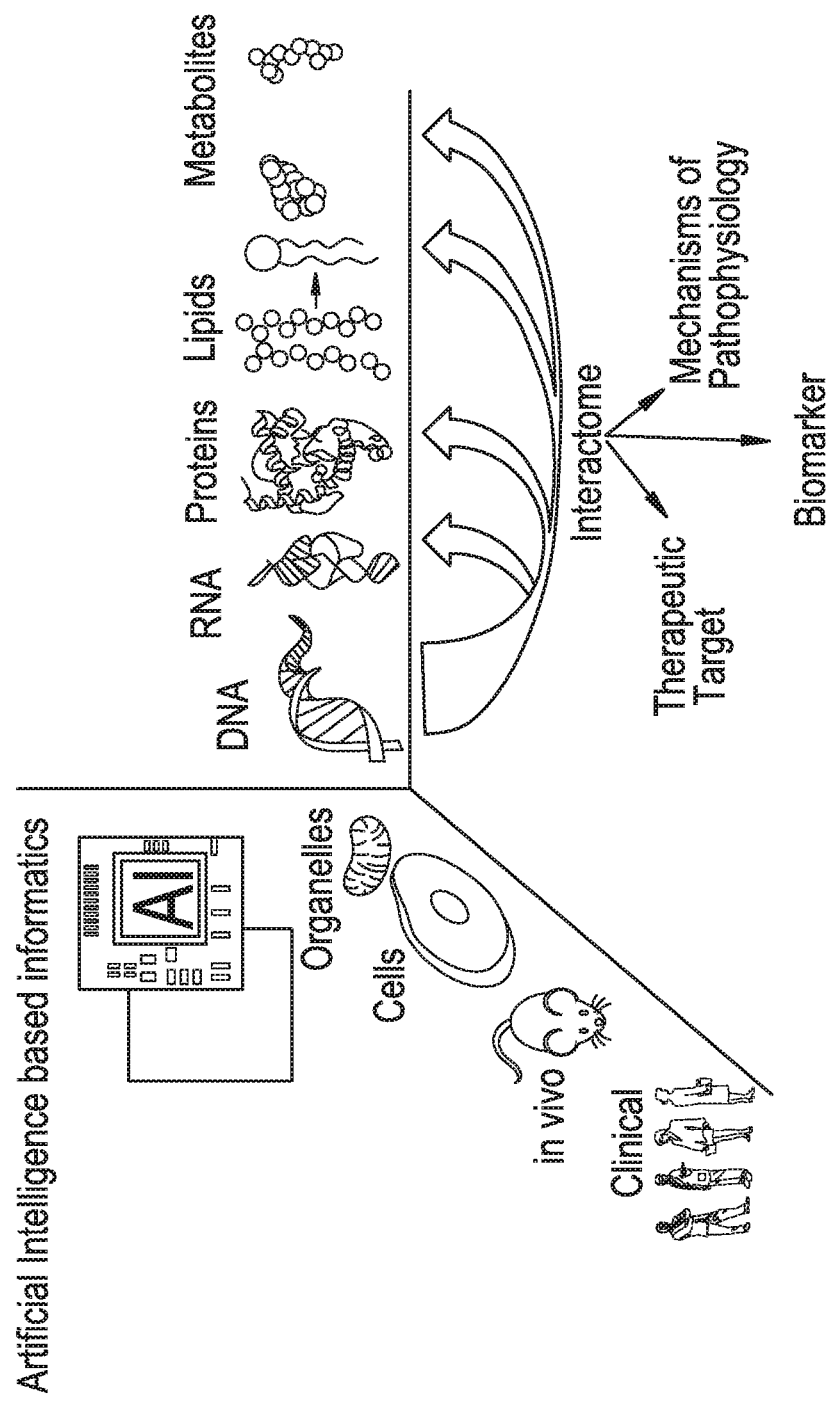
FIG. 1: Schematic representing the underlying principles of the Interrogative Platform Technology provided in WO2012119129.
Figure 2A:
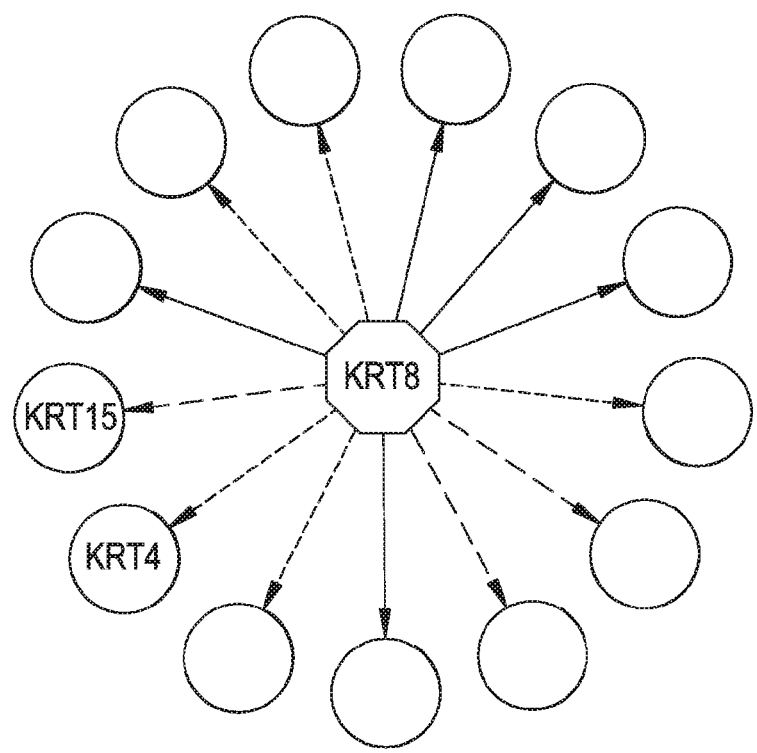
FIGS. 2A-C: Causal associations of Keratins, including (A-B) KRT8, KRT18 and (C) KRT19 in human prostate cancer cells as inferred by the Interrogative Platform Technology.
Figure 2B:
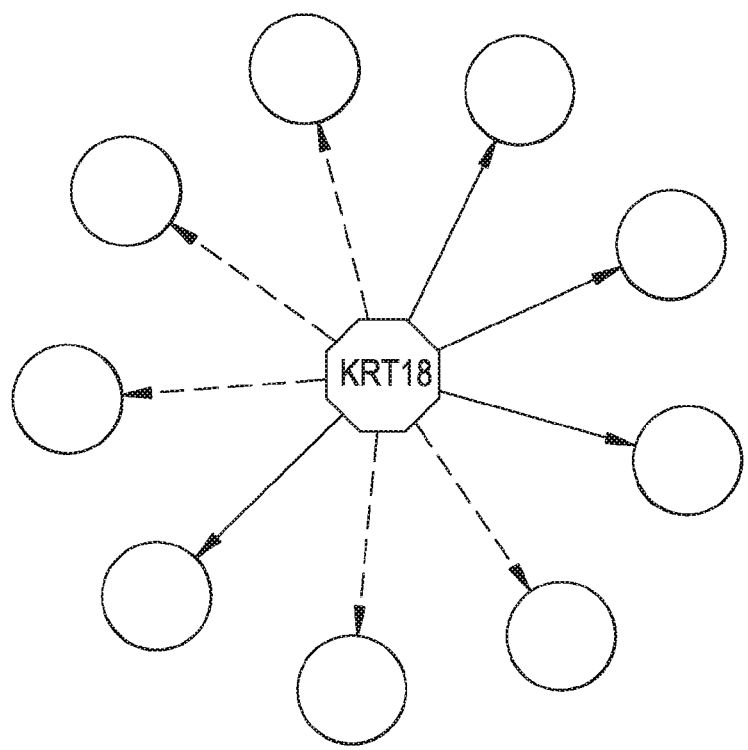
Figure 2C:
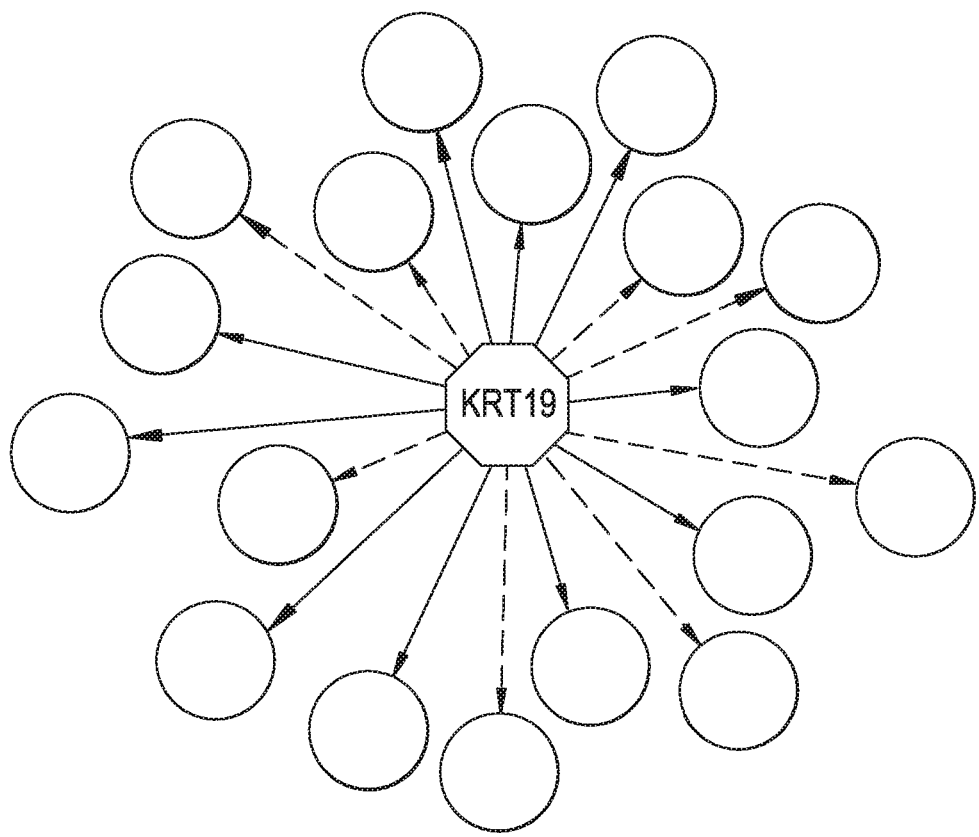
Figure 3A:
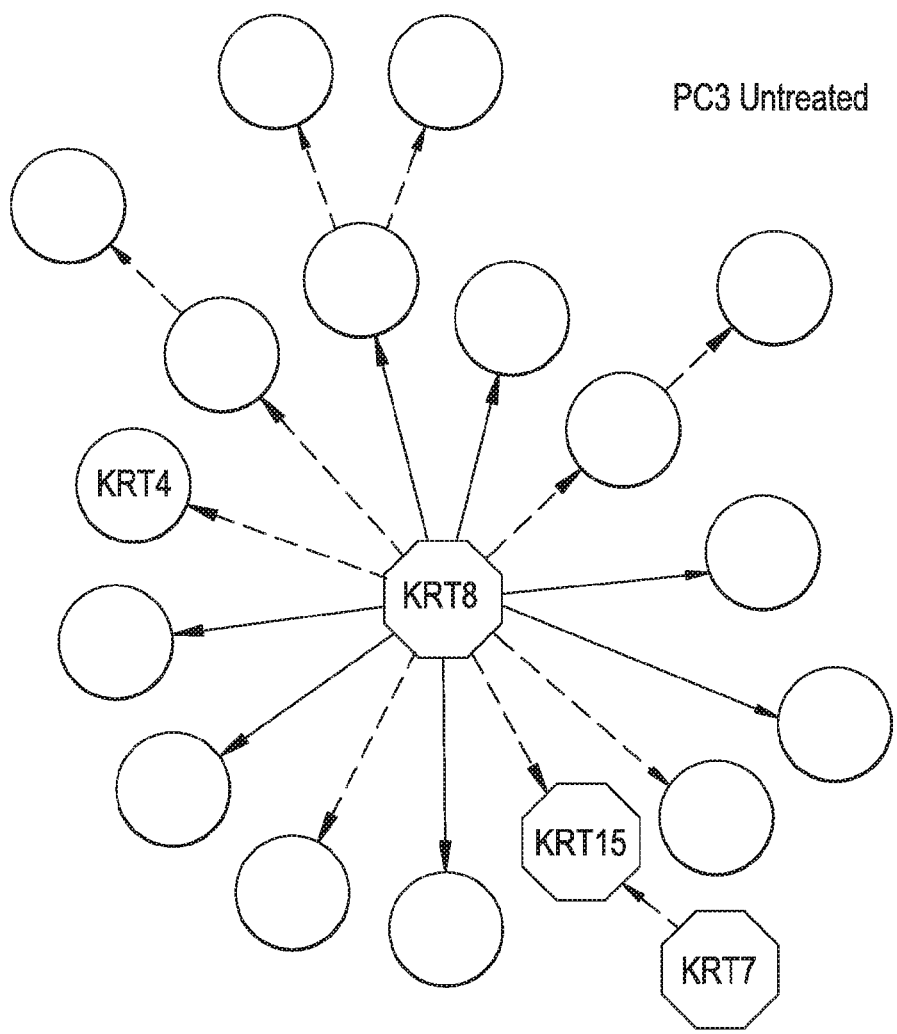
FIGS. 3A-D: Mechanistic insight into regulation of keratins by mitochondrial function inferred by the Interrogative Platform Technology. (A-B) KRT8-KRT15 association is abolished upon ubidecaronone treatment. Note change of direction of arrow between and positions of KRT7 and KRT15 before treatment (A) and after treatment (B). (C) Tubulin-beta 3 interacts with a number of proteins. (D) Expression levels of keratin 19 in biological samples from subjects with prostate cancer or control samples.
Figure 3B:
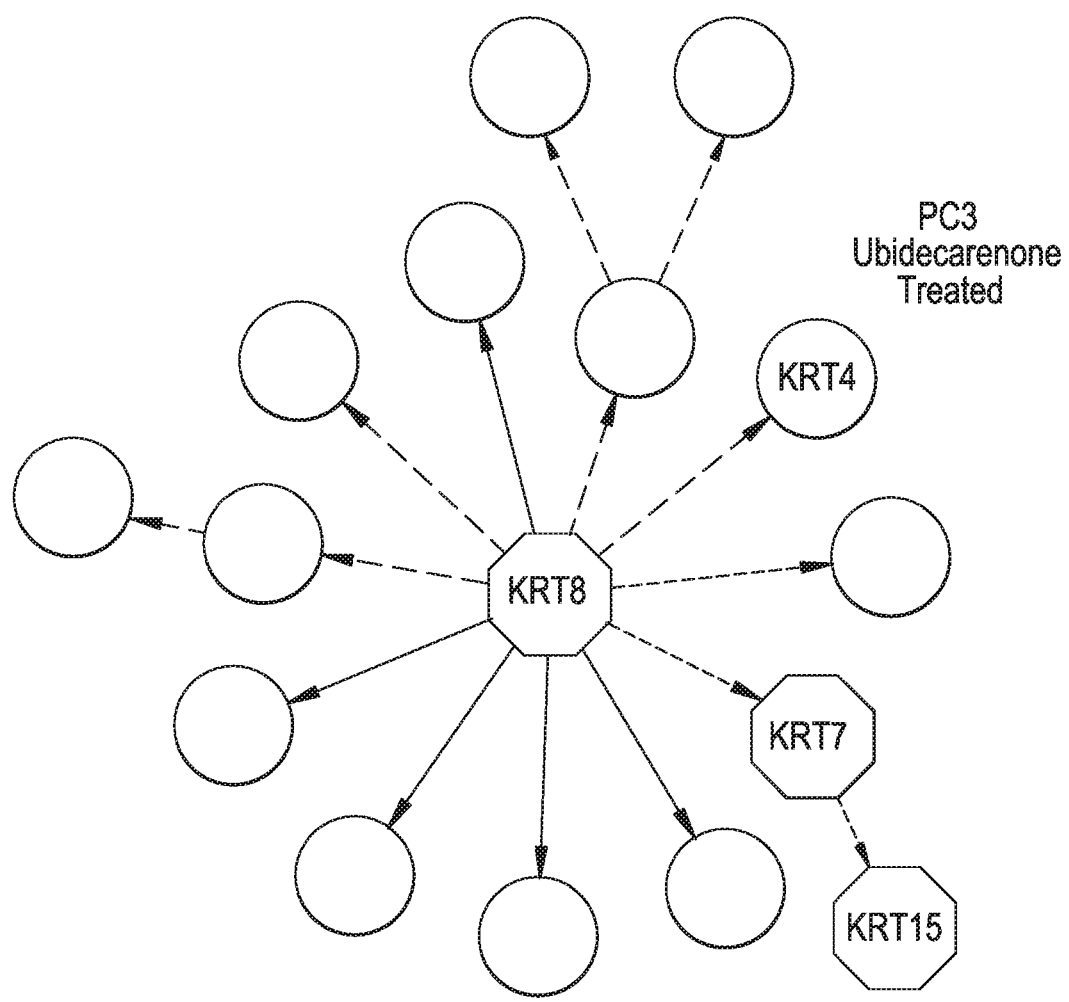
Figure 3C:
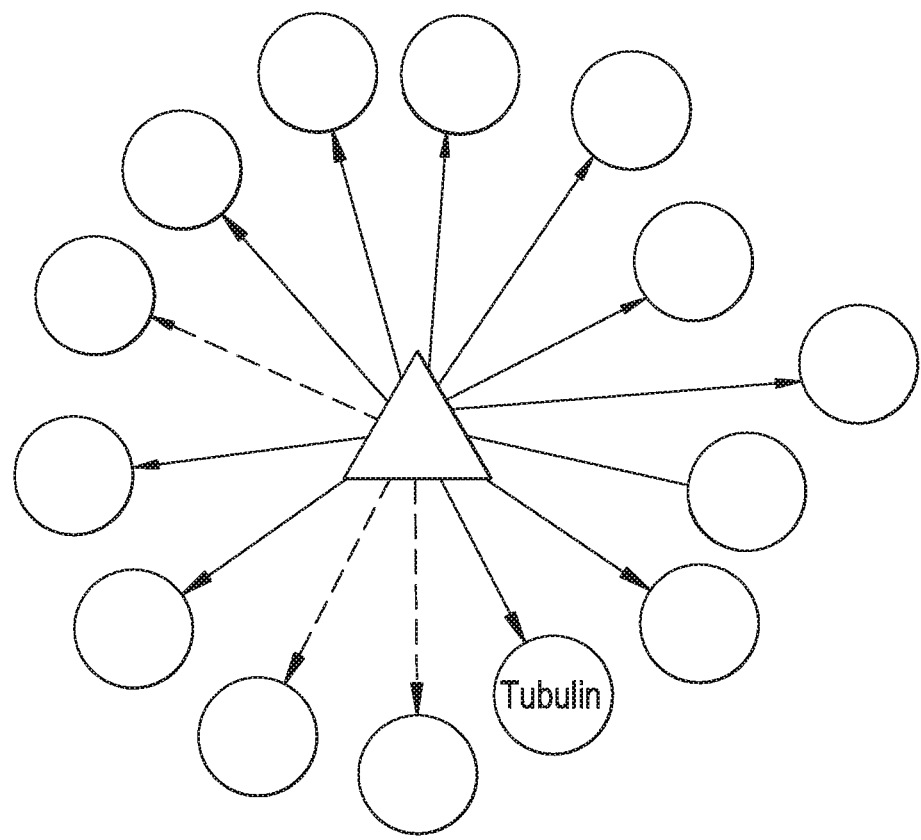
Figure 3D:
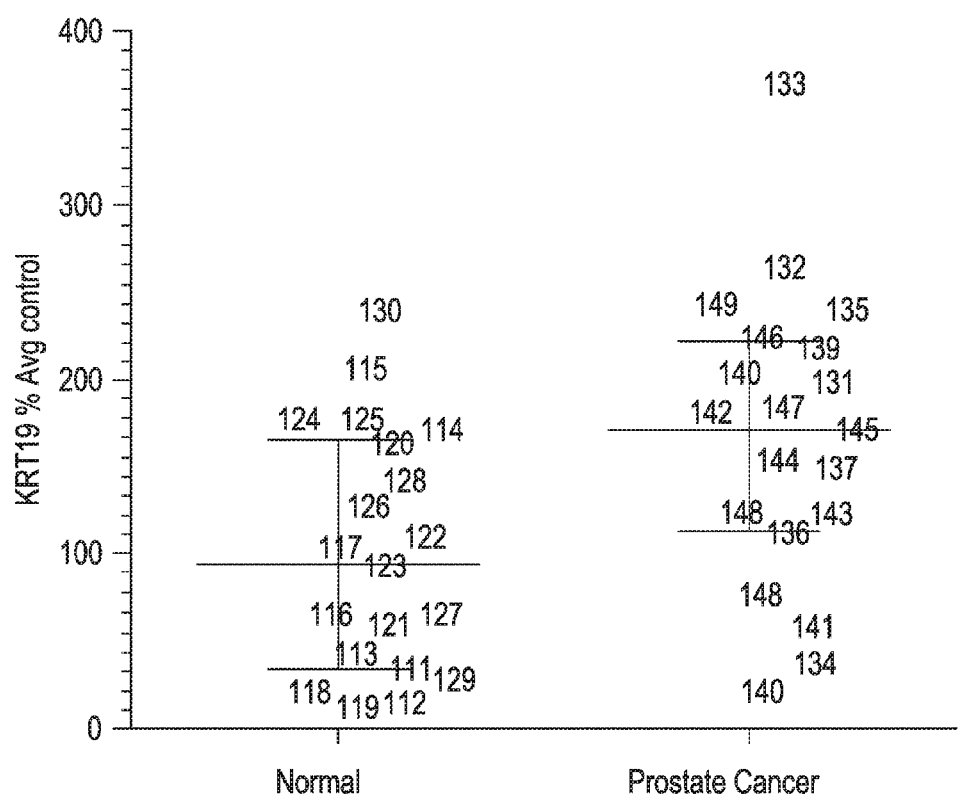

Extracellular Keratins are known to influence the cell proliferation and metastasis of epithelial derived prostate cancers. Androgen refractory prostate cancers exhibit differential expression keratin 8 (K8) when compared to normal tissue. Modulation and degradation of keratins is in turn mediated by mitochondrial generation of Reactive Oxygen Species (ROS). Despite these advances a systematic approach to understanding of keratins and other EC proteins in prostate cancer metastasis and proliferation is lacking. An interrogative systems biology based discovery platform disclosed in WO2012119129 (incorporated herein by reference), and shown schematically in FIG. 1, provides new mechanistic insights into understanding mitochondrial role in behavior of prostate cancer cells. The discovery platform involves discovery across a hierarchy of systems including in vitro human cell based models and human serum samples from prostate cancer patients and downstream data integration and mathematical modeling employing an Artificial Intelligence (AI) based informatic module. For cellular models, androgen sensitive LnCAP cell line and metastatic, androgen refractory PC3 cell line were treated with ubidecarenone (coenzyme Q10) in order to engage the mitochondrial machinery. Proteomic signatures were captured using a 2D LC-MS orbitrap technology. Total protein signatures were input to an AI based informatics module to generate causal protein networks (FIGS. 2A-C). Wet lab assays that specifically measure mitochondrial ROS, ATP and caspase 3 activation confirmed changes in intracellular levels of these markers. Several novel protein causal interactions that govern induction of mitochondrial machinery by ubidecarenone in PC3 cells were observed. Causal protein maps revealed association of keratins 8 and 15 in PC3 models and not LnCAP. The keratin 8/15 association was lost upon treatment with ubidecarenone, and a direct association of keratins 7 and 15 was established (FIGS. 3A-D). These results suggest that a change in the interaction among keratins 7, 8, and 15 is particularly useful in demonstrating a response to treatment or a change in prostate cancer status in a subject. Further, keratins 8 and 15 were differentially associated in the androgen refractory, metastatic PC3 cell line and the androgen sensitive LnCAP cell line. This indicates that keratins 8 and 15 could be useful do differentiate between prostate cancer states, e.g., between androgen sensitive and metastatic, androgen refractory prostate cancer.

An increase in the expression of keratin 19 in relation to prostate cancer was confirmed using a panel of serum samples from subjects suffering from prostate cancer as compared to an appropriate matched control population.

Thus novel mechanistic insight into prostate cancer proliferation and mitochondrial role in modulating metastasis was gained with a novel chemical systems biology approach.

The results provided herein demonstrate that modulation of keratin and potential causal association in androgen refractory prostate cancer was inferred by the Platform technology. This provides a potential mechanisms of keratin regulation in response to modulation of mitochondrial function was deciphered by the Platform technology. Thus, novel drivers of cancer pathophysiology were validated in patient serum samples.

EXAMPLE 2

Identification of Filamin B as a Prostate Cancer Marker

An interrogative systems biology based discovery platform was used to obtain mechanistic insights into understanding mitochondrial role in behavior of prostate cancer cells. The Platform technology, which is described in detail in WO2012119129, involves discovery across a hierarchy of systems including in vitro human cell based models and human serum samples from prostate cancer patients and downstream data integration and mathematical modeling employing an Artificial Intelligence (AI) based informatics module.

The results provided herein demonstrate the modulation of filamin B and LY9, and potential causal association in androgen refractory prostate cancer that was inferred using the Platform technology. The application provides potential mechanisms of filamin B and LY9 regulation in response to modulation of mitochondrial function was deciphered by the Platform technology and provides validation of the markers in patient serum samples.

Using the Platform methods, human prostate cancer cells PC3 (androgen insensitive, metastatic) and LnCap (androgen sensitive) were modeled in cancer microenvironments including hypoxia, reduced environments, and hyperglycemia and in presence of coenzyme Q10. Normal cells (human dermal fibroblasts (HDFa) and SV40 transformed human liver cells (THLE2)) were modeled under similar conditions mentioned above. Proteomics of cellular proteins and proteins secreted in the supernatant were carried out by LCMS. Data were input into the Bayesian Network Inference (BNI) algorithms REFS™.

Figure 4:
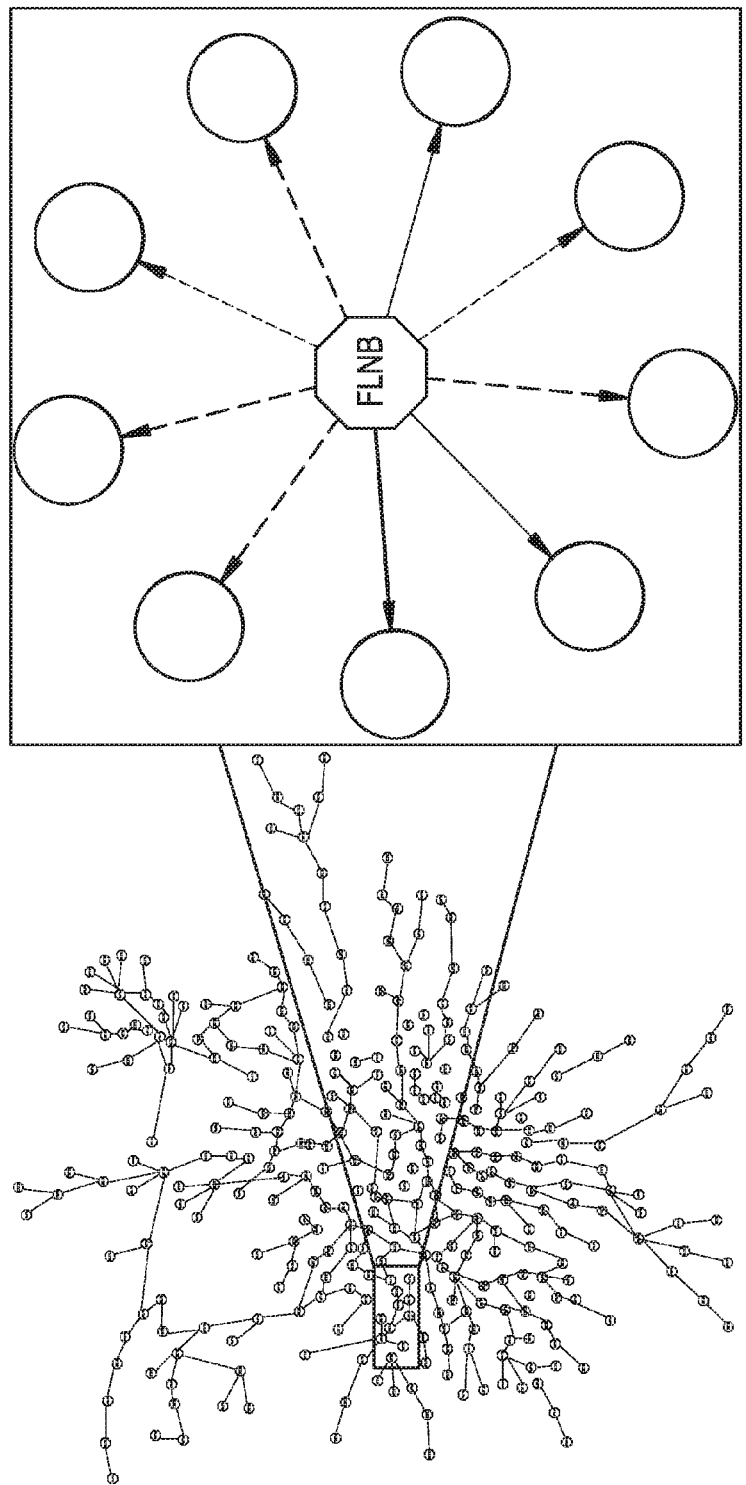
FIG. 4: Inference of filamin B (FLNB) as a hub of activity in prostate cancer and as a biomarker using the Interrogative Platform Technology provided in WO2012119129.
Figure 5:
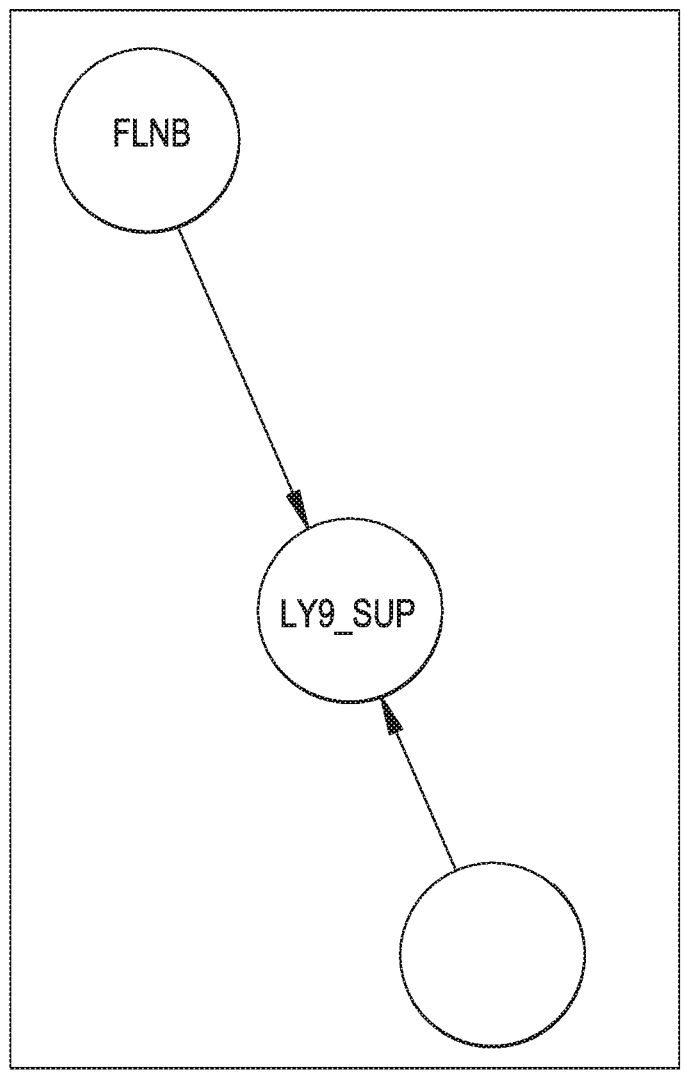
FIG. 5: Portion of an inference map showing filamin B is connected directly to LY9, which is, in turn, connected to at least one other marker.

Causal associations between proteins were derived by the BNI. Differential network analysis was employed to tease out the hubs of activity in prostate cancer when compared to normal cells in normal microenvironments. Filamin B was identified as differential hub of activity in PC3 and not in LnCap and normal cells. That is, Filamin B was found to differ between androgen sensitive LnCAP cell line and metastatic, androgen refractory PC3 cell line. This indicates that Filamin B could be useful do differentiate between prostate cancer states, e.g., between androgen sensitive and metastatic, androgen refractory prostate cancer. The interaction matrix placing filamin B at the center of an interaction hub is shown in FIG. 4. The interaction of LY9 with filamin B is shown in FIG. 5.

EXAMPLE 3

Validation of Filamin B as a Prostate Cancer Marker in Human Samples

Having identified filamin B as a prostate cancer marker using the platform technology, human serum samples from normal subjects and subjects with prostate cancer were used to confirm filamin B as a prostate cancer marker.

Specifically, human serum samples were procured from a commercial vendor that sources human serum. Twenty samples were from normal donors and 20 samples were from patients diagnosed with prostate cancer. Prostate cancer samples were from patients with different prognosis and aggressiveness of cancers reported. Clinical characteristics of the subjects are provided in the table.

|  | Prostate Cancer | Control Group |
| --- | --- | --- |
| Median Age | 61 (47-86) | 58 (45-72) |
| Ethnicity |  |  |
| Caucasian | 75% | 85% |
| African American | 15% | 10% |
| Hispanic | 10% | 5% |
| Tumor Stage |  |  |
| Stage I | 20% |  |
| Stage II | 35% |  |
| Stage III | 5% |  |
| Stage IV | 40% |  |

Figure 6A:
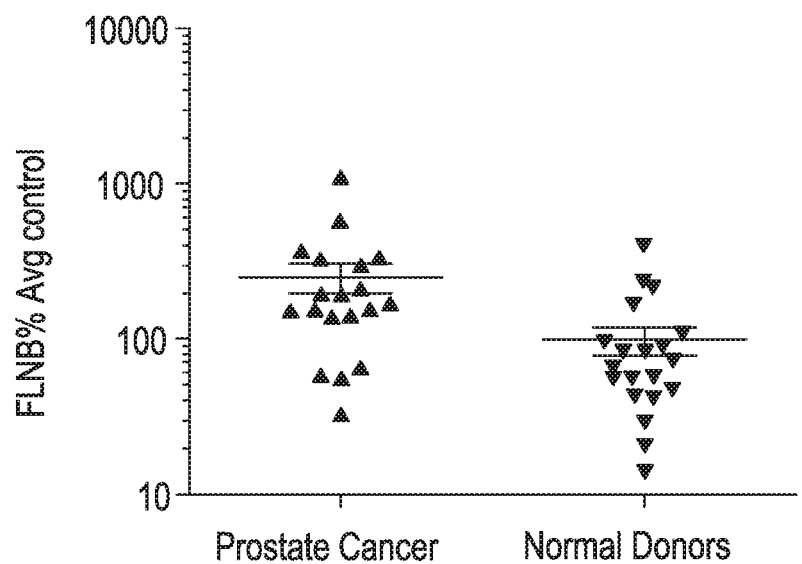
FIGS. 6A-B: Validation of filamin B levels in human serum samples. Levels of (A) filamin B and (B) PSA were elevated in prostate cancer samples when compared to normal serum. Data represents percent average change, with normal donors set to 100% on a log scale.
Figure 6B:
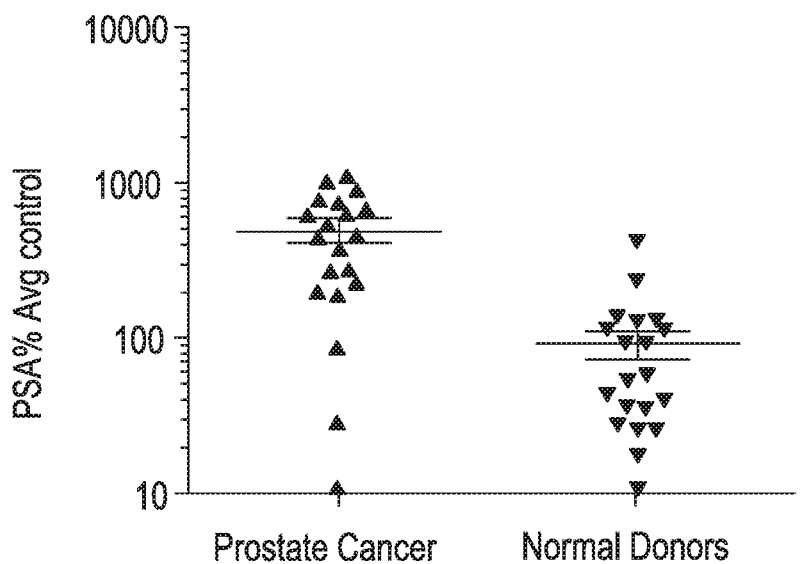

Commercially available ELISA tests for filamin B and PSA were procured from commercial source. The assays were performed using the manufactures' instructions. The results from the assay are shown in FIGS. 6A-B. The results show the differential levels of FlnB and PSA in patients with a diagnosis for prostate cancer as compared to control subjects without prostate cancer.

As shown, both filamin B and PSA levels were elevated in serum samples from patients diagnosed with prostate cancer. The correlation between PSA and FlnB expression in serum samples is 0.20075, indicating a relatively low correlation between the variables. This demonstrates that filamin B and PSA are useful for the detection of prostate cancer in different subjects. These results demonstrate that filamin B is useful for the diagnosis of prostate cancer, and that filamin B is useful for improving the detection of prostate cancer by PSA. Additional samples can be analyzed to further refine the results.

EXAMPLE 4

Stratification of Subjects with Prostate Cancer Using LY9

Figure 7:
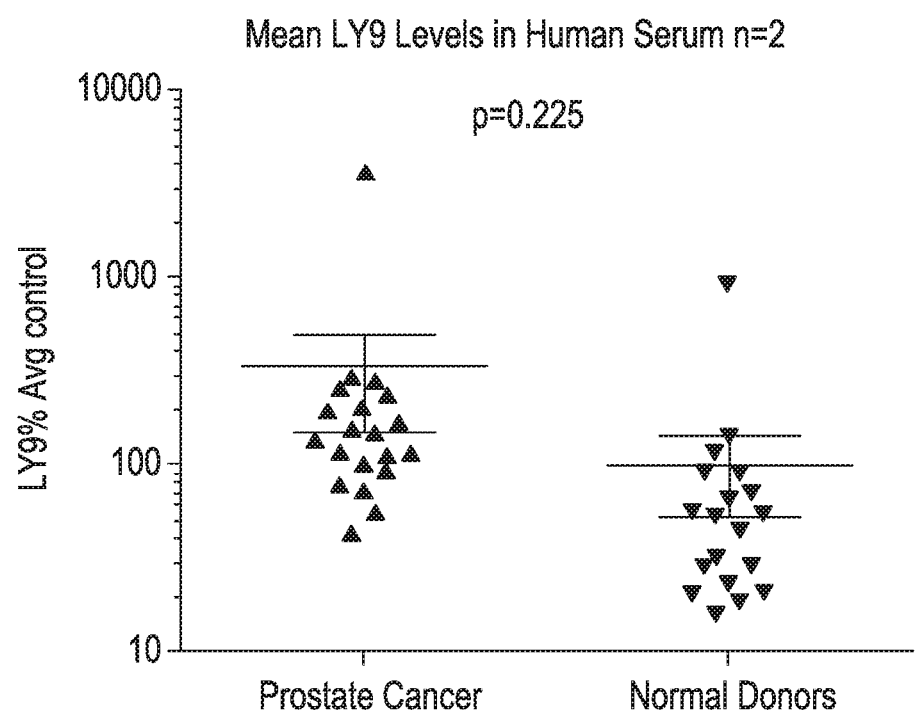
FIG. 7: Validation of LY9 levels in human serum samples. Levels of LY9 were elevated in prostate cancer samples when compared to normal serum. Data represents percent average change, with normal donors set to 100% on a log scale.
Figure 8A:
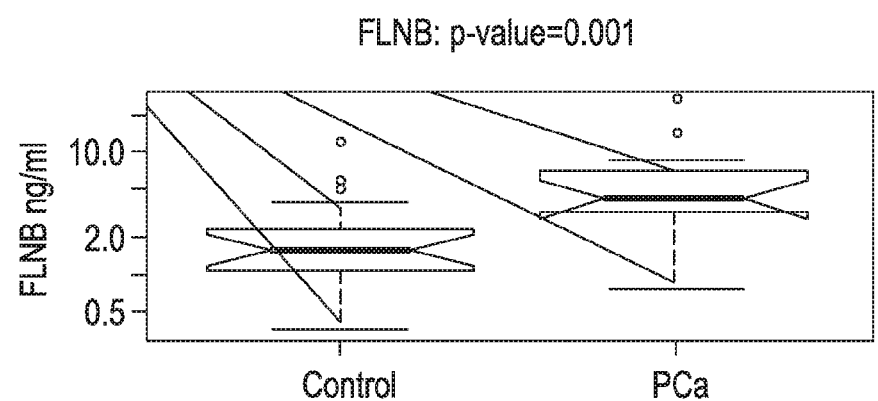
FIGS. 8A-C: Validation of (A) filamin B, (B) LY9, and (C) PSA levels in human serum samples. Data are shown as ng/ml of the marker in serum.
Figure 8B:
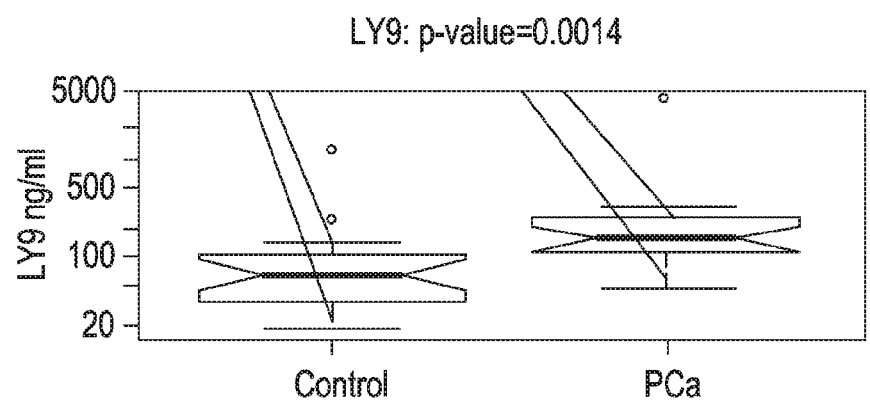
Figure 8C:
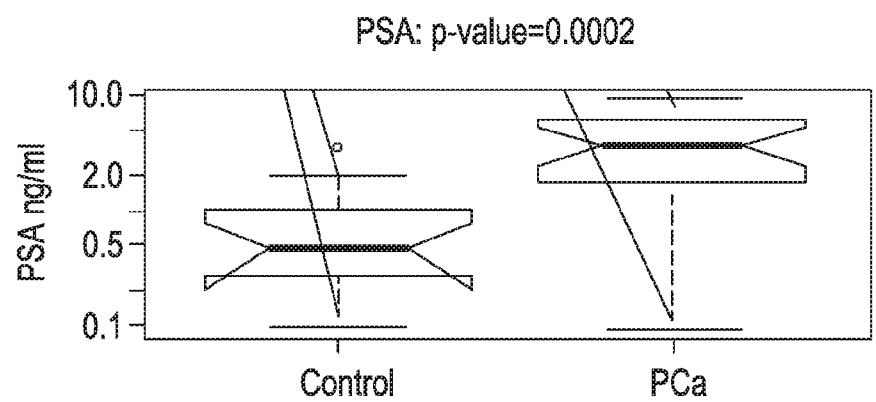

The same human serum samples used in Example 4 were further tested to detect the presence of LY9. A commercially available ELISA test for LY9 was procured from commercial source. The assay was performed using the manufactures' instructions. The results from the assay are shown in FIG. 7. The results show the differential levels of LY9 in patients with a diagnosis for prostate cancer as compared to control subjects without prostate cancer. As shown, samples from subjects with prostate cancer were found to have higher levels of LY9 as compared to normal subjects. Results from assays of expression levels of both filamin B and LY9 in human serum with results expressed as ng/ml of protein are shown in FIGS. 8A-C. Additional samples can be analyzed to further refine the results.

EXAMPLE 5

Figures 9A, 9B:
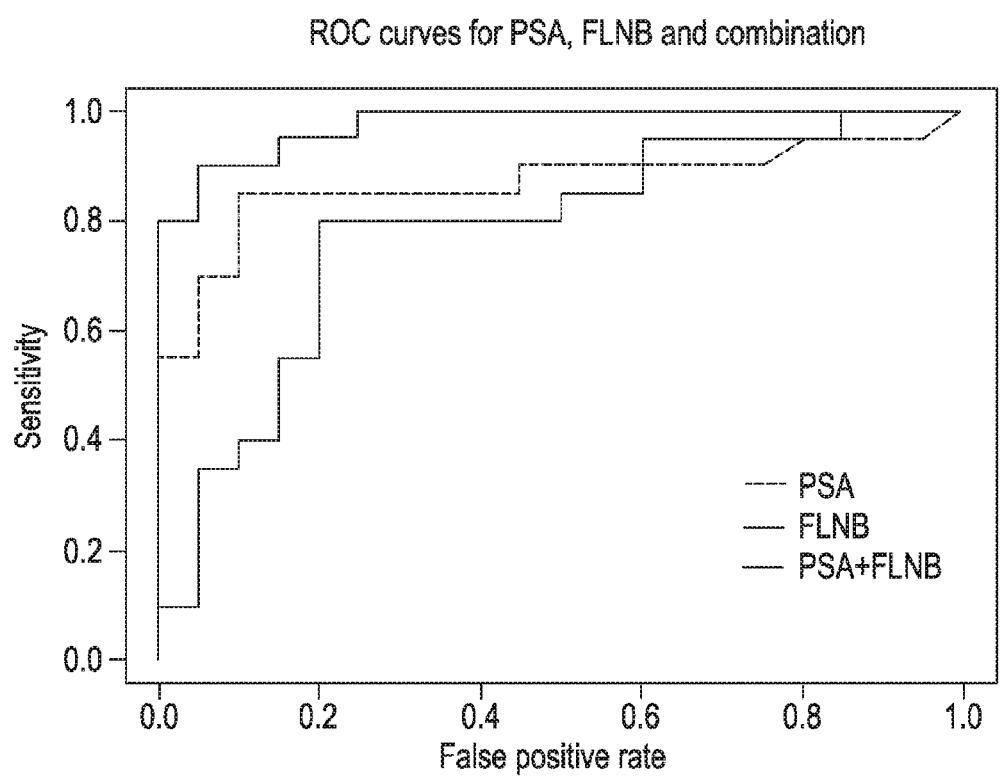
FIGS. 9A-B: ROC curve analysis of sensitivity and false positive rate (FPR) of PSA, FLNB and the combination of PSA and FLNB (A) and area under the curve values (AUC)

Analysis of Filamin B Levels Improves the Detection of Prostate Cancer as Compared to PSA Alone Having demonstrated that level of filamin B is increased in the serum of subjects with prostate cancer, the results were analyzed in conjunction with the study of PSA levels in the same samples to determine the predictive value of filamin B and PSA together was better than either of the markers alone. Receiver operating characteristic (ROC) curve analysis of sensitivity and false positive rate (FPR) of PSA, filamin B, and the combination of PSA and filamin B was generated. The curves and the area under the curve (AUC) values are shown in FIGS. 9A and B. The goal of this analysis is to gauge the predictive power of the test independent of a specific cut-off. When using an ROC analysis, a test that provides perfect discrimination or accuracy between normal and disease states would have AUC=1, whereas a very poor test that provides no better discrimination than random chance would have AUC=0.5

As demonstrated by the analysis, filamin B alone performs very well and most importantly somewhat orthogonal to PSA. PSA is reported to have a very high false positive rate, e.g., about 75% (as reported in, Gilligan, The new data on prostate cancer screening: What should we do now? Cleveland Clin. J. Med. 76: 446-448, 2009, incorporated herein by reference). That is, it has a high sensitivity and low specificity. In the specific study presented, the AUC for FLNB is lower than that for PSA. However, the correlation level of 0.20075 determined in Example 3, indicates a relatively low correlation between the variables. That is, subjects identified as having an elevated filamin B level did not necessarily have a high PSA level, and the reverse was also true, suggesting that the markers in combination can provide a predictive test than either marker alone.

This was confirmed in the ROC analysis. As shown, the combination of PSA and filamin B was found to have a higher AUC indicating better discrimination of the test than PSA alone, and to be more predictive than either of the markers alone. The combination of PSA and filamin B is very good and provides a drastic increase PSA test specificity, which is the main problem with the test.

EXAMPLE 6

Analysis of Filamin B, LY9, and PSA Levels Together Improves the Detection of Prostate Cancer as Compared to Any Marker Alone Having demonstrated that each filamin B, LY9, and PSA are all elevated in serum samples from subjects with prostate cancer, the ROC curve analysis was performed comparing each of the three markers individually to the combination of all three markers using a linear scoring function, and comparing the combination of filamin B and LY9, and the combination of filamin B and PSA, against the combination of all three markers using a non-linear scoring function to determine which combinations of the markers were more effective than each single marker for the detection of prostate cancer in a subject. As shown, the combination of all three markers was more predictive than any of the markers alone (FIG. 10A). The combination of filamin B with PSA, either with or without LY9, was more predictive than the combination of filamin B with LY9 (FIG. 10B). Additional samples can be analyzed to further refine the results. The AUC results are summarized in the table.

| Marker | AUC |
| --- | --- |
| LY9 | 0.85 |
| FLNB | 0.78 |
| PSA | 0.87 |
| LY9 + FLNB + PSA | 0.98 |

EXAMPLE 7

Stratification of Subjects with Prostate Cancer Using Keratin 4, Keratin 7, Keratin 8, Keratin 15, Keratin 18, Keratin 19, Tubulin-beta 3

As demonstrated in Examples 3 and 4 respectively, filamin B levels and LY9 levels can be used to distinguish subjects who are or are not suffering from prostate cancer. Further, as demonstrated in Examples 6 and 7, the analysis of both filamin B and PSA, optionally further in combination with LY9, is more sensitive than an analysis based on either marker alone.

A series of subject samples are obtained from an appropriate source, e.g., a commercial source, wherein the samples were obtained from subjects with different stages of prostate cancer, e.g., aggressive prostate cancer, androgen sensitive, androgen insensitive, metastatic; or from subjects not suffering from prostate cancer, e.g., subjects with normal prostate or subjects with BPH. The samples are analyzed for the expression level of at least one of keratin 4, keratin 7, keratin 8, keratin 15, keratin 18, keratin 19, tubulin-beta 3, preferably at least one of keratin 7, keratin 15, and keratin 19; and optionally further at least one of filamin B, LY9, and PSA. The level of the expression of the makers, alone and in various combinations, correlate with the presence or absence of disease, and with the severity of prostate cancer. For example, an increase in the expression level of one or more of keratin 19, filamin B, LY9, and PSA, as compared to a normal sample from a subject not suffering from prostate cancer, is indicative of prostate cancer in the subject. Expression levels of keratins 7, 8, and 15 may also be particularly useful in the stratification of subjects with prostate cancer.

EXAMPLE 8

Monitoring of Prostate Cancer Treatment Using Keratin 4, Keratin 7, Keratin 8, Keratin 15, Keratin 18, Keratin 19, Tubulin-beta 3

At the time of diagnosis with prostate cancer, subjects are invited to participate in a trial. A subject sample, e.g., blood, is obtained. Periodically, throughout the monitoring, watchful waiting, or active treatment of the subject, e.g., chemotherapy, radiation therapy, surgery, hormone therapy, a new subject sample is obtained. At the end of the study, all subject samples are tested for the expression level of at least one of keratin 4, keratin 7, keratin 8, keratin 15, keratin 18, keratin 19, tubulin-beta 3, preferably at least one of keratin 7, keratin 15, and keratin 19; and optionally further at least one of filamin B, LY9, and PSA. The subject samples are matched to the medical records of the subjects to correlate marker levels with prostate cancer status at the time of diagnosis, rate of progression of disease, response of subjects to one or more interventions, and transitions between androgen dependent and independent status. An increase in the expression level of one or more of keratin 19, filamin B, LY9, and PSA, as compared to a normal sample from a subject not suffering from prostate cancer, is indicative of prostate cancer in the subject. Expression levels of keratins 7, 8, and 15 may also be particularly useful in the diagnosis and monitoring of subjects with prostate cancer.

EXAMPLE 9

Detection and Monitoring of Prostate Cancer Using Keratin 4, Keratin 7, Keratin 8, Keratin 15, Keratin 18, Keratin 19, Tubulin-beta 3

Despite its limitations, including a positive predictive value of only 25-40%, PSA remains the only generally accepted biomarker for prostate cancer. Moreover, as prostate cancer is most commonly a slow growing tumor in men of advanced age, treatment of the cancer may do more harm to the subject than the tumor itself would. Therefore, the tests together for the expression level of at least one of keratin 4, keratin 7, keratin 8, keratin 15, keratin 18, keratin 19, tubulin-beta 3, preferably at least one of keratin 7, keratin 15, and keratin 19; and optionally further at least one of filamin B, LY9, and PSA are used for the detection an monitoring of prostate cancer. The level of the expression of the makers, alone and in various combinations are used in detection, including in routine, preventative, screening methods in men having an increased risk of prostate cancer (e.g., increased age, family history, race, etc.) or in monitoring of subjects diagnosed with prostate cancer prior to or during treatment may be useful to better identify subjects in need of further, potentially more invasive, diagnostic tests, e.g., prostate exam or biopsy, digital rectal exam; or more aggressive treatment. Detection of levels of expression of the markers, or various combinations thereof, may also be indicative of a good or poor response to a specific treatment regimen prior to changes in other signs or symptoms, e.g., loss of tumor response to hormone therapy.

In routine screening methods for prostate cancer, a serum sample from a subject is tested for the level of expression of at least one of keratin 4, keratin 7, keratin 8, keratin 15, keratin 18, keratin 19, tubulin-beta 3, preferably at least one of keratin 7, keratin 15, and keratin 19; and optionally further at least one of filamin B, LY9, and PSA. The levels are compared to one or more appropriate controls, e.g., other normal subjects, subjects with prostate cancer. Detection of an abnormal level of one or more of at least one of keratin 4, keratin 7, keratin 8, keratin 15, keratin 18, keratin 19, tubulin-beta 3, preferably at least one of keratin 7, keratin 8, keratin 15, and keratin 19; indicates that the subject should be considered for further tests for the presence of prostate cancer. Changes in the level of at least one of keratin 4, keratin 7, keratin 8, keratin 15, keratin 18, keratin 19, tubulin-beta 3, preferably at least one of keratin 7, keratin 8, keratin 15, and keratin 19, in the subject may be more indicative of a change in prostate cancer status than comparison to a population control.

In determining a therapeutic regimen for a subject with prostate cancer not yet being actively treated for prostate cancer (i.e., watchful waiting) can be tested at regular intervals to determine if there is a change in the level of expression of at least one of keratin 4, keratin 7, keratin 8, keratin 15, keratin 18, keratin 19, tubulin-beta 3, preferably at least one of keratin 7, keratin 15, and keratin 19; and optionally further at least one of filamin B, LY9, and PSA. An modulation in the level of at least one of keratin 4, keratin 7, keratin 8, keratin 15, keratin 18, keratin 19, tubulin-beta 3, preferably at least one of keratin 7, keratin 8, keratin 15, and keratin 19; and optionally further at least one of filamin B, LY9, and PSA indicates that the subject should be considered for further tests to monitor the prostate cancer and more active therapeutic interventions should be considered.

In a subject undergoing treatment for prostate cancer (e.g., hormone therapy, chemotherapy, radiation therapy, surgery) is tested prior to the initiation of the treatment and during and/or after the treatment to determine if the treatment results in a decrease in the level of expression of at least one of keratin 4, keratin 7, keratin 8, keratin 15, keratin 18, keratin 19, tubulin-beta 3, preferably at least one of keratin 7, keratin 15, and keratin 19; and optionally further at least one of filamin B, LY9, and PSA. A decrease in the level of keratin 19, filamin B, LY9, or PSA is indicative of response to treatment. Expression levels of keratins 7, 8, and 15 may also be particularly useful in the diagnosis and monitoring of subjects with prostate cancer.

EXAMPLE 10

Stratification of Subjects with Prostate Cancer Using Filamin B, PSA, or LY9

As demonstrated in Examples 3 and 4 respectively, filamin B levels and LY9 levels can be used to distinguish subjects who are or are not suffering from prostate cancer. Further, as demonstrated in Examples 6 and 7, the analysis of both filamin B and PSA, optionally further in combination with LY9, is more sensitive than an analysis based on either marker alone.

A series of subject samples are obtained from an appropriate source, e.g., a commercial source, wherein the samples were obtained from subjects with different stages of prostate cancer, e.g., aggressive prostate cancer, androgen sensitive, androgen insensitive, metastatic; or from subjects not suffering from prostate cancer, e.g., subjects with normal prostate or subjects with BPH. The samples are analyzed for the expression level of filamin B and PSA, and optionally the level of LY9, and further with one or more of keratin 4, keratin 7, keratin 8, keratin 15, keratin 18, keratin 19, and tubulin-beta 3, especially keratin 19. The level of filamin B, LY9, and PSA, alone and in various combinations, optionally with other markers, e.g., keratin 4, keratin 7, keratin 8, keratin 15, keratin 18, keratin 19, and tubulin-beta 3, especially keratin 19, correlate with the presence or absence of disease, and with the severity of prostate cancer.

EXAMPLE 11

Monitoring of Prostate Cancer Treatment Using Filamin B, PSA, or LY9

At the time of diagnosis with prostate cancer, subjects are invited to participate in a trial. A subject sample, e.g., blood, is obtained. Periodically, throughout the monitoring, watchful waiting, or active treatment of the subject, e.g., chemotherapy, radiation therapy, surgery, hormone therapy, a new subject sample is obtained. At the end of the study, all subject samples are tested for the level of filamin B, PSA, and optionally in further combination with one or more of LY9, keratin 4, keratin 7, keratin 8, keratin 15, keratin 18, keratin 19, and tubulin-beta 3. The subject samples are matched to the medical records of the subjects to correlate filamin B, PSA, LY9, keratin 4, keratin 7, keratin 8, keratin 15, keratin 18, keratin 19, or tubulin-beta 3 levels, as appropriate, with prostate cancer status at the time of diagnosis, rate of progression of disease, response of subjects to one or more interventions, and transitions between androgen dependent and independent status.

EXAMPLE 12

Detection and Monitoring of Prostate Cancer Using Filamin B, PSA, or LY9

Despite its limitations, including a positive predictive value of only 25-40%, PSA remains the only generally accepted biomarker for prostate cancer. Moreover, as prostate cancer is most commonly a slow growing tumor in men of advanced age, treatment of the cancer may do more harm to the subject than the tumor itself would. As demonstrated herein, there is a low correlation between elevated levels of filamin B and PSA in subjects with prostate cancer. Further, elevated levels of LY9 have been demonstrated to be associated with prostate cancer. Therefore, the tests together, particularly filamin B and PSA, optionally in combination with one or more of LY9, keratin 4, keratin 7, keratin 8, keratin 15, keratin 18, keratin 19, and tubulin-beta 3, especially keratin 19, in detection, including in routine, preventative, screening methods in men having an increased risk of prostate cancer (e.g., increased age, family history, race, etc.) or in monitoring of subjects diagnosed with prostate cancer prior to or during treatment may be useful to better identify subjects in need of further, potentially more invasive, diagnostic tests, e.g., prostate exam or biopsy, digital rectal exam; or more aggressive treatment. Detection of levels of expression of filamin B, PSA, LY9 keratin 4, keratin 7, keratin 8, keratin 15, keratin 18, keratin 19, and tubulin-beta 3, especially keratin 19, may also be indicative of a good or poor response to a specific treatment regimen prior to changes in other signs or symptoms, e.g., loss of tumor response to hormone therapy.

In routine screening methods for prostate cancer, a serum sample from a subject is tested for the level of expression of both filamin B and PSA, and optionally one or more of LY9, keratin 4, keratin 7, keratin 8, keratin 15, keratin 18, keratin 19, and tubulin-beta 3, especially keratin 19. The levels are compared to one or more appropriate controls, e.g., other normal subjects, subjects with prostate cancer. Detection of an abnormal level of one or more of filamin B, PSA, LY9, keratin 4, keratin 7, keratin 8, keratin 15, keratin 18, keratin 19, and tubulin-beta 3, especially keratin 19 indicates that the subject should be considered for further tests for the presence of prostate cancer. Changes in the level of filamin B, optionally in combination with one or more of PSA, LY9, keratin 4, keratin 7, keratin 8, keratin 15, keratin 18, keratin 19, or tubulin-beta 3, especially keratin 19 with PSA in the subject may be more indicative of a change in prostate cancer status than comparison to a population control.

In determining a therapeutic regimen for a subject with prostate cancer not yet being actively treated for prostate cancer (i.e., watchful waiting) can be tested at regular intervals to determine if there is a change in the level of expression of filamin B, PSA, LY9 keratin 4, keratin 7, keratin 8, keratin 15, keratin 18, keratin 19, and tubulin-beta 3. An increase in the level of filamin B, PSA, keratin 19, or LY9 indicates that the subject should be considered for further tests to monitor the prostate cancer and more active therapeutic interventions should be considered.

In a subject undergoing treatment for prostate cancer (e.g., hormone therapy, chemotherapy, radiation therapy, surgery) is tested prior to the initiation of the treatment and during and/or after the treatment to determine if the treatment results in a change in the level of expression of one or more of filamin B, PSA, LY9, keratin 4, keratin 7, keratin 8, keratin 15, keratin 18, keratin 19, and tubulin-beta 3. A decrease in the level of filamin B, PSA, keratin 19, or LY9 is indicative of response to treatment.

Equivalents:

Those skilled in the art will recognize, or be able to ascertain using no more than routine experimentation, many equivalents to the specific embodiments and methods described herein. Such equivalents are intended to be encompassed by the scope of the following claims.

The invention claimed is:

1. A method for diagnosing and treating prostate cancer in a subject comprising:
   (1) detecting the protein level of one or more of the prostate cancer related markers filamin B and keratin 19 in a serum sample isolated from a subject suspected of having prostate cancer;
   (2) comparing the protein level of the one or more prostate cancer related markers in the serum sample with the protein level of the one or more prostate cancer related markers in a normal control sample;
   (3) diagnosing the subject as having prostate cancer when an increased protein level of the one or more prostate cancer related markers is detected in the serum sample relative to the normal control sample; and
   (4) performing surgical prostate resection on the diagnosed subject, thereby diagnosing and treating prostate cancer in the subject.

2. The method of claim 1, wherein detecting the level of one or more of the prostate cancer related markers filamin B and keratin 19 comprises contacting the sample with one or more reagents that selectively bind at least one of filamin B and keratin 19.

3. The method of claim 2, wherein the one or more reagent is an antibody.

4. The method of claim 1, wherein the prostate cancer related marker is filamin B.

5. The method of claim 1, wherein the prostate cancer related marker is keratin 19.

6. The method of claim 1, wherein no increase in one or more of filamin B and keratin 19 in the biological sample relative to the normal control sample is indicative of a normal prostate state in the subject.

7. The method of claim 1, further comprising detecting the level of prostate specific antigen (PSA) in the sample.

8. The method of claim 7, further comprising comparing the level of PSA in the sample to the level of PSA in a normal control sample.

9. The method of claim 8, wherein an increase in the detected level of one or more of filamin B and keratin 19 in the sample relative to the normal control sample, in combination with an increase in the level of PSA in the sample relative to the level of PSA in the normal control sample, is indicative of prostate cancer in the subject.

10. The method of claim 8, wherein no increase in the detected level of one or more of filamin B and keratin 19 in the sample relative to the normal control sample, in combination with a decreased or normal level of PSA in the sample as compared to the level of PSA in the normal control sample, is indicative of a normal prostate state in the subject.

11. The method of claim 1, wherein prior to step (1), the subject has been determined to be at an increased risk of prostate cancer.

12. The method of claim 11, wherein the increased risk for prostate cancer is due to increased age.

13. A method for diagnosing and treating prostate cancer in a subject comprising:
   (1) detecting the protein level of the prostate cancer related marker filamin B in a serum sample isolated from a subject suspected of having prostate cancer;
   (2) comparing the protein level of filamin B in the serum sample with the protein level of filamin B in a normal control sample;
   (3) diagnosing the subject as having prostate cancer when an increased protein level of filamin B is detected in the serum sample relative to the normal control sample; and
   (4) performing surgical resection on the diagnosed subject, thereby diagnosing and treating prostate cancer in the subject.

14. The method of claim 13, wherein detecting the level of filamin B comprises contacting the sample with one or more reagents that selectively bind filamin B.

15. The method of claim 14, wherein the one or more reagent is an antibody.

16. The method of claim 13, wherein no increase in filamin B in the biological sample relative to the normal control sample is indicative of a normal prostate state in the subject.

17. The method of claim 13, further comprising detecting the level of prostate specific antigen (PSA) in the sample.

18. The method of claim 17, further comprising comparing the level of PSA in the sample to the level of PSA in a normal control sample.

19. The method of claim 18, wherein an increase in the detected level of filamin B in the sample relative to the normal control sample, in combination with an increase in the level of PSA in the sample relative to the level of PSA in the normal control sample, is indicative of prostate cancer in the subject.

20. The method of claim 18, wherein no increase in the detected level of filamin B in the sample relative to the normal control sample, in combination with a decreased or normal level of PSA in the sample as compared to the level of PSA in the normal control sample, is indicative of a normal prostate state in the subject.

21. The method of claim 13, wherein prior to step (1), the subject has been determined to be at an increased risk of prostate cancer.

22. The method of claim 21, wherein the increased risk is due to increased age.

23. A method for diagnosing and treating prostate cancer in a subject comprising:
   (1) detecting the protein level of the prostate cancer related marker filamin B in a serum sample isolated from a subject suspected of having prostate cancer;
   (2) comparing the protein level of filamin B in the serum sample with the protein level of filamin B in a normal control sample;
   (3) diagnosing the subject as having prostate cancer when an increased protein level of filamin B is detected in the serum sample relative to the normal control sample; and
   (4) administering radiation therapy to the diagnosed subject, thereby diagnosing and treating prostate cancer in the subject.

24. The method of claim 23, wherein the radiation therapy is brachytherapy.

25. The method of claim 23, wherein detecting the level of filamin B comprises contacting the sample with one or more reagents that selectively bind filamin B.

26. The method of claim 25, wherein the one or more reagent is an antibody.

27. The method of claim 23, wherein no increase in filamin B in the biological sample relative to the normal control sample is indicative of a normal prostate state in the subject.

28. The method of claim 23, further comprising detecting the level of prostate specific antigen (PSA) in the sample.

29. The method of claim 28, further comprising comparing the level of PSA in the sample to the level of PSA in a normal control sample.

30. The method of claim 21, wherein an increase in the detected level of filamin B in the sample relative to the normal control sample, in combination with an increase in the level of PSA in the sample relative to the level of PSA in the normal control sample, is indicative of prostate cancer in the subject.

31. The method of claim 21, wherein no increase in the detected level of filamin B in the sample relative to the normal control sample, in combination with a decreased or normal level of PSA in the sample as compared to the level of PSA in the normal control sample, is indicative of a normal prostate state in the subject.

32. The method of claim 23, wherein prior to step (1), the subject has been determined to be at an increased risk of prostate cancer.

33. The method of claim 24, wherein the increased risk is due to increased age.

* * * * *

SEQUENCE LISTING

```
<160> NUMBER OF SEQ ID NOS: 45

<210> SEQ ID NO 1
<211> LENGTH: 520
<212> TYPE: PRT
<213> ORGANISM: Homo sapiens

<400> SEQUENCE: 1

Met Ile Ala Arg Gln Gln Cys Val Arg Gly Gly Pro Arg Gly Phe Ser
1               5                   10                  15

Cys Gly Ser Ala Ile Val Gly Gly Gly Lys Arg Gly Ala Phe Ser Ser
            20                  25                  30

Val Ser Met Ser Gly Gly Ala Gly Arg Cys Ser Ser Gly Gly Phe Gly
        35                  40                  45

Ser Arg Ser Leu Tyr Asn Leu Arg Gly Asn Lys Ser Ile Ser Met Ser
    50                  55                  60

Val Ala Gly Ser Arg Gln Gly Ala Cys Phe Gly Gly Ala Gly Gly Phe
```

```
                65                  70                  75                  80
Gly Thr Gly Gly Phe Gly Gly Phe Gly Gly Ser Phe Ser Gly Lys
                    85                  90                  95
Gly Gly Pro Gly Phe Pro Val Cys Pro Ala Gly Gly Ile Gln Glu Val
                    100                 105                 110
Thr Ile Asn Gln Ser Leu Leu Thr Pro Leu His Val Glu Ile Asp Pro
                    115                 120                 125
Glu Ile Gln Lys Val Arg Thr Glu Arg Glu Gln Ile Lys Leu Leu
    130                 135                 140
Asn Asn Lys Phe Ala Ser Phe Ile Asp Lys Val Gln Phe Leu Glu Gln
145                 150                 155                 160
Gln Asn Lys Val Leu Glu Thr Lys Trp Asn Leu Leu Gln Gln Gln Thr
                    165                 170                 175
Thr Thr Thr Ser Ser Lys Asn Leu Glu Pro Leu Phe Glu Thr Tyr Leu
                    180                 185                 190
Ser Val Leu Arg Lys Gln Leu Asp Thr Leu Gly Asn Asp Lys Gly Arg
            195                 200                 205
Leu Gln Ser Glu Leu Lys Thr Met Gln Asp Ser Val Glu Asp Phe Lys
    210                 215                 220
Thr Lys Tyr Glu Glu Glu Ile Asn Lys Arg Thr Ala Ala Glu Asn Asp
225                 230                 235                 240
Phe Val Val Leu Lys Lys Asp Val Asp Ala Ala Tyr Leu Asn Lys Val
                    245                 250                 255
Glu Leu Glu Ala Lys Val Asp Ser Leu Asn Asp Glu Ile Asn Phe Leu
                    260                 265                 270
Lys Val Leu Tyr Asp Ala Glu Leu Ser Gln Met Gln Thr His Val Ser
                    275                 280                 285
Asp Thr Ser Val Val Leu Ser Met Asp Asn Asn Arg Asn Leu Asp Leu
    290                 295                 300
Asp Ser Ile Ile Ala Glu Val Arg Ala Gln Tyr Glu Glu Ile Ala Gln
305                 310                 315                 320
Arg Ser Lys Ala Glu Ala Glu Ala Leu Tyr Gln Thr Lys Val Gln Gln
                    325                 330                 335
Leu Gln Ile Ser Val Asp Gln His Gly Asp Asn Leu Lys Asn Thr Lys
                    340                 345                 350
Ser Glu Ile Ala Glu Leu Asn Arg Met Ile Gln Arg Leu Arg Ala Glu
            355                 360                 365
Ile Glu Asn Ile Lys Lys Gln Cys Gln Thr Leu Gln Val Ser Val Ala
    370                 375                 380
Asp Ala Glu Gln Arg Gly Glu Asn Ala Leu Lys Asp Ala His Ser Lys
385                 390                 395                 400
Arg Val Glu Leu Glu Ala Ala Leu Gln Gln Ala Lys Glu Glu Leu Ala
                    405                 410                 415
Arg Met Leu Arg Glu Tyr Gln Glu Leu Met Ser Val Lys Leu Ala Leu
                    420                 425                 430
Asp Ile Glu Ile Ala Thr Tyr Arg Lys Leu Leu Glu Gly Glu Glu Tyr
            435                 440                 445
Arg Met Ser Gly Glu Cys Gln Ser Ala Val Ser Ile Ser Val Val Ser
    450                 455                 460
Gly Ser Thr Ser Thr Gly Gly Ile Ser Gly Leu Gly Ser Gly Ser
465                 470                 475                 480
Gly Phe Gly Leu Ser Ser Gly Phe Gly Ser Gly Ser Gly Ser Gly Phe
                    485                 490                 495
```

Gly Phe Gly Gly Ser Val Ser Gly Ser Ser Ser Lys Ile Ile Ser
        500                 505                 510

Thr Thr Thr Leu Asn Lys Arg Arg
        515                 520

<210> SEQ ID NO 2
<211> LENGTH: 2147
<212> TYPE: DNA
<213> ORGANISM: Homo sapiens

<400> SEQUENCE: 2

| | | | | |
|---|---|---|---|---|
| actcaccggc | ctgggccctg | tcacttctct | gatagctccc | agctcgctct | ctgcagccat | 60 |
| gattgccaga | cagcagtgtg | tccgaggcgg | gccccggggc | ttcagctgtg | gctcggccat | 120 |
| tgtaggcggt | ggcaagagag | gtgccttcag | ctcagtctcc | atgtctggag | gtgctggccg | 180 |
| atgctcttct | gggggatttg | gcagcagaag | cctctacaac | ctcaggggga | acaaaagcat | 240 |
| ctccatgagt | gtggctgggt | cacgacaagg | tgcctgcttt | ggggtgctg | gaggctttgg | 300 |
| cactggtggc | tttggtggtg | gatttggggg | ctccttcagt | ggtaagggtg | ccctggctt | 360 |
| ccccgtctgc | cccgctgggg | gaattcagga | ggtcaccatc | aaccagagct | tgctcaccc | 420 |
| cctccacgtg | gagattgacc | ctgagatcca | gaaagtccgg | acggaagagc | gcgaacagat | 480 |
| caagctcctc | aacaacaagt | ttgcctcctt | catcgacaag | gtgcagttct | tagagcaaca | 540 |
| gaataaggtc | ctggagacca | atggaacct | gctccagcag | cagacgacca | ccacctccag | 600 |
| caaaaaccct | gagcccctct | ttgagaccta | cctcagtgtc | ctgaggaagc | agctagatac | 660 |
| cttgggcaat | gacaaagggc | gcctgcagtc | tgagctgaag | accatgcagg | acagcgtgga | 720 |
| ggacttcaag | actaagtatg | aagaggagat | caacaaacgc | acagcagccg | agaatgactt | 780 |
| tgtggtccta | aagaaggacg | tggatgctgc | ctacctgaac | aaggtggagt | tggaggccaa | 840 |
| ggtgacagt | cttaatgacg | agatcaactt | cctgaaggtc | ctctatgatg | cggagctgtc | 900 |
| ccagatgcag | acccatgtca | gcgacacgtc | cgtggtcctt | tccatggaca | acaaccgcaa | 960 |
| cctggacctg | gacagcatta | ttgccgaggt | ccgtgcccag | tacgaggaga | ttgcccagag | 1020 |
| gagcaaggct | gaggctgaag | ccctgtacca | gaccaaggtc | cagcagctcc | agatctcggt | 1080 |
| tgaccaacat | ggtgacaacc | tgaagaacac | caagagtgaa | attgcagagc | tcaacaggat | 1140 |
| gatccagagg | ctgcgggcag | agatcgagaa | catcaagaag | cagtgccaga | ctcttcaggt | 1200 |
| atccgtggct | gatgcagagc | agcgaggtga | gaatgccctt | aaagatgccc | acagcaagcg | 1260 |
| cgtagagctg | gaggctgccc | tgcagcaggc | caaggaggag | ctggcacgaa | tgctgcgtga | 1320 |
| gtaccaggag | ctcatgagtg | tgaagctggc | cttggacatc | gagatcgcca | cctaccgcaa | 1380 |
| actgctggag | ggcgaggagt | acagaatgtc | tggagaatgc | cagagtgccg | tgagcatctc | 1440 |
| tgtggtcagc | ggtagcacca | gcactggagg | catcagcgga | ggattaggaa | gtggctccgg | 1500 |
| gtttggcctg | agtagtggct | ttggctccgg | ctctggaagt | ggctttgggt | ttggtggcag | 1560 |
| tgtctctggc | agttccagca | gcaagatcat | ctctaccacc | accctgaaca | agagacgata | 1620 |
| gaggagacga | ggtccctgca | gctcactgtg | tccagctggg | cccagcactg | gtgtctctgt | 1680 |
| gcttccttca | cttcacctcc | atcctctgtc | tctgggctc | atcttactag | tatccctcc | 1740 |
| actatcccat | gggctctctc | tgccccagga | tgatcttctg | tgctgggaca | gggactctgc | 1800 |
| ctcttggagt | ttggtagcta | cttcttgatt | tgggcctggt | gacccacctg | gaatgggaag | 1860 |
| gatgtcagct | gacctctcac | ctcccatgga | cagagaagaa | aatgaccagg | agtgtcatct | 1920 |

```
ccagaattat tggggtcaca tatgtccctt cccagtccaa tgccatctcc cactagatcc    1980
tgtattatcc atctcatca gaaccaaact acttctccaa cacccggcag cacttggccc    2040
tgcaagctta ggatgagaac cacttagtgt cccattctac tcctctcatt ccctcttatc   2100
catctgcagg tgaatcttca ataaaatgct tttgtcattc attctga                 2147
```

```
<210> SEQ ID NO 3
<211> LENGTH: 469
<212> TYPE: PRT
<213> ORGANISM: Homo sapiens

<400> SEQUENCE: 3

Met Ser Ile His Phe Ser Ser Pro Val Phe Thr Ser Arg Ser Ala Ala
1               5                   10                  15

Phe Ser Gly Arg Gly Ala Gln Val Arg Leu Ser Ser Ala Arg Pro Gly
            20                  25                  30

Gly Leu Gly Ser Ser Ser Leu Tyr Gly Leu Gly Ala Ser Arg Pro Arg
        35                  40                  45

Val Ala Val Arg Ser Ala Tyr Gly Gly Pro Val Gly Ala Gly Ile Arg
    50                  55                  60

Glu Val Thr Ile Asn Gln Ser Leu Leu Ala Pro Leu Arg Leu Asp Ala
65                  70                  75                  80

Asp Pro Ser Leu Gln Arg Val Arg Gln Glu Glu Ser Glu Gln Ile Lys
                85                  90                  95

Thr Leu Asn Asn Lys Phe Ala Ser Phe Ile Asp Lys Val Arg Phe Leu
            100                 105                 110

Glu Gln Gln Asn Lys Leu Leu Glu Thr Lys Trp Thr Leu Leu Gln Glu
        115                 120                 125

Gln Lys Ser Ala Lys Ser Ser Arg Leu Pro Asp Ile Phe Glu Ala Gln
    130                 135                 140

Ile Ala Gly Leu Arg Gly Gln Leu Glu Ala Leu Gln Val Asp Gly Gly
145                 150                 155                 160

Arg Leu Glu Ala Glu Leu Arg Ser Met Gln Asp Val Val Glu Asp Phe
                165                 170                 175

Lys Asn Lys Tyr Glu Asp Glu Ile Asn His Arg Thr Ala Ala Glu Asn
            180                 185                 190

Glu Phe Val Val Leu Lys Lys Asp Val Asp Ala Ala Tyr Met Ser Lys
        195                 200                 205

Val Glu Leu Glu Ala Lys Val Asp Ala Leu Asn Asp Glu Ile Asn Phe
    210                 215                 220

Leu Arg Thr Leu Asn Glu Thr Glu Leu Thr Glu Leu Gln Ser Gln Ile
225                 230                 235                 240

Ser Asp Thr Ser Val Val Leu Ser Met Asp Asn Ser Arg Ser Leu Asp
                245                 250                 255

Leu Asp Gly Ile Ile Ala Glu Val Lys Ala Gln Tyr Glu Glu Met Ala
            260                 265                 270

Lys Cys Ser Arg Ala Glu Ala Glu Ala Trp Tyr Gln Thr Lys Phe Glu
        275                 280                 285

Thr Leu Gln Ala Gln Ala Gly Lys His Gly Asp Asp Leu Arg Asn Thr
    290                 295                 300

Arg Asn Glu Ile Ser Glu Met Asn Arg Ala Ile Gln Arg Leu Gln Ala
305                 310                 315                 320

Glu Ile Asp Asn Ile Lys Asn Gln Arg Ala Lys Leu Glu Ala Ala Ile
                325                 330                 335
```

```
Ala Glu Ala Glu Glu Arg Gly Glu Leu Ala Leu Lys Asp Ala Arg Ala
            340                 345                 350
Lys Gln Glu Glu Leu Glu Ala Ala Leu Gln Arg Gly Lys Gln Asp Met
        355                 360                 365
Ala Arg Gln Leu Arg Glu Tyr Gln Glu Leu Met Ser Val Lys Leu Ala
    370                 375                 380
Leu Asp Ile Glu Ile Ala Thr Tyr Arg Lys Leu Leu Glu Gly Glu Glu
385                 390                 395                 400
Ser Arg Leu Ala Gly Asp Gly Val Gly Ala Val Asn Ile Ser Val Met
                405                 410                 415
Asn Ser Thr Gly Gly Ser Ser Ser Gly Gly Gly Ile Gly Leu Thr Leu
            420                 425                 430
Gly Gly Thr Met Gly Ser Asn Ala Leu Ser Phe Ser Ser Ala Gly
        435                 440                 445
Pro Gly Leu Leu Lys Ala Tyr Ser Ile Arg Thr Ala Ser Ala Ser Arg
    450                 455                 460
Arg Ser Ala Arg Asp
465

<210> SEQ ID NO 4
<211> LENGTH: 1753
<212> TYPE: DNA
<213> ORGANISM: Homo sapiens

<400> SEQUENCE: 4
cagccccgcc cctacctgtg aagcccagc cgcccgctcc cgcggataaa aggcgcggag     60
tgtccccgag gtcagcgagt gcgcgctcct cctcgcccgc cgctaggtcc atcccggccc    120
agccaccatg tccatccact tcagctcccc ggtattcacc tcgcgctcag ccgccttctc    180
gggccgcggc gcccaggtgc gcctgagctc cgctcgcccc ggcggccttg gcagcagcag    240
cctctacggc ctcggcgcct cacggccgcg cgtggccgtg cgctctgcct atggggcc     300 ggtgggcgcc ggcatccgcg aggtcaccat taaccagagc ctgctggccc cgctgcggct    360
ggacgccgac ccctccctcc agcgggtgcg ccaggaggag agcgagcaga tcaagaccct    420
caacaacaag tttgcctcct tcatcgacaa ggtgcggttt ctggagcagc agaacaagct    480
gctggagacc aagtggacgc tgctgcagga gcagaagtcg ccaagagca gccgcctccc    540 agacatcttt gaggcccaga ttgctggcct tcggggtcag cttgaggcac tgcaggtgga    600
tgggggccgc ctggaggcgg agctgcggag catgcaggat gtggtggagg acttcaagaa    660
taagtacgaa gatgaaatta accaccgcac agctgctgag aatgagtttg tggtgctgaa    720
gaaggatgtg gatgctgcct acatgagcaa ggtggagctg gaggccaagg tggatgccct    780
gaatgatgag atcaacttcc tcaggaccct caatgagacg gagttgacag agctgcagtc    840
ccagatctcc gacacatctg tggtgctgtc catggacaac agtcgctccc tggacctgga    900
cggcatcatc gctgaggtca aggcgcagta tgaggagatg gccaaatgca gccgggctga    960
ggctgaagcc tggtaccaga ccaagtttga ccctccag gcccaggctg gaagcatgg    1020 ggacgacctc cggaatacccc ggaatgagat tcagagatg aaccgggcca tccagaggct    1080
gcaggctgag atcgacaaca tcaagaacca gcgtgccaag ttggaggccg ccattgccga    1140
ggctgaggag cgtggggagc tggcgctcaa ggatgctcgt gccaagcagg aggagctgga    1200
agccgccctg cagcggggca agcaggatat ggcacgcgca gctgcgtgagt accaggaact    1260 catgagcgtg aagctggccc tggacatcga gatcgccacc taccgcaagc tgctggaggg    1320
```

```
cgaggagagc cggttggctg gagatggagt gggagccgtg aatatctctg tgatgaattc    1380
cactggtggc agtagcagtg gcggtggcat tgggctgacc ctcgggggaa ccatgggcag    1440
caatgccctg agcttctcca gcagtgcggg tcctgggctc ctgaaggctt attccatccg    1500
gaccgcatcc gccagtcgca ggagtgcccg cgactgagcc gcctcccacc actccactcc    1560
tccagccacc acccacaatc acaagaagat tcccacccct gcctcccatg cctggtccca    1620
agacagtgag acagtctgga aagtgatgtc agaatagctt ccaataaagc agcctcattc    1680
tgaggcctga gtgatccacg tgaaaaaaaa aaaaaaaaaa aaaaaaaaaa aaaaaaaaaa    1740
aaaaaaaaaa aaa                                                       1753
```

<210> SEQ ID NO 5
<211> LENGTH: 511
<212> TYPE: PRT
<213> ORGANISM: Homo sapiens

<400> SEQUENCE: 5

```
Met Asn Gly Val Ser Trp Ser Gln Asp Leu Gln Glu Gly Ile Ser Ala
1               5                   10                  15

Trp Phe Gly Pro Pro Ala Ser Thr Pro Ala Ser Thr Met Ser Ile Arg
            20                  25                  30

Val Thr Gln Lys Ser Tyr Lys Val Ser Thr Ser Gly Pro Arg Ala Phe
        35                  40                  45

Ser Ser Arg Ser Tyr Thr Ser Gly Pro Gly Ser Arg Ile Ser Ser Ser
    50                  55                  60

Ser Phe Ser Arg Val Gly Ser Ser Asn Phe Arg Gly Gly Leu Gly Gly
65                  70                  75                  80

Gly Tyr Gly Gly Ala Ser Gly Met Gly Gly Ile Thr Ala Val Thr Val
                85                  90                  95

Asn Gln Ser Leu Leu Ser Pro Leu Val Leu Glu Val Asp Pro Asn Ile
            100                 105                 110

Gln Ala Val Arg Thr Gln Glu Lys Glu Gln Ile Lys Thr Leu Asn Asn
        115                 120                 125

Lys Phe Ala Ser Phe Ile Asp Lys Val Arg Phe Leu Glu Gln Gln Asn
    130                 135                 140

Lys Met Leu Glu Thr Lys Trp Ser Leu Leu Gln Gln Gln Lys Thr Ala
145                 150                 155                 160

Arg Ser Asn Met Asp Asn Met Phe Glu Ser Tyr Ile Asn Asn Leu Arg
                165                 170                 175

Arg Gln Leu Glu Thr Leu Gly Gln Glu Lys Leu Lys Leu Glu Ala Glu
            180                 185                 190

Leu Gly Asn Met Gln Gly Leu Val Glu Asp Phe Lys Asn Lys Tyr Glu
        195                 200                 205

Asp Glu Ile Asn Lys Arg Thr Glu Met Glu Asn Glu Phe Val Leu Ile
    210                 215                 220

Lys Lys Asp Val Asp Glu Ala Tyr Met Asn Lys Val Glu Leu Glu Ser
225                 230                 235                 240

Arg Leu Glu Gly Leu Thr Asp Glu Ile Asn Phe Leu Arg Gln Leu Tyr
                245                 250                 255

Glu Glu Glu Ile Arg Glu Leu Gln Ser Gln Ile Ser Asp Thr Ser Val
            260                 265                 270

Val Leu Ser Met Asp Asn Ser Arg Ser Leu Asp Met Asp Ser Ile Ile
        275                 280                 285

Ala Glu Val Lys Ala Gln Tyr Glu Asp Ile Ala Asn Arg Ser Arg Ala
```

```
                    290                 295                 300
Glu Ala Glu Ser Met Tyr Gln Ile Lys Tyr Glu Leu Gln Ser Leu
305                 310                 315                 320

Ala Gly Lys His Gly Asp Asp Leu Arg Arg Thr Lys Thr Glu Ile Ser
                325                 330                 335

Glu Met Asn Arg Asn Ile Ser Arg Leu Gln Ala Glu Ile Glu Gly Leu
                340                 345                 350

Lys Gly Gln Arg Ala Ser Leu Glu Ala Ala Ile Ala Asp Ala Glu Gln
                355                 360                 365

Arg Gly Glu Leu Ala Ile Lys Asp Ala Asn Ala Lys Leu Ser Glu Leu
                370                 375                 380

Glu Ala Ala Leu Gln Arg Ala Lys Gln Asp Met Ala Arg Gln Leu Arg
385                 390                 395                 400

Glu Tyr Gln Glu Leu Met Asn Val Lys Leu Ala Leu Asp Ile Glu Ile
                405                 410                 415

Ala Thr Tyr Arg Lys Leu Leu Glu Gly Glu Glu Ser Arg Leu Glu Ser
                420                 425                 430

Gly Met Gln Asn Met Ser Ile His Thr Lys Thr Thr Ser Gly Tyr Ala
                435                 440                 445

Gly Gly Leu Ser Ser Ala Tyr Gly Gly Leu Thr Ser Pro Gly Leu Ser
            450                 455                 460

Tyr Ser Leu Gly Ser Ser Phe Gly Ser Gly Ala Gly Ser Ser Ser Phe
465                 470                 475                 480

Ser Arg Thr Ser Ser Arg Ala Val Val Val Lys Lys Ile Glu Thr
                485                 490                 495

Arg Asp Gly Lys Leu Val Ser Glu Ser Ser Asp Val Leu Pro Lys
                500                 505                 510

<210> SEQ ID NO 6
<211> LENGTH: 1807
<212> TYPE: DNA
<213> ORGANISM: Homo sapiens

<400> SEQUENCE: 6
attcagcaaa tgtttgcgga atgaatgggg tgagctggag ccaggacctg caggaaggga      60
tctccgcctg gttcggcccg cctgcctcca ctcctgcctc taccatgtcc atcagggtga     120
cccagaagtc ctacaaggtg tccacctctg cccccgggc cttcagcagc cgctcctaca     180
cgagtgggcc cggttcccgc atcagctcct cgagcttctc ccgagtgggc agcagcaact     240
ttcgcggtgg cctgggcggc ggctatggtg gggccagcgg catgggaggc atcaccgcag     300
ttacggtcaa ccagagcctg ctgagccccc ttgtcctgga ggtggacccc aacatccagg     360
ccgtgcgcac ccaggagaag gagcagatca gaccctcaa caacaagttt gcctccttca     420
tagacaaggt acggttcctg gagcagcaga caagatgct ggagaccaag tggagcctcc     480
tgcagcagca gaagacggct cgaagcaaca tggacaacat gttcgagagc tacatcaaca     540
accttaggcg gcagctggag actctgggcc aggagaagct gaagctggag gcggagcttg     600
gcaacatgca ggggctggtg gaggacttca agaacaagta tgaggatgag atcaataagc     660
gtacagagat ggagaacgaa tttgtcctca tcaagaagga tgtggatgaa gcttacatga     720
acaaggtaga gctggagtct cgcctggaag ggctgaccga cgagatcaac ttcctcaggc     780
agctatatga agaggagatc cgggagctgc agtcccagat ctcggacaca tctgtggtgc     840
tgtccatgga caacagccgc tccctggaca tggacagcat cattgctgag gtcaaggcac     900
```

```
agtacgagga tattgccaac cgcagccggg ctgaggctga gagcatgtac cagatcaagt   960
atgaggagct gcagagcctg gctgggaagc acggggatga cctgcggcgc acaaagactg  1020
agatctctga gatgaaccgg aacatcagcc ggctccaggc tgagattgag ggcctcaaag  1080
gccagagggc ttccctggag gccgccattg cagatgccga gcagcgtgga gagctggcca  1140
ttaaggatgc caacgccaag ttgtccgagc tggaggccgc cctgcagcgg gccaagcagg  1200
acatggcgcg gcagctgcgt gagtaccagg agctgatgaa cgtcaagctg ccctggaca   1260
tcgagatcgc cacctacagg aagctgctgg agggcgagga gagccggctg gagtctggga  1320
tgcagaacat gagtattcat acgaagacca ccagcggcta tgcaggtggt ctgagctcgg  1380
cctatggggg cctcacaagc cccggcctca gctacagcct gggctccagc tttggctctg  1440
gcgcgggctc cagctccttc agccgcacca gctcctccag gccgtggtt gtgaagaaga   1500
tcgagacacg tgatgggaag ctggtgtctg agtcctctga cgtcctgccc aagtgaacag  1560
ctgcggcagc ccctcccagc ctaccccctcc tgcgctgccc cagagcctgg gaaggaggcc  1620
gctatgcagg gtagcactgg gaacaggaga cccacctgag gctcagccct agccctcagc  1680
ccacctgggg agtttactac ctggggaccc cccttgccca tgcctccagc tacaaaacaa  1740
ttcaattgct ttttttttt ggtccaaaat aaaacctcag ctagctctgc caatgtcaaa   1800
aaaaaaa                                                            1807
```

```
<210> SEQ ID NO 7
<211> LENGTH: 483
<212> TYPE: PRT
<213> ORGANISM: Homo sapiens

<400> SEQUENCE: 7

Met Ser Ile Arg Val Thr Gln Lys Ser Tyr Lys Val Ser Thr Ser Gly
1               5                   10                  15

Pro Arg Ala Phe Ser Ser Arg Ser Tyr Thr Ser Gly Pro Gly Ser Arg
            20                  25                  30

Ile Ser Ser Ser Ser Phe Ser Arg Val Gly Ser Ser Asn Phe Arg Gly
        35                  40                  45

Gly Leu Gly Gly Gly Tyr Gly Gly Ala Ser Gly Met Gly Gly Ile Thr
    50                  55                  60

Ala Val Thr Val Asn Gln Ser Leu Leu Ser Pro Leu Val Leu Glu Val
65                  70                  75                  80

Asp Pro Asn Ile Gln Ala Val Arg Thr Gln Glu Lys Glu Gln Ile Lys
                85                  90                  95

Thr Leu Asn Asn Lys Phe Ala Ser Phe Ile Asp Lys Val Arg Phe Leu
            100                 105                 110

Glu Gln Gln Asn Lys Met Leu Glu Thr Lys Trp Ser Leu Leu Gln Gln
        115                 120                 125

Gln Lys Thr Ala Arg Ser Asn Met Asp Asn Met Phe Glu Ser Tyr Ile
    130                 135                 140

Asn Asn Leu Arg Arg Gln Leu Glu Thr Leu Gly Gln Glu Lys Leu Lys
145                 150                 155                 160

Leu Glu Ala Glu Leu Gly Asn Met Gln Gly Leu Val Glu Asp Phe Lys
                165                 170                 175

Asn Lys Tyr Glu Asp Glu Ile Asn Lys Arg Thr Glu Met Glu Asn Glu
            180                 185                 190

Phe Val Leu Ile Lys Lys Asp Val Asp Glu Ala Tyr Met Asn Lys Val
        195                 200                 205
```

Glu Leu Glu Ser Arg Leu Glu Gly Leu Thr Asp Glu Ile Asn Phe Leu
    210                 215                 220

Arg Gln Leu Tyr Glu Glu Ile Arg Glu Leu Gln Ser Gln Ile Ser
225                 230                 235                 240

Asp Thr Ser Val Val Leu Ser Met Asp Asn Ser Arg Ser Leu Asp Met
                245                 250                 255

Asp Ser Ile Ile Ala Glu Val Lys Ala Gln Tyr Glu Asp Ile Ala Asn
            260                 265                 270

Arg Ser Arg Ala Glu Ala Glu Ser Met Tyr Gln Ile Lys Tyr Glu Glu
        275                 280                 285

Leu Gln Ser Leu Ala Gly Lys His Gly Asp Asp Leu Arg Arg Thr Lys
    290                 295                 300

Thr Glu Ile Ser Glu Met Asn Arg Asn Ile Ser Arg Leu Gln Ala Glu
305                 310                 315                 320

Ile Glu Gly Leu Lys Gly Gln Arg Ala Ser Leu Glu Ala Ala Ile Ala
                325                 330                 335

Asp Ala Glu Gln Arg Gly Glu Leu Ala Ile Lys Asp Ala Asn Ala Lys
            340                 345                 350

Leu Ser Glu Leu Glu Ala Ala Leu Gln Arg Ala Lys Gln Asp Met Ala
        355                 360                 365

Arg Gln Leu Arg Glu Tyr Gln Glu Leu Met Asn Val Lys Leu Ala Leu
    370                 375                 380

Asp Ile Glu Ile Ala Thr Tyr Arg Lys Leu Leu Glu Gly Glu Glu Ser
385                 390                 395                 400

Arg Leu Glu Ser Gly Met Gln Asn Met Ser Ile His Thr Lys Thr Thr
                405                 410                 415

Ser Gly Tyr Ala Gly Gly Leu Ser Ser Ala Tyr Gly Gly Leu Thr Ser
            420                 425                 430

Pro Gly Leu Ser Tyr Ser Leu Gly Ser Ser Phe Gly Ser Gly Ala Gly
        435                 440                 445

Ser Ser Ser Phe Ser Arg Thr Ser Ser Arg Ala Val Val Val Lys
    450                 455                 460

Lys Ile Glu Thr Arg Asp Gly Lys Leu Val Ser Glu Ser Ser Asp Val
465                 470                 475                 480

Leu Pro Lys

<210> SEQ ID NO 8
<211> LENGTH: 1901
<212> TYPE: DNA
<213> ORGANISM: Homo sapiens

<400> SEQUENCE: 8
acaggccttt ccttacctcc ctccatgctg tccacttcct ctgtaaagct ctcaaccctg      60
tccccttccc cctctctcct gggaaagagc cctcccatgc ctagctgctg ctcttaggga    120
ccctgtggct aggtgcgcgg atggaaatcc aggatctccg cctggttcgg cccgcctgcc    180
tccactcctg cctctaccat gtccatcagg gtgacccaga agtcctacaa ggtgtccacc    240
tctggccccc gggccttcag cagccgctcc tacacgagtg ggcccggttc ccgcatcagc    300
tcctcgagct ctcccgagt gggcagcagc aactttcgcg gtggcctggg cggcggctat    360 ggtgggggcca gcggcatggg aggcatcacc gcagttacgg tcaaccagag cctgctgagc    420 cccccttgtcc tggaggtgga ccccaacatc caggccgtgc gcacccagga gaaggagcag    480
atcaagaccc tcaacaacaa gtttgcctcc ttcatagaca aggtacggtt cctggagcag    540

```
cagaacaaga tgctggagac caagtggagc ctcctgcagc agcagaagac ggctcgaagc    600
aacatggaca acatgttcga gagctacatc aacaacctta ggcggcagct ggagactctg    660
ggccaggaga agctgaagct ggaggcggag cttggcaaca tgcagggggct ggtggaggac   720 ttcaagaaca agtatgagga tgagatcaat aagcgtacag atggagaa cgaatttgtc      780 ctcatcaaga aggatgtgga tgaagcttac atgaacaagg tagagctgga gtctcgcctg    840
gaagggctga ccgacgagat caacttcctc aggcagctat atgaagagga gatccgggag    900
ctgcagtccc agatctcgga cacatctgtg gtgctgtcca tggacaacag ccgctccctg    960
gacatggaca gcatcattgc tgaggtcaag gcacagtacg aggatattgc aaccgcagc    1020 cgggctgagg ctgagagcat gtaccagatc aagtatgagg agctgcagag cctggctggg   1080
aagcacgggg atgacctgcg cgcacacaaag actgagatct ctgagatgaa ccggaacatc   1140
agccggctcc aggctgagat tgagggcctc aaaggccaga gggcttccct ggaggccgcc   1200
attgcagatg ccgagcagcg tggagagctg gccattaagg atgccaacgc caagttgtcc   1260
gagctggagg ccgccctgca gcgggccaag caggacatgg cgcggcagct gcgtgagtac   1320
caggagctga tgaacgtcaa gctggccctg gacatcgaga tcgccaccta caggaagctg   1380
ctggagggcg aggagagccg gctggagtct gggatgcaga acatgagtat tcatacgaag   1440
accaccagcg gctatgcagg tggtctgagc tcggcctatg ggggcctcac aagccccggc   1500
ctcagctaca gcctgggctc cagctttggc tctggcgcgg gctccagctc cttcagccgc   1560
accagctcct ccagggccgt ggttgtgaag aagatcgaga cacgtgatgg gaagctggtg   1620
tctgagtcct ctgacgtcct gcccaagtga acagctgcgg cagcccctcc cagcctaccc   1680
ctcctgcgct gccccagagc ctgggaagga ggccgctatg cagggtagca ctgggaacag   1740
gagacccacc tgaggctcag ccctagcccct cagcccacct ggggagttta ctacctgggg   1800
accccccttg cccatgcctc cagctacaaa acaattcaat tgcttttttt ttttggtcca   1860
aaataaaacc tcagctagct ctgccaatgt caaaaaaaaa a                       1901
```

<210> SEQ ID NO 9
<211> LENGTH: 456
<212> TYPE: PRT
<213> ORGANISM: Homo sapiens

<400> SEQUENCE: 9

```
Met Thr Thr Thr Phe Leu Gln Thr Ser Ser Ser Thr Phe Gly Gly Gly
1               5                   10                  15

Ser Thr Arg Gly Gly Ser Leu Leu Ala Gly Gly Gly Phe Gly Gly
            20                  25                  30

Gly Ser Leu Ser Gly Gly Gly Ser Arg Ser Ile Ser Ala Ser Ser
        35                  40                  45

Ala Arg Phe Val Ser Ser Gly Ser Gly Gly Gly Tyr Gly Gly Gly Met
    50                  55                  60

Arg Val Cys Gly Phe Gly Gly Gly Ala Gly Ser Val Phe Gly Gly Gly
65                  70                  75                  80

Phe Gly Gly Gly Val Gly Gly Gly Phe Gly Gly Gly Phe Gly Gly Gly
                85                  90                  95

Asp Gly Gly Leu Leu Ser Gly Asn Glu Lys Ile Thr Met Gln Asn Leu
            100                 105                 110

Asn Asp Arg Leu Ala Ser Tyr Leu Asp Lys Val Arg Ala Leu Glu Glu
        115                 120                 125

Ala Asn Ala Asp Leu Glu Val Lys Ile His Asp Trp Tyr Gln Lys Gln
```

```
                130             135             140
Thr Pro Thr Ser Pro Glu Cys Asp Tyr Ser Gln Tyr Phe Lys Thr Ile
145                 150                 155                 160

Glu Glu Leu Arg Asp Lys Ile Met Ala Thr Thr Ile Asp Asn Ser Arg
                165                 170                 175

Val Ile Leu Glu Ile Asp Asn Ala Arg Leu Ala Ala Asp Asp Phe Arg
            180                 185                 190

Leu Lys Tyr Glu Asn Glu Leu Ala Leu Arg Gln Gly Val Glu Ala Asp
        195                 200                 205

Ile Asn Gly Leu Arg Arg Val Leu Asp Glu Leu Thr Leu Ala Arg Thr
    210                 215                 220

Asp Leu Glu Met Gln Ile Glu Gly Leu Asn Glu Glu Leu Ala Tyr Leu
225                 230                 235                 240

Lys Lys Asn His Glu Glu Glu Met Lys Glu Phe Ser Ser Gln Leu Ala
                245                 250                 255

Gly Gln Val Asn Val Glu Met Asp Ala Ala Pro Gly Val Asp Leu Thr
            260                 265                 270

Arg Val Leu Ala Glu Met Arg Glu Gln Tyr Glu Ala Met Ala Glu Lys
        275                 280                 285

Asn Arg Arg Asp Val Glu Ala Trp Phe Phe Ser Lys Thr Glu Glu Leu
    290                 295                 300

Asn Lys Glu Val Ala Ser Asn Thr Glu Met Ile Gln Thr Ser Lys Thr
305                 310                 315                 320

Glu Ile Thr Asp Leu Arg Arg Thr Met Gln Glu Leu Glu Ile Glu Leu
                325                 330                 335

Gln Ser Gln Leu Ser Met Lys Ala Gly Leu Glu Asn Ser Leu Ala Glu
            340                 345                 350

Thr Glu Cys Arg Tyr Ala Thr Gln Leu Gln Gln Ile Gln Gly Leu Ile
        355                 360                 365

Gly Gly Leu Glu Ala Gln Leu Ser Glu Leu Arg Cys Glu Met Glu Ala
    370                 375                 380

Gln Asn Gln Glu Tyr Lys Met Leu Leu Asp Ile Lys Thr Arg Leu Glu
385                 390                 395                 400

Gln Glu Ile Ala Thr Tyr Arg Ser Leu Leu Glu Gly Gln Asp Ala Lys
                405                 410                 415

Met Ala Gly Ile Gly Ile Arg Glu Ala Ser Ser Gly Gly Gly Gly Ser
            420                 425                 430

Ser Ser Asn Phe His Ile Asn Val Glu Glu Ser Val Asp Gly Gln Val
        435                 440                 445

Val Ser Ser His Lys Arg Glu Ile
450                 455

<210> SEQ ID NO 10
<211> LENGTH: 1861
<212> TYPE: DNA
<213> ORGANISM: Homo sapiens

<400> SEQUENCE: 10
cactcaaggt gtgcaggcag ctgtgtttgt caggaaggca gaaggagttg gctttgcttt       60 agggaggag acgaggtccc acaacaccct ctgaagggta tataaggagc cccagcgtgc      120
agcctggcct ggtacctcct gccagcatct cttgggtttg ctgagaactc acgggctcca      180
gctacctggc catgaccacc acatttctgc aaacttcttc ctccaccttt ggggtggct      240 caacccgagg gggttccctc ctggctgggg gaggtggctt tggtgggggg agtctctctg      300
```

```
ggggaggtgg aagccgaagt atctcagctt cttctgctag gtttgtctct tcagggtcag      360
gaggaggata tggggtggc atgagggtct gtggctttgg tggaggggct ggtagtgttt       420
tcggtggagg cttggaggg ggcgttggtg ggggttttgg tggtggcttt ggtggtggcg       480
atggtggtct cctctctggc aatgagaaaa ttaccatgca gaacctcaat gaccgcctgg      540
cctcctacct ggacaaggta cgtgccctgg aggaggccaa tgctgacctg gaggtgaaga      600
tccatgactg gtaccagaag cagaccccaa ccagcccaga atgcgactac agccaatact      660
tcaagaccat tgaagagctc cgggacaaga tcatggccac caccatcgac aactcccggg      720
tcatcctgga gatcgacaat gccaggctgg ctgcggacga cttcaggctc aagtatgaga      780
atgagctggc cctgcgccag ggcgttgagg ctgacatcaa cggcttgcgc cgagtcctgg      840
atgagctgac cctggccagg actgacctgg agatgcagat cgagggcctg aatgaggagc      900
tagcctacct gaagaagaac cacgaagagg agatgaagga gttcagcagc agctggccg       960
gccaggtcaa tgtggagatg gacgcagcac cgggtgtgga cctgaccgt gtgctggcag      1020
agatgaggga gcagtacgag gccatggcgg agaagaaccg ccgggatgtc gaggcctggt      1080
tcttcagcaa gactgaggag ctgaacaaag aggtggcctc caacacagaa atgatccaga     1140
ccagcaagac ggagatcaca gacctgagac gcacgatgca ggagctggag atcgagctgc     1200
agtcccagct cagcatgaaa gctggctgg agaactcact ggccgagaca gagtgccgct      1260
atgccacgca gctgcagcag atccagggc tcattggtgg cctggaggcc agctgagtg       1320
agctccgatg cgagatggag gctcagaacc aggagtacaa gatgctgctt gacataaaga     1380
cacggctgga gcaggagatc gctacttacc gcagcctgct cgagggccag gatgccaaga     1440
tggctggcat tggcatcagg gaagcctctt caggaggtgg tggtagcagc agcaatttcc     1500
acatcaatgt agaagagtca gtggatggac aggtggtttc ttcccacaag agagaaatct    1560
aagtgtctat tgcaggagaa acgtcccttg ccactcccca ctctcatcag gccaagtgga    1620
ggactggcca gagggcctgc acatgcaaac tccagtccct gccttcagag agctgaaaag    1680
ggtccctcgg tcttttattt cagggctttg catgcgctct attccccctc tgcctctccc    1740
caccttcttt ggagcaagga gatgcagctg tattgtgtaa caagctcatt tgtacagtgt    1800
ctgttcatgt aataaagaat tacttttcct tttgcaaata aaaaaaaaaa aaaaaaaaa     1860
a                                                                    1861
```

<210> SEQ ID NO 11
<211> LENGTH: 430
<212> TYPE: PRT
<213> ORGANISM: Homo sapiens

<400> SEQUENCE: 11

```
Met Ser Phe Thr Thr Arg Ser Thr Phe Ser Thr Asn Tyr Arg Ser Leu
1               5                   10                  15

Gly Ser Val Gln Ala Pro Ser Tyr Gly Ala Arg Pro Val Ser Ser Ala
            20                  25                  30

Ala Ser Val Tyr Ala Gly Ala Gly Gly Ser Gly Ser Arg Ile Ser Val
        35                  40                  45

Ser Arg Ser Thr Ser Phe Arg Gly Gly Met Gly Ser Gly Gly Leu Ala
    50                  55                  60

Thr Gly Ile Ala Gly Gly Leu Ala Gly Met Gly Gly Ile Gln Asn Glu
65                  70                  75                  80

Lys Glu Thr Met Gln Ser Leu Asn Asp Arg Leu Ala Ser Tyr Leu Asp
```

```
            85                  90                  95
Arg Val Arg Ser Leu Glu Thr Glu Asn Arg Arg Leu Glu Ser Lys Ile
            100                 105                 110

Arg Glu His Leu Glu Lys Lys Gly Pro Gln Val Arg Asp Trp Ser His
            115                 120                 125

Tyr Phe Lys Ile Ile Glu Asp Leu Arg Ala Gln Ile Phe Ala Asn Thr
            130                 135                 140

Val Asp Asn Ala Arg Ile Val Leu Gln Ile Asp Asn Ala Arg Leu Ala
145                 150                 155                 160

Ala Asp Asp Phe Arg Val Lys Tyr Glu Thr Glu Leu Ala Met Arg Gln
                165                 170                 175

Ser Val Glu Asn Asp Ile His Gly Leu Arg Lys Val Ile Asp Asp Thr
            180                 185                 190

Asn Ile Thr Arg Leu Gln Leu Glu Thr Glu Ile Glu Ala Leu Lys Glu
            195                 200                 205

Glu Leu Leu Phe Met Lys Lys Asn His Glu Glu Glu Val Lys Gly Leu
            210                 215                 220

Gln Ala Gln Ile Ala Ser Ser Gly Leu Thr Val Glu Val Asp Ala Pro
225                 230                 235                 240

Lys Ser Gln Asp Leu Ala Lys Ile Met Ala Asp Ile Arg Ala Gln Tyr
                245                 250                 255

Asp Glu Leu Ala Arg Lys Asn Arg Glu Glu Leu Asp Lys Tyr Trp Ser
            260                 265                 270

Gln Gln Ile Glu Glu Ser Thr Thr Val Val Thr Thr Gln Ser Ala Glu
            275                 280                 285

Val Gly Ala Ala Glu Thr Thr Leu Thr Glu Leu Arg Arg Thr Val Gln
290                 295                 300

Ser Leu Glu Ile Asp Leu Asp Ser Met Arg Asn Leu Lys Ala Ser Leu
305                 310                 315                 320

Glu Asn Ser Leu Arg Glu Val Glu Ala Arg Tyr Ala Leu Gln Met Glu
                325                 330                 335

Gln Leu Asn Gly Ile Leu Leu His Leu Glu Ser Glu Leu Ala Gln Thr
            340                 345                 350

Arg Ala Glu Gly Gln Arg Gln Ala Gln Glu Tyr Glu Ala Leu Leu Asn
            355                 360                 365

Ile Lys Val Lys Leu Glu Ala Glu Ile Ala Thr Tyr Arg Arg Leu Leu
            370                 375                 380

Glu Asp Gly Glu Asp Phe Asn Leu Gly Asp Ala Leu Asp Ser Ser Asn
385                 390                 395                 400

Ser Met Gln Thr Ile Gln Lys Thr Thr Thr Arg Arg Ile Val Asp Gly
                405                 410                 415

Lys Val Val Ser Glu Thr Asn Asp Thr Lys Val Leu Arg His
            420                 425                 430

<210> SEQ ID NO 12
<211> LENGTH: 1485
<212> TYPE: DNA
<213> ORGANISM: Homo sapiens

<400> SEQUENCE: 12
tccggggcgg gggcggggcc tcactctgcg atataactcg ggtcgcgcgg ctcgcgcagg      60
ccgccaccgt cgtccgcaaa gcctgagtcc tgtcctttct ctctccccgg acagcatgag     120
cttcaccact cgctccacct tctccaccaa ctaccgggtcc ctgggctctg tccaggcgcc     180
```

-continued

```
cagctacggc gcccggccgg tcagcagcgc ggccagcgtc tatgcaggcg ctggggctc    240 tggttcccgg atctccgtgt cccgctccac cagcttcagg ggcggcatgg ggtccggggg    300
cctggccacc gggatagccg ggggtctggc aggaatggga ggcatccaga acgagaagga    360
gaccatgcaa agcctgaacg accgcctggc ctcttacctg gacagagtga ggagcctgga    420
gaccgagaac cggaggctgg agagcaaaat ccgggagcac ttggagaaga agggacccca    480
ggtcagagac tggagccatt acttcaagat catcgaggac ctgagggctc agatcttcgc    540
aaatactgtg gacaatgccc gcatcgttct gcagattgac aatgcccgtc ttgctgctga    600
tgactttaga gtcaagtatg agacagagct ggccatgcgc cagtctgtgg agaacgacat    660
ccatgggctc cgcaaggtca ttgatgacac caatatcaca cgactgcagc tggagacaga    720
gatcgaggct ctcaaggagg agctgctctt catgaagaag aaccacgaag aggaagtaaa    780
aggcctacaa gcccagattg ccagctctgg gttgaccgtg gaggtagatg cccccaaatc    840
tcaggacctc gccaagatca tggcagacat ccgggcccaa tatgacgagc tggctcggaa    900
gaaccgagag gagctagaca gtactggtc tcagcagatt gaggagagca ccacagtggt    960
caccacacag tctgctgagg ttggagctgc tgagacgacg ctcacagagc tgagacgtac   1020
agtccagtcc ttggagatcg acctggactc catgagaaat ctgaaggcca gcttggagaa   1080
cagcctgagg gaggtggagg cccgctacgc cctacagatg gagcagctca acgggatcct   1140
gctgcacctt gagtcagagc tggcacagac ccgggcagag ggacagcgcc aggcccagga   1200
gtatgaggcc ctgctgaaca tcaaggtcaa gctggaggct gagatcgcca cctaccgccg   1260
cctgctggaa gatggcgagg actttaatct tggtgatgcc ttggacagca gcaactccat   1320
gcaaaccatc caaaagacca ccacccgccg gatagtggat ggcaaagtgg tgtctgagac   1380
caatgacacc aaagttctga ggcattaagc cagcagaagc agggtaccct ttggggagca   1440
ggaggccaat aaaaagttca gagttcaaaa aaaaaaaaa aaaaa                    1485
```

<210> SEQ ID NO 13
<211> LENGTH: 430
<212> TYPE: PRT
<213> ORGANISM: Homo sapiens

<400> SEQUENCE: 13

```
Met Ser Phe Thr Thr Arg Ser Thr Phe Ser Thr Asn Tyr Arg Ser Leu
1               5                   10                  15

Gly Ser Val Gln Ala Pro Ser Tyr Gly Ala Arg Pro Val Ser Ser Ala
            20                  25                  30

Ala Ser Val Tyr Ala Gly Ala Gly Gly Ser Gly Ser Arg Ile Ser Val
        35                  40                  45

Ser Arg Ser Thr Ser Phe Arg Gly Gly Met Gly Ser Gly Gly Leu Ala
    50                  55                  60

Thr Gly Ile Ala Gly Gly Leu Ala Gly Met Gly Gly Ile Gln Asn Glu
65                  70                  75                  80

Lys Glu Thr Met Gln Ser Leu Asn Asp Arg Leu Ala Ser Tyr Leu Asp
                85                  90                  95

Arg Val Arg Ser Leu Glu Thr Glu Asn Arg Arg Leu Glu Ser Lys Ile
            100                 105                 110

Arg Glu His Leu Glu Lys Lys Gly Pro Gln Val Arg Asp Trp Ser His
        115                 120                 125

Tyr Phe Lys Ile Ile Glu Asp Leu Arg Ala Gln Ile Phe Ala Asn Thr
    130                 135                 140
```

| | | | | | | | | | | | | | | |
|---|---|---|---|---|---|---|---|---|---|---|---|---|---|---|
|Val|Asp|Asn|Ala|Arg|Ile|Val|Leu|Gln|Ile|Asp|Asn|Ala|Arg|Leu|Ala|
|145| | | | |150| | | | |155| | | | |160|

Ala Asp Asp Phe Arg Val Lys Tyr Glu Thr Glu Leu Ala Met Arg Gln
                165                 170                 175

Ser Val Glu Asn Asp Ile His Gly Leu Arg Lys Val Ile Asp Asp Thr
                180                 185                 190

Asn Ile Thr Arg Leu Gln Leu Glu Thr Glu Ile Glu Ala Leu Lys Glu
                195                 200                 205

Glu Leu Leu Phe Met Lys Lys Asn His Glu Glu Val Lys Gly Leu
210                 215                 220

Gln Ala Gln Ile Ala Ser Ser Gly Leu Thr Val Glu Val Asp Ala Pro
225                 230                 235                 240

Lys Ser Gln Asp Leu Ala Lys Ile Met Ala Asp Ile Arg Ala Gln Tyr
                245                 250                 255

Asp Glu Leu Ala Arg Lys Asn Arg Glu Glu Leu Asp Lys Tyr Trp Ser
                260                 265                 270

Gln Gln Ile Glu Glu Ser Thr Thr Val Val Thr Thr Gln Ser Ala Glu
                275                 280                 285

Val Gly Ala Ala Glu Thr Thr Leu Thr Glu Leu Arg Arg Thr Val Gln
                290                 295                 300

Ser Leu Glu Ile Asp Leu Asp Ser Met Arg Asn Leu Lys Ala Ser Leu
305                 310                 315                 320

Glu Asn Ser Leu Arg Glu Val Glu Ala Arg Tyr Ala Leu Gln Met Glu
                325                 330                 335

Gln Leu Asn Gly Ile Leu Leu His Leu Glu Ser Glu Leu Ala Gln Thr
                340                 345                 350

Arg Ala Glu Gly Gln Arg Gln Ala Gln Glu Tyr Glu Ala Leu Leu Asn
                355                 360                 365

Ile Lys Val Lys Leu Glu Ala Glu Ile Ala Thr Tyr Arg Arg Leu Leu
                370                 375                 380

Glu Asp Gly Glu Asp Phe Asn Leu Gly Asp Ala Leu Asp Ser Ser Asn
385                 390                 395                 400

Ser Met Gln Thr Ile Gln Lys Thr Thr Thr Arg Arg Ile Val Asp Gly
                405                 410                 415

Lys Val Val Ser Glu Thr Asn Asp Thr Lys Val Leu Arg His
                420                 425                 430

<210> SEQ ID NO 14
<211> LENGTH: 1439
<212> TYPE: DNA
<213> ORGANISM: Homo sapiens

<400> SEQUENCE: 14
gcagcctcga gggccaacaa cacctgctgt ccgtgtccat gcccggttgg ccaccccgtt     60
tctgggggca tgagcttcac cactcgctcc accttctcca ccaactaccg gtccctgggc    120
tctgtccagg cgcccagcta cggcgcccgg ccggtcagca gcgcggccag cgtctatgca    180
ggcgctgggg gctctggttc ccggatctcc gtgtcccgct ccaccagctt caggggcggc    240
atggggtccg gggcctggc accgggata gccgggggtc tggcaggaat gggaggcatc    300
cagaacgaga aggagaccat gcaaagcctg aacgaccgcc tggcctctta cctggacaga    360
gtgaggagcc tggagaccga gaaccggagg ctgagagca aaatccggga gcacttggag    420
aagaagggac cccaggtcag agactggagc cattacttca gatcatcga ggacctgagg    480 gctcagatct tcgcaaatac tgtggacaat gcccgcatcg ttctgcagat tgacaatgcc    540

-continued

```
cgtcttgctg ctgatgactt tagagtcaag tatgagacag agctggccat gcgccagtct      600
gtggagaacg acatccatgg gctccgcaag gtcattgatg acaccaatat cacacgactg      660
cagctggaga cagagatcga ggctctcaag gaggagctgc tcttcatgaa gaagaaccac      720
gaagaggaag taaaaggcct acaagcccag attgccagct ctgggttgac cgtggaggta      780
gatgccccca atctcagga cctcgccaag atcatggcag acatccgggc ccaatatgac       840
gagctggctc ggaagaaccg agaggagcta gacaagtact ggtctcagca gattgaggag      900
agcaccacag tggtcaccac acagtctgct gaggttggag ctgctgagac gacgctcaca      960
gagctgagac gtacagtcca gtccttggag atcgacctgg actccatgag aaatctgaag     1020
gccagcttgg agaacagcct gagggaggtg gaggcccgct acgccctaca gatggagcag     1080
ctcaacggga tcctgctgca ccttgagtca gagctggcac agacccgggc agagggacag     1140
cgccaggccc aggagtatga ggccctgctg aacatcaagg tcaagctgga ggctgagatc     1200
gccacctacc gccgcctgct ggaagatggc gaggactta atcttggtga tgccttggac      1260
agcagcaact ccatgcaaac catccaaaag accaccaccc gccggatagt ggatggcaaa     1320
gtggtgtctg agaccaatga caccaaagtt ctgaggcatt aagccagcag aagcagggta     1380 cccttttgggg agcaggaggc caataaaaag ttcagagttc aaaaaaaaaa aaaaaaaa      1439
```

```
<210> SEQ ID NO 15
<211> LENGTH: 400
<212> TYPE: PRT
<213> ORGANISM: Homo sapiens

<400> SEQUENCE: 15

Met Thr Ser Tyr Ser Tyr Arg Gln Ser Ala Thr Ser Ser Phe Gly
1               5                  10                  15

Gly Leu Gly Gly Gly Ser Val Arg Phe Gly Pro Gly Val Ala Phe Arg
            20                  25                  30

Ala Pro Ser Ile His Gly Gly Ser Gly Gly Arg Gly Val Ser Val Ser
        35                  40                  45

Ser Ala Arg Phe Val Ser Ser Ser Ser Gly Ala Tyr Gly Gly Gly
    50                  55                  60

Tyr Gly Gly Val Leu Thr Ala Ser Asp Gly Leu Leu Ala Gly Asn Glu
65                  70                  75                  80

Lys Leu Thr Met Gln Asn Leu Asn Asp Arg Leu Ala Ser Tyr Leu Asp
                85                  90                  95

Lys Val Arg Ala Leu Glu Ala Ala Asn Gly Glu Leu Glu Val Lys Ile
            100                 105                 110

Arg Asp Trp Tyr Gln Lys Gln Gly Pro Gly Pro Ser Arg Asp Tyr Ser
        115                 120                 125

His Tyr Tyr Thr Thr Ile Gln Asp Leu Arg Asp Lys Ile Leu Gly Ala
    130                 135                 140

Thr Ile Glu Asn Ser Arg Ile Val Leu Gln Ile Asp Asn Ala Arg Leu
145                 150                 155                 160

Ala Ala Asp Asp Phe Arg Thr Lys Phe Glu Thr Glu Gln Ala Leu Arg
                165                 170                 175

Met Ser Val Glu Ala Asp Ile Asn Gly Leu Arg Arg Val Leu Asp Glu
            180                 185                 190

Leu Thr Leu Ala Arg Thr Asp Leu Glu Met Gln Ile Glu Gly Leu Lys
        195                 200                 205

Glu Glu Leu Ala Tyr Leu Lys Lys Asn His Glu Glu Glu Ile Ser Thr
```

```
                     210                 215                 220
Leu Arg Gly Gln Val Gly Gly Gln Val Ser Val Glu Val Asp Ser Ala
225                 230                 235                 240

Pro Gly Thr Asp Leu Ala Lys Ile Leu Ser Asp Met Arg Ser Gln Tyr
                245                 250                 255

Glu Val Met Ala Glu Gln Asn Arg Lys Asp Ala Glu Ala Trp Phe Thr
                260                 265                 270

Ser Arg Thr Glu Glu Leu Asn Arg Glu Val Ala Gly His Thr Glu Gln
            275                 280                 285

Leu Gln Met Ser Arg Ser Glu Val Thr Asp Leu Arg Arg Thr Leu Gln
        290                 295                 300

Gly Leu Glu Ile Glu Leu Gln Ser Gln Leu Ser Met Lys Ala Ala Leu
305                 310                 315                 320

Glu Asp Thr Leu Ala Glu Thr Glu Ala Arg Phe Gly Ala Gln Leu Ala
                325                 330                 335

His Ile Gln Ala Leu Ile Ser Gly Ile Glu Ala Gln Leu Gly Asp Val
                340                 345                 350

Arg Ala Asp Ser Glu Arg Gln Asn Gln Glu Tyr Gln Arg Leu Met Asp
            355                 360                 365

Ile Lys Ser Arg Leu Glu Gln Glu Ile Ala Thr Tyr Arg Ser Leu Leu
        370                 375                 380

Glu Gly Gln Glu Asp His Tyr Asn Asn Leu Ser Ala Ser Lys Val Leu
385                 390                 395                 400

<210> SEQ ID NO 16
<211> LENGTH: 1490
<212> TYPE: DNA
<213> ORGANISM: Homo sapiens

<400> SEQUENCE: 16
agatatccgc ccctgacacc attcctccct tcccccctcc accggccgcg ggcataaaag      60
gcgccaggtg agggcctcgc cgctcctccc gcgaatcgca gcttctgaga ccagggttgc     120
tccgtccgtg ctccgcctcg ccatgacttc ctacagctat cgccagtcgt cggccacgtc     180
gtccttcgga ggcctgggcg gcggctccgt gcgttttggg ccggggtcg cctttcgcgc      240 gcccagcatt cacgggggct ccggcggccg cggcgtatcc gtgtcctccg cccgctttgt     300
gtcctcgtcc tcctcggggg cctacggcgg cggctacggc ggcgtcctga ccgcgtccga     360
cgggctgctg gcgggcaacg agaagctaac catgcagaac ctcaacgacc gcctggcctc     420
ctacctggac aaggtgcgcg ccctggaggc ggccaacggc gagctagagg tgaagatccg     480
cgactggtac cagaagcagg ggcctgggcc ctcccgcgac tacagccact actacacgac     540
catccaggac ctgcgggaca gattcttgg tgccaccatt gagaactcca ggattgtcct      600
gcagatcgac aatgcccgtc tggctgcaga tgacttccga accaagtttg agacggaaca     660
ggctctgcgc atgagcgtgg aggccgacat caacggcctg cgcagggtgc tggatgagct     720 gacccctggcc aggaccgacc tggagatgca gatcgaaggc ctgaaggaag agctggccta     780
cctgaagaag aaccatgagg aggaaatcag tacgctgagg ggccaagtgg aggccaggt      840 cagtgtggag gtggattccg ctccgggcac cgatctcgcc aagatcctga gtgacatgcg     900
aagccaatat gaggtcatgg ccgagcagaa ccggaaggat gctgaagcct ggttcaccag     960
ccggactgaa gaattgaacc gggaggtcgc tggccacacg gagcagctcc agatgagcag    1020
gtccgaggtt actgacctgc ggcgcaccct tcagggtctt gagattgagc tgcagtcaca    1080
```

```
gctgagcatg aaagctgcct tggaagacac actggcagaa acggaggcgc gctttggagc   1140
ccagctggcg catatccagg cgctgatcag cggtattgaa gcccagctgg gcgatgtgcg   1200
agctgatagt gagcggcaga atcaggagta ccagcggctc atggacatca agtcgcggct   1260
ggagcaggag attgccacct accgcagcct gctcgaggga caggaagatc actacaacaa   1320
tttgtctgcc tccaaggtcc tctgaggcag caggctctgg ggcttctgct gtcctttgga   1380
gggtgtcttc tgggtagagg gatgggaagg aagggaccct taccccggc tcttctcctg   1440 acctgccaat aaaaatttat ggtccaaggg aaaaaaaaaa aaaaaaaaa                1490
```

<210> SEQ ID NO 17
<211> LENGTH: 378
<212> TYPE: PRT
<213> ORGANISM: Homo sapiens

<400> SEQUENCE: 17

```
Met Asp Ser Val Arg Ser Gly Ala Phe Gly His Leu Phe Arg Pro Asp
1               5                   10                  15

Asn Phe Ile Phe Gly Gln Ser Gly Ala Gly Asn Asn Trp Ala Lys Gly
                20                  25                  30

His Tyr Thr Glu Gly Ala Glu Leu Val Asp Ser Val Leu Asp Val Val
            35                  40                  45

Arg Lys Glu Cys Glu Asn Cys Asp Cys Leu Gln Gly Phe Gln Leu Thr
        50                  55                  60

His Ser Leu Gly Gly Gly Thr Gly Ser Gly Met Gly Thr Leu Leu Ile
65                  70                  75                  80

Ser Lys Val Arg Glu Glu Tyr Pro Asp Arg Ile Met Asn Thr Phe Ser
                85                  90                  95

Val Val Pro Ser Pro Lys Val Ser Asp Thr Val Val Glu Pro Tyr Asn
            100                 105                 110

Ala Thr Leu Ser Ile His Gln Leu Val Glu Asn Thr Asp Glu Thr Tyr
        115                 120                 125

Cys Ile Asp Asn Glu Ala Leu Tyr Asp Ile Cys Phe Arg Thr Leu Lys
    130                 135                 140

Leu Ala Thr Pro Thr Tyr Gly Asp Leu Asn His Leu Val Ser Ala Thr
145                 150                 155                 160

Met Ser Gly Val Thr Thr Ser Leu Arg Phe Pro Gly Gln Leu Asn Ala
                165                 170                 175

Asp Leu Arg Lys Leu Ala Val Asn Met Val Pro Phe Pro Arg Leu His
            180                 185                 190

Phe Phe Met Pro Gly Phe Ala Pro Leu Thr Ala Arg Gly Ser Gln Gln
        195                 200                 205

Tyr Arg Ala Leu Thr Val Pro Glu Leu Thr Gln Gln Met Phe Asp Ala
    210                 215                 220

Lys Asn Met Met Ala Ala Cys Asp Pro Arg His Gly Arg Tyr Leu Thr
225                 230                 235                 240

Val Ala Thr Val Phe Arg Gly Arg Met Ser Met Lys Glu Val Asp Glu
                245                 250                 255

Gln Met Leu Ala Ile Gln Ser Lys Asn Ser Ser Tyr Phe Val Glu Trp
            260                 265                 270

Ile Pro Asn Asn Val Lys Val Ala Val Cys Asp Ile Pro Pro Arg Gly
        275                 280                 285

Leu Lys Met Ser Ser Thr Phe Ile Gly Asn Ser Thr Ala Ile Gln Glu
    290                 295                 300
```

```
Leu Phe Lys Arg Ile Ser Glu Gln Phe Thr Ala Met Phe Arg Arg Lys
305                 310                 315                 320

Ala Phe Leu His Trp Tyr Thr Gly Glu Gly Met Asp Glu Met Glu Phe
                325                 330                 335

Thr Glu Ala Glu Ser Asn Met Asn Asp Leu Val Ser Gly Tyr Gln Gln
            340                 345                 350

Tyr Gln Asp Ala Thr Ala Glu Glu Gly Glu Met Tyr Glu Asp Asp
        355                 360                 365

Glu Glu Glu Ser Glu Ala Gln Gly Pro Lys
    370                 375

<210> SEQ ID NO 18
<211> LENGTH: 1851
<212> TYPE: DNA
<213> ORGANISM: Homo sapiens

<400> SEQUENCE: 18
```

| | | | | |
|---|---|---|---|---|
| agacactcac | cccggactcc | cttgaacagg | gacagggagg | aacccaggc agctagaccc | 60 |
| cagcagcagc | cacacgagca | cactgtgggg | cagggagggg | catctcttga gaacaaaaga | 120 |
| tccatttctc | gactttccaa | actggagagc | ttcttgagag | aaaagagaga gacaggtaca | 180 |
| ggtccacgcc | acccacacac | agccctgtgc | acacagaccg | gacacaggcg tccacagttc | 240 |
| tgggaagtca | tcagtgatga | gcatggcatc | gaccccagcg | gcaactacgt gggcgactcg | 300 |
| gacttgcagc | tggagcggat | cagcgtctac | tacaacgagg | cctcttctca caagtacgtg | 360 |
| cctcgagcca | ttctggtgga | cctggaaccc | ggaaccatgg | acagtgtccg ctcaggggcc | 420 |
| tttggacatc | tcttcaggcc | tgacaatttc | atctttggtc | agagtggggc cggcaacaac | 480 |
| tgggccaagg | gtcactacac | ggagggggcg | gagctggtgg | attcggtcct ggatgtggtg | 540 |
| cggaaggagt | gtgaaaactg | cgactgcctg | cagggcttcc | agctgaccca ctcgctgggg | 600 |
| ggcggcacgg | gctccggcat | gggcacgttg | ctcatcagca | aggtgcgtga ggagtatccc | 660 |
| gaccgcatca | tgaacacctt | cagcgtcgtg | ccctcaccca | aggtgtcaga cacggtggtg | 720 |
| gagccctaca | cgccacgct | gtccatccac | cagctggtgg | agaacacgga tgagacctac | 780 |
| tgcatcgaca | cgaggcgct | ctacgacatc | tgcttccgca | ccctcaagct ggccacgccc | 840 |
| acctacgggg | acctcaacca | cctggtatcg | gccaccatga | gcggagtcac cacctccttg | 900 |
| cgcttcccgg | gccagctcaa | cgctgacctg | cgcaagctgg | ccgtcaacat ggtgcccttc | 960 |
| ccgcgcctgc | acttcttcat | gcccggcttc | gccccctca | cagcccgggg cagccagcag | 1020 |
| tacgggccc | tgaccgtgcc | cgagctcacc | cagcagatgt | tcgatgccaa gaacatgatg | 1080 |
| gccgcctgcg | acccgcgcca | cggccgctac | ctgacggtgg | ccaccgtgtt ccggggccgc | 1140 |
| atgtccatga | aggaggtgga | cgagcagatg | ctggccatcc | agagcaagaa cagcagctac | 1200 |
| ttcgtggagt | ggatccccaa | caacgtgaag | gtggccgtgt | gtgacatccc gccccgcggc | 1260 |
| ctcaagatgt | cctccacctt | catcgggaac | agcacggcca | tccaggagct gttcaagcgc | 1320 |
| atctccgagc | agttcacggc | catgttccgg | cgcaaggcct | tcctgcactg gtacacgggc | 1380 |
| gagggcatgg | acgagatgga | gttcaccgag | gccgagagca | acatgaacga cctggtgtcc | 1440 |
| gagtaccagc | agtaccagga | cgccacggcc | gaggaagagg | gcgagatgta cgaagacgac | 1500 |
| gaggaggagt | cggaggccca | gggccccaag | tgaagctgct | cgcagctgga gtgagaggca | 1560 |
| ggtggcggcc | ggggccgaag | ccagcagtgt | ctaaaccccc | ggagccatct tgctgccgac | 1620 |
| accctgcttt | cccctcgccc | tagggctccc | ttgccgccct | cctgcagtat ttatggcctc | 1680 |

-continued

```
gtcctcccca cctaggccac gtgtgagctg ctcctgtctc tgtcttattg cagctccagg    1740
cctgacgttt tacggttttg ttttttactg gtttgtgttt atattttcgg ggatacttaa    1800
taaatctatt gctgtcagat acccttaaaa aaaaaaaaaa aaaaaaaaaa a            1851
```

<210> SEQ ID NO 19
<211> LENGTH: 450
<212> TYPE: PRT
<213> ORGANISM: Homo sapiens

<400> SEQUENCE: 19

```
Met Arg Glu Ile Val His Ile Gln Ala Gly Gln Cys Gly Asn Gln Ile
1               5                  10                  15

Gly Ala Lys Phe Trp Glu Val Ile Ser Asp Glu His Gly Ile Asp Pro
            20                  25                  30

Ser Gly Asn Tyr Val Gly Asp Ser Asp Leu Gln Leu Glu Arg Ile Ser
        35                  40                  45

Val Tyr Tyr Asn Glu Ala Ser Ser His Lys Tyr Val Pro Arg Ala Ile
    50                  55                  60

Leu Val Asp Leu Glu Pro Gly Thr Met Asp Ser Val Arg Ser Gly Ala
65                  70                  75                  80

Phe Gly His Leu Phe Arg Pro Asp Asn Phe Ile Phe Gly Gln Ser Gly
                85                  90                  95

Ala Gly Asn Asn Trp Ala Lys Gly His Tyr Thr Glu Gly Ala Glu Leu
            100                 105                 110

Val Asp Ser Val Leu Asp Val Val Arg Lys Glu Cys Glu Asn Cys Asp
        115                 120                 125

Cys Leu Gln Gly Phe Gln Leu Thr His Ser Leu Gly Gly Gly Thr Gly
    130                 135                 140

Ser Gly Met Gly Thr Leu Leu Ile Ser Lys Val Arg Glu Glu Tyr Pro
145                 150                 155                 160

Asp Arg Ile Met Asn Thr Phe Ser Val Val Pro Ser Pro Lys Val Ser
                165                 170                 175

Asp Thr Val Val Glu Pro Tyr Asn Ala Thr Leu Ser Ile His Gln Leu
            180                 185                 190

Val Glu Asn Thr Asp Glu Thr Tyr Cys Ile Asp Asn Glu Ala Leu Tyr
        195                 200                 205

Asp Ile Cys Phe Arg Thr Leu Lys Leu Ala Thr Pro Thr Tyr Gly Asp
    210                 215                 220

Leu Asn His Leu Val Ser Ala Thr Met Ser Gly Val Thr Thr Ser Leu
225                 230                 235                 240

Arg Phe Pro Gly Gln Leu Asn Ala Asp Leu Arg Lys Leu Ala Val Asn
                245                 250                 255

Met Val Pro Phe Pro Arg Leu His Phe Phe Met Pro Gly Phe Ala Pro
            260                 265                 270

Leu Thr Ala Arg Gly Ser Gln Gln Tyr Arg Ala Leu Thr Val Pro Glu
        275                 280                 285

Leu Thr Gln Gln Met Phe Asp Ala Lys Asn Met Met Ala Ala Cys Asp
    290                 295                 300

Pro Arg His Gly Arg Tyr Leu Thr Val Ala Thr Val Phe Arg Gly Arg
305                 310                 315                 320

Met Ser Met Lys Glu Val Asp Glu Gln Met Leu Ala Ile Gln Ser Lys
                325                 330                 335

Asn Ser Ser Tyr Phe Val Glu Trp Ile Pro Asn Asn Val Lys Val Ala
            340                 345                 350
```

```
Val Cys Asp Ile Pro Pro Arg Gly Leu Lys Met Ser Ser Thr Phe Ile
        355                 360                 365

Gly Asn Ser Thr Ala Ile Gln Glu Leu Phe Lys Arg Ile Ser Glu Gln
    370                 375                 380

Phe Thr Ala Met Phe Arg Arg Lys Ala Phe Leu His Trp Tyr Thr Gly
385                 390                 395                 400

Glu Gly Met Asp Glu Met Glu Phe Thr Glu Ala Glu Ser Asn Met Asn
                405                 410                 415

Asp Leu Val Ser Glu Tyr Gln Gln Tyr Gln Asp Ala Thr Ala Glu Glu
            420                 425                 430

Glu Gly Glu Met Tyr Glu Asp Asp Glu Glu Glu Ser Glu Ala Gln Gly
        435                 440                 445

Pro Lys
    450

<210> SEQ ID NO 20
<211> LENGTH: 1794
<212> TYPE: DNA
<213> ORGANISM: Homo sapiens

<400> SEQUENCE: 20
gacatcagcc gatgcgaagg gcggggccgc ggctataaga gcgcgcggcc gcggtccccg      60
accctcagca gccagcccgg cccgcccgcg cccgtccgca gccgcccgcc agacgcgccc     120
agtatgaggg agatcgtgca catccaggcc ggccagtgcg gcaaccagat cggggccaag     180
ttctgggaag tcatcagtga tgagcatggc atcgacccca gcggcaacta cgtgggcgac     240
tcggacttgc agctggagcg gatcagcgtc tactacaacg aggcctcttc tcacaagtac     300
gtgcctcgag ccattctggt ggacctggaa cccggaacca tggacagtgt ccgctcaggg     360
gcctttggac atctcttcag gcctgacaat ttcatctttg gtcagagtgg ggccggcaac     420
aactgggcca aggtcactac acgaggggg cggagctgg tggattcggt cctggatgtg     480
gtgcggaagg agtgtgaaaa ctgcgactgc ctgcagggct ccagctgac ccactcgctg     540 gggggcggca cgggctccgg catgggcacg ttgctcatca gcaaggtgcg tgaggagtat     600
cccgaccgca tcatgaacac cttcagcgtc gtgccctcac ccaaggtgtc agacacggtg     660
gtggagccct acaacgccac gctgtccatc accagctgg tggagaacac ggatgagacc     720
tactgcatcg acaacgaggc gctctacgac atctgcttcc gcaccctcaa gctggccacg     780
cccacctacg ggaccctcaa ccacctggta tcggccacca tgagcggagt caccaccctcc     840 ttgcgcttcc cgggccagct caacgctgac ctgcgcaagc tggccgtcaa catggtgccc     900
ttcccgcgcc tgcacttctt catgcccggc ttcgcccccc tcacagcccg ggcagccag     960 cagtaccggg ccctgaccgt gcccgagctc acccagcaga tgttcgatgc caagaacatg    1020
atggccgcct gcgacccgcg ccacggccgc tacctgacgg tggccaccgt gttccggggc    1080
cgcatgtcca tgaaggaggt ggacgagcag atgctggcca tccagagcaa gaacagcagc    1140
tacttcgtgg agtggatccc caacaacgtg aaggtggccg tgtgtgacat cccgcccgc     1200 ggcctcaaga tgtcctccac cttcatcggg aacagcacgg ccatccagga gctgttcaag    1260
cgcatctccg agcagttcac ggccatgttc cggcgcaagg ccttcctgca ctggtacacg    1320
ggcgagggca tggacgagat ggagttcacc gaggccgaga gcaacatgaa cgacctggtg    1380
tccgagtacc agcagtacca ggacgccacg gccgaggaag agggcgagat gtacgaagac    1440
gacgaggagg agtcggaggc ccagggcccc aagtgaagct gctcgcagct ggagtgagag    1500
```

```
gcaggtggcg gccggggccg aagccagcag tgtctaaacc cccggagcca tcttgctgcc    1560
gacaccctgc tttcccctcg ccctagggct cccttgccgc cctcctgcag tatttatggc    1620
ctcgtcctcc ccacctaggc cacgtgtgag ctgctcctgt ctctgtctta ttgcagctcc    1680
aggcctgacg ttttacggtt ttgttttttta ctggtttgtg tttatatttt cggggatact   1740
taataaatct attgctgtca gataccctta aaaaaaaaaa aaaaaaaaaa aaaa          1794

<210> SEQ ID NO 21
<211> LENGTH: 163856
<212> TYPE: DNA
<213> ORGANISM: Homo sapiens

<400> SEQUENCE: 21
gcggccaggg gcgggcggcc gcagagcagc accggccgtg gctccggtag cagcaagttc      60
gaaccccgct cccgctccgc ttcggttctc gctccttcgg cccttgggcc tccaaacacc     120
agtccccggc agctcgttgc gcattgcgct ctccccgcca ccaggatgcc ggtaaccgag     180
aaggatctag ctgaggacgc gccttggaag aagatccagc agaacacgtt cacacgctgg     240
tgcaacgagc acctcaagtg cgtgaacaaa cgcatcggca acctgcagac cgacctgagc     300
gacgggctgc ggctcatcgc gctgctcgag gtgctcagcc agaagcgcat gtaccgcaag     360
taccatcagc ggcccacctt cgccagatg cagctcgaga tgtgtccgt ggcgctcgag      420 ttcctggacc gtgagagcat caagctcgtg tccatcggtg agttctctgg ccgggcccag     480
gcgcccactg tggtgccgac ccgccccgc gcgtgcaccc ctgcggaggg cgaggatttc      540
ccgcagcgcg ccccccacctc ggagataagg gggagtcgtc cccaggggtg ggttataggg    600
ggcctagacc ccctccccgg tgtcttcccc tgggatggga cctgttgtga tcgctccccg     660
ccatccgccc cagcagtgca cctttggctg gctaagggtt gagggtttgg gctggggtca     720
caggaggaga ggtggagttg ttgcatttct ctacacctgg ggcgcccta tgggagctag      780 gggactagaa accctcgttc gctgtccccg ggggcgggcc ctagggtcag atgctccgcg     840
gagtgctctc cctgctgcgc ccaggttggt gctctcagag gcagctgaat gggcgttggc     900
tcggaggccg ggccgtgaga cctgaggagg aaccgttctc tgcgcctggg gcctccctgc     960
ccaggtggag acagagacct ggtaccttcc cctgccgtcg ctggaatggg tgtgggcccc    1020
gaggttgcaa gggtaggcgc gggtgtgtgt cctcgctctc tctgctccca gctcagctct    1080
ggccgcgcgc cgcaggttga acccactcct tgctgccgaa gttataattt agagatggtg    1140
gtggtaacag taattgctgt cttgtaggga gcccaactag cgtccactgt gtaccgtcag    1200
ccttctaagt tatctccgtc cctacgcatc ctgccatctg ggtgaggct agacccattt     1260 tacagataag ggggtccgga gggttaattg acctgtccaa ggtcagcaag tagggcccag    1320
ctgagaactg aaggaagtgg gcaacagtta gaaggaggct ttgttttcct ctcctctccc    1380
aaacctacac cagggtcttc ctgaaaggag ggagggaatt ggtgtctctt gctggactgg    1440
gccttctggt ctggggagga agaataagga tgaagtctcc cttgtggtct gagatagttg    1500
gaggcttccc agagggccac aaggctactg atagtgtggg ctgtgatggt aggggctgtg    1560
atgtgtgtgt gcatgtgggc gtttgtgcag agaacgtgtg tacacacata gcatgtgtgt    1620
atagcatgtg catatgcaaa gagtttgcat gtacacggaa tgtatgcaga gaatgtgtat    1680
ccacctacac gtgtgtatgg gtgtgtgtat gtgtgtgtgt gtatgtgggt gggtgggtgt    1740
gggttggggc agaggagggt tctgggtctg gatctcttcc taaggagaac cagggactgg    1800
```

-continued

```
ccctggcctg tgatttgggt ctcttcctga ggaaaccagg tcactatagt gaccctagtg    1860
acaggaagaa agggagatgg gtgtggctgc caggactttc tccagtggaa aagggattcc    1920
ctctaggctg agcctcccct gggccttagg gcctcaccct tccctteccc cacacctgtc    1980
ctggcaggta aggctgcttc ctgcttcctg ggcccagatg gcagccgcac cacccagctg    2040
atctccagca gccctccccc tccccaaggg tggcttccct gcagaagaat ctgcatggca    2100
cgctgttgtc ttcttcctgg ggtccatctc ctgtactggg gagggagaac ctcagaatct    2160
cctggaattc tttaccattc agaaaccagc ctcccctctg aagaatccca aggcccagct    2220
gggctcaatt tggatctgtt ctttgtttta aaatgtgta tttatttaat taactgaata    2280
aagaaactta aagtaaacca gaagtatcca aatacgacat gaaatctcta aaacaacaac    2340
aaaaccaaac caaaccgcag cactagcaaa tcacagactg cctgatctac ccactgttta    2400
cagaggcagc agctacttcc agcactgtct ctcatcagtg cccggggctg tgggtctcat    2460
tctagatttt gtctacattt ttttacatgg ttctcctgat tccctgctcc ccctccccac    2520
caccgccccg cctggagatg gagccttgct ctgtctccag gctggagtac aatggtgcca    2580
tctctgctca ctgcaacctc cacctcccgg gttcaagcga ttcttctgcc tcagcctcct    2640
gagtagctag aattacaggc acatgccacc acgcccggct aattttttgta ttcttagtag    2700
agatggggtt tcaccatgtt ggccaggctg gtctcgaact cttgacctca tgatatgccc    2760
gcctcggcct cccaagtgcg ggggttacag ccctgagcca ccgcgcccag cccggtcctc    2820
cttttatttt cgaatccact caggccctag ctactcccat tgtcccgacg ttccagggtt    2880
agttagcttc ccttcctctg tgctgggcct gtgggctgtt ggcagcttct tcctgttcct    2940
accacaactt gcattctatt ttttccttt taatgatttt cttggatcat attccccaga    3000
gtgacattcc tgggttaaag ggtgtgacca catttatgac ttgtatcatt ggctgcctaa    3060
ttgctctccc gagagatctt gcaacaaaca ggttttccag cctctggaga ccacagagag    3120
ccctggcaag tgccaggact gctgtgggga taaagcagga ggcttcttcc ctaagctctt    3180
gaggctgttg tgggtaatgg tccttcatcc ttcaaggcaa agttacctcc agcttggact    3240
aaggttcata tattcactgc ttaggttgtg ttacattgtg ctgacaatga cactagcttc    3300
aatttggggg cacctactgg gtgttaagtg tgttctgttg atcaccccat tgaattttca    3360
tgctaatcat tgattgacag caactactgc cctatctcta atgatctgct tctgcaagtc    3420
acttagagag ttcagggctt aacactgtcc tgggcatgtg ttgcttagaa aatggcgcct    3480
gttaattaaa taaggtgctg tctaataatt atctcaaaag taatgccagg gctggatgcc    3540
gtggctcacg cctgtaatcc cagcacttta ggaggccaag gtgggtggat cacctgaggt    3600
caggagttcg agaccagcct ggacaacatg gtgaaaccct agctctacta aaaatacaaa    3660
aattagctgg gcatggtggt gcacacctgt agtcccagct actcgggagg ctgaggcagg    3720
agaattgctt gaacccggga ggtggaggtt gcagtgagcc gaggtctttg tgtaactgca    3780
ctccagcctg ggagagcgag actctgactc aaaaaaaaaa aaaaaaaaaa aagtcatgcc    3840
cgaatggttt gcacaccgaa gggacgttca aaattagggg agaacagcct ggttgtttgt    3900
ttctgtttgg ttgatcatac tcttgccatg gttagtatta ttatctttat ttaaagatgg    3960
gaaacaggag tgaagccact tgtggaggtg acccagctag ctagtaaatg gtgtctgaaa    4020
cccaggtctg cccagctgtt gaattggagc cttaactgac ttgccttcca gtttcagaga    4080
tgagtaaaat acagcttttc tctccacatc agagggtccc tgcaacacta ggtttgcaag    4140
tcttaggtgt tagggtggtg gctggatacc cacactctga acctctgacc ttggacaaaa    4200
```

```
tagggatgtc agggccttcc atgattggca ggatgaatcc tctggctgtg atgaaggtc    4260
tcacaagttg agagtcagcc gggaattaag tgggatcagt ttgcctcttg tgttttcctc   4320
attgtgtttt ggttggttgg ttgagatttc ctactaccca atggatgatg ttttattcca   4380
tcgtcaggga aggtatcatt gaatgaatac agggttttgt atgctttgga taagaccaga   4440
cagttgtgga gtcattagaa ttgtgtacat gcctccagct ctgagatagg tggtgtttca   4500
acagctgcca gaggactctg gcttttctgc ctagaattca ctgaaagaca accctggcta   4560
ttgattcaca tttgtggttc attgtaaggt aggccctag gcgccatcca aaagttgaaa    4620
atttccttac gtttcttgtt atgtgatggg cagttcatag tgaggactca gtgtctttaa   4680
ttccagctgt ttgccaggag ttggcagttt tatttacttg ttttccaaa aacctttctg    4740
acatggggca gtccagccag ctgggaggaa aaggggtctc tcagcccaag aatgatgatc   4800
aaggcctaga agtttgggtg gtgtgttttg ttttgggcct ttagagaaag gaattgtttc   4860
cttttcagag gatgtggtct aaccctaaag tttacttgac tgacttaaac caggccagcg   4920
ccagagcagg cagggtgcgt gttcccaaga cttcgggtca ctaggcagct tccagggtgg   4980
tgggtcactg gtccagtcag ctccttttcc ttcctctccc ttttgtgcta ctactaccaa   5040
aataatttcc aaataacctt aagttctgct cttttcttgca tgtctagcag atgccagcat  5100
gtcttttggg tagtacagag agtgcttaaa aagtagcaaa gttggccgga cgtggtggct   5160
catgcctgta atcccagcac cctgggaggc caaggtgggt ggatcacctg aggtctggag   5220
tttgagacca gcctgaccaa catggagaaa ccccatctct actaaaaata caaaattaga   5280
tggccgtggt ggtgcatgcc tgtaatccca gctacgtggg aggctgaggc aggacaatag   5340
cttgaatcca agggcagagg ctgtgttgag ctgagatcat gccattgcac tccagcttgg   5400
gcaacaggag caaaactcca tctcaaaaaa aagtagcaaa gtagcatgct ttgtcagaat   5460
tattaataac aagttgtggg ccatgtacaa ggtggcacat tagcattcaa tgtcacttgt   5520
gtagtagtta agagcaagga ttcttggttc aaatcccact tgccactaag tagctattag   5580
aaacttctgt gccttggttt ccttatcact aaaatgggga taataactac cttcttaaaa   5640
ggctgttata aagattaaac aagttaataa ttttttaaagt gcttggcaca gtttatggta   5700
catagtaagt gctctgtgaa tgcctgttaa ttaaataagg cactgtttaa taatctcaaa   5760
agtcatgccg gaaaggtttg cacactgaaa gggcatttga aatcagcgcg ctctggggag   5820
aacagcttgg ttggctaagg ttgatcctac ttgctaaaat acggctatgg actgcctaga   5880
gggtgtcacc tccttgaaag gggctgcccc ctgctatgtt atggctgcct ccagggccca   5940
ttcacaccag ctttgtttcc aagctggaca gggagctcca ggcgtctggt cattccagcc   6000
tcccacccct ttcaggaatc tctgggccaa atcacttcca gatggtggtt gggcctctgt   6060
ggagttctcc cagcaacggc ggagccagca tgccagtcgg cagccgcctt cgttcttgga   6120
gagtctgagc taaaggaggg ctttgatttg gagccaaatt gtgtctcttg ggtcctggtt   6180
ttgtgctgtg aggcaggtac catggagtgg gctgctggct tagttgagga tggctgccct   6240
gctccttagg ggagcagata cccagggcct ggagccttta ggccctgcct ccagtagctc   6300
catggtcagg gtgccagtca ccttgcgttt tcttttttctt ttttttgag atggagtctt   6360
gctctgtcgc ccaggttgga gtgcagtggc gtgatctcgg ctcactgcaa cctctgtctc   6420
ccggggtcaa gcaattctcc tgcctcagcc tcctgagtag ctgggattac aggcgtgcgc   6480
cactatgtct ggctaatttt tgtatttta gtagagatgg ggtttcacct tgttggtcag   6540
```

```
gctggtctcg aactcccaac ctcgtgatcc acctgcctcg gcctcccaaa gtgctgggat   6600
tacaggcgtg agccaccgga cccagccaac tttgctacat cagtttccag gtagcatatc   6660
ctaggcaaaa ctggatgtag cctagtgatt cagggcctcg gtctgaagct agactgtctg   6720
gattctaatc cgcactctgc ctgataccag ctgtgcaact ctagtccact gctttaacct   6780
ttctgtgcct gcttccctgt ctataaaatg caagagcaaa atagttgcta tcttagagtt   6840
gctgggagca ttatatttga tgaggttaag ttatagcaca gtgttgtcat tatcactatg   6900
aatattgtgc ttttggaccc aagtccagga ctttgtcttg tcttctgtct attctctggc   6960
cagtccagat atttttggaa tcctattgct gtcatctggt gtgttagctg ttccctttct   7020
ccaagttcag aacgtctgat gaagatgtct cccaagatcc tttcttcctt tcctcattca   7080
acaaatatat gaaagcccat ctctgaacca ggccctgtgc tgggtgctag acaacagga   7140 atgagaggat catgtccttt gcttgcctca gatactgctc agaggagaag agacaagcaa   7200
gcagggagag ccatgcagag gagagctgct caaaccttca ggcccatgct catcacctgg   7260
ggactttgtt aaaaatgcag gtctgattga gtaggtgctg gggtgtaggc tgggattctg   7320
cgtttccagt cagcttcaga tcctgctgtc tgtgcaccgt gctgtaagta gcaaggatct   7380
aggtgccaag ccctctgaaa aggaggagca cctgccccta ggctgggtat gggtaatcta   7440
gaaggttccc tggaggaagg gacctttcag ctaagaccta aagcgtgact agaattaggc   7500
aggcaaacag acatttacac aggagcagac gagtgtgtca gtttagaggt cttgatgctc   7560
aggtcagagg ggcagtggag gggtgggcag ggctggttta ccaagggctt tctgaaactg   7620
gaggctgcct atggggtatg ctccttgagt ttgtttgttt gttttttttt ttgagttgga   7680
gtttcaatct tgtttcctag gctggagtgc agtacagtgg catgatctcg gctcactgca   7740
gcctccatct cccgggttca agagattctc ctgcctgagc ctcccaagta gctggaatta   7800
taggcatgtg cacacctggc taattttgta ttttagtag atatggtgtt tcaccatgtt   7860
ggtcaggctg gcctcgaact cctgacctca ggtgatccac ccacctagcc tcccaaagtg   7920
ctgggattac aggcgtgagc cacggcatcc agcccttgt ttagtgtagg gtagtaaacc   7980
cagccaaaag gggtcgttta tctcaggggt ctcacctgtt gctccagtca ttcctattag   8040
cagaaagttt tgtatgtgcc ccttcctcat atatatatat atttatatat gtatttatat   8100
atatttataa gttataaaca tactctactg tcaatttgta tattaaatat tagtaaatct   8160
tagtttcttt ttagatgaca aatccaaata taaaatctgt ttttttcctg gctctaacgg   8220
attatcttat gtccccttgg ggtggacata cctcttttgg aggctcccgt gaaggtttgt   8280
gtttctacat ttagtttttt tctttttttcc atattcttgt tattctgctt ttaattttca   8340
tctttgagta ttctaaatta aggagctgga tctgtaattg taacaccttc ccccaacaat   8400
aagtttaact aatgaaaata ttcaatggaa tgagccattt taatctaaat ggggctattt   8460
cctgctttta taatgattac agttgctttt catgacattc tactagaagc catcttacat   8520
tactgttgta aatctagtta ttcattaaac gggcacagta atccctaaat tggctcaggt   8580
tattgtataa taaacaacaa tactttcttc ttcaggagct tgagaagtga tcttgtattt   8640
ttaaggtgcc taactaactt ttcatgggaa actgagtcca tgtactggga agaaagcttt   8700
ttggggaaaa tgattagaaa accaaatggg tctctttatg actgaagtga tgaaccagca   8760
ggtgagagta ggtatagatg gtacagagga cggaattact gggtatttta atcaggccca   8820
cttagtatca caatttatta ttctattcta ttttttattat tattttttga gatggagttt   8880
cgctcttgtc atccaggctg gagtgcagtg gcgctatctc agctcactgc aacctccgcc   8940
```

```
tcccgggttc aagagattct cctgcctcag cctcccaagt agctgggatt acaggcatgc    9000
gccatcacac ctggataatt tttttgcatt tttagtagag atgaggtttc tccatgttgg    9060
tcaggctggt ctcgaactcc cgatctcagg tgatccgccc gctttggcct ctcaaagtgc    9120
tgggattgca ggtgtgagcc atcgcgcctg gccagtgtca ggatttattc tgtgggaggg    9180
gaggaggaca aagaaaaata ctgagctatg tttgaagctc ctgccctcta agagccttag    9240
agcagctgac ttaaatgtgt tcctttgata aactgtagat ggttgttgta actcttctgc    9300
aaactgttta ttttttaaaaa caatttgatg agattttact tatgcccatt gtttgagtac    9360
agcatttacc aaagaacaat tttggccaga tcccatgcag tagaatgccc ttggccaaaa    9420
ttttcttgta ctataagcaa agaagcagtt tggttttca cttaggcaag actgcctatc     9480
agactgagtt attgtgacag agccgctgac tctctcccct tccccattat caaaatctgg    9540
cttttctaag cagcgcatgt aaaaagcttg gcaaggagga cccttgtcct cctacatatt    9600
attctttggc tcttcttggt accaagaata catacaaata atgctggctg tgtactgaat    9660
gttgaggtgt gcactgttga ggatattcat cctctaatat aacatctagt atttctcaca    9720
ccttccgtct gctgagcatt ggtctatctt acttatacta cttctaatcc tcgtgaactc    9780
tgcaaaacta gtggctttac atctatgaga aagaaaaga actttatcg gaagaaggtg      9840 agtccttta aagtatcagg cctggaaaga cattaaatga gacagcgaac acatcctgct     9900
accctctttg agctatgtat tcattgactt tttttttttt tttttttttt ttttgaggca    9960
gagttttgct ttgtcaccag gctggagtgt agtggtgcaa tcttggctca ctgcaacctc    10020
tgcctccggg gttcaagtga ttctcatgcc acagcctcct gagtagctgg gattacaggc    10080
gcctgccacc ttgcctggct agttttggta tttttatttt tatttattta ttttaagaca   10140
gggtctcact ctgtcaccca ggctggagta cagtggcgcg atcttggctc actgcaacct    10200
ctgcctcccg ggttccagcg attctcctgc ctcaacctct ccagtagctg ggattacagg    10260
cgccttggca ccacagccag ttaatttttt gtatttttag tagaaacggg gtttcagcat    10320
gttggccagg ctggtctcga actcccaacc tcaggtaatc cgcctgcttt ggcctcccaa    10380
agtgctggga ttacgagtgt gagccattgt gccccgccta tgtattcatt tcttaaaatt    10440
ggttgctggc taggtgtggt ggtacatgcc tgtcctataa tcacagcact ttggaaggcc    10500
ggtgctggag gatctattga ggccaggagt ttaagaccag cctgggtgag atcacatctc    10560
tacaaaaaaa aaaaaaaaaa aaaaaattat ctggatgcag tggcacaagc ctacatagtt    10620
gtagctgctt gggaggctga gttgggagga tagcttgagc ccaggagttt gagtctgcag    10680
tgagctatga ttgcgtcact gcactctagc ctgggcgaca gagtgagacc cgtttctaaa    10740
acaaagaaat tgctattgtc acaattagtt ataaattaat ctaataatgc tgcacgcagt    10800
accataatcc acaccctata gcttaacgat ggatggccaa ccactaatca atgctatttc    10860
tgtacgccaa tgagaattcc tgacaaaaaa ctttgtatca gccccactcc ctgtctgtcc    10920 cctctttgc ttttaaaaac ctgcttgtaa caaaggccaa acagagctca tatccaaggt     10980
tacttgggcc tgagtctttc aggcagctgt cttcactttg gctcaagtaa actctttaat    11040
agtttaaatt ttaagcctct gcctctttct tttaggttga catctgtttc cattttacag    11100
atgagaaaac tgaggctcag ctctgcctca ctttacaggt caggcttaat ccctaatccc    11160
tgcctgcatc atgctgtaaa ggactttgt gtcaaaactg agtttcacac tctgtaaagt     11220
aaaatagata tattgtagtg agagggtgta gaagagactg ttttctgctt ctgtggattt    11280
```

```
tttttcttcc tgttttgctt tgctccaaac tttactcatt tgcgcttgat tcatgtgaaa   11340
ctgaaatttc cttctacaga acaaaacttt ttgggggcta cttaccatat cttttcccac   11400
accgtggagc tctgactggg acctttccca gttttggag acattgctcc agttcttcc   11460 ctgcctttgg tttccagggg gcagtaatgt caccgcaggt gtggacagta gggaccagct   11520
aaaggttgct ttggaggagg tgggcagggc ttttgtttgt gaggtctaga aaccagaggt   11580
gaggaaggag gtgtccctgg aactcccct ggctgcaggg ctcacagcac acaccatgac   11640
accacagggg tgtgtgtgtg tgtgtgtgtg tgtgtgtgtg tgtgtgtgtg tgtgtgttga   11700
ggggagtgtt gttgagagcc aactatgcca ggagatcctt ggtgacagcg gacataggca   11760
cagctatgct ctgtcaggaa tgagttcacc cacacccttt tcttctgcta ccttgtttaa   11820
ctggtgggag ggtgtgctgg gttgtgtttg ctggtgagcc cagcaactgc acccttcttt   11880
ccaggcctag cacccagcct ttatcagtct catggccctg gcacaagtgg gcagcctgct   11940
tccaatccaa gcaggcagct ttccgctcat ctgcaggtag cctcgtgctg tggcagcaca   12000
aagttgtgtg agccagagct gaacttgtga tccccacggg catctcctga ggcgcacctc   12060
tcctgagaga gaaagctggt ccgtccagcc cattcagggc tcagcctccc cagccgtcgc   12120
agggctggct tgctgaaagg tctgggtgtt aacacagcac tcctgttctc tctctctgaa   12180
ggccctttat gctggcatga attccttttc tcatagagat ctgaaagctc ttttgactaa   12240
atgggtcacc tttctgagta ttttcataag gctgtcagcc tttaccatgc cagacaagtt   12300
ttctggaatt tccttttccag aaaaaaaaaa aaaaaaggct actaagagg ttggagttat   12360 ttggaacaca gggtggaatt ctggcattcg aactataggg aaacgggtgg ggatttgtgg   12420
caggcactat gtaaatttgc cgcaagccca taaattcaga ctttaagatg aaagatggca   12480
agcagcagtc agctttcctt caacaggcag gaacggtgct accttccgcc tgtgctgagt   12540
gtgactgagg gagaggcagg cctcctaggg aggccgggc aggaaaggtt tcttggtggc   12600
taaaatagga tttctcagtt tccccgtgt cccaagaaaa taagttctta tcatgcttgt   12660
accacacttc ttgtgcgtat caccctggtt tccctgcacc tccttgaagt ggtttatcag   12720
attccaggga cacaagaatg gtttggcatc tacagcctat tgtgggagca ggggcccggc   12780
ctggtgcttc ttgcccagga acaaactgat tgttcccttg gtgtggggta aagcaggcca   12840
gagtatggga ccaggccctg cctcccaggg gacctgaggt gcaaggtctt tgagctgaga   12900
ccctaaaagg cctttgtgag tctgtagtgc tatcagttga gcagagttca gggttctgtt   12960
tacaagattc cctctcagca gaggcaggga ggggtacctg ctggaagacc aggaatgtgc   13020
tgctgctggg atggggccc tcggtggagc ttctagccat ctggaggcag aacccagaat   13080
gtgttctgag tgaggcgcct tggcagagtt ggcttgaaag cacctaggca gtggcttgtc   13140
acattcctta tctccaccaa aggaggcaag ctagcacctg ggggatggct ctcccatcag   13200
ggagtccttt acaggatgtg atccaggtgt cacattacac ttcctgcagg tgtgcacctc   13260
ttacctaatt gtctctccta tccctttttc tcagcactat tgtctgacat ccatggggag   13320
tcacacccaa agttgggcat gaggtcctct cctgggcacc caacaccttg ttttttttgtt   13380 tttgttttt ttggagatag agtcttgctc tgtcacccag gctagagtgc agtggtgcca   13440
tcacagctcg ctgcagcctc gacctccttg gctcaagcga tcctcccacc tcagcctccc   13500
acgtagtcag aattacaggc acacacacca acactgctgg ctaatttgt attttttgta   13560 gattcggttt gctatgttgc ccaggctggt cttgaactcc tgggctcaag cgatctgcct   13620
gcctcagcct cccaaagtgt ggggattaca ggcatgagcc acctcacttg gccacactgc   13680
```

```
cctcttactg agccgtattg gtgttctaaa tggccttctt actctcccac gggtcatcag  13740
tgctccaggg gcaggcgctg tgtctcttgt ttacctctgt ggctctgacc ttggcactta  13800
ataggaattt aataaataac ttgttaaata aacagtctct agtataatag cttgagtatt  13860
aagactggta cattgactta tttgcaattc agaaaatgca aaacagtggt tctttgctgc  13920
ctttagtgaa gtgggaatta tatgtagtag acaactgggt ctggggtccc agtggaacac  13980 ttcgttttg gactgtgatg ctgaacttaa agaactcagc agttcatgtt cattctctgg  14040
acatctgtga tttgcttcaa caactgttag agaacaaggc cttttccagg tgaagctcag  14100
aaaatgaatt taataggaaa ttactgaaag tcacaatcat agtaacagtt tcattagtta  14160
cagtgaatat agagagagcc catacaaagt accaggcatt gtgataaacg cttcttacta  14220
atagctatac aaaacatcat tgcaattctg agaagtagtt attgttgtaa ttcccgttat  14280
gcagatgaga aaactgaggc acacccagat tggccagtga gtgtgtggtt attactcaga  14340
ttcttgtctg agattttaat cttcatattt tactgctttc ccaaggaaag ccatcagctc  14400
agcaagtctt tgaaatttgc ttcttttttt tttttgaga cagagtcttg ctgtgtctcc  14460
caggctggag tacagtggcg caatcttggc tcactgcaac ctccgcctcc tgggttcaag  14520
cgattctctt gcctcagcct cccgagtagc tgggaatata gttgcatgcc accacacctg  14580
gctattttgt attttagta gagacggggt ttcaccatgt tggccagcct ggtcctgaac  14640
tcctgatctc gagatccacc tgcctcggcc tcctaaagtg ctgggatcag gcttgagcca  14700
ccgaactcgg cctttttttt tttttttttt gaaatgatgt ctccttttgt tgcccaaact  14760
gcagtcttgg ctcactgcaa cttctgcctc ctgggttcaa gtgattctcc tgcctcagcc  14820
tcccgagtag ctgggactac aggcacgtgc caccatgccc agctaatttt tgtattttta  14880
tagagacagg ctaagcttgt cttgaactcc tgacctcaag tgatccacct acctggccct  14940
cccaaagtgc tgggattaca ggagtgagcc cctgtgccca gcctgaaatt caattctaat  15000
aaatttttat tggagcatta aaaagttaca tctgtagttg ttactctttg caaaaaattg  15060
caagaacaca gaaaaatata aagaaaaaaa tcacctgtga agaattttaa tgaatctttt  15120 tctacttta ggggattttg cttacagctg ccttttaatc agaatagga agaaagagat  15180 tcctttctca ggaaaaagt gactgtggac tggaaatgct ttgtgaaata attttggtca  15240
tactgatggt tataacaaga ttcgtcttca attgagttat tgctgagctt tgtccaacat  15300
taaaatgaaa ggtctcattt gagtctcatt gtggtttgca agtctcccttg gtctagaaa  15360 tatgtttggt caaccacggc atggaggtgt tccagccact ttctgtctct taaaagtttt  15420
taggacctac ttttattggg actgccaggg tctcttaata atagttatta tacttggtaa  15480
ctattgtgac cttgtctcat aggcagccca gcatagaaac tcatttagct tttagttgct  15540
cagctccatt agctgtttaa acatgtttca gatgtgagcc tgacaatgta cttgggcagc  15600
ttggttcacc cttgactgcc tgggaacttt gagaagtctg aaaattatat gtagccctaa  15660
ggtcttcatg gtattgtttt tttggaggca ccatttccca atagccctga ggacaccagg  15720
cccatgaagc catcctgtct cagccaggag gcagaggaga tggaatggaa accacttctg  15780
gatacagatc cagccacttc cggagtgctt cagagcatgg gtcagataga ccttgctgct  15840
ttctagctgg cagacttggg gaaggttgtt tgacctctct gagtttgtgt cccagactat  15900
agcagtaccc ccttactggc gttatcgaag ataaaatgat ataatcctga taatcactt  15960 gacccagtcc ttggaggtgg tggtgggggc tggggtaagt gccccatgaa tggtggtcat  16020
```

```
catgctcccc accaacctcc tttctctctt ctcctttccc gtctttcaca cccctaattc   16080
ctggacctgg gggtggtctc tccagactag atgaagaagc aatctaatta tctaggaagg   16140
tgaaaggtgg ttgggaatac tcccagaaat aggccaaaga taccgcctcc tacctaacag   16200
actcttttta gaagaagagg caacctgggt ttttggataa ctgttgagta ggaaccatca   16260
tgagtggcat ttctgcattt ctggtcttct ggccaagcct cctttttttt ttttttttt    16320 tttttttta accttgagac agtcttgctt tgttgccagg ctggattgca atggtgcagt    16380
cttggctcac tgcaacctcc atctcccagg ttcaagcgat tctcctgcct cagcctcctg   16440
agtagctggt actacaggtg ccgccactat gcccagctaa ttttgtatt tttagtaggg    16500 acggggtttc atcatattgg ccaggatggt ctcaatctct tgacctcata ctctgcccgc   16560
ctcggcctcc caaagtgcca gaattacaag cgtgagccac tgagcccagc cttccttttt   16620
tttttttttt tttaagtagc tccattgccc tccctcaccc tttcttttgt ctcctgtaat   16680
gtccttccct tccatttctt tttttcttt tttcttttct tctttctttc tttctttttt    16740 tttttttga gataggatct cattctgtgg caaaggctgg agtgtagtgg cacattcacg    16800
gctcattgca gcctcgacct ccaggactca ggtgatcctc acatctcagc ctcccgagta   16860
gctgggacca caggcacaca ccaccacacc cggctaattt ttgcattttt tgtagaggta   16920
gtgttttgcc atgtttccca ggctggtctt gagctcctgg gctcaagtga tactccctcc   16980
tcagcctccc aaattgctga gattacaggc ataagcctct gcacctggcc ttccctctca   17040
tttttttttc tttcctggtt ttgcctgtcc cagaccaccc tcttggaaag atgctctccc   17100
agcagcggca gtaaggtcct ggtcttgtgt ttgctcctgg gcctgagtct tggctttgct   17160
gctttgtagc tagctggctg acaccaggga gctgcttccc tccaggagcc tgtcgtccat   17220
atgctgaatg tgatccttaa atgctctgtc ttacaggggc cagacattgt ggctcatgca   17280 cttcagggg ctgaggcgtg cagatcactt gaggccagga gtttgagacc agcctggcca   17340
acatggcgaa accctgtctc tactaaaaat acaaaaatta gccggaggtg gtagtgtgtg   17400
cctttaattc cagctacttg gaaggctgag gcaggaaaat cgctagaacc tgggaggcgg   17460
aggttgcagt gagccgagat catgccactg cactccagcc tgatcaacag agcgagattg   17520
tctcaaacaa acaaacaaaa aatgttctgc cttacagagt tcttaggtat aaaagagaag   17580
gtgcctctaa agctcttggc accgtgcctg gcttatagta agtgcttggt aaacgtcagc   17640
tgctgctgtt gtggtgttag tatcagcatt gttgctgtga gaccctgcac ttcccactta   17700
gccttggaaa aataagtctt cacgttaatg ccatgggcta ccgcttctct tttcagggct   17760
tcttggagga gggtggagat ggagagacag gtgggggact gccagggtta catcctccat   17820
gaggctgagg ctgtgctgac tgccttgtgt gctttcaacc tggagtaaag ggtggctgtg   17880
ccagctgctc ccatccccca ggagtctgac tcgtccctgc cttggccctg gcagcactt    17940 tccctcctag ctctttggca tctggggtca tggtgggggct gcctgccatc tgtcaaaatt   18000
tttgctgccc tgggtgtggt ggtaaacccc cgcactatcc aacttggtgt catggagctg   18060
gcgacaatat ttttacagtg gttagtgctt ggaaactgga cttctgggtt atgccctgta   18120
caaacagcat caaagtcgct gggctagggt gacagaggag gctgccaaca gggaattctg   18180
tggctcctgg gacaggaatg gatatgggag gttgggggcc agtattttcg gttctcttga   18240
ggagttggcg agtattagtc tttgccctga tggatagaag gaatctgtct gtgtcttgca   18300
tgaaccgtgt acttccccca gttactcctt ggacaccagc tgcctgctgt tcataattgg   18360
gccagatttc taatactgca gcgctaccaa atgtcagttt taggccatct ctggtgtagc   18420
```

```
cagggaacgc caacacctt tcccaaaggt agaatttgtg tgggttttac ttcactgagt   18480
gactaatgca gatctttatg ttttaatgat gggaagaaat tcgtcagcct gggtactttt   18540
tccatgtgat ggggcaaaaa tttaaaacac ttgcacaacg cttttgtttt ctccagctac   18600
taaaggtgac tgtcatttag gcattatcag tatgatcagc tgatgttaac ccactcccct   18660
tctggagacc cgtttctgtt tctgggaaag gtgtaggaca tgctggattt ggcaagattg   18720
caggtcccag gcagatgtcc ggacttagac tctggctctt ttttttttt ccagacaggg    18780 tctccctctg tcacccagtc tggagtgcag tggcgcgatc tcggctcacc acaacctccg   18840
cctcccaggt tcaagggatt ctcctgcctc agcccctga gtagctggga ttacaggcgt    18900
gcaccactat gcccagctaa ttcttttttt tttttgaga tagaggctca ctgtcaccca    18960
ggttggagtg cggtggcccg tccgcctgc ctcagcctcc caaagtgtta ggattacagg    19020
tgtgagccac cgtgcctggc ctcagctaac ttttgtattt ttagtatcaa cgaggtttca   19080
ccatgttggc caggctggct ttgaattcct ggcctcaatt gatctgccca cctcggcctc   19140
ccaaagtgct gggattacag gcatgagcca ccgcgcctgg cccagaccct ggctcttact   19200
cctaggtcta cctctaccat cactgggcc ctcgcctgaa ccttttgccc catctataaa    19260
atgggagaac tagactaggt ctgtgtcccc caagcttcaa tcatttgtaa aggaaccacc   19320
tttactattt tgccatatcc cacggctgtc tctatttcat ttttcactta atattatttt   19380
cccctgcagt tgactcactt gtaaaacaaa tgtatttgaa aaggagactt tgtgtcacta   19440
taataacgga aaaacagcgt cactaggtaa atggaaggta accataaata aaccccaaac   19500
agttattaaa ttccagccag cactgttgcc tgttcacaac atgaggcata ctctcttttg   19560
gttaaaaagg gaaattagca agagatggag aggtgttgaa ggtaacctag cactacattg   19620
agccttttcc ttgacctgct caggaggatt gagaaagaac taggagaact gggaagagaa   19680
taacgtcttt ttgtgatgca aagtgcctga gtgtgaccaa gagctcagag tagtaatgta   19740
tagatgcttt gtttggatac ttatgcagcc attaccatgt gccaggggtg tagaggggct   19800
aggagtatag aggggattgg gacttgttca ctgacttctg gttgcttgtg gtctagtagt   19860
ggggaggtgg tcatagaata ttgaatacaa acgaagatcg aacaggctgc agggggtttaa  19920 taggaaaatc acaggactaa attctgtcat gtgtacatgg ggtctacaaa taagagttgt   19980
ttagaatttt ttttaattta aatttcccat gaaatataaa tctatttcat tccagaatga   20040
ttctagagaa gctctaaata cattaaagtt gtgttggctg ggtgcagtgg ctcatgcctg   20100
taatcccagc actttgggag gctgaggctg gagaatcact tgtggccagg agtttgagac   20160
cagcctgggc aacatgggag accttatctc taccaaaaaa aattttttt tctttctttt    20220 ttttttttt tgagacaaag tttcgctctt gttgcccagg ctagagtgca atggcatgat    20280
ctcagctcac tgcaacctcc gcctccctgg ttcaagcaat tctcctgcct cagcctccca   20340
agtagctggg attacaggca tgtaccacca cacccagcta attttgtatt ttttttagtg   20400
gaggtgggat ttcaccatgt cgatcaggct ggtcttgaac tcctgacctc aggtgatcca   20460
cccatctcag tctcacaaag tgttgggatt acaggcgata gccactgcac ctggccaaaa   20520 acatttaat aaattagctg ggtatggtgg tatgtgcctg taatcctagc tacttgggag    20580 gctgggcag gaggatccct tgagcccagg aattccaagc tgcagtgaac tataatcagg    20640
tcactgcact gaagccggag tgacagagtg agaccttgtc tcttaaaata aatttgtgtc   20700
attgtttgtt gttttatggg tgttatgaca atgatccatc ttaacccttt atgtagtggt   20760
```

```
aactaactttt ctcttttcct aaaagctgat ttgagtttta ggttctcttg gagtctgtga   20820
caattgtaaa tagataagat ataacaaaat ggcctgaaat actcttgcaa cactcatatt   20880
tcccccctca gattagcatg ttctatactc tctgcaaagc aagatataca ccagaattag   20940
gcctctaaaa agcctcatac tgctaatctc tgggaatgaa tggtgttctt tgggataatg   21000
ggatatgaag ctcagtctga ttttctgtt ctgctggtag cttagggccc cctttcttct   21060
gttgggtttt ttgggagaag ggaagttgtg attaagaatg agaattcttt tttttttttt   21120
ttgtctcaag agtcttgctc tgtcgcccag gctggagtgc aatggctcga tctcggctca   21180
ctgcagtctt cacctcctgg tgtcaagcga ttctcctgcc ttagcctcca agtagctggg   21240
aatacaggca cctgccacca tgcctggcta atttttttgta tttttagtaa agatggggtt   21300
tcaccatgtt ggccaggctg gtctcgaact actgacccca tgatcccaac ccccccgacc   21360
tccccggcct cccaaagtgc tgggattata ggggggagcc actgcgtcca gccaagaatg   21420
agaatttggg agtcaggcac ctctgggatt gaatctggaa ttgactgagt gtacatgctt   21480
tctctgaggc ctccgtcctc actgctctca tctataaact gggaataatc atagtttcta   21540
tctgaaacag tgggtgtgaa gatttaacga gctaaattgt aaagtgcctg agacatggga   21600
agaagtcagg atgtgctaat gggtaatctt acacttcccc aatggaaagg gccaggttta   21660
tattactcta ggctggtagt aagcgaggca aaggagatat caggtttcag ctttgttaga   21720
acatgctaat ggcaccagga cactcagaag agatacagag tttgagacaa atggcaccat   21780
gagccctgag acattgtgta tggggtgaat cggatagcaa aatagactt caaggaggga   21840 agtagggcag ttagaatcct ttcagctgca aggaactgaa aactggctca catagaagga   21900
aaatgattgg ctcatgtcag caagcctaga tgcagagcaa gttatgggtt tcagggatcc   21960
agcatctaaa tgatgtcatc aagaacccaa gttttttggg tctctgctct gttggtttct   22020
ttcatcctaa agctggttct cctgtggttt accatagtag agttcctgtg agaactccac   22080
tctgaccaat caggccttcc cagagccagg gatggatgga gtcgcttctt ttgaggccca   22140
tgggtcctat ctggagggga tggatccaga ctcctatcag gaatctagga ggggccgggc   22200
acggtggctc atgcctgtaa tcccagcact tcataatgcc aaggtggaca gatcacttga   22260
ggccaggagt tccagatcag cctggccagt atggtgaaac cccatctcta ctaaaaatac   22320
aaaaattagc taggcgtggt agcaggcgcc tgttgtccca gctactcggg tggctgaggt   22380
gggaggatca cttgagcctg ggcacagagg ttgcggtgag gttgtggtga gctgtggttg   22440
cgctgctgcc ctccagcctg ggcaacagag tgagaccctg tctcaaaaac aacaacaaca   22500
aaatcttatg taccccataa atatatacac ctactgtgta tccacaaaag ttaaaaatta   22560
gaaaaggcaa attgcagaga tttccatatg ctatgatacc gtttatatga agttttacat   22620
atgtcataaa aatacagata acctttaggg gaatgatcat taccaaactt ttggataacg   22680
gtttctgggg atgggcagag agggctatac agtcatgaag aggtgtatag gggctttcaa   22740
ctctttgtag tgttttattt cttcagtccc atggtggtta tatgattctt cactcccctt   22800
tttttgtgtg gaatattttt cttataaaaa gtgtgtcttt tatttattta tttatctttt   22860
tcacatggag tctcactctg tcgcccagge tggagtgcag tgttgcgatc tcggctcact   22920
gcaagctccg cctcccgggt tcgcgccatt ctcctgcctc agcctcccga gtagctggga   22980
ctacaggcgc ccgccaccac gcctggctaa ttttttgtat ttttagcaga cgggggttt   23040 cactgtgtta gccaggatgg tctcaatctg ctgaccttgt gatctgcctg cctcggcctc   23100
ccaaagtgct aggggattac agacgtgagc caccgtgccc tgccttttttt ttttttttt   23160
```

```
tttttttttta aaggcagagt cttgccctgt tggccaggct gcagtgcagt ggcctgataa  23220
tggctcactg cagcttccac ctcccaggct caagcaatcc tcccacctca gcctcctgag  23280
tagctgggac tacaggtatg tgccaccaag cctggctaat ttttccattt ttaaaggttt  23340
tgccatgttg cccaggctgg tctcgaaccc ctgggttcaa gccatcctcc cacctttggcc  23400 tcccaaattg ctgggactat agacgtgaac cactgcaccc ccatccaaaa gtgtcatttt  23460
aatgctgaca tactgcatta ctaagcttga ccaggggaag agaaaaaaaa ataccttgtg  23520
tttattattt tgtttgtttg tttgtttgag acagggtctt gctctttctc ccaggctaga  23580
gtgcagtggc atgaacatgg ctcactgcag cctccacttc ccagggtcaa gccatcctcc  23640
cacttcagcc tcccaagtag ctgggattac aggtgtgtgc caccacacct gactaatttt  23700 tcttttttc tttttttgta ttttggtag agacagggtt gcccaggctg tcttgaact  23760 cctgagctca agcaatcctc tcttcagcct cccaaagtgc tgggattaca agtatgagcc  23820
actgtgcccg gcctgtttgt ttgttttaaa gacaagtttg ggcccagttt ataagaaaag  23880
aaaacagacc atccttaggg tgtcaggatg atattttgac aaaggcattc atgcttagca  23940
ggatttctct cccctaccc ccaccccaag tgttgaaacg gctgagctaa ttaccttaga  24000
atgtaaggct tcctctgttg cttgtgaacg tggcagactt gggattctca gagacagagg  24060
gcttcagaag cttgcctctg ggagcgtcca gtcaatagct ttttgtctga gcagaaggag  24120
atattgctca aggtaccatc tcaagggact gctgaatcag ttgcattgtc tctaaaagta  24180
ggtaaaagtc tagagtaggg ctggttcaac agtggaatga gtgttaagag agagttgcat  24240
tctaagaaca cctttacact gtggccaaat tcaagcaggt ccattttgtg gtttggtggt  24300
ccccatctag tgggatgtgg tctggtatcc caggcacctg catatatgag ctcagatggg  24360 tttaatttt gaaaaactgc tttattggct gggtgtggta gctcatgcct gtaatcccaa  24420
cattttggga ggccaaggca ggaggatctc ttgagcctgg gaattcagga ccagcctggg  24480
caacattgag agatccccat ctctactccc ttccccgcca aaaaaaagct aggtgtagtg  24540
acatgcacct gtggtcccag ctactcagga ggctgaggtg ggaggattgc ttgagcccgg  24600
gaagtcaaga ctgcagtgag ctgagattgc atgactgcac tccagcctgg gcaaaagagt  24660
gagacattgt ctcaatctcc ccaccccttgc caagaaaacc caaaaatat tgaggtataa  24720 ttgttataca atgaagaaca cattttgatt agcttataca cactcctg tgtacacatg  24780 tacactcaca catcaggaaa ccatcaccat aatcaagaca gcgaacctcc ctatccagcc  24840
ccagaagttt ccttgtgcct ctttgtaatt cttgccttt atctctccat gtcttccaca  24900
cccatgctca agcattcact gatctgcttt ctgtcattat cagtcagttt tcatcttta  24960 gccttttata taaatggaat catatagtat gctgttttgt ttttttttga gacaagagtc  25020
tcactctgtt acccaggctg gagtgcagtg gtgcgacctc ggctcactac aacctccatc  25080
tccccagatt taagtgattc tcctgcccta gcttcccgag tagcagggat tacaggcaca  25140
tgctatcatg cctagctaat ttttgtattt ttagtaaaga tggggattca ccatgttggc  25200
caggctggtc ccgaactcct gacctcaggt gatcacccgc cttggcctcc caaagtgcta  25260
ggatcacagg catgagccac tacgccctgc cagtatgtac tctttttgtc tggcttcttc  25320
tagcatagtt attctgaaat tcatccttgt tgcatgtgtc aatagtccta ttccttttta  25380
ttgctgagta gtagtccatt gtatggatat actacatttt gtttatacat ccttctgttg  25440
ataacatttg ggtggtttct tatttatta tttattttg agacggagtc tcactctgtt  25500
```

```
gaacaggctg gagtgcagtg gtgtgatctt ggctcactgc aacctccacc tcccgggttc   25560
aagcaattct cctgcctcag ccttctgagt agctgggatt acaggcattt gccaccacac   25620
ctggctaatt tttgtatttt tagtagagac ggggtttcac catgttggtc atgctggtct   25680
cgaactcctg accttaggcg atccgctcac ctctgcctcc caaagtgcag ggattatagg   25740
tgtgagccac cacgcctggc cgggtggttt ctaaataaag ctatcatgaa catcttttac   25800
tactctttgt atggatgtat atttctattt ttctgagtgg aatgttagga tcatacatca   25860
taggtgtacg tttaactgtt caagaaactg ccaaactgtt tcccaaagtg gttgtattgt   25920
tttacatttc cacgagcagt gtttgagagc tccagttctt gcacatccta gccacaaaaa   25980
ggttctgttt tttaaagaca attttttttt tttttgaga gtttcgccct agtcgcccag   26040
gctggagtgc agtggtaagc gaatccctgc tacaggccag agactgttct cagttggttt   26100
ttacaccaag tatcgcactt cattctaaca ctccaccatt ttacaaatga ggaaaccgag   26160
gcactgagag gtttagtaac ttgtggcaca gccaggaagc agtagagaaa gactttgaat   26220
ataaatgtat ccattaggat gtatatggtt ccaagtcatg ggaaacctac ctaatcctgg   26280
tttatccaaa aagggagctc attggctctc gtaactgaaa agtcaagggg taggcaggca   26340
gttggacctg gaagtctcca gggcatcaga gagccttggc tctgcttctc tgattctgtt   26400
gtctctccac agacgggtgg gtgtagcagt cccaggcccg cagccacacc ccacacctcc   26460
cagaggaaga aggcgggccc tgatcccagc agtcccagga aagccctgag gttcactgtg   26520
attggaccag cctatgtcac ctgctcacat tcagcccac cactggcaag ggtgtttgac   26580
tcttgggaat gactcttggg actggcttgt cctagatcac atgttctacc tgaaatttggg   26640 gacattgcag aggattggtg gagtggacct caaggaggtg tttcacgtgg cttcctgtgt   26700
cactaggttg ccatttattc tttagaaagc ccctttgttt gatgaaaccc tggtgtcaca   26760
ggctgtgtga cttagggtaa tccccttgtc cacatctgtg aagtgagatt acctcttcac   26820
ctcacaggca gatcaaacag gaaaacaaaa acaaaaccaa acccaaaata cacgtaaatt   26880
gcagagtgct tgaggtttct tttaagctgt ctatgtaatt aaaagctgtt acttagactt   26940
ggatatgaaa taaatctga cttcaaattt aagtggtgta atttccatgc ctcttaaaat   27000
atcaggtaac ttcatttgtg agcctcagtc tgtagacttg agggatttcc atctgaagag   27060
ggggcagaat ggtggtttag ggaacgcaac atgtaccca ccccaactt ttttaagagg   27120 aagagttgaa agaaataatg aatgtgtgag aaataagggg tttgattgcc ttccagggtc   27180
catgttgaag gagaggaaaa tgtagctcaa ccacagtgac tctccccaat taaaaactaa   27240
aaaaagatcc gtggttatag ggcttggact tcggacaagc cagcagcctc agtcattgtg   27300
agtgtgattc cagattggaa ggttctgcta ggaggaaagt ggaagttttg agaattccta   27360
gttggacaga atgcctcttg atcacggcct tagctaaagg agaccactct ttgctggatg   27420
gatcagtcag ctacgtgtga agtttggctc agtacaacat tctcggcctg gggcggcagc   27480
atgggaaaga tttttattgg aattaacttt ctacagagat gtactttcaa atgagaccat   27540
ccttctctca ctggtgagct cacccgggct cttattccac aaagcttaat tgttttggac   27600
ccatacattt aaactcctta attaattgac tcaagactta ggacagattt gcttttcttt   27660
ataatgactc catggctgta aatgctgctg attcagatga aagaggaccc tagagcacag   27720
aatgagaagg acgtggactc aggatacctg tttctttatt ctgactgtgc tcttcgtcag   27780
ctctggggct ttggaccca gttttgtaac cacctaacga gttcacctttg cctgctgcct   27840 agacggagct gatttatcaa gacagaggaa ttgcaatgga gaaagagtaa gtcacccaga   27900
```

```
gccagctgtg tgggaggcta gaattttatt gttactgaaa tcagtctccc gagcatttgg   27960
gatcagagtt tttaaagata attcggcagg tagggctca ggaagtgggg agtgctgatt    28020
ggtcaagttg gagatggagt cacaggggt cgaagtgacg ttttcttgct gtcttctgtt    28080
cctgggtggg atggcagaac tggttgagcc agattaccgc tctgggaggt gtcagctgat   28140
ccatggagtg cagggtctgc aaactatctc aagcactgat gttaagtttt acagtagtga   28200
tgttatctcc agaagcaatt tgtggaggtt cagactcttg cagttctga cccctaaacc    28260 ttaatttcta atcttgtagc taatttgtta gtcctacaaa ggcagactgc tcccaaggca   28320 agaagaggg cttttgggga aagggctatt agcagtttt tttcagagtg aaaccataaa     28380
ctaaattcat tcccaaggtt agtttggcct atgcccagga atgaacaagg acagcctaaa   28440
ggttagaagc aagatggagt cggttaggtc tgacctcttt cactgtctat aattttgca    28500 aaggcagttt cagtttctca cctgtaaacg ttgaagactg agccagaatc agggtcatca   28560
aatagcaccc cggctatact ttcttctctt catgacaaac attgctgtc agttgatatg    28620 atgttctttc ccactgggcc cagacttgac attagagtct tttttttttt tttttttttt   28680
tttttgagac agtctcgctc tatcaccctg gctggagtgc agtggcacca tctcagctca   28740
ctgcaacctc cgtctccaga gttcaagcaa ttctcctgcc tcagcctctc aggtagctgg   28800
gattacagga gtgcaccacc acccccagca gatttttgta tttttagtag agacggggtt   28860
tcgccatgtt ggccaggctt gtctggaact cctgacctca ggccatccgc tcgctttggc   28920
ctcccaaagt gctaggatta taggcgtaag ccaccacgcc tggccgacat cagagtcatt   28980
ttagcctgca atgcaagttg tcctcagtgg gctgctagca ttggcttcaa ccttcatatc   29040
agccagctaa agcccctgt aatgaatggg gaggttcctt cacccttgcc tcccgctgcc    29100
tcctcttgac cactcatttt ttttcttgta gttcaggaac caattcagat gatttccctc   29160
gtgaagtcct ctcgaaagcc cccaggtaga attattcatt ttttcccttg cattcccaca   29220
gcactgtgca cacaaattag aatccttgta aaatggccat gattctgttt atgaccctgg   29280
ccctccacca gaccagcctc tctgccctct ggcttttta gatcactggc atggtttctg    29340
cctactccag gtgccagtat tattttgtga atgtttttt tcttcatatc tactcatctt    29400
tatactactt tactcgtaaa aggaaactag agaacatgat cttaaatgaa aaccacgatc   29460
acttgccaga aagaacaggt aactaggctt tgaaaaaata agttagagga gatagcataa   29520
gaaaaaatta aaaataaat aaaatcaatg aaaacaacgt gttactaaat tcttgaaaag    29580 tttttgaag actttgagcc tgaggcctgt tcttattgtt tgtttgtttg tttgtttgtt   29640 tgttttatg acagagtttc gctcttgttg cccaggctag agtgcaatgg catgatctcg    29700
gctcattgca gcatttgcct cctgtgttca agcgattctc ctgcctcagc tcccgagta    29760 gctgggatta caggtgcccg ccaccatgcc cagctaattt ttgtatttta gtagagatgg   29820
gttttgccca tgttggccag gctggtctcg aactcctgac ctcaggtgat ccacctgcct   29880
tggcctccca aagtgtgggg attacaggcg tgagccacca tgctcggcct gttcttattg   29940
ttaaaaagag agatttgtgt gaaagctgct gacgtctttt tggcaccaag tcaagactga   30000
gttagttctt gtcagaatct gattgtttgt gaattgatgg ctttttttt tttcctgagt   30060 tggggtctc gctctgttgc ccaggctgga gtacgaccac tataacctca aattgctggg   30120
ctcaagcaat ccttccgcct cagctgccca agtagctggg actactaggc atgctccacc   30180
atgcccagtt aattaatttt ttttttttt tgagagacag ggtctcacta tgttccccag   30240
```

```
gctggtctca aattcctggc ctcaagtgat ctcctgcctc agcctcccaa agctctggga   30300
ttacaggagc gagccactgt gcctggccgg attttaaagt tctgcccatg cacctcctta   30360
gctctggcag ttactacttg caggcatctc ctttgtctgc cctgccccctt gttaggaaag   30420 gctgtgctga ctgtcagctg gcacccagtg catagaagag atagttctct gtagatgatg   30480
ttgaacaatg tggtactata atcccaacct gttgtatctt tgtttactct caaaagcaac   30540
aattgggctg ggcatggtgg ctcatgcctg taatcgcagc actttgggag gctaaggtgg   30600
gagggttgct tgaagttagt tccttttttt tttttttttt aaaaaaaaga caagatctcg   30660
ctctgtcacc ccggctggaa tgcagtggca tgatcatagc tcactgcagc cttgaccacg   30720
tgggctcaag gaatgaacca ttgtgccagg agttcaacac cagcctggat aacatagcga   30780
gaccctgtct ctacaggaaa aaaaaaaaaa aagaagaatt gcataagtat catcagaact   30840
gttgaatgga aaatcagact ttgtgggttt ggtttgttaa ttacttctcg ttggattaga   30900
atttgatagg taaaaaaaaa aaaaaggtg tagaaaagtg attccagtct tgagcaaatt   30960
tttaatgaaa aacggtgtct tggttctctg ttcactacaa cttgtatcta agggaaagcc   31020
tagtgatgca gacatttcat ttcgtgatgg gaaaactgat gcccagaggt tcacagctga   31080 ccagggggcta gtctgactgg ggggatctag gtcaccaccc cccttgcctt gttttcccag   31140
ctagtgcatt tcctactaga cttgactcta ctgtaattca agttgctgag tagcaaacaa   31200
gaactacaat gactagaagg aacagaacta gcttttttgt gctctgaaag tggaaactta   31260
ttgagggttc ttttcctccc agagaatgca gaagtgccct gatttgcttt tggaaggaca   31320
ccattcactt tattgcctct tttcattgtt gcccagaata tcaccatgat ttattcatgg   31380
gtggtgggga gggtagcact agtgtatgct cccagcaaag aggaacatct cacgttgtga   31440
agagatgcgc aaaactaagc cagggcaggg tgtggtggct catgcctgta atcccagcac   31500
tttgggaagc tgaggtgggc agatcacctg aggtcaagag ttgaagacca ccctggccaa   31560
catggtgaaa ctctgtctgt actaaaaata caaaaattag ctgggtctga ttgcaggtgc   31620
ctctaattgc agctacttgg gaggctgagg caggagaatt tcttgaacct gggaggcaga   31680
ggttgcagtg agctgagact gtgccgttgt actctagcct gggcaacaag agccatctca   31740 aaaaagaag caagccagat cttttggggtg ctgtgacggc aaatcccccca gcgctggcct   31800 ctcaggttct cttgcgggat tagtgtttgt tgaataataa gcaatacacc ctgacccagc   31860
gagccaaagc aaacaggaca gtaactgaaa ctgcagggga gtgtgagtaa acagttacct   31920
tctaccctca tggagctggc ctctggccag caacatgata gctgtttgca tcttactctt   31980
atggagccat tggccctctc attaaggtgg gggcagcttc tggtccatgc ctgcaagtcc   32040
tcatgggagt gggtacctga cagggtgtaa agggtaggtc tgaggacatg gtttcttttt   32100
tttattgttg ttgagatgga atcctgctct tgtcacacag tctggagtgc agtggcctga   32160
tctcggctca ctgcaacctc cgtctcactg gttcaagcga ttctcctgcc taagcctcct   32220
gagtagctgg gactataggc gcatcctgcc atgcctggct aagttttgta ttttttagtag   32280 agacgggtt tcaccacgtt ggccaggctg gtctcgaact cctgacctca ggtgatccac   32340
ccacctcagc ctcccaaagt gctgggatta caggcgtgag ccaccgtccc agccaacat   32400 ggtttcttta aaatatactc cccgctccat cccattcatg tgtgggagtt gagctgcatc   32460 tgggttttc ttttctcttt ttctgtaaat ctttattgta ttttttttgg atcatagaat   32520
ggatacatgt ttcttaaagt ttgatcatta tagaaactta attagactat tatttgagtg   32580
ctaaccatag tgagtgagtg cttactgtgt gctaggtggc tttttatgcc tcatgtcact   32640
```

```
tacatgaggt ctgaggaacg gtgttaatcc cgttttgcag ctgaggaaac tgaggctaca   32700
tttacggtca cctagctggc aagcaagtgg ctgagcctgg agcagcagca gatctgggga   32760
actccacaaa ccagatttct gtgtggtatc cctgtggaca caaggattta acttgattct   32820
ttttgctttc agtatcactt tatgatatta caatgagctt gcagtattta ttttcagaag   32880
aaaagccaga ttattcccat ttatgagaga agcagccagg tgggcaggga tttccagcgc   32940
tgaaccagcc agtgtgtgca ttgtctcttc ccgctgagcg gccctggtgt gctgggttag   33000
tctgtgagcc acaggaaatg ttgtcagggc ctctgggctt ttggatgtca gcaggccttc   33060
agtggtgagg aggttgtggc tggactcaga ggactccttg cttttgctga acgaccctcc   33120
ccaccaacca ccaccaccac caccagtggg actagcccat gagctgtaag ccaacctttt   33180
ccttcctaac ttaattttcc aaagaatagt aacttaccca ccaccactgc agtcactggg   33240
ccgggaagac aagcactctt gccttgaatc catgccttga gccagtagcc ttgacccagg   33300
gtaaagcagt tatgtgcttg ggtcacctgg gtcatgtttt tgaaattgcc tcaagcctac   33360
cttacaaatc cttcctggaa ccctgcttgg cttttctttg tgggcttccc ttaggaggga   33420
agcttcccga gcagcttgtc ttgactgtag ccagctgggt ggtcccagcc acagaattta   33480
actgtcaaac agcaccagaa gggttcctca tccagctgtc ttgccccaag tgccctcttt   33540
gctttctttt tagagagttc tgagactcat tagagagttt agagatttta gcattcttga   33600
agttctttct gtggtcagtt tggtgaacca cttcatttct aaagtttctc agttgacccc   33660
attcttcccc agctttgcat tctccatgaa gccacctgtg tttggtgtgt atgggttttc   33720
tgcaacctag gttgaacaag tcctctagaa tcctgaacaa ttggtgattc atgctggcct   33780
ggttttctta attggcctgg aaatgtggct gtagtggaca caagtggact tggcctcctc   33840
tttgatgcgg gtaaacttta gatttgcatt agctctgttt gattagagga tcttactggt   33900
ttttgttgtt atttatttac cttttaggag ctttagtctc tgtaggtttt ttttttttt   33960 tttttaaagt ccgggtctta ctctgtcacc caggctaggg tgcagtggca tgatcacagc   34020
tcactgcagc ccccaccttc ctgggctcag gtgatcctgc caccttagtt tcctgagtag   34080
ctgggactac aggcatgtgc caccatgccc agcaaattta tttctacttt ttgaaaacag   34140
ggtctcactt tgtcacccag gccagaatgc agtagcacga tcatggctca ctgcagtctc   34200
aacctcccag gcttaaggga ttctcccacc tcagcctccc aagtagctgg gaggctactt   34260
ggcatgcatc acaaggccca gctaatttgt gttttttctt gtagaggcgg ggttttgcca   34320
tgttgcccag gctggtctcg aactcctggg gtcaagttat actctctcct tgcctccag   34380 ccatgagccg ttcgttgcgc ctgggctagt cattatagat ttatcccttc tttcatctca   34440
tgctacaaaa gcagttcttg tattttacc cgacttgtga ttttctactg ggaatgtttg   34500
tttgtgatgg ttagcagggt gctgagaggg aattaatccc aggaggccca atattgggcc   34560
atgtcgtgct gttgagcaca gtcatttgac acctataact tctcatcaat tcttctgata   34620
gactgaggag gaattgggaa atttcctaga gttttgtctg cattattggg ttgttttgag   34680
aacataaacc ttaaactcta gctatgtaaa ctggataagt catttggta atttggcatt   34740 cctttttttt tttttttttt tttttgagac agagtttcac tctgttgccc gggggaatga   34800
tctctgctca ctgcaacctc tgcctcccag gttcaagcaa ttcttctgcc tcagcctccc   34860
aagtagttgg gactacaggc acactccacc gtgtccggct aattttttgta tttttaatag   34920 agacaggatt tcatcatgtt gaccaggctg gtaatttggc attcttttga gtacaagtga   34980
```

```
gagaaactca cttgagctgg cttaagtgaa aaaattcttt gtcaggagag ttttgtgaat    35040
ttctgtttag tggcaagttg tagaaaccac ttgaaactgc ttaaaggcaa aagagggagc    35100
cacttgtccc agtaactgag acatcccaga gccgactgcc cccaagcatt acttggtccc    35160
aagtttcaaa cgggtcttca gggtttgatc tctctcctca tctccagtct gcttcattca    35220
ttttggctct atgtggtggc agaagggctt ctggcatctc tggacccttta tgcctcccag    35280 gtccaaaccc agccagaaag gagagtgaga gtgctgagtg caaaactctc ctatagctcc    35340
tatacaagtc caggatttgc tattagactc cttgaattat gtgcccagct ctgagccaat    35400
ggctgtgctt aggaggctcc tgtctcatgc acccacccca gtactgggca tcagaaacaa    35460
ccagtgatcc ctataatgaa ccacgggttc acagacttaa gtgtaatcct gcagcagggc    35520
ctcaggaaga cttgaaaccc aaaatcagaa agccatggtt tcttgtcttc ctggtgtctg    35580
ttttgtccct tccctctgta gaggagtcct gctatcactg caggcaacgg ggctgccctg    35640
cagctcctgc tgtttacatt tcactcggtg tagccatagg cagagacctc agggagaacc    35700
tgattcggct tggattgagt caggttccac cccagtccag tcagttgtgg actgagaggt    35760
gatgaggctg ggccctttaa gacaaatctg ggtgggtgga gtctgtgctt aatgaagttg    35820
tgatgttagc tgatggccca gaagggactg gtaggtgcct ctcattgtct ggttgggaag    35880
cattctctta agtccaagat gatgataaat agtattaggc caggtgccgt gtcatgcctc    35940 tatcccagc actttgagag gccaaggtgg gaggatcgct tgagcccaga agttcaaagc    36000
cagagtgggc aacataaaga gaccctgtct ctacaaaaaa caaacaaaca aacaaaccaa    36060
aaaaacccca caacaattag ccaggcatga tggcgcacac cagtagtccc agctactcag    36120
gaggctgagg tgggaggatt gcttgagcct ggcgggtcga ggttgcagca agctgtgatc    36180
acacctctgc gctccagcct gggtgacaga gtgagaccct gtctcaaaaa gtaaaaaatt    36240
caaataaata aacaaataat atcaagggcc tctctcccaa gctaggaaga tatcagctga    36300
agctctagcc cagctacgtg gatggctgct tcctgcctgg aagcgatgcc cagatcagca    36360
ccttgggacc cccctgaact tgcctctgct ccagtgtggg cccttccttc ctgcagagga    36420
gacagcactg tctgagaggc atgaatgaga atttcctcct tctaggccca agtcagcatg    36480
actcgaggat ggctttgact ggaaaaactg aatcaaagag tgtgctacag ccaaggattt    36540 ccccaaaacac taatcagtgc tgattacttc cagggtattg cctttggctc tgtggagttt    36600
tgtccactgt ggctgcaatg tctggcttct gctgcccaga agatgagaaa tgagtttgta    36660
gggatgagcc tgggtgaagg gatgtgcccc ctcaccatcc tgacctctat taggtgtaaa    36720
agaccctgat tgccaaattc ataggtcatg ggttggctct gcctccagca ttaacacttg    36780
ggggtggagt tggggaatca tagtattact tgcataaatg gaatcctaaa agtttgttgg    36840
gacagtttca taaaaatcct caccatgatc agtttgaaaa tgacgttccc ttcacatgtt    36900
tgtcttctga actgagttgc aatgctgagt atgagtttga gagtcccaag accatctaaa    36960
gcaagcctgt ccaacccaca gactgcaggc tgtaggcagc ccaggacagc tctgaatgcg    37020
ccccaacaca aattcgtaaa ctttcttaaa acattatgag atcctttcgc atttgttttt    37080
taaagctcat cagctatcat tagtgttagt gtatcttatg tggccaagac aattcttctt    37140
cttccagtgt ggcccaggga agccaagaga ttggacaccc ccgatttaaa ggaagtaact    37200
caattttgtg aacctgaaac ttgatcttgg atgaaccaaa tgaaatttta tgattctctt    37260
aagctcacga aagttcaata actgtgctgt gtaaaataga ggtaaaagac ttgagttgga    37320
ccaggaatgg ttgctcatgc ctgtaatccc agcactctgg gaggctgagg cgggtgcatc    37380
```

```
acttgaagtc aggagttcaa gaccagcccg gccaacatgg tgaaaccctg tttctactaa    37440
aaatataaaa attagccggg cgtggtagtg tacgcctgta gtcttagctt cttgggaggc    37500
tgaggcagga taatcccttg aacccaggag gtggaggttg cagtgagcaa gatcatacca    37560
ctgcactaca gcctgggcta cagagcgaga ctccgtctcc aaaaaaaaaa aaaaaaaaa     37620
aaaaagactt gagttggttc taatagaata ccttggagaa cctcaagatg ccttctggtc    37680
cagccaggtt tacagattgg aagatattct gttaatcaga atctcagaga gggacaggcc    37740
ctgatcaagg taacacagtg agttgtggta gctgggctgg gctagaacct gggcctcctt    37800
ggttccaggt cacagggacc aagggatttg gcttgtctta gtcctacttg taactacaat    37860
actgccttct gctaggaaga ataagagctt gcaggctaga ggaatttata ggaattttct    37920
ttctttaaaa aaatccccc aaaaccagct ttactgagat ataactcaca caccataaaa     37980
ttcacccttt taaagtatgc aattttagt atattcacag aattatgcaa ctatcatcac     38040
tataatttta gaattgtttt ttttttttg gagacggagt cttactcttg cccaggctgg     38100
agtgcagtgg tgcagtcttg gctcactgca acctccatct cccaggttca gcgattctc     38160
cttcctcagc cttccgagta gctgggatta taggtgcatg ccaccacacc caactaattt    38220
ttgtatttt agtagacatg gggtttcacc attttggtca ggctggtctc aaactccgcc     38280
tgccttggcc tcccaaagtg ttgggattac aggtgtgagc cactgtgcct ggccaatttt    38340
agaatatttt tattgcctca gaagaacccc tgtatccatt agcagtcact ctcccttcc    38400
cttccccaac caggcccaat aaaccactaa tctactctgt ctctatggat ctgtccattc    38460
agaacatttc atatggtaaa atcatacacg tgttctggtg ttactgactt ctttcactta    38520
gcagaatgtt ttcaaggttc agccatgtta tgtctgtact ttattctttt ttacggccaa    38580
gtgttggaat gtgtaggatt tgaattttca aataaagctt taaagttttc agatttattt    38640
ttactttgcc tggtgtgttt tttcctggaa agccaacttc tacatttgga gattaaaaga    38700
caaactttct caaactccct gtacctaagt ggttgctgct tttcttaaat gttttgacac    38760
caaagagaaa aattggtttc tggaagaaag tgtgttttct tttattgcca agaaaattag    38820
tgcatgttaa ttaatataga tgctcaggac ccagagttgt aatgaacttt ttcttatat    38880
ttattttcta gatgtttgac ttattttaac agttttcatt ttagcaataa tgtttccttc    38940
ccactcccaa atttattgga aaccctcaat caacccatt tatttattta ttttagagat    39000
gggatctcac tatgttgtcc aggctggtct ggaaaccctc actcttatag atagtatgaa    39060
agaagattat agccaactct tatataacct tccccagagc ctccaattgt taatgttttg    39120
ccatatttgc ttgctctatc acttgctcta aagatgcata tcacacactt ttttttttt    39180
taatttattt ttgagacaga gtctggctct gtcgcccagg ctgtagtgca gtggcatgat    39240
cttggcttac tgcatcctct gcctcctggg ttcaagcgat tctcctgcct tagtctcctg    39300
agtagctggg attacaggca cgggccacca tgcccagcta ttttgtat tttagtaga     39360
gatggggttg gccaagctgg tcgtgaacta ttgacctcaa gtgatcctcc tgcctcagcc    39420
tcccaaagtg ctaggattac aggagtgagc caccatgcct ggccacatgc gtgtttttta    39480
ttgaatcatt tgaaagtact cagctcgtat catgacccttt cacccccaca tactccaaca    39540
agcatctcta agaaaaagga cattctccta accacagtgt ctctgcattc ccaggacatt    39600
cttctaacca cagcgtcact gcatacccaa gaggttagca ccgatacagt aataacatct    39660
tgtgtaaaac ttcccaaaat gctcccaagt gtcctttatg acagtttaaa aaaaaatggc    39720
```

```
attttttggg atccaggaac caattaacga ttactcaatt gaatttggtt tcaaagtcac   39780
atacctcaac ttttccttta atcaagaaca gccccctgc cttttacaca ttttttgtc    39840 tttcgtgacc gtgtcatttt tgaagaaatc aggcccgttg tcttgtagaa ctggtgtttc   39900
tcaagtgtgc ttgggagggt cttggtaaaa tgcacattct gattctggag aacagggtgg   39960
agcctgggaa tctgcatttc cagccagcat cccggtgatg ccagtgcagc tggtcttcgg   40020
ctgtagaatg ttccacattc taggtctgtc tgtttccttg tgattaaatt caagttgaat   40080 attttttggct agggcacttc ctgaggtcat aggtacttcc cactgcctca cagcacaggc  40140
tcacaatctc agtttgtcct gttacttcgt ggtgctaagt gtggtcacct gcttcaagtg   40200
gtgtccgcct gctctctgtt gaaacaatac ctttctccta gtataatgat taggtaacct   40260
gtgattgtaa ttggtaagta atctttgaga ctacatgaat atcctgttcc ccagcagttt   40320
tcactcattg gtgaactgtt tgggaaaaaa taatagcatc ttacagttat aataccctgc   40380
tggtaacaca tggctcttac ataatcagca gttaattgtt tgtatgtgtg ttaatttta    40440 tttttaaaat gtaactagtg actggtaact ctcatttgta ttttaaacat tggcttttac   40500
agcttctcag tacatttcac tctgtgtatg ttttttggtag agcatttgtt gtcctgtata   40560
atggtttagg aaatcctata ggccaaatga agggctggag actcacctgt gttcccacca   40620
ctgtgtttca ctgtgtattg ccagagaaaa tacagttaaa tttgaattc agatagacaa    40680 tgaataactt tttagtataa gtatgttcca agtgtggcag acagctctca caagttacaa   40740
gtcgttgcgt aggacatacc tatgctaaac gatttgatgt ttatctaaat taatatgtaa   40800
ctgatatctt gtattttat ttgtacgatc ttccaagccc acgtcccacc gccttctcgg    40860
ggatggccac catttgtgtt tgctgcctgg tggtgtttgc agctgcgaga agggccttgg   40920
aggaggagca aagtgtagtg gtatctccgt gctgtggcct tgggcactgg ggtggggtt    40980 agatgagtaa ttagctgaat atgacctcac ccatgaagaa tgtgcccttg ctaggtatta   41040
gcagaggttt aggctccagg gagccattgt cagaagcttg tcagtgatgt catcagctgg   41100
aagggccagc tttcaggcct caggaaaaag cttgaaagtc agggctccag ttttggtaat   41160
aaatgggaat ggagttttcac aggtagggtg tggaggaatt tattgtgaca ggaagcctga   41220
tggagcctct tgcctgtgtg cagcccccag ccaggtttct gagttctgat gaactaccag   41280
aaacttccac cacggcctgt gattacactg ttggcccaat gccctggaaa aattggcttg   41340
ctctcgggga acactccagg agctgcaaag ggggtgtcag gactgttgtg cagctcccct   41400
taaattgggg aggaggggtg gctgatgtgg aaactgttca ttagactgct cagggtagtg   41460
tgagaaaacg tgtaatctgt gggcatctac ccctagctgc ccctctgatc tcacccacta   41520
ctgtgggagc accccgtgga tgggggcaga ggagggtctt ctggatttag acactcacaa   41580
aacttccttt taccttgttc attggaagaa atagaaaatg cctttttttt ttttttttc    41640 ttttttttg agacagagtc tcgctctgtt gacaggctgg agtgcagtgg catgatcttg    41700
gctcaccgca acctctgcct cccgggttct aacaattctc ctgcctcagc tctggagta   41760 gctgggacta cagccacgtg ccaccacacc cagctaattt tgtattttt agtacagacg    41820 gggtttcacc atgttggcca ggacggtctt gagctcttga cctcgttatc cacccgcctc   41880
ggcctcccaa agtgctggga ttacaggcgt gagccaccat gcctggtctc tttttcattt   41940
ttaaagggta atttgctgtg caggagtggg ctctcagacc agaagtgggg acctgaatga   42000
aatcaaggac tgagtatggt aactacagcc atttaatttt atttgaagtc tcccgtaaaa   42060
tgttctggaa aaaacagggg ttccagggct gggtgggcag tttcaatcat ggactggatt   42120
```

```
ttgtggttca gatttctctg ggcctgttgg aggttcccct taagcaatta cccaaggcag    42180
ttctgcccag ctgaagtact gattacctgc acactatacc agtgaggact catgggtgag    42240
cagatgggag gcactgagct tgattctgaa accctggcct ccatcccacc tgacattcaa    42300
tgtcagatta gaatttggaa gaccctaagt ctccagattg gtgcactggg tagctcctga    42360
aatggggtgg ctgagacagg tcctctgtgc ccccttccac agcttcctct ggggcccttc    42420
tgctcactgg catgtgcttc tgggcaaata ggcctctccc agcatttgtt ttggctctgt    42480
gaaatggggt aatatttgtt cctattgcgg gtgaagcgct gctgttggga tgctcaggta    42540
actcactccg tgggtagctg atattgcctg gcaagtggc attttagagg aaatctgtgc    42600
catcaaaaga gttggacctg atcacacttt tgcttttgaa tatgctttgt cccagcctgg    42660
ccattcgtca cttgggaccc cctgagtctc tctgacccca ctgtaaaatg gatatgccat    42720
ggagttgtcc caggaatcaa gggcaggtcc tctccagtga gtgatgggct tgcctctcac    42780
ttctctaaca cccttctgct tcctgtgta agatttcact attagtggct attctctttt    42840
acagaagaaa aagggagacg catgcctctt ccagttcact gttcaccatt gcagcatatt    42900
tattccaagg gactggccga atcatccctt tctttgttag aatgtggttt tgttgccttg    42960
agacaagtgg cccgcatgtc tgcactgaag gaggctttgc gcaatagcct tgggcacctc    43020
cggttctgca agcatgtaca gtacttgctc tcctttccct ttctttgtat acttttctg    43080 gtctgctacg tgtccatctg catgtggata aagggtcgtc gtcttgagta gtgatttgc    43140 tgtgatgtga ttcctgtgag gtctagttgc acacagtgat tccgaaggta gacccagctg    43200
gaaagctttt aaattgctga tactccagcc ccactcccca agagatgctg attttgtttt    43260
gttttgggga gggcagtttt tttgggtttt ttttttaagc ttttgatgt gtagccaggg    43320 ttgagactga agtgattttt gtgagtaacg gagaagtgtt aaggcttgag aagttggaag    43380
agccatgctt gagataggac caaggtcata tccccggcat tagcacagag caaccctgac    43440
ctgttggaga gttgggctgg atggatgcgg tcagggaga gactcgcttt attttattta    43500
tttagagata cagtttcact cttgtcaccc aggctggagt gtaatggcac gatctcggct    43560
cactgcaacc tctgcctcct gggttcaagt gattctcgtg cctcagcctc ctgagtggct    43620
gggactccag gcacgcgccg ccacaccctg ctagttttttg tgtttttact agagacaggg    43680
tttcaccatt gttggccagg ctggtcttga actcctgacc tcaggtgatc cgcccacctc    43740
ggcctaccaa agtgctggga ttatgggtgt gagccactgt gcccagcctc gactcgcttt    43800
attatatcca cacttggaat acaattcgga ttgattgtag tggggcattt tataattagg    43860
aaaaattaat caggaaaaat cactccatgt agattagtac caccatatga ggggacaaga    43920
atttcttcag attaggaact tcttccaaca ggactgacag ggtccaaaac tactcttgga    43980
tccagcttta agatggaccc agcccactgt tgagtcccct ctgaggtctt ctctctgtgg    44040
atggatttga ttgttaacaa tggctgagtc atgtggcacc cagcccggtg agtaagacag    44100
ctgagtaaga ggggaaacag ggcctttggt cagaaaaacc agactgactt cagtcttatc    44160
tgtttagaga agcccagaa gctgcaaaaa ttgcagcttc cagactttag tgtgccgtgg    44220
tcatgacatc ggtgtggatg gcaggttgtc atctgagcag tcagggtggc agcacacagc    44280
ttgcgggctg gctgatggcc gaggtgtgtg aactgacctg ccccaagtga cttcagtgct    44340
gggcacagca taggagcagt actaatgata tggacagtat gctcagagga cgttagggag    44400
cacagctttg tgtaaagggc atgccctgcc ctgtccggat ttaaagcagc tatagcactg    44460
```

```
aaacccatg gtcaccctcg catttctaca cttctgcctg tgccaagtct agtttgtgtg   44520
cctcctccat tttgtgtgta catgggggta ttttttttctg ctaggcaact gctatttatg   44580
cctctcagta ctgtacttag tgtgtaccat tcctgcaagg tatagacatt gtcagcccat   44640
tttacagatg aggaaaatgg agttttttgag agggtgagat cattcagtgg cagaatggaa   44700
tgttaaccca ggtagtctaa cctctctgct gtagatctga tgtccatttg aactttagac   44760
ttcccatctg tgtctacagt ctagccctta aaaaatgtga taaacaggtt tttaggtaag   44820
tctgttaatt tcagaaagac attattatta tttttttagaa agttagagct tatgttaggg   44880
ctcagtctat cctcctgcct cagctgcctg aatagctggg actgcaggca catgccacca   44940
tgcctggtta atttctgtgg tatacatcat tgattactga gaagtcacag tccgttgtta   45000
aataactgag ctattcatag ccaaatcatt tttaaaaaca caaatataag caaaacaaa   45060 acatttattt atttatttat tgagacggag tctcgctgtc acccgggctg gagtgcagtg   45120
gcgctatctc agctcactgc aacctctgcc tcctgggttc aagtgattct tctgcttcag   45180
cctccccagt agctgggact acagacaccc actaccatgc ccggctaatt tttttttttat   45240 ttttagtaga cagggtttt cactgtgtta gtcaggatgg tctttatctc ctgaccttgt   45300
gatctgcccg cctcggcctc ccaaagtgct gggattacag acgtgagcca ctgtacctgg   45360
cccaaacatg tggtttttt aaatgaaagt gtgttcattt tacaaacagt gcattcttac   45420
taattttaca ggccctgtgc tagggacatg gcctcgtctt ccgctatctt agagtgaaga   45480
agtaaagaca gagaaagtgt tcacaagttg ctgcacaagt ctcattgcag tgcctcccag   45540
aggcgcgaag agcaacacct ttcacctggg ctgtcctaga aggcccgtgg cagggtgggg   45600
ttggtgaaca ctggggctta aggggggtgaa ttcagaagac aaaggacctt ctgggcaaag   45660
aagggcccag tagtgggaag tgcaggagtg tgagagtgcc tggaattgcc cactcactgg   45720
ctctggagct tggtgctgag tgcttgggaa gtgttgggag gatcagttat attgctggct   45780
gggttctaaa gaacctccaa agtttacata aaagttaacct ttgatttgac tgttctaccc   45840
tccagtcacg tggctaaatt aattaaatca aatttaaaat taagctcagc cataccaagt   45900
atatccagtg ttcaataggt acatgtggct tgtggctgat gcactggaca gtgtacatat   45960
aaaacatttc catcgttgca gaaacttcta ttgaacagca gttgtattag tccgttctca   46020
acactgctgt gaagaaatac ctgagactgg gtaatttata aaggaaagag gtttaattga   46080
ttcccagttc cacagggctg gggaagtctc gggaaactta caatcatggc agaaggggaa   46140
gcaaacatgt ccttcttcac atggaggccg cagcaaggag aagtgcagag agaagagggg   46200
gaaaagcccc ttataaaacc atcagatctt gtgagaacag cagcatgggg gtaaccattc   46260
ccctgattca attcctccc accaggtccc tccaatgacc tgtggggatt atgggaacta   46320
caatttaaga tgagatttgg gtggggacat agccaagcca catcagtgtt gttacacacc   46380
acagtggtgc tgtggtgtgt aggtgggaaa actatggcat gggggccata tctggtcctc   46440
tgcctatttt tataaagttt tattggaaca taggccacac tcatttattt atgtactgtc   46500
tatggatgct ttcacactgc aacaatagat ccaaatagtt gcaagagac tgtgtggccc   46560 acaaaaccta aatatttact atccaggcca ggcatggtgg ctcatgcctg taattccagc   46620
actttgggag gttgaggtgg gcagatccct gaggtcagg agttcaagac catcctagcc   46680
aacatggtga atcctgtctc taccaaaaa tacaaaaatt agctaggctt ggtggtgctt   46740
gcctgtaatc ccagctactt gggtgtcgag acacgagaat tgcttgaacc cagaaggcag   46800
aggttgcagt gagctgggat catgccactg tactccagcc tgggtgacag agtgagattc   46860
```

```
tgtctctcaa aaaaaaaaaa cttactcttt ggcccttat ggaaagtttg ctgacctctt    46920
ctgtagatgg tagggtacgg tagaaggtgt tcaagccagg agtaacatga atgattgtat    46980
ttatggccta agaggataac tcgtggtggt gggcgggcca tatttgtgga gagacccatt    47040
ttcagtgact tccaagagtc tgcgtgagag atgactgagg tcttgccctg gcaggaatgg    47100
ttccattaat ctgtgtctca tttgacaaat gaggaactac aaatgggaac agtttaagat    47160
gagatttggg tggggacaca gccaaaccac atcagtggtg ctaatagaca gtggtgctgt    47220
ggtgtgtagt agggaaaact atggcctgtg ggccaaattt tgaagtcctt ttacttttg     47280
gttctaaaaa ttattaattg tagccagagt tgttaactta atatgtcttg gaccccttgg    47340
gctctctgaa gactgtactc tttctttcca cttaataata tacatggaat tgcaaaggaa    47400
accaatgata ttgaaataga tatcagaaat aaaattttta gatatagcaa taaatgcaca    47460
tctgtattaa aatgtgtaat aacaagatct aacagtgagt ctaagaacta ctataattat    47520
catgtagcaa tggcataaag gatagtttgt gctatctaaa acagtcaatg acaggagaaa    47580
atctgatttc tttggtgata aaacgacagg tgctgctaat acacctgtgt tttatggtct    47640
tcgtttgtaa tgaaaagaaa tgccattaat aaatttatt tatttatta tttatttatt      47700
tatttatttt tttttttttt gaggtggagt ctcactctgt cgcccaggct gaagtgcagt    47760
ggcatgatct cggctcacta ctacctcctc ctcctgggtt caagggattc ttctgcctca    47820
ggctcctgag tagctgggat tacaggcgcc caccaccatg ccaagctaat ttttgtattt    47880
ttaatagagg tggggtttc accatgttga ccaggctagt ctcgaactcc tgaccttgtg     47940
atctgcctac ctcgggctcc caaagtcctg ggattacagg tgtgagccac cgcacccggc    48000
cagatgctgg gatgtttttt aagaccttag accctaagcc tatcatatca aatacaatga    48060
aacacaccca ctttcacac tttaaaaaaa gtgtgttggt gtttattgct gtaaaatagt      48120
ttgaaacttt ttaaaaaaag ttttggtctt gctcatactt gtgttttaaa aaagtatttg    48180
gctatgacta actcagttat gtatttattt atttattttt gagacggagt ctcgctttgt    48240
tgcccaggct ggagtgcagt ggcatgacct cggctcactg cagtcgccgc ctcctgggtt    48300
caagcctcag cctctcgagt agctagaatt acaggcgtgc tccaccatac ccagctaatt    48360
tttgtatttt tagtagagat ggggttttac catattggtc aggatagtct tgatctcctg    48420
acctcctgat ctgcctgcct cggcctccca aagtgctggg attacaggcg tgagccacca    48480
cgccctgtga ctaactcagt tatttaacaa ttgactgtaa tttctcagca atcagtgtat    48540
acttggaaat tctgggatg tgagaaaact aacctataac tcattttctt ttttctttga     48600
ggtgaggtct ctctttgtta cccaggctgg cgtgcagtgg catgaacagg gctcactgca    48660
gccttgacct cctgggctca atcctcccac ctcagtctcc tgagtagctg ggactactgg    48720
cacgtgccac catgcctggt taatttttgt attttctgta gaaatggggt ctcactgtgt    48780
tgcccaggct gatcctgaac tcctgagctc aagcaatcca cccactttgg cctcccaaca    48840
taccgggatt acaggcatga atgagccacc atgcctggcc tgcaacttct ataaatagca    48900
aagttagtaa ttagtgaaga tgatggtttg caagcactga attatacttc tattaatttc    48960
atttcctttc aattttctaa tgttttgtgc ccaatctgtc ctgtctgcct ctacctagct    49020
ttagaagtgt tttgttggtt cctgagatgg agctgtgcct gaagggtatg aggttaccct    49080
ctgggttcag cggggagatt tgggaagagt tttgatttgt aggccagtaa aggggcctga    49140
cattagatga tggctgctgg gctagggaac aacttagagg cagctaacag gattcaggga    49200
```

```
gagtggattt ggtgggagag agtagtctag gatgaatcca attgggtttt tatgagtagt   49260
ttggtagttg gttgactggg tgggtggtcc cttggtaatt atttgttgat tagtggttgt   49320
tgggttaggt tggttacact tacattatag tcgatggaat ctcagatttg gatctaatac   49380
cacatgtaag tcgagtggat ttttttttga gacagagttt tgctcttgtt gctcaggctg   49440
gagtgcagtg gaacagtctc agctcaccac aacctccgcc tcccaggttc aagcgattct   49500
cctacctcag cctcccgagt agctgggatt acaggcatgc gccaccacgc cgggctaatt   49560
ttgtattttt aagagttggg gtttcacca tattggtcag gctggtctcg aactcccgac   49620
ctcaggtgat ccgcctgcct tggcctccta aagtgctggc attacagggg tgagccactg   49680
tgcctggcca gttgagtgga tttttttagc actcaagctt cgtggctcat tgctattatt   49740
gtgcatgtga gcgttttatc tttcagtagc attaggatg ctacttggat gtgtttagt    49800 tattacagaa atagttttta ctaacttta ctaagttatc tttcctctcc tgtgtaggaa    49860
gtttagagtg aagcggcagt tggctggagg ttctgaaggt ttcccccttt cacataattt   49920
gatgttccag ttgcccacat caggacgact ccctctcttt ctactgatgt aagcagtggg   49980
ccaaattatg gggctccatc cctgcatctt cctacttgtc taaatcttcg tcacagacaa   50040
catattgctc taaaggaaac ctagaaagga ggagaagctg gttttcgccc aaattcctca   50100
aaatcatcgc ctgttgttta agaattacag tttgcactgg aacaataaga tgttccttaa   50160
tgtggttttt aagtgagttg gttgtcgcct gaatttcata aacactggct aaggattgtg   50220
caaaagggtg tgcttccctt tagcatcctt aattagggac agcgttttga aaactgcttt   50280
ttattgtcct ttatctgcaa aacttcttga atccaaatag cgagattctc atttcttaat   50340
cactgccaca gaaagttgta gattagagaa agctccaatt ccttatttcc tgtcttcctt   50400
tctttctgtg tgtttattgc ctgtgtctca tcctcactcc tgccagtttt atagaatgta   50460
acctcccagc ctctgggaat gtttgggaga cttgttcata gaggatctga agagcagttt   50520
aaagtggact tacccaaact atcttctgga gaacattagt ctctttggag ataaaatttt   50580
taaacatccg ctagtccaat agtgttggca aattccctgt gacactgtag ccctctcttt   50640
gagattgtca atgtacgttg gcatgttaaa ggctctgaga agtcctgcag cagttaaaaa   50700
attgtttagt ctagtgtgcc cccagttgtt tggccactga accccctttt tctggaaaaa   50760
ccagctaaca tctggtagtc ttttctaaga ggtggtactg aagatgatac tcatgttaca   50820
catttaaaaa ttctaacatg tgttttttcat gtgtttataa aatgcaacta atgtatcaaa   50880
cctgtgattt ccaggacata attacttaag ctaaggaaaa aagaaaacat gagtgaagga   50940
aaaactttag taaataggcc aggtggtaag aggagagagc cttgtctgtg agtgtggtct   51000 aggggatgc tggacctagc ttttcagagc taggttcagg cagagctgct ctgagatgta    51060
gacactgcag ctggggttct tgttgagccg ggaagcagct tctgactaag gtgcagactg   51120
tttagatgag ctggtcataa agagccctga ctgtggactg cgtctccagc cacggcagca   51180
gctggtggat ggggtgatgc cttggatatt tatcgtgtgt ttcttgcctg gcctgccctt   51240
ggacagtgcg cctcaggaat gttagaatgt gttcccccct tagcagcaaa gccgatctgc   51300
tgtgtacttg ttctgtttat cttactgcca cgaccgttta tcacgggcca gagttcaggg   51360
gcacactgat aaatctcttt taggaggatg atgtaaccct cagcattttc cccctacttg   51420
gttctgagtt tttaaagctt ttgtaacacc atcatgtcct tgtttgggca tcttcctgtg   51480
tactcccgtt tgggtctcca gggtgaaata gccaacagtg gattctggag tcatggcctg   51540
ggttcaaatt cctgctctgc tgcttatcaa ctctgacttt ggggtttaatt gacctattca   51600
```

```
ttattttttct taatctggaa aatggagcca acagcagttc ctcataaagc agctgtaagg    51660 attcagggggg gtaactgcac agggccaagc cctcaggttt cacctctcac tgggaggtcg    51720
gacctctgca taatggacaa gctctcctag ggtgcaagtg aacggggggcg caagggagtt    51780 aggaaggtgg gtgttttttg ttttttgtttt ttggtggctt gaaaaacatg cccaaggctg    51840
ggtgtggtgg ctcatgcctg taattccagc actttggaag gcagaggcgg gagcattgtt    51900
tgagcccggg agtttgagat cagcctgggc aacatggtga gaccctgtct ctcttttttt    51960
tttttttttt ttgagatgga gtctcgctct gttgcccaga ctggagtgca gtggcgcaat    52020
ctcagctcac tgcaaccttc accccaggt tcaagtgatt ctcctgcctc agcctcccaa    52080
gtagctggga ttacaggcgt gtgccattgt gcccagctaa ttttgtgct tttagtagag    52140 atggggtttt gtcatgttgg ccaggctggt ctcgaactcc tgatcacagg tgacccatcc    52200
accttggcct cccaaagtgc taggattata ggcgtgagct actgtgcctg gctgacccaa    52260
aaaattagct gggcgtggtg gcacacaccc ctgtagtccc agctacttgt gaggctgggg    52320
caggaggatt gcttgaggcc agcctgggca acagagcaag accttgtctc aaaaaaaaaa    52380
aaaaaaaaaa aaaaaaaaaa gaaagaaaga aagaaaaga aaagaaaaga aaaacatgcc    52440
caaaggcaac caaatgactc catcttttgc aatgtaatct tcaacatcga ctcctctggc    52500
aagctgtttg gaaatggcaa agtccatctc ctgaggctgg gagattgctt gtccaggacg    52560
ggtgtgtctg gtgaggaatg gaaggcattt ggatggccac tgagaaagct gagccaagga    52620
gcatcagaaa gacaatcagg caaacccaca gagtctccag gtattccttt gctgataggt    52680
aacattgcac tagcgattta aacaaacagg tgaaaggcca ttgccctacc accccacctc    52740
acctctattc cttgctgctc tttccagaag caactgcatg gtctgggaac agttttttgt    52800
cttgtcaaga gacagtctgt acatagatga attcaattat attacttctg tagtaccctg    52860
tactcaaatt tgaacctgtc atacacattg cttttatcat ttcataatac ctgttgattt    52920
tcccacgtta gtacctatag atcctgacaa gcaattttgt taagatgaag agttcttcat    52980
atgtattgta ctatgtttct tttttgatg atgtatgtca agatttatta taaaagtaac    53040
agatgggtag ggcatggtgg ctcattcctg tgatcccagc actttgggag accgagatgg    53100
gaggattgct tgagcccggg agtttaagac aagcctggga aacctggcga atcctgtct    53160 ctacaaaaat tacgaaaatt agccaggcat ggtggtgact gtcccagcta cttgggaccc    53220
aaatgtccca gatactcagg aagctgagtc gggagcctga tcctcagagg tcgaggttgc    53280
agtgagccgt gattgcacca ctgcactcca gcctaggtga cagagtgaga ccctgtctcc    53340
ccctggcctc aaaaaaaaaa aaaaaagta acatatgtag tttaaatttt aaaattaaa     53400 tttttggggg ggctgggtgt ggtggctcat gcctgtaatc ccagcacttt gggaggccaa    53460
ggtgggcaga tcacctgaga tcaggagttc aagaccagcc tggccaacat ggtgaaaccc    53520
tgtctctaga aaaacacaaa aattagctgg gcatgatggg gggcgcctgt aatcccagct    53580
acttgggagg ctgaggtggg agaatcgctt gaacctggga ggcggaggtt gcagtaagcc    53640
gaaatcatgc cactgcactc cagcctgggc acagagcga gactccatta aaaaataaaa    53700
ataaaaaatc aagcaatgca gaataaataa caacaataaa atgaaagccc atcttccacc    53760
atcagcttct tagttttctt cctagaagga gccagtgagg acagtttggt gtttatgctt    53820
ccagatcttt ctgttcagat gcagtcatga cttctgaaaa acaggattgt acaattcata    53880
cttttctaca aattatcccc ttcccttaat acatcataga agcctattca tattggaaca    53940
```

```
aacaaacatt tcttattctt ttcacagcac cctgttttcc tcttgcttga atgtaaagtt   54000
tatttaacca cttactgtca gggaggcatt tgttttcagt tctccctccc tcccccacc   54060 agttgtcttg taatgaactg ctttaatggc taaagatcac tttaatatca aacctcccc   54120 cacctcccat tagaaaaaga aatcatgtta gggaacttca aattgaattt acggaccttg   54180
tgtttaattt tctatcagca gtggcccag cctggcccct gcagactgcc ccggaatctg   54240
tgggaggagt tggggtggcc tgcagactag agcacactgc cagttcattc agcagctcac   54300
cgagcaagaa acatcttgat tctatcagcc ttaatgctgt gtcccattag ggacccagct   54360
cttgtggtca ttagcagatg gaatgctcat ctgtgctaga aggcggaatt ctagggcatt   54420
cggctctgag cagtcttgaa ccagaattga atggcttgaa tccttttcac aatgccaacg   54480
gggaggcacc cttagctccc aaacttgtgt gtgttataat actatggtag taataacagt   54540
ggttgtagta gcccccgtga atttgatggg acagtcgtca ggcagtgctg cttgcttgct   54600
ttactccatc gtatcaccgc agcctgatga ggcgagggag ttacgactct cattttgcag   54660
gtgaggacac tgagcacagg gaatcgaccc actcatggtc acacagcttg ccaagtcgct   54720
gtgcttggga ggtgaaccag gcttctctga cgccccagca ggacgtctga acttctagct   54780
gccccatcac taactgactt aatgcccctg actcctgggt gacttggcca ccagttactt   54840
cagccagcga cctgcccttt ctttgagtgg gttccaccca tccctgcacc atgccttta   54900 ctttggatgt tggtggcatg gaattccacc cgtaagaagg aggtcggtcc ctgggctgag   54960
agagtttgca gagagctctg ttgggattgg gtgggacgtg tgtttggagg cctcctcaca   55020
taattgtggg ctgaaaggtc cagatttggg gatataaagt tgagccgtca gctgagctaa   55080
agacagggca cagggaggag ccatccagaa agtgtcagtg taggtaaagc aggcagagtt   55140 cccctatct gtcctctgag ggcctccttt cttgtggttt cctcccttt ctgtggtgat   55200 ggtcagagcc agcggttata aattatttgg aattttcctc agcttggttc ctactcaaga   55260 cttaaatta ggagttttgt tcccttttat gacttcacaa tctttgggca ggctgccatc   55320
tctacagcag gctaatatga gttgtaactt gaggtgagtt acagggaaa aatggaagct   55380 gatttctccc cttttaaacc aaggaagcca ccttgatctg actttgtaac aaagctcaac   55440
ttttgtaagt ttgcaattaa aggataaata cctatcctat ttattattat tattaacttt   55500
ttattataaa aggggaaaaa actcccagga aacatagcct aatatgaggg acaaaaagcc   55560
aaaaggtttt ttttttcttc ctttaaaagg tcctcaatgt cttgccctgt ggagacacca   55620
gttttcatta taataacgcc attatctctt tgtagagtca tttcaagcca atttaacttt   55680
ctcatttaaa agtataattg gtattcagca cagagctggg agctcagtag gcagttagaa   55740
aatatgtgta tatttttgga gacgaagttt cactcttgtc acctaggctg gagtgcagtg   55800
gtgcgatctt ggcttactgc aacctccacc tcccgggttc aagcaattct cctgcctcag   55860
cctcccaaat agctggaact acaggcactc accaccacgc ccaactaatt ttcgtatttt   55920
tagtagagat ggggtttcac catggctggt ctcaaactcc tgagtttcgc caggctggtt   55980
tcaaactcct gatttcaggt gatctacctg ccttggcctc ctaaagtgct ggcattatag   56040
gcatgagcca cagcacctgg ctgcagtta ggaaatattt attgaatatg agaaaagaaa   56100
aatagagcaa attgaatctt caagtagtat gtgagtaact ctaattcctg ttttctggaa   56160
aacacacagg ctgataggtt tgggtaaata agagcagagc tgcatcttct ctcaagttcc   56220
ctgattccct caaggagtta cctgagaata gctctgtgcc aagcagtgcg gcatgcatag   56280
gggacctctt gaatggaggg acagtccatt atcattagaa tccccagttc cagccaggtg   56340
```

```
cagtggctca tgcctgtaat cccagcactt tgagaggcca atgtgggcag attgcttgag    56400
ttcaggagtt caagactagc ctgggcaaca tggcaaaacc ttgtctcccc ccgccacaca    56460
cacaccacac agacacacag acacacacac actggctagg cgtggtggca ggtgtctgta    56520
gtcccagcta cttagaaagc tgaggtagga ggattgcttg agacttggag gtcgatactg    56580
cagtgagctg tgatcgtgcc actgcactcc agcttgggtg acagagcaag accccggacc    56640
ctgtctcaaa aaaaaattc cccagttctc agggtgtggt agaggccgag tcagtcatgg     56700
ctgagacaag gggactgtgc tctgtgtgct tctgtgccct gtgtttatat ggttcatacg    56760
ctgcctgtcc accatgtttt tcccgagagc ctcggcagcg caggcatcat gggaatgact    56820
gagtcaggtg gaaattcaga ggccctgccc tggtgggcag agaagcctgg cttacctccc    56880
aagcacagca tgtgtgtgga tcacttctgt gcactgtctc ctcatctcca aaatgggagt    56940
cataactgaa ctcacctcat caagttgtta tgagatgatg tagattcagc gaagtagcaa    57000
gagtaggagt ttgggctttg ataacagaga gaagtgagtt tccatctaga ttctcccccct   57060 gtgtcacttt tggcagttgg cttcacctct gtgggcctct gttatgtcat ctgtaaaatg    57120
ggattaaccc taaaagccac cctcacaggg tcattgtgag gattgcacaa ggtgatgcaa    57180
gtggcacagg gtctggccca ggagaggggg ctggaagaga gcgagctgcc attgtatttt    57240
ggttgctgtg gatctaagga gaagagatgt ttaggagtct ttccctggca tggttcctcc    57300
tgccttcacc catcactctt ttcctcgagg gattccctgt ggggtgcaca gccccagggt    57360
gggccagact gagctcacag gagcatgggc tgtgtttcag gtgaggtggc ctcaccacat    57420
gacaaactga gctggagtca aagggtcacg aggacctcca ttcacagcca gcatttatta    57480
tttcagctgg aaatgtttgc cgagcagttg tagctggaag ctgtgagcga gacacagact    57540
gccatcaggc tgaggcctcc agagctcatg ctgggcttta acctgagcct cttgggggct    57600
gggctctgag ctcctccact tctgctcatg cccaggcgtc cttgggggcc ttgaactgtc    57660
agttgtccag gagaactgtg tggcagcaac agaatgagtt tgtatagcaa cctgttgctt    57720
tgaggtttaa aacttagttt agaacgcaat tgctttgacc attttggagt gtctatactt    57780
tttttcttct tctttaagtt ttcttttttc tttttttctt ttttttttt ttgagacaga     57840 gttttgctct tgttgcccag tggcaacaag agtgcaatgg cgaaatctcg gctcaccaca    57900
acctctacct cctgggttca agctattctc ctgcctcggc cttctgagta gctgggatta    57960
caggcgcccg ccaccatgcc tgaccaattt ttgtattttt agtagagacg ggtttcaccg    58020
tgttcaccag gctggtctcg aactcctgac ctcaggtgat tcatctgcct tggcctccca    58080
aaatgctggg attacaggca taagccatca gccctgctt ttttgtttcc cttcttcgac     58140 cttctaaca agaggttgga atcctcgttt tgacttttaa aggatttccc agtgctagaa    58200
agtggtaaga tagttactgt atcctaggcc ctttagcaga cctgtctcat tgatcattta    58260
tttagtccag tgtggctttg ttgttggata ttaagtaatt ctcaaaattt tacctttca    58320 aaagtggcat tgaaaataaa ggcattgggt gatgaaaatg gaacttttaa atacagtgat    58380
tcctgttaac cagaaatagg gtgtttggga taatttatga agcagtacac catcatagat    58440
actatgagct gaaagttcac caaactctct atcccaaaat aacaataagg tatttatgaa    58500
gtgattcgtt ccaactattt gaggcaaaaa ttgtccagca agtgagagag aacagaagga    58560
atagttggca aaatagggaa tttgaagtct gaggttatgc ataaggaatg tgttatgggc    58620
ctatagtaga aatctcaaat cagggattag ggaatgttta ctcagttctg ttgcagagaa    58680
```

```
atcctggcca cgactccccc atgccatgcc cagggcaggc attgctaatc ttcactgcct   58740
ccattctcca tgccctgttc acggaagaca tttctaatgc attttagcag tctttttttt   58800
ttttgctgaa tccagatgtg gcctcagaat ccttctcaac acagtgtact agcaccactt   58860
ggtgctcctg atctactgta tcatctcttg aaaaactact aacatgaaaa gacctgccaa   58920
gtcaacttta tattaactga acccttgaca cagtgatgga taaaaattaa ttcaaacagc   58980
ttctttgtga tctttgagta gttcatgagc aagaaagaga attggaaatc cagccaactt   59040
cggccccctt gtctacttgt attttactgt ggtttatgtt ttctcttacc aattgagata   59100
ggcccatgag acttctggtc ttccaaagcc cagaacatcc ccacattata gtttaaccac   59160
tgtaacaaag aggttttttt tgtttgtttt tttgttttttt ttttgttttt ttttgggac    59220 agaatctcgc tctgtcgccc aggctggagt gcagtggcat gatcttggct cactgcaagc   59280
tccgcctccc aggttcacgc cattctcctg cctcagcctc ctgagtagct ggggttacag   59340
gcgcccacca tcacgcccgg ctaattttt gcattttta atagagacgg ggtgtctgga   59400
tctctgacct cgtgatccgc ccacctccgc ctcccaaagt gctgggatta caggcgtgag   59460
ccaccacgcc tggccagagg ttttcttaaa aacaataaca acaaaaacag ttgtggaaag   59520
catgtagagt gtgggttttt tcggtcttca ggttggcagg gcatctgata ctgggaccca   59580
ggttccttcc ctcaccttgc tgtgcctctc ctagtgcagg ccaaagccag gtgactgcgc   59640
tgtctgggct cctggctggc aatcggggaa agagtgcatg gagcaggcat gcccactgtt   59700
caggtcctga agccgtggct catttcatat catttgttgc ttatttgaaa gacaggcaca   59760
gcactgactt ccaggggagg ctgactgacc atctaggtgg aagttgcatg cctgggaggg   59820
agaaggggac aaaggccaca gataggcatc agttatcagg gccttaagtc tgccttgttg   59880
gcatgcagcc ttttattgga tcaaggccct ggagaaaagc cctgagcagg aggagataag   59940
ccagcttggt ccccttcatc ctacccaggg gcctctgggg tacctgagcc aaagtgcaca   60000
gttcattggc tgtgtggatg aagggatat gggacttgaa aatgggacac tggtcctggg   60060
cagctgaccg acatggtcct ccttaacctg ctgtctgggg agatgggttg catctggcta   60120
ggttttgact gaggaactga ggagagctgt cagctgtccc cgctttggtt cagaatgccc   60180
ttttgtttgg acagctgaag cctacaattc agccatggtt tgtttgggct cagaaaacag   60240
gcaaggatga agagaaactg caaagctgac ctgggctgtc agtgggcacc aggtcctgct   60300
ggcctggggt ctggatgcag gagatctgag ctcttcaatg tggggtggtc ttgcagcagc   60360
tcttcacagg ctgctgctgc tgctgctgta ggctcaccca agcagccaag acggacagga   60420
tctattctag ttttgtgcag agttggatat agaagaggca ttagagggag aggggatggg   60480
gaaggagttc caggccaggt gagcatgggg cacagtaaac tgggatgtta aggaggggcc   60540
agtttgtgac cagcctgggc aacatggcgg aaccctgtct ctataaaaaa ttaaattagc   60600
caggtgggtg gcatgtgcct gtagtcctag ctacccagga ggctgaggtg aaggatcgc    60660 ttgagcccag gaggcggatg ttgcagtgag cagagattgt accattgtat tctagcctgg   60720
atgaccgaga ccctgtcttt aaaaaaaaa aaaaggagg ggccagaccc ctgacccata    60780
tgtgctgctc ttttcttca gggaggtctg ataaaatatc agtagttcaa ttcttttttt    60840 ttttttttt ttttttctga gatggagtct tgctctgttg cccaggctgg agtgcaatgg   60900
agtgatttcg gctcactgag acctccgtct cccaggttca agtgattctt gtgcctcagc   60960
ctcccaagta gctgggatta caaggtgccc accgccatgc ctggctgatt tttgtatttt   61020
tagtagcgac agggtttcac catattgtcc aggctggtct cgaactcgtg acctcaggag   61080
```

```
gtcctcctgc ctcagcctcc caaagtgctg ggattatagg cgtgagccac catgcccggc    61140
ccatagttca gttctttagg tggttcttgg tgctgcatat gagatctctg caagaaggac    61200
acgtctgagc cgggtggttt agaagaccag catggcccaa gaccctcaga gcaacaccaa    61260
gaaccaccta aaattctttc tcagacgtgt ccttcttgca gagatctcac gtgccccagg    61320
ttcgctgcag cgttaggggt cagcctccct ttggagcagg agagcagggg ccttggaggt    61380
ggcagtcatg gccctcctaa ttaattgctt ggctcagaga agtgacaaat tgaacatttc    61440
aaccacctgt taattcacaa ggtacttctt ttcatttctt gctgcttgca caaacactt    61500 ggagtatggc ttgtggatgt ctggccctag ggaagagtgt ttggcacata gcaggtactt    61560
aagtattagg aaaatgagga tggaggggag ggagggaaca ttattaagcg gccaactgtg    61620
agacaggcat tgtgcttgac tctttctttc tttttttttt ttttttttgag acagagtctc    61680 tttctgtcac ccaggctgga gtgcagtggt gtgatctcgg atcactgcaa ccgcgcctcc    61740
tgggttcaag tgattttcgt gcctcagcct cccaagtagc tgggattaca ggcgcctgcc    61800
attatgccct gctaatttta ttttagtgg agacagggtt tcaccatgtt ggccaggctg    61860
gtctcgaact cctgacctca gtgatctgcc tgcctcggcc tcccaaagtg ccaggattac    61920
aggcgtgagc cactgtgccc ggccgacact tggcattctc taacctacct actccttata    61980
acagccctgg gaagtagttg accatggcca tttctatttg gtagatgagg aaaataagg    62040 ttcagagatg gattgttcaa accgatgtat ctagtcaagc tactggttcc cgagcctgtg    62100
tttgcaaccc ctctaccatg tagcctctcc gggtggtaga gatgaggggg cagagtgcac    62160
agtgcatggc atcctgttcc ccagatggcc aagtcttagt gcgagtgtgt gtggccttgg    62220
taacttgtgt caagcacaca ccccatctct ctctctctct cttttttttt ttttttga    62280 aacggagtct cactcggtca cccaggctgg agtgcagtgg tgctatcttg gctcactgca    62340
acctctgcct cctgggttca ggcgattctc ttgcctcagc ctcccgagta gctgggacta    62400
caggcacatg ccaccacgcc cagcaaattt ttagaagaga ctgggtttca ccatgttggc    62460
caggatggtc ttgaactcct gacctcgtga tctgccctcc ttggcctccc aaagtgctag    62520
gattacaggc tctcttgctc tctctctctc ttgtttttt tttttgaga cagagtctta    62580 ctttgttgcc cagcttggag tgcagtggcg tgatcatggt tcactgcagc ctcgatctcc    62640
tggctcaagc aatcctcctg cctcagcctc tcaagtacta gttggtacta atgggcatgc    62700
accactacac ctgactaatt ttttttatta tttgtaggga cagggtgtcc ctatgttgcc    62760
caggctctgt tcttgaactc ctgggctcga gctatcctcc tgtctcagct tcccatagtg    62820
ctgggattac agagatgaac cgcctggcct acacacccct atctctcctc gattctttt    62880 ttttttttt tttttttgag acagagtctc cctctgtctc ccaggctgga gtgcagtggg    62940
gtgatcttgg ctcactgtag cctatggctc ccaggttcaa gcgattcttg tgcttcagcc    63000
acccaagtag ctgggattac aggcacacac caccatgccc agctaatttt tgtattttga    63060
gtagagacag ggtttcaccg tgttagccag gctggcctcg aactcctgac cccaagtgat    63120
cctcctgcct cggcctccca agtgttgag attataggtg tgagccacca tgcctggcct    63180
ctccttgatt cttacagtca ctttgttggc tgtttctgac tcagcagcta cctgcattgt    63240
ggccaaagga tgacctattc cttctcagga gggcaaaaat gtggaatagt gtctgtccat    63300
gcctctcctc atgggctacc acctctgcca ccgtggttaa tcagtaacaa ccaggagaga    63360
agctgctgga actgacctct gggaactccc tggatggttt ggtgcaggaa tgtagtaggc    63420
```

```
atacacgtgg ttgcgtggat ctgggccctc ctgatgtgag tagagaggta aaaggccacc    63480
atctccttga cctctgggga actcatccac aaagaagatg tttccaagat gcttctgaag    63540
attgcctaaa aatagccggt ttccaccccc gtgaatgcat ccattctaga atgctccttc    63600
accaggacca gagaactgat ttacagaagt gacatgaaaa cattccatcc cagaatttgc    63660
agtagctcaa attaagtttc tagctattaa aaagaaaaga aaacaaaact aaacaaaaca    63720
cacccaccct gctcacttag aagcaacact gagtaatttt aagtagttcg agaaaatgta    63780
tgtggtttga gggtcagggt tgtccagagc caagaccagt tatgtgggaa ttgttattgg    63840
ctggatttgg ggaggagaaa cccatggccc aattccaacc cactgaaatc taagcagatt    63900
ctaggtggtt aggcggacct ggtaggcgtt ggtttatttt attcccgaaa aaggccctgg    63960
agcaagtctt cacatggaat cctgctgaaa ggcttccggc tcatctgcc ttttcctcct    64020 cttaaggttc tgctccatgt tttaccctcg gcgtaaacat tgcagagcac gttcagatct    64080
gaaaagtgtc tcatctacgt gatggtcaga cgttgttgac cctgtgatgc tgtgtaacat    64140
ttcattttcg aggcttgggg agtctcctat ttcatgtgga tgggaacctg gaggtctttg    64200
ggcaagtcgc catcttttta ttgttccaag agtttggtga agcgtttgaa ccttcacctg    64260
tcaaaatcag ttttggaatg agaactgctc tctctctagt cctatataata gcagaaggaa    64320 ggtatcattt atcccaatga gaccataaag ggggctttcc cgtgtggaca cccaccttga    64380
attcaattgg aaacagaaat tctgggcatt gtattttttg taaatttggc tcagacttca    64440
actggatcat atttccccca aaatcttttc gaaaaagact tgtgtctcat tcctttagac    64500
tagcatgtgt aagctgggta aaaatagagc aagccgattt catgttaatg atttcatgtt    64560
aggtttgtga atcaaatctg caagtctgct tttgaaaagc atttaacata taacttggga    64620
aagtttgagt tttgcagact aatgcctgtg gccggatgag acttcatagc tccatccaat    64680
ccctcctggt gcaagagatc aatgccttga gggtgcctgg ccaccaccat taccctgaca    64740
gtatacccac tatttatta tttatttatt tatttattta cttattatt gtttacccct    64800 ttgaagattg ctcttctccc tttaacttaa aggaattggc atggaaactt gtttgatctg    64860
gaatttctga taatcagtag gtagtaactc cgtaatcaat agcacttcaa acaacaacc    64920 aaataacagg ataactaatc caaaaaattc agtcatggtc aaggacttcc agctcaggaa    64980
atgtctggtc ccgtggggtg gattccttgg ataaccaagt tccgtgcagg gcctggagtt    65040
ttatgcagac cattgctcct tgattgacca caggacctca aaaggagggc tggcttcatg    65100
accacatgac ccgtgtgctc agaagggccc tgtacttggt ttattgctct gctgttgctg    65160
tcttgaagtt cttaattttt ttttttttt tggcactggg gagttgcagt ttcaaacaac    65220
acttattcat tgtctcacag tttctgtggg ccaggagtcc agccatggct taagaccagg    65280
tcctctgctc cgggtctcac gagactacaa ggaaggtgcc atctagggtg tgttttcatc    65340
tgaatgccta actaaggaaa aatccacttc attcaggttc attcaggttt ttaaaagaat    65400
ccatttctgt gtgattgtcc cactgacagg tcccagcttt ttactagctg ttgcttggag    65460
gctaacctca ggttttacag gctacgctca tatctctgcc atgaggcctt ctgcataggc    65520
aattcataac acaggtgcct gtttcctcac agccagcaag agaatctgtc tcctgtctgc    65580
taaagtggag tttcatgcat cgtaatatgg tcatgggagt aatagcccgt cacctctgcc    65640 attttctctgt tggttagaat aaaggcacag gttttcccca cactcaggaa gaacccatga    65700
tataaaggct ttcagtaaag gagacgacaa acagaatatg gaatgatcag aattactctt    65760
atgacccaga ccaagaacat cagcattacc tacgaattta ttggaaattc aaattctcct    65820
```

```
gtttcacccc aggcctgtta aatcagaaac tttaaaagcg agcccagcat tctgtggttt   65880
aacagatcct tcaggtgatt ctgacacctg ctgaattttg agaaccactg gtctagaggc   65940
aggcaggtct tgctccccta ggagttaagt ttgatgtatc ttctggtaat actgagaaat   66000
gagctgggaa atggttccaa aatcagatta tcctccccag gattaacaag actcatactt   66060
gcaaaagaga gtgaagaaga gaaactaaaa aaagcaagag gctgtgtgtg aagctagatt   66120
caaacagtta aagacagcaa cacatggcaa aggatgggaa tttgaggaag tgggtagtga   66180
aagcaattct tgagctaaat tacaagaaaa cacggtgaat ttgtatctgt ttcctatatt   66240
tagggggctg gcttaaacgt tagtgataca tttggggagt agaaaatgga tgttggtgtg   66300
aagttcttaa gttttggaca aggaaccctg tattttcatt tttctctgag ccccatgaat   66360
tatgtagaca gtcctgcttc gaagttatta tttatacaat tcattataga gaaagtcctt   66420
gggaacctta actttgagtg aggattgctt gagttagttt ttcttaccag ccactccatg   66480
atactctttg tttttccag gttagatgat cgagttttat tatgactgaa tctgcacctg   66540
caaaattaat tctgattaat taatttaata attaaattct gatgatttct ctctgatggt   66600
ttgggtgtgg gctcttaaag agggtctttt tttgcaagag gatataacaa taatcaggtt   66660
aattaaaaaa ataaggctct cacccttca tttttgagtg gcatgccatg caccccttat   66720
cagcatgtga gtatgctttt catgtggtcg tggttgggtt tcattaagtg taatttggca   66780
tgtgttcaac cagcattcag gtggctcttg gtgggtggct ggggagacac caagatgcag   66840
atagctcagt cactcctcaa caagcggctt agttctggaa tgaggtggga ggccaaggaa   66900
ctcacacata aatgctggtg ggagtgaagt gccaccagct gtagaatctg gtgtcagaat   66960
gatgagccag gagttatccc acaggaggat gggtgaaggt cttcccatca aagggataga   67020
gaacatgtga agaggtccag gggctcaggg caagatgtag tccaggaaca aggagtcttt   67080
gagcctgcag tatggtgggt ggaagtggca agagtggaaa gcggattgga tggggtttat   67140
gtaggttctg aggtgctgtg tatgtttaag gagctgattg tgtgcagcgg gaaccctggt   67200
gaatttggaa gcacagaggc acctgacgag aaagatggtt ctggggttat gtgaacagtg   67260
attcggcttc aaggctatca aagacaaaaa tgtttattgg gagggtatag aaaagggttt   67320
gccaaaagag ttaggtaggg atagaattga cacattgtgg aaactatacc cagagtttaa   67380
gaggtggagt ccaggatagt gcccatgttt gtagcttggg gtcctggtag aatgggagct   67440
ggctatggag tatctttgtt ggagagtggg tatagggaaa cggagagaga gagaaagttg   67500 caggggtgc gggagatgga tagctgcaga gaaggcaagg gcagggaaag tggaaacaaa   67560
tggcagtgag actcctggaa ggtgctggcc aggggcatgg catggcatgt tctgttaagc   67620
aaggaaagga ctagaaaggg gccatgattt tggctgggca cttatcctcc tcacaacagg   67680
acgcatttgt gtcatggctt actcttaaga atgactgacg tgtcagaata gcaaatatga   67740
aaatgattga taacacctag cattggtgag atttgcaggg ataactagct ggcctcttaa   67800
atctatagat aggaatgtaa acagaaacaa actttttata gggaaaagat atctaggaca   67860
taatgattaa tgaaaagaaa aaaattccta cctatcgaaa aacgtgaatt caggcagcaa   67920
acacacatgc atgtatacac atacacacgt gcacacacgc atacacacac aatctggtag   67980
gctgtatact accagtttag caggttgtta cctctgggat gcagtcactc ctttttgttg   68040
tgtatatttg tgaaatgatt tctttcaatt tttgagacag gtctcactc tgttgcccag   68100 gctggagtgc agtggcgtga cgtcagctct ctgcaacttt cacttcccgg gctcaagcga   68160
```

```
tcctccaacc tcagtctcct gagtagctgg gactacagga gtgagccacc atgctcggct    68220 aattttttt ttttttttgg gtagagaggg agttttgcca tgttgcccag gctggtcttg    68280
aactcctaag ctcaaagcaa tcctcctgcc tcggcctccc aaaagtgctg gggttacagg    68340
agtgtgccac tgcacctggc cattattatg gaaaatttta ggcgtataca aaagtagaga    68400
cagtggtgtc ttacatgctc atgaacccat gatccagtga catccgttaa tggcattttg    68460
gaatcatatt tcatctgttt ttgtcctcaa atgttttgaa gcaaatttca gcattacatc    68520
atttcactct taaatatctc agtatggttc tctaatagtt gaagactcca tttacattta    68580
tataaggagc ataatttaca cttgtgtaac ccaaaggaat gaccaagcct gtgcttctct    68640
ccccagatag caaagccatt gtggatggga acctgaagct catcttgggt ctggtgtgga    68700
cgctgatcct ccactactcc atctccatgc ccgtgtggga ggatgaaggg gatgatgatg    68760
ccaagaagca gacgccaaag cagaggctgc tggggtggat tcagaacaag atcccctact    68820
tgcccatcac caactttaac cagaactggc aagacggcaa agccctggga gccctggtag    68880
acagctgtgc tccaggtaag tggccagggc tgcctaaacc atctgtccag gatggggtg    68940 tgtgggtccc aaacattctg gttttcaacg ggaatgctat ctttgctttg attagcgtat    69000
ttctccaggt cttagcccat tataagccca ttataaggaa actaaaactg gctctgtgta    69060
cccttccaag ggcagatttt ctaggtatat ccatagacat gttgagcat caagttgagt    69120 cttttatcca aattccaatg aaggagttgg tgcttagaag caagacttgg gtttaggttc    69180
cagactccaa aatcctgtgt cttcccacat tggtgctcag tttctcattg gatttggaga    69240
aacatttggt cctattaggt ggcttggcat gaaaatctga aaacttccat ggagtggaaa    69300
gtacccattt ttattaacca ctggtttgac tatatatggc attctccacc ctttctttc    69360 tgtgttgctg tgaaatagca tttggtcagg atccagttgg agccttttcc acccttgatg    69420
ggctgctcat ttcttagtgg ttgagtgtat atgaaggttg taattattcc cactggaggg    69480
tttagattga tgggtagagt ttgctggtac acactcagta gaaagaccag agtcagagtt    69540
tacacacacc ccctaaagtt gattttaata aaaaaaaag gtattaatca tattttccat    69600
ttactgtgta ttctgtattt actgggcaca ttagtattta gttagttagt ggttcttgac    69660
atactcaaag cagaactagt gtcagttggg taggggaggg ctgaaggcct cattcttact    69720
tgagagccta taagttggtg tcatccagga aaaattcaaa gtgcagcatt aattgatttc    69780
ctaatatcct cttctttact tccatttaag gacacatttt aggatacctc tttccaattt    69840
aaacctggga gttttactc tagtccttta cctcatgtgc ttacaaaggc ttttaagata    69900
attctaggtt tgtgcctttg agcaagtgga tttttgaatc acacaggatg ctattctaga    69960
ctttttagat atatccagga atagagtaaa aaataaaatc cctcctgcat aaaggcacca    70020 ggcttttcc aagctttgtt tattttttaa caccacttct tcaaggaatg gataatcccc    70080
atcttcatgc aagaacatag cacccggagg agaagtctca gtaatggagg atagtttaca    70140
ccctggcaca ctcatacctg tgatactttt tgcctattaa atatatgatt tgctcagatt    70200
ttaggaaaaa atcattctct gaactaaaag aaaaaatggg gttagtttag gcacatggtt    70260
tcctttaatc tctttggtca gctaatgcta aaagaatctt ttgtgttctg ttaacaggtc    70320
tgtgcccaga ctgggaatcc tgggacccgc agaagcctgt ggataatgca cgagaagcca    70380
tgcagcaggc agatgactgg ctgggtgtcc cacaggtatg cacaagtgtg ccaggtcctg    70440
tgaggctgcc cccaccccact agcttgttct gtggatgcct tccgggtca ggcagcccga    70500 ccttcttggc attgagactt cagagagcat tgcctgtgat gctctctcat cttcctcagt    70560
```

```
ttacccataa taatagtagg ttctcattga ctcaggtgct tatagatctt agtgtgttgg    70620
tttaatgtag atcatccaga aattttcatg tcactcttct ttgtcacaca ctggcaaatt    70680
ttctagtatt tcttctctaa atattttgaa gactaccttt aaacccaga ctacaaatat     70740 ggaccctaac tattaggttg agccataaga aattgatagt atttgaccat ttttcaatct    70800
acattttaaa aggtaatttt aatccaatag cttaagaaaa gtcacaggac ttaaaatttt    70860
tttttttttt tgagatggag tctcgctttg tcgcccaggc tggagtgcag tggtgtgatc    70920
tccactcact gcaacctctg cctcccgggt tcaagcaatt ctcctgcctc agcctcctga    70980
gtagctggga ttataggtgc gcaccaccac acctggctaa tttttgtatt tttagtagag    71040
acagggtttt accatgttgg tcaggctagt ctcgaactcc tgacctcgtg atctgcccgc    71100
ctcagcctcc caaagtgctg ggattacagg cgtgagccac tgtgcctggc cgacttaaaa    71160
cttttaaaaa catgtaagcc aggataatcc accattaatg gaaactgtgg aagaatctct    71220
atcacccata atcctatcac aggaatataa caagagaact cagaaatcaa ataagtcttg    71280
gataccatct acagtagtca cattgcttag ttgaagtctg atcttcctag ctgggaggaa    71340
aaccagtgtt ttcttttccag aaactccctc taacagttag gcaccatgag tcccgtgtcc    71400
aaaggctagc cagggaagat tgcaggtagc cagtgccatg ggactgatgg cgtcactata    71460
ggctgcattg aggtctgagt tcagtgtatt ttgtaacagg gtcccttgga aggtagaaca    71520
acatgcctgt ttctttggtt tggttttgga gtcatgtctc tcctacatgg ctcattggtt    71580
tcttggctcg tccaccctca ggaagtggtg tggtgtgttt ttcatctccg cttaaaccta    71640
aaccgtctcc tttttacgtt cacgtgatgt tggcatgggt gaagttgttg aaggagctgc    71700
tgggaagaaa tgccaaatcg acacacatcc tacttttat ggaatgtatt gaaggcgact      71760
gttcaaaccc aagtagctct tttgttcctg caggctaatg gtcagaatgt ttctggtgc     71820 tttttatcac atggggaggg aagttggaca catctgttgt tcattgcaca tggttaacct    71880
ggtccatgag acagagcctc tgttcatctg aggaagtgtg atttacctcc ttagcaccat    71940
tactggaggc agggaggact ctgcaagctg tttagggctg ggtcagatga tggtactgaa    72000
actgaggtgg tggcaccttc agggaagtca cctgtccagg atgggtctag tcttgctcct    72060
aagctgaata tcaagagaag ttcacccatt ccctattttt tttttttttt tttgagatgg    72120
agtcttgctc tgtcacatag gctggagtgc agtggcacga tctcagctca ctgcaacctc    72180
cgcctcctag gtacaagcga ttctcctgtc tcagcctccc gagtagctgg gactgcaggt    72240
gtatgccacc atgcctggct aattttgtat tttagtaga aatgggggttt caccatgttg    72300 gccaggcttg tcttgaactc ctgacctcgt gatccaccca cctcggcctc ccaaagtgct    72360
gggattacag gtgtgagcta ctgcgtctgg ccttttttt tttttaaag agacagcgtc      72420 ttactcctct gttacccagg ctggagtgca gtggcatgat ctcggttcac tgaaacctcc    72480
acctgctggg ttcaagccat cctcctgcct cagcctccct agtagctggg attacaggtg    72540
tctgccacca cactgggcta attttgtat tttagtaga gactgggttt taccatgttg       72600
gccaggcttg tctcgaactc ctgacctcaa gtgatttctc ttgtcttggc ctcctaaagt    72660
gatgggatta cagtcatgag ctaccacgcc tggcttccct attttttaa tggctcctaa     72720 tatattgaga tcacatatct aatatttaca tgttatttct tttttattta cctttttaa     72780 ttagtagagt taatacagat acagaccatg agtatacaag caaaggaaaa agctggtaa     72840 cctgtgcact ttttttgtaac atgctctaat cccatgtgtg cttgtttctt cattttcctg   72900
```

```
ccttgctata gcttatcctt ttatcatttt tgaaattttg accagaggag taaatggact   72960
tttggggaat ggggaggaca atgaactttt ggaagttaca tgcagaattt tttggagagg   73020
ggcccctagc tttcaaaggg gtctgcaatt tctcaaaaat ggttaaaaac actgatattg   73080
gtgtgttggt ttaaagtaat ttcacttaat tgagaagctg actcagtttc ttaatatttg   73140
tagtgcttgg tttaagaggc atttgcaaac acttcaatag ttgcaaagtg atgtgttctg   73200
ggtgttcatc caccatgtca ttatcctagg tcatcactcc tgaagaaatc attcacccgg   73260
atgtggacga gcactcagtt atgacttacc tgtcccagtt ccccaaagcc aagctcaagc   73320
cgggggctcc tctcaaaccc aaactcaacc cgaagaaagc cagggcctat ggcagaggtg   73380
agtgctggtc ctctggtgtt gtattggaga catgtcctct ggtgttggag atgatttcat   73440
ggcttcaaga gtgatgttct tagaatcaaa aatagatagg tgtaatcctc aaagagaccc   73500
caagcctcct ttgtaacaca ttttatgact gtttttattct gccttgtttt tctaaggctt   73560
taagaaatgt ttctgcttag atggaaaggg caagtttgct gcttggtgat tttagtgcag   73620
tagcccattg ctcccatttt tcagaagagg aatcgcgggg tagggagtcg ggggagtttg   73680
gtcttgcccc agatcaccac agtcagtgat ggggtgggc catctggctg ctgattcatt   73740
tctccttctg ttacactaag cctgcctcag atttccagcc ggagtgggag ctattgttaa   73800
cccctggcag atacttcctt gctaagacat cctgtttatg actgcgaggc agctgcggaa   73860
caccgttttg ctcagaacat tatagtgggt agaagccatt tcaaggcatt tggtgttgtg   73920
attggcacct gacttcaagc acactagctt tgtgaagaga acagttacat ggctgcaaag   73980
tgtggtttct ggtgaagatc aacatggcca gatacaactt aatgccttt ctatggggga   74040 ggggaaggag tgcattttat ttctcatttt tcataattaa gaaaatatcg gccgggtgtg   74100
atggttcatg cctataatct cagcactttg agaggccgag gcgggcagat cacctgaggt   74160
caggagttgg agaccagcct ggccaacatg gtgaaaccct gtctctacaa aaaatacaaa   74220
aattagccag gcatggtggc gggtgcctgt aatcccagct attcaggagg ctgaggcagg   74280
agaatcgctt gaacccagga ggcagaggtt gcatcgagcc gagatcttgc cactgcactc   74340
cagcctgggt gacagagtgc gtgagcctcc gtctcaaaaa aaaaaaacga gaaagaaaat   74400
gttatcccag tgggataata gttatacaca cagtattctg tatatcttct cccagaattg   74460
acagttgtta ccattctagc ttaatagttt tctcttgccc tttgtgtgtg tttgcatatg   74520
tgttcatgtg tatgattgct gaattatttg aaaataagtt gcaagcatgg tgacagttct   74580
gtcctcagta catcactaag cttctcctaa gaataggata tcctctagca taaccacagt   74640
attcattgcc acatgtaaga aaattaacaa tagtttcata taatctaata ttcagtttgt   74700
tgtagaattt ctctattgtc ctaagattat cttttatagt tgttgctgtt ttacaaacta   74760
agatctgatt aaggttcact tactacattt gtttgttatt tctctttaga ctcttttcat   74820
gctaaataat ttccccaaac tttttttttt tttttttaa atgacactga ctttctgaat   74880
agttaagggc atgtgtcttg taggatgttc cttccctaca aatgttccct ttgaataaag   74940
tattttcctg cttggtatca gcttagtctt tttttttttt tttttttttg agagtcttgc   75000
tctgtcgccc aggctggagt gcagtggcac gatctcagct cactgcaacc tctgcctcct   75060
gggttcaagc gatcctcctg cctcagcctc ccgagtagct gggattacag gcatccacca   75120
ccatgcctgg ctaattttg tattttagt agagatgggg tttcaccatg ttggccaggc   75180
tggtctccaa ctcctggcct caggtgatct gcccggctcg gcctcccaat ccgcttattc   75240
ttaagacgac acatggctag ggcagtgatg ctgaccacgt gctgttctca cctcagtggt   75300
```

```
cgagtcttct catctgactt tttgggcatg atttagaccg gcagatagtt ctggaacaaa    75360
ccccttacca tttgaggttc cgtttgcagt gggttgtgag gtgtgtgaga catcacttgt    75420
gttatgtagg gactagggac ttcaaagccc tcctcccatt cacagtcact tgaaggctgg    75480
catgtcctca ctttctttaa aagtgctttc tttggccggg cttggtggct cacacctgta    75540
atcctagcac tttggaggct gaggcaggca gatcacaagg tcagaagatt gagaccatcc    75600
tggctaacaa ggtgaaaccc catctctact aaaaatacaa aaattagctt ggcgtggtgg    75660
tacaagcctg tagtcccagc tactcgggag gctgaggcag gagaattgct tgaacctggg    75720
aggcggaggt tgcagtgagc cgagatcgcg ccactgcact ccagcctggg tgacagaacg    75780
agactctgtc tcaaaaaaaa aaaaaaaaaa gtgctttctt taaggcatac cacaggtggt    75840
ggctggaatg aggaatctct gactttaaag gttatgcttc cttaatgaca aaacagttgc    75900
aaacaaccaa ttaaatcctt tgtcaaccag attggtcaaa tggactgaat ctaatcaagg    75960
catagtgtat gtttgtaata accttatcac tggccatccg gcttccctgt tgttaatgtg    76020
agacggtttc ctttcacggt gctatttcct agaaaatgat cacttgttat ggttcaggaa    76080
tgtggctggt cattgccatt tccttcatct gcctcttagc aagtgtggtg cacttgtaga    76140
ggaaacacac ccttttaaaa aaaaattttt ttttatatgt gtgcttttg cattttttta    76200 attgtgggaa aatatccata acataaaatt cactatttta accatttta agtgtggcat    76260 taagtgtatt cacgttgttg tgcaaccgcc actgctatcc atctccagaa cttttcaac    76320 ttcccaaact gaaactccat actcattaaa caatagcgcc ccattctccc ctctcctctg    76380
ctcctggtaa cctttattct actccctgtc tctatgaatt tgcttattct agggacctcc    76440
tagaagtgaa atcatatgct gtctgttagg tacctcctag aagtggaatc atacgctgtc    76500
tgttaggtac ctcctagaag tagaatcata tgctgtcttt ttttctctgg cttacttcat    76560
ttgtcatatg ttttcagggt tcaccatgtt gtagcatgtg ttagaatttc attccttttt    76620
aaggctgaat aatattcctt tgtacgtgta tatcacattt tgcttataca ttcgtctgct    76680
gatagacatt tgggttgtta cattcttttg gctattgtga ataatgctgc tatgaaaaca    76740
tgggtgtaca agtgctgttt gagaccctgc tttcaattct tttagggata tacccagaag    76800
tggaattggt ggatcatatg gtaattctat atgcagctta tttttcagga ggaagtggcc    76860
tcactctgct ttttaaagta gggagacaaa tggtcatatt aggtgacagg gtcacaaggc    76920
cacatgggtg gggctgtgag atatgtccct gtcatgtggt tagatgaaag ccggggtcag    76980
ttttggtctt ctctgtgtga ccacattgct tcatttctgc cacctgagcc caggaagaga    77040
gaccgtttca tcttctagtt tctaaaagat ttgaaagtgt tgtttatt ttatttcct    77100 gattgtttaa tagatgccag ttgccagcca gttagcattt gttgatccat tcactgagtc    77160
ccaccttgct tagttctagt gggttgaaag gagagagggc tggggtgagg tggacctcca    77220
gccacaaaca gatctttgtg gtgggcttcc ttgcagggtt agctatgtga aaagcattcg    77280
tccatgagct aatcagaaat ctttgtaaaa atctagttct ctatgaagca tttactgtag    77340
agcaatcctt aagcacccctt ctatctgagt aatcagaggg gtaccagttg tctcctttca    77400
tggtaagcaa agctccgcag aagtttacag agttggggtg tggttcaact ttctaaccag    77460
ccatggttag ccacgggtga ccaacccaag cccagacctt tgacaagctg cagagtacgt    77520
tgtttcttag gctgctggag tcacacgaag tggaactttt agtattttag gtgcatgttt    77580
atttacttac ttattttgt tgttgtcgtt ttcagataga gtctcactct ctctctctgt    77640
```

```
gtgtggagtg tcgtgatgcc atcacggcta actgcagcct tgaccttctg ggctcaagtg   77700
attctccctc ctcagcttcc ctagtagttc ggaccacagg tgtgcaccac catgtccagc   77760
tttttttttt tttaatattt tagtttgaga ccagcctggc catgttgccc aggctggtct   77820
caaaatcctg agctcaagca atcccctgc cttggccccc tcaaagtgct gggattacag    77880
gcatgagcca ccatgcttgg ctattaggtg tatgtttaaa tccatttgct tatatcagtt   77940
acataacctg agtgttatgt aaatcttaag caaaagaaaa atatatgaaa taaaaattga   78000
aactcacttc ccaactgcca atctcattcc tgccttcaaa gtttcaggta tttatttcta   78060
gccttttttc tatgctgagt taaactgtgt atcttctttg ctttgcattt cttactgagc   78120
agtgtgggaa ggctaccttt taaaatttat ttgtagttct ttataatttt tacctttctt   78180
tttaggcaga aagattatct tattatataa cagtctacgg ccatttttc ttaaactaaa    78240 ttattgggaa atgaatagaa atccagagta tagtaacaaa tgacctagtg tctttaacag   78300
attggtagct aggaaaagga agtggtggag agacagccgg agattaaatg agacttaaga   78360
gacttagcaa ccatttgtaa tatgtgacct tatttggatc ctattcaaac taatggttaa   78420
aaaaattcat gatagctggg catggtggct cacgcctgta atcccagtac tttgggaggc   78480
tgaggtgggt ggatcacgag gtcaggagat cgagaccatc ctggccaacg tggtgaaacc   78540 cccttacca aaatacaaa aattagctgg gcatggcggc atgtgcctgt agtcccagct     78600
acttgggagg ctgaggcagg aaaatcgctt gaacctggga ggtggaggtt gcagtgaacc   78660
gagatggcgc cactgcactc caggctggcg acagagctag actctgtctc aaacaaacaa   78720
acaaacaaat aaaaattcat gataaagcag cagctcaagg tgctgtaaga aattcatgat   78780
atttataaga taattgaaaa tttgaacact gaatatttga cattaaggaa ttatttttt    78840 ttatatggta tcgatattgt gggtactttg caagtatctt ttaaggatac atagtgattg   78900
tggataaaaa atctgaggtc taggatttgt gtcaaaataa tacaggaagg ggaggtggcg   78960
ggagtgaagg tgaaacaaga ccagctgtga gttgatagtt gttgaagctg ggtacaggag   79020
gtccactgtg cagtgctctc tacatctgtg tttgtaattc tttttttttt ttgagacgga   79080
gtctcactct gtcgcccagg ctggagtgca gtggcatgat ctcggccac tgcaacctct    79140 gctgccggg ttcaagcgtt ctcctgcctc agcctgccaa gtagctggga ttacaggcgc    79200
ccaccaccac acccggctaa ttttgtagtt ttagtagaga tggggtttca ccatcttggc   79260
caggctggtc ttgaactcct gacctcgtga tccacctgcc tcggcctccc gaagtgttgg   79320
gattacaggt gtgagccact cgcccagcc tttttttttga dacagagttt cgctcttgtt    79380
gcccaggctg gagtgcaatg gcacgatctc ggctcactgc aacctctgcc tcctggattc   79440
aagtaattct cctgcctcag cctcccaagt agctgggatt acaggcatgc accaccacac   79500
cccgccaatt ttgtattttt agtagagaca aggttacacc atgttggtca ggctggtctt   79560
gaactgctga ccttgggtga tctgcccacc ttggcctcga aagtgctgag attacaggtg   79620
tgaaccacgg cgcccagcct ttttttttt tttttttttt tgctgaagtt tcacttctgt    79680
ttcacaggtt ggagtgcaat ggtatgatct tggctcgctg caacccccgc ctctgcctcc   79740
tgggttcaag ggattctcct gcctcagcct cccgagtagc tgagattata ggcatctacc   79800
atcacacctg gctaattttt gtattttag tagagacgga gtttcaccat gttggccagg    79860
ctggtctcga actcctgacc tcaggtaatc cacctgcctt ggcctcccaa attgctggaa   79920
ttacaggtgt gagccactgt gtccagccta gtttggaatt cttcataata aaaagctttt   79980 taaaaggta atatttggac ttctgctcct gggaagatgg aataggactt ttcctaattc    80040
```

```
tttcttctaa ctacaactaa aaccctgggg ctatacataa ggaaaacaca gggagcctct   80100
gaaaaaggat gaggcagacc aaccagggat cttgggactc gaggaatgac acagtactga   80160
gttccttggg tttactttgc tttatatatc ccagacttgg agccaaagaa agaagctgac   80220
aacctgaaaa tgccagtggg cacaaacaca gaaagtgcca acaaaagctc ccctgtccag   80280
ccagaagacc aggaaagggc agcccagtga ggcagaaaac ttaaagagtc actgctctac   80340
tccaggtcca caccatagaa aaaactatgc agccccacac ttacacccgc agaggtgaat   80400
ggggagccta ggctttgaca acagtctagc aataaggaag ccactctccg gggccatgga   80460
ggagcagtaa tgaggcactc ctacttcctc cagccagaac tcccaccttc acgcaccagt   80520
aatgagcccc ccaatcttga gcatcagtcg aggttgaatg gagagcctag acttcttccc   80580
ccactgttag taacaaggtg tgtaccccttc cctcccctgc cacagtggta tcataaaatg   80640
ccagctacaa cagaacattt acagaagacc cagagtctca ttacatgata ccccaaatat   80700
ccagtttcaa aaaaaaaaag aaatcacttg tcataccaag aaccaggaag atctcaaact   80760
gaatgaaaaa gacagttgat gccaacactg aggtgataga gatgttagaa tcctatgaca   80820
aaaattttaa agcagccatt aaaaaaggct tcagtagcca ggcgtggtgg ctcactttgg   80880
gaggcttgta atcccaggac tttgggaggc cgaggcgggc agatcacctg aggtcaggaa   80940
ttcgatacca gcctgaccaa ccttatgaaa cccagtctct actaaaaata caaaaaatta   81000
gccaggtgag gtggtgggca cctgtaatcc cagctactcg ggaggctgag gcaggagaat   81060
cgcttgaaac tgggaggtgg aggttgcagt gagctgaggt catgccgttg ccctccagcc   81120
tgggcaagaa gagtgagact ccatctcaaa aaaaaaaaaa aaggcttcgg taggcagtta   81180
agaacaatca tgaaaaaaat gaaaaaatta aaatctcaa caagaaata caatgtccca   81240 gcaaataat aataaaaatt taggagataa aaagaaccaa atggacattt tagaattgga   81300
aattgcagta actgaaataa aaacttattg gataagcgca atagcagggt ggaaggacag   81360 agaaagaat ccttcaactg gacaacaatt ggttgttttg ttctgaggtg gagttttgct   81420
cttgtcaccc aggctagagt acagtggagt gatcttggct tactgcaacc tctgcctcct   81480
gggttcaagc tattctcctg cctcagcctc cctagtagct gggcttacag gtgcccacca   81540
ccacttctgg ctaatttttt tatttttagt agagacgtag tttcacccctg ttggcctggc   81600 tggtcttgaa ctcctgacct taggtgatcc acctcggtaa tccaccttag gtgatccaaa   81660
gtgctgggat tacaggtgtg agccactgga cccggcctct gtaagctttt ttctgtgttt   81720 aaaactttc attttgtac ttttaaaact tttttttttt tttaaacaca cacattagtc   81780
tagacttaca cagggtcagg atcatcatta tcactatctt ccacctccaa atcctgtccc   81840
actgtcccac tggtaggtcg tcaagagcag taatgtgtgg aaccgccgtc tcctataata   81900
acaatgcctt cttctagaat atttcctgaa ggacttgctt gaggctgctt tacagttaac   81960 ttaatttta aatagaagat gcccactcta aaatataatg ataaaagta tagcatatta   82020 aatacataaa ccagtagcat tgtcatttat catcaagtat tatgtattga acataattgt   82080
ctgtgctata tatgttttcta tggccggtag cccagtgggt ttgttttatac cagcatcatc   82140 acaaatacat gagtaatgcg atgcgttact gtgacgtcag taggcaacag gaattttttg   82200 gctctatttta taatcttacg ggaccatcat tgtatgtgtg gactattttt gactgaaact   82260
tcattattta gcaaatgact atattagcaa ataaaattga gctgtatata atgaagaagt   82320
atgcattata accaagtggg gtttattgca gggatgcaag gcctcgttca ctattagaaa   82380
```

```
atcagtcaac agcctggctc ggtggctcac gcctgtaatc ccagcacttt gggaggccga   82440
ggtgggcgat gggcggatca tgaggtcagg agatcaagac catcctggct aacacggtga   82500
aaccctgtct ctactaaaaa tacaaaaaat tagctgggcg tggtggtggg tgcctgtagt   82560
cccagctact cgggaggctg aggcaggaga atggcatgaa cccgggaggc agagcttgca   82620
gtgagccaag attgtgccac cgcactgtag cctgggcgac agagcgagac tccgtctcaa   82680
aaaaaaaaaa aaaagtcaa atagtaaaga taccacctct cctcaaattg tcattcaggt   82740
ttgatgcaat tgctgtcaaa atcccagcaa gagttttgc agatagcaag attattattt   82800
taaaacctat atgaaaaggc aaaggaatta agtagcaaa aacaattttg agaaagaagt   82860
acaacatgga ggaatcagcc ttcctgattt caagacttgc tgtatagcta cagaagtcca   82920
gattttgtag tattggtcaa aggatagaca ttatagatca gtgaaacaga attgcagccc   82980
cacacaaata tgcacaactg attattgaca aaggtgcaaa gataagtcat tgggggaaaa   83040
aaccttttcg gcacatggtg gcagagaaat tgaacatccc taggcaaaac aaaacaaaag   83100
caaaccccaa accaaaaaac aaaaaaccca tataactata aaactttgag aaaaaaacat   83160
agaagagaat ctttgagatc tagagctagg caaatagttc tcagatttga caccaaaaac   83220
atgatccatt aaaaaaaaat aagttggatt tcatcaaaat taaaaacttt ttaatgtttt   83280
aagaaggatg gtctgtctca aagactcaac atggtacatg gtggttggcc tttatgtgct   83340
gttgagggtt ttcctgcatt gaagggtgca ctcctgggtc acctactgtc ctgcaagaca   83400
agctgtctta gccctcacac tataaaagcc acccggacac cgtctcaaac agaactcaaa   83460
atgttgctga gactgggatc tggggggctgg atttttactt tacaaacaat ttaaaacttt   83520
ttacagttaa gaggatgaat atacaggcta aagactggga gaaaaaattt gcaaaccata   83580
tgtccaacag aacactagta tctagaacat gtagaaagaa ctctcaagtc ttagtcgtta   83640
aaaaacagac aaacatttaa ccaaacaacc caataagaaa atgggcaaaa gacataaaca   83700
gtttctgctg aagagaacgt ccatatgaca aaaaaacaca tcgaaatttg ttcagtatca   83760
ttaaccatga gaaaaatgcg aattaatcct agtacacact atcagaacgg ctaaaataaa   83820
aaatattaat actgataaca ctaaatgcag aacggatgga gagaaactga atctggatca   83880
ctcactcata cattgctggt gggaatgtaa aatggtgtag ctactttgga acactgtttg   83940
gtagtttctt aataaagaaa taggctgggc acagtgactc ccttctgtaa tcccagcact   84000
ttgggaggct gaggctggag gatcacttga gcccaggagt ttgagaccag cctgggcaac   84060
atagggagat tgcatctcta caaataattt ttaaaaatta tacaggtgtg gtggtatgca   84120
cctgtggtcc cagctactca ggagattgag gcaggaggat tgcctgagcc tgggaggtcg   84180
aggttgcagt gagccgtaat tgtgccactg tgctccagcc tgggctacag agtgagactt   84240
ggtctcaaaa caaaaacaaa aacaaaacct caaaaaacag tacatgcaac taccatatgg   84300
cccaacaatt gcactccttg gcatttatcc cagaggaatg aaaacttact gtatatgaga   84360
gccactgttt ttccttctat agtctcacag ctaaagaaaa aaactttc tcatcttctc   84420 tactactcct ctcagtattt cgcttccggt caccaaaatc tatggatttc tgtcccccat   84480
actgacaagt tctccaattt tatgtggaca acaagtaggg gtcctataat caattccctt   84540
caattctgac actatctacc tgaagttagt gcagacgcca ttaagggctc ggtccctcaa   84600
aactgcccct gacttcagag gccagtcaga agtggtgggt cctcaggtaa cccacagctt   84660
ctgtccaggt ttgctacaaa tcagaaggtc ccattacccc ttcctcatgt tatgttattt   84720
gctagagtgg ctcacagaac tcagggaaac acttaccttt agcagttgtg tagtgaagga   84780
```

```
tatgatagag gatacagatg atgccccaga tgaagaggtg cacgggggcaa agtttagagg    84840 cgttttgaac acaggagcgt ctgtccccat gaagttgggg tgggccatcc tcttggcaca    84900
tggatgtgtt caccaaccca gaagctctct aaactccata cttcagggat gtggaggcta    84960
agtcacgtag gcgtgattga cattaactga gactacagtt cctctccctt ccctgtagga    85020
tggggagtgg ggccgaaagt tctaagcttc tgatcatgac ttggtctttc tgttgattag    85080
ccacatcttg aaagctatcc gggagcccac taagagttgc ctgattagaa cagaagatgc    85140
tcttgtcacc aaggacattc caaggggttt aggaactctg gaaccagggg cagagaccta    85200
tatatataat ttcttactat tttatactta tgttcacaca cacacacaca cacacacaca    85260
cccctatgca cagatgttta cagcagcttt attggtaaga gacaactaga aacaacccag    85320
atgttcttca gtgggcgaat ggttaaactg tggtacatct ataccatgga atattagcta    85380
ctcagcaata aaaggaaaa aaaccattga cagaagcaac aacctgggtg aacctgtaga    85440
caattatatg tagtgaaaaa ggccactcct aaaaggttac atagttatga ttccattgat    85500
gtgacgttac cgaaataata aaattacagt gtggagaacg ggttagtggt tatcagggct    85560
aaggagagtg tgggtgtggt tatgcaaggg cagcaggagg gctccctgtg ctaaagggaa    85620
tgttctctat tttgattgta tcaacgtcaa taccctggtt gtgagattga gtcatagctt    85680
tttaccgtgt taccactggg gaaactattt tgagatggag tcatgctctg ccgcctagga    85740
tgcgatctgg gctcactgca acctccacct ccctggttca agcaattctc ctgcctcagc    85800
ctcccaagta gctgggatta caggcatgtg ccaccacgtt gtattttag tagagacagg    85860 gtttcaccat gttggccagg ctggtcttga acgcctgact tcaggtgatc cacctgcctc    85920
agcctcccaa agtgctggga ttacaggcat gagccaccgc tcccagcaag ggcattgttt    85980
cttacaccta caggtaaaat ctgtctcgat gaatttgctc gatcatctta aaataaaaag    86040
gttaattaaa aaaatgattg aatataattt ttaaaaatgt caggcaatac aataaatgct    86100
gtttaatgag aaataagctt cgctcctccc tgctgtgttg cttccatcaa ggcaagctct    86160
gctactactt attaaccaca ttatttccac aattttatat agactcctga ctgaggttct    86220
ctgaatatca aaattggata ttacttcaat aacatgggca aaattaaggc tttcgacctg    86280
cctgattttc cttgtcaagg cagttttgtcc ccatttccca catgggatct gcagggctgg    86340
gtcccatctc tcagttccct gaaagagatg cagtgggcga tggctcatga cacaccctcg    86400
cctggcttct aacatgtctg tgtaaacctg tggcaggaat cgagcccact ggaaacatgg    86460
tgaagcagcc agccaagttc actgtggaca ccatcagcgc cgggcaagga gacgtgatgg    86520
tgtttgttga ggacccagaa gggaacaaag aggaggtatg ttggaggatg ctgcctctcc    86580
tttccagcac ctcatggagc ttttgggggct tgtaatgcgg ccagggactg tgcctccatt    86640
ttcatttcag ctcacaacca aaagtgtttt ttaccaaaag gatactgagg cttatagctg    86700
ttaaagtaac ctgcccaaga ggtgagcctt gaaatcaaat ttaaattgat tgccagggac    86760
acagtgttta atgaaataaa ggatactttg gatttagcaa aggtgccttg tcagttgagg    86820
tttatgtatg tatttattta tttatttatt tattttattga gacagagttt cactcctgtt    86880
gcccgggttg gagtgcagtg gcacaatctt ggctcacggc aacattcacc tactgggttc    86940
aggcgattct cctgcctcag cccggctaat ttttgtaacc caagtaactg ggattacagg    87000
gacctgccac cacgcctggc taatttttgt atttttagta gagacagggt ttcaccacat    87060
tggccaggct ggtcttgaac tcctgacctc aggtgatcca cctgcctctg cctcccaaac    87120
```

```
tgctgggatt acaggtgtga gccaccgtgc ccagcctcag ttgaggtttt atatactgat    87180
ggccagaata ataagagtct tgccctgctc tcttcccaca ttggccattc tttggttcct    87240
ccctcagagc ctttgcacat gctgttcttt ctgtcactta ttttcgtagg accatatttt    87300
attcttggca tttagcataa tttgcaattc taagtttaca gatggatggt ccatttcccc    87360
caccggggca gggattgtat ctgacttgct catgttttat ttttagtacc taacactggg    87420
ccctgcattt cataagcttt caatgaacta ttgagtggat aaaggtttaa gtttcttgct    87480
tcatattctc tcttacctag agagtgccag cctgacactg gacactggag agtcctgact    87540
ctgttatgcc tctgtgctgc atggttttgt ttctgtgact tcaagcagtt tctctctagg    87600
ggcgttgtgc aagagggaca ggagctcgcc agcaccttca gtgtttccga cctggcagct    87660
cctgcagaac ccctgctgac acagcatgct ccttactcac acccggcacc ttttctaact    87720
gttgcccacc ttccctccta ggcacaagtg acccctgaca gtgacaagaa caagacatac    87780
tctgtggagt atctgcccaa ggtcaccggg ctacacaaag taagatgaag cagcatggct    87840
gtggcttggg ctgctctggg gctaggagaa gaaagatagc ccaggaagaa gagtgttttt    87900
cttaagtgaa tttctgattt tcctttctga ttatagaagg atctatgctc atgatagaaa    87960
attggaatca ctaggattcc ctctactagc taggatgagt tgtttgcaat gtcgtaagat    88020
ttttccaact ccatctaggt aactaatggt tgcagctgtg tgtctggagt gtagatgctg    88080
tggtgactac actatagatg ggttcttgt ccttgattct ttttttggag acagggtctt    88140
gctctgtcac ccaagctgga gtgcagtggt gtggtctcag ctcactgcaa ccccgcctc    88200 ctgggctcaa gcgatcctct cacctcagcc tcccaagtag gtgggattat aggcacccac    88260
aaccactccc agctaatttt tgcatttta gtagagacca ggttcacca ggtcacctag    88320 actgttcttg aactcctgac ctcaaactat cctcctgcct cagcctccca aagtgctggg    88380
attatagaca tgagccacca caccctgctg gctctttgtc cttaatgctt tcttaagaac    88440
tctccttgga ggtgctctgg aggagctgtc agcattgaag gctgaggatg gagtagttca    88500
gctgaatata gtagagggaa atggccctct cagcacctgg agaaatgata gggattgagg    88560
cctcaggctc tttgtcttgg cagccttcg agttctgttt gagatgacat ccaggtgacc    88620
tatagggcaa gggctgagag agcctgtctt gcaggagagt ggggtgaccc aggagtacac    88680
ttttcattgg aagaaagccc tcaacagcac ataaaggcca atcccatcat gtacctgccc    88740
agactttgga atacagactg tactcaccac cttgggcttt agtgaattca cctggaatga    88800
tggccttagc gttctcttag actcttagac tatgatgcat ttggagtaaa tgctcttgaa    88860
gggagcattt ataatgtaat taattaattc cagtcaagta taggttcaca tgaaacccaa    88920
cccaattacc ccccaaaaat ttcagagatg agaacagtga ctcaagtttt agatggaaat    88980
cattctactt tgtcccaaat ccatgtatct aagaatgatt ttcgtccctt gaaaaaacag    89040
tttggctgtg gatttgaaat cctggaactg catatttat tctgagggat agtggcccat    89100
tcagcccccg aaaggactca atgtccagag attgaaatgt gtttgtttcc tattaaagag    89160
actaagtgta tataaggtca gcattttat tttgctaaag gtgtgatgtc ccagacccag    89220
ctgtatggct gaaggggcca ggtgggagtc ccattcaggc tgttaaactt ggttccaggg    89280
ctccttattc tagacacctt gtgtgtgcca tcatgggagg gtaggagagg tgatcatcaa    89340
tgtatgtggc ttgatgtcag tcttgctggg cacagagaag tgattatgta tttctcacct    89400
atctgtcacc tataggtcac agtcctcttt gcaggacaga acatctccaa gagcccattt    89460
gaagtgagtg ttgacaaggc ccagggagat gccagtaaag tcactgcaaa aggtccaggg    89520
```

```
ttggaagctg tagggaacat cgccaataag cccacctact ttgacatcta tacggcaggt    89580
aacgtgcctc tcctccatgg atctgacctt tgcgctttct tccagaggct gaaatataat    89640
cctcggggac ttgaaggcct gaccttttgt cttttaaatc aaataaataa tcacaaagac    89700
aattttttca aatgtgttat attagatttt tcaaaaccag cttttcttct ctaaaatact    89760
caggcttcac ttgaataaga catacttctt gaattgttgg cttcttttcc atgtagtaaa    89820
tagaaaatgc agaagaagga aacattcaac cataaaccct tcaaccccta gaaaatagtt    89880
gttaacatct tggtgtggac ctctctgagg gcctgtctcc tgtttacttg ttttgttgtt    89940
gttgttgggg gaacagagaa tcactctatt gcccagactg gagtgcagtg gcgtgatctt    90000
ggctcaacgc aacctccgcc tcctgggttc aagcgattct catacatcag cctctcaagt    90060
agctgggatt acaggcgtgc gccaccatgc ttggctaatt tttgtatttt ttttagtaga    90120
gacggatttc accatgttgg ccaggctggt ctcgaaatcc tgacctcaag tgatctaccc    90180
acctcggcct ctcgaagtgc tgggattaca agcatgagcc accacactgg tcctgtttgc    90240
attttgcact cagcagcagt gagctttcag agagggtgac ttgggctcat ggaatgcttg    90300 cttcttgta ggagctggtg tgggtgacat tggtgtggag gtggaagatc cccaggggaa    90360
gaacaccgtg gagttgctcg tggaagacaa aggaaaccag gtgtatcgat gtgtgtacaa    90420
acccatgcag cctggccctc acgtggtcaa gatcttcttt gctggggaca ctattcctaa    90480
gagtcccttc gttgtgcagg ttggggaagg tgagtgctgg gctgctggcc acatgtgctt    90540 ctcatagggaa agctgactgc acagctgggc agggaggcca ggaaaacagt cagggcccaa    90600
cattgacctt atgcctatcc cttttctgcc agggctactt cagcagtaag tggcttactt    90660
tgtcctcaat atattaatat taatatcttc tatgagccac gcagagacct aaatgctttg    90720
cttatattaa ctcatttact tctctccaaa acacatgtac aggagagtaa ttatcctcat    90780
ggagggaggt gggactgagg cagtgggagg actcggtagc ataactgaag ttagcagcag    90840
caacatgggc cctgcagcct ccattgcttg gcctttactg gcccaggcac ttaccatgac    90900
tgcatctaat cattgcacca gcctgtgtgt tgcaggtgct attattatcc ctagcttgca    90960
ggtggagatg ctgaggctta gatagcgtta ggtatcagta ctacaaggca tcagcagggc    91020
tagaaccaca gactctgttg gccttaccct taactactct gctaaactcc ctctggcgct    91080
gggggtacgc attttttctca aatgttagac tctctccctc tgactttgtt gccccttttt    91140
ttctgttttg ttttgttttg ttttgttttc caactgtact accttttcta acccacactt    91200
gcctttccct gttctgtcct ctgaatctgc gtctgcagac gtggcttcct cttccgaatc    91260
ctacctctgg gccagcctgg accctgaagc tgttggcttc ctagttgaga ccactgggcc    91320
agaggcctct tgcttggtaa gggctggttg ggtgggactt ccttgccagt tctttgtgct    91380
gcttgtgaat gttagctggg cccgtgttct gtgtgatttt aggaaactct gtgcaggtgt    91440
tattattaca gcctgtccag ccggaaccca aacccactgt ctaattgcct ttaaacacat    91500
ctagggcttt tttagatggt gaaggagctg gtggtgccct tcagactcta gccccattta    91560
atgtttatat gaactcagca attactcttt tgatgttgag actgttgcac atgttcataa    91620
tttccatgag tgtgtgtgtg tttcttaaga cacattaaag ccctccgagg aagtcctgtc    91680
attgtattgt gactgacttc tggtatgacc aactttctc cccttgacaa agaaaaaaca    91740
ggcaaaaaaa attctaacat attcctaagc aaagctcttt tttacataag agagcatttt    91800
gaatagcttt cctaattcta ctattgtttt ccaacctttc ctcactcgtg gacttccttt    91860
```

```
ttcttttctg gcctgtacat cctatactat ttagcattta atgaataacc ttttctttt    91920
aatttactaa catcctctct cccacctaaa tgattttaca tatgtaaaaa aaaaatatat    91980
atatatttgc aggggcgcgg tgggaaggat acagggtctc actctgtctt ttgggctgga   92040
gtgcagtggt accatcatgg ctcacttgta gcctcgacct cccaggctca aatgatcctc   92100
ccacttcagc ctcttgagta gctaagactg tagatgtgcg ccaccatgcc tggttacatt   92160
ttttacccct tttttttctt tttctttttc tttttttttt tgttttgttt tgttttgaga   92220
cagagtctca ctctctcacc catgctggag tgtggtggtg tgatcttggc tcactgcagc   92280
ttctgcttcc ctggttcaag tgattcttgc ctcagccacc tgagtagctg ggactacagg   92340
tgcacaccac cacgcctggc taagtttttt tgtacttttta gcagacacag ggtttcacta   92400
tgttggccag gctggtctcg aactcctgat gtcaagtgat ccacctgcct cggcctccca   92460
aaatgctggg tttacaggca taagccacca tgcctgacct aattttttctt tttttgtag    92520
aggtggggtc tcactctgtt gtccagactg gtcttaaacc cctggactca agcaatctcc   92580
ccgcctcagc ctcccaaagt gctgggttta cagatgtaaa ttatttatg ttaaagaaa    92640
ctttatatca ctttcacaat ggaaaaccaa agtcacttgc cataaagtgc caccgtaagc   92700
ttatgttcat ccataaacca tctaaaatca tctctaactc caagggtatg tgtatgactc   92760
tttgggaagc agttgtttgc caaatagcca gctaaggcca ttgcaggaag gaggaaccag   92820
aggaggaatt accttccgtc tgtggagtag agtcccgtct tctggagtct gtgaccttcc   92880
tgtatagaga tttgtcaaat tttcagtgtt agatttggaa aggaaaagcc acttaataac   92940
atgcattttt ccccactagt ctcccgtttc tatttactga aaaggttgtc cgtgctgggc   93000
agaagattta ttctagggca taaaggtatc ttttatcaac ctctagatac catggaacag   93060
tagttctgtg gacatttcaa gtaaggcata ttggaagcta tcttcgccct taactttag    93120
acttacaact ctaggttttc aagctagacc cggaaatgaa atcagcaatg gtgtttactg   93180
ctaattattg cctttatagc cacccacatt ctgaaggcct gtaacagac agcacgaaaa    93240
gattggtctg cctcagccaa ggtggggctg aactggtctc tttccaagct gtgttggttg   93300
ttttttgcctg gttgttcagg cggaagacaa caacatttag acacttaaaa atggctgacc   93360
caggttttgg aacccagaca ggcattttca agtactgcat tttccaagaa gacttgaaaa   93420
agtccagtct atccaattac tgagcccttg agtatggcag tgaggtttga ataatgtcca   93480
gcactcggcc ttaactccct ttcacaaatg aaaggttaaa tgctggaagc aggagcacag   93540
catgatgttg ctgtgctctc ctgttttctt tgccaaagtc acttttctcc agtccttctg   93600
tggtgtcact ggacaaagtt atattgtgtc tgtatttgct agcctggtgt gctccctgag   93660
tgggaccccct ggtcttgggc aactactgca tactatttgt gcaaagcaaa tattttcttg   93720
gcgggtggct ccaggttacc ttggctttca cgactctgac taaagaatga aagattgaat   93780
tgatgtcaaa actgtgcttg cagcctgcaa tccaaatgcc tgccgggcca gtggccgagg   93840
cctacaaccc aaaggcgtcc gtatccggga gaccacagat ttcaaggttg acaccaaagc   93900
tgcaggaagt ggggagctcg gtgtaaccat gaagggtcct agtaagtgtt cctttgtttc   93960
tctatctcag gtgtggtttt ggctaacttt gcagccatgg catatggatt tcatcccacg   94020
gccagttgtc ctcaataatc ccagaaggct atgtcaagga tttgaggcta tctgggctcc   94080
ttgggaagaa cggcagtgat tgattagtaa tgtctgccct ggatgcggcc agtgggtggc   94140
ttgacagctt tacattacat caagacttct gggagtagaa aaagcagtga tgtaaaggag   94200
ttggggaaat gctgctgttg gaacaagtgg ctcatttttt attttagaca tctgggctca   94260
```

```
gagaggaagg ctcttgccta aggtcataca gcgtttgtaa tcatctgagc tggaattcaa    94320
gcacagtctc caaagccagt gattttccca ctacaggtta cattttatag agtatgaaat    94380
tatgtcaagt acttaattac tatgatcagt gcttatagaa ggagaataaa attccctaag    94440
attaagtttt ctttgtagat aaatgccatt tgtggaggta caggttaaac cctgcaaccc    94500
attctctctc cctcttttgg ggaaggagac agcagatgtg gggatgggtg tcttcacttt    94560
tttcgttgga acagagaagc atttcagcac ttctagtctc gggtgtagca gcctttggtg    94620
gttttactcc catgcctgtg gaatcttgag cttcctgtac caggattgct cttaccttct    94680
gtgttcccaa caggctgggg caggagcatt ctgagctcca gaaagttaat atttgacttc    94740
acagcaccag gctttgggtc aggctgtgcc ctgagggtag ccgaggttct agactgccca    94800
gacctggagt caagctgctt ggggactgtc ttccctccca gattattcca acaggagcca    94860
aggagggtgt gtgtgtgtgt gtgtgtgtgt gtgtgcacgc gcgtgcatgc ctctgcgtat    94920
gtgtgcgtac gtgtgtgttt tctcctgacc ttgaatactt gcttgactca acggctttcc    94980
tggccaaacc tcagggctca acacaaaaca agttcctgcc tgatggctgg gtttggagtt    95040
tgcagcgtca catctaaaac ctgtcctctt gcagatagcg tctgaggact ttcttgcttt    95100
tgttgtccag ctttagatgg aaaagtatac gctggaacac tgaacctaaa actcatacca    95160
aatacttcta aaggtttact tcttccccag tttttgtggg ggactaggaa gggtagctat    95220
gattattggg aaatactgaa atgtgactgg atttatcttt atgcaggccc agggagttca    95280
ggacctcagg gcccctcgta gccaagcaag atttctaaag ccaattagct gggaaatcct    95340
ccatttcctc ataccttgaa gcagagatgg ctgtgttttt agctttgaaa taatctccca    95400
ggctttgagg ggagaggtcc catactctgg ggcagcccac ttggttttta tgtatggttt    95460
atgttttgtt cagtgtggct gcctctctgt tcttgtcctt ttgattctca tttgggcct    95520 aggattgtgt tggaaagatt atctccttcc ttcccacaga gggtctggag gagctggtga    95580
agcagaaaga ctttctggat ggggtctacg cattcgagta ttaccccagc accccgggga    95640
gatacagcat tgccatcaca tgggggggac accacattcc aaagaggtga ggctcctgct    95700
gcagaggggt cttctctgga gggtgctcgg cccagggcgg actcatgggt agttgcttcc    95760
cgggctgcag gagggaaaga gatctgcttt gttgaaaact tttttttttt tttttcgga    95820 gcagcacaga catttggcct gttctcaaaa gcagcagaaa gttgctgtgg ttttagctga    95880
cttgctttaa atcaaatgct ggtggttagg ggctggtggg aggcagggga ggcagaagga    95940
gcagttagag caaatgggct gtgtgtctag atgcccgcat ataaactgag attctctttt    96000
tcaatgaact cctttgttca tgaatgccac ggggcagaat ctgctgtggt ttacattaag    96060
accgtctacg tgagtgctgt cagggccaa gggacgcagt ctacagcttt gccttgtggg    96120
cattgcactt gccctctgc gttctgtgtt ttccagctcc cctggaggtg caactttaaa    96180
ctccgaataa attcagttag ccttgagaaa tatttgggca ttattgggtt ccgaatacct    96240
accacgcttt ttttttaag cctcccatgc caaggttaca gcacattcat tcatgtatga    96300
gataaagccc attcaaccaa gttttctggt tatagcataa gcaggatata gtgtgtggac    96360
tctctcactt tccagggtca tagtctgggg aggcctgcac acaaaggtaa agggccagga    96420
ggctggtgca aagcagcgtg gcttgagtgc caacccagtg gccacctgag ctcccagaag    96480
cagtcacatt acattatatt gttgacataa cagtagctat gggtgagagg cctgcaggag    96540
gaagggcttg gctgcagttt gggatgccag atgaaaggat caggcaagtg gaaagaatgt    96600
```

```
gcaaaggaac tgcagcttat ggctatagtg acaccttact ttactcttct ttgatgcttc   96660
ttctattcct ttccctgtag cccctttgaa gttcaagttg ccctgaagc gggtatgcag    96720 aaagtccgtg cttggggccc tgggctccat ggtgggattg tcggcggtc agcggacttc    96780 gtggtagaat ccattggctc tgaagtgggg tctctgggta agtggacaca gctgaccagc   96840
atcttctgga ggactgagga ttacagggct tccgggctgt gtcaggctgg atgttgggc    96900 cttgcctagc ctcaatacct ttagcttcct ggcctcctgg ccaccctaag ccatctctgc   96960
gtgctgctgt acatttgcag ttgcctctga taccagcatt gattcattca ggagaccttg   97020
agggcagaaa ccttatgtgg gtattgtgcc taaaacaatg cttggaacgt agtaaacact   97080
tagcaaatag tgttgactga cctttatagt ttagatgaat gaatgaatga attttgctga   97140
aatttggatt tggaagataa atatttcctt tggagcacag ctgaagtata ttttaaatac   97200
atgtctaatg tatatatgat cattttatat caggagtcag ccagcttttt ctataaaagg   97260
ccagatggca atattttcc acctgtgggc cttatggtct ctgtcacagt tatttgactc    97320
tgccgttgta gcctgaaagc agctatagga atacgtaaac aaacgtgtgt ggccatgttc   97380
cagtaaaact ttatttgcaa aagtaagcaa tgggccagat gtggccttca gactgtcgtt   97440
tagcaacccg ttttaggtaa tagcaataag caaaagagaa aaataagaaa tcacatttaa   97500
ttttcccttc tagagagatg atatgaatcg tcttgtatat tcttagtcta gagataatat   97560
taagtctttt agtgtatcct tctagacttt tttctctata tatgcatgca atattgatt    97620 tggtacagaa aatatcttag acaagtcttt atatctttat gcgtaaatat agggtatgcc   97680
ttcattttcc atagcttcca tggaattcca ttgtatggct ctatccattg tcaggctctt   97740
cagttatttc cagggttttg ctataaaaac agtgctgact gtgtatcctt ggtaattgcc   97800
ttcagataaa acccagaag tggatttggt ggtgctaaga gtgggtgttg gttcaaggct    97860
tttgccacat gttgccacat ctccaacaga agggtttgct ggttggactt ccctgttgg    97920 atgatgataa atacatata atgtatttaa tactatatat atatatatat atatatatcc   97980
tcctggcctc aagtgatcca cctgcctcgg ccctcccaaa gtgctgggat gacaggtgtg   98040
agccaccaca cccagcccag gcctacattt gaaaaaaaaa aaatatatat atattttcca   98100 cccccttccat ctctactgaa gacttaatga gcttggtttt ggaagaaagg gatacaaaca  98160
gatttcaatc ttctggccaa cacttggctt ttagggaggc agcgggaatg agctgtcgta   98220
acatagaata ggtgctttcc accatataac cagggagacc cttccacctc cacccccag   98280 ggtttgccat tgaaggcccc tctcaggcaa agattgagta caacgaccag aatgatggat   98340
cgtgtgatgt caaatactgg cccaaggagc ctggcgaata tgctgttcac atcatgtgtg   98400
acgacgaaga catcaaggac agcccgtaca tggccttcat ccaccagcc acggaggct    98460 acaaccctga tctggtgaat cagctgctgt gcttctgtct tcttgtccct ggccctggt    98520 tcctcacccc catgcccgaa gttgccttaa gcagcatgtt gagagatggc agagaggaat   98580
catttggatt ttaggaagga aacaggcctg catttgtttg tttgtttgtt tgtttgtttg   98640
tttgttttga gacagactct tgctctgtcg cccaggctgg ggtacggtgg catgatcaca   98700
gctcactgga acctctgcct cctggggttca agtgattctc gtgccttagc ctcccaagta   98760
gctggaacta caggcatgtg ccaccacagc tggctaatct ttgtattgtt tagtagagat   98820 ggggttttcac catgttggcc aggctggtct cgaactcctg gcctcaagtg atccacccgc  98880
ctcggccctc ccaaagtgct gggattacag gtgtgagcct ccacacccag cccaggccta   98940
catttgaatc ctggtagtag cacttagcac ttttatagtg ttgggcaagt aacttaccta   99000
```

```
tctgactctt ggtgtcttcc tctataagac aggaatgata gtagtctctg cttctagaga   99060
gcttctagga tgattcagga ggtggcatgc ataaagaccg cctttggctt atgcctggcc   99120
catgcaggga gctccataag ctgttatttt cttgcaactc cggggatcat atgtcagtct   99180
tacagccatt ttctatagtt attatttcaa ggtgctccat agataaagga ttttttttc    99240
ctagttccgt gtctcttaag ttggagcaat gtttccaaga gtgtcctctc aaacccttag   99300
caggctgata agcatcaagt ctgagccagc ctggctgaca gggagttggc cccagaggcc   99360
acgtgtgcta ctgttggccc acacgggcag ctgtccatag gctgatgtca gtctgggctg   99420
gtagctaccc cgttttggcc aaatgatatt cctttgccct ctagggcaaa tgttgtccgt   99480
ggtaaagatt ctgagtcccc tcaaagtggg aacgttgaaa ctgggcatga ctagaggtct   99540
ctgccccagt tgttagaagt tctttaggtc aactcagaat aaggcaggga gcatgggtta   99600
gtttgggcat ggttttagaa caggggtttc aatattttg ccttccctgg ccacactgg     99660
aaggagaaga attgtcttgg gccacacata aaatactaat gatagccgat gaacaaaaac   99720
aaaaacaaaa aaaaaattgc aaaaaatttt ataacatttt aagaaagttt acaaatttgt   99780
gttgggctgc attcaaagcc atcctgggcc gcatgcgggc ttcaggccgt gggttggatt   99840
tgtttagaga gttttctccc ttatgaggga gagacatttg tttttaagtt acaacctact   99900
ttagcacttt acttcccata accaacctct tatgtggata ctgtaaaacc agacacaggt   99960
cattttgttc ttccccacc ccctggttac ctgtctttgt ataagggttt agttggggca   100020
ttacacagaa agagacttac tatctgcctt tgcttcaggt tcgagcatac gggccaggtt   100080
tggagaaatc tggatgcatt gtcaacaacc tggccgagtt cactgtggat cctaaggatg   100140
ctggaaaagc tcccttaaag atatttgctc aggtaaattt cagggggcca cctgtgcagg   100200
taattgtcag gtaacaagat ctgaccacgt aatggcaagt tgctgagtcc atctgatctt   100260
cagtttcctc atctgcaccg tggaaatgat aagaagatta tcttataggg ttatgtgagg   100320
gttcagtgag actaccatgt agagtactgg gcttaaaaa aatcagcttt ctgatttata    100380
ttctgtggaa atgaggcttg tttgtttcag gttattctat aatgtctttt ggtgtggctg   100440
aagctgctga ggccatgggg ggagatttgt aaacaaggat ttaaaagta tgtttattta    100500
atctaattga atttggccaa aggacttaaa tgcaggaatt gagtggccaa agctttgttt   100560
ttgggtcact tgctcttaat aactaaaaat aaataaatgc atgtcatatt ttgtcactgg   100620
ttgtcaccgt gttgtgaaaa tatggcacat tgtagttggt ccatgaagtt ttgttgtata   100680
agcaagtggt gacttggctg tcttgggagg ccacagtgac cctgtctgat agagacagtg   100740
tgagggccac ctctggtcct agctctggct tttttgcagg atggggaagg ccaacgcatt   100800
gacatccaga tgaagaaccg gatggacggc acatatgcat gctcatacac cccggtgaag   100860
gccatcaagc acaccattgc tgtggtctgg ggaggcgtga acatcccgca cagcccctac   100920
agggtaggtt gtgaggcaga atcctggctg ttttatggaa atgcctggtc atacaccagg   100980
tctgggatcc atgcctgaca gccaaggcag acatatggaa ggaacccatc cctggtgggc   101040
cttgaatgat ggaggggccc gaagggcaga gtgctccagc ctgctcagaa gaactatttc   101100
taacaatgtt ttttaatagt attttactgg gtccaagtgg aggagaactt gatgaccttc   101160
tccatgtctt ctctaggtca acatcgggca aggtagccat cctcagaagg tcaaagtgtt   101220
tgggccaggt gtggagagaa gtggtctgaa ggcaaatgaa cctacacact tcacggtgga   101280
ctgtactgag gctggggaag gtgagaaagg gctttgttca acccagtgat cattgctccg   101340
```

```
tggggaaggc agttctttc ataacgtttc aatgccttt gaactaggaa gtagtccatc  101400
tgaataggta atcatctact gagcctctga gtcattcctt agtgatatct ttgctaatcc  101460
atcatccctt tccccaaatc cttactcttt ctcaggtttc ttactagaaa cttcccaatt  101520 gcttttgag ggtgttaacc tgagctggaa gagattgcac aggacatgct gttcttgta  101580 agctggtgct aataagctgg tctgttccag gtgatgtcag tgttggcatt aagtgtgatg  101640
cccgggtgtt aagtgaagat gaggaagacg tggatttga cattattcac aatgccaatg  101700
atacgttcac agtcaaatat gtgcctcctg ctgctgggcg atacactatc aaagttctct  101760
ttgcatctca ggtacgtggt ggggcctggg aggagatggg tggagtaggc ctggattctc  101820
tttggccact tgtgtgcatg tctcatctac tttttggtgt tttgttagta ttattatttt  101880
tgagatggag tctcactctt tcacccaagc tagagtgcag tggtgtgatc ttggctcact  101940
gcaacctctg cctcccaggt tcaagtgatc ctcccacctc agcctcccaa gtagctgggg  102000
actacaggct cataccacca cccagctaat ttttttttaa tttgttttta ttttttatt  102060 ttttttga gatggagttt tgctcttgtt gcccaagctg gagtgcaatg gcatgatctt  102120
ggctcactgc aacctctgcc tcccgggttc aagtgattct cctgcctcag cctcccaagt  102180
agctgggatt acaggccacc acgcctggct aatttttttg tatttttata gaatgggt  102240 ttcaccatgt tagccaggct ggtctcaaac ttctgacctc agatgatacg cctgccttgg  102300
cctcccaaag tgctgggatt ctaggtgtga gccaccgtgc ctggccactc agctaattgt  102360
tttgcatttt tagtagagac ggttgcccag actgctctcg agctcctgac ctcaggccca  102420
cctggcctcc caaagtgttg ggattatagg catgagccac cacatttggc ctcctttg  102480 gtgttttact gacagggaag ttgtcttgag aacactgctc aatcgttttc tctctggctc  102540
cttacaacca agaaggaaaa aaaatttacc cagagctaaa ttattaccac tttctaacaa  102600
aagtgaggca gtgtgttcag tggttaaaag caggggtctg gagagagact agtttgtaat  102660
aaattttcat caatattttg gttgaaatgc agttagcttc tagatatgtt ctactttgat  102720
gcctttgaag caatgactgt ggtctccacc cttaaattt tatagagaga ggtgattga  102780 agtttcaggt atgcaatagt gaagataggg tgagcaggat cctgaaagag agaaattga  102840 aatcctaggg attaaaatta accttacata aaaatggaaa tcttagtaga atgttctgtg  102900
cctaaaggta gtggtcttga catccatta acctcttctg cctttattcc aatagtctgc  102960
aacattcttt ttgaagaatt ataatcattc tgtctctgat cacttcttgc atttcccag  103020 accttagctc tcagctgtcc ctggaggaca tttccttccc ccagccccat gtattattgt  103080 cgttttggt tttattcttg ttggcatttt tcatcctgag tactcaacat tcagtattaa  103140
aggctcaaag tcctcgggtt tgtttgtgac atcagggatc caggcattag agagtgacct  103200
gttatagaag gccctttccc aatgctgggc cctttggct tatcttaccc ttctgtttac  103260
ctgtggtaat agaagtctgc tcaccactcg ctaagtcaga gtgatgctaa ggttcacccct  103320 ttgtttgaagg ctccctgagc tctggctgtt gcttcagggg ctttcctact aagactgtgt  103380
ctctgctaca ggaaatcccc gccagcccct tcagagtcaa agttgaccct tcccacgatg  103440
ccagcaaagt gaaggcagaa ggcccagggc tcagcaaagc aggtaagatg gcacgtctag  103500
gttgtcctgg gccctctgc cagccggtgg cactgggcgt gtttcatcca cggccttgag  103560
gaacttcatc tccaccaaca ccaacaccaa gctggcaggt tttctgtgca gctctgatgc  103620
agcagtggct ggccaggccc gttgctggct gtcataatag acctggtgct gttgaacctg  103680
tctgacgggt tctcaaagtg aaactactcc agctggtctg tctcctcact tcacagtata  103740
```

```
tctttccagg tgtggaaaat gggaaaccga cccacttcac tgtctacacc aaggggctg   103800 ggaaagcccc gctcaacgtg cagttcaaca gccctcttcc tggcgatgca gtgaaggatt  103860
tggatatcat cgataattat gactactctc acacggttaa atatacaccc acccaacagg  103920
tagggtcctt ctccctctg ctcccctggc ccccagccag gccccttct atgcagtcgg    103980 tgctgggtca ctgtggacac caaggggtgt gagaggtgct ctgccaaagt gctccctgat  104040
gggaggcagc tcctggcact ttgaacccct ctgggagcac ctataggaag cccaatgggt  104100
tctatcaggt gaactgcaga attccccaaa agcaagcagg aagctggtcc catatctcca  104160
cctttggttt gcattttatc agagaaatgc tcagttcttg atattcaggc cctaatatct  104220
atctttctgt tacacatgtg cacacatgtg cacacacaca cacatacaca cacacacgtg  104280
cattccctcg cggcctcacc agctgccttt tagtcttttc attaattacc cacagaaaaa  104340
gagctgctac accttttgtgt ttccttcctg gtccttttag cttagtttac ccttttttatg 104400 aggtgttgga atgaggtctt ttctcaaaga gccagttcag cctttcgtcc ctaaggccca  104460
gcacactatt tagggcagca aattattccc ctttacaaaa tgcaggattt cacatgtgat  104520
cttaccatct aggctggctt actctgatta tttcaggcca taaggccctt aaaactgcct  104580
ctctgtacaa gttaatgttt atttgtttaa aaacattaaa aaaaatttgt atcgtggtaa  104640
aatacacata acacaaaatt taccgtctta accatttta agtgtatagt tcattagtgt   104700
taagtgcatt cattatgtcg tgcacccatc accaccatcc atctccataa ttctttacat  104760
cttgtaaaac tgaagccctg tatccattat atttgtttaa aatttgtttt cgcttcatgt  104820
tcacacctct ggggtctgga gagcagacat cctggcagaa aagtctggat tttaatactt  104880
aagcctagtg ttcgaagtgg ttgttccaag cctctgagat tcctttattc ttaagggaaa  104940
tgatcctgct gtgtttgaaa tgccatttgt aggagaagaa gggcaacgct ttctgcagaa  105000
gcactgctca gaagccttgc tcccgtctgg gtcctctcag cgaggagcag tcaagagtca  105060
agtggggaag aaagaggatt atagtgagga aggggtcatg gtgtaactgt cccctgagtt  105120
tgggggctgc actcccttgg agatggaatc cttactgtga gaacatccct gcagtgggag  105180
ggattccctg ggcgaaggga ttctgtgtgt cgtgttataa atgtggcccc ttacatccag  105240
gcttgctgct gtttgtgctt tcttccccaa attttattt ttatttattt attttttaga   105300
caaaagtctt gctctgttgc ccaagctgga gtgcagtggc atgatctcag ctcactgcaa  105360
cctctgcctc ccaggttcaa gcgattctcc tgcctcagcc tcccgagcag gtgggattac  105420
aggcacatgc caccacacct ggctaatttt tgtattttg gtagagacgg ggtttcgcca   105480
tgttggccag gctggtctcc aactcctggg ctgaggcaat cctttcacct cagcctccaa  105540
acctgcggat attacaggca tgagccactg cgcctgacct cagtatttgt cttttgtga   105600 ctgatttatt tttcttccta tatgtcctcc atgttgtagc acgtgtcaga acttcattcc  105660
ttttcgaggc tgcattccac tgtatgtata tatgttttgc ttctctcttc gtctgttttt  105720
tgtttgtttt ttcttgagac tcgctctgtt cctcaagctg gagtggcact gtctcggctc  105780
actgcaacct ctgtctcctg ggttcaagtg attgtcctgc ctcagcctac cgagtagctg  105840
gaagtacagg cacgtgccac catgcccagc taatttttgt attttttagta tagatgtttc 105900 accatgttgg ccaaggtttc accatggggt ttcaccatgt tggccaggcc ggtcttgaat  105960
tcctgatctc aggtgatctg cccacctcag cctccgaaag tgctgggatt ataggcatga  106020
gccaccgcgc ccggccatct tcatttgttg aagaacattt gggttgcttc cgtcttttgt  106080
```

```
ctgttgtgaa taatgctggg tgtacaaata tctctttgag tctctgcatt taattcttgt    106140
gattataaac ccgaaatgga attgctggat catatggaaa tctcttttta attttttgag    106200
aaactactat actgtattcc acagtggctg cactacttta cagtcctgcc aacagcatgc    106260
aagggtcctg gtttctccac atccttgcta acatttgttt tttttctgtt ttttttttt    106320 gttgttgttg ttgttgttga tagtgaccat cctgttgagt gtaagatggt gtcttattgt    106380
ggttttgatt tgcatttttcc taatgattag tgatgctgat catcttttca tgtgcttatt    106440
ggtcctttgc atattttctt tggagaatta tctacttgcc cattttata tcaaccttct     106500 taattttatg ttgagttttta ggaattctcc atgtattctg gatattagtt ccttatcaga    106560
taaatgattt gcaaatatat tctctcactc cttggtttgc cttttcacgc cgttaacagt    106620
tctcgtgtgc aggttataaa cgcggcttct tatctccaga cttgctcttc ctgtgcttta    106680
aaataaaaaa tccaaaacaa aacattcatt attagtaatg ataaaactaa cacttttata    106740
gatagagcat tcttttctca tcaggccact caatagtaag taggtaatta ttttcctgct    106800
gatggttctg agggttggtg ggagccttac tactgggtgc accacgctga atcttctttg    106860
ttgccaaatt ctccatattc tttaggagaa agcaccagaa agccatagct gtctgcgtac    106920
aatgactggg atcacaaggc catgacgtct tctaaaaaca ttttgtgact tctgctttat    106980
tctatgtcta tatgcctttt agtgttttgg ctgagccgtt agaaagtaag ttgcagatat    107040
caggacaggg tcagggtttg acctgcatcc ttggaaagga ctgcagaacc cagtacccca    107100
gacgtcccct gctgctggtt gaggcagaag tggagattag gagcctaggt ccggttttgt    107160 ccccttttgaa gtaatgctgg agtgggaggc tccttacttc agagtcaccc caaggtcaca    107220
ttcatccagt tctctgatag cagcaggttt gagaactgct gccatgctga gtactcactt    107280
agggctttgt gtccggatgc tcccaggatg cattcaagga gccgggtggg ccttggtggc    107340
ggtcgttgcc accaagtggc aacatccaag ctgcttgaag ccacccacaa ccccacaacc    107400
aagagaagag aagaccaaag tcctcaggta aatcacaagt gtgaatgact tgcagggtgg    107460
cactggggtc cttcttgttg tttgttgctt ggagctgggt ttattgtttc attatttggg    107520
caacttgcaa ttctgcctat ttttctatgg caaagaacac attaaatctc tccttagatt    107580
gaatttcctt cccaccccca ccccagcac agagcctggc cctataagtg ctctgtgtgg    107640
attaatggct gtgagtgagc gaataaatga catggcgcct ggattcacaa gcggagatgg    107700
cctaagaacg ttgtaatctg gtagaggagt gatgccaaca cctcctcatt ctcctttgaa    107760
ctctgttttc tgaagagcag ctaaaagctc aagactgggc taaggaagtg tgcccttgga    107820
tgtggttaag agacctgggt cagcccagaa agccaccccc tgacacgggg gagggagcat    107880
actttgaggg ctgacaccca caggcacacc ttctcatggt agttttaggg tataacaggc    107940
tggaaatccc cagaaaggtg gctgcttggg catgggtgtg tcctggcctg gtgtgggcgc    108000 ttcccccctca gaacacaggc tgtgccacgt ggggagccga ggtcctgcct gagtaaccca    108060
ggtccctgat tgctggtttt gctccctgac acctgcaggc ctgccactcc acctcgcaaa    108120
gtccctgagt gacagcttgc aggtgcttgc ctgcctgggg tggatgagtg atgtggatgg    108180
ctgtaggatc ctgtgagtcc cttgaggatg caaaagtaga gcgcgttttg ccttagagga    108240
atggacttgt tggcttgggg cttgaggacc ctcccagagg tcaaagactc ggttttatag    108300
aagggaagtg atttccctga ggactttggt cttctcttct cttggttgtg ggtggcttca    108360
agcagcttaa atttctcacc gcacgttccc ctgcgcagag cagtttgaga agctggtggc    108420
aatgtctcca ttacgtgctg tgctgggagc cactaggatt ggggaccact ccatgtagta    108480
```

```
ctctggcacc tttagaaatc cctgtgagct cacagaccct cacagagtaa cagcttctac    108540
cttgaaatgt tcttaacgtg gtggtcctgg ctgctcctgg agggccctaa aagggatggt    108600
gctgagggtg gctctctcag tcccatcctc ttctgagctg tctggtcagt gtcttgtgta    108660
tgtatatttt gaagaataag attcaggttt cagaagcatg tagaggagag tgaaactgtc    108720
ttgcagcctg cgaagtcgtg gcgaaatgca ctggccatca ctacccagac atccctcact    108780 tcatagcccct gttggggaat aaacacagtc cattccttag ttggggcctc aggggacact    108840
ttaaaatgct gtaggcattg taggtgtaaa tctccgagat ttttcccctc cccttctta     108900 ggttatttaa ggtacagttc attttctatc tgagttttg ttttgttttt gactggtaac     108960
aagagcatac tttcttttat gggatgggtg ggcttaactg gaagagggtt tttccctctc   109020 tttttagca cttcagagaa gaggccagaa aactttatgc gggtgaggga ggaggtatcc    109080
ccaagacctc tggttagcct gaggtctgct tagtgagccc ctgaattgtt aggggctgtg   109140
gggaaacgga agctcgggaa gagttggcac gttgggaatg ccacgttggc tgaagtagcg   109200
agtcagtcct gccttaaaca gtacaaaaag gagacctttc ctgccccttg gctggctccc    109260
agctctgttg aatttgacct gtacacattt taccaggaaa tgttgttcac atgaggcagg    109320
gggccaattg gttttgtgtg cagtgcttaa aaatgctgga aaattaatcc tctcttcatt    109380
gatgcaacca gttttttttt tttttcttg gcctttaccc ccttccttat tacaaaagga    109440
atgtgacaaa atatacatag gccaaatgct acacccttt aacacttgat cagcaacagc    109500
tttcagcagg gcctgcattc cagcaaggct gctggattct tggggggaac tcgtctctcc   109560
ctcacacttt cctgttacat tatgcctggc cgattgtggt gaagggatc ttgatctact     109620 gagacagcca tgagatttct tggagcctcg atttggaggg agggaacttg gccaaccatg   109680
gagagaagaa gccggctgtg tgccagcctg gaaccggcga gaggagagaa atggcgcaca   109740
catggctatc gcgtgccacc cggccacccg tgagggtgcc tgccaatcct gcaagcacca   109800
tctgccttca cacttgcaat tttattttct ttcacatgga aatggaagtt cagatattgt    109860
gcgatggtct tagcacaggt ctaggtgaac tcttgcaaat ccctgttgca gcctgggggc   109920
ctcaaactga ttcctaggac agaaatggtt ctgtttggtg agtggcccca ggcccagctg   109980
cactggctgg cactgggtat gatgatgggg aggtggtgtg gcagagcagc taggacacag   110040 atttggggc catgggtatg aggcccagct cgcacccta ccaaggtgtg tgacttgggg     110100
cacgttcctt taccagtctg agccacagtt tcctctcctg aaaaaatgag atgacagtag   110160
gaactacccc ttaggactgt tttgatcttg aattgaggaa atgcataaaa gcacatagca   110220
tggtgcttgg tgtgtagaaa atgctcatta agttgcttct gttattatta gctgctctta   110280
tttgatctaa ttttctgtt attcttgcct tgtggtcaaa agctagaaga aatagatcta    110340
agatactttc tacattgatt ggaatcaagt ctcccctgtc cgtgagaaga atgagggatc   110400
ttgaggggat tttaaatgcc aagttagctt tttggtaccc aaaggtaaac tgagttttct   110460
ctcttgttcc agggcaacat gcaggttctg gtgacttacg gtggcgatcc catccctaaa   110520 agcccttttca ctgtgggtgt tgctgcaccg ctggatctga gcaagataaa actcaatggg  110580
ctggaaaaca gtaagtgcct gaatggagag cagatgggtt gttgatgacc ccccaacgtg   110640
gctgctggtt agattttctt caaaaggtga aatttgcaga gaagcaaatt ctatgttaag   110700
agactttgca gttgcacaga ctttggttcg aattaaggcc gtggtgtgaa gtaactgtga   110760
ctgtgtctgc cccttagcca caccgagact cagctttctc atttgtacag tgggggtgg    110820
```

```
tcggcgggga gaggttgaga acacccatgg gaatattttg aaaattatat gagctaatgg    110880
ttcagaggct ggcacgtagt cagcccctg gcattgcagt aggaagtttt cattaaaaag    110940
agaatttggg ctatgttgct ttctgatgag tttctaactg tgccagctat ccttggcaac   111000
tgaatccgca ctaaggttgc gagtcaagca taaatgccaa atccctggca ctcagaagtc   111060
actaccacca cacctctgcc ccatcccaat gttcctttag cttgttaggg attttactag   111120
tataagctca tttcgcttat tttcaatttt ctgattattt tttagtaggg aaaatttcaa   111180
acagaaaagg aaagagaata gtataacatg aacactgatg tacttatcac tcagcttcag   111240
atgtgcaaca catgctcata aaatgatttt tttatacaag taaaaatata tccattttc    111300 atctaaaaaa cattacagtt aagggataat tccactttaa ccctcacctc tccttctccc   111360
tagggttaac caaagttttc aattcagttt ctgttcttcc agatcttctc tctgcatcta   111420
tacatataga tgtgcctgtg gaacacattt ggctgtattt attttgcatt aaagttgccc   111480
tgctgtataa acctacttct tcggcctgcc ttccaacagt gcatctcggg aatcattcac   111540
tcctacatct tttccgtctg tgtttactgc tgagtggctc cagactggat gtacctcagg   111600
gctcacattc acctggtttc aggcttactg aggcagggct gagtgcatac ccccaggacg   111660
gggcctcctg tattcacctg tgagggtttc tccagagtac cactagcagt gccattagtg   111720
agcatcttcc ttcactcgtg acccaagtgc acaagttgca agcaaggcca gctcccagtt   111780
gcagagatcc aaagtgagag ctcactgttg gcttttgtgg ctggagcagc cagctctgag   111840
tgtgtaaacg tccactgccc aaccctgtca tgtgtcccct tgtcactcct ttccccaaga   111900
cactgagagc tttgactcca gaacaggaaa agcagggtgc caattaggaa agcctctttt   111960
ccggtgggaa gtagcgatcc gggacctcct tgcctgtggt tcggcagtgt ccatcttgcc   112020
aggccctatg ttccttcaga gtcaaggttc tctgggttgt ggcaggggcc ctgtgttccc   112080
agtgcttttg ttttgggtaa agtccttttcc ctgttcttgt ctaatctaac acttgggctt   112140
cctgcagccc tgctttgcag agaccttttg gaaaccatca cggtacagtc agttctcagc   112200
acttgcttca atcggctcgc atttggcagc tctgtgactt ctgctttctt gaggggggagg   112260 ggtgcctata agatggagtt ggctgccaag aattagtaaa taaaacattg acttatgagg   112320
gtgtttggat atcaagttaa caccaaaagt aagtaaataa gagacgacag tgtcagatta   112380
caactttctg gtcagcaaag attgtggggt caggtaaatt tcactttgag tcccagcttg   112440
gcaggctgct gcatatgtca ccctggacaa gttacttaac ctctctgagc atcagtttcc   112500
ccatctgtga aagccattgg ttaataataa atacccata ggattgtggt gaaaattaag    112560
acaataacct atttgtgctt ggcatataaa atgcattcag taaatgatag ccgttattgc   112620
tgtcatcact aattgattat tgtgccgaca cttgttgtta ctgaggctga gatgctgatg   112680
atacttactc agctttgctg cttgtcctct gcagcagctg ttgcttacag tggaggctga   112740
gataagtccc cgtgtccaaa gaaccattgc ttctgtgctc tggattgttc ctgctgctga   112800
aaagggtcag ctcttcacct cagcttgtgt ttcttttcca ggggtggaag ttgggaagga   112860
tcaggagttc accgttgata ccagggggc aggaggccag gggaagctgg acgtgacaat   112920
cctcagcccc tctcggaagg tcgtgccatg cctagtgaca cctgtgacag gccgggagaa   112980
cagcacggcc aagttcatcc ctcgggagga ggggctgtat gctgtagacg tgacctacga   113040
tggacaccct gtgcccggga gcccctacac agtggaggcc tcgctgccac cagatcccag   113100
caaggtcagc ctttgctttt gtcccagaac ttgtctcatt gctgtcaaac atgacaccat   113160
agtccttctc tggttcttcc tggcaaagac cttctgaaaa tcgtttttgtg atgaaagtta   113220
```

```
gcacaattca ctgtgaaagg tccctgggt aggtgggtca caaccctgct cctcctcttg 113280
ctctctgact acaagacttt ggtgaggggc tccctgtccc agagtcttct ttcttcgctt 113340
gttagcataa tcacagtcct cactacaaag ccagcctgta aggggtaggt gagttagcaa 113400
acgtggaggc ctctgcccag cacccagctc acagacggag ctcaccctcc agaagctaga 113460
atcatgtaat ataaaaatac attattctgg ccaggcgcgg tggctcatgc ctgtaatccc 113520
agcactttgg gaggccgagg cgggcggatc atgaggtcag gagatcaaga ccatcctggc 113580
taccacggtg aaaccccgtc tccactaaaa atacaaaaaa ttagctgggc atggtggcgg 113640
gcacctgtag tcccagctac tcgggaggct gaggcaggag aatggtgtga acctgggagg 113700
cggagcttgc agtgagctga gatcacacca ctgcactcca gcctgggcga cagagcaaga 113760
ctccgtctca aaaaaaaaa aaaaaaacc acaaaaaaaa acattattct ggctgggcg 113820 cagcggctca cgcctgtaat cactgcactt gggaggcca aggtggatgg ataacttgag 113880
gtcaggagtt tgagaccaac ctggccaaca tggtgaaacc ccatctctac taaaaataca 113940
aagattagct gggtgtggtg acgcatgcct gtaatcccag ctactcggga ggctgaggtg 114000
ggataatcgc ttgaacctgg gaggcagagg ttgcagtgag ctgagattgt gccactgcac 114060
tccagcctgg gcaacagagt gagattccgt ccctccaaa aaaaaaaa aaagttcatc 114120 gtcatttctt catagtaacc ctgactcaag gggttttgga agattccag tggtctcaat 114180 ggtgtgaatc ctatgaaggt gtcttatttg ttgaattaga ggtgaaagcc tccttcctca 114240 ctcttttta gaaacagttt agttttatta ttatgcagaa tttgttgagc aaattgcaac 114300
agcccaagcc acagctagct ccacaagagc ccttccatga gccctcaacc tgggatctcg 114360
tgtatctttg ttggaatgga cattaggttt ccaagtccag gctgtgatt tagaagggtc 114420 aggttgggta ggagagagga gagtcttgga ggggctgctc catgggggtc acacctctct 114480
cctgtgggtt ttcgctggtg attgagttct gaggcatttg ctgcattgac tgttgtagct 114540
ttaactcgtg tgcacgtgtg acacataaag ccccaagaga agggctgcct ggctcagatg 114600
cacttccatg ctgattatat gcatgggtgt tgaaagcagt gctggctgag cagcgatccc 114660
agtgcagttt gactttattc tttgctcaaa taggtgaagg cccacggtcc cggcctcgaa 114720
ggtggtctcg tgggcaagcc tgccgagttc accatcgata ccaaaggagc tggtactgga 114780
ggtctgggct taacggtgga aggtccgtgc gaggccaaaa tcgagtgctc cgacaatggt 114840
gatgggacct gctccgtctc ttaccttccc acaaaacccg gggagtactt cgtcaacatc 114900
ctctttgaag aagtccacat acctgggtct cccttcaaag ctgacattga aatgcccttt 114960
gacccctcta aagtcgtggc atcggggcca ggtctcgagc acgggaaggt gggtgaagct 115020
ggcctcctta gcgtcgactg ctcggaagcg ggaccggggg cctgggcct ggaagctgtc 115080 tcggactcgg gaacaaaagc cgaagtcagt attcagaaca caaagatgg cacctacgcg 115140 gtgacctacg tgcccctgac ggccggcatg tacacgttga ccatgaagta tggtggcgaa 115200
ctcgtgccac acttccccgc ccgggtcaag gtggagcccg ccgtggacac cagcaggatc 115260
aaagtctttg gaccaggaat agaagggaaa ggtgggtttc atttaaaaaa aaaaaaaaa 115320 aaaaaagac aagctgggac ttaagggcta cctgaaactt ggagctgcaa actcagccac 115380
ctgcaggagc caggtgacat ataaggcggt gctcacctgt tccctctgcc tcggggagta 115440 gttgggggc cctggtgaag gttaagcaca ttgcatttct ggggaccgtg ctactcaacc 115500
cctgttttct gtttctccat ggggaacagg acctagcatt gtcagcagaa tctctagttt 115560
```

```
tttggcaaag gcagaaatct tgatttttct ctggaaactc aacatacaac atgttggcat    115620
ttaattggaa aaaagtttaa aatgtagtgt tgtctaacac ctgcatgcca cacagcaggt    115680
tagtcttcaa cctttaacct gtcctcgagc ccggtgtgag cagtcgtgtt gtcacttagc    115740
cgtggctact ctagaaaggc cttctttggg atggagggggg ttaatattct tgatttgaga    115800
gttagaaaaa ccagttttcc agttactgaa attggacttc atgtgtcctg aagtgccaag    115860
aaccttggtt ctggggtttg cttttgggtc tggggtactg gtggcagtgt tagctatgtg    115920
cttgctctgc agatgtgttc cgggaagcta ccaccgactt tacagttgac tctcggccgc    115980
tgacccaggt tgggggtgac cacatcaagg cccacattgc caacccctca ggggcctcca    116040
ccgagtgctt tgtcacagac aatgcggatg ggacctacca ggtggaatac acacccttg     116100 agaaaggtga gccgccctgt cctcggactg gaccctcgtt cagagctgcc cttggtcatt    116160
gcctcctggt ggctggtact gatgcctgcc ccatgtgcta ggcctgtctc agcagggcca    116220
cgtgcagagt gacagagtgg aagtcagcgt ccgctgcagt cacctgccca ctcagtgcct    116280
ggcttgctgg ccttgtgtaa taggtgggct gggtttagcc tcagtctcac ctcagcaagt    116340
tatggggtaa tgtcatgatg ttgctcattt gtgccatttt tctttgcgta tgaatttctt    116400
tcttcttgag tattaggaat tataaaaaat ttcaataaat agaaaaccat aaagaaaaaa    116460
aagtgccatg tatatctcca ctacctggag atcggaagcc tgcgatattc tgatatagat    116520
attttcagtc ttcttgtgga tgcctgtttc ttctgtttca cgggtttcgc ttttctttt     116580 ggttaatggc tggatggtgt tttcccgaat gagagtagtc tgtttaggat gactgacttg    116640
aatatttgct tggttgggt ggagtggctt atgtgactgc agatagacgg tttgtattat      116700
ttaaaagtca gatcatacct acattactgt gggattgttt tgttttgttt tgaaacagga    116760
tgtcactctg ttgcccaggc tggagtgcag tggtgtgatc acggctcact gcaggctcaa    116820
cctcctgggc tcaaatgatc ctcctgcctc agccccctga gtagctggaa ctgcaggtgt    116880
gcaccaccac actcagctaa ttttttgtatt ttttgtagag atggggtctc gccatgttgc    116940
ccaggctggt cttgaactcc tggactcaag tgatctaccc acctcggcct cccaaagtgc    117000
tgggattata ggtgtaagcc actgccccca gccacattac tgtgttttta accccctttt    117060
ccaaataaca tagtatagca tgcagacttc gatgctagat gaaactctga gtagagaat     117120 cattttcac aaatagggga tttgtatgca aatatgcgtt tctgtttgtt gttttgagca     117180
ggtctccatg tagtggaggt gacatatgat gacgtgccta tcccaaacag tcccttcaag    117240
gtggctgtca ctgaaggctg ccagccatct agggtgcaag cccaaggacc tggattgaaa    117300
gaggccttta ccaacaagcc caatgtcttc accgtggtta ccaggtaggc aaggccctac    117360
atttggtgtc ttgagtctca cttttgtggc tagattctac ctatgtgtca tggtttccta    117420
acttttgata agatgaattt ttatttttat aacatgtatt tccttctgta gagacttatg    117480
ttacatagaa agaccaagca tacctaaaaa acataccaaa gcacttgata atggtcatga    117540
aactatttag caaaccagga gtcaatcaag ctctataact tgataatgta aaaatttgta    117600
gccaaccttg taagtatttt tattaaagtt ggttgcaagg catatgcctg cgttgtactt    117660
gcagtcctag ccagtgcaat tagataagaa aaataggctg ggtgtggcgg ctcacacctg    117720
taatctcagc acttcaggtg gccgagacgg gacaattgct tgaggccagg agtttgagac    117780
cagcctggcc aacatggcaa aaccccatcc ctacaagaaa tataaaaatt agctgggctt    117840
ggtagtacac gcctgtaatc ccagctacta cttgggaggc tgaggcatgt gaattgcttg    117900
aacccaagag acataggttg cagtgagccg agaccgcgcc actgcactcc agcctgggca    117960
```

```
atggagtgag actctgtctc aggaaaaaga aaataaatg  aagcataagc attgaaaatg    118020
aggggtcaga gtgtctttac ttacattata ctaatgtgaa attccctatg tgagaggtgt    118080
agtaattgag ttggggtggc tacgtggaat agtttataaa gggaatttgc atgaattttg    118140
gcaataagca gaccagcata aataaatggt gcacatttca cttctttttc cactcttttcc   118200
agaggcgcag gaattggtgg gcttggcata actgttgagg gaccatcaga gtcgaagata   118260
aattgcagag acaacaagga tggcagctgc agtgctgagt acattccttt cgcaccgggg   118320
gattacgatg ttaatatcac atatggagga gcccacatcc ccggtgagct attcctcaga   118380
gaggacccca gagaataatt gattttgcag gaaaatgggt ttgattttgg ttatctctct   118440
gagtggggaa aacaatctga tatttgtaat agctgcaaaa ggagagtttt cttagggct    118500
acatctccaa gattatctca actcccagta gaaccggtaa catggcaaaa agcatcggct   118560
tagaattttg actggaaaca gttgtgcgtg tgttggagga cctagttctt gattcagggg   118620
aaagctggtt cttacaaag  ttgaaaatca cagtggctca cacctgtaat ccccaaactt    118680
tgggaggcca aggcatgcag attgcttcag gtcaggagtt tgagaccagc ccaggcaaca   118740
tgggaatcc  ccatctttac aagaaataca aaacttagct gagtgtgatg gtgcgtgcct   118800
gtaatcctag ctatgtgggg tggggctgt  gatgggacga tgtctgagat gggagcctgg   118860
gaggttgagt gagctgagat tgcgccactg cgctccagct tgggtgacag aggaagaccc   118920
tgtctcaaaa aaaaaaaaa  agaaaaagaa agaaaatttc taccttattt tgtgcttggc    118980
tccttattca tgtgtcttgg tttctttttt ttcactgaca atactagtag ctgatcaaga   119040
tatgcagatt caaattcttt cttttgtatt tagtgatgtc atgtgtaatc actgtgaaac   119100
acggtttctc aactccggca ctatgacact ttgggctaga tgattcttg  tggtgtgggg    119160
ctgtcctgtt cattgtagac ttttgtcagc atccctgccc tgtacctgct agatgcccat   119220
agcagacttc tccttcccca ttcttatttg tggcaaccaa aaatgtctcc atatcttgcc   119280
agatgtctta agggacaaaa tcacttcagc ctgaaccact gctgtaaaga ttcaaacaat   119340
aaataaatat atgacttaag tagtgaaaga ccctcctcca tttgttttgg ggggaggact   119400
ctccataggt tctagttatc tactcaaatg attgtcaccc ccacacattt tatttattta   119460
tttcaatagc tttggggtac aagtcgtttg tggttacatg gatgaattct atagtggtga   119520
attctgagac cacctccccc gcccccattt ctaaaagggc aggcaagtgt gtggtgtgga   119580
cagaagaccg agggctgggg ctgttctggg ccacttatgc cttgtcttag gtgtggtgtg   119640
aagagggcaa agccccaccc caggaccca  ggagcagaaa gagcctcagc ggggtcttgt    119700
tcttctttct ctgggtcacg ctgagagggg aagggcaggt tgaggggccc actgctgggt   119760
tctgggttaa ctctcaggca gctggagtgt ccactgacca cacgctttcc tgattccatt   119820
cctgcttccc ccttaccaca tggaaatgtg cacacacact cacactcact ctctctcaca   119880
ctgatcagaa agtattgaca ttcaactcag actgattcta ctcagatact catttaagcc   119940
tcaagtcatt taaaacaaca tgtttctcct caaacttgtg cttgcggctc attcaatata   120000
gatttaaaaa attcctataa tcactagtct agggggactt cagctgtggg caagacaaag   120060
tcctgccctc agggagctta ctgtctaggg cttttacaac taaaacttgt gatgactgct   120120
atgaagaatg agaatggggc tcggtgacag aattcagagc tacgggcttg ttttggagtt   120180
ttgtaacact tgcgttagga gagagttggg cacaggaaac gggtagaagg ctgctcccag   120240
gagggggtgat gtggctccga cctggcaggc aacagtggag atgaacatct cctgtggcaa   120300
```

```
tgaaactttt tgactatggg gaaaggctgg tgagtgccac cagcttccga atccccctta    120360
cagaaagggg tcagagtttg tccctgtgg ccgacctgtg agcttaaagc aaatggtcgt    120420
ctttgagcat aacaacagaa agacactcat ttgtggtttt cccatcaggt gtggatggtg    120480 ccttttatg tttcaggctc tctgttgcct cccagagagc caaatgccgg cttttccaga    120540
accccagaac tttcccaggc agagatattt agtgaagtgt tggttggttt tctaagcatc    120600
aggcttctta gctaaggcaa cctatggggg tactgccggg aaacagtcgg ctacctgcca    120660
ccttctaatt tgctttcatg gtaattctgg gtgcttaaat attagcctag ttttcctgg     120720 cctggttaaa aacccggagt ggagttattt ttaacaacgt gtcctgtctt acccgtaatg    120780
gcatgttgat ttcctgtggt aggccagctg tggttggttg gtggcggctc cctagaccac    120840
tggattgact ggggttcaga gtgcatgagg aagaagatct ggcatgaggg aatggtgaca    120900
tgtgtctggg catggaacag gggagtggcg gataatgctt ggggtctgcc atcttggaca    120960
gtttatctta cccgggtttg ttggttttg gctactctca tgctgagctc agacaacttc     121020
tagtggaggc tctgacttaa agattggcct cagaggtagt cccttgccat cagctgttga    121080
cattgaaatc ctcaactgtc actctctaaa gtaaagcccc cttttgttcc tctcacccca    121140
gtgtggaggc ctgtgcttgt ttgccagggc cagccattta tttcacgtag ctaaagacct    121200
ggatgccgtt gaaacccagc tgttgttaga aagccaggga ctcaattctt tgtgtgtctt    121260
ggctgtctac catctctaat tctacaaagt ataaattctc tgggatgcaa agcagagatc    121320
cctcagcttt cacggcagtc attaactttg ccagatacca tggggagcac caggactccc    121380
atgcgaggca gaggtgcacg tagcccttg gtgatgggcg tggtagcctg aggcatgctg    121440
ccgttcgctg gatggggagg tccccctcca cagtggagtc catgagtgtc cttggcctag    121500
cccttgtttc tctgttagc acttctctag caaatcacta tctcctctcc tcgactcctc    121560
tgtgcttcat cttaaaact gacaccctca aggagtcaga ggccctcagg gtccccggg      121620 gggtcagcca tgtagcagga gctcagctta cactcaggaa gacggcaagg cttcaccagg    121680
tggccgagtg accgagaagg ctgagtgtgg tcagaaggtg ccagctgcat tggagggaga    121740
ggagtctggg ggacacacag gagccatgtg tgggggacag ggctggatgt gggctgcagg    121800
gcctgcccat ctctctccgt tctgttgttc caccacttgg cttcctcctt cagttgctcc    121860
agcagcctgt ctcctccctc gcctctaggc tcctgcatgt gctgaggcct ctctacttga    121920
agcacctctc tgtctgctcc ctcttgtgcc gcaactgaga tgttactgga aagctttctc    121980
tggtctcccg cagaccaggt taattgcctc ctgagtgctc caccttccac accccaaata    122040
tgttatgtag gatgttagag tgacttgctt gcctcatcct tctcctgcag ttgtgggttc    122100 ctgggggtt ttaaccgctc aggatccagc acgtggcaca acatctgcac gtagtaggtg     122160
ttctgtgaga atggttgaca acaatgagta ggcacatgag cagtgcacac agtgaggcag    122220
ggggagctga ccgaggcctg catggccgag gtcccggggg agcagcagtg ctattctggg    122280
tgtgcacaag gtggtctcca attcccagct tgtgctcaga atcccacaac ctctcttcca    122340
ggcagcccct tcagggttcc tgtgaaggat gttgtggacc ccagcaaggt caagattgcc    122400
ggccccgggc tgggctcagg cgtccgagcc cgtgtcctgc agtccttcac ggtggacagc    122460
agcaaggctg gcctggctcc gctggaagtg agggttctgg gcccacgagg taagtgtgca    122520
ccctgccttc ctgcagacat tcatctgccc caggcagggg cagctgtaac ccagagcaga    122580
tgctttgctt ttgagtttgc tcatgagctt aaaattaaat taaaaaaaat tattgtttca    122640
tttctagtta aacagtagaa attcctgctt acaagtaagc aggcttgtta tttctccagt    122700
```

```
gatctgtccc cccatttaat aatatggcta tcaatttctt agaggaagca gcagtatttg   122760
ggctgtcata tgtaatatgg tggcgactgt ttcattatgt gtttcagcat ttgtgagggg   122820
gtgggttgct ctggatgtgg cagatggtgg ggtttggagg tgataactca ttgagatatc   122880
ttggtgtcca tgtggtacat accagaacct ctgggaatgc caggcacatg atgcacgtga   122940
tacgtggctt tgtcattgtc ttagttcccc agagagagag tgtgtcttgg ggaatgggct   123000
ttgttggcaa tttggcctgc cttgttggca gcttggaact tgggtttggt aaggctagcg   123060
ggccatatag ggacaaagcc ctgaagtgca ttggaacttg cctttttga taagtgacca    123120 tgtttcctcc tccagcactt aaaatgtgcc tttctcccac atagaggaca gtgtgcctaa   123180
tttcttacgt aatctggatt ttcctcgcca atgatatgtt cttggattca cagaagtggc   123240
aaatggggtt ttccctcttt gaagaggaac cttctcttc atggggttca gcaggaggtt    123300
ttatcttttg aagctcaggg cagaaatggt ttgggggaaa ttaggtcatg ggtctgggat   123360
cagattctgt gaagttactg agcttcagga cctgcatgtg tttgtgtgca tgtatgtgtc   123420
cctgtgtatg tgtgaatgag agagggagaa aaagaagaaa gagaagcttt acttggatat   123480
ctgcctctat tatgaaggac tctcaagtaa cagccttttg attttagctg acgacacgga   123540
ttcccagtca tggcgcagcc ccttgaaagc cctttcagag ttctttaaag gtgacccgaa   123600
gggtgacttt aataagacag gtttgcattt tcccatggct gctgaattat gtaacccaaa   123660
tgcttcttgc tggcctcact tctaaaattg cttacacctg cctcatctgc tttgcttaat   123720
gagcatgcca tcctttgatt aacctaccct ggagttgacc catccttgac tgtcacgttg   123780
gaagctggga tctggactct gcaacccaac gcgtgccttg attatgtttt agcataatct   123840
ctaacatctc cacaggcttc accttgaggg tccccttgcc ccatgagatt ggcaccctca   123900
cctgccctgc acctatgccc cagcatgctg gtaccacagt gttctttgct caaaggtggc   123960
cacaagtctt gactagccag cccattggtt aattttgct cttcacaatt ctggactctt    124020
tggcagtgtc tcagctgtag agtaaaattg ccacatccta agcgtgccta accagcttga   124080
aaggttatat tgtgtcttca acacacatca tccacataca ccctccagca gcaagcacag   124140
gcagtctcct taattatact ctagggcaga ctgagtgtat tttagccaac aaaaagctaa   124200
aggtgtctct cggggtcatt tctgcaacca tgaattgggg atcctgtgat tttttcagg    124260 cctgtgatta tggttgctgg cctttttgtt actcatcagt ggaaaccaat agctcttggg   124320
gatggatgtg gtcctatttc agactcagcc aagggtggag taaaggtgag gccaggcagc   124380
tccttaaacc tctcatctct gtcctcaggc ttggtggagc cagtgaacgt ggtggacaat   124440
ggagatggca cacacacagt aacctacacc ccatctcagg agggacctta catggtctca   124500
gttaaatatg ctgatgaaga gattcctcgc aggtaagctc catccatctg cccatccatt   124560
cctccatcag tctatctgtc cacccatcca ttcctccatc agtccatcca cccatccgtt   124620
cctccatcat tccatccatc cactcatcca ttcctccatc agtccatcca tccacccatc   124680
cattcctcca tcagtccatc catccatcca ttctttcatc attccatcca tccacccatc   124740
cattcctcca tcagtccgtc tacccattca tagaggcagc aagtattaca tagaacctgc   124800
aacttgtcac cacacactag ccttgatatt tgtggctccc gctctctcac tcccccagtt   124860
cctttcagac atctttagtt taaaggtgag ctgaaattaa gaagttggaa atcctaacca   124920
cgtgtggtgg gattcgcctg taatcccagc tacttgggag actgagatga gaggatcact   124980
tgagcccaag agtttgaggc cagcctgggc aacatagacc ctcccctgac atctctggaa   125040
```

```
aaaaaaaaaa aaaaaaaaaa aaaaaagcaa tagtagtaga caatcattga tgaaataaat   125100
aatttattag tttattagag gcttccttt ggtgttttgg tgaacctgca agtagtttc     125160 tgattgggac aggacaaagg tctttacttc agggtttgct tgataaaagc atttccaaaa   125220
ggttttacat agaaaccttg ttccttgttg atattaatac aaaaaaaaat gttacataag   125280
ctcttcacct cttggaacaa tctctaaggg ttttcttttc ttttttttaaa aaatcatgcc   125340 ccttaagatg aaaaactttc acccatatcc cctaacacat atttatata gagataagca    125400 tattagctct atgtagaaat atgtaattta taaattacat ttgtatattg ctttactaat   125460
ataccatgta ccatatgaag catactatag aataattata gatacagaat atagaataag   125520
atgagatata aatattaaaa ctgaagttcc agtattctct ttccatttgg tgaccatgat   125580
cttagcataa caaagtggg gtaaatgtgt ttaaccctgt gtttcccaaa ctaatttgtg    125640
aactcttcct ccccaaacta cttgtatccc ttggaacaga ggtccccaac ccttggagcg   125700
tggactggtg tgggtgcacg gcatgttagg aattgggccg cacggtggtg ggtgagccat   125760
cattactgcc tgagccctgc ctcctgtcag atcagcagct gcattagatt ctcataggag   125820
tgcgaaccct attgtgaact gcacatgaga aggatctaga ttgcacactc cttgtgagaa   125880
tctaactagt gcctgatgat ctgaggtgga acagttttat cctgaaagca ttcccccacc   125940
aggccccctg gtcttctacg aaaccagtcc ctagtgccaa aaaggttggg gaccgctgcc   126000
ttggaacaca ctcaggacaa aaccagtctg tcatatgatg gttactacct catagttgta   126060
aatttctgct agacttaggc accttgacta actcactgtc ttatctgctg tagaaatccc   126120
cttttccatc ccactcttat gtgtaagaaa agtcagatgc agctgggttg acatgtatct   126180
ttattgacta gggtgtgtgt gtgtgtgtct atcaagtccc ttcaaggtca aggtccttcc   126240
cacatatgat gccagcaaag tgactgccag tggccccggc cttagttcct atggtgtgcc   126300
tgccagtcta cctgtggact ttgcaattga tgcccgagat gccggggaag gcctgcttgc   126360
tgttcaaata acgtaacttt ggagttattt tctgagccaa accttaatcc taagacttaa   126420
tttctgggcc agatttaaga acaagggttt caataaccga tttctgactc aatgcaagtt   126480
gtttgttaga ttttcccacc aaagagtcag taaatgtgca gaagcagaag cagctcacct   126540
gagagatttg agggtgtagc tccaagaacc acttttggt gaattttcat gtttttttac    126600
tacatctatt cctatgtttt tatttttatt ttttttaaag atggggtttc accatgttgc   126660
ccaatctggt cttgaactct cttgggttca agcagtctgc ctgcctcaac ctcccaaagt   126720
gctgggattg cagacatgag acactgtgcc cgtcccctat gttttatttt ttaaatgttt   126780
taaattactc tttggttcat ttaagactaa gttatgctgc atatcacagt aaaccttaaa   126840
ataagagtgg ctgaaataaa tgagattatt ctctcttgtt aaggaacccc aggctaagcc   126900
acctgggtgc cctgcagctc accaaggaag tcagctccat ctctctgctc ctctacctag   126960
catgtggctt ctgtccttaa ggtctcctcc tggaccataa ggctgccagt gctctggcca   127020
tcacatccac atggcaggcc agaaggagga agaaagaagg gaaaagggg tcctcccagc    127080 tcagtgggct ctcttaagca gccctgccaa aagtccatca tagacttcca ttcccttctg   127140
atttgttggg ggttggtcac aattcacatt acctagtggc aaggatgcta ggaagtggat   127200
tcccatcttc tgggagcggt gcacctagct aagagttatg gtcctgttaa taaagagaaa   127260
agggagactg gatgtggtgg tgtgtgagca gaagcctctg cctcctcccc tccctacatt   127320
tcagaggatt tcgagctaaa acactcttgg ttcacctgac aacaaaatta ctaaaaattg   127380
gccatgtctg tcatggtgtt aaagggatct gtgaccctct actctcccta ccaaaaaaca   127440
```

```
aaacaaaact agattgtatt aagccatcaa ttctgtctgt ttccactaga ggcactaatt  127500
ggaaaatatg tcagggtttt ccatgaatgt tttctacatc ttgacaacat cctaaatagc  127560
atttctctat gatccacagg accaagaagg aaaacccaaa agagccattg tccatgacaa  127620
taaagatggc acgtatgctg tcacctacat ccccgacaag actgggcgct atatgattgg  127680
agtcacctac gggggtgacg acatcccact ttctccttat cgcatccgag ccacacagac  127740
gggtgatgcc agcaagtgcc tggccacggg tgagtacagg gcatctcaag gtcagggca  127800 caggctttgc aatcagaaag ccgggccgta gcccttctct gtgacttaca agctacatga  127860
tctgggcacg ttgctcaacc tcactgaact tcagtttgac atagattgaa gctctttgtt  127920
tttatttgga gaacatttag atccaagaag ctcttctaag aacagagac tgttttacag  127980 ggttactgca aagattagat gaggtcaggc atgaaaaatg cttagcacag tgctaggtac  128040
atgataacta ttattatatg cttttgaaat gttgagaacc caactctgat ggcggctccc  128100
atgaaaagca gcacatttct gcctttatg agtagatagt tactcaggat tcattcaaga  128160
gcatttcagg tcagcattag agaaacacat ttaaggatct aggttttttt catcatgcat  128220
atgtaaacct ctcaggaatt ctccatgaat atttgagcat cacagtttct ttggtttctt  128280 tcttttttt tccctcctt tttccttcag tttctaagac acaactattg actgtcacag  128340
gccattcttt tttttttttt tttttttttt gagatggagt cttgctctgt tgcccaggct  128400
ggagtgcagt gacgcaatct cagctcactg cagcctcagc ctcctgagta gctgggacca  128460
caggtgccca cgaccatgcc cggctaagtt ttgtattttt agtggattca gggtttcacc  128520
ataattggcc aggctggtct cgaactcctg gcctcaagtg atctgccctc ctcagcctcc  128580
caaagtgctg ggattacagg tgtgagcacc acgcctggcc ggcctttcag tttttaagaa  128640
cagcccttgg gcagctcagt gctgctgctc aagcagattt taaaacacga atccccatct  128700
ctaaaatgag acagatttac ttcttttaa ataagaagac taaacacagg accacccttg  128760
atgtgttctg tttctctctt agcccatctt tttttgaatg gagaaaatct gggctttcac  128820
ggcaaggttg tgaattgctc agcgtggccc tttttggctc acccatggca aaaaatggaa  128880
aaattttgga atgcaggcca atccaccacc tcctaggtct atgcagctgc cagcgacaac  128940
cagatcatct ttactaattg atggcatgtt aacgttggat ggggacttcc cccttgcctt  129000
gcaggcccta tttcctcccc cagcttgggc agaagcctga gctgaatact tgccttttgg  129060
ccacacctct gggtctgtca ttcagggtct tccacagatt gactccagtc ttctcttcca  129120
ctcctccctg aacaaactgt tcttgccacc ctccctatta ctcctacgca cttggctcat  129180
atctaccaat gtgcttttag ttcatgcttt tctgcatttc ctgatatgtg atcctgtgt  129240 aaagggggcgc cagaaatcaa gagagagact ggtcactggg gagaggttgc aagtctccct  129300
tagctaacag cacccatcct tcagggttca gccatgtttc ctttctttag gaagcccttt  129360
gtcagtgcgg caaccctggg atataaattc ttagaacctt tgcctagata tgctgccaga  129420
cacttctctg aggaacagtt tgttatttt tctgtaactt agttcctctt cagcatttcc  129480
actgcagttg gaaatgtcgt tcttggtgcc tggccctgtt aacatcttga gagcagggac  129540
tgtgtcttgc ccacctttat gtgtacctgg cacttaagaa aatgcccaat atgtttgcta  129600
ttgaaagtca accttcattg ccatacccttt aaatgctggc aaacccaggc taacctttag  129660
tcaacactca gagcttacag atgctcctta tttagtaagt aattgatgac gtaacccttt  129720
gagcaacacc tgatcagggg atctttggga tatccctctg aatggcagca gttggaggcc  129780
```

```
taacatttac aggcacagac aacatggatg ggtatgattt gttcttgggc ctccaggatg   129840
tgtgtccata cttccattct cttcccctga actcttctcc aggtcctgga atcgcctcca   129900
ctgtgaaaac tggcgaagaa gtaggctttg tggttgatgc caagactgcc gggaagggta   129960
aagtgacctg cacggttctg accccagatg cactgaggc cgaggccgat gtcattgaga    130020
atgaagatgg aacctatgac atcttctaca cagctgccaa gccgggcaca tatgtgatct   130080
atgtgcgctt cggtggtgtt gatattccta acagccccct cactgtcatg gtaaggaaaa   130140
ttccttctcc cgagcatgct gttattggtg gaaactgtaa cagctgccgt tgttgaacc    130200
ctgactagga tatcctcttc acctttttt tcctttggaa aaaaatttgt taagcagtca    130260
tgaccttgta gagtcccaga gtaatctcta gaaactcaga gacccctttgg ctgtaagggt   130320
ttttagggaa tcttactggc caccaaggtg tctatcataa taagggactt gggcaatatc   130380
ctggcctaag cccaggcatt ttgaaagata actcctcaga aaaacacacc tttatgaaaa   130440
tgtttctaca taaaacatga caggttttta accggccagc tcttccttct tccatcttca    130500
tggccattct ccatggctgg aggagagagc ttcctgatgc tgtttgttt ggagacttga    130560
ctctgaaatc ccaggactca aagtacctcc acttgtgttt tggaaagatt cacactttat   130620
gtatgagggg gaaatacctc gtcttttgca gctaggaaca tctggaataa aaggaggaaa   130680
ccattatgca aacacctggg ttagtgaatg accaaggtct ttcatttta gttgtgagtt    130740
acttatagat cttcctctgt ttatttattt ttattattac ataatagatc ttcttctgaa   130800
tattcttcaa ccaggaaaag ggttagaaac cttggggaca ttacctcatt gaaccctcaa   130860
aaccaagcat cgttggcttt tttacaaatg aagcatgctt ggtctagaca gacaccaaat   130920
accatgctgt catcctcact ggtgtccttt gatactgtgg tcagcagccg cacttgacca   130980
caaggtttat aggcccttaa tgacctggcc ttgtgcacag ccgacaaagc accttctaat   131040
tatttcattt tgtgcagcaa tggagaggtg catgaagact ccattccaaa ctccaaagct   131100
cagggacttt cttccgaaca gtctatactc tgttgtagta ttattccctt ccatcgacgt   131160
ctgtttatct gtaaacagca tgccagagat ctggaggctc ttttatgtct caagtatgta   131220
aatgtaaaca cttgtcaact tttgacattg ttcatttaag agtgttttc tcctgtagga   131280
agaaagaaat acagctggga agttgatgtc cttattcaca gagaagggta ccagttgtag   131340
ttttcagaat ctgttttag cccatagtgg gttttatctg gttggttaga attaggtgga    131400
aggagggaag agcagccaag cactgagcag tggtcatggg cctgctggtg caatgatttg   131460
ggggtaagag aagaccatat tgggaaggtc tacgtgagaa agtcagagta aaaaaattga   131520
ggacccttttt tgcagaagtg gaggcttcca aactcagtaa taagtgtctt ctagcccctg   131580
aatacacaca aagcaagaat actttgtgtt tacccactgc cccctgacca ctgctgaagg   131640
cagaaaggga cgatcaccta cagtacctgg tttgggtctt tattctctca ttccagggag   131700
agaaccttaa ctagatggac tgactgactg ttcattggct ttggttgggt agattccctg   131760
cttccctcta taagtttgac gccaaaaaag gacaccgacc agcactgcag tcatagcaaa   131820
tgtctcaagg agacccacag ggtggtttct tcaaatacac tactcacaca cagcacatgg   131880
agtcatggac aaaacagctta actgcccatt gcctttgaga agtcctggac caaaggccat   131940
agctcagcca ttgaaagatc ttccttctga ctgatatgtc cctgcatagc tccaacctgt   132000
gcaggcagag gatagggctg ttccaaatgt cgctcacaga gctgcctttg cctttctgca   132060
gatcccaaga tacacacaaa gcagttaaca tgggtaaata ggccttcctc tgtaggagag   132120
ggcttctgat tcttattctt tcttatggcg gaagagggtg ttgagagggg ttcccttgct   132180
```

```
gttggttctg ttgaatcagg agcattaaat cttttttgtt ttttttttgag acagaatctc    132240
actctgtcac ccaggctgga gtacagtggt gcaatctcag ctctctgcaa cctccacctc    132300
ctgggtttaa gcgattctcc tgcctcagcc tcccgagtag ctgggattat aggcacctgc    132360
caccacgcct ggctattttt tgtatattta gtagagatgg ggtttcacca tgttggccag    132420
gctggtaact cctgacctcc agtgatccac ctgccttggc ctcccaaagt gctgggatta    132480
ccggcatgag ccactgcgcc cagccatgag cattaaagct aagatttgtt gaaaatgaat    132540
ttataaaaaa ctttagaaac attaactgct gagcatggtg gctcatgcct gaaatctcag    132600
cagtttggga ggccaaggtg agaggggttgc tggatcccag gagtttaaga ccagcctggg    132660
caatacagtg agaccccatc tctaccaaaa aaaaaaaata ataattagcc tggtgtggtg    132720
gtgcacgcct ctagtcccaa ctgctcagga ggctgaggtg ggaggatcac ctgggcccag    132780
aaggttgagg ctgtagtaag ctgagattgc gccactgcac tccagcctgg atgacagagc    132840
aaaactctgc ctcaaaaaaa attaaataat taaccacagt agacatttat caagtaaaaa    132900
aagaactttt tcctgattct gtgctgcaga gatgccttgt gttagttttt acctacttac    132960
acttcacaca cctcactttc atgcctgggg tcacaccgta catactgctt tcgcaccttg    133020
cttccttccc tcaatgtgtc ataggtaccc ttacatattg attcattgga cctgactgcc    133080
atgttccact ggacagactc accagaattt atttgaccaa atcccttcca gatggacatt    133140
gggttgcttt agttttgcac gaccacagac agcaccagtc aaggtcctta cacacatcaa    133200
ttaactatgg agtctcccgc cagcttaggt ctgcgtgcta caagtggggt tgtgggctca    133260
cagggcatgc gcatctgaca gttgaagaga ggacaccaac tgccttccaa aagggcagta    133320
agaaagtgtc cttcgctaga gtgagtggct cactgcagtt caagatggag cagtggggga    133380
agcagctctg tggtggtagt ctactgagtg tatccttcca gtatggttcc caactaatct    133440
ccatttgcca ctgaccaggc cacagatggg gaagtcacag ccgtggagga ggcaccggta    133500
aatgcatgtc cccctggatt caggccctgg gtacaatttt ggttttttcc tttttgtgtt    133560
tctgtgttta ctcagccttc atttcagaaa atctgccatc tgcttctggg attgcttaag    133620
ccctgtgggt gtcctggtca ttggtgtgcc cctcactgat cagcccatca cgatgatccc    133680
tgctttttct gtaataagat caccctttgcg tcaccatccg tgctccacga atcgccagcc    133740
gtcgtgtctg tgatcacgct cggtgcagtt tgtctctgtg tttaaagaga aagacagaca    133800
gctgtctgca gccctcctgc tgcctctcaa agccgccact tgcacattca gtttctgttc    133860
aggggggaaag ccacccactg ctactctctg ccacttaaaa tgcaccttct tttccaggcc    133920
acaagcaact aaacctttcc agatggagcc tcttgggact catagacatt gctgtctctc    133980
acttttccac tttcccgtgg gtgctgctgg gaattttaca aacagactcc cgagtgattg    134040
ctaacagttg gtcagcatga cctctccagt ccctcaggtt ctaccctggg tctggagcca    134100
cttagacaaa gcccatacca caatgggcag ccgcattccc aaatcccggc ctcactggct    134160
tgtagaattc ccagcagctc taacccctgt agcttcacca gctcccgctg ttgtctgctt    134220
tacccagtga ccactgcctt ctgttttttag gtgaccgaag aggcctatgt cccagtgagt    134280
gacatgaacg gcctgggatt taagccttttt gacctggtca ttccgtttgc tgtcaggaaa    134340
ggagaaatca ctggtaagca cttgccataa aggccgtctc attctcactt gctctcacga    134400
gcttcccaga atggtgctgg ggaggtgtgt ccactgtccc ccagacccag gctccttaac    134460
ccagggtcac gagttcttgg tctccggtgt tgggccgtgg gctcctgaaa ctacagaata    134520
```

```
tgccacgtgt gtgtttctct gaagaagtgg ctcactgaca acttgcatta ctttcttgag   134580
cagtcccatg attctctcta ggttaaaaac tgctgtgttt agatacctca tgactgtcgg   134640
gttcttgttt gccccttttt cctgccttct cttatttgac ttttccagat gtgactttga   134700
cactgagtct gtcatacagg agttcctttc tccctcagc ctcttttcaa tgcccactt    134760
ctctttggtt tgatgctcta tgtatccagc tggtttcatg gtgttctcaa gtcctttctg   134820
agcttgattt tgccagttgt agaaaactct ttaagagttg tctgctatat tttgtggaag   134880
ccaaatggaa ctgaaaaaa aaaaagaaa agagcaaatg gtctctccca ttgtgggact    134940
tgaatgtttt aggcagcaac gaatgttctt gggtctggaa acctttattt tgaatacatc   135000
tgtgccttgg gctctgcttc tctggggaag gttgctggtg ggcttcattg ccccgtctct   135060
ctgtgctcca taggagaggt ccacatgcct tctgggaaga cagccacacc tgagattgtg   135120
gacaacaagg acggcacggt cactgttaga tatgccccca ctgaggtcgg gctccatgag   135180
atgcacatca aatacatggg cagccacatc cctggtaagc tgagtcagca ggcccagcag   135240
ggctccacca ttcaggggca tccgggcagc ctgcagacac tcctcagccg ctttgcaggg   135300
agcagctctc ggcagcaggc tggagaatgc agcgttggta ccctgtgaa accaaacagt    135360
ctgggaccct agcaggtcca gctgattct ggaagggatg atgtagctca gtgtcttggg    135420
tcacagtgca ggcctttggg tctgtggttg tttatctttg tcactacgct gagtgtggcc   135480
agaggtcaag ctgggagaaa aatgggaggc atggtgaggg actttccagc ctggcctgca   135540
gagccctgtg tgggctggag gcttgggcc aggtcagagg tggaagaaga ggaccagcag    135600
ccctggaaga agaggaccag cagccctcta caagggaagc cagcccaggt ttcatgggtc   135660
accaaccagc acagtgtcac cagttcattc tttcttttg tagttgtatt tgttttttaa    135720
tttagtattt tgaataggta acacattctc atggttcaaa aataaaatg atacgaagaa    135780
agttttcctt cctacccctc tccttgaact agactatcat aaatttttt atgttcgatt    135840
tcagagtttc agggttttat tttttatttt tttgtggaga tagggtctca ctgtgttgca   135900
cagattggtc tcaaactcct gtcctcaagc agacctcccg cctttgtctc ctaaagtgtt   135960
gggataacag gcatgagccg ccacgcctgg ccaatttcag agtatttta agactctcca    136020
tgcaaacgga aatacagata tataagagag tgtcttccca gccttccctc atgtggacga   136080
accattacat atttgaccat ttccctattg gagggcattt tggttcttcc tgccctcgct   136140
gtccccagtg ttgctgcgca aatcgacttt tccctagtc acctcacact cacaaagatg    136200
tatctgtgag atttagttac cagaggaggc aatgctaggg ccccagtgca ggcatctatg   136260
attttgacag atcttgccaa attgcccttc agagggctg ttgcagttca cacgccctct    136320
ggccatggag aagagcacct tcttttccac aaaatttgcc agtagaatat ggtatcaaat   136380
ttttggagct ttgccagtct gatggttgga aagaaacaga atctcagcgt tgctttattt   136440
gtatttctct tgtgaatgag accacacaac tttccctatg tctatttgta tttctttttc   136500
tgtgaactga acatttggat ccacggcctg ttttctatt tggttattgg cctttgtcat    136560
atagtttcta agagcaatgt aaacattgga gagattagcc ctttgtggta ggagttgcaa   136620
atgtttctct gagattggca tttacttag ttgtctgtat gtaatattgg tttaaagcaa    136680
aaatgtatta tctgcttcta tttaaatatt ctaaagcggc agatggagag agaggaaaaa   136740
atgtctttct cacatctgcc atccacttcc actgctggtg tgagttgtgt atcttttcag   136800
atgtttctct ctgtatctac aaacatacat ataattttat tctatttgt ttttaaagga    136860
atagcataat ggtattcata gtttatagca acttgctttt tttctttta atgcatcata    136920
```

```
ttatggataa tttctcaagt cagtaaacat gggtcttcct cactcttttt aatggcccat   136980
gagtagatca gcatttattt aaccggtccc ctgttgtgaa cacttaggtc ttttcctgat   137040
gtgcacccga acactgcaga aatgaaagtg cttacatagg gctaggagtc ggggtgggca   137100
gagaagacca ctgtggggtt gattccttac aggttgaatg gcatgggcaa atggccttcc   137160
aaaagccctt tccacttacc ttccctctgg ccatgggtcc tttcaccacc cagtgcaaaa   137220
gtttcttcct tatttgtcag gttgggctgg taccttacct tagccccctt cctcatctgg   137280
agcagcttcc aggattgttt ttcttatgtt gtgattgaag gaataatact gcgtagaccc   137340
tctctgatgt cctaggatgg cggggatgg gaggtgcatg tgcatctcct tctgtctctt   137400
catgcctctg cttaggaggc gccagacctg tagagaggtg gacgtcaaga tgccagttgt   137460
ccagggtctt cgttcacccc ttaatgagca ccaattttgt ttgtgtccttt cgtaaaccca   137520 gagagcccac tccagttcta cgtgaactac cccaacagtg gaagtgtttc tgcatacggt   137580
ccaggcctcg tgtatggagt ggccaacaaa actgccacct tcaccatcgt cacagaggat   137640
gcaggagaag gtactgtgtg gtttacgtgt ttatacgcct ccagctgtcc atttggaggg   137700
tgaagtggac acggttccag ggtggctttt aaaagtgaga caatcgaatg gtagtatttg   137760
tcttgtcttt tctctcgtgt aaatctgttt cttctttaga gccgcttcgt cttctaccca   137820
gacagacatt tttgaagtcc tttgtgttct aactgaaatc agattcatgc tatgaaatac   137880
tttatgtgac ttgtctggaa tttaagtgtg ttttggttgg tgatgttttt gttcttgttg   137940
cacatgtatc cacaagacca catgacttac tgagtggctc ttttgataa agctgtgtgc   138000 ccattcccgt ggtattcatg gataatccca aatctgtggt tctaatggga tttccgtgat   138060
ggcagccagt gcctgatggg cagggacaat ccacctctgc cctccaccac ccaccgtctc   138120
ctatgtgtaa ttgatgtaca cggctccttc cttttctcat cccatgcatc ctgagagtag   138180
agagagctcc agggttactt gcagtgaaga actcagatgt ttggggtttc ttctcagtgg   138240
gtgtttttac tgcgtggact gcttcattct gacagatgtc cctttgccca cagctcacgt   138300
ggagtgcgtc aatccattgt ccccagcatc agggctgccc tggatgagtt gttaaaagga   138360
aactcttaaa acaaggcaac tctctcccta acaccctgc atccctgttc ccacttgtag   138420
gtggtctgga cttggctatt gagggcccct caaaagcaga aatcagctgc attgacaata   138480
aagatgggac atgcacagtg acctacctgc cgactctgcc aggcgactac agcattctgg   138540
tcaagtacaa tgacaagcac atccctggca gccccttcac agccaagatc acaggtaggg   138600
ttgtctggct tctggggtct tcctcgtggg aagtatggct gcctctgact gccaccctcc   138660
ttatcagacc cctggcagca ggctagacgt ctctttgagt ttaggtttca cagagacttg   138720
ttgaggagga gcaggggatg gaatgcaatt ttggattagc taaatccttc tcttgctgat   138780
aatccaggaa aatgcgagag ctagtatttg gagcacactt ttattgtgcc agtgtgactc   138840
tagggtgcaa agagaaagct ctcagatgga gtgttcgaat catacttact gcaatagtgc   138900
atgaagtgca tgagcttaga catgcccttc agcgtcacta ctaggtaaat tttctgctat   138960
cccttttaca gatgggaaaa ctgaggcttg gcaaggtagt ggtgtagcca agttcacata   139020
taggtaaaca gatccaggtt atcaaattcc aaagcccatg ctcctcacct tgctgtgttc   139080
aggttatgct ttcagtgggt tataaggaag atgcacaagg cagatcctgt ttccccaccg   139140
tatttagacc tgtctgtgaa gcagccagta gtactgtgtg gaatgtggtc attgtttacc   139200
tagaaatgcc cacagccatg ccaggcaggt atgaggtgcc ttcaactaac aaaaattcct   139260
```

```
atatttatt ttattttga gacagagtct cactctatca cccaggctgg agttttagtg   139320
gcatgatctc ggctcactgt gacctctacc tcctgggttc aagcgattct cctgcctcag   139380
cctcctgaat agctgggatt acagcaccca ccaccacacc cagcttattt ttgtattttt   139440
aatagagatg aagtttcacc atgttggaca ggctggtctt gaactcctga cctcaagtga   139500
ttcgtctgcc tcagcctctc aaagtgttgg gattaggcac ctggcccaaa gattccttta   139560
aaatgtggtc catgaggact caagtctcta ggtcctgcca gcttcttgtc tttgctgcaa   139620
gcaggcatga atcccatcat tcttcattgg ttgggtctac tcagtgttca aggctcattt   139680
tttttcact taactttgtg taattagttc ttgcgtgttc atccgtgaac agcatatggc   139740
atggcagctc tgtgaagcca gggtaaccac atgtaacggg agtccttttt gggggatgtt   139800
tcccagatga cagcaggcgg tgctcccagg tgaagttggg ctcagccgct gacttcctgc   139860
tcgacatcag tgagactgac ctcagcagcc tgacggccag cattaaggcc ccatctggcc   139920
gagacgagcc ctgtctcctg aagaggctgc ccaacaacca cattggtgag ctaggctacc   139980
cttcctggct ggagccagga catcttgggt gggagatggg gactcttgca gtcctttctt   140040
gggaatgggt agcacaatgg agtgtgatgt gataaacctg ctgggtcaca cgcacgataa   140100
atgcccaagc gtatttgtgc attgtgatat cgacactctg gattgttggg tgtcaggaaa   140160
gaggacatat ttctatttct gagagtgtgt ctctctcctg cttcctctcc gccatcccct   140220
tacaagcccc aatctgtgtt ctggtccagg catctccttc atccccgggg aagtgggcga   140280
acatctggtc agcatcaaga aaaatggcaa ccatgtggcc aacagccccg tgtctatcat   140340
ggtggtccag tcggagattg gtgacgcccg ccgagccaaa gtctatggcc gcggcctgtc   140400
agaaggccgg actttcgaga tgtctgactt catcgtggac acaagggatg caggtctgtg   140460
tggtcccagg ggagaggccc agagcttgtg ggaaccgact tattttgctg aggcagcgtc   140520
atcttttcat cctaccaact cctttttctt tctgagcatc cttcaagcta taggtccttc   140580
tgcctgcatt gtcttttatg cctcatgacc attggcaaaa atgggattgt ctttgttttt   140640
tagatgatga aactgaggct tgcaaggttt agagccccct ctgcactagg atctgaaccc   140700
agagccacaa cacctcgcaa acccctgttt tcttatctgc tctcccaccc ttgttctcag   140760
cttcccagcg tctctccaag caaagaatgt tgggttgatt ggccaagacc atggtcatct   140820
gagcagagct tttgtggaaa tgaagcatct cttttctgttt tctctttgag atggtttgag   140880
ttagattgtg tctcttccaa gcttgccaca ccccagtgcc tccagtcatc tgcttttcttg   140940
aaggatggcc acgctggtga attctagaca aattctaacc cggggagagg gctggagaat   141000
ttctggtcct ggttgggaga tactccctgt taaaccttcg gatatgctga cctagctgag   141060
gtagccaggg gctatttaaa aattcaaaat ctcagatctg gctgtggata aaccccccaag   141120
gtggtacgtg cagtacttgg aggcgtgagg gcagaaggtc ctccccagca gtttgtacgg   141180
gacacatcat ctatgggata ttagtaaata tccttaagga aaggcttctg tggtcaaaac   141240
caggttcagc aggttatttc actatggggc ttctcaggac gcttaaccta ctcatccccc   141300
tctgggcttt gcaaacgagg ccgccattgc tttctttctg ctatgtagaa atagattgag   141360
gcgtaagggt cggatgtcct ttctccattc atcaggctcc ctcttcctga ggagctgctg   141420
tcagaacagc ctggggctgc tgtgttgcag gttatggtgg catatccttg gcggtggaag   141480
gccccagcaa agtggacatc cagacggagg acctggaaga tggcacctgc aaagtctcct   141540
acttccctac cgtgcctggg gtttatatcg tctccaccaa attcgctgac gagcacgtgc   141600
ctggtatgtg cattccattc ccctccaggt gggatgcttg ggttttctgt aaatgctgtg   141660
```

```
ccttggcctc tggcctgctc acaggagcct tcttgggtct tgcagggagc ccatttaccg   141720
tgaagatcag tggggaggga agagtcaaag agagcatcac ccgcaccagt cgggcccgt   141780 ccgtggccac tgtcgggagc atttgtgacc tgaacctgaa atcccaggt gggcgtcggg    141840 gactagtagg gtggggaagc cttggctcca gccttcaggg cagtgggtgc ctttgggaac   141900
caagtttagg catggcccag aacacagtat ccaagtcggc tgtgctgacc ttttcatttc   141960
acttcatttc attatgttct tctatgttta ttttcacaga gtctcatcca agaaaaacaa   142020
atgtttacct tgctacccttt ttcctcttcc aaataaaaat agctttattg tgtcacatgg  142080
gggaaacgta gatatgcttt tagatttta gattaactat ctgtcaaata gaatcatgtc    142140
agtgaaagaa ctggccctgc cgatgccagg gtctggaagt atttaagagg tggcagccca   142200
gcggcatcct tctagtattt ctctttcatt cctgaaatta gaacgagggc tgtgctgcag   142260
aactcgctgg gccacatcta gccctttggt ggtgaattgt tcttcttggg ccccgattag   142320
ccagtcaaca ggtcacacag tctgtctgaa atgtgttcca agttctttct ataaagaatc   142380
cttccagagg gaagccactg tgagtgaaaa ttttgaggct cctctgccca gaagttggca   142440
tgtcctgtgg aattgcacaa attctacaga gaagggaaat ctaaatcgtc ttcagatgga   142500
gcttgtgttg cgagctctgg agagggggtt gtctttctac actgcatctc ccatccttcc   142560
taacgagtca cggagctgtc gactccgcct tcttggcttt agttaacagg ttcttcttgt   142620
gtagtcacat caacgtcggg tcacatggga atgtggtaaa gcctcattac tgtagagttc   142680
agacatgatc acttaaaaag agctttattg ggccgggcgc ggtggcttac tcctataatc   142740
ccagcacttt gggggggccga ggcaggcaga tcacctgagg tcaggagttc gagaccagcc   142800
tggctaacat ggcaaaaccc tatctcttct aaaaatacaa aaataagcag ggcgtggtgg   142860
cgggcacctg taatcccacc tactcaggag gctgaggcac aagaattgcg taaacctggg   142920
aggtggaggt tgcagtgagc tgaaattgca ccgctgcact ccagcctggg caacaaagtg   142980
agactccttc tcaaaaaaaa aaaaaaaaaa aaaaagagc tgtactgatc gtttgtagtc    143040
ataaacagtt cgtgtgcctc aaggtggggg gaggaagtgt cacctcccag agagagcttg   143100
gttcacattt taggtacaga gttggaccct ggctgcccca tcctcatagc cacgtctgct   143160
cactttccag tcacattggt gtactcatcc actgttttg tgggcatctt cccacctcaa    143220
aaaatagaca tccacatcat ctcttcatg accctgataa aatgccattt cattcaatgg    143280
aactattggt gatagaaaaa gagagattcc atttcatgtc tagatgcatc aaccttcgtt   143340
actcatctct gtgcctcagc tcccatcatc agggctgctg tgacatttgc caccctgtgc   143400
tcaggctgtg ggctggatgc ccaggagtgg gctgggctgg tgcatttcag atgctgccat   143460
gccttggcag accgccctcc acatttctcc atactccccc accagcactg gggctgtctc   143520
tccttctcac tttggccaac ctgatggaaa acatggcat tcagtgttca gtttcatatc    143580
ttcgattact agtgatatgt gtactgtgtt ttcttttcat ttgctttaca tttctcatttt  143640 ggcaaaattt ctgtgctctg cttatttctt gaggaactag caagtatctg cagtgtggac   143700 gtttacccctt tctcttaagt ctcttccagc tcttggccat tttgttattc ttttagttac   143760
ttagtaccag atgactctgg gtgaggctcg atttccact cattacccaa atgatcctct     143820
cggagatccc ctcctcctta atggaggaca gctcactaac ttcagatgtc ctccggaccc   143880
aggttttgcg gggcatcttt gtcagttttgg gctgctgtag caaaatcaca tgaactaggt  143940
ggcaaccaac agaaatgtat gcctcacagt tgtggaggct ggaagtccaa gatcaggtgc   144000
```

```
cagcatggcc agattgtggt gagggcctcc ttccaggctg caaaccgaca gcgtcccctt 144060
gtatcctcac atgctggaga acggagggag ccagctgtct gggactctta caaggccact 144120
gaccccatca cagggtcgct ccactttcat gaccttatct aatcctaatt gcctcctcaa 144180
ggcccatgat aatcccatca cattgttggg ggtagggttt caatatttga attttggagg 144240
gacacaaaca ttcagttcat tacatgggtg accctctttt caacctccct tccctttcct 144300
gtcctcaggg gtcagagtca tgaactgctc tgcccagatc ctgtggggct ggagggtgca 144360
gtttcatact ggctctaggt gatggcagtg ctccgtgccc cgcatgcggc cgcctggcct 144420
caccacggca gtgcaggcac agtcgttggc atgacgtgag cagctcacgg agagtgatgt 144480
ggtcttgcgt cctagcactg gtgacccgag acattgcttt tctgaaagtg tggcccctgg 144540
tctttggttt gctcaaagct ttgctcacgc atggtttccc ctctgccatt gggacttaca 144600
tatgttcacc tttttctcta actttgtctt gttgcctaaa agaaatgcca aagcttcttg 144660
acggtaaagg atgatggctc ttgttttcta cccttaccta tctgtggaaa ggagcccgtc 144720
tgtgcatgat ggatgaccac gtcacctttg gcaaaaagtc tcagtgcccc cagcatgggt 144780
ggcctgaagg gccctgccca ctccatgctg gccacagaag ggcaggcacc cagcctgaag 144840
ggaaggaagc ctgggcacct cacgtccacc gggctgcaca caccttgctc tcggctgctt 144900
gccctgcatg tcctgccctg tctcaggccc ttgccctaac cctcttctct cccccaacct 144960
ccctccctct ttcagaaatc aacagcagtg atatgtcggc ccacgtcacc agcccctctg 145020
gccgtgtgac tgaggcagag attgtgccca tggggaagaa ctcacactgc gtccggtttg 145080
tgccccagga gatgggcgtg cacacggtca gcgtcaagta ccgtgggcag cacgtcaccg 145140
gcagcccctt ccagttcacc gtggggccac ttggtgaagg aggcgcccac aaggtgcggg 145200
caggaggccc tggcctggag agaggagaag cgggagtccc aggtgagcat tgcgggcagg 145260
attttcactt gggaagaata gagttgagcc caggcagtgt gggcacccac atactttttt 145320
gccccatttg aaagagaaga cttctgatag gtggcattaa gggcattatt taaaacaagg 145380
catcatgact aagtctggca cagtttgtaa ctaagctttg ctcacttacg taaagccaaa 145440
caggtttctt actgggagcc tccttggagc ccgtatctta ttagtgtgca cctgagtctc 145500
taattgggga gcagagtaat acggtttcca gagcatcttt cagggctgat gttctgtgga 145560
acatactaga aagctacaaa actgactgta agcatccttt cctgtggttg ccgctggtgg 145620
gaagatctgt agggaaaaaa tggaacattc tcatctttct ctggcttggt taaggtgtat 145680
tcatttttta aatttttat ttaatatctt tttctctctt gtttgttaga gatgggtccc 145740
cactatcttg ctcagactgg tcttgaactc ctgggctcaa gtgatcctcc tgccttggcc 145800
tcctaaagtg ctgggattat aggcatgagc cactgtgcct ggccggttaa gatgtattca 145860
gggctgggcg tggtggctca cacctgtaac tctagcactt tgcaaggccg aggcaggcag 145920
actgcctgag ctcaggagtt caagaccagc ctgggcaaca cggtgaaacc ccatctttac 145980
taaaatataa aagaaattag ctgggcatgg cggcatgagc ctgtagtctc agctactcgg 146040
gaggctgaga caggagaatt gcttgaacac aggagatgga gcttgcagtg agctgagatt 146100
gcaccactgc actccagcct gggcagcaga gcaagactcc gtctcaaaaa aaaaaaaaa 146160 aagacatgtc ttcagaggac tccagatgtc ctgtgaattt agttatcact agtgatgctt 146220
aggaaacttc agcaatggac cttggacctt gcttgggttc tgcttggggt tggagaaaga 146280
ggaaagggct agcaacagac gaaacctagc actgcaggtt tgaacaagga tggaagaggg 146340
acaggggctc tgtgggctc agtcactaac caggtttctc tttgctctca gctgagttca 146400
```

```
gcatttggac ccgggaagca ggcgctggag gcctctccat cgctgttgag ggccccagta  146460
aggccgagat tacattcgat gaccataaaa atgggtcgtg cggtgtatct tatattgccc  146520
aagagcctgg tatgtattca gggttcacaa gaggacattt tccttgtttg aacatgatta  146580
ggttgcaagg aacagaaatc catcaagttt gctgaagtca atgaggaatc tatgtgtatg  146640
ggcacatggg acagcctcct agaaatccag ttgcaagata catggccaga cctcttaagg  146700
gtgggaacgc ttgttctggt tgccttttgc ctttctccat tagcctctct gcttcttgct  146760
ttcattcaat tgctccattc tttccaccaa ccagcctctg tctgcccacc catggctacc  146820
ctggctggct gccccagaag agtggccttg gcatctgagc tccctctagc aggagctctt  146880
aaccttttgt gtgccattga ctcttgccat ctggcgaagc ctatggggac tgttcttggg  146940
ataatgtttt aaagcacata aaatgaaata tgtcacatta taaagaaat cattgatatt  147000 atagtacagt taccaaaatc ttacaagaac aaatatgcaa catagaaaca tgcatatctt  147060
cgttaataca ttaaatcata agatttggtg acagtatatt aactgtcatc aaagtgacaa  147120
agtaataagt gaaatgata cgtcaaaata actgtaaaat gacataaaaa tatatgattt  147180
ttaatggtga tgtaagtcat atgtacttat aatgtgctgt gatttcttgt caacatttct  147240
gaagaaagga aatggtaaat ttcagttaga gaatggtgaa aattaaaacg taattttttc  147300
cccattgaag tccatggatc tgctgaattc aatacaggcc atttggggac cctgtgagcc  147360
ccggttaaga gtccctggcc ttaccccact aaggaaatca tatcggccca gcctcagcca  147420
ggcgactccc actcaaccaa tcagctgtgg ccattgagga gggctgggtc tctctgaagg  147480
cattttagcc cttggtgaga agcaagagtc cactctgggt ccagagtctc tgaaatgatg  147540
ggactttcct gtcctcatag gtaactacga ggtgtccatc aagttcaatg atgagcacat  147600
cccggaaagc ccctacctgg tgccggtcat cgcaccctcc gacgacgccc gccgcctcac  147660
tgttatgagc cttcaggtga gatgcaagga agcatccatc tccttggccg caggccacca  147720
gtgagacccc tggactcctg aggctgcttc aatgtcccct taggtgctga ggcccctttt  147780
cacattttga ccacagatgt cacccagtca ctggggagct ttcctgtggc agagtcaact  147840
ccccatacac ttagggcgga tgacacttgg ggcgagcaaa acagagcca cagtcaacaa  147900 cacaccttaa tgtttgggga cacgtttgtt tttaaaggtt tatttaagag aaacaaagga  147960
agcctgttca taactggtta agggataaca agggctttca aaacaaaacc aacacaaaaa  148020
taacagtgca gtgatgtttt agcctgctgt tgttggctgc ctttcttcaa gaaagtcagt  148080
tgcaacttac tgtgattcat taataagtgt gcagggaact atattaagag ctttatcagt  148140
gttacctcag taaatccttg caatagcctg acaagtaggt tctcttgacc ccattttaat  148200 gatgaaaaa cagagataca aggaggtttt gtccactggg aaccagctag tatgaggcag  148260
aacaggcaca gtgtggctcc agaacctgta tttttgtttg tttgttgttg ttgttgaggc  148320
agagtctcgc tctgtcaccc aggctggagt gcagtggcat gatctcggct cactgaaacc  148380
tctgcctccc aggttcaagt gattcttctg cctcagcctc ctgagtagct gagactccag  148440
gcacgcgcca tcacacccgg ctaatttttg gattttcgt agagatgggg ttgcaccatg  148500
ttggccaggc tggtctcaaa ctcctgacct gaggtgatcc accccactca acctcccaaa  148560
gtgctgggat tacagacgtg agccactgtg cctggccaga acctgtgccc ttaacggcaa  148620
cctctctaac ccccacctga tgttgtggca cacggttgca tagtccatcc cattaggata  148680
ccaggagatg caacattttt cctcgtccta aacaggtcac ttaattcaag gttgtactag  148740
```

```
caccttcagc caaactaaga accatcgggg atgcctctgg gttttttgccc aggacactga   148800
aaaataatta ggtgtctgaa ctgggagtag caattaagtt gtgaaataac atcgaaatcc   148860
caaagtatga tttctgggta agagtttcta aatagccttg agctgccccc agttcttgaa   148920
aatattggat tcattaaaat ccaatctgat gtctaagatt ggtgatatca ttggctttag   148980
ttccatacac ttggtttaca tttgagattc taatcttact ctgagggaa ctgggatacc    149040
tccagttgtt ccaaacatta gtctttcatt tagagacgta aacagaaccc aaaccagact   149100
cagtccacac attgaagcgg cctcatccgg agaataccaa gggtactaac tggttactgt   149160
ggtgtagatg ttttttcttgt gtttcattta aaggcttctt aacagaagtg tcttttgtgg   149220
ccaacttaac taaaacctac ggagggagat aaacccagca cttattgagg gcaggagctg   149280
ccctcatgca tctcgaagat ttctttcaaa tctgccgagg catttatctc cctcttgagg   149340
atttagcggc aagcggattc aggtaatgta atgattctg tctaaaagga gctggtttgg    149400
aaaaatcccc tccaggaaac ttctgtagag tgctctcgtc atagctgggt cataaatgtt   149460
tcagtaagtg cacagcaggc tgtttcttaa gcttttgtaa ccagctgctg ccgcaggaga   149520
agtgtgttca tcagcatcgc cccctgttct tcccgggtca tttgatgccg agtgatatgt   149580
aaaattattga tcagagattt tgcggaggcc cacgcaagca acatctggtg ctggttagca   149640
aagagaggca tgtatcgttt tgtcttgctt ttgagacttt ttaggaaatt ggagtaggct   149700
ggcacttggg gtgggggtgg gatgggagtg atctggtgat caaagaccct ctaattctgt   149760
gttctgtcct ccctcctcag tctatatccc ctagggcagc acagtccaat agtaggttct   149820
gcagtgatca aaatgcttca agtctatgct atgcagcatg atagccacta accatatgtg   149880
actattgaac atctgaaatg tggccagagg aaccaaggag ctggatgttt agttttattt   149940
aagtgcatta agttgaaata tatgtatata tggcctcgtg gctggtgact accaaattag   150000
ccagtgcagc tttaggacct tgccatgaag atgtggttct tgggccagtt cttggacctc   150060
agcatcacct gagaacttca gtcccagacc cactggaaaa gaatctgtat tttaataaga   150120
tccccagatg gtttgcttac acattaagtg tgagccatgc tgcttcagag ttattgcctg   150180
aggagtggct gtccgaccaa gtctaaatca aaattactga cttgtaaaat gctgctgttc   150240
aggattggct agtcttaaaa tatctcaaat gttgttgctc agctttgttc ttaaccatct   150300
gaacttctaa tccctcctc ccagaagagg agatagtttc caagacaaag tatgggagt    150360
gaaactgatc cagggaagag caaaagctat gtctttctat ggcttcttgt ggggatacaa   150420
cctctaaatg catattaata tttaataata agctgacgtt ttcgagcctc tctgtgtatg   150480
ggctaggccc tgtgataaat gttttgcatg cacagcttca tttgatcttt atagtagccc   150540
tcgagataga tcgttattat gcccatttta cagatgagga aactgagact cgaagaggtt   150600
tggcacccta gatatatagc taggaaatgg taggaaatcc agatccagct gattcttaac   150660
tgctatggag tactgccttc tttgcacacg tagccctta taatatgttc ctccaggtct    150720
gcccttgaga taacaaacag cataacataa aactgtgttc gtgttcgtga gtgcatgact   150780
ttgttagctg cagtatcctc ttaaaagagg acacttttt gacctggaac atactgggtt    150840
ttctggcctg catgggcatt attttggatg ctgagatgat agtcctttg accaggatgt    150900
ctcaagtatc caagcccaga aatcatctct tctaggctga atcaagatgg tttgcataag   150960
agaccatgca gatgcacgtc tctgctatct tacattaaaa atgcagaatg gctcacctgc   151020
cctttgttgt catatgttat atagaaaaac ctatttgcat gagaactgtc acccacagtt   151080
ttgggtaggg tcagtgtgtg ccactgagca ggaacgccga gggccataac ctgtctgatg   151140
```

```
tattaaattc tcaggaatcg ggattaaaag ttaaccagcc agcatccttt gctataaggt   151200
tgaatggcgc aaaaggcaag attgatgcaa aggtgcacag cccctctgga gccgtggagg   151260
agtgccacgt gtctgagctg gagccaggtg agcaggaggc ctgctggggg gtcccagcac   151320
cagcactttc cagcagaatg ttcctgtaaa tgtgtgtccc aagggagggc tgatcagttt   151380
cattactgcc agtgagcctc tgaattccct ttgctgttgc cagatattgt ttataaatta   151440
gggtttaaac atgtgccagg gatagggaga ccctttatgc taggagagaa tgctcattct   151500
ttctttcttt tttaaacaaa tgctgggctg ggtacagtgc cttaacctga gaggtcaagg   151560
ctgcagtgag ctatgatgca gtgagctatg attgtgccac tgaactccag cctgggtgac   151620
agagtgagac cctgtctcca gaaaaaaaac aaaaaaacaa aaaacacat acacacaaca    151680 caaaaacaaa tgcttctttg ttttctgtta gttttcaga ttccttttgc atgcattca     151740 tcataatttt tctttcatat tgtaacaaca tcttacagat ttttattcat tgaccttatg   151800
gcacgagtaa gcatattttg atctcacttt actctaaagg aaaagtaggt taatgttctg   151860
taaatttaaa aagaaaatc tgggtctcta ggccctaatg tcctaagatt tttcttgctt    151920
ggtgccttgg tatatggaat tctctgattt aatcaacttt aaagagacag tgttaccggt   151980
gaacataata aatttattaa gtgtcagaaa cttgaaggaa ggtataaggc tcaaagagtt   152040
gctcaaagtt tagtgaaggc ctggccaaaa agcagatgat gacccaaat gatcactagt    152100 accacaggag aactgtgaag caaatggtaa agatggtcag agcaggagag agaaatagtt   152160
tctgcctcgg tgagttcagg agggcttctc agaggaggtg acatttgatg tgggccttga   152220
tgtatgagga ggagacctat gattactgcc ttatagggca tttgttgtgt gcctggctgt   152280
atttgtatag tgtagttgga aatctaggct ctgaccaggc atggtggctc acacctgtaa   152340
tctcagcact ttgggaggat cagttgagcc caggagtttg gaccaacct gggtaacata    152400 gtgagacccc ttctctacaa aaaaagtaa aaaaaaatt agccaggcat ggtggcacac     152460
acctgtagtc tacttgtggg ggatgaggtg ggaggattgc ttatgtccag gaggtcgaga   152520
ctgctgtgag ctgtgatcat gccattgcac tccagcctgg gtaacacagc aagaccctgt   152580
ctcaaaaaga aagaaaaaagg aatgtaggct ctgtgtgaac atttagatct atgtttccta  152640
gtaggcagaa aggcagtggg gagcctcagg aggaacaagt gtaaaggatg gggtcagatc   152700
ctggttttag tctgaaaggc caagtggcaa gctggtgctc ccagagtggt ccatttgagg   152760
aagcagtggc actggaaatg gagaggaggg acttgaggcc agagatctat ggtggctata   152820
gagagtgaga gagagaatcc attccaaaat gttccacgta gcttagtgat tgggtcgaa   152880 gatgacagtg cagttatcag aactagggcc agccaggcag agggtgggtg aggattggtc   152940
agggccttaa agggtttaat attttacttt gaggggtttt gaaggatccc caatacccaa   153000
atggagatgt ttactagatc actgtgaggt ttggtggcct cagccccaac agtccctcac   153060
tgggtacccc cctcttctc ttaaagccaa tgtgcttcag gggaagctaa ctccacccca   153120
gacaggattt gaaccctac agatgtatga gatcattagc atgacacagt tactattgat    153180
tgcaaattac agaatacccca gctcaagcca actcacacaa taaggggcc cagtaagttg    153240 cataactaga aagttcaaga catccaagac aggtttcagc aatttgattt ggtcattgag   153300
ctgcgccctg caaggcgtca aatatttctg ctgttctgct ttgtgggcct ggttctggcc   153360
ttcctcttgg tggcaggatg gccttcctct tggtggcagg atggctgcag cagcaccaga   153420
tgtcccacct tcacgccaca tcaattaaga gagacaccct ctcaggattc ttagaagtcg   153480
```

-continued

```
agagcctcct ttcccagaag tctccagcac gtctgccttc ccctctcact gacctggaca     153540
catgcccact gctgagtcat ttcctgtggc taaagaaatg ccatgtgctc attgactaag     153600
gcttagtgaa gaaggatttt tccctgatcc actcagggac cacacctgga catggcggtg     153660
gagccagctt ccactacaac acattggctt taagggaggc ggatggggac tgttggagga     153720
tgttcagtgc caaaggacgt agggtgcaca gcttcatgga ggtgcacctc tgtggagacg     153780
tccagaggca gggagaagag ctttgggggaa cacaaattct gagagggatg aagagtacta     153840
ggcaccaggg agagaccgag agactacctg gagaggtagg aggagaacag gctctgcacc     153900
ctgggcagga gggcttcaag gaggaagcgg cagtcaggtg gtgcacaatg ggtagatgtt     153960
ctaggtgccc acttcagtta acagattacc ttgctacatg ctgtgaccca aacgcacagc     154020
cacaaacctg ccctgtgggg gcagttccta gctttgagct taattaagga gcattaatgc     154080
cagttggaac cgttttttt ccccttcaag tggccaaata gagaaacata gaagaagtga     154140
ggttttcttt tttcccttca tatatattcc ttttattc ttgttatgcc ttcccaaaac     154200
agagacattg aacagtagtt agaatggcca tctcccaatg tttaaaaaca aactgaactc     154260
cccaatgggt gaacaaagta aagagtagta acctggagtt cagctgagta agccgctgcg     154320
gagccttaag tggtgaggtc ttccaatttc agagtgctgt gtcttcaact tgtatcatca     154380
ttttagtgga aaaacataat ttaattttgg tgaaatgaga ttcatctcgt gacaggatta     154440
gtaacagcat tcacagaatt tcacactgaa gaagtgaggt tttctaaaga aaggaagtgt     154500
tcttctgagg caggggtcag agtcttgtcc tgtgtttata ggatttgcaa tgtggatgcg     154560
tttcccttgg ggctgatgag ggatacccag ggggtctgtc tggttctgaa atccaggatg     154620
ctgagtgcca ggctccctgt agaactgttg attttaaatg gccatctca gcttggcctc     154680
catcctttat cctcactgaa ctcagggtgt tccatttgct tgatttcacc ctgtgccttt     154740
gctcattctc ctagataagt atgctgttcg cttcatccct catgagaatg tgtccacac     154800
catcgatgtc aagttcaatg ggagccacgt ggttggaagc cccttcaaag tgcgcgttgg     154860
ggagcctgga caagcgggga accctgccct ggtgtccgcc tatggcacgg gactcgaagg     154920
gggcaccaca ggtaacccac tcttctgctt cttgaagcct taactgaacc agctccaggg     154980
accaagccag atggaaatcc tcaagcccca tgaaagcttt ttacacgtac tccccgtgga     155040
aactgggggtc atgcacactt cggaggcgct tgctgtccaa agctgttttg ggagttgcgg     155100
tttgacccac gataaatcca gagtgagagc tcgatggccg tgttatcaca cctcattact     155160
gttagttgtg attcagattc cttcctctgc caagtttctt gactttcaga acaggatgct     155220
gatagtcagg gaacacagca cagtgtcatt aattttgagg gtttctttgc ctgcacagaa     155280
ttcatgatgc gtccaagtgg gctcctaccc gtctgttctt tcatggtacc aggctcccag     155340
aaatgcactg aagcagcaat aagacctgtc ccagcctatc tcctcctctt tttactctca     155400
gatcttaatg gaggaggaga aaagactgaa atgttcaaag aattctgaag cttttagac     155460
ccgttacaat ttactttat tctttgccac agatgggaca tgtttgatta tgaaagatac     155520
aggcagtgaa gaagtaaata aagtgagact cactccatct tctctcctcc tcccccacct     155580
gggtctggaa gcaaacggct ctgggaaggg aggaccttca ccctgtctgt catctcattg     155640
tctgtcttca ttcttggttg ctgggttggt tagctaattg gttcattaga caagcagaca     155700
cagagttttg cttttgtctt acagaaagaa tcttactgta tccactgtgt ggtatagctt     155760
gtgttttgc tttgacatct taaagatctt tccatgtcag aacagatctt cccctccttt     155820
tcctggctgt agtgagaatt cctgctgtga atcgcagtta tttgaacagg tggcatcggg     155880
```

```
tggtgcgcag tgagtgcgtc actgttatgg aggctgccag ggtggagagt cagtccttag    155940
tctttgcagg ggaagtgcgc agtgtggact cactggggca tgtttgcatt tggtgttact    156000
ttggaccctc ttgggaaagc agtatgtcct ggtttcttga gtctcttgtg tgtgtacccc    156060 cacccccgcat aaggagagtg ggatggagca gacttgcctc ccaggggtga ggggtgagtg    156120
gctgcatggt tgcctggcat ccagccctag gagcaagtga cctgtgtggc caaggggccc    156180
tctccgggtg caggagtgac tggtgggctg cagggctgcc cgggactctg gccaaagcag    156240
tggcctcagc aaagccaccc acaggggtgg tgtgagtgct gccagactcc ccaggcaaat    156300
ccagcccggc tccacgctga actctgggcc tgcggcttgc cttttgtgaa aggcatggta    156360 tcatttacc gtaagtgatg tccattttac agatgtggaa agtgagatgc agaggttgag    156420
tcactcccca aacaacactc ccccaaaaag cagtcagctg ggaggaggca gaaccaggaa    156480
tcagtctaca tccgtgacct cagagcctat gcgctgaacc cccgagcttg gcccccctctc    156540 taagtggctg gctcacccag aggcagtgac tgcatcccca gcccactttg gggatgtcct    156600
aaaccaggac ccctgtcctc ccagccactc aggagtactt tccaggcagc agtgctggca    156660
cttgggccct gacaaggtac tcacctttga gggcccaggt ggggtcctct cggcacttgg    156720
agcgcgtggc aggcttcagg ccaggcctca cagcagctgc tggggtctcc cacactggcc    156780
aggaagcatc tcaccctcct gctggctcat gccgctgtgc ctgggccctc tcccatttcc    156840
ttttggctgt tcgcacacct tttttgggagc ttgggtttca ggctgtgctc tgcaagtgct    156900
ggacgctgct gagagaagga gttgctcttg cagggaagct cctagccagg aggggagagg    156960
tacagaaccg cctgcttcaa accctgtgta aatattgctc ttgtcacagg gaaggcgcct    157020 tgttttttcca gccctcctgc tcccaagcct ttccctaaat atccattctg agattacaca    157080
gctgcagtgt gcatggaatg aaaaggtatc tgtgcttggc cgccagagcg cccagtatcc    157140
tgaccttctg aacaaagcaa acctccctct gttttttaatg ggtgagtttg ctgtatctct    157200
tggctcaagc tttaaatggt ccattctgta gattttggag taggggaatg tggagaattt    157260
ggggcgggac cctgctggag gcggcttgag aggctgggag atagaccagg gagctccaga    157320
ttctttggag ccgctgagca attttcctaa tgaaatggtc caggaacccc agtgtgctcg    157380
gggtatacca gaagggcctc cttccttaac tgccttgaag aacaagcagt gctgcgttta    157440
acatgcatta aactcacagg aactgagctg gacatatttg aggggggtggg ggaagaccgc    157500 cacgcccaga gatgtttgt ggtgtcagat acaggttata gctagaggca gtggtgagag    157560
acttctgctt gtggattttt ttccttccat cttctctcag gtaagtgctt tagctccaag    157620
ttggacagac tttatgttta aatcccagtt ctgctggtcc ccagctgtgt gactccagat    157680
gaattatctg acttcactgt gcctctgctt cctttcctgt aaaacaggat taataacagg    157740
acccacctaa taggcttgtt tggagctgta gaggaggtaa cagccaagta gtagctcttg    157800
tcccataacc cctgctttct cttttcccac ctcgtcttcc ctgcccttttt gggccctcac    157860 agtcaagatg aactgatttt tggttggtca aaatattgca ttagggccaa atgggtgcgg    157920
tggctcatgc ctgtaatcaa agcactttgg aaggccaagg cagaaagatt gtttgaggcc    157980
aagagtttga gaccagcctg ggtgacatag taaaactcca tctctaccaa aaaaaaaaat    158040
ttttaaagac gaacttagga atgaaacagc ttgttaaaaa atggtggaac tttcccctgc    158100
agccacatca tttcaacttc actttaaaaa tatcttttttg gcctggcaca gtggctcaca    158160
cctgtaatcc cagcactttg ggaggtggag gtgggaggat cacttgagcc taggagtttg    158220
```

```
agaccagccc aggcaacaca gcaaaacccc atctctacaa aaaaatttaa aaattagcca  158280
ggcgtggtgg tgcatgcctg aagtcccagc tactttggag gctgaggcag gaggatggct  158340
tgagcctgga agattgacgc tgtggtgagc tgtgatcatg ccaccgtact ccagcctggg  158400
caacagagga agactttatc taaaaaaaaa aatattagta ataaggccgg gtgcgttggc  158460
tcatgcctgt aatcctagca ctttgggaga ccaaggtggg cagatcactt gaggtcagga  158520
gctcaagacc agcctggcca acatggtgag accccatctc tactaaagaa atacaaaaat  158580
tagctgggca tggtggcgag tgcctgtaat cccagctaat caggaagctg aagcaggaga  158640
atcgcttgaa cctgggaggc ggaggttgca ataagccaag atcatggtac tgcactccag  158700
cctgggcaac agagcgagac tctatctcaa tcaatcaatc aataaaatat ctttccttat  158760
catcacctta cagctgcttc ctggatggac acactgtctc cttgttgctc acctcccgct  158820
tcttccctac gtagcccag gcctcagagc tgctgcttga ggggcttctt ggctgcacag  158880
attagatacc atgatgaggt tgagatagtg ttggggtgg accttgggc aggagcctca  158940 agagcttcca ggaacagctg ggttgtgttt gagagttgca cgatagcagc tcttttgttt  159000
ttattgatat ccagaacaat aattctttct ctggactagg agctataatt aaaccaaaat  159060
atttcccagc tggggcagtg tctagggctc tggcagaagc atagccctgc atggggatgc  159120
tatgccaggc atgccccata gagggcactg tagcaggcat gcgccagacc tgatgactga  159180
aggaggctct ccctgggcca gctaagttgt ctcaggctg cagttagggg atctgaggca  159240
gctccactgc ccatccaggg gtcaagagat gagcctggca ccagagccat gcagacatgg  159300
ttcaaacccg gctctaccac tttctggttg tgtagcgtga ctggccccct ccctgagccg  159360
cagagtcatt tgtgaagcag gaatcacgga aaggattcca taccacatgc gtaaatggtg  159420
ctgtgcacag gacctggagc cggagtgggg tacgcatgcc ccgtcagcgg gagctgctgt  159480
tctgttcctg tgcttgttgc tggaattcac ggcaaagtgg gtgggctggc aggtcacagt  159540
ggctgcaccc ggtctgcagc acagtgcctg gggtgagggc tgaggaggaa gggaggagat  159600
gcttggcctc cctggcttct ccaagtctac ccggagaaga aaggacagtc agagggccc  159660 acgcctcccc cacaccctg gagggagagc tggactctgg tggctgaagc agcacttcag  159720
gctcacagtg tgactcaggc ttcttgccct cagccacaat ggctcatgcc cagaggagag  159780
aacagggtgt ccaggctgtt ggtgcttgtg ggcgaaatgt cagccatgct cctcctgcct  159840
tggcctagaa aagggagccc ccaccccgca gggcctgagg ttctctctgc cagaagttca  159900
gagctagtgc cagtgggttc ccatgccacc agggtgagcc ctctgtaagg ggatctatgt  159960
gtgtccctca ccacggcctc agtgctccca ggaaagccct ccaagtcatc aacacagcat  160020
tttctattcc tttctcccag gtatccagtc ggaattcttt attaacacca cccgagcagg  160080
tccagggaca ttatccgtca ccatcgaagg cccatccaag gttaaaatgg attgccagga  160140
aacacctgaa gggtacaaag tcatgtacac ccccatggct cctggtaact acctgatcag  160200
cgtcaaatac ggtgggccca accacatcgt gggcagtccc ttcaaggcca aggtgacagg  160260
taacgaacaa ccaccttcgg agttactctc ccttcctggg gagctggttg tgtcagatca  160320
atcatagtgg aaactatgga tggttttaga tgtgttaaag ctactttgaa ctttgaatgt  160380
cagtaaatag tatgagatgt cagagggcag tgtttgaaac ttacaaaagt ccacagagtg  160440
gagccgtgca gaagttgaga aagcatgtta ggatgttagg tggttttcta tctctaacag  160500 gaaagaaatac atattgaaat cttacgtatt tgtttagatc agggtctgaa aaatccctg  160560 atttctaatt ttcacttgaa aaataatcaa aaagtttcc tatacttata aaaatgtgtc  160620
```

```
tcctccaaaa cactggaaaa aataccaaac tatgaaaacc acttcacagc caccacccaa 160680
ggtaaccacc ataaacactg tagtaaatcc cttccacacg tcatgattca ctgttacata 160740
aagaatgtag gttcatcgca ggaaaattag aaaattcaga tagaaaaatc atcctttctc 160800
atccacagaa tcattttttg atatttcatt atatgtcatc ccaaacttt acactgctta 160860 tacatagact atttatgtc aatagaaaga tgtgaattcc acaggcacat ctttggtggg 160920 taggggtgg gggattggg agggtccttg gccttgtcag ccaaggccag actcatccat 160980
ttgcccagaa agccagatcc tagttgtatg ggggtgggat cctagggtt tagaagacat 161040 tatgggtgtg agatacaggt gtggtggctt ttgtgttggg gtgcgcgggc tctcctgggg 161100
ttactgtgta gggtactcgc ctgtcctctg gctgagagac ccctcttgat ctggccattc 161160
atgcctgtcc ccctccctcc tgtatcttag gccagcgtct agttagccct ggctcagcca 161220
acgagacctc atccatcctg gtggagtcag tgaccaggtc gtctacagag acctgctata 161280
gcgccattcc caaggcatcc tcggacgcca gcaaggtgac ctctaagggg gcagggctct 161340
caaaggcctt tgtgggccag aagagttcct tcctggtgga ctgcagcaaa gctggtaggt 161400
gtctgggcct tttcaagggt ggggtggggc aggggcaggc tgggcaccct gggtacactg 161460
gccttccctg ctgaggtctc ctgcagtgcc caccccatg taggccagcc gtttgcaagt 161520
aaccatcgtc atgaccctgt tctcctgcac ttaatatttt taaatgattt ccttctcttt 161580
tgccttttga acttgggtat ttatttgggt ttcaagggtc ggttgcctgg gttctggcat 161640
ccagtacacc tgggctggaa acctagtacc gccacttcat tcattcattc gtttgttcta 161700
aaacttattt agccatgtga ccttggaaag ttattaaatc tctttccaaa agtcagtttc 161760
ctcttctcgg aagtaccttc cttaaggtgc ttgtgagagt aaacaagaag attctcatag 161820
ccaacactta gaatagccct tactgtgtgc taggttttga cacccataac tcttaaacct 161880
cacaactagt tcgtgaggta tgtgctgttc tcattccctg tttacagatg gggaagctga 161940
gctagggaga ggtgagattc cagtccaagg tcacccaggt agcaagtggc agggcaggga 162000
ttcgaaccca caccgtcagg ctctatgagc ctctgcttgt aattgccacg ctctcccacc 162060
tcttaggggc cccagcatta tcgtggaagc accttacctt tggctctcat atttcctctt 162120
cttcctgtgc ctgtcctgat gcatccgggt ggagtaacca cctttttgcct cctaggctcc 162180 aacatgctgc tgatcgggt ccatgggccc accaccccct gcgaggaggt ctccatgaag 162240
catgtaggca accagcaata caacgtcaca tacgtcgtca aggagagggg cgattatgtg 162300
ctggctgtga agtgggggga ggaacacatc cctggcagcc cttttcatgt cacagtgcct 162360
taaaacagtt ttctcaaatc ctggagagag ttcttgtggt tgcttttgtt gcttgtttgt 162420
aattcatttt atacaaagcc ctccagcctg tttgtgggc tgaaacccca tccctaaaat 162480
attgctgttg taaaatgcct tcagaaataa gtcctagact ggactcttga gggacatatt 162540
ggagaatctt aagaaatgca agcttgttca ggggctgag aagatcctga gtacactagg 162600
tgcaaaccag aactcttggt ggaacagacc agccactgca gcagacagac caggaacaca 162660
atgagactga catttcaaaa aaacaaaact ggctagcctg agctgctggt tcactcttca 162720
gcatttatga aacaaggcta ggggaagatg ggcagagaaa aaggggacac ctagtttggt 162780
tgtcatttgg caaaggagat gacttaaaat ccgcttaatc tcttccagtg tccgtgttaa 162840
tgtatttggc tattagatca ctagcactgc tttaccgctc ctcatcgcca acaccccat 162900 gctctgtggc cttcttacac ttctcagagg gcagagtggc agccgggcac cctacagaaa 162960
```

```
ctcagagggc agagtggcag ccaggcccac atgtctctca agtacctgtc ccctcgctct    163020
ggtgattatt tcttgcagaa tcaccacacg agaccatccc ggcagtcatg gtttgctt      163080 agttttccaa gtccgtttca gtcccttcct tggtctgaag aaattctgca gtggcgagca    163140
gtttcccact tgccaaagat cccttttaac caacactagc ccttgttttt aacacacgct    163200 ccagccctt atcagcctgg gcagtcttac caaaatgttt aaagtgatct cagaggggcc     163260
catggattaa cgccctcatc ccaaggtccg tcccatgaca taacactcca cacccgcccc    163320
agccaacttc atgggtcact ttttctggaa aataatgatc tgtacagaca ggacagaatg    163380
aaactcctgc gggtctttgg cctgaaagtt gggaatggtt gggggagaga agggcagcag    163440
cttattggtg gtcttttcac cattggcaga aacagtgaga gctgtgtggt gcagaaatcc    163500
agaaatgagg tgtagggaat tttgcctgcc ttcctgcaga cctgagctgg ctttggaatg    163560
aggttaaagt gtcagggacg ttgcctgagc ccaaatgtgt agtgtggtct gggcaggcag    163620
acctttaggt tttgctgctt agtcctgagg aagtggccac tcttgtggca ggtgtagtat    163680
ctggggcgag tgttgggggt aaaagccac cctacagaaa gtgaacagc ccggagcctg      163740 atgtgaaagg accacgggtg ttgtaagctg ggacacggaa gccaaactgg aatcaaacgc    163800
cgactgtaaa ttgtatctta taacttatta aataaaacat ttgctccgta aagttg        163856

<210> SEQ ID NO 22
<211> LENGTH: 2633
<212> TYPE: PRT
<213> ORGANISM: Homo sapiens

<400> SEQUENCE: 22

Met Pro Val Thr Glu Lys Asp Leu Ala Glu Asp Ala Pro Trp Lys Lys
1               5                   10                  15

Ile Gln Gln Asn Thr Phe Thr Arg Trp Cys Asn Glu His Leu Lys Cys
            20                  25                  30

Val Asn Lys Arg Ile Gly Asn Leu Gln Thr Asp Leu Ser Asp Gly Leu
        35                  40                  45

Arg Leu Ile Ala Leu Leu Glu Val Leu Ser Gln Lys Arg Met Tyr Arg
    50                  55                  60

Lys Tyr His Gln Arg Pro Thr Phe Arg Gln Met Gln Leu Glu Asn Val
65                  70                  75                  80

Ser Val Ala Leu Glu Phe Leu Asp Arg Glu Ser Ile Lys Leu Val Ser
                85                  90                  95

Ile Asp Ser Lys Ala Ile Val Asp Gly Asn Leu Lys Leu Ile Leu Gly
            100                 105                 110

Leu Val Trp Thr Leu Ile Leu His Tyr Ser Ile Ser Met Pro Val Trp
        115                 120                 125

Glu Asp Glu Gly Asp Asp Asp Ala Lys Lys Gln Thr Pro Lys Gln Arg
    130                 135                 140

Leu Leu Gly Trp Ile Gln Asn Lys Ile Pro Tyr Leu Pro Ile Thr Asn
145                 150                 155                 160

Phe Asn Gln Asn Trp Gln Asp Gly Lys Ala Leu Gly Ala Leu Val Asp
                165                 170                 175

Ser Cys Ala Pro Gly Leu Cys Pro Asp Trp Glu Ser Trp Asp Pro Gln
            180                 185                 190

Lys Pro Val Asp Asn Ala Arg Glu Ala Met Gln Gln Ala Asp Asp Trp
        195                 200                 205

Leu Gly Val Pro Gln Val Ile Thr Pro Glu Glu Ile Ile His Pro Asp
    210                 215                 220
```

```
Val Asp Glu His Ser Val Met Thr Tyr Leu Ser Gln Phe Pro Lys Ala
225                 230                 235                 240

Lys Leu Lys Pro Gly Ala Pro Leu Lys Pro Lys Leu Asn Pro Lys Lys
            245                 250                 255

Ala Arg Ala Tyr Gly Arg Gly Ile Glu Pro Thr Gly Asn Met Val Lys
        260                 265                 270

Gln Pro Ala Lys Phe Thr Val Asp Thr Ile Ser Ala Gly Gln Gly Asp
    275                 280                 285

Val Met Val Phe Val Glu Asp Pro Glu Gly Asn Lys Glu Glu Ala Gln
290                 295                 300

Val Thr Pro Asp Ser Asp Lys Asn Lys Thr Tyr Ser Val Glu Tyr Leu
305                 310                 315                 320

Pro Lys Val Thr Gly Leu His Lys Val Thr Val Leu Phe Ala Gly Gln
            325                 330                 335

His Ile Ser Lys Ser Pro Phe Glu Val Ser Val Asp Lys Ala Gln Gly
        340                 345                 350

Asp Ala Ser Lys Val Thr Ala Lys Gly Pro Gly Leu Glu Ala Val Gly
    355                 360                 365

Asn Ile Ala Asn Lys Pro Thr Tyr Phe Asp Ile Tyr Thr Ala Gly Ala
370                 375                 380

Gly Val Gly Asp Ile Gly Val Glu Val Glu Asp Pro Gln Gly Lys Asn
385                 390                 395                 400

Thr Val Glu Leu Leu Val Glu Asp Lys Gly Asn Gln Val Tyr Arg Cys
            405                 410                 415

Val Tyr Lys Pro Met Gln Pro Gly Pro His Val Val Lys Ile Phe Phe
        420                 425                 430

Ala Gly Asp Thr Ile Pro Lys Ser Pro Phe Val Val Gln Val Gly Glu
    435                 440                 445

Ala Cys Asn Pro Asn Ala Cys Arg Ala Ser Gly Arg Gly Leu Gln Pro
450                 455                 460

Lys Gly Val Arg Ile Arg Glu Thr Thr Asp Phe Lys Val Asp Thr Lys
465                 470                 475                 480

Ala Ala Gly Ser Gly Glu Leu Gly Val Thr Met Lys Gly Pro Lys Gly
            485                 490                 495

Leu Glu Glu Leu Val Lys Gln Lys Asp Phe Leu Asp Gly Val Tyr Ala
        500                 505                 510

Phe Glu Tyr Tyr Pro Ser Thr Pro Gly Arg Tyr Ser Ile Ala Ile Thr
    515                 520                 525

Trp Gly Gly His His Ile Pro Lys Ser Pro Phe Glu Val Gln Val Gly
530                 535                 540

Pro Glu Ala Gly Met Gln Lys Val Arg Ala Trp Gly Pro Gly Leu His
545                 550                 555                 560

Gly Gly Ile Val Gly Arg Ser Ala Asp Phe Val Val Glu Ser Ile Gly
            565                 570                 575

Ser Glu Val Gly Ser Leu Gly Phe Ala Ile Glu Gly Pro Ser Gln Ala
        580                 585                 590

Lys Ile Glu Tyr Asn Asp Gln Asn Asp Gly Ser Cys Asp Val Lys Tyr
    595                 600                 605

Trp Pro Lys Glu Pro Gly Glu Tyr Ala Val His Ile Met Cys Asp Asp
610                 615                 620

Glu Asp Ile Lys Asp Ser Pro Tyr Met Ala Phe Ile His Pro Ala Thr
625                 630                 635                 640
```

```
Gly Gly Tyr Asn Pro Asp Leu Val Arg Ala Tyr Gly Pro Gly Leu Glu
            645                 650                 655

Lys Ser Gly Cys Ile Val Asn Asn Leu Ala Glu Phe Thr Val Asp Pro
        660                 665                 670

Lys Asp Ala Gly Lys Ala Pro Leu Lys Ile Phe Ala Gln Asp Gly Glu
            675                 680                 685

Gly Gln Arg Ile Asp Ile Gln Met Lys Asn Arg Met Asp Gly Thr Tyr
        690                 695                 700

Ala Cys Ser Tyr Thr Pro Val Lys Ala Ile Lys His Thr Ile Ala Val
705                 710                 715                 720

Val Trp Gly Gly Val Asn Ile Pro His Ser Pro Tyr Arg Val Asn Ile
                725                 730                 735

Gly Gln Gly Ser His Pro Gln Lys Val Lys Val Phe Gly Pro Gly Val
            740                 745                 750

Glu Arg Ser Gly Leu Lys Ala Asn Glu Pro Thr His Phe Thr Val Asp
        755                 760                 765

Cys Thr Glu Ala Gly Glu Gly Asp Val Ser Val Gly Ile Lys Cys Asp
770                 775                 780

Ala Arg Val Leu Ser Glu Asp Glu Asp Val Asp Phe Asp Ile Ile
785                 790                 795                 800

His Asn Ala Asn Asp Thr Phe Thr Val Lys Tyr Val Pro Pro Ala Ala
                805                 810                 815

Gly Arg Tyr Thr Ile Lys Val Leu Phe Ala Ser Gln Glu Ile Pro Ala
                820                 825                 830

Ser Pro Phe Arg Val Lys Val Asp Pro Ser His Asp Ala Ser Lys Val
        835                 840                 845

Lys Ala Glu Gly Pro Gly Leu Ser Lys Ala Gly Val Glu Asn Gly Lys
850                 855                 860

Pro Thr His Phe Thr Val Tyr Thr Lys Gly Ala Gly Lys Ala Pro Leu
865                 870                 875                 880

Asn Val Gln Phe Asn Ser Pro Leu Pro Gly Asp Ala Val Lys Asp Leu
                885                 890                 895

Asp Ile Ile Asp Asn Tyr Asp Tyr Ser His Thr Val Lys Tyr Thr Pro
            900                 905                 910

Thr Gln Gln Gly Asn Met Gln Val Leu Val Thr Tyr Gly Gly Asp Pro
        915                 920                 925

Ile Pro Lys Ser Pro Phe Thr Val Gly Val Ala Ala Pro Leu Asp Leu
        930                 935                 940

Ser Lys Ile Lys Leu Asn Gly Leu Glu Asn Arg Val Glu Val Gly Lys
945                 950                 955                 960

Asp Gln Glu Phe Thr Val Asp Thr Arg Gly Ala Gly Gly Gln Gly Lys
                965                 970                 975

Leu Asp Val Thr Ile Leu Ser Pro Ser Arg Lys Val Val Pro Cys Leu
            980                 985                 990

Val Thr Pro Val Thr Gly Arg Glu Asn Ser Thr Ala Lys Phe Ile Pro
            995                 1000                1005

Arg Glu Glu Gly Leu Tyr Ala Val Asp Val Thr Tyr Asp Gly His
    1010                1015                1020

Pro Val Pro Gly Ser Pro Tyr Thr Val Glu Ala Ser Leu Pro Pro
    1025                1030                1035

Asp Pro Ser Lys Val Lys Ala His Gly Pro Gly Leu Glu Gly Gly
    1040                1045                1050

Leu Val Gly Lys Pro Ala Glu Phe Thr Ile Asp Thr Lys Gly Ala
```

-continued

```
              1055                1060                1065
Gly Thr Gly Gly Leu Gly Leu Thr Val Glu Gly Pro Cys Glu Ala
              1070                1075                1080
Lys Ile Glu Cys Ser Asp Asn Gly Asp Gly Thr Cys Ser Val Ser
              1085                1090                1095
Tyr Leu Pro Thr Lys Pro Gly Glu Tyr Phe Val Asn Ile Leu Phe
              1100                1105                1110
Glu Glu Val His Ile Pro Gly Ser Pro Phe Lys Ala Asp Ile Glu
              1115                1120                1125
Met Pro Phe Asp Pro Ser Lys Val Val Ala Ser Gly Pro Gly Leu
              1130                1135                1140
Glu His Gly Lys Val Gly Glu Ala Gly Leu Leu Ser Val Asp Cys
              1145                1150                1155
Ser Glu Ala Gly Pro Gly Ala Leu Gly Leu Glu Ala Val Ser Asp
              1160                1165                1170
Ser Gly Thr Lys Ala Glu Val Ser Ile Gln Asn Asn Lys Asp Gly
              1175                1180                1185
Thr Tyr Ala Val Thr Tyr Val Pro Leu Thr Ala Gly Met Tyr Thr
              1190                1195                1200
Leu Thr Met Lys Tyr Gly Gly Glu Leu Val Pro His Phe Pro Ala
              1205                1210                1215
Arg Val Lys Val Glu Pro Ala Val Asp Thr Ser Arg Ile Lys Val
              1220                1225                1230
Phe Gly Pro Gly Ile Glu Gly Lys Asp Val Phe Arg Glu Ala Thr
              1235                1240                1245
Thr Asp Phe Thr Val Asp Ser Arg Pro Leu Thr Gln Val Gly Gly
              1250                1255                1260
Asp His Ile Lys Ala His Ile Ala Asn Pro Ser Gly Ala Ser Thr
              1265                1270                1275
Glu Cys Phe Val Thr Asp Asn Ala Asp Gly Thr Tyr Gln Val Glu
              1280                1285                1290
Tyr Thr Pro Phe Glu Lys Gly Leu His Val Val Glu Val Thr Tyr
              1295                1300                1305
Asp Asp Val Pro Ile Pro Asn Ser Pro Phe Lys Val Ala Val Thr
              1310                1315                1320
Glu Gly Cys Gln Pro Ser Arg Val Gln Ala Gln Gly Pro Gly Leu
              1325                1330                1335
Lys Glu Ala Phe Thr Asn Lys Pro Asn Val Phe Thr Val Val Thr
              1340                1345                1350
Arg Gly Ala Gly Ile Gly Gly Leu Gly Ile Thr Val Glu Gly Pro
              1355                1360                1365
Ser Glu Ser Lys Ile Asn Cys Arg Asp Asn Lys Asp Gly Ser Cys
              1370                1375                1380
Ser Ala Glu Tyr Ile Pro Phe Ala Pro Gly Asp Tyr Asp Val Asn
              1385                1390                1395
Ile Thr Tyr Gly Gly Ala His Ile Pro Gly Ser Pro Phe Arg Val
              1400                1405                1410
Pro Val Lys Asp Val Val Asp Pro Ser Lys Val Lys Ile Ala Gly
              1415                1420                1425
Pro Gly Leu Gly Ser Gly Val Arg Ala Arg Val Leu Gln Ser Phe
              1430                1435                1440
Thr Val Asp Ser Ser Lys Ala Gly Leu Ala Pro Leu Glu Val Arg
              1445                1450                1455
```

```
Val Leu Gly Pro Arg Ala Asp Asp Thr Asp Ser Gln Ser Trp Arg
    1460                1465                1470

Ser Pro Leu Lys Ala Leu Ser Glu Phe Phe Lys Gly Asp Pro Lys
    1475                1480                1485

Gly Asp Phe Asn Lys Thr Gly Leu Val Glu Pro Val Asn Val Val
    1490                1495                1500

Asp Asn Gly Asp Gly Thr His Thr Val Thr Tyr Thr Pro Ser Gln
    1505                1510                1515

Glu Gly Pro Tyr Met Val Ser Val Lys Tyr Ala Asp Glu Glu Ile
    1520                1525                1530

Pro Arg Ser Pro Phe Lys Val Lys Val Leu Pro Thr Tyr Asp Ala
    1535                1540                1545

Ser Lys Val Thr Ala Ser Gly Pro Gly Leu Ser Ser Tyr Gly Val
    1550                1555                1560

Pro Ala Ser Leu Pro Val Asp Phe Ala Ile Asp Ala Arg Asp Ala
    1565                1570                1575

Gly Glu Gly Leu Leu Ala Val Gln Ile Thr Asp Gln Glu Gly Lys
    1580                1585                1590

Pro Lys Arg Ala Ile Val His Asp Asn Lys Asp Gly Thr Tyr Ala
    1595                1600                1605

Val Thr Tyr Ile Pro Asp Lys Thr Gly Arg Tyr Met Ile Gly Val
    1610                1615                1620

Thr Tyr Gly Gly Asp Asp Ile Pro Leu Ser Pro Tyr Arg Ile Arg
    1625                1630                1635

Ala Thr Gln Thr Gly Asp Ala Ser Lys Cys Leu Ala Thr Gly Pro
    1640                1645                1650

Gly Ile Ala Ser Thr Val Lys Thr Gly Glu Glu Val Gly Phe Val
    1655                1660                1665

Val Asp Ala Lys Thr Ala Gly Lys Gly Lys Val Thr Cys Thr Val
    1670                1675                1680

Leu Thr Pro Asp Gly Thr Glu Ala Glu Ala Asp Val Ile Glu Asn
    1685                1690                1695

Glu Asp Gly Thr Tyr Asp Ile Phe Tyr Thr Ala Ala Lys Pro Gly
    1700                1705                1710

Thr Tyr Val Ile Tyr Val Arg Phe Gly Gly Val Asp Ile Pro Asn
    1715                1720                1725

Ser Pro Phe Thr Val Met Ala Thr Asp Gly Glu Val Thr Ala Val
    1730                1735                1740

Glu Glu Ala Pro Val Asn Ala Cys Pro Pro Gly Phe Arg Pro Trp
    1745                1750                1755

Val Thr Glu Glu Ala Tyr Val Pro Val Ser Asp Met Asn Gly Leu
    1760                1765                1770

Gly Phe Lys Pro Phe Asp Leu Val Ile Pro Phe Ala Val Arg Lys
    1775                1780                1785

Gly Glu Ile Thr Gly Glu Val His Met Pro Ser Gly Lys Thr Ala
    1790                1795                1800

Thr Pro Glu Ile Val Asp Asn Lys Asp Gly Thr Val Thr Val Arg
    1805                1810                1815

Tyr Ala Pro Thr Glu Val Gly Leu His Glu Met His Ile Lys Tyr
    1820                1825                1830

Met Gly Ser His Ile Pro Glu Ser Pro Leu Gln Phe Tyr Val Asn
    1835                1840                1845
```

```
Tyr Pro Asn Ser Gly Ser Val Ser Ala Tyr Gly Pro Gly Leu Val
1850                 1855                 1860

Tyr Gly Val Ala Asn Lys Thr Ala Thr Phe Thr Ile Val Thr Glu
1865                 1870                 1875

Asp Ala Gly Glu Gly Gly Leu Asp Leu Ala Ile Glu Gly Pro Ser
1880                 1885                 1890

Lys Ala Glu Ile Ser Cys Ile Asp Asn Lys Asp Gly Thr Cys Thr
1895                 1900                 1905

Val Thr Tyr Leu Pro Thr Leu Pro Gly Asp Tyr Ser Ile Leu Val
1910                 1915                 1920

Lys Tyr Asn Asp Lys His Ile Pro Gly Ser Pro Phe Thr Ala Lys
1925                 1930                 1935

Ile Thr Asp Asp Ser Arg Arg Cys Ser Gln Val Lys Leu Gly Ser
1940                 1945                 1950

Ala Ala Asp Phe Leu Leu Asp Ile Ser Glu Thr Asp Leu Ser Ser
1955                 1960                 1965

Leu Thr Ala Ser Ile Lys Ala Pro Ser Gly Arg Asp Glu Pro Cys
1970                 1975                 1980

Leu Leu Lys Arg Leu Pro Asn Asn His Ile Gly Ile Ser Phe Ile
1985                 1990                 1995

Pro Arg Glu Val Gly Glu His Leu Val Ser Ile Lys Lys Asn Gly
2000                 2005                 2010

Asn His Val Ala Asn Ser Pro Val Ser Ile Met Val Val Gln Ser
2015                 2020                 2025

Glu Ile Gly Asp Ala Arg Arg Ala Lys Val Tyr Gly Arg Gly Leu
2030                 2035                 2040

Ser Glu Gly Arg Thr Phe Glu Met Ser Asp Phe Ile Val Asp Thr
2045                 2050                 2055

Arg Asp Ala Gly Tyr Gly Gly Ile Ser Leu Ala Val Glu Gly Pro
2060                 2065                 2070

Ser Lys Val Asp Ile Gln Thr Glu Asp Leu Glu Asp Gly Thr Cys
2075                 2080                 2085

Lys Val Ser Tyr Phe Pro Thr Val Pro Gly Val Tyr Ile Val Ser
2090                 2095                 2100

Thr Lys Phe Ala Asp Glu His Val Pro Gly Ser Pro Phe Thr Val
2105                 2110                 2115

Lys Ile Ser Gly Glu Gly Arg Val Lys Glu Ser Ile Thr Arg Thr
2120                 2125                 2130

Ser Arg Ala Pro Ser Val Ala Thr Val Gly Ser Ile Cys Asp Leu
2135                 2140                 2145

Asn Leu Lys Ile Pro Glu Ile Asn Ser Ser Asp Met Ser Ala His
2150                 2155                 2160

Val Thr Ser Pro Ser Gly Arg Val Thr Glu Ala Glu Ile Val Pro
2165                 2170                 2175

Met Gly Lys Asn Ser His Cys Val Arg Phe Val Pro Gln Glu Met
2180                 2185                 2190

Gly Val His Thr Val Ser Val Lys Tyr Arg Gly Gln His Val Thr
2195                 2200                 2205

Gly Ser Pro Phe Gln Phe Thr Val Gly Pro Leu Gly Glu Gly Gly
2210                 2215                 2220

Ala His Lys Val Arg Ala Gly Gly Pro Gly Leu Glu Arg Gly Glu
2225                 2230                 2235

Ala Gly Val Pro Ala Glu Phe Ser Ile Trp Thr Arg Glu Ala Gly
```

|  | 2240 |  |  |  | 2245 |  |  |  | 2250 |  |
|---|---|---|---|---|---|---|---|---|---|---|

Ala Gly Gly Leu Ser Ile Ala Val Glu Gly Pro Ser Lys Ala Glu
  2255                    2260                    2265

Ile Thr Phe Asp Asp His Lys Asn Gly Ser Cys Gly Val Ser Tyr
  2270                    2275                    2280

Ile Ala Gln Glu Pro Gly Asn Tyr Glu Val Ser Ile Lys Phe Asn
  2285                    2290                    2295

Asp Glu His Ile Pro Glu Ser Pro Tyr Leu Val Pro Val Ile Ala
  2300                    2305                    2310

Pro Ser Asp Asp Ala Arg Arg Leu Thr Val Met Ser Leu Gln Glu
  2315                    2320                    2325

Ser Gly Leu Lys Val Asn Gln Pro Ala Ser Phe Ala Ile Arg Leu
  2330                    2335                    2340

Asn Gly Ala Lys Gly Lys Ile Asp Ala Lys Val His Ser Pro Ser
  2345                    2350                    2355

Gly Ala Val Glu Glu Cys His Val Ser Glu Leu Glu Pro Asp Lys
  2360                    2365                    2370

Tyr Ala Val Arg Phe Ile Pro His Glu Asn Gly Val His Thr Ile
  2375                    2380                    2385

Asp Val Lys Phe Asn Gly Ser His Val Val Gly Ser Pro Phe Lys
  2390                    2395                    2400

Val Arg Val Gly Glu Pro Gly Gln Ala Gly Asn Pro Ala Leu Val
  2405                    2410                    2415

Ser Ala Tyr Gly Thr Gly Leu Glu Gly Gly Thr Thr Gly Ile Gln
  2420                    2425                    2430

Ser Glu Phe Phe Ile Asn Thr Thr Arg Ala Gly Pro Gly Thr Leu
  2435                    2440                    2445

Ser Val Thr Ile Glu Gly Pro Ser Lys Val Lys Met Asp Cys Gln
  2450                    2455                    2460

Glu Thr Pro Glu Gly Tyr Lys Val Met Tyr Thr Pro Met Ala Pro
  2465                    2470                    2475

Gly Asn Tyr Leu Ile Ser Val Lys Tyr Gly Gly Pro Asn His Ile
  2480                    2485                    2490

Val Gly Ser Pro Phe Lys Ala Lys Val Thr Gly Gln Arg Leu Val
  2495                    2500                    2505

Ser Pro Gly Ser Ala Asn Glu Thr Ser Ser Ile Leu Val Glu Ser
  2510                    2515                    2520

Val Thr Arg Ser Ser Thr Glu Thr Cys Tyr Ser Ala Ile Pro Lys
  2525                    2530                    2535

Ala Ser Ser Asp Ala Ser Lys Val Thr Ser Lys Gly Ala Gly Leu
  2540                    2545                    2550

Ser Lys Ala Phe Val Gly Gln Lys Ser Ser Phe Leu Val Asp Cys
  2555                    2560                    2565

Ser Lys Ala Gly Ser Asn Met Leu Leu Ile Gly Val His Gly Pro
  2570                    2575                    2580

Thr Thr Pro Cys Glu Glu Val Ser Met Lys His Val Gly Asn Gln
  2585                    2590                    2595

Gln Tyr Asn Val Thr Tyr Val Val Lys Glu Arg Gly Asp Tyr Val
  2600                    2605                    2610

Leu Ala Val Lys Trp Gly Glu Glu His Ile Pro Gly Ser Pro Phe
  2615                    2620                    2625

His Val Thr Val Pro
  2630

<210> SEQ ID NO 23
<211> LENGTH: 9560
<212> TYPE: DNA
<213> ORGANISM: Homo sapiens

<400> SEQUENCE: 23

```
gcggccaggg gcgggcggcc gcagagcagc accggccgtg gctccggtag cagcaagttc      60
gaaccccgct cccgctccgc ttcggttctc gctccttcgg cccttgggcc tccaaacacc     120
agtccccggc agctcgttgc gcattgcgct ctccccgcca ccaggatgcc ggtaaccgag     180
aaggatctag ctgaggacgc gccttggaag aagatccagc agaacacgtt cacacgctgg     240
tgcaacgagc acctcaagtg cgtgaacaaa cgcatcggca acctgcagac cgacctgagc     300
gacgggctgc ggctcatcgc gctgctcgag gtgctcagcc agaagcgcat gtaccgcaag     360
taccatcagc ggcccacctt tcgccagatg cagctcgaga atgtgtccgt ggcgctcgag     420
ttcctggacc gtgagagcat caagctcgtg tccatcgata gcaaagccat tgtggatggg     480
aacctgaagc tcatcttggg tctggtgtgg acgctgatcc tccactactc catctccatg     540
cccgtgtggg aggatgaagg ggatgatgat gccaagaagc agacgccaaa gcagaggctg     600
ctggggtgga ttcagaacaa gatcccctac ttgcccatca ccaactttaa ccagaactgg     660
caagacggca aagccctggg agccctggta gacagctgtg ctccaggtct gtgcccagac     720
tgggaatcct gggacccgca gaagcctgtg gataatgcac gagaagccat gcagcaggca     780
gatgactggc tgggtgtccc acaggtcatc actcctgaag aaatcattca cccggatgtg     840
gacgagcact cagttatgac ttacctgtcc cagttcccca agccaagct caagccgggg      900 gctcctctca acccaaaact caaccccgaag aaagccaggg cctatggcag aggaatcgag     960
cccactggaa acatggtgaa gcagccagcc aagttcactg tggacaccat cagcgccggg    1020
caaggagacg tgatggtgtt tgttgaggac ccagaaggga caaagagga ggcacaagtg    1080 accctgaca gtgacaagaa caagacatac tctgtggagt atctgcccaa ggtcaccggg    1140
ctacacaaag tcacagtcct ctttgcagga cagcacatct ccaagagccc atttgaagtg    1200
agtgttgaca aggcccaggg agatgccagt aaagtcactg caaaaggtcc aggggttggaa    1260 gctgtaggga acatcgccaa taagcccacc tactttgaca tctatacggc aggagctggt    1320
gtgggtgaca ttggtgtgga ggtggaagat ccccagggga gaacaccgt ggagttgctc     1380 gtggaagaca aggaaaacca ggtgtatcga tgtgtgtaca acccatgca gcctggccct    1440 cacgtggtca agatcttctt tgctggggac actattccta gagtcccctt cgttgtgcag    1500
gttggggaag cctgcaatcc aaatgcctgc cgggccagtg gccgaggcct acaacccaaa    1560
ggcgtccgta tccgggagac cacagatttc aaggttgaca ccaaagctgc aggaagtggg    1620
gagctcggtg taaccatgaa gggtcctaag ggtctggagg agctggtgaa gcagaaagac    1680
tttctggatg ggtctacgc attcgagtat accccagca ccccggggag atacagcatt     1740
gccatcacat gggggggaca ccacattcca aagagccct ttgaagttca agttggccct    1800
gaagcgggta tgcagaaagt ccgtgcttgg ggccctgggc tccatggtgg gattgtcggg    1860
cggtcagcgg acttcgtggt agaatccatt ggctctgaag tggggtctct ggggtttgcc    1920
attgaaggcc cctctcaggc aaagattgag tacaacgacc agaatgatgg atcgtgtgat    1980
gtcaaatact ggcccaagga gcctggcgaa tatgctgttc acatcatgtg tgacgacgaa    2040
gacatcaagg acagcccgta catggccttc atccacccag ccacgggagg ctacaaccct    2100
```

-continued

```
gatctggttc gagcatacgg gccaggtttg gagaaatctg gatgcattgt caacaacctg    2160
gccgagttca ctgtggatcc taaggatgct ggaaaagctc ccttaaagat atttgctcag    2220
gatggggaag gccaacgcat tgacatccag atgaagaacc ggatggacgg cacatatgca    2280
tgctcataca ccccggtgaa ggccatcaag cacaccattg ctgtggtctg ggaggcgtg     2340
aacatcccgc acagcccta  cagggtcaac atcgggcaag gtagccatcc tcagaaggtc    2400
aaagtgtttg ggccaggtgt ggagagaagt ggtctgaagg caaatgaacc tacacacttc    2460
acggtggact gtactgaggc tggggaaggt gatgtcagtg ttggcattaa gtgtgatgcc    2520
cgggtgttaa gtgaagatga ggaagacgtg gattttgaca ttattcacaa tgccaatgat    2580
acgttcacag tcaaatatgt gcctcctgct gctgggcgat acactatcaa agttctcttt    2640
gcatctcagg aaatccccgc cagcccttc  agagtcaaag ttgacccttc ccacgatgcc    2700
agcaaagtga aggcagaagg cccagggctc agcaaagcag gtgtggaaaa tgggaaaccg    2760
acccacttca ctgtctacac caaggggggct gggaaagccc cgctcaacgt gcagttcaac    2820
agccctcttc ctggcgatgc agtgaaggat ttggatatca tcgataatta tgactactct    2880
cacacggtta aatatacacc cacccaacag gcaacatgc  aggttctggt gacttacggt    2940
ggcgatccca tccctaaaag ccctttcact gtgggtgttg ctgcaccgct ggatctgagc    3000
aagataaaac tcaatgggct ggaaaacagg gtggaagttg gaaggatca  ggagttcacc    3060
gttgatacca gggggcagg  aggccagggg aagctggacg tgacaatcct cagcccctct    3120
cggaaggtcg tgccatgcct agtgacacct gtgacaggcc gggagaacag cacggccaag    3180
ttcatccctc ggaggaggg  gctgtatgct gtagacgtga cctacgatgg acaccctgtg    3240
cccgggagcc cctacacagt ggaggcctcg ctgccaccag atcccagcaa ggtgaaggcc    3300
cacggtcccg gcctcgaagg tggtctcgtg ggcaagcctg ccgagttcac catcgatacc    3360
aaaggagctg gtactggagg tctgggctta acggtggaag gtccgtgcga ggccaaaatc    3420
gagtgctccg acaatggtga tgggacctgc tccgtctctt accttcccac aaaacccggg    3480
gagtacttcg tcaacatcct cttttgaagaa gtccacatac ctgggtctcc cttcaaagct    3540
gacattgaaa tgcccttga  cccctctaaa gtcgtggcat cggggccagg tctcgagcac    3600
gggaaggtgg gtgaagctgg cctccttagc gtcgactgct cggaagcggg accgggggcc    3660
ctgggcctgg aagctgtctc ggactcggga acaaaagccg aagtcagtat tcagaacaac    3720
aaagatggca cctacgcggt gacctacgtg cccctgacgg ccggcatgta cacgttgacc    3780
atgaagtatg gtggcgaact cgtgccacac ttccccgccc gggtcaaggt ggagcccgcc    3840
gtggacacca gcaggatcaa agtctttgga ccaggaatag aagggaaaga tgtgttccgg    3900
gaagctacca ccgactttac agttgactct cggccgctga cccaggttgg gggtgaccac    3960
atcaaggccc acattgccaa cccctcaggg gcctccaccg agtgctttgt cacagacaat    4020
gcggatggga cctaccaggt ggaatacaca ccctttgaga aggtctcca  tgtagtggag    4080
gtgacatatg atgacgtgcc tatcccaaac agtcccttca aggtggctgt cactgaaggc    4140
tgccagccat ctagggtgca agcccaagga cctggattga agaggccttt accaacaag    4200
cccaatgtct tcaccgtggt taccagaggc gcaggaattg gtgggcttgg cataactgtt    4260
gagggaccat cagagtcgaa gataaattgc agagacaaca aggatggcag ctgcagtgct    4320
gagtacattc ctttcgcacc gggggattac gatgttaata tcacatatgg aggagcccac    4380
atccccggca gccccttcag ggttcctgtg aaggatgttg tggaccccag caaggtcaag    4440
attgccggcc ccgggctggg ctcaggcgtc cgagcccgtg tcctgcagtc cttcacggtg    4500
```

```
gacagcagca aggctggcct ggctccgctg gaagtgaggg ttctgggccc acgagctgac    4560
gacacggatt cccagtcatg gcgcagcccc ttgaaagccc tttcagagtt ctttaaaggt    4620
gacccgaagg gtgactttaa taagacaggc ttggtggagc cagtgaacgt ggtggacaat    4680
ggagatggca cacacacagt aacctacacc ccatctcagg agggaccttta catggtctca    4740 gttaaatatg ctgatgaaga gattcctcgc agtcccttca aggtcaaggt ccttcccaca    4800
tatgatgcca gcaaagtgac tgccagtggc cccggcctta gttcctatgg tgtgcctgcc    4860
agtctacctg tggactttgc aattgatgcc cgagatgccg gggaaggcct gcttgctgtt    4920
caaataacgg accaagaagg aaaacccaaa agagccattg tccatgacaa taaagatggc    4980
acgtatgctg tcacctacat ccccgacaag actgggcgct atatgattgg agtcacctac    5040
gggggtgacg acatcccact ttctccttat cgcatccgag ccacacagac gggtgatgcc    5100
agcaagtgcc tggccacggg tcctggaatc gcctccactg tgaaaactgg cgaagaagta    5160
ggctttgtgg ttgatgccaa gactgccggg aagggtaaag tgacctgcac ggttctgacc    5220
ccagatggca ctgaggccga ggccgatgtc attgagaatg aagatggaac ctatgacatc    5280
ttctacacag ctgccaagcc gggcacatat gtgatctatg tgcgcttcgg tggtgttgat    5340
attcctaaca gccccttcac tgtcatggcc acagatgggg aagtcacagc cgtggaggag    5400
gcaccggtaa atgcatgtcc ccctggattc aggccctggg tgaccgaaga ggcctatgtc    5460
ccagtgagtg acatgaacgg cctgggattt aagccttttg acctggtcat tccgtttgct    5520
gtcaggaaag gagaaatcac tggagaggtc cacatgcctt ctgggaagac agccacacct    5580
gagattgtgg acaacaagga cggcacggtc actgttagat atgccccac tgaggtcggg    5640 ctccatgaga tgcacatcaa atacatgggc agccacatcc ctgagagccc actccagttc    5700
tacgtgaact accccaacag tggaagtgtt tctgcatacg gtccaggcct cgtgtatgga    5760
gtggccaaca aaactgccac cttcaccatc gtcacagagg atgcaggaga aggtggtctg    5820
gacttggcta ttgagggccc ctcaaaagca gaaatcagct gcattgacaa taaagatggg    5880
acatgcacag tgacctacct gccgactctg ccaggcgact acagcattct ggtcaagtac    5940
aatgacaagc acatccctgg cagccccttc acagccaaga tcacagatga cagcaggcgg    6000
tgctcccagg tgaagttggg ctcagccgct gacttcctgc tcgacatcag tgagactgac    6060
ctcagcagcc tgacggccag cattaaggcc ccatctggcc gagacgagcc ctgtctcctg    6120
aagaggctgc caacaaccca cattggcatc tccttcatcc cccgggaagt gggcgaacat    6180
ctggtcagca tcaagaaaaa tggcaaccat gtggccaaca gccccgtgtc tatcatggtg    6240
gtccagtcgg agattggtga cgcccgccga gccaaagtct atggccgcgg cctgtcagaa    6300
ggccggactt tcgagatgtc tgacttcatc gtggacacaa gggatgcagg ttatggtggc    6360
atatccttgg cggtggaagg ccccagcaaa gtggacatcc agacggagga cctggaagat    6420
ggcacctgca aagtctccta cttccctacc gtgcctgggg tttatatcgt ctccaccaaa    6480
ttcgctgacg agcacgtgcc tgggagccca tttaccgtga agatcagtgg ggagggaaga    6540
gtcaaagaga gcatcacccg caccagtcgg gcccgtccg tggccactgt cgggagcatt    6600
tgtgacctga acctgaaaat cccagaaatc aacagcagtg atatgtcggc ccacgtcacc    6660
agcccctctg gccgtgtgac tgaggcagag attgtgccca tggggaagaa ctcacactgc    6720
gtccggtttg tgcccagga gatgggcgtg cacacggtca cgtcaagta ccgtgggcag    6780 cacgtcaccg gcagccccc tccagttcac cgtggggcac ttggtgaagg aggcgcccac    6840
```

| | |
|---|---|
| aaggtgcggg caggaggccc tggcctggag agaggagaag cgggagtccc agctgagttc | 6900 |
| agcatttgga cccgggaagc aggcgctgga ggcctctcca tcgctgttga gggccccagt | 6960 |
| aaggccgaga ttacattcga tgaccataaa aatgggtcgt gcggtgtatc ttatattgcc | 7020 |
| caagagcctg gtaactacga ggtgtccatc aagttcaatg atgagcacat cccggaaagc | 7080 |
| ccctacctgg tgccggtcat cgcaccctcc gacgacgccc gccgcctcac tgttatgagc | 7140 |
| cttcaggaat cgggattaaa agttaaccag ccagcatcct ttgctataag gttgaatggc | 7200 |
| gcaaaaggca agattgatgc aaaggtgcac agccctctg gagccgtgga ggagtgccac | 7260 |
| gtgtctgagc tggagccaga taagtatgct gttcgcttca tccctcatga gaatggtgtc | 7320 |
| cacaccatcg atgtcaagtt caatgggagc cacgtggttg gaagccccttt caaagtgcgc | 7380 |
| gttgggagc ctgacaagc ggggaaccct gccctggtgt ccgcctatgg cacgggactc | 7440 |
| gaaggggca ccacaggtat ccagtcggaa ttctttatta acaccacccg agcaggtcca | 7500 |
| gggacattat ccgtcaccat cgaaggccca tccaaggtta aaatggattg ccaggaaaca | 7560 |
| cctgaagggt acaaagtcat gtacaccccc atggctcctg gtaactacct gatcagcgtc | 7620 |
| aaatacggtg ggcccaacca atcgtgggc agtcccttca aggccaaggt gacaggccag | 7680 |
| cgtctagtta gccctggctc agccaacgag acctcatcca tcctggtgga gtcagtgacc | 7740 |
| aggtcgtcta cagagacctg ctatagcgcc attcccaagg catcctcgga cgccagcaag | 7800 |
| gtgacctcta aggggcagg gctctcaaag gcctttgtgg gccagaagag ttccttcctg | 7860 |
| gtggactgca gcaaagctgg ctccaacatg ctgctgatcg gggtccatgg gcccaccacc | 7920 |
| ccctgcgagg aggtctccat gaagcatgta ggcaaccagc aatacaacgt cacatacgtc | 7980 |
| gtcaaggaga ggggcgatta tgtgctggct gtgaagtggg gggaggaaca catccctggc | 8040 |
| agccctttc atgtcacagt gccttaaaac agttttctca aatcctggag agagttcttg | 8100 |
| tggttgcttt tgttgcttgt ttgtaattca ttttatacaa agccctccag cctgtttgtg | 8160 |
| gggctgaaac cccatcccta aaatattgct gttgtaaaat gccttcagaa ataagtccta | 8220 |
| gactggactc ttgagggaca tattggagaa tcttaagaaa tgcaagcttg ttcaggggc | 8280 |
| tgagaagatc ctgagtacac taggtgcaaa ccagaactct tggtgaaca gaccagccac | 8340 |
| tgcagcagac agaccaggaa cacaatgaga ctgacatttc aaaaaaacaa aactggctag | 8400 |
| cctgagctgc tggttcactc ttcagcattt atgaaacaag gctagggaa gatgggcaga | 8460 |
| gaaaagggg acacctagtt tggttgtcat ttggcaaagg agatgactta aaatccgctt | 8520 |
| aatctcttcc agtgtccgtg ttaatgtatt tggctattag atcactagca ctgctttacc | 8580 |
| gctcctcatc gccaacaccc ccatgctctg tggccttctt acacttctca gagggcagag | 8640 |
| tggcagccgg gcaccctaca gaaactcaga gggcagagtg gcagccaggc ccacatgtct | 8700 |
| ctcaagtacc tgtcccctcg ctctggtgat tatttcttgc agaatcacca cacgagacca | 8760 |
| tcccggcagt catggttttg ctttagtttt ccaagtccgt ttcagtccct tccttggtct | 8820 |
| gaagaaattc tgcagtggcg agcagtttcc cacttgccaa agatccctttt taaccaacac | 8880 |
| tagcccttgt tttaacaca cgctccagcc cttcatcagc ctgggcagtc ttaccaaaat | 8940 |
| gtttaaagtg atctcagagg ggccatgga ttaacgccct catcccaagg tccgtcccat | 9000 |
| gacataacac tccacacccg ccccagccaa cttcatgggt cacttttct ggaaaataat | 9060 |
| gatctgtaca gacaggacag aatgaaactc ctgcgggtct ttggcctgaa agttgggaat | 9120 |
| ggttggggga gagaagggca gcagcttatt ggtggtcttt tcaccattgg cagaaacagt | 9180 |
| gagagctgtg tggtgcagaa atccagaaat gaggtgtagg gaattttgcc tgccttcctg | 9240 |

-continued

```
cagacctgag ctggctttgg aatgaggtta aagtgtcagg gacgttgcct gagcccaaat    9300
gtgtagtgtg gtctgggcag gcagacccttt aggttttgct gcttagtcct gaggaagtgg    9360
ccactcttgt ggcaggtgta gtatctgggg cgagtgttgg gggtaaaagc ccaccctaca    9420
gaaagtggaa cagcccggag cctgatgtga aggaccacg ggtgttgtaa gctgggacac    9480
ggaagccaaa ctggaatcaa acgccgactg taaattgtat cttataactt attaaataaa    9540
acatttgctc cgtaaagttg                                                 9560
```

<210> SEQ ID NO 24
<211> LENGTH: 2591
<212> TYPE: PRT
<213> ORGANISM: Homo sapiens

<400> SEQUENCE: 24

```
Met Pro Val Thr Glu Lys Asp Leu Ala Glu Asp Ala Pro Trp Lys Lys
1               5                   10                  15

Ile Gln Gln Asn Thr Phe Thr Arg Trp Cys Asn Glu His Leu Lys Cys
            20                  25                  30

Val Asn Lys Arg Ile Gly Asn Leu Gln Thr Asp Leu Ser Asp Gly Leu
        35                  40                  45

Arg Leu Ile Ala Leu Leu Glu Val Leu Ser Gln Lys Arg Met Tyr Arg
    50                  55                  60

Lys Tyr His Gln Arg Pro Thr Phe Arg Gln Met Gln Leu Glu Asn Val
65                  70                  75                  80

Ser Val Ala Leu Glu Phe Leu Asp Arg Glu Ser Ile Lys Leu Val Ser
                85                  90                  95

Ile Asp Ser Lys Ala Ile Val Asp Gly Asn Leu Lys Leu Ile Leu Gly
            100                 105                 110

Leu Val Trp Thr Leu Ile Leu His Tyr Ser Ile Ser Met Pro Val Trp
        115                 120                 125

Glu Asp Glu Gly Asp Asp Asp Ala Lys Lys Gln Thr Pro Lys Gln Arg
    130                 135                 140

Leu Leu Gly Trp Ile Gln Asn Lys Ile Pro Tyr Leu Pro Ile Thr Asn
145                 150                 155                 160

Phe Asn Gln Asn Trp Gln Asp Gly Lys Ala Leu Gly Ala Leu Val Asp
                165                 170                 175

Ser Cys Ala Pro Gly Leu Cys Pro Asp Trp Glu Ser Trp Asp Pro Gln
            180                 185                 190

Lys Pro Val Asp Asn Ala Arg Glu Ala Met Gln Gln Ala Asp Asp Trp
        195                 200                 205

Leu Gly Val Pro Gln Val Ile Thr Pro Glu Glu Ile Ile His Pro Asp
    210                 215                 220

Val Asp Glu His Ser Val Met Thr Tyr Leu Ser Gln Phe Pro Lys Ala
225                 230                 235                 240

Lys Leu Lys Pro Gly Ala Pro Leu Lys Pro Lys Leu Asn Pro Lys Lys
                245                 250                 255

Ala Arg Ala Tyr Gly Arg Gly Ile Glu Pro Thr Gly Asn Met Val Lys
            260                 265                 270

Gln Pro Ala Lys Phe Thr Val Asp Thr Ile Ser Ala Gly Gln Gly Asp
        275                 280                 285

Val Met Val Phe Val Glu Asp Pro Glu Gly Asn Lys Glu Glu Ala Gln
    290                 295                 300

Val Thr Pro Asp Ser Asp Lys Asn Lys Thr Tyr Ser Val Glu Tyr Leu
```

```
            305                 310                 315                 320
        Pro Lys Val Thr Gly Leu His Lys Val Thr Val Leu Phe Ala Gly Gln
                        325                 330                 335
        His Ile Ser Lys Ser Pro Phe Glu Val Ser Val Asp Lys Ala Gln Gly
                        340                 345                 350
        Asp Ala Ser Lys Val Thr Ala Lys Gly Pro Gly Leu Glu Ala Val Gly
                        355                 360                 365
        Asn Ile Ala Asn Lys Pro Thr Tyr Phe Asp Ile Tyr Thr Ala Gly Ala
        370                 375                 380
        Gly Val Gly Asp Ile Gly Val Glu Val Glu Asp Pro Gln Gly Lys Asn
        385                 390                 395                 400
        Thr Val Glu Leu Leu Val Asp Lys Gly Asn Gln Val Tyr Arg Cys
                        405                 410                 415
        Val Tyr Lys Pro Met Gln Pro Gly Pro His Val Val Lys Ile Phe Phe
                        420                 425                 430
        Ala Gly Asp Thr Ile Pro Lys Ser Pro Phe Val Val Gln Val Gly Glu
                        435                 440                 445
        Ala Cys Asn Pro Asn Ala Cys Arg Ala Ser Gly Arg Gly Leu Gln Pro
        450                 455                 460
        Lys Gly Val Arg Ile Arg Glu Thr Thr Asp Phe Lys Val Asp Thr Lys
        465                 470                 475                 480
        Ala Ala Gly Ser Gly Glu Leu Gly Val Thr Met Lys Gly Pro Lys Gly
                        485                 490                 495
        Leu Glu Glu Leu Val Lys Gln Lys Asp Phe Leu Asp Gly Val Tyr Ala
                        500                 505                 510
        Phe Glu Tyr Tyr Pro Ser Thr Pro Gly Arg Tyr Ser Ile Ala Ile Thr
                        515                 520                 525
        Trp Gly Gly His His Ile Pro Lys Ser Pro Phe Glu Val Gln Val Gly
                        530                 535                 540
        Pro Glu Ala Gly Met Gln Lys Val Arg Ala Trp Gly Pro Gly Leu His
        545                 550                 555                 560
        Gly Gly Ile Val Gly Arg Ser Ala Asp Phe Val Val Glu Ser Ile Gly
                        565                 570                 575
        Ser Glu Val Gly Ser Leu Gly Phe Ala Ile Glu Gly Pro Ser Gln Ala
                        580                 585                 590
        Lys Ile Glu Tyr Asn Asp Gln Asn Asp Gly Ser Cys Asp Val Lys Tyr
                        595                 600                 605
        Trp Pro Lys Glu Pro Gly Glu Tyr Ala Val His Ile Met Cys Asp Asp
        610                 615                 620
        Glu Asp Ile Lys Asp Ser Pro Tyr Met Ala Phe Ile His Pro Ala Thr
        625                 630                 635                 640
        Gly Gly Tyr Asn Pro Asp Leu Val Arg Ala Tyr Gly Pro Gly Leu Glu
                        645                 650                 655
        Lys Ser Gly Cys Ile Val Asn Asn Leu Ala Glu Phe Thr Val Asp Pro
                        660                 665                 670
        Lys Asp Ala Gly Lys Ala Pro Leu Lys Ile Phe Ala Gln Asp Gly Glu
                        675                 680                 685
        Gly Gln Arg Ile Asp Ile Gln Met Lys Asn Arg Met Asp Gly Thr Tyr
                        690                 695                 700
        Ala Cys Ser Tyr Thr Pro Val Lys Ala Ile Lys His Thr Ile Ala Val
        705                 710                 715                 720
        Val Trp Gly Gly Val Asn Ile Pro His Ser Pro Tyr Arg Val Asn Ile
                        725                 730                 735
```

```
Gly Gln Gly Ser His Pro Gln Lys Val Lys Val Phe Gly Pro Gly Val
            740                 745                 750

Glu Arg Ser Gly Leu Lys Ala Asn Glu Pro Thr His Phe Thr Val Asp
            755                 760                 765

Cys Thr Glu Ala Gly Glu Gly Asp Val Ser Val Gly Ile Lys Cys Asp
770                 775                 780

Ala Arg Val Leu Ser Glu Asp Glu Asp Val Asp Phe Asp Ile Ile
785                 790                 795                 800

His Asn Ala Asn Asp Thr Phe Thr Val Lys Tyr Val Pro Ala Ala
                805                 810                 815

Gly Arg Tyr Thr Ile Lys Val Leu Phe Ala Ser Gln Glu Ile Pro Ala
            820                 825                 830

Ser Pro Phe Arg Val Lys Val Asp Pro Ser His Asp Ala Ser Lys Val
            835                 840                 845

Lys Ala Glu Gly Pro Gly Leu Ser Lys Ala Gly Val Glu Asn Gly Lys
850                 855                 860

Pro Thr His Phe Thr Val Tyr Thr Lys Gly Ala Gly Lys Ala Pro Leu
865                 870                 875                 880

Asn Val Gln Phe Asn Ser Pro Leu Pro Gly Asp Ala Val Lys Asp Leu
                885                 890                 895

Asp Ile Ile Asp Asn Tyr Asp Tyr Ser His Thr Val Lys Tyr Thr Pro
            900                 905                 910

Thr Gln Gln Gly Asn Met Gln Val Leu Val Thr Tyr Gly Gly Asp Pro
            915                 920                 925

Ile Pro Lys Ser Pro Phe Thr Val Gly Val Ala Ala Pro Leu Asp Leu
            930                 935                 940

Ser Lys Ile Lys Leu Asn Gly Leu Glu Asn Arg Val Glu Val Gly Lys
945                 950                 955                 960

Asp Gln Glu Phe Thr Val Asp Thr Arg Gly Ala Gly Gly Gln Gly Lys
                965                 970                 975

Leu Asp Val Thr Ile Leu Ser Pro Ser Arg Lys Val Val Pro Cys Leu
            980                 985                 990

Val Thr Pro Val Thr Gly Arg Glu Asn Ser Thr Ala Lys Phe Ile Pro
            995                 1000                1005

Arg Glu Glu Gly Leu Tyr Ala Val Asp Val Thr Tyr Asp Gly His
    1010                1015                1020

Pro Val Pro Gly Ser Pro Tyr Thr Val Glu Ala Ser Leu Pro Pro
    1025                1030                1035

Asp Pro Ser Lys Val Lys Ala His Gly Pro Gly Leu Glu Gly Gly
    1040                1045                1050

Leu Val Gly Lys Pro Ala Glu Phe Thr Ile Asp Thr Lys Gly Ala
    1055                1060                1065

Gly Thr Gly Gly Leu Gly Leu Thr Val Glu Gly Pro Cys Glu Ala
    1070                1075                1080

Lys Ile Glu Cys Ser Asp Asn Gly Asp Gly Thr Cys Ser Val Ser
    1085                1090                1095

Tyr Leu Pro Thr Lys Pro Gly Glu Tyr Phe Val Asn Ile Leu Phe
    1100                1105                1110

Glu Glu Val His Ile Pro Gly Ser Pro Phe Lys Ala Asp Ile Glu
    1115                1120                1125

Met Pro Phe Asp Pro Ser Lys Val Val Ala Ser Gly Pro Gly Leu
    1130                1135                1140
```

| | | | | | | | | | | |
|---|---|---|---|---|---|---|---|---|---|---|
| Glu | His 1145 | Gly | Lys | Val 1150 | Gly | Glu | Ala | Gly 1155 | Leu | Leu | Ser | Val | Asp | Cys |

```
Glu His Gly Lys Val Gly Glu Ala Gly Leu Leu Ser Val Asp Cys
    1145          1150              1155

Ser Glu Ala Gly Pro Gly Ala Leu Gly Leu Glu Ala Val Ser Asp
    1160          1165              1170

Ser Gly Thr Lys Ala Glu Val Ser Ile Gln Asn Asn Lys Asp Gly
    1175          1180              1185

Thr Tyr Ala Val Thr Tyr Val Pro Leu Thr Ala Gly Met Tyr Thr
    1190          1195              1200

Leu Thr Met Lys Tyr Gly Gly Glu Leu Val Pro His Phe Pro Ala
    1205          1210              1215

Arg Val Lys Val Glu Pro Ala Val Asp Thr Ser Arg Ile Lys Val
    1220          1225              1230

Phe Gly Pro Gly Ile Glu Gly Lys Asp Val Phe Arg Glu Ala Thr
    1235          1240              1245

Thr Asp Phe Thr Val Asp Ser Arg Pro Leu Thr Gln Val Gly Gly
    1250          1255              1260

Asp His Ile Lys Ala His Ile Ala Asn Pro Ser Gly Ala Ser Thr
    1265          1270              1275

Glu Cys Phe Val Thr Asp Asn Ala Asp Gly Thr Tyr Gln Val Glu
    1280          1285              1290

Tyr Thr Pro Phe Glu Lys Gly Leu His Val Val Glu Val Thr Tyr
    1295          1300              1305

Asp Asp Val Pro Ile Pro Asn Ser Pro Phe Lys Val Ala Val Thr
    1310          1315              1320

Glu Gly Cys Gln Pro Ser Arg Val Gln Ala Gln Gly Pro Gly Leu
    1325          1330              1335

Lys Glu Ala Phe Thr Asn Lys Pro Asn Val Phe Thr Val Val Thr
    1340          1345              1350

Arg Gly Ala Gly Ile Gly Gly Leu Gly Ile Thr Val Glu Gly Pro
    1355          1360              1365

Ser Glu Ser Lys Ile Asn Cys Arg Asp Asn Lys Asp Gly Ser Cys
    1370          1375              1380

Ser Ala Glu Tyr Ile Pro Phe Ala Pro Gly Asp Tyr Asp Val Asn
    1385          1390              1395

Ile Thr Tyr Gly Gly Ala His Ile Pro Gly Ser Pro Phe Arg Val
    1400          1405              1410

Pro Val Lys Asp Val Val Asp Pro Ser Lys Val Lys Ile Ala Gly
    1415          1420              1425

Pro Gly Leu Gly Ser Gly Val Arg Ala Arg Val Leu Gln Ser Phe
    1430          1435              1440

Thr Val Asp Ser Ser Lys Ala Gly Leu Ala Pro Leu Glu Val Arg
    1445          1450              1455

Val Leu Gly Pro Arg Gly Leu Val Glu Pro Val Asn Val Val Asp
    1460          1465              1470

Asn Gly Asp Gly Thr His Thr Val Thr Tyr Thr Pro Ser Gln Glu
    1475          1480              1485

Gly Pro Tyr Met Val Ser Val Lys Tyr Ala Asp Glu Glu Ile Pro
    1490          1495              1500

Arg Ser Pro Phe Lys Val Lys Val Leu Pro Thr Tyr Asp Ala Ser
    1505          1510              1515

Lys Val Thr Ala Ser Gly Pro Gly Leu Ser Ser Tyr Gly Val Pro
    1520          1525              1530

Ala Ser Leu Pro Val Asp Phe Ala Ile Asp Ala Arg Asp Ala Gly
```

-continued

```
            1535                1540                1545
Glu Gly Leu Leu Ala Val Gln Ile Thr Asp Gln Glu Gly Lys Pro
            1550                1555                1560
Lys Arg Ala Ile Val His Asp Asn Lys Asp Gly Thr Tyr Ala Val
            1565                1570                1575
Thr Tyr Ile Pro Asp Lys Thr Gly Arg Tyr Met Ile Gly Val Thr
            1580                1585                1590
Tyr Gly Gly Asp Asp Ile Pro Leu Ser Pro Tyr Arg Ile Arg Ala
            1595                1600                1605
Thr Gln Thr Gly Asp Ala Ser Lys Cys Leu Ala Thr Gly Pro Gly
            1610                1615                1620
Ile Ala Ser Thr Val Lys Thr Gly Glu Glu Val Gly Phe Val Val
            1625                1630                1635
Asp Ala Lys Thr Ala Gly Lys Gly Lys Val Thr Cys Thr Val Leu
            1640                1645                1650
Thr Pro Asp Gly Thr Glu Ala Glu Ala Asp Val Ile Glu Asn Glu
            1655                1660                1665
Asp Gly Thr Tyr Asp Ile Phe Tyr Thr Ala Ala Lys Pro Gly Thr
            1670                1675                1680
Tyr Val Ile Tyr Val Arg Phe Gly Gly Val Asp Ile Pro Asn Ser
            1685                1690                1695
Pro Phe Thr Val Met Ala Thr Asp Gly Glu Val Thr Ala Val Glu
            1700                1705                1710
Glu Ala Pro Val Thr Glu Glu Ala Tyr Val Pro Val Ser Asp Met
            1715                1720                1725
Asn Gly Leu Gly Phe Lys Pro Phe Asp Leu Val Ile Pro Phe Ala
            1730                1735                1740
Val Arg Lys Gly Glu Ile Thr Gly Glu Val His Met Pro Ser Gly
            1745                1750                1755
Lys Thr Ala Thr Pro Glu Ile Val Asp Asn Lys Asp Gly Thr Val
            1760                1765                1770
Thr Val Arg Tyr Ala Pro Thr Glu Val Gly Leu His Glu Met His
            1775                1780                1785
Ile Lys Tyr Met Gly Ser His Ile Pro Glu Ser Pro Leu Gln Phe
            1790                1795                1800
Tyr Val Asn Tyr Pro Asn Ser Gly Ser Val Ser Ala Tyr Gly Pro
            1805                1810                1815
Gly Leu Val Tyr Gly Val Ala Asn Lys Thr Ala Thr Phe Thr Ile
            1820                1825                1830
Val Thr Glu Asp Ala Gly Glu Gly Gly Leu Asp Leu Ala Ile Glu
            1835                1840                1845
Gly Pro Ser Lys Ala Glu Ile Ser Cys Ile Asp Asn Lys Asp Gly
            1850                1855                1860
Thr Cys Thr Val Thr Tyr Leu Pro Thr Leu Pro Gly Asp Tyr Ser
            1865                1870                1875
Ile Leu Val Lys Tyr Asn Asp Lys His Ile Pro Gly Ser Pro Phe
            1880                1885                1890
Thr Ala Lys Ile Thr Asp Asp Ser Arg Arg Cys Ser Gln Val Lys
            1895                1900                1905
Leu Gly Ser Ala Ala Asp Phe Leu Leu Asp Ile Ser Glu Thr Asp
            1910                1915                1920
Leu Ser Ser Leu Thr Ala Ser Ile Lys Ala Pro Ser Gly Arg Asp
            1925                1930                1935
```

-continued

```
Glu Pro Cys Leu Leu Lys Arg Leu Pro Asn Asn His Ile Gly Ile
    1940                1945                1950

Ser Phe Ile Pro Arg Glu Val Gly Glu His Leu Val Ser Ile Lys
    1955                1960                1965

Lys Asn Gly Asn His Val Ala Asn Ser Pro Val Ser Ile Met Val
    1970                1975                1980

Val Gln Ser Glu Ile Gly Asp Ala Arg Arg Ala Lys Val Tyr Gly
    1985                1990                1995

Arg Gly Leu Ser Glu Gly Arg Thr Phe Glu Met Ser Asp Phe Ile
    2000                2005                2010

Val Asp Thr Arg Asp Ala Gly Tyr Gly Ile Ser Leu Ala Val
    2015                2020                2025

Glu Gly Pro Ser Lys Val Asp Ile Gln Thr Glu Asp Leu Glu Asp
    2030                2035                2040

Gly Thr Cys Lys Val Ser Tyr Phe Pro Thr Val Pro Gly Val Tyr
    2045                2050                2055

Ile Val Ser Thr Lys Phe Ala Asp Glu His Val Pro Gly Ser Pro
    2060                2065                2070

Phe Thr Val Lys Ile Ser Gly Glu Gly Arg Val Lys Glu Ser Ile
    2075                2080                2085

Thr Arg Thr Ser Arg Ala Pro Ser Val Ala Thr Val Gly Ser Ile
    2090                2095                2100

Cys Asp Leu Asn Leu Lys Ile Pro Glu Ile Asn Ser Ser Asp Met
    2105                2110                2115

Ser Ala His Val Thr Ser Pro Ser Gly Arg Val Thr Glu Ala Glu
    2120                2125                2130

Ile Val Pro Met Gly Lys Asn Ser His Cys Val Arg Phe Val Pro
    2135                2140                2145

Gln Glu Met Gly Val His Thr Val Ser Val Lys Tyr Arg Gly Gln
    2150                2155                2160

His Val Thr Gly Ser Pro Phe Gln Phe Thr Val Gly Pro Leu Gly
    2165                2170                2175

Glu Gly Gly Ala His Lys Val Arg Ala Gly Gly Pro Gly Leu Glu
    2180                2185                2190

Arg Gly Glu Ala Gly Val Pro Ala Glu Phe Ser Ile Trp Thr Arg
    2195                2200                2205

Glu Ala Gly Ala Gly Gly Leu Ser Ile Ala Val Glu Gly Pro Ser
    2210                2215                2220

Lys Ala Glu Ile Thr Phe Asp Asp His Lys Asn Gly Ser Cys Gly
    2225                2230                2235

Val Ser Tyr Ile Ala Gln Glu Pro Gly Asn Tyr Glu Val Ser Ile
    2240                2245                2250

Lys Phe Asn Asp Glu His Ile Pro Glu Ser Pro Tyr Leu Val Pro
    2255                2260                2265

Val Ile Ala Pro Ser Asp Asp Ala Arg Arg Leu Thr Val Met Ser
    2270                2275                2280

Leu Gln Glu Ser Gly Leu Lys Val Asn Gln Pro Ala Ser Phe Ala
    2285                2290                2295

Ile Arg Leu Asn Gly Ala Lys Gly Lys Ile Asp Ala Lys Val His
    2300                2305                2310

Ser Pro Ser Gly Ala Val Glu Glu Cys His Val Ser Glu Leu Glu
    2315                2320                2325
```

| | | | | | | | | | | |
|---|---|---|---|---|---|---|---|---|---|---|
| Pro | Asp | Lys | Tyr | Ala | Val | Arg | Phe | Ile | Pro | His | Glu | Asn | Gly | Val |
| | 2330 | | | | 2335 | | | | 2340 | |

| His | Thr | Ile | Asp | Val | Lys | Phe | Asn | Gly | Ser | His | Val | Val | Gly | Ser |
| | 2345 | | | | 2350 | | | | 2355 | |

| Pro | Phe | Lys | Val | Arg | Val | Gly | Glu | Pro | Gly | Gln | Ala | Gly | Asn | Pro |
| | 2360 | | | | 2365 | | | | 2370 | |

| Ala | Leu | Val | Ser | Ala | Tyr | Gly | Thr | Gly | Leu | Glu | Gly | Gly | Thr | Thr |
| | 2375 | | | | 2380 | | | | 2385 | |

| Gly | Ile | Gln | Ser | Glu | Phe | Phe | Ile | Asn | Thr | Thr | Arg | Ala | Gly | Pro |
| | 2390 | | | | 2395 | | | | 2400 | |

| Gly | Thr | Leu | Ser | Val | Thr | Ile | Glu | Gly | Pro | Ser | Lys | Val | Lys | Met |
| | 2405 | | | | 2410 | | | | 2415 | |

| Asp | Cys | Gln | Glu | Thr | Pro | Glu | Gly | Tyr | Lys | Val | Met | Tyr | Thr | Pro |
| | 2420 | | | | 2425 | | | | 2430 | |

| Met | Ala | Pro | Gly | Asn | Tyr | Leu | Ile | Ser | Val | Lys | Tyr | Gly | Gly | Pro |
| | 2435 | | | | 2440 | | | | 2445 | |

| Asn | His | Ile | Val | Gly | Ser | Pro | Phe | Lys | Ala | Lys | Val | Thr | Gly | Gln |
| | 2450 | | | | 2455 | | | | 2460 | |

| Arg | Leu | Val | Ser | Pro | Gly | Ser | Ala | Asn | Glu | Thr | Ser | Ser | Ile | Leu |
| | 2465 | | | | 2470 | | | | 2475 | |

| Val | Glu | Ser | Val | Thr | Arg | Ser | Ser | Thr | Glu | Thr | Cys | Tyr | Ser | Ala |
| | 2480 | | | | 2485 | | | | 2490 | |

| Ile | Pro | Lys | Ala | Ser | Ser | Asp | Ala | Ser | Lys | Val | Thr | Ser | Lys | Gly |
| | 2495 | | | | 2500 | | | | 2505 | |

| Ala | Gly | Leu | Ser | Lys | Ala | Phe | Val | Gly | Gln | Lys | Ser | Ser | Phe | Leu |
| | 2510 | | | | 2515 | | | | 2520 | |

| Val | Asp | Cys | Ser | Lys | Ala | Gly | Ser | Asn | Met | Leu | Leu | Ile | Gly | Val |
| | 2525 | | | | 2530 | | | | 2535 | |

| His | Gly | Pro | Thr | Thr | Pro | Cys | Glu | Glu | Val | Ser | Met | Lys | His | Val |
| | 2540 | | | | 2545 | | | | 2550 | |

| Gly | Asn | Gln | Gln | Tyr | Asn | Val | Thr | Tyr | Val | Val | Lys | Glu | Arg | Gly |
| | 2555 | | | | 2560 | | | | 2565 | |

| Asp | Tyr | Val | Leu | Ala | Val | Lys | Trp | Gly | Glu | Glu | His | Ile | Pro | Gly |
| | 2570 | | | | 2575 | | | | 2580 | |

| Ser | Pro | Phe | His | Val | Thr | Val | Pro | | | | | | | |
| | 2585 | | | | 2590 | | | | | |

<210> SEQ ID NO 25
<211> LENGTH: 9434
<212> TYPE: DNA
<213> ORGANISM: Homo sapiens

<400> SEQUENCE: 25

```
gcggccaggg gcgggcggcc gcagagcagc accggccgtg gctccggtag cagcaagttc      60 gaacccgct cccgctccgc ttcggttctc gctccttcgg cccttgggcc tccaaacacc      120
agtccccggc agctcgttgc gcattgcgct ctccccgcca ccaggatgcc ggtaaccgag      180
aaggatctag ctgaggacgc gccttggaag aagatccagc agaacacgtt cacacgctgg      240
tgcaacgagc acctcaagtg cgtgaacaaa cgcatcggca acctgcagac cgacctgagc      300
gacgggctgc ggctcatcgc gctgctcgag gtgctcagcc agaagcgcat gtaccgcaag      360
taccatcagc ggcccacctt cgccagatg cagctcgaga atgtgtccgt ggcgctcgag      420
ttcctggacc gtgagagcat caagctcgtg tccatcgata gcaaagccat gtgtgatggg      480
aacctgaagc tcatcttggg tctggtgtgg acgctgatcc tccactactc catctccatg      540
```

```
cccgtgtggg aggatgaagg ggatgatgat gccaagaagc agacgccaaa gcagaggctg      600
ctggggtgga ttcagaacaa gatcccctac ttgcccatca ccaactttaa ccagaactgg      660
caagacggca aagccctggg agccctggta gacagctgtg ctccaggtct gtgcccagac      720
tgggaatcct gggacccgca gaagcctgtg gataatgcac gagaagccat gcagcaggca      780
gatgactggc tgggtgtccc acaggtcatc actcctgaag aaatcattca cccggatgtg      840
gacgagcact cagttatgac ttacctgtcc cagttcccca agccaagct caagccgggg       900 gctcctctca aacccaaact caacccgaag aaagccaggg cctatggcag aggaatcgag      960
cccactggaa acatggtgaa gcagccagcc aagttcactg tggacaccat cagcgccggg     1020
caaggagacg tgatggtgtt tgttgaggac ccagaaggga caaagagga ggcacaagtg      1080 acccctgaca gtgacaagaa caagacatac tctgtggagt atctgcccaa ggtcaccggg     1140
ctacacaaag tcacagtcct ctttgcagga cagcacatct ccaagagccc atttgaagtg     1200
agtgttgaca aggcccaggg agatgccagt aaagtcactg caaaaggtcc agggttggaa     1260
gctgtaggga acatcgccaa taagcccacc tactttgaca tctatacggc aggagctggt     1320
gtgggtgaca ttggtgtgga ggtggaagat ccccagggga gaacaccgt ggagttgctc      1380 gtggaagaca aaggaaacca ggtgtatcga tgtgtgtaca aacccatgca gcctggccct     1440
cacgtggtca agatcttctt tgctggggac actattccta agagtccctt cgttgtgcag     1500
gttggggaag cctgcaatcc aaatgcctgc cgggccagtg gccgaggcct acaacccaaa     1560
ggcgtccgta tccgggagac cacagatttc aaggttgaca ccaaagctgc aggaagtggg     1620
gagctcggtg taaccatgaa gggtcctaag gtctggagg agctggtgaa gcagaaagac     1680
tttctggatg gggtctacgc attcgagtat taccccagca ccccggggag atacagcatt     1740
gccatcacat ggggggggaca ccacattcca aagagcccct ttgaagttca agttggccct     1800
gaagcgggta tgcagaaagt ccgtgcttgg ggccctgggc tccatggtgg gattgtcggg     1860
cggtcagcgg acttcgtggt agaatccatt ggctctgaag tggggtctct ggggtttgcc     1920
attgaaggcc cctctcaggc aaagattgag tacaacgacc agaatgatgg atcgtgtgat     1980
gtcaaatact ggcccaagga gcctggcgaa tatgctgttc acatcatgtg tgacgacgaa     2040
gacatcaagg acagcccgta catggccttc atccacccag ccacgggagg ctacaaccct     2100
gatctggttc gagcatacgg gccaggtttg gagaaatctg gatgcattgt caacaacctg     2160
gccgagttca ctgtggatcc taaggatgct ggaaaagctc ccttaaagat atttgctcag     2220 gatgggaag ccaacgcat tgacatccag atgaagaacc ggatggacgg cacatatgca      2280
tgctcataca ccccggtgaa ggccatcaag cacaccattg ctgtggtctg gggaggcgtg     2340
aacatcccgc acagccccta cagggtcaac atcgggcaag tagccatcc tcagaaggtc      2400 aaagtgtttg ggccaggtgt ggagagaagt ggtctgaagg caaatgaacc tacacacttc     2460
acggtggact gtactgaggc tggggaaggt gatgtcagtg ttggcattaa gtgtgatgcc     2520
cgggtgttaa gtgaagatga ggaagacgtg gattttgaca ttattcacaa tgccaatgat     2580
acgttcacag tcaaatatgt gcctcctgct gctgggcgat acactatcaa agttctcttt     2640
gcatctcagg aaatccccgc cagcccttc agagtcaaag ttgacccttc ccacgatgcc      2700
agcaaagtga aggcagaagg cccagggctc agcaaagcag gtgtggaaaa tgggaaaccg     2760
acccacttca ctgtctacac caaggggggct gggaaagccc cgctcaacgt gcagttcaac     2820
agccctcttc ctggcgatgc agtgaaggat ttggatatca tcgataatta tgactactct     2880
```

```
cacacggtta aatatacacc cacccaacag ggcaacatgc aggttctggt gacttacggt    2940
ggcgatccca tccctaaaag ccctttcact gtgggtgttg ctgcaccgct ggatctgagc    3000
aagataaaac tcaatgggct ggaaaacagg gtggaagttg ggaaggatca ggagttcacc    3060
gttgatacca ggggggcagg aggccagggg aagctggacg tgacaatcct cagcccctct    3120
cggaaggtcg tgccatgcct agtgacacct gtgacaggcc gggagaacag cacggccaag    3180
ttcatccctc gggaggaggg gctgtatgct gtagacgtga cctacgatgg acaccctgtg    3240
cccgggagcc cctacacagt ggaggcctcg ctgccaccag atcccagcaa ggtgaaggcc    3300
cacggtcccg gcctcgaagg tggtctcgtg ggcaagcctg ccgagttcac catcgatacc    3360
aaaggagctg gtactggagg tctgggctta acggtggaag gtccgtgcga ggccaaaatc    3420
gagtgctccg acaatggtga tgggacctgc tccgtctctt accttcccac aaaacccggg    3480
gagtacttcg tcaacatcct cttttgaagaa gtccacatac ctgggtctcc cttcaaagct    3540
gacattgaaa tgcccttttga cccctctaaa gtcgtggcat cggggccagg tctcgagcac    3600
gggaaggtgg gtgaagctgg cctccttagc gtcgactgct cggaagcggg accggggcc    3660
ctgggcctgg aagctgtctc ggactcggga acaaaagccg aagtcagtat tcagaacaac    3720
aaagatggca cctacgcggt gacctacgtg cccctgacgg ccggcatgta cacgttgacc    3780
atgaagtatg gtggcgaact cgtgccacac ttccccgccc gggtcaaggt ggagcccgcc    3840
gtggacacca gcaggatcaa agtctttgga ccaggaatag aagggaaaga tgtgttccgg    3900
gaagctacca ccgactttac agttgactct cggccgctga cccaggttgg gggtgaccac    3960
atcaaggccc acattgccaa cccctcaggg gcctccaccg agtgctttgt cacagacaat    4020
gcggatggga cctaccaggt ggaatacaca cccctttgaga aggtctccca tgtagtggag    4080
gtgacatatg atgacgtgcc tatcccaaac agtcccttca aggtggctgt cactgaaggc    4140
tgccagccat ctagggtgca agcccaagga cctggattga agaggccttt taccaacaag    4200
cccaatgtct tcaccgtggt taccagaggc gcaggaattg gtgggcttgg cataactgtt    4260
gagggaccat cagagtcgaa gataaattgc agagacaaca aggatggcag ctgcagtgct    4320
gagtacattc ctttcgcacc gggggattac gatgttaata tcacatatgg aggagcccac    4380
atccccggca gcccccttcag ggttcctgtg aaggatgttg tggaccccag caaggtcaag    4440
attgccggcc ccgggctggg ctcaggcgtc cgagcccgtg tcctgcagtc cttcacggtg    4500
gacagcagca aggctggcct ggctccgctg gaagtgaggg ttctgggccc acgaggcttg    4560
gtggagccag tgaacgtggt ggacaatgga gatggcacac acacagtaac ctacaccca    4620
tctcaggagg gaccttacat ggtctcagtt aaatatgctg atgaagagat tcctcgcagt    4680
cccttcaagg tcaaggtcct tcccacatat gatgccagca agtgactgc cagtggcccc    4740
ggccttagtt cctatggtgt gcctgccagt ctacctgtgg actttgcaat tgatgcccga    4800
gatgccgggg aaggcctgct tgctgttcaa ataacggacc aagaaggaaa acccaaaaga    4860
gccattgtcc atgacaataa agatggcacg tatgctgtca cctacatccc cgacaagact    4920
gggcgctata tgattggagt cacctacggg ggtgacgaca tcccactttc tccttatcgc    4980
atccgagcca cacagacggg tgatgccagc aagtgcctgg ccacgggtcc tggaatcgcc    5040
tccactgtga aaactggcga agaagtaggc tttgtggttg atgccaagac tgccgggaag    5100
ggtaaagtga cctgcacggt tctgaccccca gatggcactg aggccgaggc cgatgtcatt    5160
gagaatgaag atggaacccta tgacatcttc tacacagctg ccaagccggg cacatatgtg    5220
atctatgtgc gcttcggtgg tgttgatatt cctaacagcc ccttcactgt catggccaca    5280
```

```
gatgggaag tcacagccgt ggaggaggca ccggtgaccg aagaggccta tgtcccagtg    5340
agtgacatga acggcctggg atttaagcct tttgacctgg tcattccgtt tgctgtcagg    5400
aaaggagaaa tcactggaga ggtccacatg ccttctggga agacagccac acctgagatt    5460
gtggacaaca aggacggcac ggtcactgtt agatatgccc ccactgaggt cgggctccat    5520
gagatgcaca tcaaatacat gggcagccac atccctgaga gcccactcca gttctacgtg    5580
aactacccca acagtggaag tgtttctgca tacggtccag gctcgtgta tggagtggcc     5640 aacaaaactg ccaccttcac catcgtcaca gaggatgcag agaaggtgg tctggacttg      5700 gctattgagg gccctcaaa agcagaaatc agctgcattg acaataaaga tgggacatgc      5760
acagtgacct acctgccgac tctgccaggc gactacagca ttctggtcaa gtacaatgac    5820
aagcacatcc ctggcagccc cttcacagcc aagatcacag atgacagcag gcggtgctcc    5880
caggtgaagt tgggctcagc cgctgacttc ctgctcgaca tcagtgagac tgacctcagc    5940
agcctgacgg ccagcattaa ggccccatct ggccgagacg agccctgtct cctgaagagg    6000
ctgcccaaca accacattgg catctccttc atccccgggg aagtgggcga acatctggtc    6060
agcatcaaga aaatggcaa ccatgtggcc aacagccccg tgtctatcat ggtggtccag      6120
tcggagattg gtgacgcccg ccgagccaaa gtctatggcc gcggcctgtc agaaggccgg    6180
actttcgaga tgtctgactt catcgtggac acaaggatg caggttatgg tggcatatcc      6240
ttggcggtgg aaggccccag caaagtggac atccagacgg aggacctgga agatggcacc    6300
tgcaaagtct cctacttccc taccgtgcct ggggtttata tcgtctccac caaattcgct    6360
gacgagcacg tgcctgggag cccatttacc gtgaagatca gtggggaggg aagagtcaaa    6420
gagagcatca cccgcaccag tcgggcccg tccgtggcca ctgtcgggag catttgtgac     6480
ctgaacctga aaatcccaga aatcaacagc agtgatatgt cggcccacgt caccagcccc    6540
tctggccgtg tgactgaggc agagattgtg cccatgggga gaactcaca ctgcgtccgg      6600 tttgtgcccc aggagatggg cgtgcacacg gtcagcgtca gtaccgtgg gcagcacgtc      6660 accggcagcc ccttccagtt caccgtgggg ccacttggtg aaggaggcgc ccacaaggtg    6720
cgggcaggag gccctggcct ggagagagga gaagcgggag tcccagctga gttcagcatt    6780
tggacccggg aagcaggcgc tggaggcctc tccatcgctg ttgagggccc cagtaaggcc    6840
gagattacat tcgatgacca taaaatggg tcgtgcggtg tatcttatat tgcccaagag      6900
cctggtaact acgaggtgtc catcaagttc aatgatgagc acatccccgga aagcccctac    6960 ctggtgccgg tcatcgcacc ctccgacgac gcccgccgcc tcactgttat gagccttcag    7020
gaatcgggat taaaagttaa ccagccagca tcctttgcta taaggttgaa tggcgcaaaa    7080
ggcaagattg atgcaaaggt gcacagcccc tctggagccg tggaggagtg ccacgtgtct    7140
gagctggagc cagataagta tgctgttcgc ttcatccctc atgagaatgg tgtccacacc    7200
atcgatgtca agttcaatgg gagccacgtg gttgaagcc ccttcaaagt gcgcgttggg      7260
gagcctggac aagcggggaa ccctgccctg tgtgccgcct atggcacggg actcgaaggg    7320
ggcaccacag gtatccagtc ggaattcttt attaacacca cccgagcagg tccagggaca    7380
ttatccgtca ccatcgaagg cccatccaag gttaaaatgg attgccagga aacacctgaa    7440
gggtacaaag tcatgtacac ccccatggct cctggtaact acctgatcag cgtcaaatac    7500
ggtgggccca accacatcgt gggcagtccc ttcaaggcca aggtgacagg ccagcgtcta    7560
gttagccctg gctcagccaa cgagacctca tccatcctgg tggagtcagt gaccaggtcg    7620
```

```
tctacagaga cctgctatag cgccattccc aaggcatcct cggacgccag caaggtgacc    7680
tctaaggggg cagggctctc aaaggccttt gtgggccaga agagttcctt cctggtggac    7740
tgcagcaaag ctggctccaa catgctgctg atcggggtcc atgggcccac caccccctgc    7800
gaggaggtct ccatgaagca gtaggcaac cagcaataca acgtcacata cgtcgtcaag    7860 gagagggcg attatgtgct ggctgtgaag tgggggagg aacacatccc tggcagccct    7920
tttcatgtca cagtgcctta aaacagtttt ctcaaatcct ggagagagtt cttgtggttg    7980
cttttgttgc ttgtttgtaa ttcattttat acaaagccct ccagcctgtt tgtgggctg     8040 aaacccatc cctaaaatat tgctgttgta aaatgccttc agaaataagt cctagactgg     8100
actcttgagg gacatattgg agaatcttaa gaaatgcaag cttgttcagg gggctgagaa    8160
gatcctgagt acactaggtg caaaccagaa ctcttggtgg aacagaccag ccactgcagc    8220
agacagacca ggaacacaat gagactgaca tttcaaaaaa acaaaactgg ctagcctgag    8280
ctgctggttc actcttcagc atttatgaaa caaggctagg ggaagatggg cagagaaaaa    8340
ggggacacct agtttggttg tcatttggca aaggagatga cttaaaatcc gcttaatctc    8400
ttccagtgtc cgtgttaatg tatttggcta ttagatcact agcactgctt taccgctcct    8460
catcgccaac ccccccatgc tctgtggcct tcttacactt ctcagagggc agagtggcag    8520
ccgggcaccc tacagaaact cagagggcag agtggcagcc aggcccacat gtctctcaag    8580
tacctgtccc ctcgctctgg tgattattc ttgcagaatc accacacgag accatcccgg    8640
cagtcatggt tttgctttag ttttccaagt ccgtttcagt cccttccttg gtctgaagaa    8700
attctgcagt ggcgagcagt ttcccacttg ccaaagatcc cttttaacca acactagccc    8760 ttgttttaa cacacgctcc agcccttcat cagcctgggc agtcttacca aaatgtttaa     8820
agtgatctca gagggccca tggattaacg ccctcatccc aaggtccgtc ccatgacata     8880
acactccaca cccgccccag ccaacttcat gggtcacttt ttctggaaaa taatgatctg    8940
tacagacagg acagaatgaa actcctgcgg gtctttggcc tgaaagttgg gaatggttgg    9000
gggagagaag ggcagcagct tattggtggt cttttcacca ttggcagaaa cagtgagagc    9060
tgtgtggtgc agaaatccag aaatgaggtg taggaatt tgcctgcctt cctgcagacc     9120
tgagctggct ttggaatgag gttaaagtgt cagggacgtt gcctgagccc aaatgtgtag    9180
tgtggtctgg gcaggcagac ctttaggttt tgctgcttag tcctgaggaa gtggccactc    9240
ttgtggcagg tgtagtatct ggggcgagtg ttgggggtaa aagcccaccc tacagaaagt    9300
ggaacagccc ggagcctgat gtgaaaggac cacgggtgtt gtaagctggg acacggaagc    9360
caaactggaa tcaaacgccg actgtaaatt gtatcttata acttattaaa taaaacattt    9420
gctccgtaaa gttg                                                     9434
```

<210> SEQ ID NO 26
<211> LENGTH: 2578
<212> TYPE: PRT
<213> ORGANISM: Homo sapiens

<400> SEQUENCE: 26

Met Pro Val Thr Glu Lys Asp Leu Ala Glu Asp Ala Pro Trp Lys Lys
1               5                   10                  15

Ile Gln Gln Asn Thr Phe Thr Arg Trp Cys Asn Glu His Leu Lys Cys
            20                  25                  30

Val Asn Lys Arg Ile Gly Asn Leu Gln Thr Asp Leu Ser Asp Gly Leu
        35                  40                  45

```
Arg Leu Ile Ala Leu Leu Glu Val Leu Ser Gln Lys Arg Met Tyr Arg
 50                  55                  60

Lys Tyr His Gln Arg Pro Thr Phe Arg Gln Met Gln Leu Glu Asn Val
 65                  70                  75                  80

Ser Val Ala Leu Glu Phe Leu Asp Arg Glu Ser Ile Lys Leu Val Ser
                 85                  90                  95

Ile Asp Ser Lys Ala Ile Val Asp Gly Asn Leu Lys Leu Ile Leu Gly
                100                 105                 110

Leu Val Trp Thr Leu Ile Leu His Tyr Ser Ile Ser Met Pro Val Trp
                115                 120                 125

Glu Asp Glu Gly Asp Asp Ala Lys Lys Gln Thr Pro Lys Gln Arg
130                 135                 140

Leu Leu Gly Trp Ile Gln Asn Lys Ile Pro Tyr Leu Pro Ile Thr Asn
145                 150                 155                 160

Phe Asn Gln Asn Trp Gln Asp Gly Lys Ala Leu Gly Ala Leu Val Asp
                165                 170                 175

Ser Cys Ala Pro Gly Leu Cys Pro Asp Trp Glu Ser Trp Asp Pro Gln
                180                 185                 190

Lys Pro Val Asp Asn Ala Arg Glu Ala Met Gln Gln Ala Asp Asp Trp
                195                 200                 205

Leu Gly Val Pro Gln Val Ile Thr Pro Glu Glu Ile Ile His Pro Asp
210                 215                 220

Val Asp Glu His Ser Val Met Thr Tyr Leu Ser Gln Phe Pro Lys Ala
225                 230                 235                 240

Lys Leu Lys Pro Gly Ala Pro Leu Lys Pro Lys Leu Asn Pro Lys Lys
                245                 250                 255

Ala Arg Ala Tyr Gly Arg Gly Ile Glu Pro Thr Gly Asn Met Val Lys
                260                 265                 270

Gln Pro Ala Lys Phe Thr Val Asp Thr Ile Ser Ala Gly Gln Gly Asp
                275                 280                 285

Val Met Val Phe Val Glu Asp Pro Glu Gly Asn Lys Glu Glu Ala Gln
                290                 295                 300

Val Thr Pro Asp Ser Asp Lys Asn Lys Thr Tyr Ser Val Glu Tyr Leu
305                 310                 315                 320

Pro Lys Val Thr Gly Leu His Lys Val Thr Val Leu Phe Ala Gly Gln
                325                 330                 335

His Ile Ser Lys Ser Pro Phe Glu Val Ser Val Asp Lys Ala Gln Gly
                340                 345                 350

Asp Ala Ser Lys Val Thr Ala Lys Gly Pro Gly Leu Glu Ala Val Gly
                355                 360                 365

Asn Ile Ala Asn Lys Pro Thr Tyr Phe Asp Ile Tyr Thr Ala Gly Ala
370                 375                 380

Gly Val Gly Asp Ile Gly Val Glu Val Glu Asp Pro Gln Gly Lys Asn
385                 390                 395                 400

Thr Val Glu Leu Leu Val Glu Asp Lys Gly Asn Gln Val Tyr Arg Cys
                405                 410                 415

Val Tyr Lys Pro Met Gln Pro Gly Pro His Val Val Lys Ile Phe Phe
                420                 425                 430

Ala Gly Asp Thr Ile Pro Lys Ser Pro Phe Val Val Gln Val Gly Glu
                435                 440                 445

Ala Cys Asn Pro Asn Ala Cys Arg Ala Ser Gly Arg Gly Leu Gln Pro
450                 455                 460

Lys Gly Val Arg Ile Arg Glu Thr Thr Asp Phe Lys Val Asp Thr Lys
```

```
               465                 470                 475                 480
Ala Ala Gly Ser Gly Glu Leu Gly Val Thr Met Lys Gly Pro Lys Gly
                    485                 490                 495

Leu Glu Glu Leu Val Lys Gln Lys Asp Phe Leu Asp Gly Val Tyr Ala
            500                 505                 510

Phe Glu Tyr Tyr Pro Ser Thr Pro Gly Arg Tyr Ser Ile Ala Ile Thr
            515                 520                 525

Trp Gly Gly His His Ile Pro Lys Ser Pro Phe Glu Val Gln Val Gly
        530                 535                 540

Pro Glu Ala Gly Met Gln Lys Val Arg Ala Trp Gly Pro Gly Leu His
545                 550                 555                 560

Gly Gly Ile Val Gly Arg Ser Ala Asp Phe Val Val Glu Ser Ile Gly
                565                 570                 575

Ser Glu Val Gly Ser Leu Gly Phe Ala Ile Glu Gly Pro Ser Gln Ala
            580                 585                 590

Lys Ile Glu Tyr Asn Asp Gln Asn Asp Gly Ser Cys Asp Val Lys Tyr
        595                 600                 605

Trp Pro Lys Glu Pro Gly Glu Tyr Ala Val His Ile Met Cys Asp Asp
610                 615                 620

Glu Asp Ile Lys Asp Ser Pro Tyr Met Ala Phe Ile His Pro Ala Thr
625                 630                 635                 640

Gly Gly Tyr Asn Pro Asp Leu Val Arg Ala Tyr Gly Pro Gly Leu Glu
                645                 650                 655

Lys Ser Gly Cys Ile Val Asn Asn Leu Ala Glu Phe Thr Val Asp Pro
            660                 665                 670

Lys Asp Ala Gly Lys Ala Pro Leu Lys Ile Phe Ala Gln Asp Gly Glu
        675                 680                 685

Gly Gln Arg Ile Asp Ile Gln Met Lys Asn Arg Met Asp Gly Thr Tyr
        690                 695                 700

Ala Cys Ser Tyr Thr Pro Val Lys Ala Ile Lys His Thr Ile Ala Val
705                 710                 715                 720

Val Trp Gly Gly Val Asn Ile Pro His Ser Pro Tyr Arg Val Asn Ile
                725                 730                 735

Gly Gln Gly Ser His Pro Gln Lys Val Lys Val Phe Gly Pro Gly Val
            740                 745                 750

Glu Arg Ser Gly Leu Lys Ala Asn Glu Pro Thr His Phe Thr Val Asp
        755                 760                 765

Cys Thr Glu Ala Gly Glu Gly Asp Val Ser Val Gly Ile Lys Cys Asp
770                 775                 780

Ala Arg Val Leu Ser Glu Asp Glu Asp Val Asp Phe Asp Ile Ile
785                 790                 795                 800

His Asn Ala Asn Asp Thr Phe Thr Val Lys Tyr Val Pro Pro Ala Ala
                805                 810                 815

Gly Arg Tyr Thr Ile Lys Val Leu Phe Ala Ser Gln Glu Ile Pro Ala
            820                 825                 830

Ser Pro Phe Arg Val Lys Val Asp Pro Ser His Asp Ala Ser Lys Val
        835                 840                 845

Lys Ala Glu Gly Pro Gly Leu Ser Lys Ala Gly Val Glu Asn Gly Lys
        850                 855                 860

Pro Thr His Phe Thr Val Tyr Thr Lys Gly Ala Gly Lys Ala Pro Leu
865                 870                 875                 880

Asn Val Gln Phe Asn Ser Pro Leu Pro Gly Asp Ala Val Lys Asp Leu
                885                 890                 895
```

-continued

```
Asp Ile Ile Asp Asn Tyr Asp Tyr Ser His Thr Val Lys Tyr Thr Pro
              900                 905                 910

Thr Gln Gln Gly Asn Met Gln Val Leu Val Thr Tyr Gly Gly Asp Pro
          915                 920                 925

Ile Pro Lys Ser Pro Phe Thr Val Gly Val Ala Ala Pro Leu Asp Leu
    930                 935                 940

Ser Lys Ile Lys Leu Asn Gly Leu Glu Asn Arg Val Glu Val Gly Lys
945                 950                 955                 960

Asp Gln Glu Phe Thr Val Asp Thr Arg Gly Ala Gly Gln Gly Lys
              965                 970                 975

Leu Asp Val Thr Ile Leu Ser Pro Ser Arg Lys Val Val Pro Cys Leu
          980                 985                 990

Val Thr Pro Val Thr Gly Arg Glu Asn Ser Thr Ala Lys Phe Ile Pro
    995                 1000                1005

Arg Glu Glu Gly Leu Tyr Ala Val Asp Val Thr Tyr Asp Gly His
    1010                1015                1020

Pro Val Pro Gly Ser Pro Tyr Thr Val Glu Ala Ser Leu Pro Pro
    1025                1030                1035

Asp Pro Ser Lys Val Lys Ala His Gly Pro Gly Leu Glu Gly Gly
    1040                1045                1050

Leu Val Gly Lys Pro Ala Glu Phe Thr Ile Asp Thr Lys Gly Ala
    1055                1060                1065

Gly Thr Gly Gly Leu Gly Leu Thr Val Glu Gly Pro Cys Glu Ala
    1070                1075                1080

Lys Ile Glu Cys Ser Asp Asn Gly Asp Gly Thr Cys Ser Val Ser
    1085                1090                1095

Tyr Leu Pro Thr Lys Pro Gly Glu Tyr Phe Val Asn Ile Leu Phe
    1100                1105                1110

Glu Glu Val His Ile Pro Gly Ser Pro Phe Lys Ala Asp Ile Glu
    1115                1120                1125

Met Pro Phe Asp Pro Ser Lys Val Val Ala Ser Gly Pro Gly Leu
    1130                1135                1140

Glu His Gly Lys Val Gly Glu Ala Gly Leu Leu Ser Val Asp Cys
    1145                1150                1155

Ser Glu Ala Gly Pro Gly Ala Leu Gly Leu Glu Ala Val Ser Asp
    1160                1165                1170

Ser Gly Thr Lys Ala Glu Val Ser Ile Gln Asn Asn Lys Asp Gly
    1175                1180                1185

Thr Tyr Ala Val Thr Tyr Val Pro Leu Thr Ala Gly Met Tyr Thr
    1190                1195                1200

Leu Thr Met Lys Tyr Gly Gly Glu Leu Val Pro His Phe Pro Ala
    1205                1210                1215

Arg Val Lys Val Glu Pro Ala Val Asp Thr Ser Arg Ile Lys Val
    1220                1225                1230

Phe Gly Pro Gly Ile Glu Gly Lys Asp Val Phe Arg Glu Ala Thr
    1235                1240                1245

Thr Asp Phe Thr Val Asp Ser Arg Pro Leu Thr Gln Val Gly Gly
    1250                1255                1260

Asp His Ile Lys Ala His Ile Ala Asn Pro Ser Gly Ala Ser Thr
    1265                1270                1275

Glu Cys Phe Val Thr Asp Asn Ala Asp Gly Thr Tyr Gln Val Glu
    1280                1285                1290
```

```
Tyr Thr Pro Phe Glu Lys Gly Leu His Val Val Glu Val Thr Tyr
1295                1300                1305

Asp Asp Val Pro Ile Pro Asn Ser Pro Phe Lys Val Ala Val Thr
1310                1315                1320

Glu Gly Cys Gln Pro Ser Arg Val Gln Ala Gln Gly Pro Gly Leu
1325                1330                1335

Lys Glu Ala Phe Thr Asn Lys Pro Asn Val Phe Thr Val Val Thr
1340                1345                1350

Arg Gly Ala Gly Ile Gly Gly Leu Gly Ile Thr Val Glu Gly Pro
1355                1360                1365

Ser Glu Ser Lys Ile Asn Cys Arg Asp Asn Lys Asp Gly Ser Cys
1370                1375                1380

Ser Ala Glu Tyr Ile Pro Phe Ala Pro Gly Asp Tyr Asp Val Asn
1385                1390                1395

Ile Thr Tyr Gly Gly Ala His Ile Pro Gly Ser Pro Phe Arg Val
1400                1405                1410

Pro Val Lys Asp Val Val Asp Pro Ser Lys Val Lys Ile Ala Gly
1415                1420                1425

Pro Gly Leu Gly Ser Gly Val Arg Ala Arg Val Leu Gln Ser Phe
1430                1435                1440

Thr Val Asp Ser Ser Lys Ala Gly Leu Ala Pro Leu Glu Val Arg
1445                1450                1455

Val Leu Gly Pro Arg Gly Leu Val Glu Pro Val Asn Val Val Asp
1460                1465                1470

Asn Gly Asp Gly Thr His Thr Val Thr Tyr Thr Pro Ser Gln Glu
1475                1480                1485

Gly Pro Tyr Met Val Ser Val Lys Tyr Ala Asp Glu Glu Ile Pro
1490                1495                1500

Arg Ser Pro Phe Lys Val Lys Val Leu Pro Thr Tyr Asp Ala Ser
1505                1510                1515

Lys Val Thr Ala Ser Gly Pro Gly Leu Ser Ser Tyr Gly Val Pro
1520                1525                1530

Ala Ser Leu Pro Val Asp Phe Ala Ile Asp Ala Arg Asp Ala Gly
1535                1540                1545

Glu Gly Leu Leu Ala Val Gln Ile Thr Asp Gln Glu Gly Lys Pro
1550                1555                1560

Lys Arg Ala Ile Val His Asp Asn Lys Asp Gly Thr Tyr Ala Val
1565                1570                1575

Thr Tyr Ile Pro Asp Lys Thr Gly Arg Tyr Met Ile Gly Val Thr
1580                1585                1590

Tyr Gly Gly Asp Asp Ile Pro Leu Ser Pro Tyr Arg Ile Arg Ala
1595                1600                1605

Thr Gln Thr Gly Asp Ala Ser Lys Cys Leu Ala Thr Gly Pro Gly
1610                1615                1620

Ile Ala Ser Thr Val Lys Thr Gly Glu Glu Val Gly Phe Val Val
1625                1630                1635

Asp Ala Lys Thr Ala Gly Lys Gly Lys Val Thr Cys Thr Val Leu
1640                1645                1650

Thr Pro Asp Gly Thr Glu Ala Glu Ala Asp Val Ile Glu Asn Glu
1655                1660                1665

Asp Gly Thr Tyr Asp Ile Phe Tyr Thr Ala Ala Lys Pro Gly Thr
1670                1675                1680

Tyr Val Ile Tyr Val Arg Phe Gly Gly Val Asp Ile Pro Asn Ser
```

-continued

```
           1685                1690                1695

Pro Phe Thr Val Met Val Thr Glu Glu Ala Tyr Val Pro Val Ser
    1700                1705                1710

Asp Met Asn Gly Leu Gly Phe Lys Pro Phe Asp Leu Val Ile Pro
    1715                1720                1725

Phe Ala Val Arg Lys Gly Glu Ile Thr Gly Glu Val His Met Pro
    1730                1735                1740

Ser Gly Lys Thr Ala Thr Pro Glu Ile Val Asp Asn Lys Asp Gly
    1745                1750                1755

Thr Val Thr Val Arg Tyr Ala Pro Thr Glu Val Gly Leu His Glu
    1760                1765                1770

Met His Ile Lys Tyr Met Gly Ser His Ile Pro Glu Ser Pro Leu
    1775                1780                1785

Gln Phe Tyr Val Asn Tyr Pro Asn Ser Gly Ser Val Ser Ala Tyr
    1790                1795                1800

Gly Pro Gly Leu Val Tyr Gly Val Ala Asn Lys Thr Ala Thr Phe
    1805                1810                1815

Thr Ile Val Thr Glu Asp Ala Gly Glu Gly Gly Leu Asp Leu Ala
    1820                1825                1830

Ile Glu Gly Pro Ser Lys Ala Glu Ile Ser Cys Ile Asp Asn Lys
    1835                1840                1845

Asp Gly Thr Cys Thr Val Thr Tyr Leu Pro Thr Leu Pro Gly Asp
    1850                1855                1860

Tyr Ser Ile Leu Val Lys Tyr Asn Asp Lys His Ile Pro Gly Ser
    1865                1870                1875

Pro Phe Thr Ala Lys Ile Thr Asp Asp Ser Arg Arg Cys Ser Gln
    1880                1885                1890

Val Lys Leu Gly Ser Ala Ala Asp Phe Leu Leu Asp Ile Ser Glu
    1895                1900                1905

Thr Asp Leu Ser Ser Leu Thr Ala Ser Ile Lys Ala Pro Ser Gly
    1910                1915                1920

Arg Asp Glu Pro Cys Leu Leu Lys Arg Leu Pro Asn Asn His Ile
    1925                1930                1935

Gly Ile Ser Phe Ile Pro Arg Glu Val Gly Glu His Leu Val Ser
    1940                1945                1950

Ile Lys Lys Asn Gly Asn His Val Ala Asn Ser Pro Val Ser Ile
    1955                1960                1965

Met Val Val Gln Ser Glu Ile Gly Asp Ala Arg Arg Ala Lys Val
    1970                1975                1980

Tyr Gly Arg Gly Leu Ser Glu Gly Arg Thr Phe Glu Met Ser Asp
    1985                1990                1995

Phe Ile Val Asp Thr Arg Asp Ala Gly Tyr Gly Gly Ile Ser Leu
    2000                2005                2010

Ala Val Glu Gly Pro Ser Lys Val Asp Ile Gln Thr Glu Asp Leu
    2015                2020                2025

Glu Asp Gly Thr Cys Lys Val Ser Tyr Phe Pro Thr Val Pro Gly
    2030                2035                2040

Val Tyr Ile Val Ser Thr Lys Phe Ala Asp Glu His Val Pro Gly
    2045                2050                2055

Ser Pro Phe Thr Val Lys Ile Ser Gly Glu Gly Arg Val Lys Glu
    2060                2065                2070

Ser Ile Thr Arg Thr Ser Arg Ala Pro Ser Val Ala Thr Val Gly
    2075                2080                2085
```

-continued

Ser Ile Cys Asp Leu Asn Leu Lys Ile Pro Glu Ile Asn Ser Ser
2090            2095            2100

Asp Met Ser Ala His Val Thr Ser Pro Ser Gly Arg Val Thr Glu
2105            2110            2115

Ala Glu Ile Val Pro Met Gly Lys Asn Ser His Cys Val Arg Phe
2120            2125            2130

Val Pro Gln Glu Met Gly Val His Thr Val Ser Val Lys Tyr Arg
2135            2140            2145

Gly Gln His Val Thr Gly Ser Pro Phe Gln Phe Thr Val Gly Pro
2150            2155            2160

Leu Gly Glu Gly Gly Ala His Lys Val Arg Ala Gly Gly Pro Gly
2165            2170            2175

Leu Glu Arg Gly Glu Ala Gly Val Pro Ala Glu Phe Ser Ile Trp
2180            2185            2190

Thr Arg Glu Ala Gly Ala Gly Gly Leu Ser Ile Ala Val Glu Gly
2195            2200            2205

Pro Ser Lys Ala Glu Ile Thr Phe Asp Asp His Lys Asn Gly Ser
2210            2215            2220

Cys Gly Val Ser Tyr Ile Ala Gln Glu Pro Gly Asn Tyr Glu Val
2225            2230            2235

Ser Ile Lys Phe Asn Asp Glu His Ile Pro Glu Ser Pro Tyr Leu
2240            2245            2250

Val Pro Val Ile Ala Pro Ser Asp Asp Ala Arg Arg Leu Thr Val
2255            2260            2265

Met Ser Leu Gln Glu Ser Gly Leu Lys Val Asn Gln Pro Ala Ser
2270            2275            2280

Phe Ala Ile Arg Leu Asn Gly Ala Lys Gly Lys Ile Asp Ala Lys
2285            2290            2295

Val His Ser Pro Ser Gly Ala Val Glu Glu Cys His Val Ser Glu
2300            2305            2310

Leu Glu Pro Asp Lys Tyr Ala Val Arg Phe Ile Pro His Glu Asn
2315            2320            2325

Gly Val His Thr Ile Asp Val Lys Phe Asn Gly Ser His Val Val
2330            2335            2340

Gly Ser Pro Phe Lys Val Arg Val Gly Glu Pro Gly Gln Ala Gly
2345            2350            2355

Asn Pro Ala Leu Val Ser Ala Tyr Gly Thr Gly Leu Glu Gly Gly
2360            2365            2370

Thr Thr Gly Ile Gln Ser Glu Phe Phe Ile Asn Thr Thr Arg Ala
2375            2380            2385

Gly Pro Gly Thr Leu Ser Val Thr Ile Glu Gly Pro Ser Lys Val
2390            2395            2400

Lys Met Asp Cys Gln Glu Thr Pro Glu Gly Tyr Lys Val Met Tyr
2405            2410            2415

Thr Pro Met Ala Pro Gly Asn Tyr Leu Ile Ser Val Lys Tyr Gly
2420            2425            2430

Gly Pro Asn His Ile Val Gly Ser Pro Phe Lys Ala Lys Val Thr
2435            2440            2445

Gly Gln Arg Leu Val Ser Pro Gly Ser Ala Asn Glu Thr Ser Ser
2450            2455            2460

Ile Leu Val Glu Ser Val Thr Arg Ser Ser Thr Glu Thr Cys Tyr
2465            2470            2475

| | | | | | | | | | | | |
|---|---|---|---|---|---|---|---|---|---|---|---|
|Ser|Ala|Ile|Pro|Lys|Ala|Ser|Ser|Asp|Ala|Ser|Lys|Val|Thr|Ser|
| |2480| | | |2485| | | |2490| | | | | |
|Lys|Gly|Ala|Gly|Leu|Ser|Lys|Ala|Phe|Val|Gly|Gln|Lys|Ser|Ser|
| |2495| | | |2500| | | |2505| | | | | |
|Phe|Leu|Val|Asp|Cys|Ser|Lys|Ala|Gly|Ser|Asn|Met|Leu|Leu|Ile|
| |2510| | | |2515| | | |2520| | | | | |
|Gly|Val|His|Gly|Pro|Thr|Thr|Pro|Cys|Glu|Glu|Val|Ser|Met|Lys|
| |2525| | | |2530| | | |2535| | | | | |
|His|Val|Gly|Asn|Gln|Gln|Tyr|Asn|Val|Thr|Tyr|Val|Val|Lys|Glu|
| |2540| | | |2545| | | |2550| | | | | |
|Arg|Gly|Asp|Tyr|Val|Leu|Ala|Val|Lys|Trp|Gly|Glu|Glu|His|Ile|
| |2555| | | |2560| | | |2565| | | | | |
|Pro|Gly|Ser|Pro|Phe|His|Val|Thr|Val|Pro|
| |2570| | | | |2575| | | | |

<210> SEQ ID NO 27
<211> LENGTH: 9395
<212> TYPE: DNA
<213> ORGANISM: Homo sapiens

<400> SEQUENCE: 27

```
gcggccaggg gcgggcggcc gcagagcagc accggccgtg gctccggtag cagcaagttc        60
gaaccccgct cccgctccgc ttcggttctc gctccttcgg cccttgggcc tccaaacacc       120
agtccccggc agctcgttgc gcattgcgct ctccccgcca ccaggatgcc ggtaaccgag       180
aaggatctag ctgaggacgc gccttggaag aagatccagc agaacacgtt cacacgctgg       240
tgcaacgagc acctcaagtg cgtgaacaaa cgcatcggca acctgcagac cgacctgagc       300
gacgggctgc ggctcatcgc gctgctcgag gtgctcagcc agaagcgcat gtaccgcaag       360
taccatcagc ggcccacctt cgccagatgc agctcgaga atgtgtccgt ggcgctcgag        420
ttcctggacc gtgagagcat caagctcgtg tccatcgata gcaaagccat tgtggatggg       480
aacctgaagc tcatcttggg tctggtgtgg acgctgatcc tccactactc catctccatg       540
cccgtgtggg aggatgaagg ggatgatgat gccaagaagc agacgccaaa gcagaggctg       600
ctggggtgga ttcagaacaa gatcccctac ttgcccatca ccaactttaa ccagaactgg       660
caagacggca aagccctggg agccctggta gacagctgtg ctccaggtct gtgcccagac       720
tgggaatcct gggaccgcca gaagcctgtg gataatgcac gagaagccat gcagcaggca       780
gatgactggc tgggtgtccc acaggtcatc actcctgaag aaatcattca cccggatgtg       840
gacgagcact cagttatgac ttacctgtcc cagttcccca agccaagct caagccgggg        900
gctcctctca acccaaaact caacccgaag aaagccaggg cctatggcag aggaatcgag       960
cccactggaa acatggtgaa gcagccagcc aagttcactg tggacaccat cagcgccggg      1020
caaggagacg tgatggtgtt tgttgaggac ccagaaggga caaagagga ggcacaagtg       1080
accccctgaca gtgacaagaa caagacatac tctgtggagt atctgcccaa ggtcaccggg      1140
ctacacaaag tcacagtcct ctttgcagga cagcacatct ccaagagccc atttgaagtg      1200
agtgttgaca ggcccagggg agatgccagt aaagtcactg caaaaggtcc agggttggaa      1260
gctgtaggga catcgccaa taagcccacc tactttgaca tctatacggc aggagctggt       1320
gtgggtgaca ttggtgtgga ggtggaagat ccccagggga gaacaccgt ggagttgctc        1380
gtggaagaca aggaaaccca ggtgtatcga tgtgtgtaca aacccatgca gcctggcccct      1440
cacgtggtca agatcttctt tgctggggac actattccta gagtcccctt cgttgtgcag      1500
```

-continued

```
gttgggaag cctgcaatcc aaatgcctgc cgggccagtg gccgaggcct acaacccaaa  1560
ggcgtccgta tccgggagac cacagatttc aaggttgaca ccaaagctgc aggaagtggg  1620
gagctcggtg taaccatgaa gggtcctaag ggtctggagg agctggtgaa gcagaaagac  1680
tttctggatg gggtctacgc attcgagtat taccccagca ccccggggag atacagcatt  1740
gccatcacat ggggggggaca ccacattcca aagagcccct ttgaagttca agttggccct  1800
gaagcgggta tgcagaaagt ccgtgcttgg ggccctgggc tccatggtgg gattgtcggg  1860
cggtcagcgg acttcgtggt agaatccatt ggctctgaag tggggtctct ggggttttgcc  1920
attgaaggcc cctctcaggc aaagattgag tacaacgacc agaatgatgg atcgtgtgat  1980
gtcaaatact ggcccaagga gcctggcgaa tatgctgttc acatcatgtg tgacgacgaa  2040
gacatcaagg acagcccgta catggccttc atccacccag ccacgggagg ctacaaccct  2100
gatctggttc gagcatacgg gccaggtttg gagaaatctg gatgcattgt caacaacctg  2160
gccgagttca ctgtggatcc taaggatgct ggaaaagctc ccttaaagat atttgctcag  2220
gatggggaag ccaacgcat tgacatccag atgaagaacc ggatggacgg cacatatgca  2280
tgctcataca ccccggtgaa ggccatcaag cacaccattg ctgtggtctg gggaggcgtg  2340
aacatcccgc acagccccta cagggtcaac atcgggcaag tagccatcc tcagaaggtc  2400
aaagtgtttg gccaggtgt ggagagaagt ggtctgaagg caaatgaacc tacacacttc  2460
acggtggact gtactgaggc tgggaaggt gatgtcagtt ttggcattaa gtgtgatgcc  2520
cgggtgttaa gtgaagatga ggaagacgtg gattttgaca ttattcacaa tgccaatgat  2580
acgttcacag tcaaatatgt gcctcctgct gctgggcgat acactatcaa agttctcttt  2640
gcatctcagg aaatccccgc cagcccttc agagtcaaag ttgacccttc ccacgatgcc  2700
agcaaagtga aggcagaagg cccagggctc agcaaagcag gtgtggaaaa tgggaaaccg  2760
acccacttca ctgtctacac caaggggggct gggaaagccc cgctcaacgt gcagttcaac  2820
agccctcttc ctggcgatgc agtgaaggat ttggatatca tcgataatta tgactactct  2880
cacacggtta aatatacacc cacccaacag gcaacatgc aggttctggt gacttacggt  2940
ggcgatccca tccctaaaag ccctttcact gtgggtgttg ctgcaccgct ggatctgagc  3000
aagataaaac tcaatgggct ggaaaacagg gtggaagttg gaaggatca ggagttcacc  3060
gttgatacca ggggggcagg aggccagggg aagctggacg tgacaatcct cagcccctct  3120
cggaaggtcg tgccatgcct agtgacacct gtgacaggcc gggagaacag cacggccaag  3180
ttcatccctc gggaggaggg gctgtatgct gtagacgtga cctacgatgg acaccctgtg  3240
cccgggagcc cctacacagt ggaggcctcg ctgccaccag atcccagcaa ggtgaaggcc  3300
cacggtcccg gcctcgaagg tggtctcgtg ggcaagcctg ccgagttcac catcgatacc  3360
aaaggagctg gtactggagg tctgggctta acggtggaag gtccgtgcga ggccaaaatc  3420
gagtgctccg acaatggtga tgggacctgc tccgtctctt accttcccac aaaacccggg  3480
gagtacttcg tcaacatcct ctttgaagaa gtccacatac ctgggtctcc cttcaaagct  3540
gacattgaaa tgcccttga ccctctaaa gtcgtggcat cggggccagg tctcgagcac  3600
gggaaggtgg gtgaagctgg cctccttagc gtcgactgct cggaagcggg accggggcc  3660
ctgggcctgg aagctgtctc ggactcggga acaaaagccg aagtcagtat tcagaacaac  3720
aaagatggca cctacgcggt gacctacgtg cccctgacgg ccggcatgta cacgttgacc  3780
atgaagtatg gtgcgaact cgtgccacac ttccccgccc gggtcaaggt ggagcccgcc  3840
gtggacacca gcaggatcaa agtctttgga ccaggaatag aagggaaaga tgtgttccgg  3900
```

```
gaagctacca ccgactttac agttgactct cggccgctga cccaggttgg gggtgaccac   3960
atcaaggccc acattgccaa cccctcaggg gcctccaccg agtgctttgt cacagacaat   4020
gcggatggga cctaccaggt ggaatacaca cccttttgaga aggtctcca tgtagtggag   4080 gtgacatatg atgacgtgcc tatcccaaac agtcccttca aggtggctgt cactgaaggc   4140
tgccagccat ctagggtgca agcccaagga cctggattga agaggcctt taccaacaag   4200 cccaatgtct tcaccgtggt taccagaggc gcaggaattg gtgggcttgg cataactgtt   4260
gagggaccat cagagtcgaa gataaattgc agagacaaca aggatggcag ctgcagtgct   4320
gagtacattc ctttcgcacc gggggattac gatgttaata tcacatatgg aggagcccac   4380
atccccggca gccccttcag ggttcctgtg aaggatgttg tggaccccag caaggtcaag   4440
attgccggcc ccgggctggg ctcaggcgtc cgagcccgtg tcctgcagtc cttcacggtg   4500
gacagcagca aggctggcct ggctccgctg gaagtgaggg ttctgggccc acgaggcttg   4560
gtggagccag tgaacgtggt ggacaatgga gatggcacac acacagtaac ctacacccca   4620
tctcaggagg gaccttacat ggtctcagtt aaatatgctg atgaagagat tcctcgcagt   4680
cccttcaagg tcaaggtcct tcccacatat gatgccagca agtgactgc cagtggcccc   4740 ggccttagtt cctatggtgt gcctgccagt ctacctgtgg actttgcaat tgatgcccga   4800
gatgccgggg aaggcctgct tgctgttcaa ataacggacc aagaaggaaa acccaaaaga   4860
gccattgtcc atgacaataa agatggcacg tatgctgtca cctacatccc cgacaagact   4920
gggcgctata tgattggagt cacctacggg ggtgacgaca tcccactttc tccttatcgc   4980
atccgagcca cacagacggg tgatgccagc aagtgcctgg ccacgggtcc tggaatcgcc   5040
tccactgtga aaactggcga agaagtaggc tttgtggttg atgccaagac tgccgggaag   5100
ggtaaagtga cctgcacggt tctgacccca gatggcactg aggccgaggc cgatgtcatt   5160
gagaatgaag atggaaccta tgacatcttc tacacagctg ccaagccggg cacatatgtg   5220
atctatgtgc gcttcggtgg tgttgatatt cctaacagcc ccttcactgt catggtgacc   5280
gaagaggcct atgtcccagt gagtgacatg aacggcctgg gatttaagcc ttttgacctg   5340
gtcattccgt ttgctgtcag gaaaggagaa atcactggag aggtccacat gccttctggg   5400
aagacagcca cacctgagat tgtgacaac aaggacggca cggtcactgt tagatatgcc   5460
cccactgagg tcgggctcca tgagatgcac atcaaataca tgggcagcca catccctgag   5520
agcccactcc agttctacgt gaactacccc aacagtggaa gtgtttctgc atacggtcca   5580
ggcctcgtgt atgagtggc caacaaaact gccaccttca ccatcgtcac agaggatgca   5640
ggagaaggtg gtctggactt ggctattgag ggcccctcaa aagcagaaat cagctgcatt   5700
gacaataaag atgggacatg cacagtgacc tacctgccga ctctgccagg cgactacagc   5760
attctggtca agtacaatga caagcacatc cctggcagcc ccttcacagc caagatcaca   5820
gatgacagca ggcggtgctc ccaggtgaag ttgggctcag ccgctgactt cctgctcgac   5880
atcagtgaga ctgacctcag cagcctgacg gccagcatta aggcccatc tggccgagac   5940 gagccctgtc tcctgaagag gctgcccaac aaccacattg gcatctcctt catccccgg   6000 gaagtgggcg aacatctggt cagcatcaag aaaaatggca accatgtggc caacagcccc   6060
gtgtctatca tggtggtcca gtcggagatt ggtgacgccc gccgagccaa agtctatggc   6120
cgcggcctgt cagaaggccg gactttcgag atgtctgact tcatcgtgga cacaagggat   6180
gcaggttatg gtggcatatc cttggcggtg gaaggcccca gcaaagtgga catccagacg   6240
```

```
gaggacctgg aagatggcac ctgcaaagtc tcctacttcc ctaccgtgcc tggggtttat   6300
atcgtctcca ccaaattcgc tgacgagcac gtgcctggga gcccatttac cgtgaagatc   6360
agtggggagg gaagagtcaa agagagcatc acccgcacca gtcgggcccc gtccgtggcc   6420
actgtcggga gcatttgtga cctgaacctg aaaatcccag aaatcaacag cagtgatatg   6480
tcggcccacg tcaccagccc ctctggccgt gtgactgagg cagagattgt gcccatgggg   6540
aagaactcac actgcgtccg gtttgtgccc caggagatgg gcgtgcacac ggtcagcgtc   6600
aagtaccgtg ggcagcacgt caccggcagc cccttccagt tcaccgtggg gccacttggt   6660
gaaggaggcg cccacaaggt gcgggcagga ggccctggcc tggagagagg agaagcggga   6720
gtcccagctg agttcagcat ttggacccgg gaagcaggcg ctggaggcct ctccatcgct   6780
gttgagggcc ccagtaaggc cgagattaca ttcgatgacc ataaaaatgg gtcgtgcggt   6840
gtatcttata ttgcccaaga gcctggtaac tacgaggtgt ccatcaagtt caatgatgag   6900
cacatcccgg aaagccccta cctggtgccg gtcatcgcac cctccgacga cgcccgccgc   6960
ctcactgtta tgagccttca ggaatcggga ttaaaagtta accagccagc atcctttgct   7020
ataaggttga atggcgcaaa aggcaagatt gatgcaaagg tgcacagccc ctctggagcc   7080
gtggaggagt gccacgtgtc tgagctggag ccagataagt atgctgttcg cttcatccct   7140
catgagaatg gtgtccacac catcgatgtc aagttcaatg ggagccacgt ggttggaagc   7200
cccttcaaag tgcgcgttgg ggagcctgga caagcgggga accctgccct ggtgtccgcc   7260
tatggcacgg gactcgaagg gggcaccaca ggtatccagt cggaattctt tattaacacc   7320
acccgagcag gtccagggac attatccgtc accatcgaag gcccatccaa ggttaaaatg   7380
gattgccagg aaacacctga agggtacaaa gtcatgtaca cccccatggc tcctggtaac   7440
tacctgatca gcgtcaaata cggtgggccc aaccacatcg tgggcagtcc cttcaaggcc   7500
aaggtgacag gccagcgtct agttagccct ggctcagcca acgagacctc atccatcctg   7560
gtggagtcag tgaccaggtc gtctacagag acctgctata gcgccattcc caaggcatcc   7620
tcggacgcca gcaaggtgac ctctaagggg gcagggctct caaaggcctt tgtgggccag   7680
aagagttcct tcctggtgga ctgcagcaaa gctggctcca acatgctgct gatcggggtc   7740
catgggccca ccaccccctg cgaggaggtc tccatgaagc atgtaggcaa ccagcaatac   7800
aacgtcacat acgtcgtcaa ggagaggggc gattatgtgc tggctgtgaa gtgggggggag   7860 gaacacatcc ctggcagccc ttttcatgtc acagtgcctt aaaacagttt tctcaaatcc   7920
tggagagagt tcttgtggtt gcttttgttg cttgtttgta attcatttta tacaaagccc   7980
tccagcctgt ttgtggggct gaaaccccat ccctaaaata ttgctgttgt aaaatgcctt   8040
cagaaataag tcctagactg gactcttgag ggacatattg gagaatctta agaaatgcaa   8100
gcttgttcag ggggctgaga agatcctgag tacactaggt gcaaaccaga actcttggtg   8160
gaacagacca gccactgcag cagacagacc aggaacacaa tgagactgac atttcaaaaa   8220
aacaaaactg gctagcctga gctgctggtt cactcttcag catttatgaa acaaggctag   8280
gggaagatgg gcagagaaaa aggggacacc tagtttggtt gtcatttggc aaaggagatg   8340
acttaaaatc cgcttaatct cttccagtgt ccgtgttaat gtatttggct attagatcac   8400
tagcactgct ttaccgctcc tcatcgccaa cacccccatg ctctgtggcc ttcttacact   8460
tctcagaggg cagagtggca gccgggcacc ctacagaaac tcagagggca gagtggcagc   8520
caggcccaca tgtctctcaa gtacctgtcc cctcgctctg gtgattattt cttgcagaat   8580
caccacacga gaccatcccg gcagtcatgg ttttgcttta gttttccaag tccgtttcag   8640
```

-continued

```
tcccttcctt ggtctgaaga aattctgcag tggcgagcag tttcccactt gccaaagatc    8700 cctttaacc aacactagcc cttgtttta acacacgctc cagcccttca tcagcctggg    8760
cagtcttacc aaaatgttta aagtgatctc agaggggccc atggattaac gccctcatcc    8820
caaggtccgt cccatgacat aacactccac acccgcccca gccaacttca tgggtcactt    8880
tttctggaaa ataatgatct gtacagacag gacagaatga aactcctgcg ggtctttggc    8940
ctgaaagttg ggaatggttg ggggagagaa gggcagcagc ttattggtgg tcttttcacc    9000
attggcagaa acagtgagag ctgtgtggtg cagaaatcca gaaatgaggt gtagggaatt    9060
ttgcctgcct tcctgcagac ctgagctggc tttggaatga ggttaaagtg tcagggacgt    9120
tgcctgagcc caaatgtgta gtgtggtctg gcaggcaga cctttaggtt ttgctgctta    9180
gtcctgagga agtggccact cttgtggcag gtgtagtatc tggggcgagt gttgggggta    9240
aaagcccacc ctacagaaag tggaacagcc cggagcctga tgtgaaagga ccacgggtgt    9300
tgtaagctgg gacacggaag ccaaactgga atcaaacgcc gactgtaaat tgtatcttat    9360
aacttattaa ataaaacatt tgctccgtaa agttg                               9395
```

<210> SEQ ID NO 28
<211> LENGTH: 2602
<212> TYPE: PRT
<213> ORGANISM: Homo sapiens

<400> SEQUENCE: 28

```
Met Pro Val Thr Glu Lys Asp Leu Ala Glu Asp Ala Pro Trp Lys Lys
1               5                   10                  15

Ile Gln Gln Asn Thr Phe Thr Arg Trp Cys Asn Glu His Leu Lys Cys
            20                  25                  30

Val Asn Lys Arg Ile Gly Asn Leu Gln Thr Asp Leu Ser Asp Gly Leu
        35                  40                  45

Arg Leu Ile Ala Leu Leu Glu Val Leu Ser Gln Lys Arg Met Tyr Arg
    50                  55                  60

Lys Tyr His Gln Arg Pro Thr Phe Arg Gln Met Gln Leu Glu Asn Val
65                  70                  75                  80

Ser Val Ala Leu Glu Phe Leu Asp Arg Glu Ser Ile Lys Leu Val Ser
                85                  90                  95

Ile Asp Ser Lys Ala Ile Val Asp Gly Asn Leu Lys Leu Ile Leu Gly
            100                 105                 110

Leu Val Trp Thr Leu Ile Leu His Tyr Ser Ile Ser Met Pro Val Trp
        115                 120                 125

Glu Asp Glu Gly Asp Asp Asp Ala Lys Lys Gln Thr Pro Lys Gln Arg
    130                 135                 140

Leu Leu Gly Trp Ile Gln Asn Lys Ile Pro Tyr Leu Pro Ile Thr Asn
145                 150                 155                 160

Phe Asn Gln Asn Trp Gln Asp Gly Lys Ala Leu Gly Ala Leu Val Asp
                165                 170                 175

Ser Cys Ala Pro Gly Leu Cys Pro Asp Trp Glu Ser Trp Asp Pro Gln
            180                 185                 190

Lys Pro Val Asp Asn Ala Arg Glu Ala Met Gln Ala Asp Asp Trp
            195                 200                 205

Leu Gly Val Pro Gln Val Ile Thr Pro Glu Glu Ile Ile His Pro Asp
    210                 215                 220

Val Asp Glu His Ser Val Met Thr Tyr Leu Ser Gln Phe Pro Lys Ala
225                 230                 235                 240
```

```
Lys Leu Lys Pro Gly Ala Pro Leu Lys Pro Lys Leu Asn Pro Lys Lys
                245                 250                 255

Ala Arg Ala Tyr Gly Arg Gly Ile Glu Pro Thr Gly Asn Met Val Lys
                260                 265                 270

Gln Pro Ala Lys Phe Thr Val Asp Thr Ile Ser Ala Gly Gln Gly Asp
            275                 280                 285

Val Met Val Phe Val Glu Asp Pro Glu Gly Asn Lys Glu Glu Ala Gln
        290                 295                 300

Val Thr Pro Asp Ser Asp Lys Asn Lys Thr Tyr Ser Val Glu Tyr Leu
305                 310                 315                 320

Pro Lys Val Thr Gly Leu His Lys Val Thr Val Leu Phe Ala Gly Gln
                325                 330                 335

His Ile Ser Lys Ser Pro Phe Glu Val Ser Val Asp Lys Ala Gln Gly
                340                 345                 350

Asp Ala Ser Lys Val Thr Ala Lys Gly Pro Gly Leu Glu Ala Val Gly
            355                 360                 365

Asn Ile Ala Asn Lys Pro Thr Tyr Phe Asp Ile Tyr Thr Ala Gly Ala
370                 375                 380

Gly Val Gly Asp Ile Gly Val Glu Val Glu Asp Pro Gln Gly Lys Asn
385                 390                 395                 400

Thr Val Glu Leu Leu Val Glu Asp Lys Gly Asn Gln Val Tyr Arg Cys
                405                 410                 415

Val Tyr Lys Pro Met Gln Pro Gly Pro His Val Val Lys Ile Phe Phe
                420                 425                 430

Ala Gly Asp Thr Ile Pro Lys Ser Pro Phe Val Val Gln Val Gly Glu
            435                 440                 445

Ala Cys Asn Pro Asn Ala Cys Arg Ala Ser Gly Arg Gly Leu Gln Pro
450                 455                 460

Lys Gly Val Arg Ile Arg Glu Thr Thr Asp Phe Lys Val Asp Thr Lys
465                 470                 475                 480

Ala Ala Gly Ser Gly Glu Leu Gly Val Thr Met Lys Gly Pro Lys Gly
                485                 490                 495

Leu Glu Glu Leu Val Lys Gln Lys Asp Phe Leu Asp Gly Val Tyr Ala
                500                 505                 510

Phe Glu Tyr Tyr Pro Ser Thr Pro Gly Arg Tyr Ser Ile Ala Ile Thr
            515                 520                 525

Trp Gly Gly His His Ile Pro Lys Ser Pro Phe Glu Val Gln Val Gly
530                 535                 540

Pro Glu Ala Gly Met Gln Lys Val Arg Ala Trp Gly Pro Gly Leu His
545                 550                 555                 560

Gly Gly Ile Val Gly Arg Ser Ala Asp Phe Val Val Glu Ser Ile Gly
                565                 570                 575

Ser Glu Val Gly Ser Leu Gly Phe Ala Ile Glu Gly Pro Ser Gln Ala
            580                 585                 590

Lys Ile Glu Tyr Asn Asp Gln Asn Asp Gly Ser Cys Asp Val Lys Tyr
                595                 600                 605

Trp Pro Lys Glu Pro Gly Glu Tyr Ala Val His Ile Met Cys Asp Asp
                610                 615                 620

Glu Asp Ile Lys Asp Ser Pro Tyr Met Ala Phe Ile His Pro Ala Thr
625                 630                 635                 640

Gly Gly Tyr Asn Pro Asp Leu Val Arg Ala Tyr Gly Pro Gly Leu Glu
                645                 650                 655
```

-continued

```
Lys Ser Gly Cys Ile Val Asn Asn Leu Ala Glu Phe Thr Val Asp Pro
            660                 665                 670

Lys Asp Ala Gly Lys Ala Pro Leu Lys Ile Phe Ala Gln Asp Gly Glu
        675                 680                 685

Gly Gln Arg Ile Asp Ile Gln Met Lys Asn Arg Met Asp Gly Thr Tyr
    690                 695                 700

Ala Cys Ser Tyr Thr Pro Val Lys Ala Ile Lys His Thr Ile Ala Val
705                 710                 715                 720

Val Trp Gly Gly Val Asn Ile Pro His Ser Pro Tyr Arg Val Asn Ile
                725                 730                 735

Gly Gln Gly Ser His Pro Gln Lys Val Lys Val Phe Gly Pro Gly Val
            740                 745                 750

Glu Arg Ser Gly Leu Lys Ala Asn Glu Pro Thr His Phe Thr Val Asp
        755                 760                 765

Cys Thr Glu Ala Gly Glu Gly Asp Val Ser Val Gly Ile Lys Cys Asp
    770                 775                 780

Ala Arg Val Leu Ser Glu Asp Glu Asp Val Asp Phe Asp Ile Ile
785                 790                 795                 800

His Asn Ala Asn Asp Thr Phe Thr Val Lys Tyr Val Pro Pro Ala Ala
                805                 810                 815

Gly Arg Tyr Thr Ile Lys Val Leu Phe Ala Ser Gln Glu Ile Pro Ala
            820                 825                 830

Ser Pro Phe Arg Val Lys Val Asp Pro Ser His Asp Ala Ser Lys Val
        835                 840                 845

Lys Ala Glu Gly Pro Gly Leu Ser Lys Ala Gly Val Glu Asn Gly Lys
    850                 855                 860

Pro Thr His Phe Thr Val Tyr Thr Lys Gly Ala Gly Lys Ala Pro Leu
865                 870                 875                 880

Asn Val Gln Phe Asn Ser Pro Leu Pro Gly Asp Ala Val Lys Asp Leu
                885                 890                 895

Asp Ile Ile Asp Asn Tyr Asp Tyr Ser His Thr Val Lys Tyr Thr Pro
            900                 905                 910

Thr Gln Gln Gly Asn Met Gln Val Leu Val Thr Tyr Gly Gly Asp Pro
        915                 920                 925

Ile Pro Lys Ser Pro Phe Thr Val Gly Val Ala Ala Pro Leu Asp Leu
    930                 935                 940

Ser Lys Ile Lys Leu Asn Gly Leu Glu Asn Arg Val Glu Val Gly Lys
945                 950                 955                 960

Asp Gln Glu Phe Thr Val Asp Thr Arg Gly Ala Gly Gly Gln Gly Lys
                965                 970                 975

Leu Asp Val Thr Ile Leu Ser Pro Ser Arg Lys Val Val Pro Cys Leu
            980                 985                 990

Val Thr Pro Val Thr Gly Arg Glu Asn Ser Thr Ala Lys Phe Ile Pro
        995                 1000                1005

Arg Glu Glu Gly Leu Tyr Ala Val Asp Val Thr Tyr Asp Gly His
    1010                1015                1020

Pro Val Pro Gly Ser Pro Tyr Thr Val Glu Ala Ser Leu Pro Pro
    1025                1030                1035

Asp Pro Ser Lys Val Lys Ala His Gly Pro Gly Leu Glu Gly Gly
    1040                1045                1050

Leu Val Gly Lys Pro Ala Glu Phe Thr Ile Asp Thr Lys Gly Ala
    1055                1060                1065

Gly Thr Gly Gly Leu Gly Leu Thr Val Glu Gly Pro Cys Glu Ala
```

-continued

```
            1070                1075               1080
Lys Ile Glu Cys Ser Asp Asn Gly Asp Gly Thr Cys Ser Val Ser
            1085                1090               1095

Tyr Leu Pro Thr Lys Pro Gly Glu Tyr Phe Val Asn Ile Leu Phe
            1100                1105               1110

Glu Glu Val His Ile Pro Gly Ser Pro Phe Lys Ala Asp Ile Glu
            1115                1120               1125

Met Pro Phe Asp Pro Ser Lys Val Val Ala Ser Gly Pro Gly Leu
            1130                1135               1140

Glu His Gly Lys Val Gly Glu Ala Gly Leu Leu Ser Val Asp Cys
            1145                1150               1155

Ser Glu Ala Gly Pro Gly Ala Leu Gly Leu Glu Ala Val Ser Asp
            1160                1165               1170

Ser Gly Thr Lys Ala Glu Val Ser Ile Gln Asn Asn Lys Asp Gly
            1175                1180               1185

Thr Tyr Ala Val Thr Tyr Val Pro Leu Thr Ala Gly Met Tyr Thr
            1190                1195               1200

Leu Thr Met Lys Tyr Gly Gly Glu Leu Val Pro His Phe Pro Ala
            1205                1210               1215

Arg Val Lys Val Glu Pro Ala Val Asp Thr Ser Arg Ile Lys Val
            1220                1225               1230

Phe Gly Pro Gly Ile Glu Gly Lys Asp Val Phe Arg Glu Ala Thr
            1235                1240               1245

Thr Asp Phe Thr Val Asp Ser Arg Pro Leu Thr Gln Val Gly Gly
            1250                1255               1260

Asp His Ile Lys Ala His Ile Ala Asn Pro Ser Gly Ala Ser Thr
            1265                1270               1275

Glu Cys Phe Val Thr Asp Asn Ala Asp Gly Thr Tyr Gln Val Glu
            1280                1285               1290

Tyr Thr Pro Phe Glu Lys Gly Leu His Val Val Glu Val Thr Tyr
            1295                1300               1305

Asp Asp Val Pro Ile Pro Asn Ser Pro Phe Lys Val Ala Val Thr
            1310                1315               1320

Glu Gly Cys Gln Pro Ser Arg Val Gln Ala Gln Gly Pro Gly Leu
            1325                1330               1335

Lys Glu Ala Phe Thr Asn Lys Pro Asn Val Phe Thr Val Val Thr
            1340                1345               1350

Arg Gly Ala Gly Ile Gly Gly Leu Gly Ile Thr Val Glu Gly Pro
            1355                1360               1365

Ser Glu Ser Lys Ile Asn Cys Arg Asp Asn Lys Asp Gly Ser Cys
            1370                1375               1380

Ser Ala Glu Tyr Ile Pro Phe Ala Pro Gly Asp Tyr Asp Val Asn
            1385                1390               1395

Ile Thr Tyr Gly Gly Ala His Ile Pro Gly Ser Pro Phe Arg Val
            1400                1405               1410

Pro Val Lys Asp Val Val Asp Pro Ser Lys Val Lys Ile Ala Gly
            1415                1420               1425

Pro Gly Leu Gly Ser Gly Val Arg Ala Arg Val Leu Gln Ser Phe
            1430                1435               1440

Thr Val Asp Ser Ser Lys Ala Gly Leu Ala Pro Leu Glu Val Arg
            1445                1450               1455

Val Leu Gly Pro Arg Gly Leu Val Glu Pro Val Asn Val Val Asp
            1460                1465               1470
```

```
Asn Gly Asp Gly Thr His Thr Val Thr Tyr Thr Pro Ser Gln Glu
    1475            1480                1485

Gly Pro Tyr Met Val Ser Val Lys Tyr Ala Asp Glu Glu Ile Pro
    1490            1495                1500

Arg Ser Pro Phe Lys Val Lys Val Leu Pro Thr Tyr Asp Ala Ser
    1505            1510                1515

Lys Val Thr Ala Ser Gly Pro Gly Leu Ser Ser Tyr Gly Val Pro
    1520            1525                1530

Ala Ser Leu Pro Val Asp Phe Ala Ile Asp Ala Arg Asp Ala Gly
    1535            1540                1545

Glu Gly Leu Leu Ala Val Gln Ile Thr Asp Gln Glu Gly Lys Pro
    1550            1555                1560

Lys Arg Ala Ile Val His Asp Asn Lys Asp Gly Thr Tyr Ala Val
    1565            1570                1575

Thr Tyr Ile Pro Asp Lys Thr Gly Arg Tyr Met Ile Gly Val Thr
    1580            1585                1590

Tyr Gly Gly Asp Asp Ile Pro Leu Ser Pro Tyr Arg Ile Arg Ala
    1595            1600                1605

Thr Gln Thr Gly Asp Ala Ser Lys Cys Leu Ala Thr Gly Pro Gly
    1610            1615                1620

Ile Ala Ser Thr Val Lys Thr Gly Glu Glu Val Gly Phe Val Val
    1625            1630                1635

Asp Ala Lys Thr Ala Gly Lys Gly Lys Val Thr Cys Thr Val Leu
    1640            1645                1650

Thr Pro Asp Gly Thr Glu Ala Glu Ala Asp Val Ile Glu Asn Glu
    1655            1660                1665

Asp Gly Thr Tyr Asp Ile Phe Tyr Thr Ala Ala Lys Pro Gly Thr
    1670            1675                1680

Tyr Val Ile Tyr Val Arg Phe Gly Gly Val Asp Ile Pro Asn Ser
    1685            1690                1695

Pro Phe Thr Val Met Ala Thr Asp Gly Glu Val Thr Ala Val Glu
    1700            1705                1710

Glu Ala Pro Val Asn Ala Cys Pro Pro Gly Phe Arg Pro Trp Val
    1715            1720                1725

Thr Glu Glu Ala Tyr Val Pro Val Ser Asp Met Asn Gly Leu Gly
    1730            1735                1740

Phe Lys Pro Phe Asp Leu Val Ile Pro Phe Ala Val Arg Lys Gly
    1745            1750                1755

Glu Ile Thr Gly Glu Val His Met Pro Ser Gly Lys Thr Ala Thr
    1760            1765                1770

Pro Glu Ile Val Asp Asn Lys Asp Gly Thr Val Thr Val Arg Tyr
    1775            1780                1785

Ala Pro Thr Glu Val Gly Leu His Glu Met His Ile Lys Tyr Met
    1790            1795                1800

Gly Ser His Ile Pro Glu Ser Pro Leu Gln Phe Tyr Val Asn Tyr
    1805            1810                1815

Pro Asn Ser Gly Ser Val Ser Ala Tyr Gly Pro Gly Leu Val Tyr
    1820            1825                1830

Gly Val Ala Asn Lys Thr Ala Thr Phe Thr Ile Val Thr Glu Asp
    1835            1840                1845

Ala Gly Glu Gly Gly Leu Asp Leu Ala Ile Glu Gly Pro Ser Lys
    1850            1855                1860
```

```
Ala Glu Ile Ser Cys Ile Asp Asn Lys Asp Gly Thr Cys Thr Val
1865                1870                1875

Thr Tyr Leu Pro Thr Leu Pro Gly Asp Tyr Ser Ile Leu Val Lys
1880                1885                1890

Tyr Asn Asp Lys His Ile Pro Gly Ser Pro Phe Thr Ala Lys Ile
1895                1900                1905

Thr Asp Asp Ser Arg Arg Cys Ser Gln Val Lys Leu Gly Ser Ala
1910                1915                1920

Ala Asp Phe Leu Leu Asp Ile Ser Glu Thr Asp Leu Ser Ser Leu
1925                1930                1935

Thr Ala Ser Ile Lys Ala Pro Ser Gly Arg Asp Glu Pro Cys Leu
1940                1945                1950

Leu Lys Arg Leu Pro Asn Asn His Ile Gly Ile Ser Phe Ile Pro
1955                1960                1965

Arg Glu Val Gly Glu His Leu Val Ser Ile Lys Lys Asn Gly Asn
1970                1975                1980

His Val Ala Asn Ser Pro Val Ser Ile Met Val Val Gln Ser Glu
1985                1990                1995

Ile Gly Asp Ala Arg Arg Ala Lys Val Tyr Gly Arg Gly Leu Ser
2000                2005                2010

Glu Gly Arg Thr Phe Glu Met Ser Asp Phe Ile Val Asp Thr Arg
2015                2020                2025

Asp Ala Gly Tyr Gly Gly Ile Ser Leu Ala Val Glu Gly Pro Ser
2030                2035                2040

Lys Val Asp Ile Gln Thr Glu Asp Leu Glu Asp Gly Thr Cys Lys
2045                2050                2055

Val Ser Tyr Phe Pro Thr Val Pro Gly Val Tyr Ile Val Ser Thr
2060                2065                2070

Lys Phe Ala Asp Glu His Val Pro Gly Ser Pro Phe Thr Val Lys
2075                2080                2085

Ile Ser Gly Glu Gly Arg Val Lys Glu Ser Ile Thr Arg Thr Ser
2090                2095                2100

Arg Ala Pro Ser Val Ala Thr Val Gly Ser Ile Cys Asp Leu Asn
2105                2110                2115

Leu Lys Ile Pro Glu Ile Asn Ser Ser Asp Met Ser Ala His Val
2120                2125                2130

Thr Ser Pro Ser Gly Arg Val Thr Glu Ala Glu Ile Val Pro Met
2135                2140                2145

Gly Lys Asn Ser His Cys Val Arg Phe Val Pro Gln Glu Met Gly
2150                2155                2160

Val His Thr Val Ser Val Lys Tyr Arg Gly Gln His Val Thr Gly
2165                2170                2175

Ser Pro Phe Gln Phe Thr Val Gly Pro Leu Gly Glu Gly Gly Ala
2180                2185                2190

His Lys Val Arg Ala Gly Gly Pro Gly Leu Glu Arg Gly Glu Ala
2195                2200                2205

Gly Val Pro Ala Glu Phe Ser Ile Trp Thr Arg Glu Ala Gly Ala
2210                2215                2220

Gly Gly Leu Ser Ile Ala Val Glu Gly Pro Ser Lys Ala Glu Ile
2225                2230                2235

Thr Phe Asp Asp His Lys Asn Gly Ser Cys Gly Val Ser Tyr Ile
2240                2245                2250

Ala Gln Glu Pro Gly Asn Tyr Glu Val Ser Ile Lys Phe Asn Asp
```

-continued

| | 2255 | | | | 2260 | | | | 2265 | | |
|---|---|---|---|---|---|---|---|---|---|---|---|

Glu His Ile Pro Glu Ser Pro Tyr Leu Val Pro Val Ile Ala Pro
     2270                      2275                      2280

Ser Asp Asp Ala Arg Arg Leu Thr Val Met Ser Leu Gln Glu Ser
     2285                      2290                      2295

Gly Leu Lys Val Asn Gln Pro Ala Ser Phe Ala Ile Arg Leu Asn
     2300                      2305                      2310

Gly Ala Lys Gly Lys Ile Asp Ala Lys Val His Ser Pro Ser Gly
     2315                      2320                      2325

Ala Val Glu Glu Cys His Val Ser Glu Leu Gly Pro Asp Lys Tyr
     2330                      2335                      2340

Ala Val Arg Phe Ile Pro His Glu Asn Gly Val His Thr Ile Asp
     2345                      2350                      2355

Val Lys Phe Asn Gly Ser His Val Val Gly Ser Pro Phe Lys Val
     2360                      2365                      2370

Arg Val Gly Glu Pro Gly Gln Ala Gly Asn Pro Ala Leu Val Ser
     2375                      2380                      2385

Ala Tyr Gly Thr Gly Leu Glu Gly Gly Thr Thr Gly Ile Gln Ser
     2390                      2395                      2400

Glu Phe Phe Ile Asn Thr Thr Arg Ala Gly Pro Gly Thr Leu Ser
     2405                      2410                      2415

Val Thr Ile Glu Gly Pro Ser Lys Val Lys Met Asp Cys Gln Glu
     2420                      2425                      2430

Thr Pro Glu Gly Tyr Lys Val Met Tyr Thr Pro Met Ala Pro Gly
     2435                      2440                      2445

Asn Tyr Leu Ile Ser Val Lys Tyr Gly Gly Pro Asn His Ile Val
     2450                      2455                      2460

Gly Ser Pro Phe Lys Ala Lys Val Thr Gly Gln Arg Leu Val Ser
     2465                      2470                      2475

Pro Gly Ser Ala Asn Glu Thr Ser Ser Ile Leu Val Glu Ser Val
     2480                      2485                      2490

Thr Arg Ser Ser Thr Glu Thr Cys Tyr Ser Ala Ile Pro Lys Ala
     2495                      2500                      2505

Ser Ser Asp Ala Ser Lys Val Thr Ser Lys Gly Ala Gly Leu Ser
     2510                      2515                      2520

Lys Ala Phe Val Gly Gln Lys Ser Ser Phe Leu Val Asp Cys Ser
     2525                      2530                      2535

Lys Ala Gly Ser Asn Met Leu Leu Ile Gly Val His Gly Pro Thr
     2540                      2545                      2550

Thr Pro Cys Glu Glu Val Ser Met Lys His Val Gly Asn Gln Gln
     2555                      2560                      2565

Tyr Asn Val Thr Tyr Val Val Lys Glu Arg Gly Asp Tyr Val Leu
     2570                      2575                      2580

Ala Val Lys Trp Gly Glu Glu His Ile Pro Gly Ser Pro Phe His
     2585                      2590                      2595

Val Thr Val Pro
     2600

<210> SEQ ID NO 29
<211> LENGTH: 9467
<212> TYPE: DNA
<213> ORGANISM: Homo sapiens

<400> SEQUENCE: 29

| | |
|---|---:|
| gcggccaggg gcgggcggcc gcagagcagc accggccgtg gctccggtag cagcaagttc | 60 |
| gaacccegct ccegcteege ttcggttete getecttegg ccettgggee tecaaacace | 120 |
| agtccccggc agctcgttgc gcattgcgct ctccccgcca ccaggatgcc ggtaaccgag | 180 |
| aaggatctag ctgaggacgc gccttggaag aagatccagc agaacacgtt cacacgctgg | 240 |
| tgcaacgagc acctcaagtg cgtgaacaaa cgcatcggca acctgcagac cgacctgagc | 300 |
| gacgggctgc ggctcatcgc gctgctcgag gtgctcagcc agaagcgcat gtaccgcaag | 360 |
| taccatcagc ggcccacctt tcgccagatg cagctcgaga atgtgtccgt ggcgctcgag | 420 |
| ttcctggacc gtgagagcat caagctcgtg tccatcgata gcaaagccat tgtggatggg | 480 |
| aacctgaagc tcatcttggg tctggtgtgg acgctgatcc tccactactc catctccatg | 540 |
| cccgtgtggg aggatgaagg ggatgatgat gccaagaagc agacgccaaa gcagaggctg | 600 |
| ctggggtgga ttcagaacaa gatcccctac ttgcccatca ccaactttaa ccagaactgg | 660 |
| caagacggca aagccctggg agccctggta gacagctgtg ctccaggtct gtgcccagac | 720 |
| tgggaatcct gggacccgca gaagcctgtg gataatgcac gagaagccat gcagcaggca | 780 |
| gatgactggc tgggtgtccc acaggtcatc actcctgaag aaatcattca cccggatgtg | 840 |
| gacgagcact cagttatgac ttacctgtcc cagttcccca agccaagct caagccgggg | 900 |
| gctcctctca aacccaaact caaccccgaag aaagccaggg cctatggcag aggaatcgag | 960 |
| cccactggaa acatggtgaa gcagccagcc aagttcactg tggacaccat cagcgccggg | 1020 |
| caaggagacg tgatggtgtt tgttgaggac ccagaaggga caaagagga ggcacaagtg | 1080 |
| acccctgaca gtgacaagaa caagacatac tctgtggagt atctgcccaa ggtcaccggg | 1140 |
| ctacacaaag tcacagtcct ctttgcagga cagcacatct ccaagagccc atttgaagtg | 1200 |
| agtgttgaca aggcccaggg agatgccagt aaagtcactg caaaaggtcc agggttggaa | 1260 |
| gctgtaggga acatcgccaa taagcccacc tactttgaca tctatacggc aggagctggt | 1320 |
| gtgggtgaca ttggtgtgga ggtggaagat ccccaggga gaacaccgt ggagttgctc | 1380 |
| gtggaagaca aaggaaacca ggtgtatcga tgtgtgtaca aacccatgca gcctggccct | 1440 |
| cacgtggtca agatcttctt tgctggggac actattccta agagtcccctt cgttgtgcag | 1500 |
| gttggggaag cctgcaatcc aaatgcctgc cgggccagtg gccgaggcct acaacccaaa | 1560 |
| ggcgtccgta tccggagac cacagatttc aaggttgaca ccaaagctgc aggaagtggg | 1620 |
| gagctcggtg taaccatgaa gggtcctaag ggtctggagg agctggtgaa gcagaaagac | 1680 |
| tttctggatg gggtctacgc attcgagtat taccccagca ccccgggag atacagcatt | 1740 |
| gccatcacat gggggggaca ccacattcca aagagcccct ttgaagttca agttggccct | 1800 |
| gaagcgggta tgcagaaagt ccgtgcttgg ggccctgggc tccatggtgg gattgtcggg | 1860 |
| cggtcagcgg acttcgtggt agaatccatt ggctctgaag tggggtctct ggggtttgcc | 1920 |
| attgaaggcc cctctcaggc aaagattgag tacaacgacc agaatgatgg atcgtgtgat | 1980 |
| gtcaaatact ggcccaagga gcctggcgaa tatgctgttc acatcatgtg tgacgacgaa | 2040 |
| gacatcaagg acagcccgta catggccttc atccacccag ccacgggagg ctacaaccct | 2100 |
| gatctggttc gagcatacgg gccaggtttg agaaatctg gatgcattgt caacaacctg | 2160 |
| gccgagttca ctgtggatcc taaggatgct ggaaaagctc ccttaaagat atttgctcag | 2220 |
| gatggggaag ccaacgcat tgacatccag atgaagaacc ggatggacgg cacatatgca | 2280 |
| tgctcataca cccccggtgaa ggccatcaag cacaccattg ctgtggtctg ggaggcgtg | 2340 |
| aacatccecgc acagecccta cagggtcaac atcgggcaag gtagccatcc tcagaaggtc | 2400 |

```
aaagtgtttg ggccaggtgt ggagagaagt ggtctgaagg caaatgaacc tacacacttc   2460
acggtggact gtactgaggc tggggaaggt gatgtcagtg ttggcattaa gtgtgatgcc   2520
cgggtgttaa gtgaagatga ggaagacgtg gattttgaca ttattcacaa tgccaatgat   2580
acgttcacag tcaaatatgt gcctcctgct gctgggcgat acactatcaa agttctcttt   2640
gcatctcagg aaatccccgc cagccctttc agagtcaaag ttgacccttc ccacgatgcc   2700
agcaaagtga aggcagaagg cccagggctc agcaaagcag gtgtggaaaa tgggaaaccg   2760
acccacttca ctgtctacac caaggggggct gggaaagccc cgctcaacgt gcagttcaac   2820
agccctcttc ctggcgatgc agtgaaggat ttggatatca tcgataatta tgactactct   2880
cacacggtta aatatacacc cacccaacag ggcaacatgc aggttctggt gacttacggt   2940
ggcgatccca tccctaaaag ccctttcact gtgggtgttg ctgcaccgct ggatctgagc   3000
aagataaaac tcaatgggct ggaaaacagg gtggaagttg gaaggatca ggagttcacc   3060 gttgatacca gggggcagg aggccagggg aagctggacg tgacaatcct cagcccctct   3120
cggaaggtcg tgccatgcct agtgacacct gtgacaggcc gggagaacag cacggccaag   3180
ttcatccctc gggaggaggg gctgtatgct gtagacgtga cctacgatgg acaccctgtg   3240
cccgggagcc cctacacagt ggaggcctcg ctgccaccag atcccagcaa ggtgaaggcc   3300
cacggtcccg gcctcgaagg tggtctcgtg ggcaagcctg ccgagttcac catcgatacc   3360
aaaggagctg gtactggagg tctgggctta acggtggaag gtccgtgcga ggccaaaatc   3420
gagtgctccg acaatggtga tgggacctgc tccgtctctt accttcccac aaaacccggg   3480
gagtacttcg tcaacatcct ctttgaagaa gtccacatac ctgggtctcc cttcaaagct   3540
gacattgaaa tgccctttga cccctctaaa gtcgtggcat cggggccagg tctcgagcac   3600
gggaaggtgg gtgaagctgg cctccttagc gtcgactgct cggaagcggg accggggggcc   3660 ctgggcctgg aagctgtctc ggactcggga acaaaagccg aagtcagtat tcagaacaac   3720
aaagatggca cctacgcggt gacctacgtg cccctgacgg ccggcatgta cacgttgacc   3780
atgaagtatg gtggcgaact cgtgccacac ttccccgccc gggtcaaggt ggagcccgcc   3840
gtggacacca gcaggatcaa agtctttgga ccaggaatag aagggaaaga tgtgttccgg   3900
gaagctacca ccgactttac agttgactct cggccgctga cccaggttgg gggtgaccac   3960
atcaaggccc acattgccaa cccctcaggg gcctccaccg agtgctttgt cacagacaat   4020
gcggatggga cctaccaggt ggaatacaca cccttttgaga aggtctccca tgtagtggag   4080
gtgacatatg atgacgtgcc tatcccaaac agtcccttca aggtggctgt cactgaaggc   4140
tgccagccat ctagggtgca agcccaagga cctggattga agaggccttt accaacaag   4200 cccaatgtct tcaccgtggt taccagaggc gcaggaattg gtgggcttgg cataactgtt   4260
gagggaccat cagagtcgaa gataaattgc agagacaaca aggatggcag ctgcagtgct   4320
gagtacattc ctttcgcacc gggggattac gatgttaata tcacatatgg aggagcccac   4380
atccccggca gccccttcag ggttcctgtg aaggatgttg tggaccccag caaggtcaag   4440
attgccggcc ccgggctggg ctcaggcgtc cgagcccgtg tcctgcagtc cttcacggtg   4500
gacagcagca aggctggcct ggctccgctg gaagtgaggg ttctgggccc acgaggcttg   4560
gtggagccag tgaacgtggt ggacaatgga gatggcacac acacagtaac ctacacccca   4620
tctcaggagg gaccttacat ggtctcagtt aaatatgctg atgaagagat tcctcgcagt   4680
cccttcaagg tcaaggtcct tcccacatat gatgccagca aagtgactgc cagtggcccc   4740
```

-continued

```
ggccttagtt cctatggtgt gcctgccagt ctacctgtgg actttgcaat tgatgcccga    4800
gatgccgggg aaggcctgct tgctgttcaa ataacggacc aagaaggaaa acccaaaaga    4860
gccattgtcc atgacaataa agatggcacg tatgctgtca cctacatccc cgacaagact    4920
gggcgctata tgattggagt cacctacggg ggtgacgaca tcccactttc tccttatcgc    4980
atccgagcca cacagacggg tgatgccagc aagtgcctgg ccacgggtcc tggaatcgcc    5040
tccactgtga aaactggcga agaagtaggc tttgtggttg atgccaagac tgccgggaag    5100
ggtaaagtga cctgcacggt tctgacccca gatggcactg aggccgaggc cgatgtcatt    5160
gagaatgaag atggaaccta tgacatcttc tacacagctg ccaagccggg cacatatgtg    5220
atctatgtgc gcttcggtgg tgttgatatt cctaacagcc ccttcactgt catggccaca    5280
gatggggaag tcacagccgt ggaggaggca ccggtaaatg catgtccccc tggattcagg    5340
ccctgggtga ccgaagaggc ctatgtccca gtgagtgaca tgaacggcct gggatttaag    5400
ccttttgacc tggtcattcc gtttgctgtc aggaaaggag aaatcactgg agaggtccac    5460
atgccttctg ggaagacagc cacacctgag attgtgacaa caaggacggc acggtcact    5520 gttagatatg cccccactga ggtcgggctc catgagatgc acatcaaata catgggcagc    5580
cacatccctg agagcccact ccagttctac gtgaactacc ccaacagtgg aagtgtttct    5640
gcatacggtc caggcctcgt gtatggagtg ccaacaaaaa ctgccacctt caccatcgtc    5700
acagaggatg caggagaagg tggtctggac ttggctattg agggcccctc aaaagcagaa    5760
atcagctgca ttgacaataa agatgggaca tgcacagtga cctacctgcc gactctgcca    5820
ggcgactaca gcattctggt caagtacaat gacaagcaca tccctggcag ccccttcaca    5880
gccaagatca cagatgacag caggcggtgc tcccaggtga agttgggctc agccgctgac    5940
ttcctgctcg acatcagtga gactgacctc agcagcctga cggccagcat taaggcccca    6000
tctggccgag acgagccctg tctcctgaag aggctgccca caaccacat tggcatctcc    6060 ttcatccccc gggaagtggg cgaacatctg gtcagcatca agaaaaatgg caaccatgtg    6120
gccaacagcc ccgtgtctat catggtggtc cagtcggaga ttggtgacgc ccgccgagcc    6180
aaagtctatg gccgcggcct gtcagaaggc cggactttcg agatgtctga cttcatcgtg    6240
gacacaaggg atgcaggtta tggtggcata tccttggcgg tggaaggccc cagcaaagtg    6300
gacatccaga cggaggacct ggaagatggc acctgcaaag tctcctactt ccctaccgtg    6360
cctggggttt atatcgtctc caccaaattc gctgacgagc acgtgcctgg gagcccatt    6420 accgtgaaga tcagtgggga gggaagagtc aaagagagca tcacccgcac cagtcgggcc    6480
ccgtccgtgg ccactgtcgg gagcatttgt gacctgaacc tgaaaatccc agaaatcaac    6540
agcagtgata tgtcggccca cgtcaccagc ccctctggcc gtgtgactga gcagagatt    6600 gtgcccatgg ggaagaactc acactgcgtc cggtttgtgc cccaggagat gggcgtgcac    6660
acggtcagcg tcaagtaccg tgggcagcac gtcaccggca gccccttcca gttcaccgtg    6720
gggccacttg gtgaaggagg cgcccacaag gtgcgggcag gaggccctgg cctggagaga    6780
ggagaagcgg gagtcccagc tgagttcagc atttggaccc gggaagcagg cgctggaggc    6840
ctctccatcg ctgttgaggg ccccagtaag gccgagatta cattcgatga ccataaaaat    6900
gggtcgtgcg gtgtatctta tattgcccaa gagcctggta actacgaggt gtccatcaag    6960
ttcaatgatg agcacatccc ggaaagcccc tacctggtgc cggtcatcgc accctccgac    7020
gacgcccgcc gcctcactgt tatgagcctt caggaatcgg gattaaaagt taaccagcca    7080
gcatcctttg ctataaggtt gaatggcgca aaaggcaaga ttgatgcaaa ggtgcacagc    7140
```

```
ccctctggag ccgtggagga gtgccacgtg tctgagctgg agccagataa gtatgctgtt    7200
cgcttcatcc ctcatgagaa tggtgtccac accatcgatg tcaagttcaa tgggagccac    7260
gtggttggaa gccccttcaa agtgcgcgtt ggggagcctg acaagcggg gaaccctgcc     7320
ctggtgtccg cctatggcac gggactcgaa gggggcacca caggtatcca gtcggaattc    7380
tttattaaca ccacccgagc aggtccaggg acattatccg tcaccatcga aggcccatcc    7440
aaggttaaaa tggattgcca ggaaacacct gaagggtaca aagtcatgta cacccccatg    7500
gctcctggta actacctgat cagcgtcaaa tacggtgggc ccaaccacat cgtgggcagt    7560
cccttcaagg ccaaggtgac aggccagcgt ctagttagcc ctggctcagc caacgagacc    7620
tcatccatcc tggtggagtc agtgaccagg tcgtctacag agacctgcta tagcgccatt    7680
cccaaggcat cctcggacgc cagcaaggtg acctctaagg gggcagggct ctcaaaggcc    7740
tttgtgggcc agaagagttc cttcctggtg gactgcagca agctggctc caacatgctg     7800
ctgatcgggt ccatgggcc caccaccccc tgcgaggagg tctccatgaa gcatgtaggc     7860
aaccagcaat acaacgtcac atacgtcgtc aaggagaggg gcgattatgt gctggctgtg    7920
aagtgggggg aggaacacat ccctggcagc ccttttcatg tcacagtgcc ttaaaacagt    7980
tttctcaaat cctggagaga gttcttgtgg ttgcttttgt tgcttgtttg taattcattt    8040
tatacaaagc cctccagcct gtttgtgggg ctgaaacccc atccctaaaa tattgctgtt    8100
gtaaaatgcc ttcagaaata agtcctagac tggactcttg agggacatat tggagaatct    8160
taagaaatgc aagcttgttc aggggctga gaagatcctg agtacactag gtgcaaacca     8220
gaactcttgg tggaacagac cagccactgc agcagacaga ccaggaacac aatgagactg    8280
acatttcaaa aaacaaaac tggctagcct gagctgctgg ttcactcttc agcatttatg     8340
aaacaaggct aggggaagat gggcagagaa aaaggggaca cctagtttgg ttgtcatttg    8400
gcaaaggaga tgacttaaaa tccgcttaat ctcttccagt gtccgtgtta atgtatttgg    8460
ctattagatc actagcactg ctttaccgct cctcatcgcc aacaccccca tgctctgtgg    8520
ccttcttaca cttctcagag ggcagagtgg cagccgggca ccctacagaa actcagaggg    8580
cagagtggca gccaggccca catgtctctc aagtacctgt cccctcgctc tggtgattat    8640
ttcttgcaga atcaccacac gagaccatcc cggcagtcat ggttttgctt tagttttcca    8700
agtccgtttc agtcccttcc ttggtctgaa gaaattctgc agtggcgagc agtttcccac    8760
ttgccaaaga tcccttttaa ccaacactag cccttgtttt taacacacgc tccagcccct    8820
catcagcctg ggcagtctta ccaaaatgtt taaagtgatc tcagaggggc ccatggatta    8880
acgccctcat cccaaggtcc gtcccatgac ataacactcc acaccgcccc cagccaactt    8940
catgggtcac ttttctgga aaataatgat ctgtacagac aggacagaat gaaactcctg     9000
cgggtctttg gcctgaaagt tgggaatggt tggggagag aagggcagca gcttattggt     9060
ggtcttttca ccattggcag aaacagtgag agctgtgtgg tgcagaaatc cagaaatgag    9120
gtgtagggaa ttttgcctgc cttcctgcag acctgagctg gctttggaat gaggttaaag    9180
tgtcagggac gttgcctgag cccaaatgtg tagtgtggtc tgggcaggca gacctttagg    9240
ttttgctgct tagtcctgag gaagtggcca ctcttgtggc aggtgtagta tctggggcga    9300
gtgttggggg taaaagccca ccctacagaa agtggaacag cccggagcct gatgtgaaag    9360
gaccacgggg gttgtaagct gggacacgga agccaaactg gaatcaaacg ccgactgtaa    9420
attgtatctt ataacttatt aaataaaaca tttgctccgt aaagttg                  9467
```

<210> SEQ ID NO 30
<211> LENGTH: 193
<212> TYPE: PRT
<213> ORGANISM: Homo sapiens

<400> SEQUENCE: 30

Met Val Ala Pro Lys Ser His Thr Asp Asp Trp Ala Pro Gly Pro Phe
1               5                   10                  15

Ser Ser Lys Pro Gln Arg Ser Gln Leu Gln Ile Phe Ser Ser Val Leu
            20                  25                  30

Gln Thr Ser Leu Leu Phe Leu Leu Met Gly Leu Arg Ala Ser Gly Lys
        35                  40                  45

Asp Ser Ala Pro Thr Val Val Ser Gly Ile Leu Gly Gly Ser Val Thr
    50                  55                  60

Leu Pro Leu Asn Ile Ser Val Asp Thr Glu Ile Glu Asn Val Ile Trp
65                  70                  75                  80

Ile Gly Pro Lys Asn Ala Leu Ala Phe Ala Arg Pro Lys Glu Asn Val
                85                  90                  95

Thr Ile Met Val Lys Ser Tyr Leu Gly Arg Leu Asp Ile Thr Lys Trp
            100                 105                 110

Ser Tyr Ser Leu Cys Ile Ser Asn Leu Thr Leu Asn Asp Ala Gly Ser
        115                 120                 125

Tyr Lys Ala Gln Ile Asn Gln Arg Asn Phe Glu Val Thr Thr Glu Glu
    130                 135                 140

Glu Phe Thr Leu Phe Val Tyr Ala Pro Phe Ile Glu Lys Leu Ser Val
145                 150                 155                 160

His Val Ile Glu Gly Asp His Arg Thr Leu Leu Glu Gly Ser Gly Leu
                165                 170                 175

Glu Ser Ile Ile Ser Thr Leu Ala Glu Pro Arg Val Ser Val Arg Glu
            180                 185                 190

Gly

<210> SEQ ID NO 31
<211> LENGTH: 1525
<212> TYPE: DNA
<213> ORGANISM: Homo sapiens

<400> SEQUENCE: 31
acatacacat acacatgcac acacacactc atatacacat gcagaagctg tgacacgtgc      60
ggaagctgtg gtaagtgcat cctccttcag tctcagttct gaaaatagat catcatggtg     120
gcaccaaaga gtcacacaga tgactgggct cctgggcctt tctccagtaa gccacagagg     180
agtcagctgc aaatattctc ttctgttcta cagacctctc tcctcttcct gctcatggga     240
ctaagagcct ctggaaagga ctcagcccca acagtggtgt cagggatcct aggggggttcc    300 gtgactctcc ccctaaacat ctcagtagac acagagattg agaacgtcat ctggattggt     360
cccaaaaatg ctcttgcttt cgcacgtccc aaagaaaatg taaccattat ggtcaaaagc     420
tacctgggcc gactagacat caccaagtgg agttactccc tgtgcatcag caatctgact     480
ctgaatgatg caggatccta caagcccag ataaaccaaa ggaattttga agtcaccact     540
gaggaggaat tcaccctgtt cgtctatgca ccatttattg aaaagttgtc cgtccacgtc     600
atcgagggtg accaccgcac actcctggag ggcagcggcc tggagtccat catcagcacc     660
ctggctgagc cacgtgtgag cgtgcgggag ggctaggccc tcgcccccac ctgccactgg     720
agaccgctcc gccatcccca cctcaccgcc gcgcagcaga gctggaaggg tcctgccgat     780

```
gggaccctgc caggcccagt gccactgccc cccgaggctg ctagacgtgg gcgttaggcg    840
tgtcccaccc acccgccgcc tcccatggca cgtcgggaac accggagccg ccaacttgga    900
gactcctggt ctgtgaagag ccgctgacgc ccgcaggaac cgggctgggc cttgtgtgcc    960
agtggggttt gtgcttggtc tttctccgct tggatttgct tatttattgc attgctggta   1020
gagactccca agcctgtcca ccctgcaaag actcctcggg cagcatgcgg gtcccgcaca   1080
ctgcacccat ttcctggatg tcccctgcag gcgcgggagg ccatccgggc ctgctggctg   1140
cggcccctc tcagccaggc ctggctcagc ccactgcgtg ggaggtcacc ggccactccc   1200
cgaggagctg ggatccccgg gatgcaggcc cacagtgcgg ggctgcaccc atgatgcgga   1260
gctggcctcc aaccctgcgg gccgcgccag gcaccaactc agtgtttgtc agtgtttgtt   1320
tttccaagaa atggttcaaa ttgctgctca gattttttaaa tttactgtag ctgccagtgt   1380
acacgtgtgg accccatttt atttttacac caatttggtg aaaatgctgc tttcctcagc   1440
ctccccacaa ttaaactgca catggtctct aaaaaaataa aataaataa ataaataaat   1500
aaataaaaag tatcttttct cccca                                        1525
```

<210> SEQ ID NO 32
<211> LENGTH: 641
<212> TYPE: PRT
<213> ORGANISM: Homo sapiens

<400> SEQUENCE: 32

```
Met Val Ala Pro Lys Ser His Thr Asp Asp Trp Ala Pro Gly Pro Phe
1               5                   10                  15

Ser Ser Lys Pro Gln Arg Ser Gln Leu Gln Ile Phe Ser Ser Val Leu
            20                  25                  30

Gln Thr Ser Leu Leu Phe Leu Leu Met Gly Leu Arg Ala Ser Gly Lys
        35                  40                  45

Asp Ser Ala Pro Thr Val Val Ser Gly Ile Leu Gly Gly Ser Val Thr
    50                  55                  60

Leu Pro Leu Asn Ile Ser Val Asp Thr Glu Ile Glu Asn Val Ile Trp
65                  70                  75                  80

Ile Gly Pro Lys Asn Ala Leu Ala Phe Ala Arg Pro Lys Glu Asn Val
                85                  90                  95

Thr Ile Met Val Lys Ser Tyr Leu Gly Arg Leu Asp Ile Thr Lys Trp
            100                 105                 110

Ser Tyr Ser Leu Cys Ile Ser Asn Leu Thr Leu Asn Asp Ala Gly Ser
        115                 120                 125

Tyr Lys Ala Gln Ile Asn Gln Arg Asn Phe Glu Val Thr Thr Glu Glu
    130                 135                 140

Glu Phe Thr Leu Phe Val Tyr Glu Gln Leu Glu Pro Gln Val Thr
145                 150                 155                 160

Met Lys Ser Val Lys Val Ser Glu Asn Phe Ser Cys Asn Ile Thr Leu
                165                 170                 175

Met Cys Ser Val Lys Gly Ala Glu Lys Ser Val Leu Tyr Ser Trp Thr
            180                 185                 190

Pro Arg Glu Pro His Ala Ser Glu Ser Asn Gly Gly Ser Ile Leu Thr
        195                 200                 205

Val Ser Arg Thr Pro Cys Asp Pro Asp Leu Pro Tyr Ile Cys Thr Ala
    210                 215                 220

Gln Asn Pro Val Ser Gln Arg Ser Ser Leu Pro Val His Val Gly Gln
225                 230                 235                 240
```

-continued

```
Phe Cys Thr Asp Pro Gly Ala Ser Arg Gly Thr Gly Glu Thr
            245                 250                 255
Val Val Gly Val Leu Gly Glu Pro Val Thr Leu Pro Leu Ala Leu Pro
                260                 265                 270
Ala Cys Arg Asp Thr Glu Lys Val Val Trp Leu Phe Asn Thr Ser Ile
        275                 280                 285
Ile Ser Lys Glu Arg Glu Ala Ala Thr Ala Asp Pro Leu Ile Lys
    290                 295                 300
Ser Arg Asp Pro Tyr Lys Asn Arg Val Trp Val Ser Ser Gln Asp Cys
305                 310                 315                 320
Ser Leu Lys Ile Ser Gln Leu Lys Ile Glu Asp Ala Gly Pro Tyr His
                325                 330                 335
Ala Tyr Val Cys Ser Glu Ala Ser Ser Val Thr Ser Met Thr His Val
            340                 345                 350
Thr Leu Leu Ile Tyr Arg Arg Leu Arg Lys Pro Lys Ile Thr Trp Ser
                355                 360                 365
Leu Arg His Ser Glu Asp Gly Ile Cys Arg Ile Ser Leu Thr Cys Ser
    370                 375                 380
Val Glu Asp Gly Gly Asn Thr Val Met Tyr Thr Trp Thr Pro Leu Gln
385                 390                 395                 400
Lys Glu Ala Val Val Ser Gln Gly Ser His Leu Asn Val Ser Trp
                405                 410                 415
Arg Ser Ser Glu Asn His Pro Asn Leu Thr Cys Thr Ala Ser Asn Pro
                420                 425                 430
Val Ser Arg Ser Ser His Gln Phe Leu Ser Glu Asn Ile Cys Ser Gly
            435                 440                 445
Pro Glu Arg Asn Thr Lys Leu Trp Ile Gly Leu Phe Leu Met Val Cys
    450                 455                 460
Leu Leu Cys Val Gly Ile Phe Ser Trp Cys Ile Trp Lys Arg Lys Gly
465                 470                 475                 480
Arg Cys Ser Val Pro Ala Phe Cys Ser Ser Gln Ala Glu Ala Pro Ala
                485                 490                 495
Asp Thr Pro Gly Tyr Glu Lys Leu Asp Thr Pro Leu Arg Pro Ala Arg
            500                 505                 510
Gln Gln Pro Thr Pro Thr Ser Asp Ser Ser Ser Asp Ser Asn Leu Thr
        515                 520                 525
Thr Glu Glu Asp Glu Asp Arg Pro Glu Val His Lys Pro Ile Ser Gly
    530                 535                 540
Arg Tyr Glu Val Phe Asp Gln Val Thr Gln Glu Gly Ala Gly His Asp
545                 550                 555                 560
Pro Ala Pro Glu Gly Gln Ala Asp Tyr Asp Pro Val Thr Pro Tyr Val
                565                 570                 575
Thr Glu Val Glu Ser Val Val Gly Glu Asn Thr Met Tyr Ala Gln Val
            580                 585                 590
Phe Asn Leu Gln Gly Lys Thr Pro Val Ser Gln Lys Glu Glu Ser Ser
        595                 600                 605
Ala Thr Ile Tyr Cys Ser Ile Arg Lys Pro Gln Val Val Pro Pro Pro
    610                 615                 620
Gln Gln Asn Asp Leu Glu Ile Pro Glu Ser Pro Thr Tyr Glu Asn Phe
625                 630                 635                 640

Thr
```

<210> SEQ ID NO 33
<211> LENGTH: 2508
<212> TYPE: DNA
<213> ORGANISM: Homo sapiens

<400> SEQUENCE: 33

```
acatacacat acacatgcac acacacactc atatacacat gcagaagctg tgacacgtgc    60
ggaagctgtg gtaagtgcat cctccttcag tctcagttct gaaaatagat catcatggtg   120
gcaccaaaga gtcacacaga tgactgggct cctgggcctt tctccagtaa gccacagagg   180
agtcagctgc aaatattctc ttctgttcta cagacctctc tcctcttcct gctcatggga   240
ctaagagcct ctggaaagga ctcagcccca acagtggtgt cagggatcct agggggttcc   300
gtgactctcc ccctaaacat ctcagtagac acagagattg agaacgtcat ctggattggt   360
cccaaaaatg ctcttgcttt cgcacgtccc aaagaaaatg taaccattat ggtcaaaagc   420
tacctgggcc gactagacat caccaagtgg agttactccc tgtgcatcag caatctgact   480
ctgaatgatg caggatccta caaagcccag ataaaccaaa ggaattttga agtcaccact   540
gaggaggaat tcaccctgtt cgtctatgag cagctgcagg agccccaagt caccatgaag   600
tctgtgaagg tgtctgagaa cttctcctgt aacatcactc taatgtgctc cgtgaagggg   660
gcagagaaaa gtgttctgta cagctggacc ccaagggaac ccatgcttc tgagtccaat   720
ggaggctcca ttcttaccgt ctcccgaaca ccatgtgacc cagacctgcc atacatctgc   780
acagcccaga accccgtcag ccagagaagc tccctccctg tccatgttgg gcagttctgt   840
acagatccag gagcctccag aggaggaaca acggggggaga ctgtggtagg ggtcctggga   900
gagccagtca ccctgccact tgcactccca gcctgccggg acacagagaa ggttgtctgg   960
ttgtttaaca catccatcat tagcaaagag agggaagaag cagcaacggc agatccactc  1020
attaaatcca gggatcctta caagaacagg gtgtgggtct ccagccagga ctgctccctg  1080
aagatcagcc agctgaagat agaggacgcc ggccccctacc atgcctacgt gtgctcagag  1140
gcctccagcg tcaccagcat gacacatgtc accctgctca tctaccgcag gctgaggaag  1200
cccaaaatca cgtggagcct caggcacagt gaggatggca tctgcaggat cagcctgacc  1260
tgctcgtgg aggacggggg aaacactgtc atgtacacat ggacccgct gcagaaggaa  1320
gctgttgtgt cccaagggga atcacacctc aatgtctcat ggagaagcag tgaaaatcac  1380
cccaacctca catgcacagc cagcaaccct gtcagcagga gttcccacca gtttctttct  1440
gagaacatct gttcaggacc tgagagaaac acaaagcttt ggattgggtt gttcctgatg  1500
gtttgccttc tgtgcgttgg gatcttcagc tggtgcattt ggaagcgaaa aggacggtgt  1560
tcagtcccag ccttctgttc cagccaagct gaggccccag cggatacacc aggatatgag  1620
aagctggaca ctcccctcag gcctgccagg caacagccta cacccacctc agacagcagc  1680
tctgacagca acacctcaca actgaggagg at gaggacaggc ctgaggtgca caagcccatc  1740
agtggaagat atgaggtatt tgaccaggtc actcaggagg cgctggaca tgacccagcc  1800
cctgagggcc aagcagacta tgatccgtc actccatatg tcacggaagt tgagtctgtg  1860
gttggagaga acaccatgta tgcacaagtg ttcaacttac agggaaagac cccagttctt  1920
cagaaggaag agagctcagc cacaatctac tgctccatac ggaaacctca ggtggtgcca  1980
ccaccacaac agaatgatct tgagattcct gaaagtccta ccctatgaaaa tttcacctga  2040
aaggaaaagc agctgctgcc tctctcctgg gaccgtgggg ttggaaagtc agctggacct  2100
catggggcct ggggctcaca gacagaagca cctcagaatt tccttcagtg cctcagagat  2160
```

```
gcctggatgt ggcccctccc cctccttctc acccttaagg actcccaaac ccattaatag    2220
ttcagacaca ggctccttct tggagcctat gggcttcaga tgtctttgcc ccatttgtca    2280
cctcgcacac ttatagcgtt tcctcctcga aattctacca agactggtca aatgttgctg    2340
aggggcctgg accagctgtc ctttacacca ccttctcaac actgctgaaa agaacccaag    2400
agaattgtca cacatgacac aagatgtaca taatatcatg ctcactgcag tgttatttaa    2460 aataaaggc aggaaataaa aaaaaaaaaa aaaaaaaaa aaaaaaa                    2508
```

<210> SEQ ID NO 34
<211> LENGTH: 565
<212> TYPE: PRT
<213> ORGANISM: Homo sapiens

<400> SEQUENCE: 34

```
Met Val Ala Pro Lys Ser His Thr Asp Asp Trp Ala Pro Gly Pro Phe
1               5                   10                  15

Ser Ser Lys Pro Gln Arg Ser Gln Leu Gln Ile Phe Ser Ser Val Leu
                20                  25                  30

Gln Thr Ser Leu Leu Phe Leu Leu Met Gly Leu Arg Ala Ser Gly Lys
            35                  40                  45

Asp Ser Ala Pro Thr Val Val Ser Gly Ile Leu Gly Gly Ser Val Thr
        50                  55                  60

Leu Pro Leu Asn Ile Ser Val Asp Thr Glu Ile Glu Asn Val Ile Trp
65                  70                  75                  80

Ile Gly Pro Lys Asn Ala Leu Ala Phe Ala Arg Pro Lys Glu Asn Val
                85                  90                  95

Thr Ile Met Val Lys Ser Tyr Leu Gly Arg Leu Asp Ile Thr Lys Trp
            100                 105                 110

Ser Tyr Ser Leu Cys Ile Ser Asn Leu Thr Leu Asn Asp Ala Gly Ser
        115                 120                 125

Tyr Lys Ala Gln Ile Asn Gln Arg Asn Phe Glu Val Thr Thr Glu Glu
    130                 135                 140

Glu Phe Thr Leu Phe Val Tyr Glu Gln Leu Gln Glu Pro Gln Val Thr
145                 150                 155                 160

Met Lys Ser Val Lys Val Ser Glu Asn Phe Ser Cys Asn Ile Thr Leu
                165                 170                 175

Met Cys Ser Val Lys Gly Ala Glu Lys Ser Val Leu Tyr Ser Trp Thr
            180                 185                 190

Pro Arg Glu Pro His Ala Ser Glu Ser Asn Gly Gly Ser Ile Leu Thr
        195                 200                 205

Val Ser Arg Thr Pro Cys Asp Pro Asp Leu Pro Tyr Ile Cys Thr Ala
    210                 215                 220

Gln Asn Pro Val Ser Gln Arg Ser Ser Leu Pro Val His Val Gly Gln
225                 230                 235                 240

Phe Cys Thr Asp Pro Gly Ala Ser Arg Gly Gly Thr Thr Gly Glu Thr
                245                 250                 255

Val Val Gly Val Leu Gly Glu Pro Val Thr Leu Pro Leu Ala Leu Pro
            260                 265                 270

Ala Cys Arg Asp Thr Glu Lys Val Val Trp Leu Phe Asn Thr Ser Ile
        275                 280                 285

Ile Ser Lys Glu Arg Glu Glu Ala Ala Thr Ala Asp Pro Leu Ile Lys
    290                 295                 300

Ser Arg Asp Pro Tyr Lys Asn Arg Val Trp Val Ser Ser Gln Asp Cys
305                 310                 315                 320
```

```
Ser Leu Lys Ile Ser Gln Leu Lys Ile Glu Asp Ala Gly Pro Tyr His
            325                 330                 335

Ala Tyr Val Cys Ser Glu Ala Ser Ser Val Thr Ser Met Thr His Val
        340                 345                 350

Thr Leu Leu Ile Tyr Arg Pro Glu Arg Asn Thr Lys Leu Trp Ile Gly
            355                 360                 365

Leu Phe Leu Met Val Cys Leu Leu Cys Val Gly Ile Phe Ser Trp Cys
        370                 375                 380

Ile Trp Lys Arg Lys Gly Arg Cys Ser Val Pro Ala Phe Cys Ser Ser
385                 390                 395                 400

Gln Ala Glu Ala Pro Ala Asp Thr Pro Glu Pro Thr Ala Gly His Thr
            405                 410                 415

Leu Tyr Ser Val Leu Ser Gln Gly Tyr Glu Lys Leu Asp Thr Pro Leu
        420                 425                 430

Arg Pro Ala Arg Gln Gln Pro Thr Pro Thr Ser Asp Ser Ser Ser Asp
            435                 440                 445

Ser Asn Leu Thr Thr Glu Glu Asp Glu Asp Arg Pro Glu Val His Lys
        450                 455                 460

Pro Ile Ser Gly Arg Tyr Glu Val Phe Asp Gln Val Thr Gln Glu Gly
465                 470                 475                 480

Ala Gly His Asp Pro Ala Pro Glu Gly Gln Ala Asp Tyr Asp Pro Val
            485                 490                 495

Thr Pro Tyr Val Thr Glu Val Glu Ser Val Val Gly Glu Asn Thr Met
        500                 505                 510

Tyr Ala Gln Val Phe Asn Leu Gln Gly Lys Thr Pro Val Ser Gln Lys
            515                 520                 525

Glu Glu Ser Ser Ala Thr Ile Tyr Cys Ser Ile Arg Lys Pro Gln Val
        530                 535                 540

Val Pro Pro Pro Gln Gln Asn Asp Leu Glu Ile Pro Glu Ser Pro Thr
545                 550                 555                 560

Tyr Glu Asn Phe Thr
            565

<210> SEQ ID NO 35
<211> LENGTH: 2280
<212> TYPE: DNA
<213> ORGANISM: Homo sapiens

<400> SEQUENCE: 35
acatacacat acacatgcac acacacactc atatacacat gcagaagctg tgacacgtgc    60
ggaagctgtg gtaagtgcat cctccttcag tctcagttct gaaaatagat catcatggtg   120
gcaccaaaga gtcacacaga tgactgggct cctgggcctt ctccagtaa gccacagagg    180 agtcagctgc aaatattctc ttctgttcta cagacctctc tcctcttcct gctcatggga   240
ctaagagcct ctggaaagga ctcagcccca acagtggtgt cagggatcct agggggttcc   300
gtgactctcc ccctaaacat ctcagtagac acagagattg agaacgtcat ctggattggt   360
cccaaaaatg ctcttgcttt cgcacgtccc aagaaaatg taaccattat ggtcaaaagc    420
tacctgggcc gactagacat caccaagtgg agttactccc tgtgcatcag caatctgact   480
ctgaatgatg caggatccta caaagcccag ataaaccaaa ggaattttga agtcaccact   540
gaggaggaat tcaccctgtt cgtctatgag cagctgcagg agccccaagt caccatgaag   600
tctgtgaagg tgtctgagaa cttctcctgt aacatcactc taatgtgctc cgtgaagggg   660
```

-continued

```
gcagagaaaa gtgttctgta cagctggacc ccaagggaac cccatgcttc tgagtccaat     720
ggaggctcca ttcttaccgt ctcccgaaca ccatgtgacc cagacctgcc atacatctgc     780
acagcccaga accccgtcag ccagagaagc tccctccctg tccatgttgg gcagttctgt     840
acagatccag gagcctccag aggaggaaca acggggaga ctgtggtagg ggtcctggga      900
gagccagtca ccctgccact tgcactccca gcctgccggg acacagagaa ggttgtctgg     960
ttgtttaaca catccatcat tagcaaagag agggaagaag cagcaacggc agatccactc    1020
attaaatcca gggatcctta caagaacagg gtgtgggtct ccagccagga ctgctccctg    1080
aagatcagcc agctgaagat agaggacgcc ggcccctacc atgcctacgt gtgctcagag    1140
gcctccagcg tcaccagcat gacacatgtc accctgctca tctaccgacc tgagagaaac    1200
acaaagcttt ggattgggtt gttcctgatg gtttgccttc tgtgcgttgg gatcttcagc    1260
tggtgcattt ggaagcgaaa aggacggtgt tcagtcccag ccttctgttc cagccaagct    1320
gaggccccag cggatacacc agaacccaca gctggccaca cgctatactc tgtgctctcc    1380
caaggatatg agaagctgga cactcccctc aggcctgcca gcaacagcc tacacccacc     1440 tcagacagca gctctgacag caacctcaca actgaggagg atgaggacag gcctgaggtg    1500
cacaagccca tcagtggaag atatgaggta tttgaccagg tcactcagga gggcgctgga    1560
catgacccag cccctgaggg ccaagcagac tatgatcccg tcactccata tgtcacggaa    1620
gttgagtctg tggttggaga gaacaccatg tatgcacaag tgttcaactt acagggaaag    1680
accccagttt ctcagaagga agagagctca gccacaatct actgctccat acggaaacct    1740
caggtggtgc caccaccaca acagaatgat cttgagattc ctgaaagtcc tacctatgaa    1800
aatttcacct gaaaggaaaa gcagctgctg cctctctcct gggaccgtgg ggttggaaag    1860
tcagctggac ctcatggggc ctggggctca cagacagaag cacctcagaa tttccttcag    1920
tgcctcagag atgcctggat gtggcccctc cccctccttc tcacccttaa ggactcccaa    1980
acccattaat agttcagaca caggctcctt cttggagcct atgggcttca gatgtctttg    2040
ccccatttgt cacctcgcac acttatagcg tttcctcctc gaaattctac caagactggt    2100
caaatgttgc tgaggggcct ggaccagctg tcctttacac caccttctca acactgctga    2160
aaagaaccca agagaattgt cacacatgac acaagatgta cataatatca tgctcactgc    2220
agtgttattt aaaataaaag gcaggaaata aaaaaaaaa aaaaaaaaa aaaaaaaaa       2280
```

<210> SEQ ID NO 36
<211> LENGTH: 655
<212> TYPE: PRT
<213> ORGANISM: Homo sapiens

<400> SEQUENCE: 36

```
Met Val Ala Pro Lys Ser His Thr Asp Asp Trp Ala Pro Gly Pro Phe
1               5                   10                  15

Ser Ser Lys Pro Gln Arg Ser Gln Leu Gln Ile Phe Ser Ser Val Leu
            20                  25                  30

Gln Thr Ser Leu Leu Phe Leu Leu Met Gly Leu Arg Ala Ser Gly Lys
        35                  40                  45

Asp Ser Ala Pro Thr Val Val Ser Gly Ile Leu Gly Gly Ser Val Thr
    50                  55                  60

Leu Pro Leu Asn Ile Ser Val Asp Thr Glu Ile Glu Asn Val Ile Trp
65                  70                  75                  80

Ile Gly Pro Lys Asn Ala Leu Ala Phe Ala Arg Pro Lys Glu Asn Val
                85                  90                  95
```

-continued

```
Thr Ile Met Val Lys Ser Tyr Leu Gly Arg Leu Asp Ile Thr Lys Trp
            100                 105                 110

Ser Tyr Ser Leu Cys Ile Ser Asn Leu Thr Leu Asn Asp Ala Gly Ser
            115                 120                 125

Tyr Lys Ala Gln Ile Asn Gln Arg Asn Phe Glu Val Thr Thr Glu Glu
            130                 135                 140

Glu Phe Thr Leu Phe Val Tyr Glu Gln Leu Gln Glu Pro Gln Val Thr
145                 150                 155                 160

Met Lys Ser Val Lys Val Ser Glu Asn Phe Ser Cys Asn Ile Thr Leu
                165                 170                 175

Met Cys Ser Val Lys Gly Ala Glu Lys Ser Val Leu Tyr Ser Trp Thr
            180                 185                 190

Pro Arg Glu Pro His Ala Ser Glu Ser Asn Gly Gly Ser Ile Leu Thr
            195                 200                 205

Val Ser Arg Thr Pro Cys Asp Pro Asp Leu Pro Tyr Ile Cys Thr Ala
            210                 215                 220

Gln Asn Pro Val Ser Gln Arg Ser Ser Leu Pro Val His Val Gly Gln
225                 230                 235                 240

Phe Cys Thr Asp Pro Gly Ala Ser Arg Gly Gly Thr Thr Gly Glu Thr
                245                 250                 255

Val Val Gly Val Leu Gly Glu Pro Val Thr Leu Pro Leu Ala Leu Pro
            260                 265                 270

Ala Cys Arg Asp Thr Glu Lys Val Val Trp Leu Phe Asn Thr Ser Ile
            275                 280                 285

Ile Ser Lys Glu Arg Glu Glu Ala Ala Thr Ala Asp Pro Leu Ile Lys
            290                 295                 300

Ser Arg Asp Pro Tyr Lys Asn Arg Val Trp Val Ser Ser Gln Asp Cys
305                 310                 315                 320

Ser Leu Lys Ile Ser Gln Leu Lys Ile Glu Asp Ala Gly Pro Tyr His
                325                 330                 335

Ala Tyr Val Cys Ser Glu Ala Ser Ser Val Thr Ser Met Thr His Val
            340                 345                 350

Thr Leu Leu Ile Tyr Arg Arg Leu Arg Lys Pro Lys Ile Thr Trp Ser
            355                 360                 365

Leu Arg His Ser Glu Asp Gly Ile Cys Arg Ile Ser Leu Thr Cys Ser
            370                 375                 380

Val Glu Asp Gly Gly Asn Thr Val Met Tyr Thr Trp Thr Pro Leu Gln
385                 390                 395                 400

Lys Glu Ala Val Val Ser Gln Gly Glu Ser His Leu Asn Val Ser Trp
                405                 410                 415

Arg Ser Ser Glu Asn His Pro Asn Leu Thr Cys Thr Ala Ser Asn Pro
            420                 425                 430

Val Ser Arg Ser Ser His Gln Phe Leu Ser Glu Asn Ile Cys Ser Gly
            435                 440                 445

Pro Glu Arg Asn Thr Lys Leu Trp Ile Gly Leu Phe Leu Met Val Cys
            450                 455                 460

Leu Leu Cys Val Gly Ile Phe Ser Trp Cys Ile Trp Lys Arg Lys Gly
465                 470                 475                 480

Arg Cys Ser Val Pro Ala Phe Cys Ser Ser Gln Ala Glu Ala Pro Ala
                485                 490                 495

Asp Thr Pro Glu Pro Thr Ala Gly His Thr Leu Tyr Ser Val Leu Ser
            500                 505                 510
```

```
Gln Gly Tyr Glu Lys Leu Asp Thr Pro Leu Arg Pro Ala Arg Gln Gln
            515                 520                 525

Pro Thr Pro Thr Ser Asp Ser Ser Asp Ser Asn Leu Thr Thr Glu
        530                 535                 540

Glu Asp Glu Asp Arg Pro Glu Val His Lys Pro Ile Ser Gly Arg Tyr
545                 550                 555                 560

Glu Val Phe Asp Gln Val Thr Gln Glu Gly Ala Gly His Asp Pro Ala
                565                 570                 575

Pro Glu Gly Gln Ala Asp Tyr Asp Pro Val Thr Pro Tyr Val Thr Glu
            580                 585                 590

Val Glu Ser Val Val Gly Glu Asn Thr Met Tyr Ala Gln Val Phe Asn
        595                 600                 605

Leu Gln Gly Lys Thr Pro Val Ser Gln Lys Glu Glu Ser Ser Ala Thr
    610                 615                 620

Ile Tyr Cys Ser Ile Arg Lys Pro Gln Val Val Pro Pro Gln Gln
625                 630                 635                 640

Asn Asp Leu Glu Ile Pro Glu Ser Pro Thr Tyr Glu Asn Phe Thr
                645                 650                 655

<210> SEQ ID NO 37
<211> LENGTH: 2550
<212> TYPE: DNA
<213> ORGANISM: Homo sapiens

<400> SEQUENCE: 37
acatacacat acacatgcac acacacactc atatacacat gcagaagctg tgacacgtgc      60
ggaagctgtg gtaagtgcat cctccttcag tctcagttct gaaaatagat catcatggtg     120
gcaccaaaga gtcacacaga tgactgggct cctgggcctt tctccagtaa gccacagagg     180
agtcagctgc aaatattctc ttctgttcta cagacctctc cctcttcct gctcatggga      240 ctaagagcct ctggaaagga ctcagcccca acagtggtgt cagggatcct agggggttcc    300
gtgactctcc ccctaaacat ctcagtagac acagagattg agaacgtcat ctggattggt    360
cccaaaaatg ctcttgcttt cgcacgtccc aaagaaaatg taaccattat ggtcaaaagc    420
tacctgggcc gactagacat caccaagtgg agttactccc tgtgcatcag caatctgact    480
ctgaatgatg caggatccta caaagcccag ataaaccaaa ggaattttga agtcaccact    540
gaggaggaat tcaccctgtt cgtctatgag cagctgcagg agcccaagt caccatgaag     600 tctgtgaagg tgtctgagaa cttctcctgt aacatcactc taatgtgctc cgtgaagggg    660
gcagagaaaa gtgttctgta cagctggacc ccaagggaac cccatgcttc tgagtccaat    720
ggaggctcca ttcttaccgt ctcccgaaca ccatgtgacc cagacctgcc atacatctgc    780
acagcccaga accccgtcag ccagagaagc tccctccctg tccatgttgg gcagttctgt    840
acagatccag gagcctccag aggaggaaca acgggggaga ctgtggtagg ggtcctggga     900
gagccagtca ccctgccact tgcactccca gcctgccggg acacagagaa ggttgtctgg    960
ttgtttaaca catccatcat tagcaaagag agggaagaag cagcaacggc agatccactc   1020
attaaatcca gggatcctta caagaacagg gtgtgggtct ccagccagga ctgctccctg   1080
aagatcagcc agctgaagat agaggacgcc ggcccctacc atgcctacgt gtgctcagag   1140
gcctccagcg tcaccagcat gacacatgtc accctgctca tctaccgcag gctgaggaag   1200
cccaaaatca gtggagcct caggcacagt gaggatggca tctgcaggat cagcctgacc   1260
tgctccgtgg aggacggggg aaacactgtc atgtacacat ggaccccgct gcagaaggaa   1320
```

```
gctgttgtgt cccaagggga atcacacctc aatgtctcat ggagaagcag tgaaaatcac    1380
cccaacctca catgcacagc cagcaaccct gtcagcagga gttcccacca gtttctttct    1440
gagaacatct gttcaggacc tgagagaaac acaaagcttt ggattgggtt gttcctgatg    1500
gtttgccttc tgtgcgttgg gatcttcagc tggtgcattt ggaagcgaaa aggacggtgt    1560
tcagtcccag ccttctgttc cagccaagct gaggcccag cggatacacc agaacccaca    1620
gctggccaca cgctatactc tgtgctctcc caaggatatg agaagctgga cactcccctc    1680
aggcctgcca ggcaacagcc tacacccacc tcagacagca gctctgacag caacctcaca    1740
actgaggagg atgaggacag gcctgaggtg cacaagccca tcagtggaag atatgaggta    1800
tttgaccagg tcactcagga gggcgctgga catgacccag cccctgaggg ccaagcagac    1860
tatgatcccg tcactccata tgtcacggaa gttgagtctg tggttggaga gaacaccatg    1920
tatgcacaag tgttcaactt acaggaaag accccagttt ctcagaagga agagagctca    1980
gccacaatct actgctccat acggaaacct caggtggtgc caccaccaca acagaatgat    2040
cttgagattc ctgaaagtcc tacctatgaa aatttcacct gaaaggaaaa gcagctgctg    2100
cctctctcct gggaccgtgg ggttggaaag tcagctggac ctcatggggc ctggggctca    2160
cagacagaag cacctcagaa tttccttcag tgcctcagag atgcctggat gtggcccctc    2220
cccctccttc tcacccttaa ggactcccaa acccattaat agttcagaca caggctcctt    2280
cttggagcct atgggcttca gatgtctttg ccccatttgt cacctcgcac acttatagcg    2340
tttcctcctc gaaattctac caagactggt caaatgttgc tgaggggcct ggaccagctg    2400
tcctttacac caccttctca acactgctga aaagaaccca agagaattgt cacacatgac    2460
acaagatgta cataatatca tgctcactgc agtgttattt aaaataaaag gcaggaaata    2520
aaaaaaaaaa aaaaaaaaaa aaaaaaaaaa                                     2550

<210> SEQ ID NO 38
<211> LENGTH: 238
<212> TYPE: PRT
<213> ORGANISM: Homo sapiens

<400> SEQUENCE: 38

Met Trp Val Pro Val Phe Leu Thr Leu Ser Val Thr Trp Ile Gly
1               5                   10                  15

Ala Ala Pro Leu Ile Leu Ser Arg Ile Val Gly Gly Trp Glu Cys Glu
            20                  25                  30

Lys His Ser Gln Pro Trp Gln Val Leu Val Ala Ser Arg Gly Arg Ala
        35                  40                  45

Val Cys Gly Gly Val Leu Val His Pro Gln Trp Val Leu Thr Ala Ala
    50                  55                  60

His Cys Ile Arg Asn Lys Ser Val Ile Leu Leu Gly Arg His Ser Leu
65                  70                  75                  80

Phe His Pro Glu Asp Thr Gly Gln Val Phe Gln Val Ser His Ser Phe
                85                  90                  95

Pro His Pro Leu Tyr Asp Met Ser Leu Leu Lys Asn Arg Phe Leu Arg
            100                 105                 110

Pro Gly Asp Asp Ser Ser His Asp Leu Met Leu Leu Arg Leu Ser Glu
        115                 120                 125

Pro Ala Glu Leu Thr Asp Ala Val Lys Val Met Asp Leu Pro Thr Gln
    130                 135                 140

Glu Pro Ala Leu Gly Thr Thr Cys Tyr Ala Ser Gly Trp Gly Ser Ile
145                 150                 155                 160
```

Glu Pro Glu Glu Phe Leu Thr Pro Lys Lys Leu Gln Cys Val Asp Leu
            165                 170                 175

His Val Ile Ser Asn Asp Val Cys Ala Gln Val His Pro Gln Lys Val
        180                 185                 190

Thr Lys Phe Met Leu Cys Ala Gly Arg Trp Thr Gly Gly Lys Ser Thr
        195                 200                 205

Cys Ser Trp Val Ile Leu Ile Thr Glu Leu Thr Met Pro Ala Leu Pro
    210                 215                 220

Met Val Leu His Gly Ser Leu Val Pro Trp Arg Gly Gly Val
225                 230                 235

<210> SEQ ID NO 39
<211> LENGTH: 1906
<212> TYPE: DNA
<213> ORGANISM: Homo sapiens

<400> SEQUENCE: 39

```
agccccaagc ttaccacctg cacccggaga gctgtgtcac catgtgggtc ccggttgtct      60
tcctcaccct gtccgtgacg tggattggtg ctgcacccct catcctgtct cggattgtgg     120
gaggctggga gtgcgagaag cattcccaac cctggcaggt gcttgtggcc tctcgtggca     180
gggcagtctg cggcggtgtt ctggtgcacc ccagtgggt cctcacagct gcccactgca     240
tcaggaacaa aagcgtgatc ttgctgggtc ggcacagcc gtttcatcct gaagacacag     300
gccaggtatt tcaggtcagc cacagcttcc acacccgct ctacgatatg agcctcctga     360
agaatcgatt cctcaggcca ggtgatgact ccagccacga cctcatgctg ctccgcctgt     420
cagagcctgc cgagctcacg gatgctgtga aggtcatgga cctgcccacc aggagccag     480 cactggggac cacctgctac gcctcaggct ggggcagcat tgaaccagag gagttcttga     540
ccccaaagaa acttcagtgt gtggacctcc atgttatttc caatgacgtg tgtgcgcaag     600
ttcaccctca gaaggtgacc aagttcatgc tgtgtgctgg acgctggaca gggggcaaaa     660
gcacctgctc gtgggtcatt ctgatcaccg aactgaccat gccagccctg ccgatggtcc     720
tccatggctc cctagtgccc tggagaggag gtgtctagtc agagagtagt cctggaaggt     780
ggcctctgtg aggagccacg gggacagcat cctgcagatg gtcctggccc ttgtcccacc     840
gacctgtcta caaggactgt cctcgtggac cctcccctct gcacaggagc tggaccctga     900
agtcccttcc ccaccggcca ggactggagc ccctaccct ctgttggaat ccctgcccac     960
cttcttctgg aagtcggctc tggagacatt tctctcttct tccaaagctg gaactgcta    1020 tctgttatct gcctgtccag gtctgaaaga taggattgcc caggcagaaa ctgggactga    1080
cctatctcac tctctccctg ctttacccct tagggtgatt ctgggggccc acttgtctgt    1140
aatggtgtgc ttcaaggtat cacgtcatgg ggcagtgaac catgtgccct gcccgaaagg    1200
ccttccctgt acaccaaggt ggtgcattac cggaagtgga tcaaggacac catcgtggcc    1260
aacccctgag cacccctatc aaccccctat tgtagtaaac ttggaacctt ggaaatgacc    1320
aggccaagac tcaagcctcc ccagttctac tgacctttgt ccttaggtgt gaggtccagg    1380
gttgctagga aaagaaatca gcagacacag gtgtagacca gagtgtttct taaatggtgt    1440
aattttgtcc tctctgtgtc ctggggaata ctggccatgc ctggagacat atcactcaat    1500
ttctctgagg acacagatag gatgggtgt ctgtgttatt tgtggggtac agagatgaaa    1560
gaggggtggg atccacactg agagagtgga gagtgacatg tgctggacac tgtccatgaa    1620
gcactgagca gaagctggag gcacaacgca ccagacactc acagcaagga tggagctgaa    1680
```

```
aacataaccc actctgtcct ggaggcactg ggaagcctag agaaggctgt gagccaagga    1740
gggagggtct tcctttggca tgggatgggg atgaagtaag gagagggact ggaccccctg    1800
gaagctgatt cactatgggg ggaggtgtat tgaagtcctc cagacaaccc tcagatttga    1860
tgatttccta gtagaactca cagaaataaa gagctgttat actgtg                   1906
```

<210> SEQ ID NO 40
<211> LENGTH: 218
<212> TYPE: PRT
<213> ORGANISM: Homo sapiens

<400> SEQUENCE: 40

```
Met Trp Val Pro Val Val Phe Leu Thr Leu Ser Val Thr Trp Ile Gly
1               5                   10                  15

Ala Ala Pro Leu Ile Leu Ser Arg Ile Val Gly Gly Trp Glu Cys Glu
            20                  25                  30

Lys His Ser Gln Pro Trp Gln Val Leu Val Ala Ser Arg Gly Arg Ala
        35                  40                  45

Val Cys Gly Gly Val Leu Val His Pro Gln Trp Val Leu Thr Ala Ala
    50                  55                  60

His Cys Ile Arg Lys Pro Gly Asp Asp Ser Ser His Asp Leu Met Leu
65                  70                  75                  80

Leu Arg Leu Ser Glu Pro Ala Glu Leu Thr Asp Ala Val Lys Val Met
                85                  90                  95

Asp Leu Pro Thr Gln Glu Pro Ala Leu Gly Thr Thr Cys Tyr Ala Ser
            100                 105                 110

Gly Trp Gly Ser Ile Glu Pro Glu Glu Phe Leu Thr Pro Lys Lys Leu
        115                 120                 125

Gln Cys Val Asp Leu His Val Ile Ser Asn Asp Val Cys Ala Gln Val
    130                 135                 140

His Pro Gln Lys Val Thr Lys Phe Met Leu Cys Ala Gly Arg Trp Thr
145                 150                 155                 160

Gly Gly Lys Ser Thr Cys Ser Gly Asp Ser Gly Gly Pro Leu Val Cys
                165                 170                 175

Asn Gly Val Leu Gln Gly Ile Thr Ser Trp Gly Ser Glu Pro Cys Ala
            180                 185                 190

Leu Pro Glu Arg Pro Ser Leu Tyr Thr Lys Val Val His Tyr Arg Lys
        195                 200                 205

Trp Ile Lys Asp Thr Ile Val Ala Asn Pro
    210                 215
```

<210> SEQ ID NO 41
<211> LENGTH: 1335
<212> TYPE: DNA
<213> ORGANISM: Homo sapiens

<400> SEQUENCE: 41

```
agccccaagc ttaccacctg cacccggaga gctgtgtcac catgtgggtc ccggttgtct      60
tcctcaccct gtccgtgacg tggattggtg ctgcacccct catcctgtct cggattgtgg     120
gaggctggga gtgcgagaag cattcccaac cctggcaggt gcttgtggcc tctcgtggca     180
gggcagtctg cggcggtgtt ctggtgcacc ccagtgggt cctcacagct gcccactgca     240
tcaggaagcc aggtgatgac tccagccacg acctcatgct gctccgcctg tcagagcctg     300
ccgagctcac ggatgctgtg aaggtcatgg acctgcccac ccaggagcca gcactgggga     360
```

```
ccacctgcta cgcctcaggc tgggcagca ttgaaccaga ggagttcttg accccaaaga      420
aacttcagtg tgtggacctc catgttattt ccaatgacgt gtgtgcgcaa gttcaccctc      480
agaaggtgac caagttcatg ctgtgtgctg gacgctggac aggggggcaaa agcacctgct      540
cgggtgattc tggggggccca cttgtctgta atggtgtgct tcaaggtatc acgtcatggg      600
gcagtgaacc atgtgccctg cccgaaaggc cttccctgta caccaaggtg gtgcattacc      660
ggaagtggat caaggacacc atcgtggcca cccctgagc accccctatca accccctatt      720
gtagtaaact tggaaccttg gaaatgacca ggccaagact caagcctccc cagttctact      780
gacctttgtc cttaggtgtg aggtccaggt ttgctaggaa aagaaatcag cagacacagg      840
tgtagaccag agtgtttctt aaatggtgta attttgtcct ctctgtgtcc tggggaatac      900
tggccatgcc tggagacata tcactcaatt tctctgagga cacagatagg atggggtgtc      960
tgtgttattt gtggggtaca gagatgaaag aggggtggga tccacactga gagagtggag     1020
agtgacatgt gctggacact gtccatgaag cactgagcag aagctggagg cacaacgcac     1080
cagacactca cagcaaggat ggagctgaaa acataaccca ctctgtcctg gaggcactgg     1140
gaagcctaga gaaggctgtg agccaaggag ggagggtctt cctttggcat gggatgggga     1200
tgaagtaagg agagggactg gaccccctgg aagctgattc actatggggg gaggtgtatt     1260
gaagtcctcc agacaaccct cagatttgat gatttcctag tagaactcac agaaataaag     1320
agctgttata ctgtg                                                      1335

<210> SEQ ID NO 42
<211> LENGTH: 69
<212> TYPE: PRT
<213> ORGANISM: Homo sapiens

<400> SEQUENCE: 42

Met Trp Val Pro Val Val Phe Leu Thr Leu Ser Val Thr Trp Ile Gly
1               5                   10                  15

Ala Ala Pro Leu Ile Leu Ser Arg Ile Val Gly Gly Trp Glu Cys Glu
            20                  25                  30

Lys His Ser Gln Pro Trp Gln Val Leu Val Ala Ser Arg Gly Arg Ala
        35                  40                  45

Val Cys Gly Gly Val Leu Val His Pro Gln Trp Val Leu Thr Ala Ala
    50                  55                  60

His Cys Ile Arg Lys
65

<210> SEQ ID NO 43
<211> LENGTH: 555
<212> TYPE: DNA
<213> ORGANISM: Homo sapiens

<400> SEQUENCE: 43
agccccaagc ttaccacctg cacccggaga gctgtgtcac catgtgggtc ccggttgtct       60
tcctcaccct gtccgtgacg tggattggtg ctgcacccct catcctgtct cggattgtgg      120
gaggctggga gtgcgagaag cattcccaac cctggcaggt gcttgtggcc tctcgtggca      180
gggcagtctg cggcggtgtt ctggtgcacc ccagtgggt cctcacagct gcccactgca      240
tcaggaagtg agtaggggcc tgggtctgg ggagcaggtg tctgtgtccc agaggaataa      300
cagctgggca ttttcccag gataacctct aaggccagcc ttgggactgg gggagagagg      360
gaaagttctg gttcaggtca catggggagg cagggttggg gctggaccac cctccccatg      420
```

```
gctgcctggg tctccatctg tgttcctcta tgtctctttg tgtcgctttc attatgtctc     480
ttggtaactg gcttcggttg tgtctctccg tgtgactatt tgttctctc  tctccctctc     540 ttctctgtct tcagt                                                      555
```

```
<210> SEQ ID NO 44
<211> LENGTH: 261
<212> TYPE: PRT
<213> ORGANISM: Homo sapiens

<400> SEQUENCE: 44
```

Met Trp Val Pro Val Val Phe Leu Thr Leu Ser Val Thr Trp Ile Gly
1               5                   10                  15

Ala Ala Pro Leu Ile Leu Ser Arg Ile Val Gly Gly Trp Glu Cys Glu
            20                  25                  30

Lys His Ser Gln Pro Trp Gln Val Leu Val Ala Ser Arg Gly Arg Ala
        35                  40                  45

Val Cys Gly Gly Val Leu Val His Pro Gln Trp Val Leu Thr Ala Ala
    50                  55                  60

His Cys Ile Arg Asn Lys Ser Val Ile Leu Leu Gly Arg His Ser Leu
65                  70                  75                  80

Phe His Pro Glu Asp Thr Gly Gln Val Phe Gln Val Ser His Ser Phe
                85                  90                  95

Pro His Pro Leu Tyr Asp Met Ser Leu Leu Lys Asn Arg Phe Leu Arg
            100                 105                 110

Pro Gly Asp Asp Ser Ser His Asp Leu Met Leu Leu Arg Leu Ser Glu
        115                 120                 125

Pro Ala Glu Leu Thr Asp Ala Val Lys Val Met Asp Leu Pro Thr Gln
    130                 135                 140

Glu Pro Ala Leu Gly Thr Thr Cys Tyr Ala Ser Gly Trp Gly Ser Ile
145                 150                 155                 160

Glu Pro Glu Glu Phe Leu Thr Pro Lys Lys Leu Gln Cys Val Asp Leu
                165                 170                 175

His Val Ile Ser Asn Asp Val Cys Ala Gln Val His Pro Gln Lys Val
            180                 185                 190

Thr Lys Phe Met Leu Cys Ala Gly Arg Trp Thr Gly Gly Lys Ser Thr
        195                 200                 205

Cys Ser Gly Asp Ser Gly Gly Pro Leu Val Cys Asn Gly Val Leu Gln
    210                 215                 220

Gly Ile Thr Ser Trp Gly Ser Glu Pro Cys Ala Leu Pro Glu Arg Pro
225                 230                 235                 240

Ser Leu Tyr Thr Lys Val Val His Tyr Arg Lys Trp Ile Lys Asp Thr
                245                 250                 255

Ile Val Ala Asn Pro
            260

```
<210> SEQ ID NO 45
<211> LENGTH: 1464
<212> TYPE: DNA
<213> ORGANISM: Homo sapiens

<400> SEQUENCE: 45
```

```
agccccaagc ttaccacctg cacccggaga gctgtgtcac catgtgggtc ccggttgtct     60
tcctcaccct gtccgtgacg tggattggtg ctgcacccct catcctgtct cggattgtgg    120
gaggctggga gtgcgagaag cattcccaac cctggcaggt gcttgtggcc tctcgtggca    180
```

```
gggcagtctg cggcggtgtt ctggtgcacc cccagtgggt cctcacagct gcccactgca      240
tcaggaacaa aagcgtgatc ttgctgggtc ggcacagcct gtttcatcct gaagacacag      300
gccaggtatt tcaggtcagc cacagcttcc cacacccgct ctacgatatg agcctcctga      360
agaatcgatt cctcaggcca ggtgatgact ccagccacga cctcatgctg ctccgcctgt      420
cagagcctgc cgagctcacg gatgctgtga aggtcatgga cctgcccacc caggagccag      480
cactggggac cacctgctac gcctcaggct ggggcagcat tgaaccagag gagttcttga      540
ccccaaagaa acttcagtgt gtggacctcc atgttatttc caatgacgtg tgtgcgcaag      600
ttcaccctca gaaggtgacc aagttcatgc tgtgtgctgg acgctggaca gggggcaaaa      660
gcacctgctc gggtgattct gggggcccac ttgtctgtaa tggtgtgctt caaggtatca      720
cgtcatgggg cagtgaacca tgtgccctgc ccgaaaggcc ttccctgtac accaaggtgg      780
tgcattaccg gaagtggatc aaggacacca tcgtggccaa cccctgagca ccctatcaa       840 cccctattg tagtaaactt ggaaccttgg aaatgaccag gccaagactc aagcctcccc       900
agttctactg acctttgtcc ttaggtgtga ggtccagggt tgctaggaaa agaaatcagc      960
agacacaggt gtagaccaga gtgtttctta aatggtgtaa ttttgtcctc tctgtgtcct     1020
ggggaatact ggccatgcct ggagacatat cactcaattt ctctgaggac acagatagga     1080
tggggtgtct gtgttatttg tggggtacag agatgaaaga ggggtgggat ccacactgag     1140
agagtggaga gtgacatgtg ctggacactg tccatgaagc actgagcaga agctggaggc     1200
acaacgcacc agacactcac agcaaggatg gagctgaaaa cataacccac tctgtcctgg     1260
aggcactggg aagcctagag aaggctgtga gccaaggagg gagggtcttc ctttggcatg     1320
ggatggggat gaagtaagga gagggactgg accccctgga agctgattca ctatgggggg     1380
aggtgtattg aagtcctcca gacaaccctc agatttgatg atttcctagt agaactcaca     1440
gaaataaaga gctgttatac tgtg                                            1464
```